(12) United States Patent
Fink et al.

(10) Patent No.: US 9,708,316 B2
(45) Date of Patent: Jul. 18, 2017

(54) TGFβR ANTAGONISTS

(71) Applicant: BRISTOL-MYERS SQUIBB COMPANY, Princeton, NJ (US)

(72) Inventors: Brian E. Fink, Yardley, PA (US); Yufen Zhao, Pennington, NJ (US); Robert M. Borzilleri, New Hope, PA (US); Liping Zhang, East Windsor, NJ (US); Kyoung S. Kim, Vancouver, WA (US); Muthoni G. Kamau, Lawrenceville, NJ (US); Andrew J. Tebben, New Hope, PA (US); Yong Zhang, West Windsor, NJ (US); Andrew F. Donnell, West Windsor, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/977,709

(22) Filed: Dec. 22, 2015

(65) Prior Publication Data
US 2016/0176871 A1 Jun. 23, 2016

Related U.S. Application Data

(60) Provisional application No. 62/095,328, filed on Dec. 22, 2014.

(51) Int. Cl.

| | | |
|---|---|---|
| *A61K 31/4709* | (2006.01) | |
| *A61K 31/501* | (2006.01) | |
| *C07D 487/04* | (2006.01) | |
| *C07D 471/04* | (2006.01) | |
| *A61K 31/5377* | (2006.01) | |
| *A61K 31/437* | (2006.01) | |
| *A61K 31/496* | (2006.01) | |
| *A61K 31/4985* | (2006.01) | |
| *A61K 31/506* | (2006.01) | |
| *A61K 31/541* | (2006.01) | |

(52) U.S. Cl.
CPC .......... *C07D 471/04* (2013.01); *A61K 31/437* (2013.01); *A61K 31/4709* (2013.01); *A61K 31/496* (2013.01); *A61K 31/4985* (2013.01); *A61K 31/501* (2013.01); *A61K 31/506* (2013.01); *A61K 31/5377* (2013.01); *A61K 31/541* (2013.01); *C07D 487/04* (2013.01)

(58) Field of Classification Search
CPC ............................ C07D 487/04; C07D 471/04
USPC ......................................................... 546/113
See application file for complete search history.

(56) References Cited

U.S. PATENT DOCUMENTS

| | | | | |
|---|---|---|---|---|
| 6,316,464 | B1 * | 11/2001 | Cheng | .................. C07D 213/26 514/300 |
| 2004/0176390 | A1 | 9/2004 | Blumberg et al. | |
| 2005/0014942 | A1 | 1/2005 | Maruyama et al. | |
| 2005/0261331 | A1 * | 11/2005 | Nielsen | ................ A61K 31/437 514/300 |
| 2010/0184598 | A1 * | 7/2010 | Selles | .................... A01N 43/90 504/116.1 |
| 2010/0273652 | A1 * | 10/2010 | Mattes | ................... A01N 47/16 504/116.1 |
| 2011/0207732 | A1 | 8/2011 | Heinrich et al. | |

FOREIGN PATENT DOCUMENTS

| | | |
|---|---|---|
| WO | WO 99/20624 | 4/1999 |
| WO | WO 2008/132434 | 11/2008 |
| WO | WO 2010/124793 | 11/2010 |
| WO | WO2014140591 | * 9/2014 |

OTHER PUBLICATIONS

Trejo; J. Med. Chem., 2003 46, 4702-4713.*
Koolman; Bioorganic & Medicinal Chemistry Letters 2009, 19, 1879-1882.*

* cited by examiner

*Primary Examiner* — Noble Jarrell
*Assistant Examiner* — Daniel Carcanague
(74) *Attorney, Agent, or Firm* — Elliott Korsen

(57) ABSTRACT

The invention relates generally to compounds that modulate the activity of TGFβR-1 and TGFβR-2, pharmaceutical compositions containing said compounds and methods of treating proliferative disorders and disorders of dysregulated apoptosis, such as cancer, utilizing the compounds of the invention.

13 Claims, No Drawings

TGFβR ANTAGONISTS

CROSS-REFERENCE TO RELATED APPLICATIONS

This application claims priority from U.S. Provisional Application No. 62/095,328 filed Dec. 22, 2014, the disclosures of which are incorporated herein by reference in their entirety.

FIELD OF THE INVENTION

The invention relates generally to compounds that modulate the activity of TGFβR-1 and TGFβR-2, pharmaceutical compositions containing said compounds and methods of treating proliferative disorders and disorders of dysregulated apoptosis, such as cancer, utilizing the compounds of the invention.

BACKGROUND OF THE INVENTION

TGFβ is a multifunctional cytokine that regulates a wide variety of biological processes that include cell proliferation and differentiation, migration and adhesion, extracellular matrix modification including tumor stroma and immunosuppression, angiogenesis and desmoplasia (Ling and Lee, Current Pharmaceutical Biotech. 2011, 12:2190-2202), processes supporting tumor progression and late stage disease.

The active form of TGFβ is a dimer that signals through the formation of a membrane bound heterotetramer composed of the serine threonine type 1 and type 2 receptors, TGFβR-1 (ALK5) and TGFβR-2, respectively. Upon binding of two type 1 and two type 2 receptors, the type 2 constitutively activated receptors phosphorylate the type 1 receptors in the glycine and serine rich "GS region" activating a signaling cascade through the intracellular signaling effector molecules, Smad2 or Smad3. TGFβR-1 phosphorylates the receptor Smad2 and/or Smad3 (RSmads) that form a complex with Smad4 (Shi and Massague, Cell 2003, 113:685-700). These complexes then translocate to the nucleus where they elicit a wide variety of transcriptional responses resulting in altered gene expression (Weiss and Attisano, WIREs Developmental Biology, 2013, 2:47-63). The TGFβ proteins are prototypic members of a large family of related factors in mammals with a number of these also identified in other phyla. Generally, two groups have been characterized, the TGFβ-like and BMP-like ligands. In addition, in vertebrates, seven type1 receptors and five type 2 receptors have been identified. An additional layer of complexity in ligand/receptor binding is the potential of co-receptors known as type 3 that facilitate ligand binding to the type 1 and 2 receptor complex. These type 3 receptors, also known as Betaglycan and Endoglin are comprised of large extracellular domains and short cytoplasmic tails and bind different TGFβ family members (Bernabeu et al., Biochem Biophys Acta 2009, 1792:954-73). Although type 3 receptors facilitate signaling, cleavage of the extracellular domain can generate soluble proteins that sequester ligands and can potentially inhibit signaling (Bernabeu et al., Biochem Biophys Acta 2009, 1792:954-73). While multiple redundancies in this large family present challenges to identifying a selective inhibitor, TGFβR-1 and -2 are relatively selective targets for TGFβ ligand engagement.

Alteration in TGFβ signaling are associated with a wide variety of human disorders including fibrosis, inflammatory, skeletal, muscular and cardiovascular disorders as well as cancer (Harradine, et al, 2006, Annals of Medicine 38:403-14). In human cancer, TGFβ signaling alterations can occur in the germline or arise spontaneously in various cancer types. TGFβ is also a potent inducer of angiogenesis, which provides a critical support system for solid tumors as well as a mechanism for tumor cell dissemination (Buijs et al., 2011, Curr Pharmaceutical Biotech, 12:2121-37). Therefore multiple strategies to inhibit TGFβ signaling have been exploited in various disease states.

SUMMARY OF THE INVENTION

In a first aspect of the present invention, there is provided a compound of formula (I)

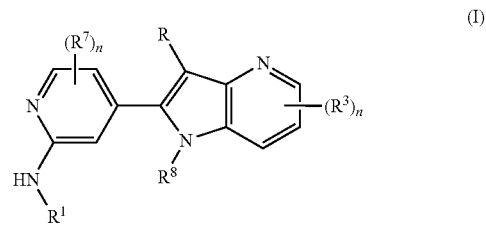

wherein:
R is

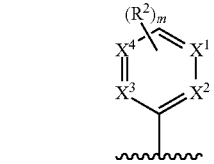

or a heterocylic or heterobicyclic group substituted with 0-4 $R^2$;

$X^1$, $X^2$, $X^3$ and $X^4$ are independently —$CR^4$ or —N—, wherein at least one is —N—;

$R^1$ is hydrogen, $(C_1$-$C_6)$alkyl, $(C_3$-$C_8)$cycloalkyl, —$CONHR^9$, —$COOR^9$, —$COR^9$ or —$SO_2R^9$, any of which except the hydrogen is substituted with 0-3 $R^x$;

$R^x$ is hydrogen, halogen, —OH, halo($C_1$-$C_3$)alkyl, hydroxy($C_1$-$C_3$)alkyl, -amino($C_1$-$C_3$)alkyl, or —CN;

$R^2$ is independently one or more hydrogen, —$CD_3$, $OCD_3$, halogen, —$CF_3$, —$CHF_2$, —CN, $(C_1$-$C_6)$alkyl, $(C_1$-$C_6)$alkoxy or —$SO_2$ $(C_1$-$C_6)$alkyl;

$R^3$ is independently one or more hydrogen, $CD_3$, $OCD_3$, halogen, —CN, $(C_1$-$C_6)$alkyl, $(C_2$-$C_6)$alkenyl, $(C_1$-$C_6)$alkoxy, $(C_3$-$C_8)$cycloalkyl, hydroxy($C_1$-$C_3$)alkyl, $(C_1$-$C_6)$alkylamino-, $(C_1$-$C_6)$alkylamino($C_1$-$C_6)$alkyl, 5-6 membered heteroaryl, heterocyclyl, O-heterocyclyl, —$NR^5R^6$, —$CONR^5R^6$, —$COOR^4$, —$COR^4$, —$SO_2R^4$, —$CHCF_2COOCH_2OH$ or —$CHCF_2CONH_2$, any of which except the hydrogen is substituted with 0-4 $R^y$;

$R^y$ is hydrogen, halogen, —OH, $(C_1$-$C_3$)alkyl, halo($C_1$-$C_3$)alkyl, hydroxy($C_1$-$C_3$)alkyl, -amino($C_1$-$C_3$)alkyl, —NHCOOH, or —CN;

$R^4$ is hydrogen or $(C_1$-$C_6)$alkyl;

$R^5$ and $R^6$ are independently hydrogen, —C(O)alkyl or $(C_1$-$C_6)$alkyl; or $R^5$ and $R^6$ can be taken together with the nitrogen atom to which they are attached to form a 5-7 membered heterocyclo ring;

$R^7$ is independently one or more hydrogen, halogen, halo($C_1$-$C_6$)alkyl or —CN;

$R^8$ is hydrogen, ($C_1$-$C_6$)alkyl, ($C_3$-$C_8$)cycloalkyl, —CONHR$^9$, —COOR$^9$, —COR$^9$ or —SO$_2$R$^9$;

$R^9$ is hydrogen, ($C_1$-$C_6$)alkyl, ($C_3$-$C_8$)cycloalkyl, heterocyclylalkyl-, heterocyclyl($C_1$-$C_3$)alkylamino($C_1$-$C_3$)alkyl- or ($C_1$-$C_3$)alkylamino($C_1$-$C_3$)alkyl;

m is 0, 1, 2, 3, or 4;

n is 0, 1, 2 or 3;

and/or a pharmaceutically acceptable salt, tautomer or stereoisomer thereof.

In another aspect, there is provided a pharmaceutical composition comprising a compound of the invention or a pharmaceutically acceptable salt thereof and one or more pharmaceutically acceptable carriers, diluents or excipients.

In another aspect, there is provided a compound of the invention or a pharmaceutically acceptable salt thereof for use in therapy. In particular, for use in the treatment of a disease or condition for which a TGFβR antagonist is indicated.

In another aspect, there is provided a method of treating cancers, fibrosis, inflammatory, skeletal, muscular and cardiovascular disorders which comprise administering to a subject in need thereof a therapeutically effective amount of a TGFβR antagonist.

DETAILED DESCRIPTION OF THE INVENTION

In a first aspect of the present invention, there is provided a compound of formula (I)

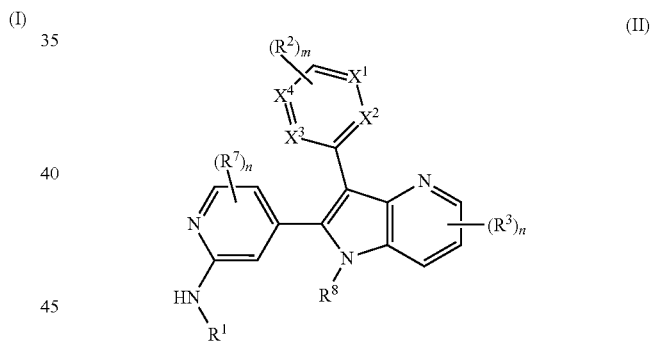

wherein:
R is

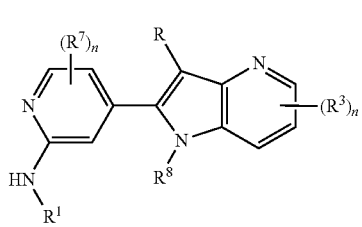

or a heterocylic or heterobicyclic group substituted with 0-4 R$^2$;

$X^1$, $X^2$, $X^3$ and $X^4$ are independently CR$^4$ or wherein at least one is —N—;

$R^1$ is hydrogen, ($C_1$-$C_6$)alkyl, ($C_3$-$C_8$)cycloalkyl, —CONHR$^9$, —COOR$^9$, —COR$^9$ or —SO$_2$R$^9$, any of which except the hydrogen is substituted with 0-3 R$^x$;

$R^x$ is hydrogen, halogen, —OH, halo($C_1$-$C_3$)alkyl, hydroxy($C_1$-$C_3$)alkyl, -amino($C_1$-$C_3$)alkyl, or —CN;

$R^2$ is independently one or more hydrogen, —CD$_3$, OCD$_3$, halogen, —CF$_3$, —CHF$_2$, —CN, ($C_1$-$C_6$)alkyl, ($C_1$-$C_6$)alkoxy or —SO$_2$ ($C_1$-$C_6$)alkyl;

$R^3$ is independently one or more hydrogen, CD$_3$, OCD$_3$, halogen, —CN, ($C_1$-$C_6$)alkyl, ($C_2$-$C_6$)alkenyl, ($C_1$-$C_6$)alkoxy, ($C_3$-$C_8$)cycloalkyl, hydroxy($C_1$-$C_3$)alkyl, ($C_1$-$C_6$)alkylamino-, ($C_1$-$C_6$)alkylamino($C_1$-$C_6$)alkyl, 5-6 membered heteroaryl, heterocyclyl, O-heterocyclyl, —NR$^5$R$^6$, —CONR$^5$R$^6$, —COOR$^4$, —COR$^4$, —SO$_2$R$^4$, —CHCF$_2$COOCH$_2$OH or —CHCF$_2$CONH$_2$, any of which except the hydrogen is substituted with 0-4 R$^y$;

$R^y$ is hydrogen, halogen, —OH, ($C_1$-$C_3$)alkyl, halo($C_1$-$C_3$)alkyl, hydroxy($C_1$-$C_3$)alkyl, -amino($C_1$-$C_3$)alkyl, —NHCOOH, or —CN;

$R^4$ is hydrogen or ($C_1$-$C_6$)alkyl;

$R^5$ and $R^6$ are independently hydrogen, —C(O)alkyl or ($C_1$-$C_6$)alkyl; or $R^5$ and $R^6$ can be taken together with the nitrogen atom to which they are attached to form a 5-7 membered heterocyclo ring;

$R^7$ is independently one or more hydrogen, halogen, halo($C_1$-$C_6$)alkyl or —CN;

$R^8$ is hydrogen, ($C_1$-$C_6$)alkyl, ($C_3$-$C_8$)cycloalkyl, —CONHR$^9$, —COOR$^9$, —COR$^9$ or —SO$_2$R$^9$;

$R^9$ is hydrogen, ($C_1$-$C_6$)alkyl, ($C_3$-$C_8$)cycloalkyl, heterocyclylalkyl-, heterocyclyl($C_1$-$C_3$)alkylamino($C_1$-$C_3$)alkyl- or ($C_1$-$C_3$)alkylamino($C_1$-$C_3$)alkyl;

m is 0, 1, 2, 3, or 4;

n is 0, 1, 2 or 3;

and/or a pharmaceutically acceptable salt, tautomer or stereoisomer thereof.

In a second aspect within the scope of the first aspect of the invention, there is provided a compound of formula (II)

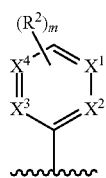

wherein:
$X^1$, $X^2$, $X^3$ and $X^4$ are independently —CR$^4$ or —N—, wherein at least one is —N—;

$R^1$ is hydrogen, ($C_1$-$C_6$)alkyl, ($C_3$-$C_8$)cycloalkyl, —CONHR$^9$, —COOR$^9$, —COR$^9$ or —SO$_2$R$^9$, any of which except the hydrogen is substituted with 0-3 R$^x$;

$R^x$ is hydrogen, halogen, —OH, halo($C_1$-$C_3$)alkyl, hydroxy($C_1$-$C_3$)alkyl, -amino($C_1$-$C_3$)alkyl, or —CN;

$R^2$ is independently one or more hydrogen, —CD$_3$, OCD$_3$, halogen, —CF$_3$, —CHF$_2$, —CN, ($C_1$-$C_6$)alkyl, ($C_1$-$C_6$)alkoxy or —SO$_2$ ($C_1$-$C_6$)alkyl;

$R^3$ is independently one or more hydrogen, CD$_3$, OCD$_3$, halogen, —CN, ($C_1$-$C_6$)alkyl, ($C_2$-$C_6$)alkenyl, ($C_1$-$C_6$)alkoxy, ($C_3$-$C_8$)cycloalkyl, hydroxy($C_1$-$C_3$)alkyl, ($C_1$-$C_6$)alkylamino-, ($C_1$-$C_6$)alkylamino($C_1$-$C_6$)alkyl, 5-6 membered heteroaryl, heterocyclyl, O-heterocyclyl, —NR$^5$R$^6$, —CONR$^5$R$^6$, —COOR$^4$, —COR$^4$, —SO$_2$R$^4$, —CHCF$_2$COOCH$_2$OH or —CHCF$_2$CONH$_2$, any of which except the hydrogen is substituted with 0-4 R$^y$;

R$^y$ is hydrogen, halogen, —OH, (C$_1$-C$_3$)alkyl, halo(C$_1$-C$_3$)alkyl, hydroxy(C$_1$-C$_3$)alkyl, -amino(C$_1$-C$_3$)alkyl, —NHCOOH, or —CN;

R$^4$ is hydrogen or (C$_1$-C$_6$)alkyl;

R$^5$ and R$^6$ are independently hydrogen, —C(O)alkyl or (C$_1$-C$_6$)alkyl; or R$^5$ and R$^6$ can be taken together with the nitrogen atom to which they are attached to form a 5-7 membered heterocyclo ring;

R$^7$ is independently one or more hydrogen, halogen, halo(C$_1$-C$_6$)alkyl or —CN;

R$^8$ is hydrogen, (C$_1$-C$_6$)alkyl, (C$_3$-C$_8$)cycloalkyl, —CONHR$^9$, —COOR$^9$, —COR$^9$ or —SO$_2$R$^9$;

R$^9$ is hydrogen, (C$_1$-C$_6$)alkyl, (C$_3$-C$_8$)cycloalkyl, heterocyclylalkyl-, heterocyclyl(C$_1$-C$_3$)alkylamino(C$_1$-C$_3$)alkyl- or (C$_1$-C$_3$)alkylamino(C$_1$-C$_3$)alkyl;

m is 0, 1, 2, 3, or 4;

n is 0, 1, 2 or 3;

and/or a pharmaceutically acceptable salt, tautomer or stereoisomer thereof.

In a third aspect within the scope of the first and second aspects of the invention, there is provided a compound of formula (II)

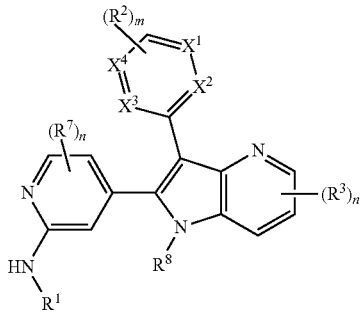

(II)

wherein:

X$^1$, X$^2$, X$^3$ and X$^4$ are independently —CR$^4$ or —N—, wherein at least one is —N—;

R$^1$ is hydrogen, (C$_1$-C$_6$)alkyl, (C$_3$-C$_8$)cycloalkyl, —CONHR$^9$, —COOR$^9$, —COR$^9$ or —SO$_2$R$^9$, any of which except the hydrogen is substituted with 0-3 R$^x$;

R$^x$ is hydrogen, halogen, —OH, halo(C$_1$-C$_3$)alkyl, hydroxy(C$_1$-C$_3$)alkyl, -amino(C$_1$-C$_3$)alkyl, or —CN;

R$^2$ is independently one or more hydrogen, —CD$_3$, OCD$_3$, halogen, —CF$_3$, —CHF$_2$, —CN, (C$_1$-C$_3$)alkyl, (C$_1$-C$_3$)alkoxy or —SO$_2$ (C$_1$-C$_3$)alkyl;

R$^3$ is independently one or more hydrogen, CD$_3$, OCD$_3$, halogen, —CN, (C$_1$-C$_3$)alkyl, (C$_2$-C$_6$)alkenyl, (C$_1$-C$_3$) alkoxy, (C$_3$-C$_8$)cycloalkyl, hydroxy(C$_1$-C$_3$)alkyl, (C$_1$-C$_3$) alkylamino-, (C$_1$-C$_3$)alkylamino(C$_1$-C$_3$)alkyl, 5-6 membered heteroaryl, heterocyclyl, O-heterocyclyl, —NR$^5$R$^6$, —CONR$^5$R$^6$, —COOR$^4$, —COR$^4$, —SO$_2$R$^4$, —CHCF$_2$COOCH$_2$OH or —CHCF$_2$CONH$_2$, any of which except the hydrogen is substituted with 0-4 R$^y$;

R$^y$ is hydrogen, halogen, —OH, (C$_1$-C$_3$)alkyl, halo(C$_1$-C$_3$)alkyl, hydroxy(C$_1$-C$_3$)alkyl, -amino(C$_1$-C$_3$)alkyl, —NHCOOH, or —CN;

R$^4$ is hydrogen or (C$_1$-C$_6$)alkyl;

R$^5$ and R$^6$ are independently hydrogen, —C(O)alkyl or (C$_1$-C$_6$)alkyl; or R$^5$ and R$^6$ can be taken together with the nitrogen atom to which they are attached to form a 5-7 membered heterocyclo ring;

R$^7$ is independently one or more hydrogen, halogen, halo(C$_1$-C$_6$)alkyl or —CN;

R$^8$ is hydrogen, (C$_1$-C$_6$)alkyl, (C$_3$-C$_8$)cycloalkyl, —CONHR$^9$, —COOR$^9$, —COR$^9$ or —SO$_2$R$^9$;

R$^9$ is hydrogen, (C$_1$-C$_6$)alkyl, (C$_3$-C$_8$)cycloalkyl, heterocyclylalkyl-, heterocyclyl(C$_1$-C$_3$)alkylamino(C$_1$-C$_3$)alkyl- or (C$_1$-C$_3$)alkylamino(C$_1$-C$_3$)alkyl;

m is 0, 1, 2, 3, or 4;

n is 0, 1, 2 or 3;

and/or a pharmaceutically acceptable salt, tautomer or stereoisomer thereof.

In a fourth aspect within the scope of the first, second and third aspects of the invention, there is provided a compound of formula (II)

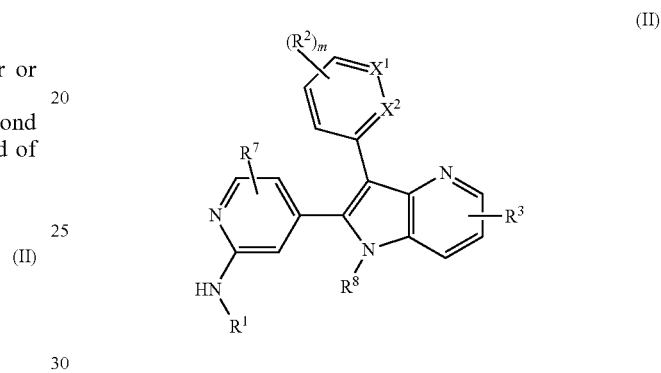

(II)

wherein:

X$^1$ and X$^2$ are independently —CH or —N—;

R$^1$ is hydrogen, (C$_1$-C$_3$)alkyl, (C$_3$-C$_8$)cycloalkyl, —CONHR$^9$, —COOR$^9$, —COR$^9$ or —SO$_2$R$^9$, any of which except the hydrogen is substituted with 0-3 R$^x$;

R$^x$ is hydrogen, halogen, —OH, halo(C$_1$-C$_3$)alkyl, hydroxy(C$_1$-C$_3$)alkyl, -amino(C$_1$-C$_3$)alkyl, or —CN;

R$^2$ is independently one or more hydrogen, —CD$_3$, OCD$_3$, halogen, —CF$_3$, —CHF$_2$, —CN, (C$_1$-C$_3$)alkyl, (C$_1$-C$_3$)alkoxy or —SO$_2$ (C$_1$-C$_3$)alkyl;

R$^3$ is independently one or more hydrogen, CD$_3$, OCD$_3$, halogen, —CN, (C$_1$-C$_3$)alkyl, (C$_2$-C$_6$)alkenyl, (C$_1$-C$_3$) alkoxy, (C$_3$-C$_8$)cycloalkyl, hydroxy(C$_1$-C$_3$)alkyl, (C$_1$-C$_3$) alkylamino-, (C$_1$-C$_3$)alkylamino(C$_1$-C$_3$)alkyl, 5-6 membered heteroaryl, heterocyclyl, O-heterocyclyl, —NR$^5$R$^6$, —CONR$^5$R$^6$, —COOR$^4$, —COR$^4$, —SO$_2$R$^4$, —CHCF$_2$COOCH$_2$OH or —CHCF$_2$CONH$_2$, any of which except the hydrogen is substituted with 0-4 R$^y$;

R$^y$ is hydrogen, halogen, —OH, (C$_1$-C$_3$)alkyl, halo(C$_1$-C$_3$)alkyl, hydroxy(C$_1$-C$_3$)alkyl, -amino(C$_1$-C$_3$)alkyl, —NHCOOH, or —CN;

R$^4$ is hydrogen or (C$_1$-C$_3$)alkyl;

R$^5$ and R$^6$ are independently hydrogen, —C(O)alkyl or (C$_1$-C$_3$)alkyl; or R$^5$ and R$^6$ can be taken together with the nitrogen atom to which they are attached to form a 5-7 membered heterocyclo ring;

R$^7$ is independently one or more hydrogen, halogen, halo(C$_1$-C$_3$)alkyl or —CN;

R$^8$ is hydrogen, (C$_1$-C$_3$)alkyl, (C$_3$-C$_6$)cycloalkyl, —CONHR$^9$, —COOR$^9$, —COR$^9$ or —SO$_2$R$^9$;

R$^9$ is hydrogen, (C$_1$-C$_3$)alkyl, (C$_3$-C$_6$)cycloalkyl, heterocyclylalkyl-, heterocyclyl(C$_1$-C$_3$)alkylamino(C$_1$-C$_3$)alkyl- or (C$_1$-C$_3$)alkylamino(C$_1$-C$_3$)alkyl;

m is 0, 1, 2, 3, or 4;

and/or a pharmaceutically acceptable salt, tautomer or stereoisomer thereof.

In a fifth aspect of the invention, there is provided a compound of formula (II)

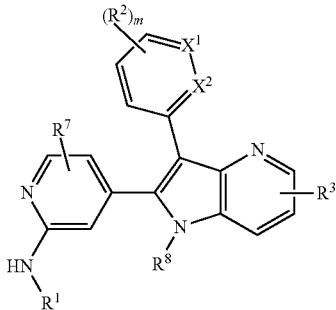

wherein:
$X^1$ and $X^2$ are independently —CH or —N—;
$R^1$ is hydrogen, $(C_1-C_3)$alkyl, $(C_4-C_6)$cycloalkyl, —CONHR$^9$, —COOR$^9$, —COR$^9$ or —SO$_2$R$^9$, any of which except the hydrogen is substituted with 0-3 R$^x$;
$R^x$ is hydrogen, halogen, —OH, halo$(C_1-C_3)$alkyl, hydroxy$(C_1-C_3)$alkyl, -amino$(C_1-C_3)$alkyl, or —CN;
$R^2$ is independently one or more hydrogen, —CD$_3$, OCD$_3$, halogen, —CF$_3$, —CHF$_2$, —CN, $(C_1-C_3)$alkyl, $(C_1-C_3)$alkoxy or —SO$_2$ $(C_1-C_3)$alkyl;
$R^3$ is independently one or more hydrogen, CD$_3$, OCD$_3$, halogen, —CN, $(C_1-C_6)$alkyl, $(C_2-C_6)$alkenyl, $(C_1-C_3)$alkoxy, $(C_3-C_8)$cycloalkyl, hydroxy$(C_1-C_3)$alkyl, $(C_1-C_3)$alkylamino-, $(C_1-C_3)$alkylamino$(C_1-C_3)$alkyl, 5-6 membered heteroaryl, heterocyclyl, O-heterocyclyl, —NR$^5$R$^6$, —CONR$^5$R$^6$, —COOR$^4$, —COR$^4$, —SO$_2$R$^4$, —CHCF$_2$COOCH$_2$OH or —CHCF$_2$CONH$_2$, any of which except the hydrogen is substituted with 0-4 R$^y$;
$R^y$ is hydrogen, halogen, —OH, $(C_1-C_3)$alkyl, halo$(C_1-C_3)$alkyl, hydroxy$(C_1-C_3)$alkyl, -amino$(C_1-C_3)$alkyl, —NHCOOH, or —CN;
$R^4$ is hydrogen or methyl;
$R^5$ and $R^6$ are independently hydrogen, —C(O)alkyl or $(C_1-C_3)$alkyl; or
$R^5$ and $R^6$ can be taken together with the nitrogen atom to which they are attached to form a 5-7 membered heterocyclo ring;
$R^7$ is independently one or more hydrogen, halogen, halo$(C_1-C_3)$alkyl or —CN;
$R^8$ is hydrogen, $(C_1-C_3)$alkyl, or —COR$^9$;
$R^9$ is hydrogen, $(C_1-C_3)$alkyl, $(C_3-C_6)$cycloalkyl, heterocyclylalkyl-, heterocyclyl$(C_1-C_3)$alkylamino$(C_1-C_3)$alkyl- or $(C_1-C_3)$alkylamino$(C_1-C_3)$alkyl;
m is 0, 1 or 2;
and/or a pharmaceutically acceptable salt, tautomer or stereoisomer thereof.

In a sixth aspect of the invention, there is provided a compound of formula (III)

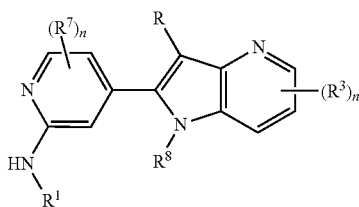

wherein:
R is a heterocylic or heterobicyclic group substituted with 0-4 R$^2$;
$R^1$ is hydrogen, $(C_1-C_6)$alkyl, $(C_3-C_8)$cycloalkyl, —CONHR$^9$, —COOR$^9$, —COR$^9$ or —SO$_2$R$^9$, any of which except the hydrogen is substituted with 0-3 R$^x$;
$R^x$ is hydrogen, halogen, —OH, halo$(C_1-C_3)$alkyl, hydroxy$(C_1-C_3)$alkyl, -amino$(C_1-C_3)$alkyl, or —CN;
$R^2$ is independently one or more hydrogen, —CD$_3$, OCD$_3$, halogen, —CF$_3$, —CHF$_2$, —CN, $(C_1-C_6)$alkyl, $(C_1-C_6)$alkoxy or —SO$_2$ $(C_1-C_6)$alkyl;
$R^3$ is independently one or more hydrogen, CD$_3$, OCD$_3$, halogen, —CN, $(C_1-C_6)$alkyl, $(C_2-C_6)$alkenyl, $(C_1-C_6)$ alkoxy, $(C_3-C_8)$cycloalkyl, hydroxy$(C_1-C_3)$alkyl, $(C_1-C_6)$ alkylamino-, $(C_1-C_6)$alkylamino$(C_1-C_6)$alkyl, 5-6 membered heteroaryl, heterocyclyl, O-heterocyclyl, —NR$^5$R$^6$, —CONR$^5$R$^6$, —COOR$^4$, —COR$^4$, —SO$_2$R$^4$, —CHCF$_2$COOCH$_2$OH or —CHCF$_2$CONH$_2$, any of which except the hydrogen is substituted with 0-4 R$^y$;
$R^y$ is hydrogen, halogen, —OH, $(C_1-C_3)$alkyl, halo$(C_1-C_3)$alkyl, hydroxy$(C_1-C_3)$alkyl, -amino$(C_1-C_3)$alkyl, —NHCOOH, or —CN;
$R^4$ is hydrogen or $(C_1-C_6)$alkyl;
$R^5$ and $R^6$ are independently hydrogen, —C(O)alkyl or $(C_1-C_6)$alkyl; or
$R^5$ and $R^6$ can be taken together with the nitrogen atom to which they are attached to form a 5-7 membered heterocyclo ring;
$R^7$ is independently one or more hydrogen, halogen, halo$(C_1-C_6)$alkyl or —CN;
$R^8$ is hydrogen, $(C_1-C_6)$alkyl, $(C_3-C_8)$cycloalkyl, —CONHR$^9$, —COOR$^9$, —COR$^9$ or —SO$_2$R$^9$;
$R^9$ is hydrogen, $(C_1-C_6)$alkyl, $(C_3-C_8)$cycloalkyl, heterocyclylalkyl-, heterocyclyl$(C_1-C_3)$alkylamino$(C_1-C_3)$alkyl- or $(C_1-C_3)$alkylamino$(C_1-C_3)$alkyl;
n is 0, 1, 2 or 3;
and/or a pharmaceutically acceptable salt, tautomer or stereoisomer thereof.

In another aspect of the invention, there is provided a compound of formula (III)

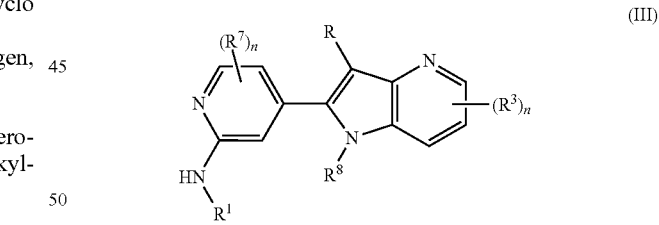

wherein:
R is a heterocylic or heterobicyclic group substituted with 0-4 R$^2$;
$R^1$ is hydrogen, $(C_1-C_3)$alkyl, $(C_3-C_6)$cycloalkyl, —CONHR$^9$, —COOR$^9$, —COR$^9$ or —SO$_2$R$^9$, any of which except the hydrogen is substituted with 0-3 R$^x$;
$R^x$ is hydrogen, halogen, —OH, halo$(C_1-C_3)$alkyl, hydroxy$(C_1-C_3)$alkyl, -amino$(C_1-C_3)$alkyl, or —CN;
$R^2$ is independently one or more hydrogen, —CD$_3$, OCD$_3$, halogen, —CF$_3$, —CHF$_2$, —CN, $(C_1-C_6)$alkyl, $(C_1-C_6)$alkoxy or —SO$_2$ $(C_1-C_6)$alkyl;
$R^3$ is independently one or more hydrogen, CD$_3$, OCD$_3$, halogen, —CN, $(C_1-C_3)$alkyl, $(C_2-C_6)$alkenyl, $(C_1-C_3)$ alkoxy, $(C_3-C_8)$cycloalkyl, hydroxy$(C_1-C_3)$alkyl, $(C_1-C_3)$ alkylamino-, $(C_1-C_3)$alkylamino$(C_1-C_3)$alkyl, 5-6 membered heteroaryl, heterocyclyl, O-heterocyclyl, —NR⁵R⁶, —CONR⁵R⁶, —COOR⁴, —COR⁴, —SO₂R⁴, —CHCF₂COOCH₂OH or —CHCF₂CONH₂, any of which except the hydrogen is substituted with 0-4 $R^y$;

$R^y$ is hydrogen, halogen, —OH, ($C_1$-$C_3$)alkyl, halo($C_1$-$C_3$)alkyl, hydroxy($C_1$-$C_3$)alkyl, -amino($C_1$-$C_3$)alkyl, —NHCOOH, or —CN;

$R^4$ is hydrogen or methyl;

$R^5$ and $R^6$ are independently hydrogen, —C(O)alkyl or ($C_1$-$C_6$)alkyl;

$R^7$ is independently one or more hydrogen, halogen, halo($C_1$-$C_6$)alkyl or —CN;

$R^8$ is hydrogen, ($C_1$-$C_6$)alkyl, ($C_3$-$C_8$)cycloalkyl, —CONHR⁹, —COOR⁹, —COR⁹ or —SO₂R⁹;

$R^9$ is hydrogen, ($C_1$-$C_6$)alkyl, ($C_3$-$C_8$)cycloalkyl, heterocyclylalkyl-, heterocyclyl($C_1$-$C_3$)alkylamino($C_1$-$C_3$)alkyl- or ($C_1$-$C_3$)alkylamino($C_1$-$C_3$)alkyl;

n is 0, 1, 2 or 3;

and/or a pharmaceutically acceptable salt, tautomer or stereoisomer thereof.

In another aspect of the invention, there is provided a compound of formula (III)

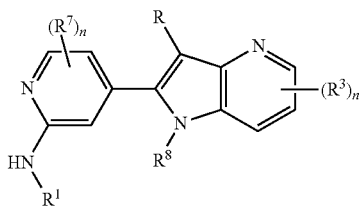

(III)

wherein:

R is thiazole, thiadiazole, thiophene, pyrazole, isoquinoline, indole or quinoline substituted with 0-4 $R^2$;

$R^1$ is hydrogen, ($C_1$-$C_3$)alkyl, ($C_3$-$C_6$)cycloalkyl, —CONHR⁹, —COOR⁹, —COR⁹ or —SO₂R⁹, any of which except the hydrogen is substituted with 0-3 $R^x$;

$R^x$ is hydrogen, halogen, —OH, halo($C_1$-$C_3$)alkyl, hydroxy($C_1$-$C_3$)alkyl, -amino($C_1$-$C_3$)alkyl, or —CN;

$R^2$ is independently one or more hydrogen, —CD₃, OCD₃, halogen, —CF₃, —CHF₂, —CN, ($C_1$-$C_6$)alkyl, ($C_1$-$C_6$)alkoxy or —SO₂ ($C_1$-$C_6$)alkyl;

$R^3$ is independently one or more hydrogen, CD₃, OCD₃, halogen, —CN, ($C_1$-$C_3$)alkyl, ($C_2$-$C_6$)alkenyl, ($C_1$-$C_3$)alkoxy, ($C_3$-$C_8$)cycloalkyl, hydroxy($C_1$-$C_3$)alkyl, ($C_1$-$C_3$)alkylamino-, ($C_1$-$C_3$)alkylamino($C_1$-$C_3$)alkyl, 5-6 membered heteroaryl, heterocyclyl, O-heterocyclyl, —NR⁵R⁶, —CONR⁵R⁶, —COOR⁴, —COR⁴, —SO₂R⁴, —CHCF₂COOCH₂OH or —CHCF₂CONH₂, any of which except the hydrogen is substituted with 0-4 $R^y$;

$R^y$ is hydrogen, halogen, —OH, ($C_1$-$C_3$)alkyl, halo($C_1$-$C_3$)alkyl, hydroxy($C_1$-$C_3$)alkyl, -amino($C_1$-$C_3$)alkyl, —NHCOOH, or —CN;

$R^4$ is hydrogen or methyl;

$R^5$ and $R^6$ are independently hydrogen, —C(O)alkyl or ($C_1$-$C_3$)alkyl;

$R^7$ is independently one or more hydrogen, halogen, halo($C_1$-$C_3$)alkyl or —CN;

$R^8$ is hydrogen, ($C_1$-$C_6$)alkyl, ($C_3$-$C_6$)cycloalkyl, —CONHR⁹, —COOR⁹, —COR⁹ or —SO₂R⁹;

$R^9$ is hydrogen, ($C_1$-$C_6$)alkyl, ($C_3$-$C_6$)cycloalkyl, heterocyclylalkyl-, heterocyclyl($C_1$-$C_3$)alkylamino($C_1$-$C_3$)alkyl- or ($C_1$-$C_3$)alkylamino($C_1$-$C_3$)alkyl;

n is 0, 1, 2 or 3;

and/or a pharmaceutically acceptable salt, tautomer or stereoisomer thereof.

In another aspect of the invention, there is provided a compound of formula (III)

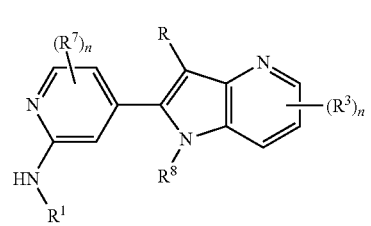

(III)

wherein:

R is thiazole, pyrazole, isoquinoline, indole or quinoline substituted with 0-4 $R^2$;

$R^1$ is —COR⁹ substituted with 0-2 $R^x$;

$R^x$ is hydrogen, halogen, —OH, halo($C_1$-$C_3$)alkyl, hydroxy($C_1$-$C_3$)alkyl, -amino($C_1$-$C_3$)alkyl, or —CN;

$R^2$ is independently one or more hydrogen, —CD₃, OCD₃, halogen, —CF₃, —CHF₂, —CN, ($C_1$-$C_3$)alkyl, ($C_1$-$C_3$)alkoxy or —SO₂ ($C_1$-$C_3$)alkyl;

$R^3$ is independently one or more hydrogen, halogen, —CN, ($C_1$-$C_3$)alkyl, ($C_1$-$C_3$)alkoxy, ($C_3$-$C_6$)cycloalkyl, 5-6 membered heteroaryl, heterocyclo, —NR⁵R⁶, —CONR⁵R⁶, —COOR⁴, —SO₂R⁴ or ($C_1$-$C_3$)alkylamino substituted with 0-2 $R^y$;

$R^y$ is hydrogen, halogen, —OH, ($C_1$-$C_3$)alkyl, halo($C_1$-$C_3$)alkyl, hydroxy($C_1$-$C_3$)alkyl, -amino($C_1$-$C_3$)alkyl, —NHCOOH, or —CN;

$R^4$ is hydrogen or methyl;

$R^5$ and $R^6$ are independently hydrogen, —C(O)alkyl or ($C_1$-$C_3$)alkyl;

$R^7$ is independently one or more hydrogen, halogen, halo($C_1$-$C_3$)alkyl or —CN;

$R^8$ is —COR⁹;

$R^9$ is hydrogen, ($C_1$-$C_3$)alkyl or ($C_3$-$C_6$)cycloalkyl;

n is 0, 1 or 2;

and/or a pharmaceutically acceptable salt, tautomer or stereoisomer thereof.

In another aspect of the invention, there is provided a compound of formula (III)

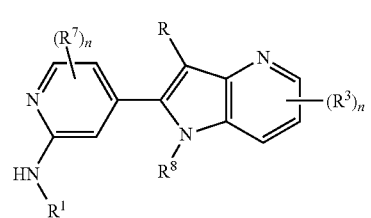

(III)

wherein:

R is thiazole, isoquinoline, indole or quinoline substituted with 0-4 $R^2$;

$R^1$ is —COR⁹;

$R^2$ is independently one or more hydrogen, halogen, —CF₃, —CN, ($C_1$-$C_3$)alkyl, ($C_1$-$C_3$)alkoxy or —SO₂ ($C_1$-$C_3$)alkyl;

$R^3$ is independently one or more hydrogen, halogen, —CN or ($C_1$-$C_3$)alkyl;

R⁷ is independently one or more hydrogen, halogen, halo($C_1$-$C_3$)alkyl or —CN;

R⁸ is hydrogen;

R⁹ is hydrogen or ($C_1$-$C_3$)alkyl;

n is 0, 1 or 2;

and/or a pharmaceutically acceptable salt, tautomer or stereoisomer thereof.

In another aspect, there is provided a compound selected from the exemplified examples within the scope of the first aspect, or a pharmaceutically acceptable salt, tautomer or stereoisomer thereof.

In another aspect, there is provided a compound selected from any subset list of compounds within the scope of any of the above aspects.

In another aspect, there is provided a compound according to claim 1 selected from the following list:

N-{4-[6-Fluoro-3-(6-methoxypyridin-3-yl)-1H-pyrrolo[3,2-b]pyridin-2-yl]pyridin-2-yl}acetamide, N-{4-[6-Chloro-3-(5-fluoropyridin-2-yl)-1H-pyrrolo[3,2-b]pyridin-2-yl]pyridin-2-yl}-2-{[3-(morpholin-4-yl)propyl]amino}acetamide, N-(4-(3-(6-(Difluoromethyl)pyridin-2-yl)-6-(methoxy-d3)-1H-pyrrolo[3,2-b]pyridin-2-yl)pyridin-2-yl)acetamide, N-(4-(3-(6-(Difluoromethyl)pyridin-2-yl)-6-ethoxy-1H-pyrrolo[3,2-b]pyridin-2-yl)pyridin-2-yl)acetamide, N-(4-{3-[6-(Difluoromethyl)pyridin-2-yl]-7-ethoxy-1H-pyrrolo[3,2-b]pyridin-2-yl}pyridin-2-yl)acetamide, N-(4-{3-[6-(Difluoromethyl)pyridin-2-yl]-7-[(dimethylamino)methyl]-1H-pyrrolo[3,2-b]pyridin-2-yl}pyridin-2-yl)acetamide, N-(4-{3-[6-(Difluoromethyl)pyridin-2-yl]-7-(hydroxymethyl)-1H-pyrrolo[3,2-b]pyridin-2-yl}pyridin-2-yl)acetamide, N-(4-{3-[6-(Difluoromethyl)pyridin-2-yl]-7-(1-hydroxyethyl)-1H-pyrrolo[3,2-b]pyridin-2-yl}pyridin-2-yl)acetamide, N-(4-{3-[6-(Difluoromethyl)pyridin-2-yl]-7-[(1R)-1-hydroxyethyl]-1H-pyrrolo[3,2-b]pyridin-2-yl}pyridin-2-yl)acetamide, N-(4-{3-[6-(Difluoromethyl)pyridin-2-yl]-7-[(1S)-1-hydroxyethyl]-1H-pyrrolo[3,2-b]pyridin-2-yl}pyridin-2-yl)acetamide, N-(4-{3-[6-(Difluoromethyl)pyridin-2-yl]-7-[(methylamino)methyl]-1H-pyrrolo[3,2-b]pyridin-2-yl}pyridin-2-yl)acetamide, N-(4-{3-[6-(Difluoromethyl)pyridin-2-yl]-7-(2-hydroxypropan-2-yl)-1H-pyrrolo[3,2-b]pyridin-2-yl}pyridin-2-yl)acetamide, N-(4-(7-(1-Hydroxyethyl)-3-(6-methoxypyridin-3-yl)-1H-pyrrolo[3,2-b]pyridin-2-yl)pyridin-2-yl)acetamide, N-(4-(3-(6-(Difluoromethyl)pyridin-2-yl)-6-methoxy-1H-pyrrolo[3,2-b]pyridin-2-yl)pyridin-2-yl)acetamide, or N-(4-(6-Methoxy-3-(6-methoxypyridin-3-yl)-1H-pyrrolo[3,2-b]pyridin-2-yl)pyridin-2-yl)acetamide;

and/or a pharmaceutically acceptable salt, tautomer or stereoisomer thereof.

In another aspect, there is provided a compound according to claim 1 selected from the following list:

N-{4-[3-(6-Methoxypyridin-3-yl)-1H-pyrrolo[3,2-b]pyridin-2-yl]pyridin-2-yl}acetamide, N-{4-[6-Chloro-3-(5-methoxypyridin-2-yl)-1H-pyrrolo[3,2-b]pyridin-2-yl]pyridin-2-yl}acetamide, N-(4-(3-(5-(Methoxy-d3)pyridin-2-yl)-1H-pyrrolo[3,2-b]pyridin-2-yl)pyridin-2-yl)acetamide, N-(4-(6-Chloro-3-(5-(methoxy-d3)pyridin-2-yl)-1H-pyrrolo[3,2-b]pyridin-2-yl)pyridin-2-yl)acetamide, N-(4-(6-Fluoro-3-(5-(methoxy-d3)pyridin-2-yl)-1H-pyrrolo[3,2-b]pyridin-2-yl)pyridin-2-yl)acetamide, 106

N-(4-(6-Methoxy-3-(5-(methoxy-d3)pyridin-2-yl)-1H-pyrrolo[3,2-b]pyridin-2-yl)pyridin-2-yl)acetamide, N-(4-(3-(6-(Difluoromethyl)pyridin-2-yl)-1H-pyrrolo[3,2-b]pyridin-2-yl)pyridin-2-yl)acetamide, or N-(4-(6-Methoxy-3-(5-methoxypyridin-2-yl)-1H-pyrrolo[3,2-b]pyridin-2-yl)pyridin-2-yl)acetamide and/or a pharmaceutically acceptable salt, tautomer or stereoisomer thereof.

Other Embodiments of the Invention

In another embodiment, the invention provides a pharmaceutical composition, comprising a pharmaceutically acceptable carrier and a therapeutically effective amount of at least one of the compounds of the invention or a stereoisomer, a tautomer, a pharmaceutically acceptable salt, or a solvate thereof.

In another embodiment, the invention provides a process for making a compound of the invention or a stereoisomer, a tautomer, a pharmaceutically acceptable salt, or a solvate thereof.

In another embodiment, the invention provides a method for the treatment and/or prophylaxis of various types of cancer, comprising administering to a patient in need of such treatment and/or prophylaxis a therapeutically effective amount of one or more compounds of the invention, alone, or, optionally, in combination with another compound of the invention and/or at least one other type of therapeutic agent.

In another embodiment, the invention provides a method for the treatment and/or prophylaxis of various types of cancer, including without limitation, small cell lung cancer, non-small cell lung cancer, colorectal cancer, multiple myeloma, acute myeloid leukemia (AML), acute lymphoblastic leukemia (ALL), pancreatic cancer, liver cancer, hepatocellular cancer, neuroblastoma, other solid tumors or other hematological cancers.

In another embodiment, the invention provides a method for the treatment and/or prophylaxis of various types of cancer, including without limitation, small cell lung cancer, non-small cell lung cancer, triple-negative breast cancer, colorectal cancer, prostate cancer, melanoma, pancreatic cancer, multiple myeloma, T-acute lymphoblastic leukemia or AML.

In another embodiment, the invention provides a method for the treatment and/or prophylaxis of Marfan's syndrome and associated diseases, disorders and conditions associated with aberrant TGF-β expression.

In another embodiment, the invention provides a method for the treatment and/or prophylaxis of fibrosis such as hepatic or pulmonary fibrosis.

In another embodiment, the invention provides a compound of the present invention for use in therapy.

In another embodiment, the invention provides a combined preparation of a compound of the present invention and additional therapeutic agent(s) for simultaneous, separate or sequential use in therapy.

Therapeutic Applications

The compounds of formula (I) of the invention are TGFβR antagonists and have potential utility in the treatment of diseases and conditions for which a TGFβR antagonist is indicated.

In one embodiment there is provided a method for the treatment of a disease or condition, for which a TGFβR antagonists is indicated, in a subject in need thereof which comprises administering a therapeutically effective amount of compound of formula (I) or a pharmaceutically acceptable salt thereof.

In another embodiment there is provided a method for treatment of a chronic autoimmune and/or inflammatory condition, in a subject in need thereof which comprises administering a therapeutically effective amount of one or more compounds of formula (I) or a pharmaceutically acceptable salt thereof.

In a further embodiment there is provided a method for treatment of cancer in a subject in need thereof which comprises administering a therapeutically effective amount of one or more compounds of formula (I) or a pharmaceutically acceptable salt thereof.

In one embodiment the subject in need thereof is a mammal, particularly a human.

TGFβR antagonists are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

TGFβR antagonists may be useful in the treatment of fibrotic conditions such as idiopathic pulmonary fibrosis, renal fibrosis, post-operative stricture, keloid formation, scleroderma and cardiac fibrosis.

TGFβR antagonists may be useful in the treatment of cancer, including hematological, epithelial including lung, breast and colon carcinomas, midline carcinomas, mesenchymal, hepatic, renal and neurological tumours.

The term "diseases or conditions for which a TGFβR antagonists is indicated" is intended to include any of or all of the above disease states.

While it is possible that for use in therapy, a compound of formula (I) as well as pharmaceutically acceptable salts thereof may be administered as the compound itself, it is more commonly presented as a pharmaceutical composition.

Pharmaceutical compositions may be presented in unit dose forms containing a predetermined amount of active ingredient pep unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Types of cancers that may be treated with the compounds of this invention include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

In addition to apoptosis defects found in tumors, defects in the ability to eliminate self-reactive cells of the immune system due to apoptosis resistance are considered to play a key role in the pathogenesis of autoimmune diseases. Autoimmune diseases are characterized in that the cells of the immune system produce antibodies against its own organs and molecules or directly attack tissues resulting in the destruction of the latter. A failure of those self-reactive cells to undergo apoptosis leads to the manifestation of the disease. Defects in apoptosis regulation have been identified in autoimmune diseases such as systemic lupus erythematosus or rheumatoid arthritis.

Compounds of the invention are useful for the treatment of certain types of cancer by themselves or in combination or co-administration with other therapeutic agents or radiation therapy. Thus, in one embodiment, the compounds of the invention are co-administered with radiation therapy or a second therapeutic agent with cytostatic or antineoplastic activity. Suitable cytostatic chemotherapy compounds include, but are not limited to (i) antimetabolites; (ii) DNA-fragmenting agents, (iii) DNA-crosslinking agents, (iv) intercalating agents (v) protein synthesis inhibitors, (vi) topoisomerase I poisons, such as camptothecin or topotecan; (vii) topoisomerase II poisons, (viii) microtubule-directed agents, (ix) kinase inhibitors (x) miscellaneous investigational agents (xi) hormones and (xii) hormone antagonists. It is contemplated that compounds of the invention may be useful in combination with any known agents falling into the above 12 classes as well as any future agents that are currently in development. In particular, it is contemplated that compounds of the invention may be useful in combination with current Standards of Care as well as any that evolve over the foreseeable future. Specific dosages and dosing regimens would be based on physicians' evolving knowledge and the general skill in the art.

Further provided herein are methods of treatment wherein compounds of the invention are administered with one or more immuno-oncology agents. The immuno-oncology agents used herein, also known as cancer immunotherapies, are effective to enhance, stimulate, and/or up-regulate immune responses in a subject. In one aspect, the administration of a compound of the invention with an immuno-oncology agent has a synergic effect in inhibiting tumor growth.

In one aspect, the compound(s) of the invention are sequentially administered prior to administration of the immuno-oncology agent. In another aspect, compound(s) of the invention are administered concurrently with the immunology-oncology agent. In yet another aspect, compound(s) of the invention are sequentially administered after administration of the immuno-oncology agent.

In another aspect, compounds of the invention may be co-formulated with an immuno-oncology agent.

Immuno-oncology agents include, for example, a small molecule drug, antibody, or other biologic or small molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α 1β2, FAS, FASL, RELT, DR6, TROY, NGFR.

In another aspect, the immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In one aspect, T cell responses can be stimulated by a combination of a compound of the invention and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with compounds of the invention for the treatment of cancer include antagonists of inhibitory receptors on NK cells or agonists of activating receptors on NK cells. For example, compounds of the invention can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In another aspect, compounds of the invention can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. Suitable PD-1 antibodies include, for example, OPDIVO (nivolumab), KEYTRUDA (pembrolizumab), or MEDI-0680 (AMP-514; WO2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224

In another aspect, the immuno-oncology agent is a PD-L1 antagonist, such as an antagonistic PD-L1 antibody. Suitable PD-L1 antibodies include, for example, MPDL3280A (RG7446; WO2010/077634), durvalumab (MEDI4736), BMS-936559 (WO2007/005874), and MSB0010718C (WO2013/79174).

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In another aspect, the immuno-oncology agent is a CD137 (4-1BB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO06/105021, WO09/009116) and MK-4166 (WO11/028683).

In another aspect, the immuno-oncology agent is an IDO antagonist. Suitable IDO antagonists include, for example, INCB-024360 (WO2006/122150, WO07/75598, WO08/36653, WO08/36642), indoximod, or NLG-919 (WO09/73620, WO09/1156652, WO11/56652, WO12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO11/109400).

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

Pharmaceutical Compositions and Dosing

The invention also provides pharmaceutically acceptable compositions which comprise a therapeutically effective amount of one or more of the compounds of Formula I, formulated together with one or more pharmaceutically acceptable carriers (additives) and/or diluents, and optionally, one or more additional therapeutic agents described above. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained release formulation; (3) topical application, for example, as a cream, ointment, or a controlled release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the patient being treated and the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, troches and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

DEFINITIONS

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

When a substituent is noted as "optionally substituted", the substituents are selected from, for example, substituents such as alkyl, cycloalkyl, aryl, heterocyclo, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g. —SO$_2$NH$_2$, substituted sulfonamido, nitro, cyano, carboxy, carbamyl, e.g. —CONH$_2$, substituted carbamyl e.g. —CONHalkyl, —CONHaryl, —CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl, unless otherwise defined.

For purposes of clarity and in accordance with standard convention in the art, the symbol

is used in formulas and tables to show the bond that is the point of attachment of the moiety or substituent to the core/nucleus of the structure.

Additionally, for purposes of clarity, where a substituent has a dash (-) that is not between two letters or symbols; this is used to indicate a point of attachment for a substituent. For example, —CONH$_2$ is attached through the carbon atom.

Additionally, for purposes of clarity, when there is no substituent shown at the end of a solid line, this indicates that there is a methyl (CH$_3$) group connected to the bond.

As used herein, the term "alkyl" or "alkylene" is intended to include both branched and straight-chain saturated aliphatic hydrocarbon groups having the specified number of carbon atoms. For example, "C$_1$-C$_6$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

The term "alkenyl" denotes a straight- or branch-chained hydrocarbon radical containing one or more double bonds and typically from 2 to 20 carbon atoms in length. For example, "C$_2$-C$_8$ alkenyl" contains from two to eight carbon atoms. Alkenyl groups include, but are not limited to, for example, ethenyl, propenyl, butenyl, 1-methyl-2-buten-1-yl, heptenyl, octenyl and the like.

The term "alkynyl" denotes a straight- or branch-chained hydrocarbon radical containing one or more triple bonds and typically from 2 to 20 carbon atoms in length. For example, "C$_2$-C$_8$ alkenyl" contains from two to eight carbon atoms. Representative alkynyl groups include, but are not limited to, for example, ethynyl, 1-propynyl, 1-butynyl, heptynyl, octynyl and the like.

The term "alkoxy" or "alkyloxy" refers to an O-alkyl group. "C$_{1-6}$ alkoxy" (or alkyloxy), is intended to include C$_1$, C$_2$, C$_3$, C$_4$, C$_5$, and C$_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

The term "aryl", either alone or as part of a larger moiety such as "aralkyl", "aralkoxy", or "aryloxyalkyl", refers to monocyclic, bicyclic and tricyclic ring systems having a total of five to 15 ring members, wherein at least one ring in the system is aromatic and wherein each ring in the system contains three to seven ring members. In certain embodiments of the invention, "aryl" refers to an aromatic ring system which includes, but not limited to phenyl, biphenyl, indanyl, 1-naphthyl, 2-naphthyl and terahydronaphthyl. The term "aralkyl" or "arylalkyl" refers to an alkyl residue attached to an aryl ring. Non-limiting examples include benzyl, phenethyl and the like. The fused aryls may be connected to another group either at a suitable position on the cycloalkyl ring or the aromatic ring. For example:

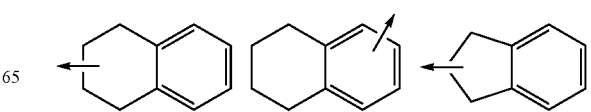

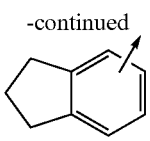

Arrowed lines drawn from the ring system indicate that the bond may be attached to any of the suitable ring atoms.

The term "cycloalkyl" refers to cyclized alkyl groups. $C_{3-6}$ cycloalkyl is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

The term "cycloalkylalkyl" refers to a cycloalkyl or substituted cycloalkyl bonded to an alkyl group connected to the core of the compound.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluoroethoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "benzyl," as used herein, refers to a methyl group on which one of the hydrogen atoms is replaced by a phenyl group.

As used herein, the term "heterocycle," "heterocyclyl," or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "heterocyclylalkyl" refers to a heterocyclyl or substituted heterocyclyl bonded to an alkyl group connected to the core of the compound.

The term "counter ion" is used to represent a negatively charged species such as chloride, bromide, hydroxide, acetate, and sulfate or a positively charged species such as sodium (Na+), potassium (K+), ammonium ($R_nNH_m$+ where n=0-4 and m=0-4) and the like.

The term "electron withdrawing group" (EWG) refers to a substituent which polarizes a bond, drawing electron density towards itself and away from other bonded atoms. Examples of EWGs include, but are not limited to, $CF_3$, $CF_2CF_3$, CN, halogen, haloalkyl, $NO_2$, sulfone, sulfoxide, ester, sulfonamide, carboxamide, alkoxy, alkoxyether, alkenyl, alkynyl, OH, C(O)alkyl, $CO_2H$, phenyl, heteroaryl, —O-phenyl, and —O— heteroaryl. Preferred examples of EWG include, but are not limited to, $CF_3$, $CF_2CF_3$, CN, halogen, $SO_2(C_{1-4}$ alkyl), $CONH(C_{1-4}$ alkyl), $CON(C_{1-4}$ alkyl)$_2$, and heteroaryl. More preferred examples of EWG include, but are not limited to, $CF_3$ and CN.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. and Greene, T. W. *Protecting Groups in Organic Synthesis*, 4th Edition, Wiley (2007) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington: The Science and Practice of Pharmacy*, 22$^{nd}$ Edition, Allen, L. V. Jr., Ed.; Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);
b) Bundgaard, H., Chapter 5, "Design and Application of Prodrugs," A *Textbook of Drug Design and Development*, pp. 113-191, Krosgaard-Larsen, P. et al., eds., Harwood Academic Publishers (1991);
c) Bundgaard, H., *Adv. Drug Deliv. Rev.*, 8:1-38 (1992);
d) Bundgaard, H. et al., *J. Pharm. Sci.*, 77:285 (1988);
e) Kakeya, N. et al., *Chem. Pharm. Bull.*, 32:692 (1984); and
f) Rautio, J (Editor). *Prodrugs and Targeted Delivery (Methods and Principles in Medicinal Chemistry)*, Vol 47, Wiley-VCH, 2011.

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxy methyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art. Preparation of prodrugs is well known in the art and described in, for example, King, F. D., ed., *Medicinal Chemistry: Principles and Practice*, The Royal Society of Chemistry, Cambridge, UK (2$^{nd}$ edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3$^{rd}$ edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. The isotopes of hydrogen can be denoted as $^1$H (hydrogen), $^2$H (deuterium) and $^3$H (tritium). They are also commonly denoted as D for deuterium and T for tritium. In the application, $CD_3$ denotes a methyl group wherein all of the hydrogen atoms are deuterium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent, i.e., a compound of the invention, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

METHODS OF PREPARATION

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The compounds of this invention may be prepared using the reactions and techniques described in this section. The reactions are performed in solvents appropriate to the reagents and materials employed and are suitable for the transformations being affected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Third Edition, Wiley and Sons, 1999).

Compounds of Formula (I) may be prepared by reference to the methods illustrated in the following Schemes. As shown therein the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

The synthesis of the compounds of Formula (I) can be made using the methods summarized in Schemes 1 to 4.

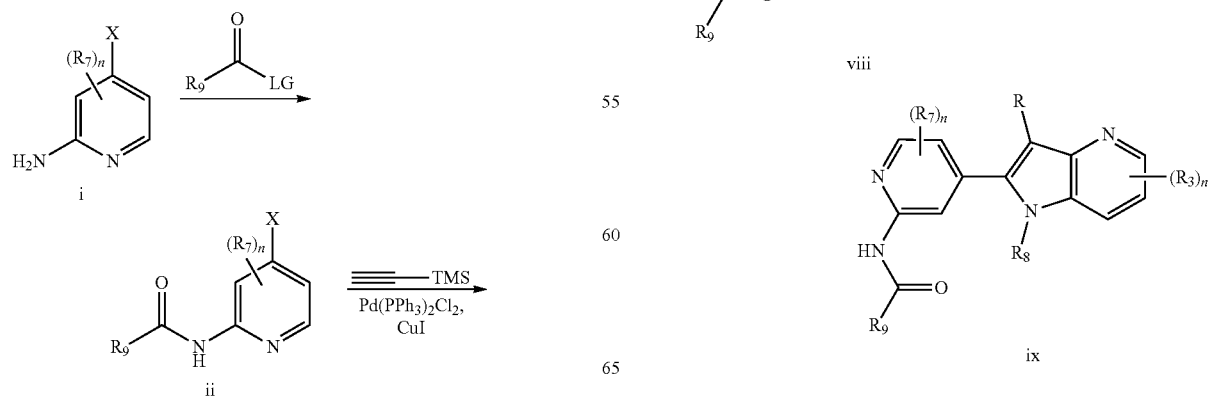

Compounds of general formula ii may be prepared from suitably substituted 2-aminopyridines i (X=halogen or other appropriate functionality) by treatment with an acylating agent such as acetic anhydride (LG=—OAc) in the presence of a base such as DMAP using a suitable solvent such as dimethylformamide at an appropriate temperature. Treatment of compound ii with a protected acetylene such as trimethylsilylacetylene in the presence of a catalyst such as $Pd(PPh_3)_2Cl_2$ with an additive such as CuI in the presence of a base such as triethylamine at elevated temperature may be used to effect transformation to compounds of formula iii. Deprotection may be accomplished by treatment with tetrabutylammonium fluoride in a solvent such as THF or other means known to one skilled in the art to afford compounds of formula iv. The reaction of compounds of formula iv with suitably substituted 3-aminopyridines (v, X=halogen) in the presence of a catalyst such as $Pd(PPh_3)_2Cl_2$ with an additive such as CuI in the presence of a base such as triethylamine in an appropriate solvent such as dimethylformamide at elevated temperature may be used to produce compounds of formula vi. Further, treatment of compounds of formula vi with trifluoracetic anhydride, or other appropriate acylating reagent in a solvent such as dichloromethane in the presence of a base such as triethylamine at an appropriate temperature may be used to afford compounds of formula vii. Cyclization of compounds of formula vii in the presence of an appropriately substituted heteroaryl halide (R—X) in the presence of a catalyst such as $Pd(PPh_3)_4$ and a base such as $Cs_2CO_3$ in an appropriate solvent such as acetonitrile at an elevated temperature such as 100° C. may afford compounds of formula viii. Compounds of formula viii may be further elaborated to compounds of general formula ix by treatment with an appropriately functionalized reagent ($R_8$—X) where X is leaving group, for example halogen, in the presence of a base such as triethylamine in an appropriate solvent such as dimethylformamide.

Scheme 2

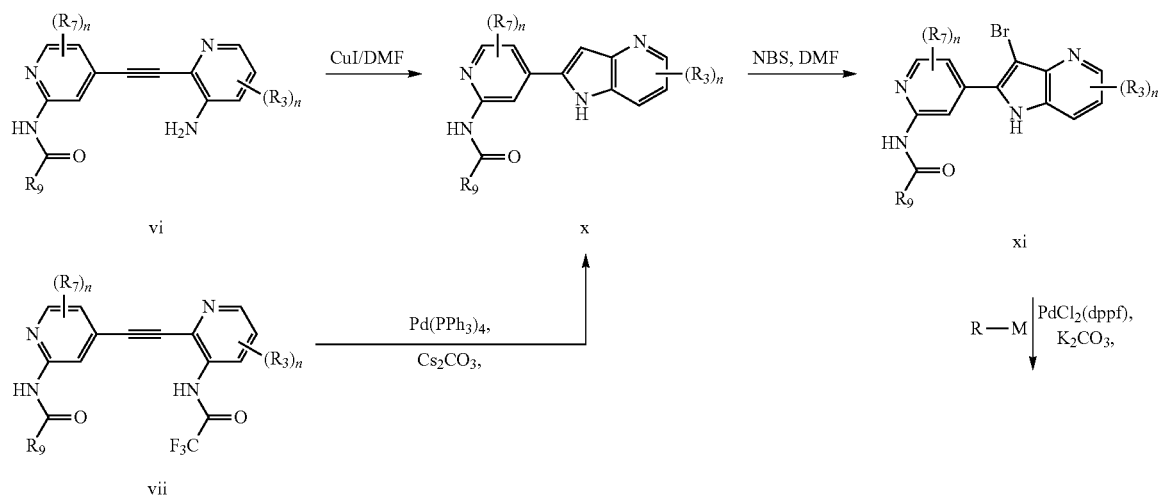

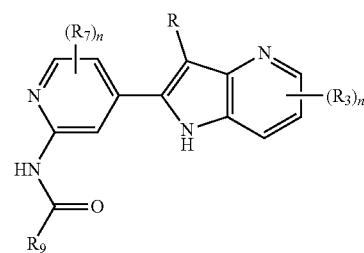

Alternatively, as described in Scheme 2, compounds of formula vi may be cyclized directly through treatment with an appropriate reagent such as CuI in an appropriate solvent such as DMF at elevated temperature to afford compounds of formula x. Additionally, compounds of formula x may be prepared by treatment of compounds of formula vii with a catalyst such as $Pd(PPh_3)_4$ in the presence of a base such as $Cs_2CO_3$ in an appropriate solvent such as acetonitrile at elevated temperatures such as 100° C. Compounds of formula x may be treated with a halogenating reagent, such as N-bromosuccinimide in a solvent such as dimethylformamide to provide compounds of formula xi. Compounds of formula xi may be further elaborated to afford compounds of formula viii by treatment with an organometallic reagent, such as a boronic acid (M=B(OH)$_2$) or boronate ester in the presence of a catalyst such as $PdCl_2(dppf)$ with a base such as $K_2CO_3$ in an appropriate solvent such as 1,4-dioxane.

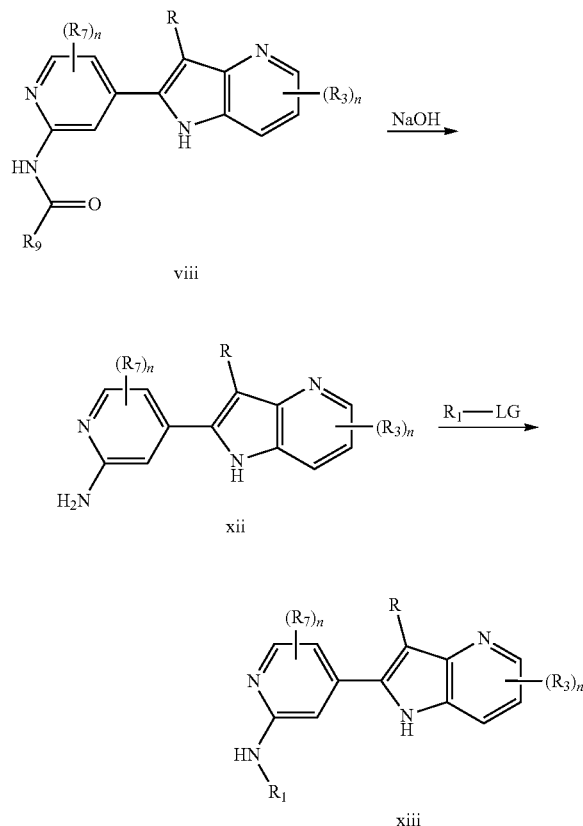

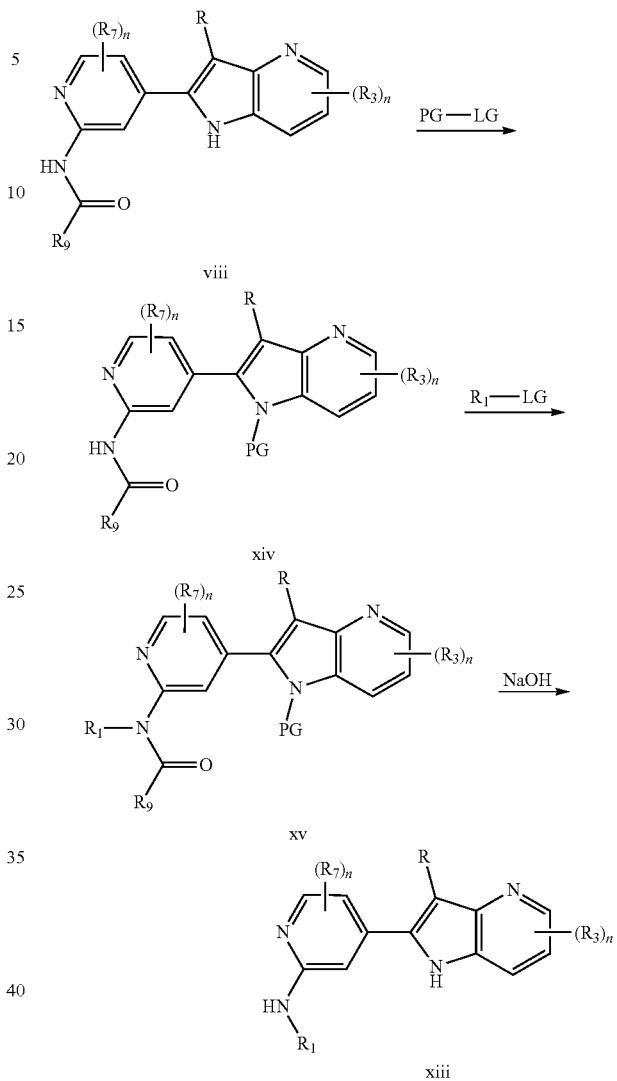

Compounds of formula viii may also be further elaborated as described in Scheme 3. Treatment of compounds of formula viii with a base, such as sodium hydroxide, in a solvent such as water or a mixture of water and methanol, at elevated temperature may provide free amines of formula xii. Reaction of compounds of formula xii with an appropriately substituted reagent containing a leaving group, for example halogen (LG=Hal), in the presence of a base in an appropriate solvent such as dimethylformamide may provide compounds of formula xiii. Alternatively, compounds of formula xiii may be treated with a carboxylic acid (LG=OH) and a peptide coupling reagent such as EDC to afford compounds of general formula xiii.

Alternatively, compounds of formula viii may be selectively protected by several methods known to one skilled in the art. For example, treatment with a sulfonyl chloride (PG-LG=pTsCl) in the presence of a base such as triethylamine in an appropriate solvent such as dimethylformamide may be used to afford compounds of general formula xiv. Reaction of compounds of formula xiv with an appropriately substituted reagent containing a leaving group, for example halogen (LG=Hal), in the presence of a base in an appropriate solvent such as dimethylformamide may provide compounds of formula xv. Protecting group removal may be effected in many ways known to one skilled in the art, for example by treatment with a base such as sodium hydroxide in a solvent or solvent mixture such as aqueous methanol to afford compounds of general formula xiii.

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein below, but rather is defined by the claims appended hereto.

| Abbreviations | |
|---|---|
| Ac₂O | acetic anhydride |
| ACN | Acetonitrile |
| CH₃CN | Acetonitrile |
| Cs₂CO₃ | cesium carbonate |
| DCM | dichloromethane |
| DMAP | dimethylaminopyridine |
| DMF | dimethylformamide |
| DMSO | dimethyl sulfoxide |
| Et₃N | triethyl amine |
| EtOAc | ethyl acetate |
| g | Gram |
| h | hour(s) |
| H₂O | Water |
| HPLC | high pressure liquid chromatography |
| K₂CO₃ | potassium carbonate |
| LCMS | Liquid Chromatography-Mass Spectroscopy |
| MeI | methyl iodide |
| MeOH | Methanol |
| min | minute(s) |
| MgSO₄ | magnesium sulfate |
| mL | Milliliter |
| mmol | Millimolar |
| NaHCO₃ | sodium bicarbonate |
| NaOH | sodium hydroxide |
| NBS | N-bromosuccinamide |
| NH₄OAc | ammonium acetate |
| NH₄OH | ammonium hydroxide |
| PdCl₂(dppf) | [1,1'-bis(diphenylphosphino)ferrocene]dichloropalladium |
| Pd(Ph₃P)₄ | tetrakis(triphenylphosphine)palladium |
| RT | retention time |
| TBAF | tetrabutylammonium fluoride |
| TEA | triethylamine |
| TFA | trifluoroacetic acid |
| THF | tetrahydrofuran |
| Ac₂O | acetic anhydride |

Example 1

N-{4-[3-(6-Methylpyridin-2-yl)-1H-pyrrolo[3,2-b]pyridin-2-yl]pyridin-2-yl}acetamide

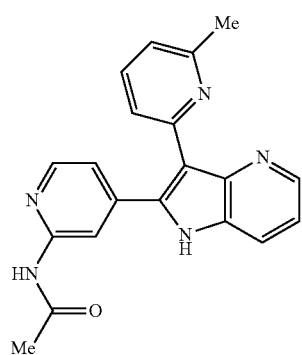 [SMILES: CC(=O)Nc1cc(-c2[nH]c3cccnc3c2-c2cccc(C)n2)ccn1]

1A): N-(4-Bromopyridin-2-yl)acetamide

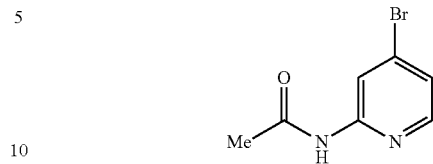

To a mixture of 4-bromopyridin-2-amine (3.8 g, 22 mmol) in Ac₂O (20 mL) was added DMAP (0.054 g, 0.44 mmol). The mixture was heated in a sealed pressure reaction vessel at 140° C. for 1 h, and then cooled to room temperature. The reaction mixture was poured into ice-water, and the resulting mixture was adjusted to pH=8.4 with NH₄OH. The resulting precipitate was collected by filtration, washed with water and dried to afford Example 1A (4.2 g, 88%). HPLC: RT=0.587 min (H₂O/MeOH with 0.1% TFA, Chromolith SpeedROD, 4.6×50 mm, gradient=4 min, wavelength=220 nm); MS (ES): m/z=217 [M+H]⁺; ¹H NMR (400 MHz, Chloroform-d) δ ppm 10.71 (br. s., 1H), 8.32 (d, J=0.1.8 Hz, 1H), 8.22 (d, J=5.5 Hz, 1H), 7.35 (dd, J=5.3, 1.8 Hz, 1H), 2.11 (s, 3H).

1B): N-(4-Ethynylpyridin-2-yl)acetamide

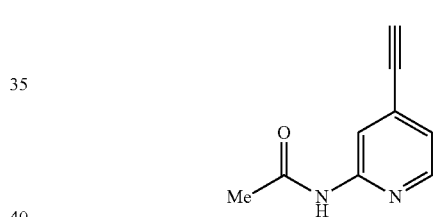

A mixture of Example 1A (4.2 g, 19.3 mmol), ethynyltrimethylsilane (2.28 g, 23.2 mmol), bis(triphenylphosphine)palladium(II) dichlororide (0.27 g, 0.39 mmol) and copper (I) iodide (0.15 g, 0.77 mmol) in TEA (20 mL, 143 mmol) was purged with nitrogen and heated to 76° C. for 2.5 h, and then cooled to room temperature. The mixture was filtered through a short silica gel column, eluting with EtOAc. The filtrate was concentrated to give N-(4-((trimethylsilyl)ethynyl)pyridin-2-yl)acetamide (5.10 g, 114%). The above solid was dissolved in THF (60 mL), and treated with TBAF (12.6 g, 48.2 mmol) in one portion. The reaction mixture was stirred at room temperature for 2 h and then concentrated to dryness. The residue was treated with water and extracted with EtOAc (3×). The combined extracts were washed with brine, dried (MgSO₄), and then concentrated. The residue was purified by silica gel flash chromatography (12 g column, EtOAc/DCM=0-100%) to afford Example 1B (2.89 g, 94%) as a light yellow solid. HPLC: RT=0.43 min (H₂O/MeOH with 0.1% TFA, Chromolith SpeedROD, 4.6×50 mm, gradient=4 min, wavelength=220 nm); MS (ES): m/z=161 [M+H]⁺; ¹H NMR (400 MHz, Chloroform-d) δ ppm 8.32 (s, 1H), 8.24 (dd, J=5.1, 0.7 Hz, 1H), 8.05 (br. s., 1H), 7.11 (dd, J=5.1, 1.5 Hz, 1H), 3.30 (s, 1H), 2.23 (s, 3H).

1C): N-(4-((3-Aminopyridin-2-yl)ethynyl)pyridin-2-yl)acetamide

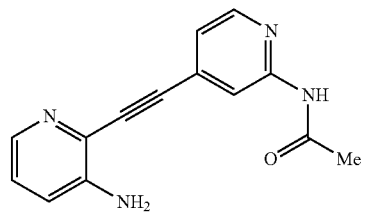

A mixture of 2-bromopyridin-3-amine (3.40 g, 19.7 mmol), Example 1B (3 g, 18.7 mmol), bis(triphenylphosphine)palladium(II) dichloride (0.13 g, 0.19 mmol) and copper(I) iodide (0.11 g, 0.56 mmol) in TEA (24 mL) and DMF (8 mL) was purged with N2, and then heated at 76° C. for 1 h. The reaction mixture was cooled to room temperature, and then concentrated and the residue was purified by silica gel flash chromatography (40 g column, MeOH/DCM=0-12%) to afford Example 1C (5.5 g) as a yellow solid. HPLC: RT=0.953 min ($H_2O$/MeOH with 0.1% TFA, Chromolith SpeedROD, 4.6×50 mm, gradient=4 min, wavelength=220 nm); MS (ES): m/z=253 [M+H]$^+$; $^1$H NMR (400 MHz, Chloroform-d) δ ppm 8.38 (s, 1H), 8.28 (dd, J=5.1, 0.9 Hz, 1H), 8.08 (dd, J=4.5, 1.4 Hz, 1H), 7.96 (br. s., 1H), 7.23 (dd, J=5.2, 1.4 Hz, 1H), 7.16-7.10 (m, 1H), 7.09-7.04 (m, 1H), 4.34 (br. s., 2H), 2.25 (s, 3H).

1D): N-(2-((2-Acetamidopyridin-4-yl)ethynyl)pyridin-3-yl)-2,2,2-trifluoroacetamide

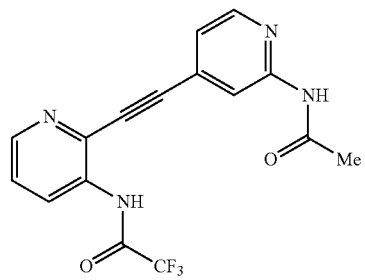 [SMILES: CC(=O)Nc1cc(C#Cc2ncccc2NC(=O)C(F)(F)F)ccn1]

To a suspension of Example 1C (335 mg, 1.33 mmol) in $CH_2Cl_2$ (15 mL) was added TEA, and the mixture was cooled to 0° C. Trifluoroacetic anhydride (0.28 mL, 1.99 mmol) was slowly added. The reaction mixture was stirred at 0° C. for 30 min and then diluted with DCM. The solution was washed with sat.aq.NaHCO$_3$ and brine, dried (MgSO$_4$), and then concentrated. The residue was sonicated with DCM/hexane, and the resulting solid was collected by filtration to afford Example 1D (412 mg, 71%) as a yellow solid. HPLC: RT=1.530 min ($H_2O$/MeOH with 0.1% TFA, Chromolith SpeedROD, 4.6×50 mm, gradient=4 min, wavelength=220 nm); MS (ES): m/z=349 [M+H]$^+$; $^1$H NMR (400 MHz, Chloroform-d) δ ppm 8.86-8.69 (m, 2H), 8.54 (dd, J=4.8, 1.5 Hz, 1H), 8.45 (s, 1H), 8.35 (dd, J=5.1, 0.9 Hz, 1H), 7.99 (br. s., 1H), 7.44 (dd, J=4.7 Hz, 1H), 7.21 (dd, J=5.1, 1.3 Hz, 1H), 2.26 (s, 3H).

Example 1): N-{4-[3-(6-Methylpyridin-2-yl)-1H-pyrrolo[3,2-b]pyridin-2-yl]pyridin-2-yl}acetamide

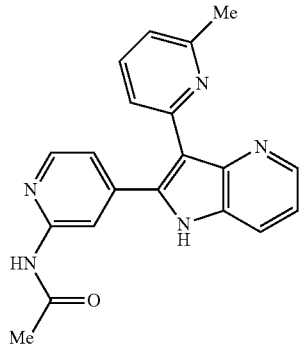

A mixture of Example 1D (40 mg, 0.12 mmol), 2-bromo-6-methylpyridine (23.7 mg, 0.14 mmol), Pd(Ph$_3$P)$_4$ (6.6 mg, 5.7 μmol) and Cs$_2$CO$_3$ (112 mg, 0.35 mmol) in acetonitrile (1 mL) was purged with N$_2$. The mixture was then heated at 100° C. in a sealed vial for 2 h, and then cooled to room temperature. The solid was filtered off, and rinsed with 10% MeOH/DCM, and the filtrate was concentrated. The residue was dissolved in DMF, and purified by preparative HPLC (YMC-Pack C-18 30×100 mm, eluting with 10%-70% aqueous CH$_3$CN containing 5 mmol NH$_4$OAc over 20 min, 30 mL/min, wavelength=254 nm) to give Example 1E (12.5 mg, 31%) as a white solid. HPLC: RT=1.040 min ($H_2O$/MeOH with 0.1% TFA, Chromolith SpeedROD, 4.6×50 mm, gradient=4 min, wavelength=220 nm); MS (ES): m/z=344 [M+H]$^+$; $^1$H NMR (400 MHz, methanol-d$_4$) δ ppm 8.39 (dd, J=4.6, 1.3 Hz, 1H), 8.31-8.21 (m, 2H), 7.97 (dd, J=8.1, 1.3 Hz, 1H), 7.83 (t, J=7.7 Hz, 1H), 7.50 (d, J=7.7 Hz, 1H), 7.32 (dt, J=8.4, 4.2 Hz, 2H), 7.13 (dd, J=5.2, 1.7 Hz, 1H), 2.53 (s, 3H), 2.17 (s, 3H).

Example 2

N-{4-[3-(6-Methoxypyridin-2-yl)-1H-pyrrolo[3,2-b]pyridin-2-yl]pyridin-2-yl}acetamide

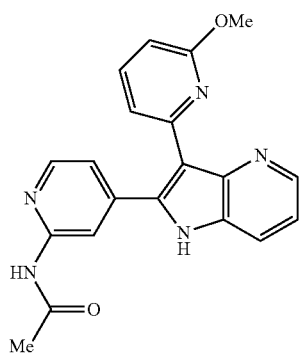

Example 2 was prepared from Example 1D and 2-bromo-6-methoxypyridine by the general methods shown for Example 1. HPLC: RT=0.72 min ($H_2O$/ACN with 0.1% TFA, Waters Acquity UPLC BEH C18, 2.1×50 mm, 1.7-μm particles, gradient=3 min, wavelength=220 nm); MS (ES): m/z=360 [M+H]$^+$; $^1$H NMR (500 MHz, DMSO-d$_6$) δ ppm 10.73 (s, 1H), 8.67 (d, J=5.0 Hz, 1H), 8.57-8.30 (m, 3H), 7.96 (s, 1H), 7.81-7.65 (m, 2H), 7.35-7.20 (m, 2H), 6.81 (d, J=8.4 Hz, 1H), 2.51 (br. s., 3H), 2.11 (s, 3H).

Example 3

N-{4-[3-(6-Chloropyridin-2-yl)-1H-pyrrolo[3,2-b]pyridin-2-yl]pyridin-2-yl}acetamide

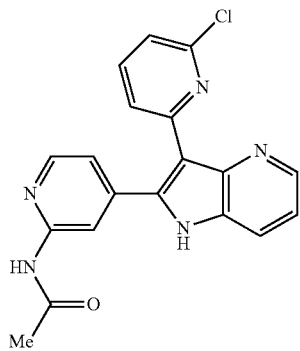

Example 3 was prepared from Example 1D, and 2-bromo-6-chloropyridine by the general methods shown for Example 1. HPLC: RT=0.77 min (H$_2$O/ACN with 0.1% TFA, Waters Acquity UPLC BEH C18, 2.1×50 mm, 1.7-μm particles, gradient=3 min, wavelength=220 nm); MS (ES): m/z=364 [M+H]$^+$; $^1$H NMR (500 MHz, DMSO-d$_6$) δ ppm 10.69 (s, 1H), 8.63 (d, J=5.0 Hz, 1H), 8.42 (d, J=5.0 Hz, 1H), 8.38-8.27 (m, 2H), 7.94-7.86 (m, 1H), 7.80 (d, J=7.1 Hz, 1H), 7.59 (dd, J=7.9, 5.6 Hz, 1H), 7.46 (d, J=8.1 Hz, 1H), 7.26 (d, J=4.4 Hz, 1H), 2.10 (s, 3H).

Example 4

N-{4-[3-(6-Fluoropyridin-3-yl)-1H-pyrrolo[3,2-b]pyridin-2-yl]pyridin-2-yl}acetamide

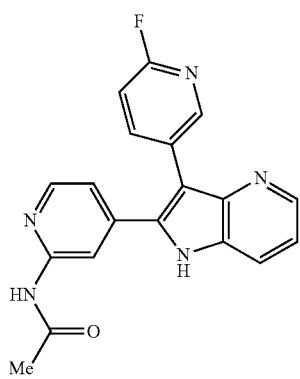 [SMILES: CC(=O)Nc1cc(-c2[nH]c3cccnc3c2-c2ccc(F)nc2)ccn1]

Example 4 was prepared from Example 1D and 2-fluoro-5-iodopyridine by the general methods shown for Example 1. HPLC: RT=0.58 min (H$_2$O/ACN with 0.1% TFA, Waters Acquity UPLC BEH C18, 2.1×50 mm, 1.7-μm particles, gradient=3 min, wavelength=220 nm); MS (ES): m/z=348 [M+H]$^+$; $^1$H NMR (500 MHz, DMSO-d$_6$) δ ppm 12.18 (s, 1H), 10.61 (s, 1H), 8.44 (d, J=4.4 Hz, 1H), 8.36 (d, J=5.0 Hz, 1H), 8.29 (s, 2H), 8.16-8.05 (m, 1H), 7.91 (d, J=8.1 Hz, 1H), 7.34-7.21 (m, 2H), 7.17 (d, J=5.0 Hz, 1H), 2.09 (s, 3H).

Example 5

N-{4-[3-(5-Chloropyridin-2-yl)-1H-pyrrolo[3,2-b]pyridin-2-yl]pyridin-2-yl}acetamide

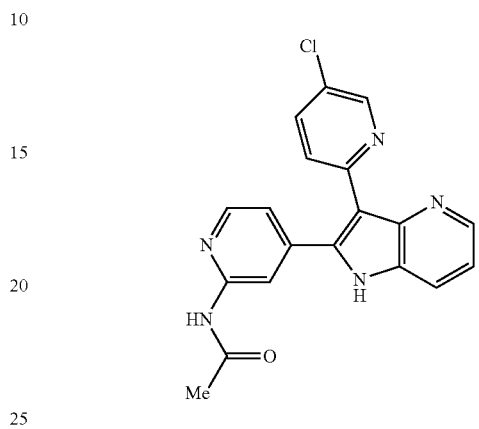

Example 5 was prepared from Example 1D and 5-chloro-2-iodopyridine by the general methods shown for Example 1. HPLC: RT=0.85 min (H$_2$O/ACN with 0.1% TFA, Waters Acquity UPLC BEH C18, 2.1×50 mm, 1.7-μm particles, gradient=3 min, wavelength=220 nm); MS (ES): m/z=364 [M+H]$^+$; $^1$H NMR (500 MHz, DMSO-d$_6$) δ ppm 10.77 (s, 1H), 8.75-8.62 (m, 2H), 8.55-8.43 (m, 2H), 8.37 (s, 1H), 8.00-7.91 (m, 1H), 7.75-7.58 (m, 2H), 7.30 (d, J=4.4 Hz, 1H), 2.12 (s, 3H).

Example 6

N-{4-[3-(5-Fluoropyridin-2-yl)-1H-pyrrolo[3,2-b]pyridin-2-yl]pyridin-2-yl}acetamide

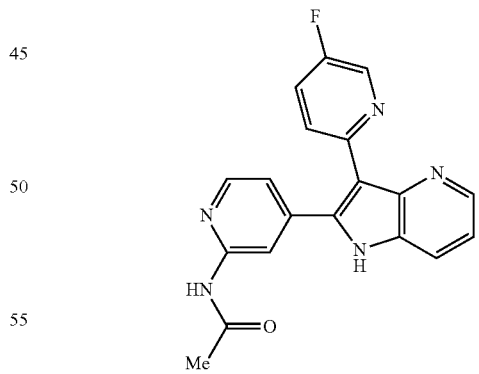

Example 6 was prepared from Example 1D and 2-bromo-5-fluoropyridine by the general methods shown for Example 1. HPLC: RT=0.70 min (H$_2$O/ACN with 0.1% TFA, Waters Acquity UPLC BEH C18, 2.1×50 mm, 1.7-μm particles, gradient=3 min, wavelength=220 nm); MS (ES): m/z=348 [M+H]$^+$; $^1$H NMR (500 MHz, DMSO-d$_6$) δ ppm 10.77 (s, 1H), 8.75-8.63 (m, 2H), 8.57 (d, J=8.4 Hz, 1H), 8.48 (d, J=5.4 Hz, 1H), 8.34 (s, 1H), 7.84-7.70 (m, 2H), 7.56 (dd, J=8.1, 3.7 Hz, 1H), 7.31 (d, J=5.0 Hz, 1H), 2.11 (s, 3H).

Example 7

N-(4-{3-[6-(Trifluoromethyl)pyridin-2-yl]-1H-pyrrolo[3,2-b]pyridin-2-yl}pyridin-2-yl)acetamide

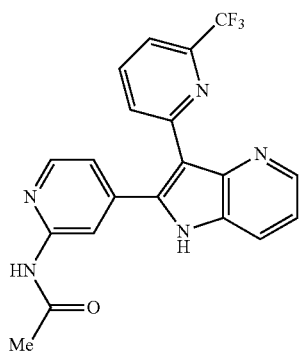

Example 7 was prepared from Example 1D and 2-bromo-6-(trifluoromethyl)pyridine by the general methods shown for Example 1. HPLC: RT=0.87 min (H$_2$O/ACN with 0.1% TFA, Waters Acquity UPLC BEH C18, 2.1×50 mm, 1.7-μm particles, gradient=3 min, wavelength=220 nm); MS (ES): m/z=398 [M+H]$^+$; $^1$H NMR (500 MHz, DMSO-d$_6$) δ ppm 10.63 (s, 1H), 8.62 (d, J=4.4 Hz, 1H), 8.41-8.30 (m, 2H), 8.29-8.20 (m, 2H), 8.17 (t, J=7.7 Hz, 1H), 7.84-7.78 (m, 1H), 7.53 (dd, J=8.1, 5.0 Hz, 1H), 7.26 (d, J=4.4 Hz, 1H), 2.08 (s, 3H).

Example 8

N-{4-[3-(Pyrimidin-2-yl)-1H-pyrrolo[3,2-b]pyridin-2-yl]pyridin-2-yl}acetamide

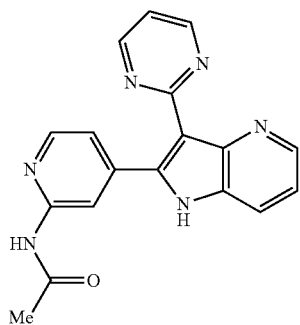 [SMILES: CC(=O)Nc1cc(-c2[nH]c3cccnc3c2-c2ncccn2)ccn1]

Example 8 was prepared from Example 1D and 2-bromopyrimidine by the general methods shown for Example 1. HPLC: RT=0.54 min (H$_2$O/ACN with 0.1% TFA, Waters Acquity UPLC BEH C18, 2.1×50 mm, 1.7-μm particles, gradient=3 min, wavelength=220 nm); MS (ES): m/z=331 [M+H]$^+$; $^1$H NMR (500 MHz, DMSO-d$_6$) δ ppm 10.77 (s, 1H), 8.86 (d, J=5.0 Hz, 2H), 8.78 (d, J=5.7 Hz, 1H), 8.71 (d, J=8.4 Hz, 1H), 8.54-8.45 (m, 2H), 7.85 (dd, J=8.1, 6.1 Hz, 1H), 7.50-7.41 (m, 2H), 2.13 (s, 3H).

Example 9

N-{4-[3-(6-Chloropyridin-3-yl)-1H-pyrrolo[3,2-b]pyridin-2-yl]pyridin-2-yl}acetamide

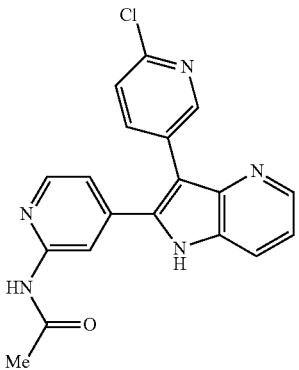

Example 9 was prepared from Example 1D and 5-bromo-2-chloropyridine by the general methods shown for Example 1. HPLC: RT=0.64 min (H$_2$O/ACN with 0.1% TFA, Waters Acquity UPLC BEH C18, 2.1×50 mm, 1.7-μm particles, gradient=3 min, wavelength=220 nm); MS (ES): m/z=364 [M+H]$^+$; $^1$H NMR (500 MHz, DMSO-d$_6$) δ ppm 12.24 (s, 1H), 10.63 (s, 1H), 8.52-8.40 (m, 2H), 8.36 (d, J=5.0 Hz, 1H), 8.30 (s, 1H), 8.00 (dd, J=8.4, 2.4 Hz, 1H), 7.91 (d, J=8.1 Hz, 1H), 7.55 (d, J=8.1 Hz, 1H), 7.29 (dd, J=8.2, 4.5 Hz, 1H), 7.16 (d, J=4.4 Hz, 1H), 2.09 (s, 3H).

Example 10

N-{4-[3-(5,6-Difluoropyridin-3-yl)-1H-pyrrolo[3,2-b]pyridin-2-yl]pyridin-2-yl}acetamide

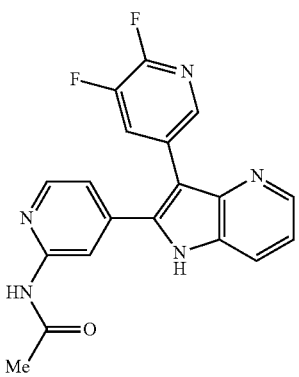

Example 10 was prepared from Example 1D and 2,3-difluoro-5-iodopyridine by the general methods shown for Example 1. HPLC: RT=0.70 min (H$_2$O/ACN with 0.1% TFA, Waters Acquity UPLC BEH C18, 2.1×50 mm, 1.7-μm particles, gradient=3 min, wavelength=220 nm); MS (ES): m/z=366 [M+H]$^+$; $^1$H NMR (500 MHz, DMSO-d$_6$) δ ppm 12.28 (s, 1H), 10.61 (s, 1H), 8.46 (d, J=4.4 Hz, 1H), 8.38 (d, J=5.0 Hz, 1H), 8.27 (br. s., 1H), 8.17 (t, J=9.8 Hz, 1H), 8.08 (s, 1H), 7.92 (d, J=8.4 Hz, 1H), 7.30 (dd, J=8.1, 4.4 Hz, 1H), 7.25 (d, J=4.7 Hz, 1H), 2.08 (s, 3H).

Example 11

N-{4-[3-(6-Fluoro-5-methylpyridin-3-yl)-1H-pyrrolo[3,2-b]pyridin-2-yl]pyridin-2-yl}acetamide

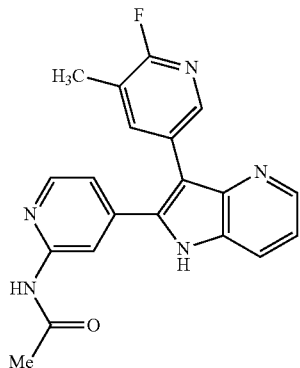 [SMILES: CC(=O)Nc1cc(-c2[nH]c3cccnc3c2-c2cnc(F)c(C)c2)ccn1]

Example 11 was prepared from Example 1D and 5-bromo-2-fluoro-3-methylpyridine by the general methods shown for Example 1. HPLC: RT=0.70 min (H$_2$O/ACN with 0.1% TFA, Waters Acquity UPLC BEH C18, 2.1×50 mm, 1.7-μm particles, gradient=3 min, wavelength=220 nm); MS (ES): m/z=362 [M+H]$^+$; $^1$H NMR (500 MHz, DMSO-d$_6$) δ ppm 10.60 (s, 1H), 8.43 (d, J=3.7 Hz, 1H), 8.37-8.25 (m, 2H), 8.10-7.94 (m, 2H), 7.90 (d, J=7.7 Hz, 1H), 7.28 (dd, J=8.1, 4.7 Hz, 1H), 7.16 (d, J=4.4 Hz, 1H), 2.28 (s, 3H), 2.09 (s, 3H).

Example 12

N-{4-[3-(6-Cyanopyridin-3-yl)-1H-pyrrolo[3,2-b]pyridin-2-yl]pyridin-2-yl}acetamide

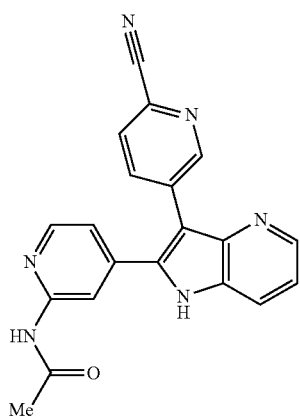 [SMILES: CC(=O)Nc1cc(-c2[nH]c3cccnc3c2-c2ccc(C#N)nc2)ccn1]

Example 12 was prepared from Example 1D and 5-bromopicolinonitrile by the general methods shown for Example 1. HPLC: RT=0.58 min (H$_2$O/ACN with 0.1% TFA, Waters Acquity UPLC BEH C18, 2.1×50 mm, 1.7-μm particles, gradient=3 min, wavelength=220 nm); MS (ES): m/z=355 [M+H]$^+$; $^1$H NMR (500 MHz, DMSO-d$_6$) δ ppm 10.70 (br. s., 1H), 8.84 (s, 1H), 8.58 (br. s., 1H), 8.41 (br. s., 1H), 8.29-8.16 (m, 3H), 8.11 (d, J=8.1 Hz, 1H), 7.95 (s, 1H), 7.53 (br. s., 1H), 7.20 (d, J=4.0 Hz, 1H), 2.09 (s, 3H).

Example 13

N-(4-{3-[6-(Trifluoromethyl)pyridin-3-yl]-1H-pyrrolo[3,2-b]pyridin-2-yl}pyridin-2-yl)acetamide

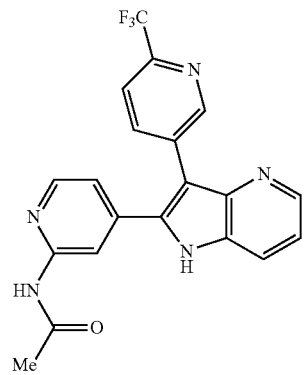 [SMILES: CC(=O)Nc1cc(-c2[nH]c3cccnc3c2-c2ccc(C(F)(F)F)nc2)ccn1]

Example 13 was prepared from Example 1D and 5-bromo-2-(trifluoromethyl)pyridine by the general methods shown for Example 1. HPLC: RT=0.78 min (H$_2$O/ACN with 0.1% TFA, Waters Acquity UPLC BEH C18, 2.1×50 mm, 1.7-μm particles, gradient=3 min, wavelength=220 nm); MS (ES): m/z=398 [M+H]$^+$; $^1$H NMR (500 MHz, DMSO-d$_6$) δ ppm 12.36 (s, 1H), 10.64 (s, 1H), 8.84 (s, 1H), 8.47 (d, J=4.4 Hz, 1H), 8.37 (d, J=5.0 Hz, 1H), 8.30 (s, 1H), 8.23 (d, J=8.1 Hz, 1H), 7.94 (m, 2H), 7.32 (dd, J=8.2, 4.5 Hz, 1H), 7.18 (d, J=4.7 Hz, 1H), 2.08 (s, 3H).

Example 14

N-{4-[3-(6-Methoxypyridin-3-yl)-1H-pyrrolo[3,2-b]pyridin-2-yl]pyridin-2-yl}acetamide

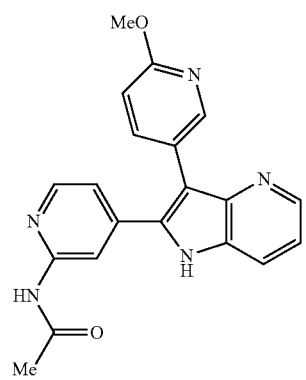

Method A:

Example 14 was prepared from Example 1D and 5-bromo-2-methoxypyridine by the general methods shown for Example 1. HPLC: RT=0.62 min (H$_2$O/ACN with 0.1% TFA, Waters Acquity UPLC BEH C18, 2.1×50 mm, 1.7-μm particles, gradient=3 min, wavelength=220 nm); MS (ES): m/z=360 [M+H]$^+$; $^1$H NMR (500 MHz, DMSO-d$_6$) δ ppm 12.01 (s, 1H), 10.58 (s, 1H), 8.41 (dd, J=4.5, 1.4 Hz, 1H), 8.37-8.29 (m, 2H), 8.26 (d, J=2.0 Hz, 1H), 7.87 (dd, J=8.1, 1.3 Hz, 1H), 7.80 (dd, J=8.5, 2.3 Hz, 1H), 7.25 (dd, J=8.3, 4.5 Hz, 1H), 7.13 (dd, J=5.1, 1.5 Hz, 1H), 6.87 (d, J=8.6 Hz, 1H), 2.10 (s, 3H).

Example 14 may also be prepared by the alternative Method B:

14A): N-(4-(1H-Pyrrolo[3,2-b]pyridin-2-yl)pyridin-2-yl)acetamide

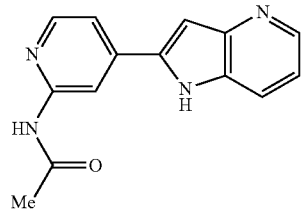 [SMILES: CC(=O)Nc1cc(-c2cc3ncccc3[nH]2)ccn1]

A mixture of Example 1D (5 g, 14.36 mmol), Pd(Ph$_3$P)$_4$ (0.829 g, 0.718 mmol) and Cs$_2$CO$_3$ (9.36 g, 28.7 mmol) in acetonitrile (60 mL) was purged with N$_2$. The mixture was then heated at 100° C. in a sealed pressure reaction vessel overnight, and then cooled to room temperature. The reaction mixture was diluted with MeOH/DCM, and directly loaded onto celite, and then purified by silica gel flash chromatography (80 g column, MeOH/DCM=0-10%) to give Example 14A (2.37 g, 65%). HPLC: RT=0.850 min (H$_2$O/MeOH with 0.1% TFA, Chromolith SpeedROD, 4.6× 50 mm, gradient=4 min, wavelength=220 nm); MS (ES): m/z=253 [M+H]$^+$; $^1$H NMR (400 MHz, DMSO-d$_6$) δ ppm 12.03 (s, 1H), 10.57 (s, 1H), 8.53 (s, 1H), 8.39 (ddd, J=6.8, 5.0, 1.0 Hz, 2H), 7.82 (dt, J=8.0, 1.2 Hz, 1H), 7.61 (dd, J=5.3, 1.5 Hz, 1H), 7.21-7.11 (m, 2H), 2.15 (s, 3H).

14B): N-(4-(3-Bromo-1H-pyrrolo[3,2-b]pyridin-2-yl)pyridin-2-yl)acetamide

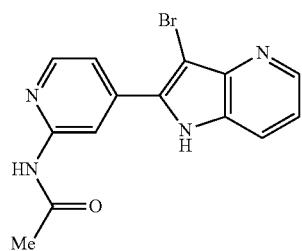 [SMILES: CC(=O)Nc1cc(-c2[nH]c3cccnc3c2Br)ccn1]

To a suspension of Example 14A (6.55 g, 26.0 mmol) in DMF (70 mL) at 0° C. was added NBS (4.62 g, 26.0 mmol). The reaction was then stirred at room temperature for 30 min, quenched with MeOH, and then concentrated. The residue was treated with MeOH, and the solid precipitate was collected by filtration and dried to give Example 14B (7.7 g, 90%) as a light yellow solid. HPLC: RT=0.953 min (H$_2$O/MeOH with 0.1% TFA, Chromolith SpeedROD, 4.6× 50 mm, gradient=4 min, wavelength=220 nm); MS (ES): m/z=332 [M+H]$^+$; $^1$H NMR (400 MHz, DMSO-d$_6$) δ ppm 12.31 (s, 1H), 10.67 (s, 1H), 8.76 (s, 1H), 8.58-8.33 (m, 2H), 7.88 (dd, J=8.4, 1.3 Hz, 1H), 7.60 (dd, J=5.3, 1.8 Hz, 1H), 7.30 (dd, J=8.3, 4.5 Hz, 1H), 2.15 (s, 3H).

Example 14): N-{4-[3-(6-Methoxypyridin-3-yl)-1H-pyrrolo[3,2-b]pyridin-2-yl]pyridin-2-yl}acetamide

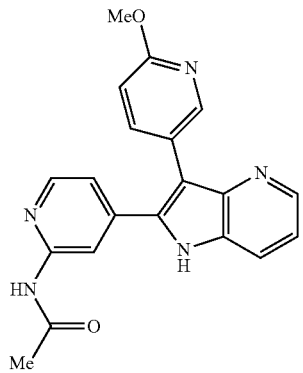 [SMILES: COc1ccc(-c2c(-c3ccnc(NC(C)=O)c3)[nH]c3cccnc23)cn1]

A mixture of Example 14B (7.5 g, 22.65 mmol), (6-methoxypyridin-3-yl)boronic acid (8.66 g, 56.6 mmol), PdCl$_2$(dppf)-CH$_2$Cl$_2$ adduct (0.555 g, 0.679 mmol) and 2M K$_2$CO$_3$ (34.0 mL, 67.9 mmol) in 1,4-Dioxane (200 mL) was purged with N$_2$. The mixture was heated to reflux for 5 h and then cooled to room temperature. The reaction mixture was then diluted with EtOAc, washed with brine, dried and concentrated. The residue was purified by silica gel flash chromatography (120 g column, MeOH/DCM=0-10%) to give Example 14 (3.85 g, 47%) as an off white solid.

Example 15

N-{4-[3-(6-Cyanopyridin-2-yl)-1H-pyrrolo[3,2-b]pyridin-2-yl]pyridin-2-yl}acetamide

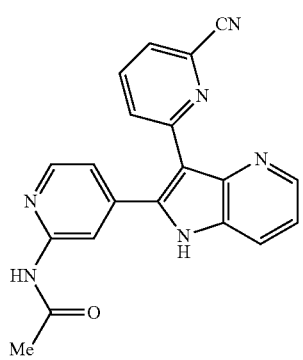

Example 15 was prepared from Example 1D and 6-bromopicolinonitrile by the general methods shown for Example 1. HPLC: RT=0.74 min (H$_2$O/ACN with 0.1% TFA, Waters Acquity UPLC BEH C18, 2.1×50 mm, 1.7-μm particles, gradient=3 min, wavelength=220 nm); MS (ES): m/z=355 [M+H]$^+$; $^1$H NMR (500 MHz, DMSO-d$_6$) δ ppm 10.55 (s, 1H), 8.54 (d, J=8.1 Hz, 1H), 8.49 (d, J=4.0 Hz, 1H), 8.36 (d, J=5.0 Hz, 1H), 8.25 (s, 1H), 8.10 (t, J=7.9 Hz, 1H), 7.98-7.90 (m, 1H), 7.85 (d, J=7.4 Hz, 1H), 7.32 (dd, J=8.2, 4.5 Hz, 1H), 7.25 (d, J=5.0 Hz, 1H), 2.08 (s, 3H).

Example 16

N-{4-[3-(6-Fluoropyridin-2-yl)-1H-pyrrolo[3,2-b]pyridin-2-yl]pyridin-2-yl}acetamide

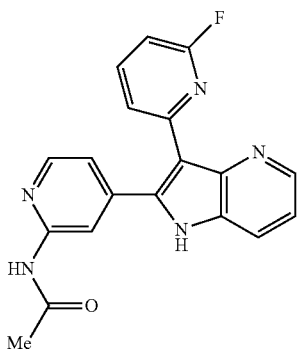 [SMILES: CC(=O)Nc1cc(-c2[nH]c3cccnc3c2-c2cccc(F)n2)ccn1]

Example 16 was prepared from Example 1D and 2-bromo-6-fluoropyridine by the general methods shown for Example 1. HPLC: RT=0.73 min (H$_2$O/ACN with 0.1% TFA, Waters Acquity UPLC BEH C18, 2.1×50 mm, 1.7-μm particles, gradient=3 min, wavelength=220 nm); MS (ES): m/z=348 [M+H]$^+$; $^1$H NMR (500 MHz, DMSO-d$_6$) δ ppm 10.75 (s, 1H), 8.67 (d, J=5.0 Hz, 1H), 8.52-8.41 (m, 2H), 8.33 (s, 1H), 8.03 (q, J=8.1 Hz, 1H), 7.68 (dd, 5.6 Hz, 1H), 7.58 (d, J=7.1 Hz, 1H), 7.30 (d, J=4.0 Hz, 1H), 7.16 (d, J=9.8 Hz, 1H), 2.11 (s, 3H).

Example 17

N-{4-[3-(Isoquinolin-6-yl)-1H-pyrrolo[3,2-b]pyridin-2-yl]pyridin-2-yl}acetamide

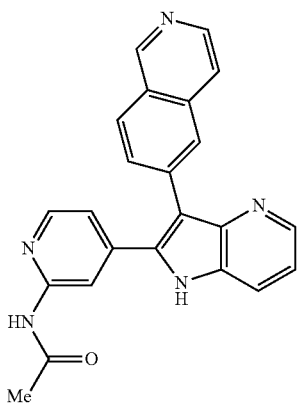 [SMILES: CC(=O)Nc1cc(-c2[nH]c3cccnc3c2-c2ccc3cnccc3c2)ccn1]

Example 17 was prepared from Example 1D and 6-bromoisoquinoline by the general methods shown for Example 1. HPLC: RT=0.55 min (H$_2$O/ACN with 0.1% TFA, Waters Acquity UPLC BEH C18, 2.1×50 mm, 1.7-μm particles, gradient=3 min, wavelength=220 nm); MS (ES): m/z=380 [M+H]$^+$; $^1$H NMR (500 MHz, DMSO-d$_6$) δ ppm 10.62 (s, 1H), 9.30 (s, 1H), 8.53-8.43 (m, 2H), 8.38 (s, 1H), 8.29 (d, J=5.4 Hz, 1H), 8.24 (s, 1H), 8.08 (d, J=8.4 Hz, 1H), 7.93 (d, J=8.1 Hz, 1H), 7.82 (d, J=5.7 Hz, 1H), 7.71 (d, J=8.4 Hz, 1H), 7.30 (dd, J=8.1, 4.4 Hz, 1H), 7.09 (d, J=5.0 Hz, 1H), 2.07 (s, 3H).

Example 18

N-{4-[3-(5-Methylpyridin-2-yl)-1H-pyrrolo[3,2-b]pyridin-2-yl]pyridin-2-yl}acetamide

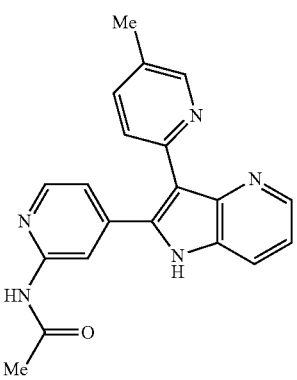 [SMILES: CC(=O)Nc1cc(-c2[nH]c3cccnc3c2-c2ccc(C)cn2)ccn1]

Example 18 was prepared from Example 1D and 2-bromo-5-methylpyridine by the general methods shown for Example 1. HPLC: RT=0.72 min (H$_2$O/ACN with 0.1% TFA, Waters Acquity UPLC BEH C18, 2.1×50 mm, 1.7-μm particles, gradient=3 min, wavelength=220 nm); MS (ES): m/z=344 [M+H]$^+$; $^1$H NMR (500 MHz, DMSO-d$_6$) δ ppm 10.80 (s, 1H), 8.73-8.64 (m, 2H), 8.49 (d, J=5.0 Hz, 1H), 8.45 (d, J=8.1 Hz, 1H), 8.36 (s, 1H), 7.91 (d, J=7.7 Hz, 1H), 7.67 (dd, J=8.1, 5.4 Hz, 1H), 7.52 (d, J=8.4 Hz, 1H), 7.32 (d, J=4.0 Hz, 1H), 2.42 (s, 3H), 2.12 (s, 3H).

Example 19

N-{4-[3-(Isoquinolin-8-yl)-1H-pyrrolo[3,2-b]pyridin-2-yl]pyridin-2-yl}acetamide

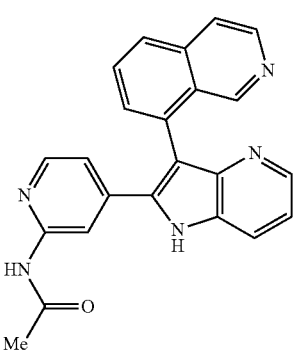 [SMILES: CC(=O)Nc1cc(-c2[nH]c3cccnc3c2-c2cccc3ccncc23)ccn1]

Example 19 was prepared from Example 1D and 8-bromoisoquinoline by the general methods shown for Example 1. HPLC: RT=0.56 min (H$_2$O/ACN with 0.1% TFA, Waters Acquity UPLC BEH C18, 2.1×50 mm, 1.7-μm particles, gradient=3 min, wavelength=220 nm); MS (ES): m/z=380 [M+H]$^+$; $^1$H NMR (500 MHz, DMSO-d$_6$) δ ppm 10.46 (s, 1H), 8.88 (s, 1H), 8.46 (d, J=5.7 Hz, 1H), 8.31 (d, J=3.7 Hz, 1H), 8.25 (s, 1H), 8.13 (d, J=5.4 Hz, 1H), 8.02 (d, J=8.4 Hz, 1H), 7.96 (s, 1H), 7.91 (d, J=5.7 Hz, 1H), 7.82 (t, J=7.6 Hz, 1H), 7.57 (d, J=6.7 Hz, 1H), 7.28 (dd, J=8.2, 4.5 Hz, 1H), 6.90 (d, J=4.4 Hz, 1H), 2.02 (s, 3H).

Example 20

N-{4-[3-(1H-Indol-5-yl)-1H-pyrrolo[3,2-b]pyridin-2-yl]pyridin-2-yl}acetamide

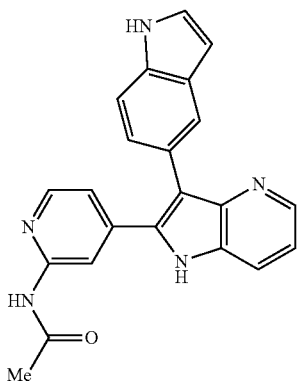 [SMILES: CC(=O)Nc1cc(-c2[nH]c3cccnc3c2-c2ccc3[nH]ccc3c2)ccn1]

Example 20 was prepared from Example 1D and 5-bromo-1H-indole by the general methods shown for Example 1. HPLC: RT=0.81 min (H₂O/ACN with 0.1% TFA, Waters Acquity UPLC BEH C18, 2.1×50 mm, 1.7-µm particles, gradient=3 min, wavelength=220 nm); MS (ES): m/z=368 [M+H]⁺; ¹H NMR (500 MHz, DMSO-d₆) δ ppm 11.33 (br. s., 1H), 10.69 (s, 1H), 8.62 (d, J=8.1 Hz, 1H), 8.55 (d, J=5.7 Hz, 1H), 8.45 (s, 1H), 8.26 (d, J=5.4 Hz, 1H), 7.77-7.67 (m, 2H), 7.53-7.41 (m, 2H), 7.06 (d, J=8.1 Hz, 1H), 6.98 (d, J=4.7 Hz, 1H), 6.50 (br. s., 1H), 2.10 (s, 3H).

Example 21

N-{4-[3-(Quinolin-8-yl)-1H-pyrrolo[3,2-b]pyridin-2-yl]pyridin-2-yl}acetamide

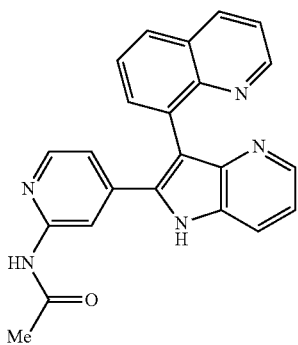 [SMILES: CC(=O)Nc1cc(-c2[nH]c3cccnc3c2-c2cccc3cccnc23)ccn1]

Example 21 was prepared from Example 1D and 8-bromoquinoline by the general methods shown for Example 1. HPLC: RT=0.64 min (H₂O/ACN with 0.1% TFA, Waters Acquity UPLC BEH C18, 2.1×50 mm, 1.7-µm particles, gradient=3 min, wavelength=220 nm); MS (ES): m/z=380 [M+H]⁺; ¹H NMR (500 MHz, DMSO-d₆) δ ppm 10.37 (s, 1H), 8.58 (d, J=2.7 Hz, 1H), 8.41 (d, J=8.1 Hz, 1H), 8.26 (d, J=4.4 Hz, 1H), 8.20 (br. s., 1H), 8.08-7.99 (m, 2H), 7.93 (d, J=8.1 Hz, 1H), 7.81 (d, J=6.7 Hz, 1H), 7.70 (t, J=7.6 Hz, 1H), 7.46 (dd, J=8.4, 4.0 Hz, 1H), 7.23 (dd, J=8.1, 4.4 Hz, 1H), 6.83 (d, J=5.0 Hz, 1H), 2.01 (s, 3H).

Example 22

N-{4-[3-(Quinolin-6-yl)-1H-pyrrolo[3,2-b]pyridin-2-yl]pyridin-2-yl}acetamide

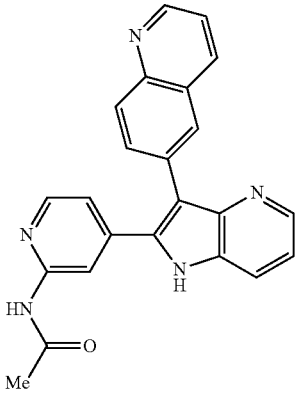 [SMILES: CC(=O)Nc1cc(-c2[nH]c3cccnc3c2-c2ccc3ncccc3c2)ccn1]

Example 22 was prepared from Example 1D and 6-bromoquinoline by the general methods shown for Example 1. HPLC: RT=0.54 min (H₂O/ACN with 0.1% TFA, Waters Acquity UPLC BEH C18, 2.1×50 mm, 1.7-µm particles, gradient=3 min, wavelength=220 nm); MS (ES): m/z=380 [M+H]⁺; ¹H NMR (500 MHz, DMSO-d₆) δ ppm 12.15 (s, 1H), 10.61 (s, 1H), 8.89 (d, J=2.7 Hz, 1H), 8.46 (d, J=3.7 Hz, 1H), 8.42-8.32 (m, 2H), 8.27 (d, J=5.4 Hz, 1H), 8.22 (s, 1H), 7.99 (d, J=8.8 Hz, 1H), 7.93 (d, J=8.1 Hz, 1H), 7.79 (dd, J=8.8, 1.3 Hz, 1H), 7.53 (dd, J=8.2, 4.2 Hz, 1H), 7.30 (dd, J=8.2, 4.5 Hz, 1H), 7.09 (d, J=4.4 Hz, 1H), 2.07 (s, 3H).

Example 23

N-{4-[3-(5-Fluoro-6-methylpyridin-2-yl)-1H-pyrrolo[3,2-b]pyridin-2-yl]pyridin-2-yl}acetamide

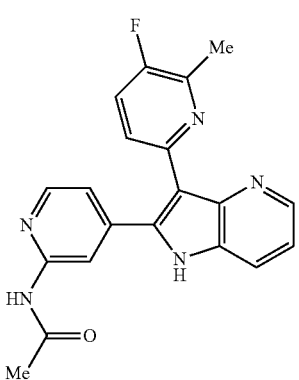

Example 23 was prepared from Example 1D and 6-bromo-3-fluoro-2-methylpyridine by the general methods shown for Example 1. HPLC: RT=0.80 min (H₂O/ACN with 0.1% TFA, Waters Acquity UPLC BEH C18, 2.1×50 mm, 1.7-µm particles, gradient=3 min, wavelength=220 nm); MS (ES): m/z=362 [M+H]⁺; ¹H NMR (500 MHz, DMSO-d₆) δ ppm 10.56 (s, 1H), 8.49 (d, J=4.4 Hz, 1H), 8.38-8.28 (m, 2H), 8.05-7.89 (m, 2H), 7.68 (t, J=9.1 Hz, 1H), 7.35 (dd, J=8.1, 4.7 Hz, 1H), 7.25 (d, J=5.4 Hz, 1H), 2.33 (d, J=2.4 Hz, 3H), 2.10 (s, 3H).

Example 24

N-{4-[3-(5-Fluoro-4-methylpyridin-2-yl)-1H-pyrrolo[3,2-b]pyridin-2-yl]pyridin-2-yl}acetamide

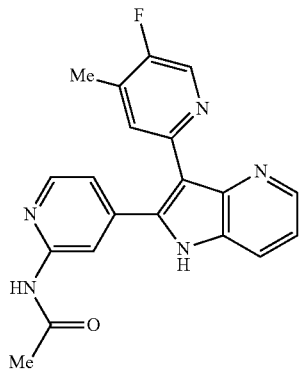 [SMILES: CC(=O)Nc1cc(-c2[nH]c3cccnc3c2-c2cc(C)c(F)cn2)ccn1]

Example 24 was prepared from Example 1D and 2-bromo-5-fluoro-4-methylpyridine by the general methods shown for Example 1. HPLC: RT=0.82 min (H₂O/ACN with 0.1% TFA, Waters Acquity UPLC BEH C18, 2.1×50 mm, 1.7-μm particles, gradient=3 min, wavelength=220 nm); MS (ES): m/z=362 [M+H]⁺; ¹H NMR (500 MHz, DMSO-d₆) δ ppm 10.74 (s, 1H), 8.65 (d, J=5.0 Hz, 1H), 8.59-8.49 (m, 2H), 8.46 (d, J=5.4 Hz, 1H), 8.35 (s, 1H), 7.71 (dd, J=8.1, 5.7 Hz, 1H), 7.54 (d, J=5.7 Hz, 1H), 7.29 (d, J=4.7 Hz, 1H), 2.26 (s, 3H), 2.11 (s, 3H).

Example 25

N-{4-[3-(5-Methanesulfonylpyridin-2-yl)-1H-pyrrolo[3,2-b]pyridin-2-yl]pyridin-2-yl}acetamide

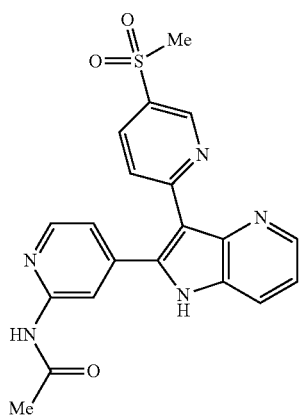 [SMILES: CC(=O)Nc1cc(-c2[nH]c3cccnc3c2-c2ccc(S(C)(=O)=O)cn2)ccn1]

Example 25 was prepared from Example 1D and 2-bromo-5-(methylsulfonyl)pyridine by the general methods shown for Example 1. HPLC: RT=0.63 min (H₂O/ACN with 0.1% TFA, Waters Acquity UPLC BEH C18, 2.1×50 mm, 1.7-μm particles, gradient=3 min, wavelength=220 nm); MS (ES): m/z=408 [M+H]⁺; ¹H NMR (500 MHz, DMSO-d₆) δ ppm 10.61 (s, 1H), 8.84 (d, J=2.0 Hz, 1H), 8.61 (d, J=8.4 Hz, 1H), 8.53 (d, J=4.7 Hz, 1H), 8.43-8.32 (m, 2H), 8.29 (s, 1H), 7.94 (d, J=8.1 Hz, 1H), 7.33 (dd, J=8.1, 4.7 Hz, 1H), 7.25 (d, J=5.0 Hz, 1H), 3.45-3.35 (m, 3H), 2.10 (s, 3H).

Example 26

N-{4-[3-(5-Methoxypyridin-2-yl)-1H-pyrrolo[3,2-b]pyridin-2-yl]pyridin-2-yl}acetamide

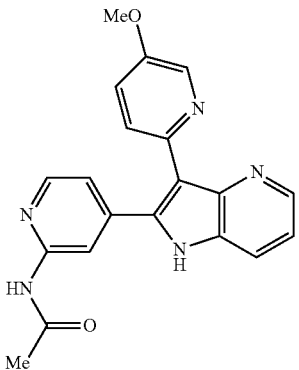 [SMILES: COc1ccc(-c2c(-c3ccnc(NC(C)=O)c3)[nH]c3cccnc23)nc1]

Example 26 was prepared from Example 1D and 2-bromo-5-methoxypyridine by the general methods shown for Example 1. HPLC: RT=0.70 min (H₂O/ACN with 0.1% TFA, Waters Acquity UPLC BEH C18, 2.1×50 mm, 1.7-μm particles, gradient=3 min, wavelength=220 nm); MS (ES): m/z=360 [M+H]⁺; ¹H NMR (500 MHz, DMSO-d₆) δ ppm 13.40 (br. s., 1H), 10.77 (s, 1H), 8.68 (d, J=5.7 Hz, 1H), 8.58 (d, J=8.4 Hz, 1H), 8.53-8.46 (m, 2H), 8.39 (s, 1H), 7.75 (dd, J=8.1, 5.7 Hz, 1H), 7.53 (dd, J=8.8, 3.1 Hz, 1H), 7.41 (d, J=8.8 Hz, 1H), 7.30 (dd, 1.5 Hz, 1H), 3.91 (s, 3H), 2.12 (s, 3H).

Example 27

N-{4-[3-(2-Methoxypyrimidin-5-yl)-1H-pyrrolo[3,2-b]pyridin-2-yl]pyridin-2-yl}acetamide

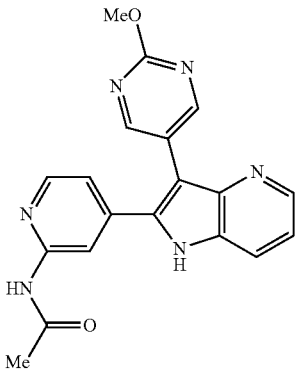 [SMILES: COc1ncc(-c2c(-c3ccnc(NC(C)=O)c3)[nH]c3cccnc23)cn1]

Example 27 was prepared from Example 1D and 5-bromo-2-methoxypyrimidine by the general methods shown for Example 1. HPLC: RT=0.55 min (H₂O/ACN with 0.1% TFA, Waters Acquity UPLC BEH C18, 2.1×50 mm, 1.7-μm particles, gradient=3 min, wavelength=220 nm); MS (ES): m/z=361 [M+H]⁺; ¹H NMR (500 MHz, DMSO-d₆) δ ppm 10.63 (s, 1H), 8.68 (s, 1H), 8.47 (d, J=4.0 Hz, 1H), 8.37 (d, J=5.0 Hz, 1H), 8.32 (s, 1H), 8.03 (d, J=8.1 Hz, 1H), 7.37 (dd, J=8.1, 4.7 Hz, 1H), 7.21 (d, J=4.0 Hz, 1H), 3.97 (s, 3H), 2.09 (s, 3H).

Example 28

N-{4-[3-(4-Methoxypyridin-2-yl)-1H-pyrrolo[3,2-b]pyridin-2-yl]pyridin-2-yl}acetamide

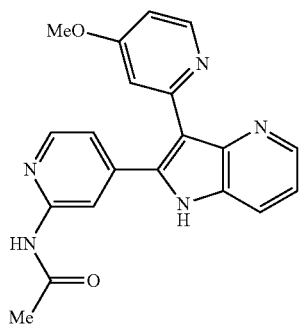 [SMILES: COc1ccnc(-c2c(-c3ccnc(NC(C)=O)c3)[nH]c3cccnc23)c1]

Example 28 was prepared from Example 1D and 2-bromo-4-methoxypyridine by the general methods shown for Example 1. HPLC: RT=0.58 min (H$_2$O/ACN with 0.1% TFA, Waters Acquity UPLC BEH C18, 2.1×50 mm, 1.7-μm particles, gradient=3 min, wavelength=220 nm); MS (ES): m/z=360 [M+H]$^+$; $^1$H NMR (500 MHz, DMSO-d$_6$) δ ppm 10.57 (s, 1H), 8.48 (d, J=4.0 Hz, 1H), 8.38-8.19 (m, 3H), 7.90 (d, J=8.4 Hz, 1H), 7.72 (d, J=2.0 Hz, 1H), 7.28 (dd, J=8.1, 4.4 Hz, 1H), 7.18 (d, J=5.0 Hz, 1H), 6.91 (d, J=3.4 Hz, 1H), 3.89 (s, 3H), 2.10 (s, 3H).

Example 29

N-{4-[3-(4-Ethylpyridin-2-yl)-1H-pyrrolo[3,2-b]pyridin-2-yl]pyridin-2-yl}acetamide

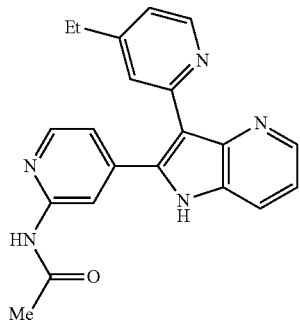 [SMILES: CCc1ccnc(-c2c(-c3ccnc(NC(C)=O)c3)[nH]c3cccnc23)c1]

Example 29 was prepared from Example 1D and 2-bromo-4-ethylpyridine by the general methods shown for Example 1. HPLC: RT=0.93 min (H$_2$O/ACN with 0.1% TFA, Waters Acquity UPLC BEH C18, 2.1×50 mm, 1.7-μm particles, gradient=3 min, wavelength=220 nm); MS (ES): m/z=358 [M+H]$^+$; $^1$H NMR (500 MHz, DMSO-d$_6$) δ ppm 10.57 (s, 1H), 8.49 (d, J=4.0 Hz, 1H), 8.38 (d, J=5.0 Hz, 1H), 8.35-8.26 (m, 2H), 7.98-7.87 (m, 2H), 7.31 (dd, J=7.9, 4.5 Hz, 1H), 7.17 (dd, J=16.7, 4.5 Hz, 2H), 2.70 (q, J=7.5 Hz, 2H), 2.10 (s, 3H), 1.23 (t, J=7.6 Hz, 3H).

Example 30

N-{4-[3-(6-Chloro-4-methylpyridin-2-yl)-1H-pyrrolo[3,2-b]pyridin-2-yl]pyridin-2-yl}acetamide

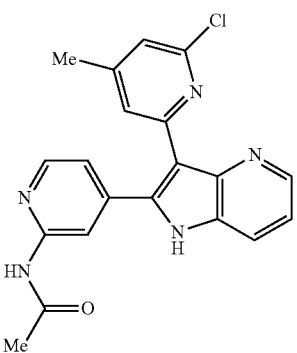 [SMILES: CC(=O)Nc1cc(-c2[nH]c3cccnc3c2-c2cc(C)cc(Cl)n2)ccn1]

Example 30 was prepared from Example 1D and 2-bromo-6-chloro-4-methylpyridine by the general methods shown for Example 1. HPLC: RT=0.88 min (H$_2$O/ACN with 0.1% TFA, Waters Acquity UPLC BEH C18, 2.1×50 mm, 1.7-μm particles, gradient=3 min, wavelength=220 nm); MS (ES): m/z=378 [M+H]$^+$; $^1$H NMR (500 MHz, DMSO-d$_6$) δ ppm 10.67 (s, 1H), 8.62 (d, J=4.7 Hz, 1H), 8.40 (d, J=5.0 Hz, 1H), 8.36-8.21 (m, 2H), 7.72 (br. s., 1H), 7.62-7.48 (m, 1H), 7.33 (s, 1H), 7.24 (d, J=4.0 Hz, 1H), 2.36 (s, 3H), 2.11 (s, 3H).

Example 31

N-{4-[3-(4-Methylpyridin-2-yl)-1H-pyrrolo[3,2-b]pyridin-2-yl]pyridin-2-yl}acetamide

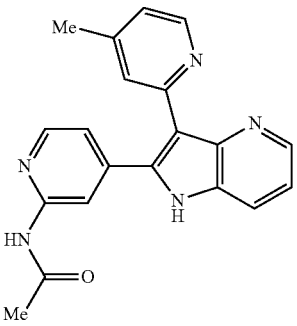

Example 31 was prepared from Example 1D and 2-bromo-4-methylpyridine by the general methods shown for Example 1. HPLC: RT=0.57 min (H$_2$O/ACN with 0.1% TFA, Waters Acquity UPLC BEH C18, 2.1×50 mm, 1.7-μm particles, gradient=3 min, wavelength=220 nm); MS (ES): m/z=344 [M+H]$^+$; $^1$H NMR (500 MHz, DMSO-d$_6$) δ ppm 10.54 (s, 1H), 8.47 (d, J=4.0 Hz, 1H), 8.35-8.21 (m, 3H), 7.94 (s, 1H), 7.89 (d, J=7.7 Hz, 1H), 7.27 (dd, J=8.2, 4.5 Hz, 1H), 7.12 (dd, J=10.3, 5.2 Hz, 2H), 2.40 (s, 3H), 2.10 (s, 3H).

Example 32

N-{4-[3-(4-Chloropyridin-2-yl)-1H-pyrrolo[3,2-b]pyridin-2-yl]pyridin-2-yl}acetamide

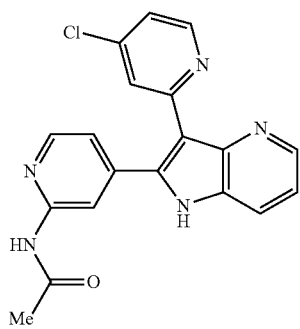 [SMILES: CC(=O)Nc1cc(-c2[nH]c3cccnc3c2-c2cc(Cl)ccn2)ccn1]

Example 32 was prepared from Example 1D and 2-bromo-4-chloropyridine by the general methods shown for Example 1. HPLC: RT=1.02 min (H₂O/ACN with 0.1% TFA, Waters Acquity UPLC BEH C18, 2.1×50 mm, 1.7-μm particles, gradient=3 min, wavelength=220 nm); MS (ES): m/z=364 [M+H]⁺; ¹H NMR (500 MHz, DMSO-d₆) δ ppm 10.74 (s, 1H), 8.71-8.54 (m, 2H), 8.46 (d, J=5.0 Hz, 1H), 8.37 (br. s., 2H), 7.86 (br. s., 1H), 7.69-7.57 (m, 1H), 7.51 (d, J=3.7 Hz, 1H), 7.31 (d, J=4.0 Hz, 1H), 2.12 (s, 3H).

Example 33

N-{4-[3-(5-Chloro-6-methylpyridin-2-yl)-1H-pyrrolo[3,2-b]pyridin-2-yl]pyridin-2-yl}acetamide

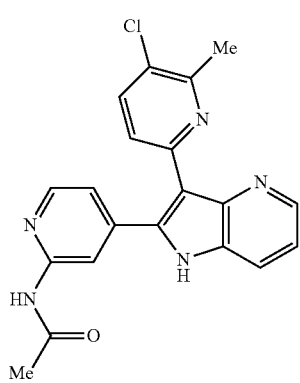 [SMILES: CC(=O)Nc1cc(-c2[nH]c3cccnc3c2-c2ccc(Cl)c(C)n2)ccn1]

Example 33 was prepared from Example 1D and 6-bromo-3-chloro-2-methylpyridine by the general methods shown for Example 1. HPLC: RT=0.98 min (H₂O/ACN with 0.1% TFA, Waters Acquity UPLC BEH C18, 2.1×50 mm, 1.7-μm particles, gradient=3 min, wavelength=220 nm); MS (ES): m/z=378 [M+H]⁺; ¹H NMR (500 MHz, DMSO-d₆) δ ppm 10.73 (s, 1H), 8.67 (d, J=5.0 Hz, 1H), 8.54-8.40 (m, 2H), 8.36 (s, 1H), 7.88 (d, J=8.4 Hz, 1H), 7.73-7.63 (m, 1H), 7.46 (d, J=7.7 Hz, 1H), 7.30 (d, J=4.4 Hz, 1H), 2.61 (s, 3H), 2.11 (s, 3H).

Example 34

N-{4-[3-(6-Chloropyridin-2-yl)-5-fluoro-1H-pyrrolo[3,2-b]pyridin-2-yl]pyridin-2-yl}acetamide

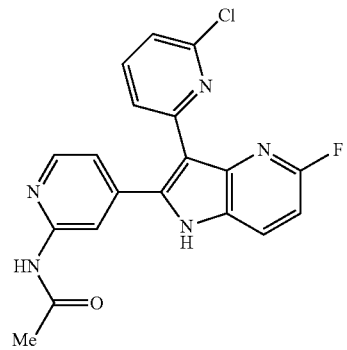 [SMILES: CC(=O)Nc1cc(-c2[nH]c3ccc(F)nc3c2-c2cccc(Cl)n2)ccn1]

34A): N-(4-((3-Amino-6-fluoropyridin-2-yl)ethynyl)pyridin-2-yl)acetamide

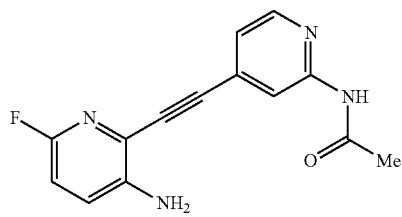 [SMILES: CC(=O)Nc1cc(C#Cc2nc(F)ccc2N)ccn1]

Example 34A was prepared from Example 1B and 2-bromo-6-fluoropyridin-3-amine by similar methods as shown for Example 1C. HPLC: RT=1.27 min (H₂O/MeOH with 0.1% TFA, Chromolith SpeedROD, 4.6×50 mm, gradient=4 min, wavelength=220 nm); MS (ES): m/z=271 [M+H]⁺.

34B): N-(2-((2-Acetamidopyridin-4-yl)ethynyl)-6-fluoropyridin-3-yl)-2,2,2-trifluoroacetamide

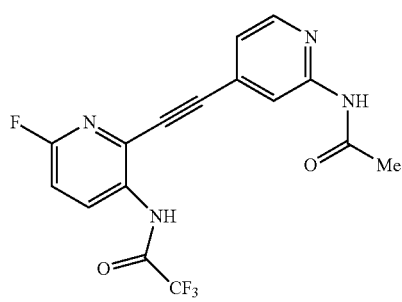 [SMILES: CC(=O)Nc1cc(C#Cc2nc(F)ccc2NC(=O)C(F)(F)F)ccn1]

Example 34B was prepared from Example 34A by methods similar to those shown for Example 1D. HPLC: RT=1.69 min (H₂O/MeOH with 0.1% TFA, Chromolith SpeedROD, 4.6×50 mm, gradient=4 min, wavelength=220 nm); MS (ES): m/z=367 [M+H]⁺, ¹H NMR (400 MHz, Chloroform-d) δ ppm 8.82 (br. s., 1H), 8.58 (dd, J=9.5, 2.6

Hz, 1H), 8.49-8.30 (m, 3H), 8.05 (br. s., 1H), 7.20 (dd, J=5.2, 1.4 Hz, 1H), 2.26 (s, 3H).

N-{4-[3-(6-Chloropyridin-2-yl)-5-fluoro-1H-pyrrolo[3,2-b]pyridin-2-yl]pyridin-2-yl}acetamide

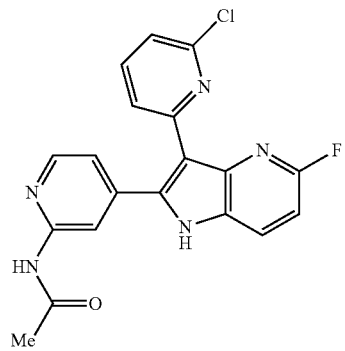 [SMILES: CC(=O)Nc1cc(-c2[nH]c3ccc(F)nc3c2-c2cccc(Cl)n2)ccn1]

Example 34 was prepared from Example 34B and 2-bromo-6-chloropyridine by the general methods shown for Example 1. HPLC: RT=0.98 min (H$_2$O/ACN with 0.1% TFA, Waters Acquity UPLC BEH C18, 2.1×50 mm, 1.7-μm particles, gradient=3 min, wavelength=220 nm); MS (ES): m/z=382 [M+H]$^+$; $^1$H NMR (500 MHz, DMSO-d$_6$) δ ppm 12.39 (s, 1H), 10.57 (s, 1H), 8.50 (s, 1H), 8.34 (d, J=5.0 Hz, 1H), 8.28 (s, 1H), 8.16 (d, J=7.4 Hz, 1H), 7.92 (t, J=7.7 Hz, 1H), 7.80 (dd, J=9.3, 2.2 Hz, 1H), 7.36 (d, J=7.7 Hz, 1H), 7.21 (d, J=5.0 Hz, 1H), 2.09 (s, 3H).

Example 35

N-{4-[5-Fluoro-3-(5-fluoropyridin-2-yl)-1H-pyrrolo[3,2-b]pyridin-2-yl]pyridin-2-yl}acetamide

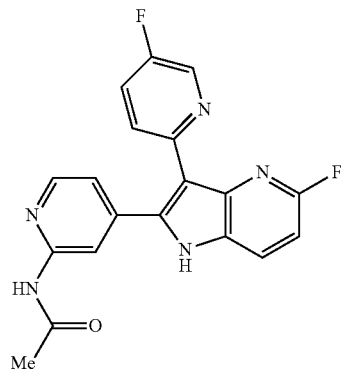 [SMILES: CC(=O)Nc1cc(-c2[nH]c3ccc(F)nc3c2-c2ccc(F)cn2)ccn1]

Example 35 was prepared from Example 34B and 2-bromo-5-fluoropyridine by the general methods shown for Example 1. HPLC: RT=0.91 min (H$_2$O/ACN with 0.1% TFA, Waters Acquity UPLC BEH C18, 2.1×50 mm, 1.7-μm particles, gradient=3 min, wavelength=220 nm); MS (ES): m/z=366 [M+H]$^+$; $^1$H NMR (500 MHz, DMSO-d$_6$) δ ppm 12.37 (s, 1H), 10.54 (s, 1H), 8.46 (d, J=3.0 Hz, 1H), 8.31 (d, J=5.0 Hz, 1H), 8.23 (s, 1H), 8.06 (t, J=7.9 Hz, 1H), 7.98 (dd, J=8.6, 4.5 Hz, 1H), 7.83 (td, J=8.8, 3.0 Hz, 1H), 7.15 (d, J=4.4 Hz, 1H), 7.02 (d, J=8.8 Hz, 1H), 2.08 (s, 3H).

Example 36

N-{4-[5-Fluoro-3-(6-methoxypyridin-3-yl)-1H-pyrrolo[3,2-b]pyridin-2-yl]pyridin-2-yl}acetamide

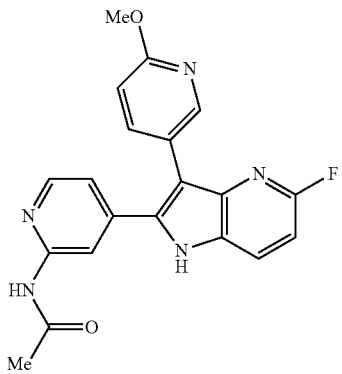 [SMILES: COc1ccc(-c2c(-c3ccnc(NC(C)=O)c3)[nH]c3ccc(F)nc23)cn1]

Example 36 was prepared from Example 34B and 5-iodo-2-methoxypyridine by the general methods shown for Example 1. HPLC: RT=0.96 min (H$_2$O/ACN with 0.1% TFA, Waters Acquity UPLC BEH C18, 2.1×50 mm, 1.7-μm particles, gradient=3 min, wavelength=220 nm); MS (ES): m/z=378 [M+H]$^+$; $^1$H NMR (500 MHz, DMSO-d$_6$) δ ppm 12.28 (s, 1H), 10.60 (s, 1H), 8.40-8.25 (m, 2H), 8.19 (d, J=1.7 Hz, 1H), 8.04 (t, J=7.9 Hz, 1H), 7.72 (dd, J=8.6, 2.2 Hz, 1H), 7.10 (d, J=5.4 Hz, 1H), 7.00 (d, J=8.8 Hz, 1H), 6.88 (d, J=8.4 Hz, 1H), 3.88 (s, 3H), 2.09 (s, 3H).

Example 37

N-{4-[5-Fluoro-3-(5-methoxypyridin-2-yl)-1H-pyrrolo[3,2-b]pyridin-2-yl]pyridin-2-yl}acetamide

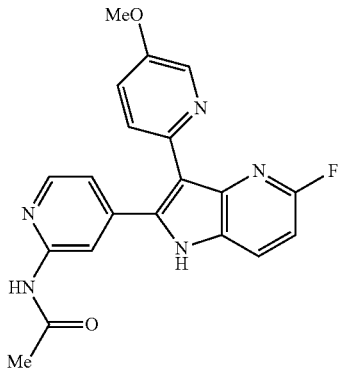 [SMILES: COc1ccc(-c2c(-c3ccnc(NC(C)=O)c3)[nH]c3ccc(F)nc23)nc1]

Example 37 was prepared from Example 34B and 2-bromo-5-methoxypyridine by the general methods shown for Example 1. HPLC: RT=0.82 min (H$_2$O/ACN with 0.1% TFA, Waters Acquity UPLC BEH C18, 2.1×50 mm, 1.7-μm particles, gradient=3 min, wavelength=220 nm); MS (ES): m/z=378 [M+H]$^+$; $^1$H NMR (500 MHz, DMSO-d$_6$) δ ppm 12.24 (s, 1H), 10.55 (s, 1H), 8.28 (d, J=5.4 Hz, 2H), 8.21 (d, J=2.7 Hz, 1H), 8.04 (t, J=8.1 Hz, 1H), 7.85 (d, J=8.4 Hz, 1H), 7.52 (dd, J=8.6, 2.9 Hz, 1H), 7.11 (d, J=4.0 Hz, 1H), 6.99 (d, J=8.4 Hz, 1H), 3.86 (s, 3H), 2.09 (s, 3H).

Example 38

N-{4-[3-(6-Chloropyridin-2-yl)-6-fluoro-1H-pyrrolo[3,2-b]pyridin-2-yl]pyridin-2-yl}acetamide

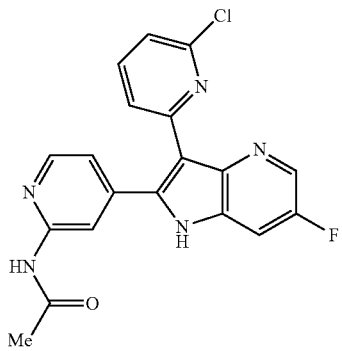 [SMILES: CC(=O)Nc1cc(-c2[nH]c3cc(F)cnc3c2-c2cccc(Cl)n2)ccn1]

38A): N-(4-((3-Amino-5-fluoropyridin-2-yl)ethynyl)pyridin-2-yl)acetamide

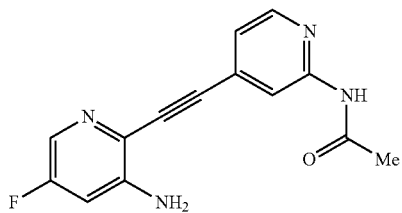 [SMILES: CC(=O)Nc1cc(C#Cc2ncc(F)cc2N)ccn1]

Example 38A was prepared from Example 1B and 2-bromo-5-fluoropyridin-3-amine by the methods shown for Example 1C. HPLC: RT=1.25 min (H₂O/MeOH with 0.1% TFA, Chromolith SpeedROD, 4.6×50 mm, gradient=4 min, wavelength=220 nm); MS (ES): m/z=271 [M+H]⁺, ¹H NMR (400 MHz, DMSO-d₆) δ 10.60 (s, 1H), 8.36 (d, J=5.3 Hz, 1H), 8.23 (s, 1H), 7.79 (d, J=2.6 Hz, 1H), 7.35 (dd, J=5.1, 1.3 Hz, 1H), 6.95 (dd, J=11.1, 2.5 Hz, 1H), 6.17 (s, 2H), 2.12 (s, 3H).

38B): N-(2-((2-Acetamidopyridin-4-yl)ethynyl)-5-fluoropyridin-3-yl)-2,2,2-trifluoroacetamide

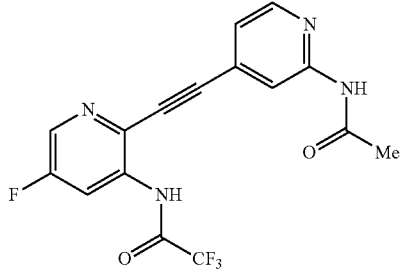 [SMILES: CC(=O)Nc1cc(C#Cc2ncc(F)cc2NC(=O)C(F)(F)F)ccn1]

Example 38B was prepared from Example 38A by the methods shown for Example 1D. HPLC: RT=1.69 min (H₂O/MeOH with 0.1% TFA, Chromolith SpeedROD, 4.6× 50 mm, gradient=4 min, wavelength=220 nm); MS (ES): m/z=367 [M+H]⁺, ¹H NMR (400 MHz, DMSO-d₆) δ ppm 11.74 (s, 1H), 10.67 (s, 1H), 8.70 (d, J=2.9 Hz, 1H), 8.41 (dd, J=5.1, 0.7 Hz, 1H), 8.24 (s, 1H), 8.09 (dd, J=9.1, 2.8 Hz, 1H), 7.19 (dd, J=5.1, 1.3 Hz, 1H), 2.12 (s, 3H).

N-{4-[3-(6-Chloropyridin-2-yl)-6-fluoro-1H-pyrrolo[3,2-b]pyridin-2-yl]pyridin-2-yl}acetamide

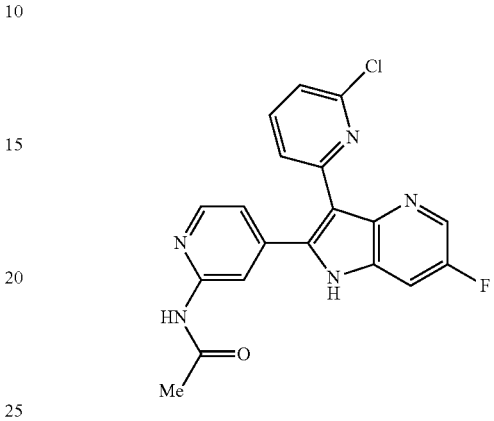

Example 38 was prepared from Example 38B and 2-bromo-6-chloropyridine by the general methods shown for Example 1. HPLC: RT=0.98 min (H₂O/ACN with 0.1% TFA, Waters Acquity UPLC BEH C18, 2.1×50 mm, 1.7-μm particles, gradient=3 min, wavelength=220 nm); MS (ES): m/z=382 [M+H]⁺; ¹H NMR (500 MHz, DMSO-d₆) δ ppm 10.57 (s, 1H), 8.50 (s, 1H), 8.34 (d, J=5.4 Hz, 1H), 8.28 (s, 1H), 8.16 (d, J=7.7 Hz, 1H), 7.93 (t, J=7.7 Hz, 1H), 7.80 (dd, J=9.3, 2.5 Hz, 1H), 7.36 (d, J=7.7 Hz, 1H), 7.21 (d, J=5.4 Hz, 1H), 2.09 (s, 3H).

Example 39

N-{4-[6-Fluoro-3-(5-methoxypyridin-2-yl)-1H-pyrrolo[3,2-b]pyridin-2-yl]pyridin-2-yl}acetamide

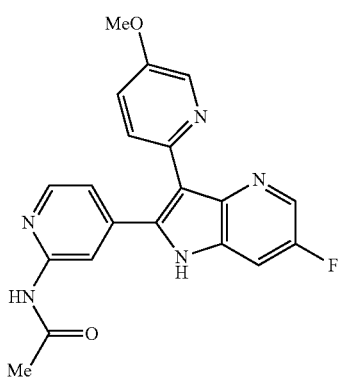

Example 39 was prepared from Example 38B and 2-bromo-5-methoxypyridine by the general methods shown for Example 1. HPLC: RT=0.77 min (H₂O/ACN with 0.1% TFA, Waters Acquity UPLC BEH C18, 2.1×50 mm, 1.7-μm particles, gradient=3 min, wavelength=220 nm); MS (ES): m/z=378 [M+H]⁺; ¹H NMR (500 MHz, DMSO-d₆) δ ppm 12.15 (s, 1H), 10.54 (s, 1H), 8.45 (s, 1H), 8.35-8.24 (m, 2H), 8.21 (d, J=2.7 Hz, 1H), 7.95 (d, J=8.4 Hz, 1H), 7.74 (dd, J=9.4, 2.4 Hz, 1H), 7.50 (dd, J=8.6, 2.9 Hz, 1H), 7.12 (d, J=4.4 Hz, 1H), 3.86 (s, 3H), 2.10 (s, 3H).

Example 40

N-{4-[6-Fluoro-3-(6-methoxypyridin-3-yl)-1H-pyrrolo[3,2-b]pyridin-2-yl]pyridin-2-yl}acetamide

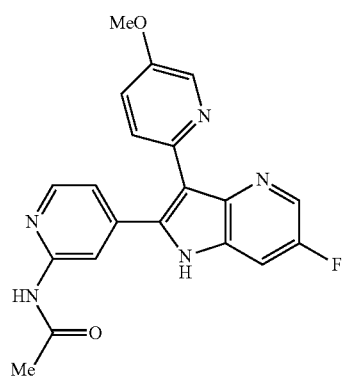 [SMILES: COc1ccc(-c2c(-c3ccnc(NC(C)=O)c3)[nH]c3cc(F)cnc23)nc1]

Example 40 was prepared from Example 38B and 5-bromo-2-methoxypyridine by the general methods shown for Example 1. HPLC: RT=0.88 min (H₂O/ACN with 0.1% TFA, Waters Acquity UPLC BEH C18, 2.1×50 mm, 1.7-μm particles, gradient=3 min, wavelength=220 nm); MS (ES): m/z=378 [M+H]⁺; ¹H NMR (500 MHz, DMSO-d₆) δ ppm 12.24 (s, 1H), 10.67 (s, 1H), 8.43 (s, 1H), 8.33 (d, J=5.0 Hz, 1H), 8.29 (s, 1H), 8.24 (d, J=2.0 Hz, 1H), 7.81-7.72 (m, 2H), 7.13 (d, J=5.0 Hz, 1H), 6.88 (d, J=8.8 Hz, 1H), 3.88 (s, 1H), 2.10 (s, 1H).

Example 41

N-{4-[3-(6-Chloropyridin-2-yl)-6-chloro-1H-pyrrolo[3,2-b]pyridin-2-yl]pyridin-2-yl}acetamide

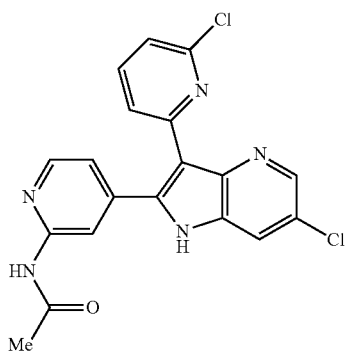 [SMILES: CC(=O)Nc1cc(-c2[nH]c3cc(Cl)cnc3c2-c2cccc(Cl)n2)ccn1]

41A): N-(4-((3-Amino-5-chloropyridin-2-yl)ethynyl)pyridin-2-yl)acetamide

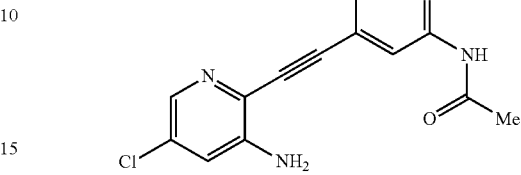

Example 41A was prepared from Example 1B and 2-bromo-5-chloropyridin-3-amine by the methods similar to those shown for Example 1C. HPLC: RT=1.53 min (H₂O/MeOH with 0.1% TFA, Chromolith SpeedROD, 4.6×50 mm, gradient=4 min, wavelength=220 nm); MS (ES): m/z=287 [M+H]⁺, ¹H NMR (400 MHz, DMSO-d₆) δ 10.61 (s, 1H), 8.36 (d, J=5.1 Hz, 1H), 8.24 (s, 1H), 7.80 (d, J=2.0 Hz, 1H), 7.36 (dd, J=5.1, 1.5 Hz, 1H), 7.20 (d, J=2.2 Hz, 1H), 6.14 (s, 2H), 2.12 (s, 3H).

41B): N-(2-((2-Acetamidopyridin-4-yl)ethynyl)-5-chloropyridin-3-yl)-2,2,2-trifluoroacetamide

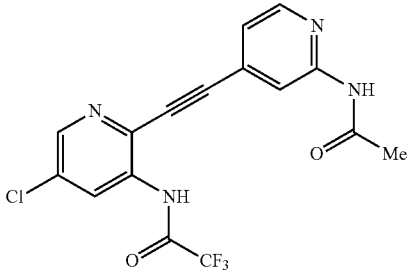 [SMILES: CC(=O)Nc1cc(C#Cc2ncc(Cl)cc2NC(=O)C(F)(F)F)ccn1]

Example 41B was prepared from Example 41A by the methods similar to those shown for Example 1D. HPLC: RT=1.93 min (H₂O/MeOH with 0.1% TFA, Chromolith SpeedROD, 4.6×50 mm, gradient=4 min, wavelength=220 nm); MS (ES): m/z=383 [M+H]⁺, ¹H NMR (400 MHz, DMSO-d) δ ppm 11.73 (s, 1H), 10.68 (s, 1H), 8.72 (d, J=2.2 Hz, 1H), 8.41 (dd, J=5.1, 0.7 Hz, 1H), 8.25 (d, J=2.2 Hz, 2H), 7.20 (dd, J=5.2, 1.4 Hz, 1H), 2.12 (s, 3H).

Example 41): N-{4-[3-(6-Chloropyridin-2-yl)-6-chloro-1H-pyrrolo[3,2-b]pyridin-2-yl]pyridin-2-yl}acetamide

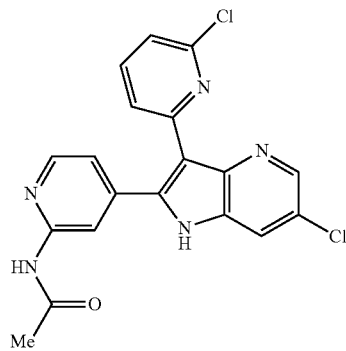 [SMILES: CC(=O)Nc1cc(-c2[nH]c3cc(Cl)cnc3c2-c2cccc(Cl)n2)ccn1]

Example 41 was prepared from Example 41B and 2-bromo-6-chloropyridine by the general methods shown for Example 1. HPLC: RT=1.14 min (H$_2$O/ACN with 0.1% TFA, Waters Acquity UPLC BEH C18, 2.1×50 mm, 1.7-μm particles, gradient=3 min, wavelength=220 nm); MS (ES): m/z=398 [M+H]$^+$; $^1$H NMR (500 MHz, DMSO-d$_6$) δ ppm 12.45 (s, 1H), 10.59 (s, 1H), 8.49 (d, J=2.0 Hz, 1H), 8.35 (d, J=5.4 Hz, 1H), 8.30 (s, 1H), 8.16 (d, J=7.7 Hz, 1H), 8.00 (d, J=2.0 Hz, 1H), 7.93 (t, J=7.7 Hz, 1H), 7.37 (d, J=7.7 Hz, 1H), 7.22 (d, J=4.0 Hz, 1H), 2.10 (s, 1H).

Example 42

N-{4-[6-Chloro-3-(5-fluoropyridin-2-yl)-1H-pyrrolo[3,2-b]pyridin-2-yl]pyridin-2-yl}acetamide

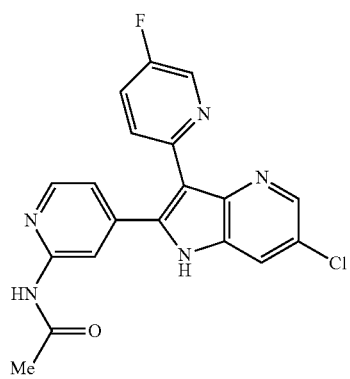 [SMILES: CC(=O)Nc1cc(-c2[nH]c3cc(Cl)cnc3c2-c2ccc(F)cn2)ccn1]

Example 42 was prepared from Example 41B and 2-bromo-5-fluoropyridine by the general methods shown for Example 1. HPLC: RT=0.95 min (H$_2$O/ACN with 0.1% TFA, Waters Acquity UPLC BEH C18, 2.1×50 mm, 1.7-μm particles, gradient=3 min, wavelength=220 nm); MS (ES): m/z=382 [M+H]$^+$; $^1$H NMR (500 MHz, DMSO-d$_6$) δ ppm 12.34 (s, 1H), 10.57 (s, 1H), 8.47 (dd, J=4.9, 2.5 Hz, 2H), 8.33 (d, J=5.0 Hz, 1H), 8.27 (s, 1H), 8.10 (dd, J=8.6, 4.5 Hz, 1H), 7.98 (d, J=2.0 Hz, 1H), 7.83 (td, J=8.8, 2.7 Hz, 1H), 7.17 (d, J=4.7 Hz, 1H), 2.09 (s, 1H).

Example 43

N-{4-[6-Chloro-3-(6-methoxypyridin-3-yl)-1H-pyrrolo[3,2-b]pyridin-2-yl]pyridin-2-yl}acetamide

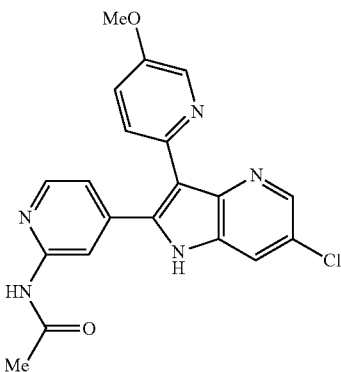

Example 43 was prepared from Example 41B and 5-bromo-2-methoxypyridine by the general methods shown for Example 1. HPLC: RT=1.03 min (H$_2$O/ACN with 0.1% TFA, Waters Acquity UPLC BEH C18, 2.1×50 mm, 1.7-μm particles, gradient=3 min, wavelength=220 nm); MS (ES): m/z=394 [M+H]$^+$; $^1$H NMR (500 MHz, DMSO-d$_6$) δ ppm 12.29 (s, 1H), 10.68 (s, 1H), 8.42 (s, 1H), 8.34 (d, J=5.4 Hz, 1H), 8.30 (s, 1H), 8.24 (s, 1H), 7.98 (s, 1H), 7.77 (d, J=8.4 Hz, 1H), 7.14 (d, J=4.7 Hz, 1H), 6.88 (d, J=8.4 Hz, 1H), 3.88 (s, 3H), 2.10 (s, 3H).

Example 44

N-{4-[6-Chloro-3-(5-fluoro-4-methylpyridin-2-yl)-1H-pyrrolo[3,2-b]pyridin-2-yl]pyridin-2-yl}acetamide

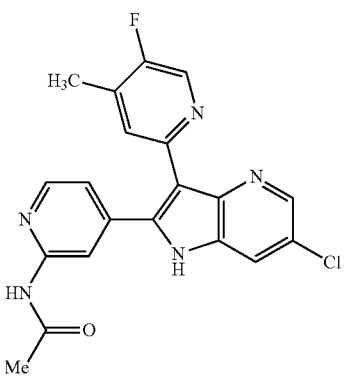 [SMILES: CC(=O)Nc1cc(-c2[nH]c3cc(Cl)cnc3c2-c2cc(C)c(F)cn2)ccn1]

Example 44 was prepared from Example 41B and 2-bromo-5-fluoro-4-methylpyridine by the general methods shown for Example 1. HPLC: RT=1.03 min (H$_2$O/ACN with 0.1% TFA, Waters Acquity UPLC BEH C18, 2.1×50 mm, 1.7-μm particles, gradient=3 min, wavelength=220 nm); MS (ES): m/z=396 [M+H]$^+$; $^1$H NMR (500 MHz, DMSO-d$_6$) δ ppm 12.32 (s, 1H), 10.56 (s, 1H), 8.46 (br. s., 1H), 8.34 (s, 1H), 8.31 (d, J=5.0 Hz, 1H), 8.26 (br. s., 1H), 7.98 (d, J=1.7 Hz, 1H), 7.94 (d, J=6.1 Hz, 1H), 7.14 (d, J=4.4 Hz, 1H), 2.36 (s, 1H), 2.09 (s, 1H).

Example 45

N-{4-[6-Chloro-3-(6-fluoropyridin-2-yl)-1H-pyrrolo[3,2-b]pyridin-2-yl]pyridin-2-yl}acetamide

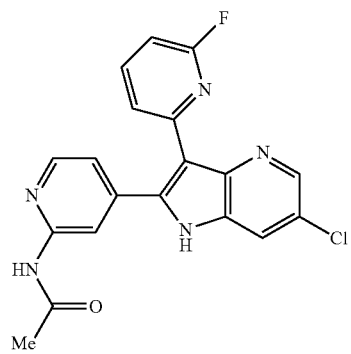 [SMILES: CC(=O)Nc1cc(-c2[nH]c3cc(Cl)cnc3c2-c2cccc(F)n2)ccn1]

Example 45 was prepared from Example 41B and 2-bromo-6-fluoropyridine by the general methods shown for Example 1. HPLC: RT=1.03 min (H₂O/ACN with 0.1% TFA, Waters Acquity UPLC BEH C18, 2.1×50 mm, 1.7-μm particles, gradient=3 min, wavelength=220 nm); MS (ES): m/z=382 [M+H]⁺; ¹H NMR (500 MHz, DMSO-d₆) δ ppm 12.44 (s, 1H), 10.59 (s, 1H), 8.48 (s, 1H), 8.36 (d, J=5.0 Hz, 1H), 8.26 (s, 1H), 8.07 (d, J=4.4 Hz, 2H), 8.00 (d, J=1.7 Hz, 1H), 7.22 (d, J=4.7 Hz, 1H), 7.03 (d, J=7.1 Hz, 1H), 2.09 (s, 3H).

Example 46

N-{4-[6-Chloro-3-(5-chloropyridin-2-yl)-1H-pyrrolo[3,2-b]pyridin-2-yl]pyridin-2-yl}acetamide

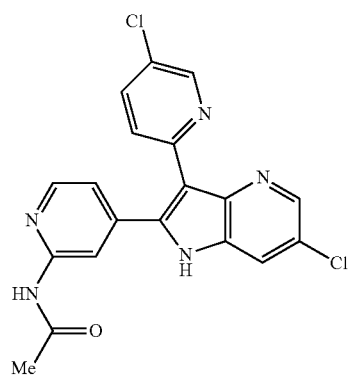

Example 46 was prepared from Example 41B and 2-bromo-5-chloropyridine by the general methods shown for Example 1. HPLC: RT=1.15 min (H₂O/ACN with 0.1% TFA, Waters Acquity UPLC BEH C18, 2.1×50 mm, 1.7-μm particles, gradient=3 min, wavelength=220 nm); MS (ES): m/z=398 [M+H]⁺; ¹H NMR (500 MHz, DMSO-d₆) δ ppm 10.61 (s, 1H), 8.47 (br. s., 2H), 8.33 (d, J=5.4 Hz, 1H), 8.25 (br. s., 1H), 8.11 (d, J=8.4 Hz, 1H), 8.04-7.97 (m, 2H), 7.18 (d, J=5.0 Hz, 1H), 2.09 (s, 3H).

Example 47

N-{4-[6-Chloro-3-(5-methoxypyridin-2-yl)-1H-pyrrolo[3,2-b]pyridin-2-yl]pyridin-2-yl}acetamide

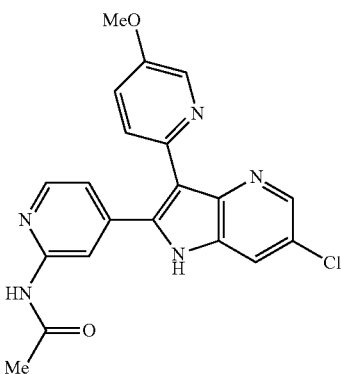

Example 47 was prepared from Example 41B and 2-bromo-5-methoxypyridine by the general methods shown for Example 1. HPLC: RT=0.89 min (H₂O/ACN with 0.1% TFA, Waters Acquity UPLC BEH C18, 2.1×50 mm, 1.7-μm particles, gradient=3 min, wavelength=220 nm); MS (ES): m/z=394 [M+H]⁺; ¹H NMR (500 MHz, DMSO-d₆) δ ppm 12.22 (s, 1H), 10.55 (s, 1H), 8.43 (d, J=2.0 Hz, 1H), 8.35-8.24 (m, 2H), 8.20 (d, J=2.7 Hz, 1H), 8.01-7.86 (m, 2H), 7.50 (dd, J=8.8, 3.0 Hz, 1H), 7.12 (d, J=6.1 Hz, 1H), 3.86 (s, 3H), 2.09 (s, 3H).

Example 48

N-{4-[3-(6-Chloropyridin-2-yl)-6-methoxy-1H-pyrrolo[3,2-b]pyridin-2-yl]pyridin-2-yl}acetamide

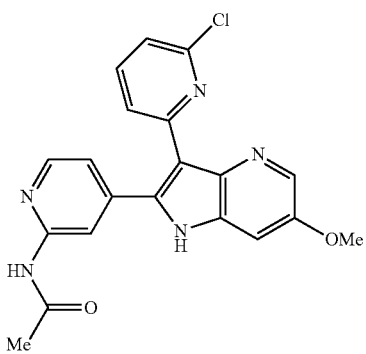 [SMILES: COc1cnc2c(-c3cccc(Cl)n3)c(-c3ccnc(NC(C)=O)c3)[nH]c2c1]

48A): N-(4-((3-Amino-5-methoxypyridin-2-yl)ethynyl)pyridin-2-yl)acetamide

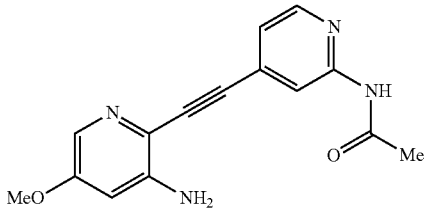 [SMILES: COc1cnc(C#Cc2ccnc(NC(C)=O)c2)c(N)c1]

Example 48A was prepared from Example 1B and 2-bromo-5-methoxypyridin-3-amine by methods similar to those shown for Example 1C. HPLC: RT=1.22 min (H$_2$O/MeOH with 0.1% TFA, Chromolith SpeedROD, 4.6×50 mm, gradient=4 min, wavelength=220 nm); MS (ES): m/z=283 [M+H]$^+$, $^1$H NMR (400 MHz, Chloroform-d) δ 8.34 (s, 1H), 8.25 (dd, J=5.2, 0.8 Hz, 1H), 7.93 (br. s., 1H), 7.82 (d, J=2.4 Hz, 1H), 7.20 (dd, J=5.1, 1.3 Hz, 1H), 6.56 (d, J=2.6 Hz, 1H), 4.36 (br. s., 2H), 3.87 (s, 3H), 2.24 (s, 3H).

48B): N-(2-((2-Acetamidopyridin-4-yl)ethynyl)-5-methoxypyridin-3-yl)-2,2,2-trifluoroacetamide

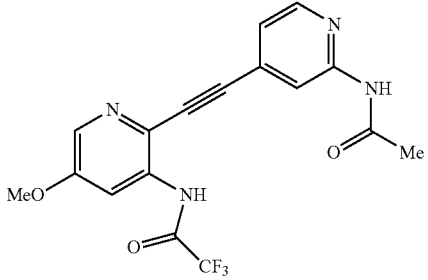 [SMILES: COc1cnc(C#Cc2ccnc(NC(C)=O)c2)c(NC(=O)C(F)(F)F)c1]

Example 48B was prepared from Example 48A by methods similar to those shown for Example 1D. HPLC: RT=1.73 min (H$_2$O/MeOH with 0.1% TFA, Chromolith SpeedROD, 4.6×50 mm, gradient=4 min, wavelength=220 nm); MS (ES): m/z=379 [M+H]$^+$, $^1$H NMR (400 MHz, Chloroform-d) δ ppm 8.78 (br. s., 1H), 8.41 (s, 1H), 8.36-8.27 (m, 2H), 8.24 (d, J=2.6 Hz, 1H), 7.94 (br. s., 1H), 7.18 (dd, J=5.1, 1.3 Hz, 1H), 3.97 (s, 3H), 2.26 (s, 3H).

N-{4-[3-(6-Chloropyridin-2-yl)-6-methoxy-1H-pyrrolo[3,2-b]pyridin-2-yl]pyridin-2-yl}acetamide

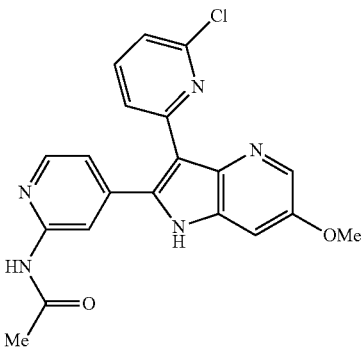 [SMILES: COc1cnc2c(-c3cccc(Cl)n3)c(-c3ccnc(NC(C)=O)c3)[nH]c2c1]

Example 48 was prepared from Example 48B and 2-bromo-6-chloropyridine by the general methods shown for Example 1. HPLC: RT=0.81 min (H$_2$O/ACN with 0.1% TFA, Waters Acquity UPLC BEH C18, 2.1×50 mm, 1.7-μm particles, gradient=3 min, wavelength=220 nm); MS (ES): m/z=394 [M+H]$^+$; $^1$H NMR (500 MHz, DMSO-d$_6$) δ ppm 12.07 (s, 1H), 10.50 (s, 1H), 8.31 (d, J=5.2 Hz, 1H), 8.23 (d, J=2.4 Hz, 2H), 8.14 (d, J=7.3 Hz, 1H), 7.90 (t, J=7.8 Hz, 1H), 7.42 (s, 1H), 7.33 (d, J=7.9 Hz, 1H), 7.19 (d, J=3.7 Hz, 1H), 3.89 (s, 3H), 2.08 (s, 3H).

Example 49

N-{4-[3-(5-Fluoropyridin-2-yl)-6-methoxy-1H-pyrrolo[3,2-b]pyridin-2-yl]pyridin-2-yl}acetamide

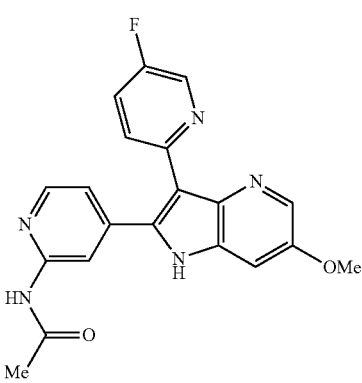 [SMILES: COc1cnc2c(-c3ccc(F)cn3)c(-c3ccnc(NC(C)=O)c3)[nH]c2c1]

Example 49 was prepared from Example 48B and 2-bromo-5-fluoropyridine by the general methods shown for Example 1. HPLC: RT=0.84 min (H$_2$O/ACN with 0.1% TFA, Waters Acquity UPLC BEH C18, 2.1×50 mm, 1.7-μm particles, gradient=3 min, wavelength=220 nm); MS (ES): m/z=378 [M+H]$^+$; $^1$H NMR (500 MHz, DMSO-d$_6$) δ ppm 11.95 (s, 1H), 10.50 (s, 1H), 8.44 (d, J=2.4 Hz, 1H), 8.28 (d, J=5.0 Hz, 1H), 8.23 (d, J=6.7 Hz, 2H), 8.10 (dd, J=8.6, 4.5 Hz, 1H), 7.85-7.77 (m, 1H), 7.39 (s, 1H), 7.15 (d, J=5.0 Hz, 1H), 3.89 (s, 3H), 2.08 (s, 3H).

Example 50

N-{4-[3-(5-Chloropyridin-2-yl)-6-methoxy-1H-pyrrolo[3,2-b]pyridin-2-yl]pyridin-2-yl}acetamide

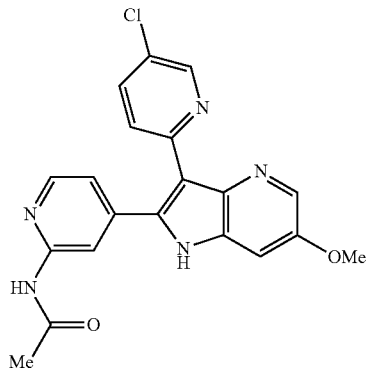 [SMILES: COc1cnc2c(-c3ccc(Cl)cn3)c(-c3ccnc(NC(C)=O)c3)[nH]c2c1]

Example 50 was prepared from Example 48B and 2-bromo-5-chloropyridine by the general methods shown for Example 1. HPLC: RT=0.95 min (H₂O/ACN with 0.1% TFA, Waters Acquity UPLC BEH C18, 2.1×50 mm, 1.7-μm particles, gradient=3 min, wavelength=220 nm); MS (ES): m/z=394 [M+H]⁺; ¹H NMR (500 MHz, DMSO-d₆) δ ppm 10.67 (s, 1H), 8.56 (d, J=2.0 Hz, 1H), 8.36 (d, J=5.0 Hz, 1H), 8.31 (d, J=2.4 Hz, 1H), 8.26 (br. s., 1H), 8.00-7.95 (m, 1H), 7.94-7.89 (m, 1H), 7.66 (br. s., 1H), 7.22 (d, J=5.0 Hz, 1H), 3.94 (s, 3H), 2.10 (s, 3H).

Example 51

N-{4-[3-(5-Fluoro-6-methylpyridin-2-yl)-6-methoxy-1H-pyrrolo[3,2-b]pyridin-2-yl]pyridin-2-yl}acetamide

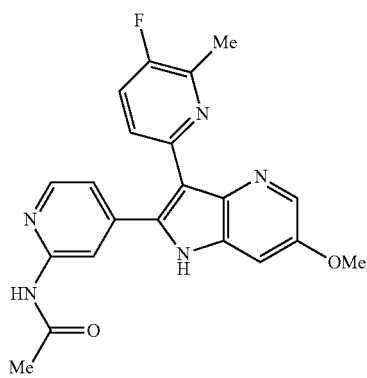 [SMILES: COc1cnc2c(-c3ccc(F)c(C)n3)c(-c3ccnc(NC(C)=O)c3)[nH]c2c1]

Example 51 was prepared from Example 48B and 6-bromo-3-fluoro-2-methylpyridine by the general methods shown for Example 1. HPLC: RT=0.91 min (H₂O/ACN with 0.1% TFA, Waters Acquity UPLC BEH C18, 2.1×50 mm, 1.7-μm particles, gradient=3 min, wavelength=220 nm); MS (ES): m/z=392 [M+H]⁺; ¹H NMR (500 MHz, DMSO-d₆) δ ppm 11.94 (s, 1H), 10.47 (s, 1H), 8.33-8.23 (m, 2H), 8.21 (d, J=2.0 Hz, 1H), 7.90 (dd, J=8.2, 3.2 Hz, 1H), 7.66 (t, J=9.1 Hz, 1H), 7.40 (s, 1H), 7.20 (d, J=5.0 Hz, 1H), 3.89 (s, 3H), 2.29 (d, J=2.4 Hz, 3H), 2.08 (s, 3H).

Example 52

4-[3-(6-Methoxypyridin-3-yl)-1H-pyrrolo[3,2-b]pyridin-2-yl]pyridin-2-amine

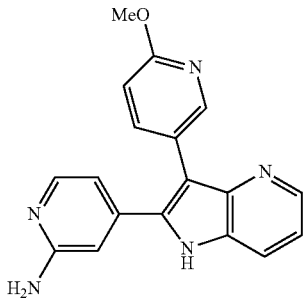 [SMILES: COc1ccc(-c2c(-c3ccnc(N)c3)[nH]c3cccnc23)cn1]

To a solution of Example 14 (38 mg, 0.106 mmol) in MeOH (8 mL) was added 1N NaOH (1.057 mL, 1.057 mmol). The mixture was then heated at 80° C. for 1.5 h, and then concentrated. The solid residue was suspended in water, collected by filtration, and dried to give the title product (27.4 mg, 80%) as a white solid. HPLC: RT=0.87 min (H₂O/ACN with 0.1% TFA, Waters Acquity UPLC BEH C18, 2.0×50 mm, 1.7-μm particles, gradient=3 min, wavelength=220 nm); MS (ES): m/z=318 [M+H]⁺; ¹H NMR (400 MHz, DMSO-d₆) δ ppm 11.85 (s, 1H), 8.39 (dd, J=4.5, 1.4 Hz, 1H), 8.30 (d, J=2.0 Hz, 1H), 7.95 (d, J=5.3 Hz, 1H), 7.82 (ddd, J=8.4, 3.9, 1.9 Hz, 2H), 7.22 (dd, J=8.3, 4.5 Hz, 1H), 6.87 (dd, J=8.5, 0.6 Hz, 1H), 6.63-6.51 (m, 2H), 6.06 (s, 2H), 3.89 (s, 3H).

Example 53

N-{4-[3-(6-Methoxypyridin-3-yl)-1H-pyrrolo[3,2-b]pyridin-2-yl]pyridin-2-yl}cyclopropanecarboxamide

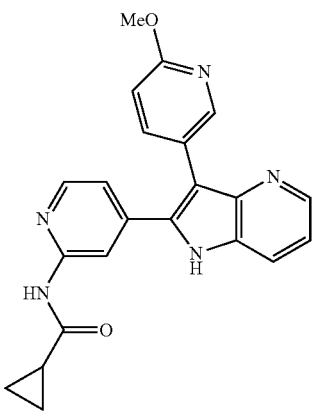 [SMILES: COc1ccc(-c2c(-c3ccnc(NC(=O)C4CC4)c3)[nH]c3cccnc23)cn1]

To a solution of Example 52 (12.1 mg, 0.038 mmol) and TEA (10.6 μl, 0.076 mmol) in THF (0.6 mL) was added a solution of cyclopropanecarbonyl chloride (6.8 mg, 0.065 mmol) in THF (70 μL). The reaction was stirred for 2 h, and then concentrated NH₄OH (1 drop) was added. The resulting reaction mixture was stirred at room temperature overnight. The mixture was diluted with DMF and purified by preparative HPLC (Column: Waters XBridge C18, 19×200 mm, 5-μm particles; Mobile Phase A: 5:95 acetonitrile: water with 10 mM ammonium acetate; Mobile Phase B: 95:5 acetonitrile: water with 10-mM ammonium acetate; Gradient: 10-55% B over 20 minutes, then a 5-minute hold at 100% B; Flow: 20 mL/min.) to give Example 53 (4.0 mg, 23%). HPLC: RT=0.82 min (H$_2$O/ACN with 0.1% TFA, Waters Acquity UPLC BEH C18, 2.1×50 mm, 1.7-μm particles, gradient=3 min, wavelength=220 nm); MS (ES): m/z=386 [M+H]$^+$; $^1$H NMR (500 MHz, DMSO-d$_6$) δ ppm 12.06 (br. s., 1H), 10.93 (s, 1H), 8.41 (d, J=3.7 Hz, 1H), 8.38 (s, 1H), 8.31 (d, J=5.1 Hz, 1H), 8.24 (d, J=1.9 Hz, 1H), 7.88 (d, J=8.1 Hz, 1H), 7.80 (dd, J=8.5, 2.2 Hz, 1H), 7.26 (dd, J=8.2, 4.6 Hz, 1H), 7.08 (d, J=4.1 Hz, 1H), 6.87 (d, J=8.6 Hz, 1H), 3.88 (s, 3H), 2.03 (br. s., 1H), 0.88-0.75 (m, 4H).

Example 54

N-{4-[3-(6-Methoxypyridin-3-yl)-1-methyl-1H-pyrrolo[3,2-b]pyridin-2-yl]pyridin-2-yl}acetamide

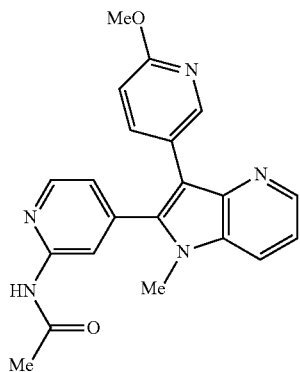 [SMILES: COc1ccc(-c2c(-c3ccnc(NC(C)=O)c3)n(C)c3cccnc23)cn1]

To a solution of Example 14 (12 mg, 0.033 mmol) in DMF (0.5 mL) was added Cs$_2$CO$_3$ (21.76 mg, 0.067 mmol), followed by a solution of methyl iodide (2.088 μl, 0.033 mmol) in DMF (0.5 mL). The reaction mixture was stirred at room temperature for 30 min and then filtered and purified by preparative HPLC (Column: Waters XBridge C18, 19×200 mm, 5-μm particles; Mobile Phase A: 5:95 acetonitrile: water with 10 mM ammonium acetate; Mobile Phase B: 95:5 acetonitrile: water with 10-mM ammonium acetate; Gradient: 5-65% B over 20 minutes, then a 5 minute hold at 100% B; Flow: 20 mL/min.) to give the title compound (8.2 mg, 66%). HPLC: RT=0.61 min (H$_2$O/ACN with 0.1% TFA, Waters Acquity UPLC BEH C18, 2.1×50 mm, 1.7-μm particles, gradient=3 min, wavelength=220 nm); MS (ES): m/z=374 [M+H]$^+$; $^1$H NMR (500 MHz, DMSO-d$_6$) δ ppm 10.73 (s, 1H), 8.46 (d, J=15.4, 4.7 Hz, 2H), 8.22-8.12 (m, 2H), 8.08 (d, J=8.2 Hz, 1H), 7.79 (dd, J=8.6, 2.2 Hz, 1H), 7.34 (dd, J=8.3, 4.6 Hz, 1H), 7.18 (d, J=5.0 Hz, 1H), 6.81 (d, J=8.6 Hz, 1H), 3.83 (s, 3H), 3.70 (s, 3H), 2.10 (s, 3H).

Example 55

N-{4-[7-(6-Chloropyridin-2-yl)-5H-pyrrolo[2,3-b]pyrazin-6-yl]pyridin-2-yl}acetamide

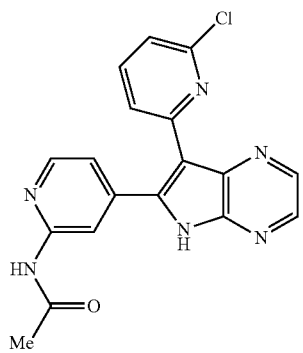

55A) N-(4-((3-Aminopyrazin-2-yl)ethynyl)pyridin-2-yl)acetamide

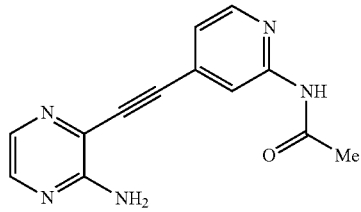 [SMILES: CC(=O)Nc1cc(C#Cc2nccnc2N)ccn1]

Example 55A was prepared from Example 1B and 3-chloropyrazin-2-amine by methods similar to those shown for Example 1C. HPLC: RT=0.906 min (H$_2$O/acetonitrile with 0.1% TFA, Waters Aquity BEH C18, 1.7 μm particles, 2.0×50 mm, gradient=1.5 min, wavelength=220 nm); MS (ES): m/z=254 [M+H]$^+$.

55B) N-(3-((2-Acetamidopyridin-4-yl)ethynyl)pyrazin-2-yl)-2,2,2-trifluoroacetamide

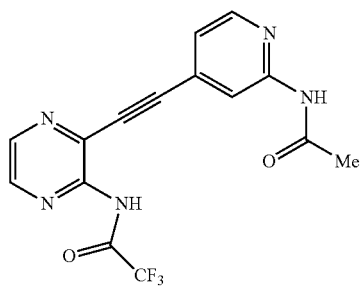 [SMILES: CC(=O)Nc1cc(C#Cc2nccnc2NC(=O)C(F)(F)F)ccn1]

Example 55B was prepared from 55A by methods similar to those shown for Example 1D. HPLC: RT=0.998 min (H$_2$O/acetonitrile with 0.1% TFA, Waters Aquity BEH C18, 1.7-μm particles, 2.0×50 mm, gradient=1.5 min, wavelength=220 nm); MS (ES): m/z=350 [M+H]$^+$.

N-{4-[7-(6-Chloropyridin-2-yl)-5H-pyrrolo[2,3-b]pyrazin-6-yl]pyridin-2-yl}acetamide

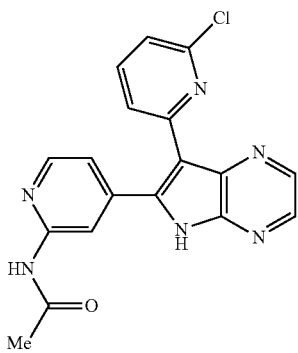 [SMILES: CC(=O)Nc1cc(-c2[nH]c3nccnc3c2-c2cccc(Cl)n2)ccn1]

Example 55 was prepared from Example 55B and 2-bromo-6-chloropyridine by the general methods shown for Example 1. HPLC: RT=0.89 min (H$_2$O/ACN with 0.1% TFA, Waters Acquity UPLC BEH C18, 2.1×50 mm, 1.7-μm particles, gradient=3 min, wavelength=220 nm); MS (ES): m/z=365 [M+H]$^+$; $^1$H NMR (500 MHz, DMSO-d$_6$) δ ppm 10.56 (s, 1H), 8.56 (d, J=2.4 Hz, 1H), 8.42 (d, J=2.4 Hz, 1H), 8.37 (d, J=5.1 Hz, 1H), 8.27 (s, 1H), 8.11 (d, J=7.7 Hz, 1H), 7.93 (t, J=7.8 Hz, 1H), 7.37 (d, J=7.9 Hz, 1H), 7.28 (d, J=5.1 Hz, 1H), 2.08 (s, 3H).

Example 56

5-Chloro-2-(2-acetamidopyridin-4-yl)-3-(6-methoxypyridin-3-yl)-N-methyl-1H-pyrrolo[3,2-b]pyridine-7-carboxamide

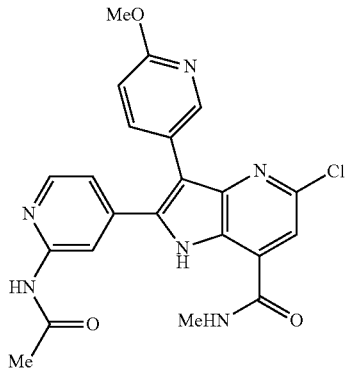 [SMILES: CNC(=O)c1cc(Cl)nc2c(-c3ccc(OC)nc3)c(-c3ccnc(NC(C)=O)c3)[nH]c12]

56A): Ethyl 5-amino-2-chloroisonicotinate

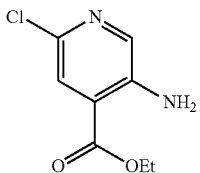 [SMILES: CCOC(=O)c1cc(Cl)ncc1N]

To a solution of ethyl 3-aminoisonicotinate (4.0 g, 24.07 mmol) in DMF (25 mL) was added NCS (3.54 g, 26.5 mmol) at room temperature. The reaction mixture was then heated at 50° C. under nitrogen for 18 h. The reaction mixture was cooled to room temperature and treated with saturated aqueous NaHCO$_3$ solution and ethyl acetate. The organic layer was separated and washed with brine, dried (MgSO$_4$) and filtered. The filtrate was concentrated in vacuo. The residue was dissolved in DCM and purified by silica gel flash chromatography, eluting with 30% ethyl acetate in hexane to give the desired product as a light yellow solid (2.0 g, 41%); HPLC: RT=0.84 min (H$_2$O/ACN with 0.05% TFA, Waters Acquity SDS BEH C18, 2.1×50 mm, 1.7-μm particles, gradient=1.8 min, wavelength=220 nm); MS (ES): m/z=200.9 [M+H]$^+$; $^1$H NMR (400 MHz, CDCl$_3$) δ ppm 7.98 (d, J=0.4 Hz, 1H), 7.66 (d, J=0.4 Hz, 1H), 4.38 (q, J=7.3 Hz, 2H), 1.42 (t, J=7.2 Hz, 3H).

56B): Ethyl 3-amino-2-bromo-6-chloroisonicotinate

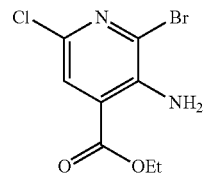 [SMILES: CCOC(=O)c1cc(Cl)nc(Br)c1N]

To a solution of Example 56A (2.0 g, 9.97 mmol) in DMF (15 mL) was added NBS (1.95 g, 10.97 mmol). The reaction mixture was stirred at room temperature for 20 h. To the reaction mixture was added a saturated aqueous NaHCO$_3$ solution and ethyl acetate. The organic layer was separated and washed with saturated NaHCO$_3$ solution, dried (MgSO$_4$), and filtered. The filtrate was concentrated in vacuo. The crude product was dissolved in DCM and purified by silica gel flash chromatography, eluting with 10% ethyl acetate in hexane to give the desired product as a light yellow solid (2.4 g, 86%); HPLC: RT=1.01 min (H$_2$O/ACN with 0.05% TFA, Waters Acquity SDS BEH C18, 2.1×50 mm, 1.7-μm particles, gradient=1.8 min, wavelength=220 nm); MS (ES): m/z=278.9, 280.9 [M+H]$^+$; $^1$H NMR (400 MHz, CDCl$_3$) δ ppm 7.68 (s, 1H), 6.24 (br. s., 2H), 4.40 (q, J=7.0 Hz, 2H), 1.42 (t, J=7.2 Hz, 3H).

56C): Ethyl 2-((2-acetamidopyridin-4-yl)ethynyl)-3-amino-6-chloroisonicotinate

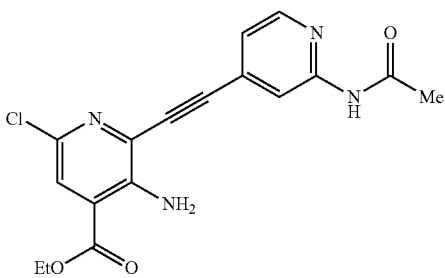 [SMILES: CCOC(=O)c1cc(Cl)nc(C#Cc2ccnc(NC(C)=O)c2)c1N]

To a solution of Example 56B (2.45 g, 8.77 mmol) and Example 1B (1.544 g, 9.64 mmol) in DMF (18 mL) were added CuI (0.134 g, 0.701 mmol) and TEA (12.2 mL, 88 mmol). The reaction mixture was purged with nitrogen, followed by the addition of PdCl$_2$(PPh$_3$)$_2$ (0.369 g, 0.526 mmol). The resulting mixture was heated at 78° C. for 2 h under nitrogen. The reaction mixture was then cooled to room temperature and diluted with ethyl acetate and saturated aqueous NaHCO$_3$ solution. The aqueous layer was extracted with EtOAc (3×) and the combined extracts were washed with saturated NaHCO$_3$ solution, and dried over MgSO$_4$. The mixture was filtered and then concentrated in vacuo. To the residue were added ethyl acetate and DCM and the precipitate was collected to give a yellow solid as the desired product. The filtrate further was concentrated in vacuo and the residue was purified by silica gel flash chromatography, eluting with 30% ethyl acetate in DCM to give additional desired product as a yellow solid (2.65 g, 84%); MS (ES): m/z=359.0 [M+H]$^+$; $^1$H NMR (400 MHz, DMSO-d$_6$) δ ppm 10.65 (s, 1H), 8.40 (dd, J=5.1, 0.7 Hz, 1H), 8.30 (s, 1H), 7.67 (s, 1H), 7.40 (dd, J=5.1, 1.3 Hz, 1H), 6.99 (s, 2H), 4.35 (q, J=7.0 Hz, 2H), 2.12 (s, 3H), 1.34 (t, J=7.2 Hz, 3H).

56D): Methyl 2-(2-acetamidopyridin-4-yl)-5-chloro-1H-pyrrolo[3,2-b]pyridine-7-carboxylate

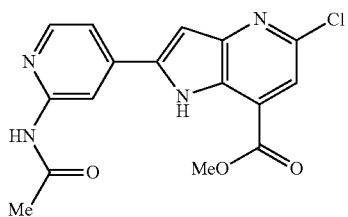

A suspension of Example 56C (160 mg, 0.446 mmol) in acetonitrile (6.0 mL) was sonicated and then treated with Cs$_2$CO$_3$ (436 mg, 1.338 mmol). The resulting mixture was purged with nitrogen for and Pd(PPh$_3$)$_4$ (51.5 mg, 0.045 mmol) was added. The reaction mixture was heated at 100° C. for 2 h under nitrogen. The reaction mixture was cooled to room temperature and the mixture was filtered. The solid was washed with ethyl acetate and the filtrate was concentrated in vacuo to give a the desired product; MS (ES): m/z=345.2 [M+H]$^+$; $^1$H NMR (400 MHz, DMSO-d$_6$) δ 11.76 (s, 1H), 10.64 (s, 1H), 8.53 (s, 1H), 8.44 (d, J=5.1 Hz, 1H), 7.67 (dd, J=5.2, 1.4 Hz, 1H), 7.60 (s, 1H), 7.23 (d, J=2.0 Hz, 1H), 4.02 (s, 3H), 2.15 (s, 3H).

56E): 2-(2-Acetamidopyridin-4-yl)-5-chloro-1H-pyrrolo[3,2-b]pyridine-7-carboxylic acid

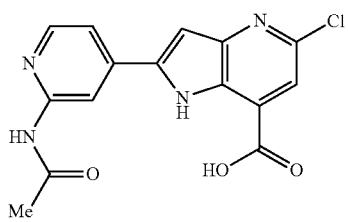

To a suspension of Example 56D (0.24 g, 0.696 mmol) in MeOH (1 mL) and 1,4-dioxane (6 mL) was added 1 M NaOH solution (3.48 mL, 3.48 mmol) dropwise. The reaction mixture was stirred at room temperature for 1 h. To the reaction mixture was added water and 1 N HCl solution was used to adjust the pH to 1-2. The reaction mixture was filtered to give a solid as the desired product (0.12 g, 52%); MS (ES): m/z=331.0 [M+H]$^+$; $^1$H NMR (400 MHz, DMSO-d$_6$) δ ppm 11.31 (br. s., 1H), 10.60 (s, 1H), 8.46 (s, 1H), 8.37 (d, J=5.3 Hz, 1H), 7.61 (dd, J=5.3, 1.5 Hz, 1H), 7.33 (s, 1H), 7.11 (s, 1H), 2.14 (s, 3H).

56F): 2-(2-Acetamidopyridin-4-yl)-5-chloro-N-methyl-1H-pyrrolo[3,2-b]pyridine-7-carboxamide

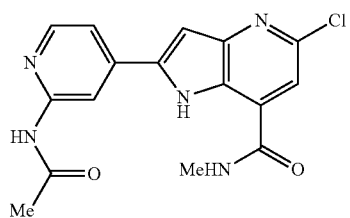 [SMILES: CNC(=O)c1cc(Cl)nc2cc(-c3ccnc(NC(C)=O)c3)[nH]c12]

To a suspension of Example 56E (90 mg, 0.272 mmol) in DMF (3 mL) was added HATU (124 mg, 0.327 mmol). The reaction mixture was stirred at room temperature for 5 min, followed by the addition of methylamine hydrochloride (0.049 mL, 0.544 mmol) and 4-methylmorpholine (0.06 mL, 0.544 mmol). The resulting mixture was stirred at room temperature for 30 min. The reaction mixture was then concentrated in vacuo and the residue was mixed with MeOH and purified by preparative HPLC (YMC-Pack C-18 30×100 mm, eluting with 5%-70% aqueous CH$_3$CN containing 0.1% TFA over 12 min, 25 mL/min, wavelength=254 nm). Fractions containing the desired product were combined, concentrated, and lyophilized to give the product (83 mg, 53%); MS (ES): m/z=344.0 [M+H]$^+$; $^1$H NMR (400 MHz, DMSO-d$_6$) δ ppm 11.74 (d, J=1.5 Hz, 1H), 10.66 (s, 1H), 8.93 (d, J=4.6 Hz, 1H), 8.50 (s, 1H), 8.40 (d, J=5.3 Hz, 1H), 7.71 (dd, J=5.4, 1.7 Hz, 1H), 7.55 (s, 1H), 7.20 (d, J=2.2 Hz, 1H), 2.89 (d, J=4.6 Hz, 3H), 2.15 (s, 3H).

56G): 2-(2-Acetamidopyridin-4-yl)-3-bromo-5-chloro-N-methyl-1H-pyrrolo[3,2-b]pyridine-7-carboxamide

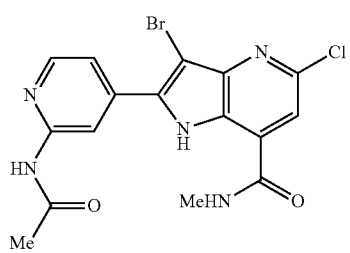 [SMILES: CNC(=O)c1cc(Cl)nc2c(Br)c(-c3ccnc(NC(C)=O)c3)[nH]c12]

To a solution of Example 56F (80 mg, 0.140 mmol) in DMF (1.5 mL) was added NBS (29.9 mg, 0.168 mmol). The reaction mixture was stirred at room temperature for 30 min. The reaction mixture was then diluted with a saturated NaHCO$_3$ solution and ethyl acetate. The organic layer was separated and dried over MgSO$_4$. The mixture was filtered and the filtrate was concentrated in vacuo. To the residue was added DCM and MeOH and the residue was filtered to give the desired product as a light yellow solid (42 mg, 71%); MS (ES): m/z=422.0, 424.0 [M+H]$^+$; $^1$H NMR (400 MHz, DMSO-d$_6$) δ ppm 12.22 (s, 1H), 10.66 (s, 1H), 8.94 (d, J=4.4 Hz, 1H), 8.61 (s, 1H), 8.47 (dd, J=5.3, 0.7 Hz, 1H), 7.64 (s, 1H), 7.52 (dd, J=5.1, 1.5 Hz, 1H), 2.87 (d, J=4.4 Hz, 3H), 2.14 (s, 3H).

Example 56): 5-Chloro-2-(2-acetamidopyridin-4-yl)-3-(6-methoxypyridin-3-yl)-N-methyl-1H-pyrrolo[3,2-b]pyridine-7-carboxamide

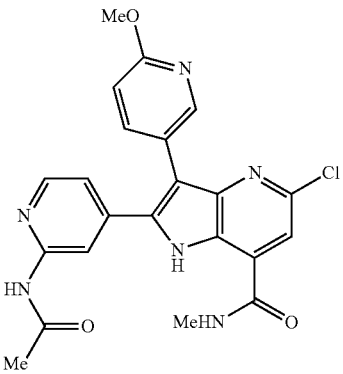 [SMILES: CNC(=O)c1cc(Cl)nc2c(-c3ccc(OC)nc3)c(-c3ccnc(NC(C)=O)c3)[nH]c12]

A suspension of Example 56G (42 mg, 0.099 mmol), 2-methoxy-5-(4,4,5,5-tetramethyl-1,3,2-dioxaborolan-2-yl)pyridine (28.0 mg, 0.119 mmol) and $Na_2CO_3$ (0.248 mL, 0.248 mmol) in dioxane (2 mL) and was purged with nitrogen, and treated with $PdCl_2$(dppf) (7.27 mg, 9.94 μmol). The resulting mixture was heated at 90° C. for 2 h. The reaction mixture was concentrated in vacuo. To the residue was added MeOH and DMF, and the mixture was purified by preparative HPLC (Sunfire C-18 19×150 mm, eluting with 5%-100% aqueous $CH_3CN$ containing 5 mmol $NH_4OAc$ over 12 min, 20 mL/min, wavelength=254 nm). Fractions containing the desired product were combined, concentrated, and lyophilized to give the product as a yellow solid (15 mg, 33%); HPLC: RT=1.02 min ($H_2O$/ACN with 0.1% TFA, Waters Acquity BEH C18, 2.0×50 mm, 1.7-μm particles, gradient=1.5 min, wavelength=220 nm) MS (ES): m/z=451.3 [M+H]$^+$; $^1$H NMR (400 MHz, MeOH-$d_4$) δ ppm 8.32 (dd, J=5.3, 0.7 Hz, 1H), 8.28 (s, 1H), 8.20 (d, J=1.8 Hz, 1H), 7.80 (dd, J=8.6, 2.4 Hz, 1H), 7.56 (s, 1H), 7.21 (dd, J=5.2, 1.7 Hz, 1H), 6.89-6.84 (m, 1H), 3.94 (s, 3H), 3.01 (s, 3H), 2.16 (s, 3H).

Example 57

2-(2-Acetamidopyridin-4-yl)-3-(6-methoxypyridin-3-yl)-N-methyl-1H-pyrrolo[3,2-b]pyridine-7-carboxamide

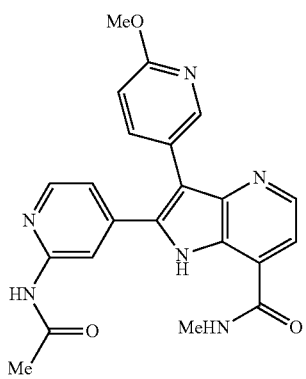 [SMILES: CNC(=O)c1ccnc2c(-c3ccc(OC)nc3)c(-c3ccnc(NC(C)=O)c3)[nH]c12]

To a suspension of Example 56 (8 mg, 0.018 mmol) in methanol (3 mL) and ethyl acetate (1 mL) was added Pd(OH)$_2$ (3.74 mg, 5.32 μmol). The reaction mixture was stirred under a nitrogen atmosphere over night. The reaction mixture was then diluted with MeOH and ethyl acetate and filtered. The filtrate was concentrated in vacuo. The residue was purified by preparative HPLC (Sunfire C-18 19×150 mm, eluting with 5%-100% aqueous $CH_3CN$ containing 5 mmol $NH_4OAc$ over 12 min, 20 mL/min, wavelength=220 nm). Fractions containing the desired product were combined, concentrated, and lyophilized to give the desired product as a yellow solid (3 mg, 40%); HPLC: RT=0.95 min ($H_2O$/ACN with 0.1% TFA, Waters Acquity BEH C18, 2.0×50 mm, 1.7-μm particles, gradient=1.5 min, wavelength=220 nm) MS (ES): m/z=417.4 [M+H]$^+$; $^1$H NMR (400 MHz, MeOH-$d_4$) δ ppm 8.47 (d, J=4.8 Hz, 1H), 8.31 (dd, J=5.3, 0.7 Hz, 1H), 8.28 (s, 1H), 8.18 (dd, J=2.4, 0.7 Hz, 1H), 7.80 (dd, J=8.5, 2.3 Hz, 1H), 7.54 (d, J=4.8 Hz, 1H), 7.24-7.18 (m, 1H), 6.89 (dd, J=8.6, 0.7 Hz, 1H), 3.95 (s, 3H), 3.03 (s, 3H), 2.16 (s, 3H).

Example 58

5-Chloro-N-(1,3-dihydroxypropan-2-yl)-2-(2-acetamidopyridin-4-yl)-3-(6-methoxypyridin-3-yl)-1H-pyrrolo[3,2-b]pyridine-7-carboxamide

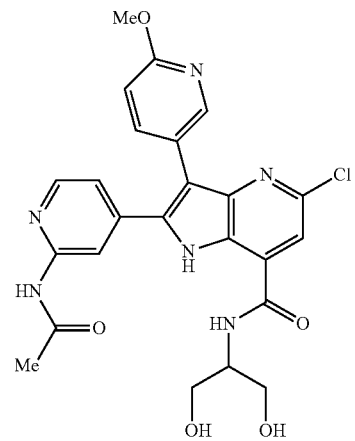 [SMILES: COc1ccc(-c2c(-c3ccnc(NC(C)=O)c3)[nH]c3c(C(=O)NC(CO)CO)cc(Cl)nc23)cn1]

58A): 2-(2-Acetamidopyridin-4-yl)-5-chloro-N-(1,3-dihydroxypropan-2-yl)-1H-pyrrolo[3,2-b]pyridine-7-carboxamide

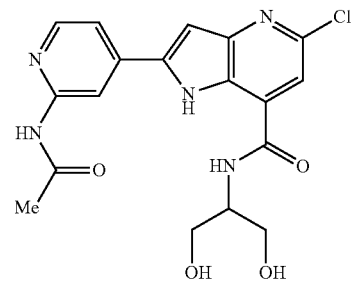 [SMILES: CC(=O)Nc1cc(-c2cc3nc(Cl)cc(C(=O)NC(CO)CO)c3[nH]2)ccn1]

Example 58A was prepared from Example 56E and 2-aminopropane-1,3-diol by similar method shown for Example 56F. HPLC: RT=0.54 min (H₂O/ACN with 0.05% TFA, Waters Acquity SDS BEH C18, 2.1×50 mm, 1.7-μm particles, gradient=1.8 min, wavelength=220 nm); MS (ES): m/z=404.1 [M+H]⁺.

58B): 2-(2-Acetamidopyridin-4-yl)-3-bromo-5-chloro-N-(1,3-dihydroxypropan-2-yl)-1H-pyrrolo[3,2-b]pyridine-7-carboxamide

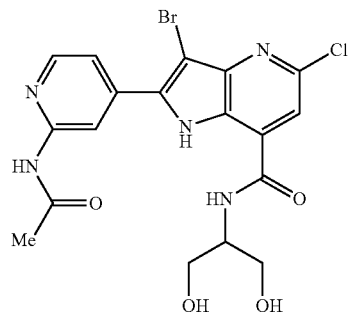 [SMILES: CC(=O)Nc1cc(-c2[nH]c3c(C(=O)NC(CO)CO)cc(Cl)nc3c2Br)ccn1]

Example 58B was prepared using similar methods as those shown for Example 56G. HPLC: RT=0.61 min (H₂O/ACN with 0.05% TFA, Waters Acquity SDS BEH C18, 2.1×50 mm, 1.7-μm particles, gradient=1.8 min, wavelength=220 nm). MS (ES): m/z=482.0, 484.0 [M+H]⁺. ¹H NMR (400 MHz, DMSO-d₆) δ ppm 12.16 (s, 1H), 10.69 (s, 1H), 8.68-8.57 (m, 2H), 8.46 (d, J=5.1 Hz, 1H), 7.81 (s, 1H), 7.52 (dd, J=5.3, 1.5 Hz, 1H), 4.11-4.00 (m, 1H), 3.64-3.51 (m, 4H), 2.14 (s, 3H).

Example 58): 5-Chloro-N-(1,3-dihydroxypropan-2-yl)-2-(2-acetamidopyridin-4-yl)-3-(6-methoxypyridin-3-yl)-1H-pyrrolo[3,2-b]pyridine-7-carboxamide

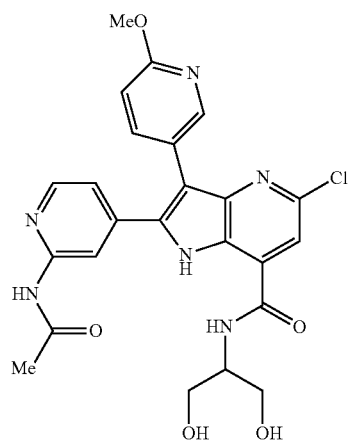 [SMILES: COc1ccc(-c2c(-c3ccnc(NC(C)=O)c3)[nH]c3c(C(=O)NC(CO)CO)cc(Cl)nc23)cn1]

Example 58 was prepared from Example 58B by the general method shown for Example 56H. HPLC: RT=0.64 min (H₂O/ACN with 0.05% TFA, Waters Acquity SDS BEH C18, 2.1×50 mm, 1.7-μm particles, gradient=1.8 min, wavelength=220 nm); MS (ES): m/z=511.2 [M+H]⁺. ¹H NMR (400 MHz, DMSO-d₆) δ ppm 11.85 (s, 1H), 10.58 (s, 1H), 8.59 (d, J=8.4 Hz, 1H), 8.31 (d, J=5.3 Hz, 1H), 8.28 (s, 1H), 8.19 (d, J=1.8 Hz, 1H), 7.76 (s, 1H), 7.72-7.66 (m, 1H), 7.11 (dd, J=5.3, 1.5 Hz, 1H), 6.87 (d, J=8.6 Hz, 1H), 4.11-4.03 (m, 1H), 3.88 (s, 3H), 3.64-3.56 (m, 4H), 2.09 (s, 3H).

Example 59

N-(1,3-Dihydroxypropan-2-yl)-2-(2-acetamidopyridin-4-yl)-3-(6-methoxypyridin-3-yl)-1H-pyrrolo[3,2-b]pyridine-7-carboxamide

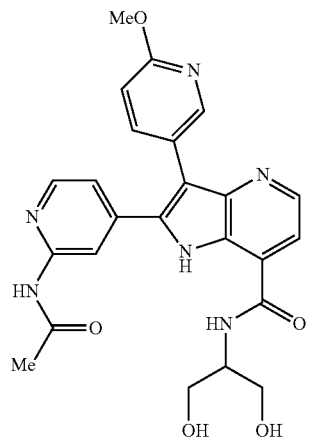 [SMILES: COc1ccc(-c2c(-c3ccnc(NC(C)=O)c3)[nH]c3c(C(=O)NC(CO)CO)ccnc23)cn1]

Example 59 was prepared from Example 58C by similar methods shown for Example 57. HPLC: RT=0.97 min (H₂O/ACN with 0.1% TFA, Waters Acquity BEH C18, 2.0×50 mm, 1.7-μm particles, gradient=1.5 min, wavelength=220 nm); MS (ES): m/z=477.3 [M+H]⁺; ¹H NMR (400 MHz, MeOH-d₄) δ ppm 8.48 (d, J=5.1 Hz, 1H), 8.30 (d, J=5.7 Hz, 1H), 8.27 (s, 1H), 8.18 (d, J=2.0 Hz, 1H), 7.79 (dd, J=8.6, 2.4 Hz, 1H), 7.64 (d, J=5.1 Hz, 1H), 7.21 (dd, 1.5 Hz, 1H), 6.89 (dd, J=8.6, 0.7 Hz, 1H), 4.42-4.27 (m, 1H), 3.95 (s, 3H), 3.86-3.75 (m, 4H), 2.16 (s, 3H).

Example 60

5-Chloro-N-(1,3-dihydroxypropan-2-yl)-2-(2-acetamidopyridin-4-yl)-3-(pyridin-3-yl)-1H-pyrrolo[3,2-b]pyridine-7-carboxamide

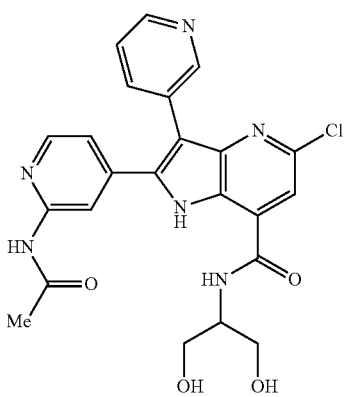 [SMILES: CC(=O)Nc1cc(-c2[nH]c3c(C(=O)NC(CO)CO)cc(Cl)nc3c2-c2cccnc2)ccn1]

Example 60 was prepared from Example 58B by similar methods as shown for Example 56. HPLC: RT=0.92 min (H₂O/ACN with 0.1% TFA, Waters Acquity BEH C18, 2.0×50 mm, 1.7-μm particles, gradient=1.5 min, wavelength=220 nm); MS (ES): m/z=481.3 [M+H]⁺; ¹H NMR (400 MHz, MeOH-d₄) δ ppm 8.60 (s, 1H), 8.46 (d, J=4.0 Hz, 1H), 8.34-8.28 (m, 1H), 8.25 (s, 1H), 8.00 (dt, J=8.0, 1.8 Hz, 1H), 7.68 (s, 1H), 7.46 (dd, J=7.8, 5.0 Hz, 1H), 7.16 (dd, J=5.2, 1.7 Hz, 1H), 4.29 (t, J=5.7 Hz, 1H), 3.90-3.73 (m, 4H), 2.15 (s, 3H).

Example 61

N-{4-[7-Chloro-3-(5-fluoropyridin-2-yl)-1H-pyrrolo[3,2-b]pyridin-2-yl]pyridin-2-yl}acetamide

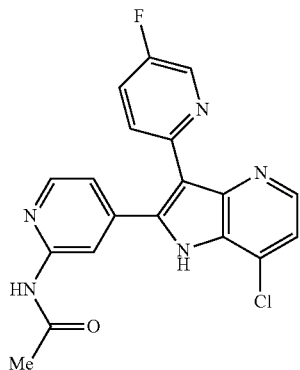 [SMILES: CC(=O)Nc1cc(-c2[nH]c3c(Cl)ccnc3c2-c2ccc(F)cn2)ccn1]

61A): 2-Bromo-4-chloropyridin-3-amine

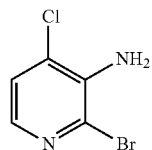

A solution of 4-chloropyridin-3-amine (2.0 g, 15.56 mmol) in TFA (17.98 ml, 233 mmol) was stirred at ice bath temperature and then treated with NBS (3.05 g, 17.11 mmol) slowly.

The reaction mixture was stirred at room temperature for 5 h. The reaction mixture was then concentrated in vacuo to a small volume. To the reaction mixture was added 1N NaOH solution and ethyl acetate. The organic layer was separated and washed with a saturated NaHCO₃ solution, dried over MgSO₄, and then filtered. The filtrate was concentrated in vacuo. The residue was purified by silica gel flash chromatography, eluting with 15% ethyl acetate in hexane to give the desired product as a white solid (1.65 g, 51%). HPLC: RT=1.03 min (H₂O/ACN with 0.1% TFA, Waters Acquity BEH C18, 2.0×50 mm, 1.7-μm particles, gradient=1.5 min, wavelength=220 nm); MS (ES): m/z=207.1, 209.1 [M+H]⁺; ¹H NMR (400 MHz, CDCl₃) δ ppm 7.70 (d, J=5.1 Hz, 1H), 7.17 (d, J=5.1 Hz, 1H), 4.52 (br. s., 2H).

61B): N-(4-((3-Amino-4-chloropyridin-2-yl)ethynyl)pyridin-2-yl)acetamide

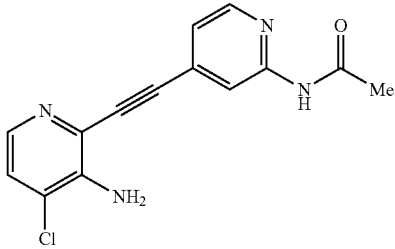 [SMILES: CC(=O)Nc1cc(C#Cc2nccc(Cl)c2N)ccn1]

To a solution of Example 61A (1.55 g, 7.47 mmol) and Example 1B (1.257 g, 7.85 mmol) in DMF (6 mL) were added CuI (0.142 g, 0.747 mmol) and TEA (10.41 mL, 74.7 mmol). The reaction mixture was purged with nitrogen, and treated with PdCl₂(PPh₃)₂ (0.367 g, 0.523 mmol). The resulting mixture was heated at 78° C. for 1.5 h under nitrogen. The reaction mixture was then cooled to room temperature, diluted with ethyl acetate and filtered. The brown filtrate was diluted with ethyl acetate and a saturated NaHCO₃ solution. The aqueous layer was extracted with ethyl acetate (2×) and the combined extracts were washed with a saturated NaHCO₃ solution, and dried over MgSO₄. The mixture was filtered and the filtrate was concentrated in vacuo. The residue was triturated with DCM and filtered to give a yellow solid as the desired product. The filtrate was further purified by silica gel flash chromatography, eluting with 10% MeOH in DCM to give the desired product as a yellow solid (1.55 g, 72%); HPLC: RT=0.61 min (H₂O/ACN with 0.05% TFA, Waters Acquity SDS BEH C18, 2.1×50 mm, 1.7-μm particles, gradient=1.8 min, wavelength=220 nm); MS (ES): m/z=287.0 [M+H]⁺; ¹H NMR (400 MHz, CDCl₃) δ ppm 8.37 (s, 1H), 8.28 (d, J=5.1 Hz, 1H), 7.95 (d, J=5.1 Hz, 2H), 7.24-7.19 (m, 2H), 4.71 (br. s., 2H), 2.24 (s, 3H).

61C): N-(2-((2-Acetamidopyridin-4-yl)ethynyl)-4-chloropyridin-3-yl)-2,2,2-trifluoroacetamide

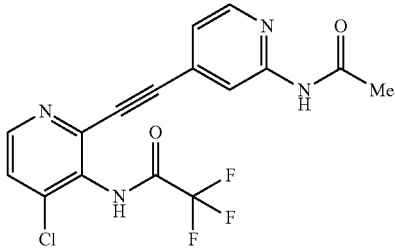 [SMILES: CC(=O)Nc1cc(C#Cc2nccc(Cl)c2NC(=O)C(F)(F)F)ccn1]

To a suspension of Example 61B (0.95 g, 3.31 mmol) in DCE (12 mL) at ice bath temperature was added TEA (1.62 mL, 11.60 mmol), followed by the addition of trifluoroacetic anhydride (0.74 mL, 5.30 mmol) slowly. The reaction mixture was stirred at 0° C. for 20 min. To the mixture was added more TEA (1.0 mL) and trifluoroacetic anhydride (0.45 mL) and the reaction mixture was stirred at 0° C. for another 40 min. The reaction mixture was quenched with a cold saturated NaHCO₃ solution and the resulting mixture was extracted with ethyl acetate (2×). The organic layer was separated and washed with a saturated NaHCO₃ solution, and dried over MgSO₄. The mixture was filtered and the filtrate was concentrated in vacuo to give a tan solid. The crude product was purified by silica gel flash chromatography, eluting with 70% ethyl acetate in DCM to give the desired product as a yellow solid (0.4 g, 32%); HPLC: RT=1.04 min (H₂O/ACN with 0.1% TFA, Waters Acquity BEH C18, 2.0×50 mm, 1.7-μm particles, gradient=1.5 min, wavelength=220 nm); MS (ES): m/z=383.0 [M+H]⁺; ¹H NMR (400 MHz, CDCl₃) δ ppm 8.54 (d, J=5.3 Hz, 1H), 8.34 (s, 1H), 8.28 (d, J=5.1 Hz, 1H), 8.17 (br. s., 1H), 7.93 (br. s., 1H), 7.50 (d, J=5.3 Hz, 1H), 7.13 (dd, 1.5 Hz, 1H), 2.24 (s, 3H).

Example 61): N-{4-[7-Chloro-3-(5-fluoropyridin-2-yl)-1H-pyrrolo[3,2-b]pyridin-2-yl]pyridin-2-yl}acetamide

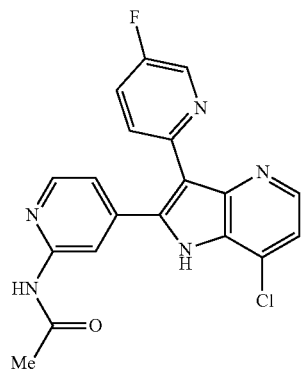 [SMILES: CC(=O)Nc1cc(-c2[nH]c3c(Cl)ccnc3c2-c2ccc(F)cn2)ccn1]

A mixture of Example 61C (30 mg, 0.078 mmol), Cs₂CO₃ (77 mg, 0.235 mmol) and 2-bromo-5-fluoropyridine (17.93 mg, 0.102 mmol) in acetonitrile (2 mL) in a sealed tube was purged with nitrogen, and treated with Pd(PPh₃)₄ (9.06 mg, 7.84 μmol). The reaction mixture was heated at 100° C. for 1.5 h and then cooled to room temperature. The reaction mixture was diluted with MeOH and ethyl acetate and filtered. The filtrate was concentrated in vacuo. The residue was purified by preparative HPLC (Column: Waters XBridge C18, 19×200 mm, 5-μm particles; Mobile Phase A: 5:95 acetonitrile: water with 10 mM ammonium acetate; Mobile Phase B: 95:5 acetonitrile: water with 10-mM ammonium acetate; Gradient: 5-50% B over 20 minutes, then a 5 minute hold at 100% B; Flow: 20 mL/min.). Fractions containing the desired product were combined, concentrated, and lyophilized to give the desired product as a yellow solid (1.6 mg, 5.3%); %); HPLC: RT=0.72 min (H₂O/ACN with 0.1% TFA, Waters Acquity UPLC BEH C18, 2.1×50 mm, 1.7-μm particles, gradient=3 min, wavelength=220 nm); MS (ES): m/z=382.2 [M+H]⁺; ¹H NMR (400 MHz, DMSO-d₆) δ ppm 12.53 (br. s., 1H), 10.55 (s, 1H), 8.47-8.38 (m, 2H), 8.31 (d, J=5.1 Hz, 1H), 8.22 (br. s., 1H), 8.12 (d, J=8.7 Hz, 1H), 7.81 (td, J=8.8, 2.8 Hz, 1H), 7.44 (d, J=5.0 Hz, 1H), 7.19 (d, J=4.3 Hz, 1H), 2.07 (s, 3H).

Example 62

N-{4-[7-Chloro-3-(5-methoxypyridin-2-yl)-1H-pyrrolo[3,2-b]pyridin-2-yl]pyridin-2-yl}acetamide

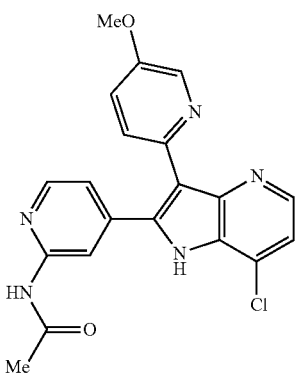 [SMILES: COc1ccc(-c2c(-c3ccnc(NC(C)=O)c3)[nH]c3c(Cl)ccnc23)nc1]

Example 62 was prepared from Example 61C and 2-bromo-5-methoxypyridine by the general method shown for Example 61. HPLC: RT=0.73 min (H₂O/ACN with 0.1% TFA, Waters Acquity UPLC BEH C18, 2.1×50 mm, 1.7-μm particles, gradient=3 min, wavelength=220 nm); MS (ES): m/z=394.0 [M+H]⁺; ¹H NMR (500 MHz, DMSO-d₆) δ ppm 12.80-12.08 (m, 1H), 10.53 (s, 1H), 8.38 (d, J=5.0 Hz, 1H), 8.28 (d, J=5.1 Hz, 1H), 8.26 (br. s., 1H), 8.16 (d, J=2.7 Hz, 1H), 7.95 (d, J=8.7 Hz, 1H), 7.48 (dd, J=8.7, 2.8 Hz, 1H), 7.41 (d, J=5.0 Hz, 1H), 7.14 (d, J=4.9 Hz, 1H), 3.90-3.79 (m, 3H), 2.08 (s, 3H).

Example 63

N-{4-[7-Chloro-3-(5-chloropyridin-2-yl)-1H-pyrrolo[3,2-b]pyridin-2-yl]pyridin-2-yl}acetamide

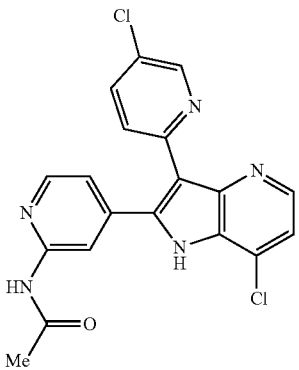

Example 63 was prepared from Example 61C and 2-bromo-5-chloropyridine by the general method shown for Example 61. HPLC: RT=0.97 min (H₂O/ACN with 0.1% TFA, Waters Acquity BEH C18, 2.0×50 mm, 1.7-μm particles, gradient=1.5 min, wavelength=220 nm); MS (ES): m/z=398.2 [M+H]⁺; ¹H NMR (400 MHz, DMSO-d₆) δ ppm 12.59 (s, 1H), 10.56 (s, 1H), 8.50-8.40 (m, 2H), 8.33 (d, J=5.3 Hz, 1H), 8.27 (s, 1H), 8.20 (d, J=8.6 Hz, 1H), 8.00 (dd, J=8.6, 2.6 Hz, 1H), 7.46 (d, J=5.1 Hz, 1H), 7.20 (dd, J=5.2, 1.4 Hz, 1H), 2.13-2.07 (m, 3H).

Example 64

N-{4-[7-Chloro-3-(6-fluoropyridin-2-yl)-1H-pyrrolo[3,2-b]pyridin-2-yl]pyridin-2-yl}acetamide

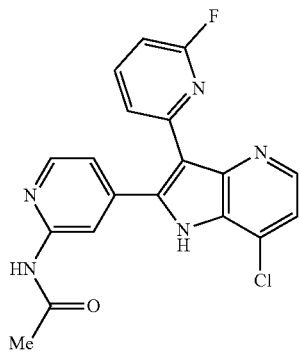 [SMILES: CC(=O)Nc1cc(-c2[nH]c3c(Cl)ccnc3c2-c2cccc(F)n2)ccn1]

Example 64 was prepared from Example 61C and 2-bromo-6-fluoropyridine by the general method shown for Example 61. HPLC: RT=0.71 min (H$_2$O/ACN with 0.1% TFA, Waters Acquity UPLC BEH C18, 2.1×50 mm, 1.7-μm particles, gradient=3 min, wavelength=220 nm); MS (ES): m/z=382.0 [M+H]$^+$; $^1$H NMR (500 MHz, DMSO-d$_6$) δ ppm 10.56 (s, 1H), 8.41 (d, J=5.0 Hz, 1H), 8.34 (d, J=5.0 Hz, 1H), 8.21 (s, 1H), 8.12 (d, J=5.4 Hz, 1H), 8.03 (q, J=8.1 Hz, 1H), 7.43 (d, J=5.0 Hz, 1H), 7.23 (d, J=5.0 Hz, 1H), 6.99 (d, J=6.2 Hz, 1H), 2.07 (s, 3H).

Example 65

N-{4-[6-Chloro-3-(6-methoxypyridin-2-yl)-1H-pyrrolo[3,2-b]pyridin-2-yl]pyridin-2-yl}acetamide

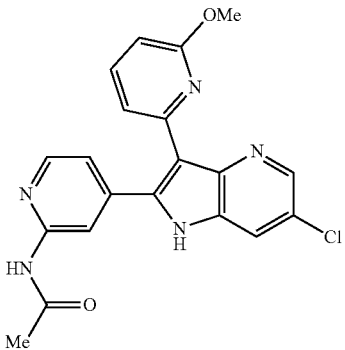 [SMILES: COc1cccc(-c2c(-c3ccnc(NC(C)=O)c3)[nH]c3cc(Cl)cnc23)n1]

Example 65 was prepared from Example 41B and 2-bromo-6-methoxypyridine by the general methods shown for Example 1. HPLC: RT=0.73 min (H$_2$O/ACN with 0.1% TFA, Waters Acquity UPLC BEH C18, 2.1×50 mm, 1.7-μm particles, gradient=3 min, wavelength=220 nm); MS (ES): m/z=394.1 [M+H]$^+$; $^1$H NMR (500 MHz, DMSO-d$_6$) δ ppm 10.57 (s, 1H), 8.48 (d, J=2.0 Hz, 1H), 8.35 (d, J=5.1 Hz, 1H), 8.27 (br. s., 1H), 8.02-7.90 (m, 2H), 7.76 (t, J=7.8 Hz, 1H), 7.19 (d, J=5.0 Hz, 1H), 6.62 (d, J=8.2 Hz, 1H), 3.48 (br. s., 3H), 2.08 (s, 3H).

Example 66

N-{4-[6-Chloro-3-(6-methylpyridin-2-yl)-1H-pyrrolo[3,2-b]pyridin-2-yl]pyridin-2-yl}acetamide

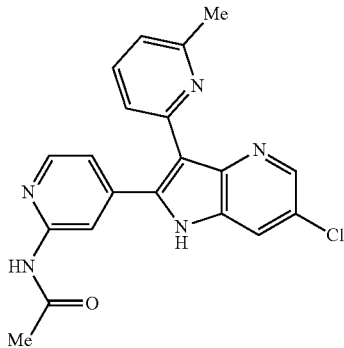 [SMILES: CC(=O)Nc1cc(-c2[nH]c3cc(Cl)cnc3c2-c2cccc(C)n2)ccn1]

Example 66 was prepared from Example 41B and 2-bromo-6-methylpyridine by the general methods shown for Example 1. HPLC: RT=0.91 min (H$_2$O/ACN with 0.1% TFA, Waters Acquity UPLC BEH C18, 2.1×50 mm, 1.7-μm particles, gradient=3 min, wavelength=220 nm); MS (ES): m/z=378.0 [M+H]$^+$; $^1$H NMR (500 MHz, DMSO-d$_6$) δ ppm 12.26 (s, 1H), 10.51 (s, 1H), 8.42 (d, J=1.9 Hz, 1H), 8.35-8.23 (m, 2H), 7.96 (d, J=1.9 Hz, 1H), 7.85-7.77 (m, 1H), 7.75-7.67 (m, 1H), 7.19 (d, J=4.0 Hz, 1H), 7.13 (d, J=7.6 Hz, 1H), 2.29 (s, 3H), 2.07 (s, 3H).

Example 67

N-(4-{6-Chloro-3-[6-(hydroxymethyl)pyridin-2-yl]-1H-pyrrolo[3,2-b]pyridin-2-yl}pyridin-2-yl)acetamide

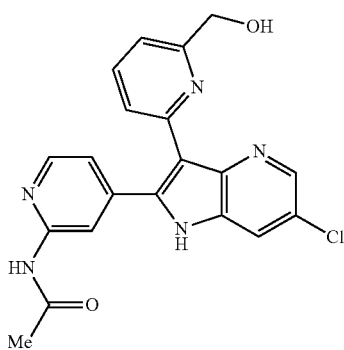 [SMILES: CC(=O)Nc1cc(-c2[nH]c3cc(Cl)cnc3c2-c2cccc(CO)n2)ccn1]

Example 67 was prepared from Example 41B and (6-bromopyridin-2-yl)methanol by the general methods shown for Example 1. HPLC: RT=0.78 min (H$_2$O/ACN with 0.1% TFA, Waters Acquity UPLC BEH C18, 2.1×50 mm, 1.7-μm particles, gradient=3 min, wavelength=220 nm); MS (ES): m/z=394.3 [M+H]$^+$; $^1$H NMR (500 MHz, DMSO-d$_6$) δ ppm 10.65 (s, 1H), 8.50 (d, J=1.9 Hz, 1H), 8.37 (d, J=5.1 Hz, 1H), 8.27 (s, 1H), 8.11 (t, J=7.8 Hz, 1H), 8.07 (d, J=1.7 Hz, 1H), 7.87 (d, J=7.9 Hz, 1H), 7.57 (d, J=7.7 Hz, 1H), 7.25 (d, J=3.2 Hz, 1H), 4.59 (s, 2H), 2.08 (s, 3H).

Example 68

N-[4-(6-Chloro-3-{6-[(2-hydroxyethyl)amino]pyridin-2-yl}-1H-pyrrolo[3,2-b]pyridin-2-yl)pyridin-2-yl]acetamide

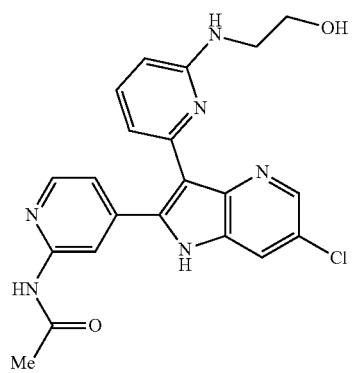 [SMILES: CC(=O)Nc1cc(-c2[nH]c3cc(Cl)cnc3c2-c2cccc(NCCO)n2)ccn1]

Example 68 was prepared from Example 41B and 2-((6-bromopyridin-2-yl)amino)ethanol by the general methods shown for Example 1. HPLC: RT=0.90 min (H$_2$O/ACN with 0.1% TFA, Waters Acquity UPLC BEH C18, 2.1×50 mm, 1.7-μm particles, gradient=3 min, wavelength=220 nm); MS (ES): m/z=423.0 [M+H]$^+$; $^1$H NMR (500 MHz, DMSO-d$_6$) δ ppm 10.71 (s, 1H), 8.54 (d, J=1.8 Hz, 1H), 8.45 (d, J=5.0 Hz, 1H), 8.31 (s, 1H), 8.11 (s, 1H), 7.82 (br. s., 1H), 7.31 (d, J=4.5 Hz, 1H), 6.96 (br. s., 1H), 6.87 (br. s., 1H), 2.54 (s, 4H), 2.09 (s, 3H).

Example 69

Methyl 5-chloro-2-(2-acetamidopyridin-4-yl)-3-(5-fluoropyridin-2-yl)-1H-pyrrolo[3,2-b]pyridine-7-carboxylate

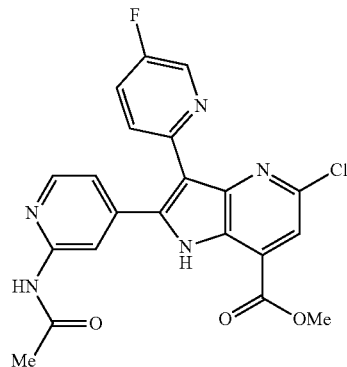 [SMILES: COC(=O)c1cc(Cl)nc2c(-c3ccc(F)cn3)c(-c3ccnc(NC(C)=O)c3)[nH]c12]

69A): Ethyl 2-((2-acetamidopyridin-4-yl)ethynyl)-6-chloro-3-(2,2,2-trifluoroacetamido)isonicotinate

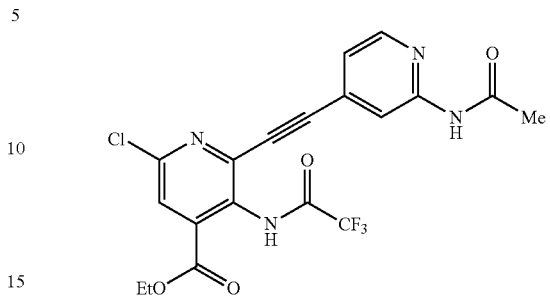

To a suspension of Example 56C (0.2 g, 0.557 mmol) in DCE (4 mL) and diethyl ether (10 mL) was added CaCO$_3$ (0.223 g, 2.230 mmol) at ice bath temperature. To the reaction mixture was added TFAA (0.17 mL, 1.226 mmol) slowly and the reaction mixture was stirred at ice bath temperature for 2 h. To the reaction mixture was added cold water and ethyl acetate. The organic layer was separated and washed with brine and dried over MgSO$_4$. The mixture was filtered and the filtrate was concentrated in vacuo. To the residue was added DCM and the resulting solid was filtered to give the desired product as a yellow solid (0.15 g, 60%). HPLC: RT=0.90 min (H$_2$O/ACN with 0.05% TFA, Waters Acquity SDS BEH C18, 2.1×50 mm, 1.7-μm particles, gradient=1.8 min, wavelength=220 nm); MS (ES): m/z=455.0 [M+H]$^+$; $^1$H NMR (400 MHz, DMSO-d$_6$) δ ppm 11.90 (s, 1H), 10.70 (s, 1H), 8.48-8.39 (m, 1H), 8.26 (s, 1H), 7.99 (s, 1H), 7.22 (dd, J=5.1, 1.5 Hz, 1H), 4.32 (q, J=7.1 Hz, 2H), 2.12 (s, 3H), 1.29 (t, J=7.0 Hz, 3H).

Example 69): Methyl 5-chloro-2-(2-acetamidopyridin-4-yl)-3-(5-fluoropyridin-2-yl)-1H-pyrrolo[3,2-b]pyridine-7-carboxylate

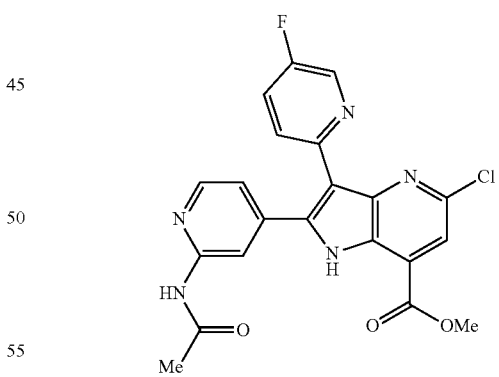

Example 69 was prepared from Example 69A and 2-bromo-5-fluoropyridine by the general methods shown for Example 1. HPLC: RT=1.13 min (H$_2$O/ACN with 0.1% TFA, Waters Acquity BEH C18, 2.0×50 mm, 1.7-μm particles, gradient=1.5 min, wavelength=220 nm); MS (ES): m/z=440.3 [M+H]$^+$; $^1$H NMR (400 MHz, DMSO-d$_6$) δ ppm 12.07 (s, 1H), 10.59 (s, 1H), 8.45 (d, J=3.1 Hz, 1H), 8.34 (d, J=5.1 Hz, 1H), 8.20 (s, 1H), 8.01 (dd, J=8.8, 4.6 Hz, 1H), 7.84 (td, J=8.7, 3.0 Hz, 1H), 7.70 (s, 1H), 7.17 (dd, J=5.1, 1.5 Hz, 1H), 4.02 (s, 3H), 2.09 (s, 3H).

Example 70

Methyl 5-chloro-3-(5-chloropyridin-2-yl)-2-(2-acetamidopyridin-4-yl)-1H-pyrrolo[3,2-b]pyridine-7-carboxylate

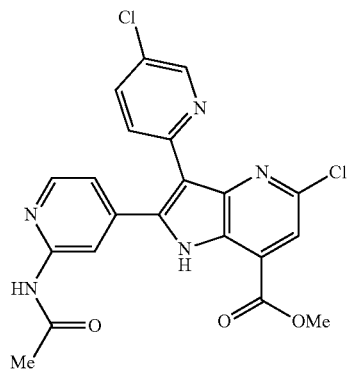 [SMILES: COC(=O)c1cc(Cl)nc2c(-c3ccc(Cl)cn3)c(-c3ccnc(NC(C)=O)c3)[nH]c12]

Example 70 was prepared from Example 69A and 2-bromo-5-chloropyridine by the general methods shown for Example 1. HPLC: RT=0.92 min (H$_2$O/ACN with 0.05% TFA, Waters Acquity SDS BEH C18, 2.1×50 mm, 1.7-μm particles, gradient=1.8 min, wavelength=220 nm); MS (ES): m/z=456.1 [M+H]$^+$; $^1$H NMR (400 MHz, DMSO-d$_6$) δ ppm 12.14 (s, 1H), 10.59 (s, 1H), 8.46 (s, 1H), 8.34 (d, J=5.1 Hz, 1H), 8.23 (s, 1H), 8.04 (s, 2H), 7.70 (s, 1H), 7.15 (d, J=3.8 Hz, 1H), 4.01 (s, 3H), 2.09 (s, 3H).

Example 71

Methyl 2-(2-acetamidopyridin-4-yl)-3-(5-fluoropyridin-2-yl)-1H-pyrrolo[3,2-b]pyridine-7-carboxylate

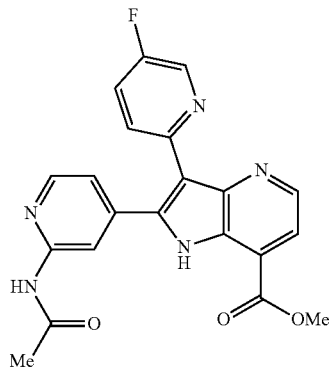 [SMILES: COC(=O)c1ccnc2c(-c3ccc(F)cn3)c(-c3ccnc(NC(C)=O)c3)[nH]c12]

Example 71 was prepared from Example 69B by the general methods shown for Example 57. HPLC: RT=0.96 min (H$_2$O/ACN with 0.1% TFA, Waters Acquity BEH C18, 2.0×50 mm, 1.7-μm particles, gradient=1.5 min, wavelength=220 nm); MS (ES): m/z=406.3 [M+H]$^+$; $^1$H NMR (400 MHz, CDCl$_3$+MeOH-d$_4$) δ ppm 8.15 (br. s., 1H), 8.03 (br. s., 1H), 7.87 (d, J=5.3 Hz, 1H), 7.83 (s, 1H), 7.39 (br. s., 2H), 7.25-7.17 (m, 1H), 6.82-6.72 (m, 1H), 3.68 (s, 3H), 1.76 (s, 3H).

Example 72

N-{4-[6-Chloro-3-(5-fluoropyridin-2-yl)-1H-pyrrolo[3,2-b]pyridin-2-yl]pyridin-2-yl}-2-hydroxyacetamide

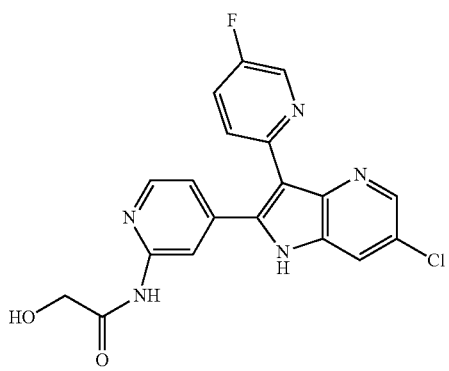 [SMILES: O=C(CO)Nc1cc(-c2[nH]c3cc(Cl)cnc3c2-c2ccc(F)cn2)ccn1]

72A): 4-(6-Chloro-3-(5-fluoropyridin-2-yl)-1H-pyrrolo[3,2-b]pyridin-2-yl)pyridin-2-amine

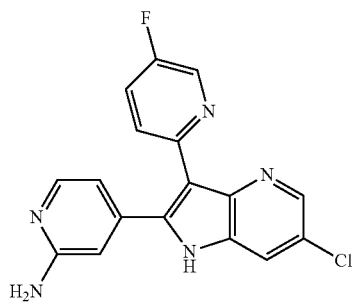 [SMILES: Nc1cc(-c2[nH]c3cc(Cl)cnc3c2-c2ccc(F)cn2)ccn1]

Example 72A was prepared from Example 42 by similar method as those shown for Example 52. HPLC: RT=0.98 min (H$_2$O/ACN with 0.1% TFA, Waters Acquity BEH C18, 2.0×50 mm, 1.7-μm particles, gradient=1.5 min, wavelength=220 nm); MS (ES): m/z=340.2 [M+H]$^+$; $^1$H NMR (400 MHz, DMSO-d$_6$) δ ppm 12.15 (br. s., 1H), 8.51 (d, J=3.1 Hz, 1H), 8.41 (d, J=2.2 Hz, 1H), 8.02 (dd, J=9.0, 4.4 Hz, 1H), 7.94-7.89 (m, 2H), 7.80 (td, J=8.8, 3.1 Hz, 1H), 6.57 (s, 1H), 6.53 (dd, J=5.3, 1.5 Hz, 1H), 6.00 (s, 2H).

72B) 2-((4-(6-Chloro-3-(5-fluoropyridin-2-yl)-1H-pyrrolo[3,2-b]pyridin-2-yl)pyridin-2-yl)amino)-2-oxoethyl acetate

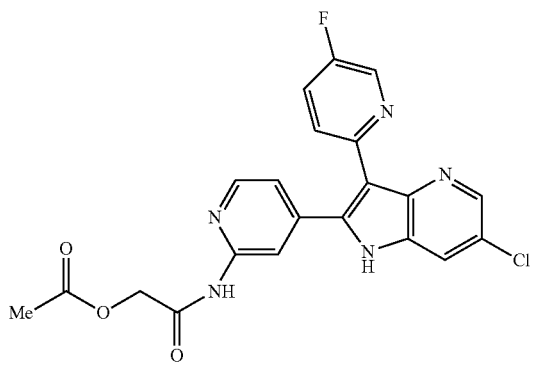 [SMILES: CC(=O)OCC(=O)Nc1cc(-c2[nH]c3cc(Cl)cnc3c2-c2ccc(F)cn2)ccn1]

To a suspension of Example 72A (60 mg, 0.177 mmol) in DCE (3 mL) were added acetoxyacetyl chloride (0.06 mL, 0.54 mmol) and TEA (0.1 mL, 0.71 mmol). The reaction was stirred at room temperature for 2 h. To the reaction mixture was added 0.5 mL of an ammonia hydroxide solution and the mixture was stirred at room temperature for 1 h. The resulting reaction mixture was concentrated in vacuo. The residue was purified by preparative HPLC (Sunfire C-18 19×150 mm, eluting with 10%-100% aqueous CH$_3$CN containing 5 mmol NH$_4$OAc over 18 min, 20 mL/min, wavelength=220 nm). Fractions containing the desired product were combined, concentrated, and lyophilized to give the desired product as a yellow solid (46 mg, 58%); HPLC: RT=1.04 min (H$_2$O/ACN with 0.1% TFA, Waters Acquity BEH C18, 2.0×50 mm, 1.7-μm particles, gradient=1.5 min, wavelength=220 nm); MS (ES): m/z=440.2 [M+H]$^+$; $^1$H NMR (400 MHz, DMSO-d$_6$) δ ppm 10.74 (s, 1H), 8.45 (dd, J=4.6, 2.6 Hz, 2H), 8.33 (d, J=5.3 Hz, 1H), 8.25 (br. s., 1H), 8.12 (dd, J=8.8, 4.6 Hz, 1H), 7.97 (d, J=2.2 Hz, 1H), 7.82 (td, J=8.8, 3.1 Hz, 1H), 7.18 (dd, J=5.3, 1.5 Hz, 1H), 4.72 (s, 2H), 2.11 (s, 3H).

N-{4-[6-Chloro-3-(5-fluoropyridin-2-yl)-1H-pyrrolo[3,2-b]pyridin-2-yl]pyridin-2-yl}-2-hydroxyacetamide

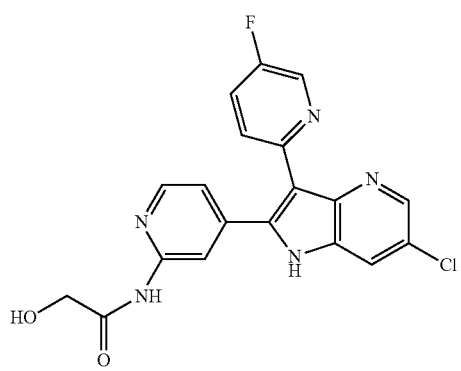 [SMILES: O=C(CO)Nc1cc(-c2[nH]c3cc(Cl)cnc3c2-c2ccc(F)cn2)ccn1]

A solution of Example 72B (35 mg, 0.08 mmol) in methanol (2 mL) was treated with aqueous NaOH (0.8 mL, 0.80 mmol). The reaction mixture was stirred at room temperature for 30 min. The reaction mixture was then concentrated in vacuo. The residue was purified by preparative HPLC (Sunfire C-18 19×150 mm, eluting with 5%-70% aqueous CH$_3$CN containing 5 mmol NH$_4$OAc over 14 min, 20 mL/min, wavelength=220 nm). Fractions containing the desired product were combined, concentrated, and lyophilized to give the desired product as a yellow solid (22 mg, 69%); HPLC: RT=1.0 min (H$_2$O/ACN with 0.1% TFA, Waters Acquity BEH C18, 2.0×50 mm, 1.7-μm particles, gradient=1.5 min, wavelength=220 nm); MS (ES): m/z=398.2 [M+H]$^+$; $^1$H NMR (400 MHz, DMSO-d$_6$) δ ppm 12.34 (br. s., 1H), 9.72 (s, 1H), 8.46 (d, J=2.2 Hz, 2H), 8.35 (dd, J=5.3, 0.7 Hz, 1H), 8.29 (s, 1H), 8.12 (dd, J=8.8, 4.6 Hz, 1H), 7.98 (d, J=2.2 Hz, 1H), 7.83 (td, J=8.8, 3.1 Hz, 1H), 7.23 (dd, 1.5 Hz, 1H), 5.73 (t, J=6.1 Hz, 1H), 4.03 (d, J=5.9 Hz, 2H).

Example 73

2S)—N-{4-[6-Chloro-3-(5-fluoropyridin-2-yl)-1H-pyrrolo[3,2-b]pyridin-2-yl]pyridin-2-yl}-2-hydroxypropanamide

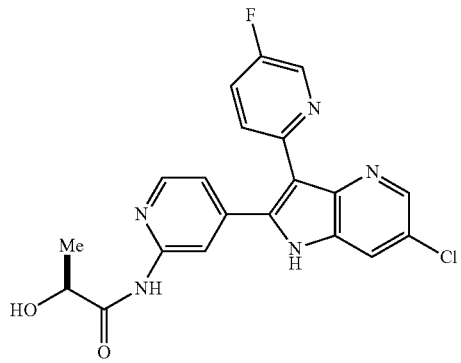 [SMILES: C[C@H](O)C(=O)Nc1cc(-c2[nH]c3cc(Cl)cnc3c2-c2ccc(F)cn2)ccn1]

Example 73 was prepared from Example 72A and (S)-1-Chloro-1-oxopropan-2-yl acetate by the general methods shown for Example 72. HPLC: RT=1.11 min (H$_2$O/ACN with 0.1% TFA, Waters Acquity UPLC BEH C18, 2.1×50 mm, 1.7-μm particles, gradient=3.0 min, wavelength=220 nm); MS (ES): m/z=412.0 [M+H]$^+$; $^1$H NMR (500 MHz, DMSO-d$_6$) δ ppm 9.68 (s, 1H), 8.45 (br. s., 2H), 8.33 (d, J=5.1 Hz, 1H), 8.30 (s, 1H), 8.10 (dd, J=8.5, 4.5 Hz, 1H), 7.98 (d, J=1.7 Hz, 1H), 7.87-7.78 (m, 1H), 7.20 (d, J=4.5 Hz, 1H), 5.96 (d, J=5.2 Hz, 1H), 4.27-4.16 (m, 1H), 3.45 (s, 1H), 1.29 (d, J=6.7 Hz, 3H).

Example 74

N-{4-[6-Chloro-3-(5-fluoropyridin-2-yl)-1H-pyrrolo[3,2-b]pyridin-2-yl]pyridin-2-yl}-2-(morpholin-4-yl)acetamide

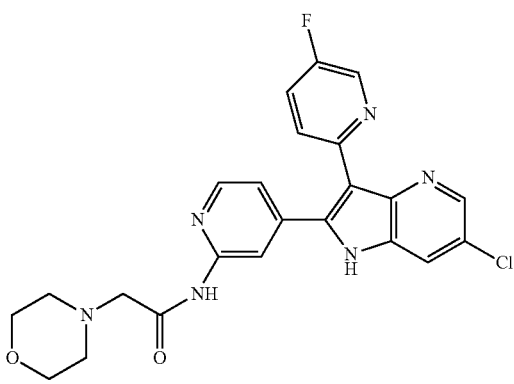 [SMILES: O=C(CN1CCOCC1)Nc1cc(-c2[nH]c3cc(Cl)cnc3c2-c2ccc(F)cn2)ccn1]

74A): 2-Chloro-N-(4-(6-chloro-3-(5-fluoropyridin-2-yl)-1H-pyrrolo[3,2-b]pyridin-2-yl)pyridin-2-yl)acetamide

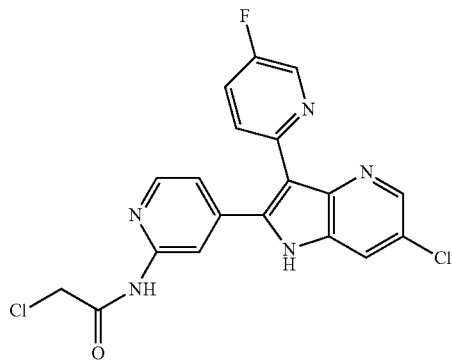 [SMILES: O=C(CCl)Nc1cc(-c2[nH]c3cc(Cl)cnc3c2-c2ccc(F)cn2)ccn1]

To a suspension of Example 72A (115 mg, 0.338 mmol) in DCE (7 mL) were added chloroacetyl chloride (0.14 mL, 1.70 mmol) and TEA (0.25 mL, 1.70 mmol) slowly. The reaction was stirred at room temperature for 1 h. To the reaction mixture was added 1 mL of ammonia hydroxide solution and the mixture was stirred at room temperature for 0.5 h. The reaction mixture was then diluted with CHCl$_3$:2-propanol (2.5:1) and saturated NaHCO$_3$ solution. The organic layer was separated and dried over MgSO$_4$. The mixture was filtered and the filtrate was concentrated in vacuo. To the residue was added DCM and the mixture was filtered to give the desired product (75 mg, 53%). HPLC: RT=1.09 min (H$_2$O/ACN with 0.1% TFA, Waters Acquity BEH C18, 2.0×50 mm, 1.7-µm particles, gradient=1.5 min, wavelength=220 nm); MS (ES): m/z=416.0 [M+H]$^+$; $^1$H NMR (400 MHz, DMSO-d$_6$) δ ppm 10.90 (br. s., 1H), 8.45 (d, J=3.1 Hz, 2H), 8.35 (d, J=5.1 Hz, 1H), 8.26 (s, 1H), 8.12 (dd, J=8.6, 4.6 Hz, 1H), 7.98 (d, J=1.5 Hz, 1H), 7.82 (td, J=8.7, 2.6 Hz, 1H), 7.24 (d, J=4.6 Hz, 1H), 4.34 (s, 2H).

N-{4-[6-Chloro-3-(5-fluoropyridin-2-yl)-1H-pyrrolo[3,2-b]pyridin-2-yl]pyridin-2-yl}-2-(morpholin-4-yl)acetamide

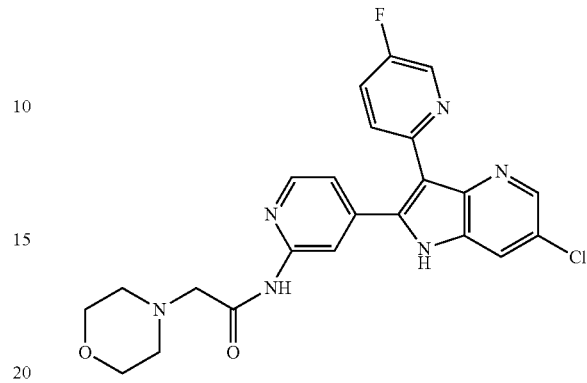

To a mixture of Example 74A (35 mg, 0.084 mmol) in acetonitrile (2 mL) were added morpholine (0.074 mL, 0.841 mmol) and Ag$_2$O (39.0 mg, 0.168 mmol). The reaction mixture was stirred at room temperature for 22 h. The reaction mixture was then diluted with MeOH, and filtered. The filtrate was concentrated in vacuo. The residue was purified by preparative HPLC (Column: Waters XBridge C18, 19×200 mm, 5-µm particles; Mobile Phase A: 5:95 acetonitrile: water with 10 mM ammonium acetate; Mobile Phase B: 95:5 acetonitrile: water with 10-mM ammonium acetate; Gradient: 15-100% B over 20 minutes, then a 5 minute hold at 100% B; Flow: 20 mL/min.). Fractions containing the desired product were combined, concentrated, and lyophilized to give the desired product as a yellow solid (9.1 mg, 23%); HPLC: RT=0.85 min (H$_2$O/ACN with 0.1% TFA, Waters Acquity UPLC BEH C18, 2.1×50 mm, 1.7-µm particles, gradient=3 min, wavelength=220 nm); MS (ES): m/z=467.3 [M+H]$^+$; $^1$H NMR (400 MHz, DMSO-d$_6$) δ ppm 12.37 (s, 1H), 8.44 (br. s., 2H), 8.33 (d, J=5.1 Hz, 1H), 8.25 (s, 1H), 8.07 (dd, J=8.7, 4.5 Hz, 1H), 7.99 (s, 1H), 7.81 (td, J=8.7, 2.8 Hz, 1H), 7.21 (d, J=4.8 Hz, 1H), 3.63 (br. s., 2H), 3.57-3.36 (m, 4H), 2.54 (br. s., 4H).

Example 75

N-{4-[6-Chloro-3-(5-fluoropyridin-2-yl)-1H-pyrrolo[3,2-b]pyridin-2-yl]pyridin-2-yl}-2-[(2-hydroxyethyl)amino]acetamide

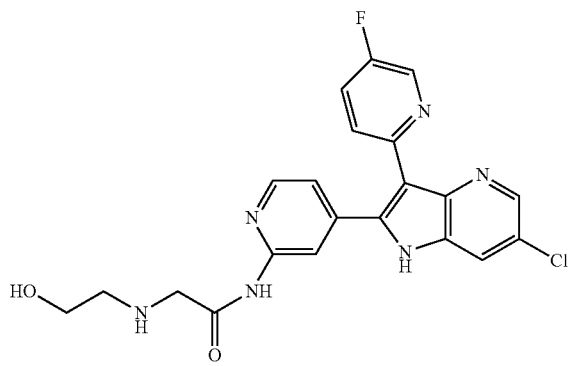 [SMILES: O=C(CNCCO)Nc1cc(-c2[nH]c3cc(Cl)cnc3c2-c2ccc(F)cn2)ccn1]

Example 75 was prepared from Example 74A and 2-aminoethanol by the general methods shown for Example 74. HPLC: RT=1.00 min (H₂O/ACN with 0.1% TFA, Waters Acquity BEH C18, 2.0×50 mm, 1.7-μm particles, gradient=1.5 min, wavelength=220 nm); MS (ES): m/z=441.1 [M+H]⁺; ¹H NMR (400 MHz, MeOH-d₄) δ ppm 8.46 (d, J=2.9 Hz, 1H), 8.37 (d, J=2.0 Hz, 1H), 8.33-8.26 (m, 2H), 7.95 (d, J=2.0 Hz, 1H), 7.84 (dd, J=8.6, 4.6 Hz, 1H), 7.72 (td, J=8.5, 3.0 Hz, 1H), 7.20 (dd, 1.5 Hz, 1H), 3.69 (t, J=5.4 Hz, 2H), 3.48 (s, 2H), 2.80 (t, J=5.4 Hz, 2H).

Example 76

N-(4-(5-Methoxy-3-(6-methoxypyridin-3-yl)-1H-pyrrolo[3,2-b]pyridin-2-yl)pyridin-2-yl)acetamide

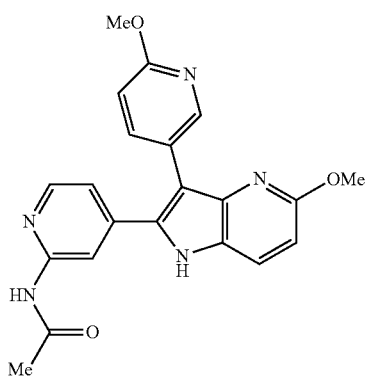 [SMILES: COc1ccc(-c2c(-c3ccnc(NC(C)=O)c3)[nH]c3ccc(OC)nc23)cn1]

76A): N-(4-((3-Amino-6-methoxypyridin-2-yl)ethynyl)pyridin-2-yl)acetamide

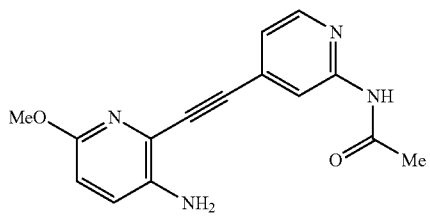 [SMILES: COc1ccc(N)c(C#Cc2ccnc(NC(C)=O)c2)n1]

Example 76A was prepared from Example 1B and 2-bromo-6-methoxypyridin-3-amine following the general procedure for Example 1C. HPLC: RT=0.63 min (H₂O/acetonitrile with 0.1% TFA, Waters Aquity BEH C18, 1.7-μm particles, 2.0×50 mm, gradient=1.5 min, wavelength=220 nm); MS (ES): m/z=283 [M+H]⁺.

76B): N-(2-((2-Acetamidopyridin-4-yl)ethynyl)-6-methoxypyridin-3-yl)-2,2,2-trifluoroacetamide

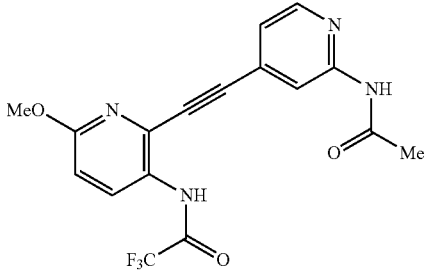 [SMILES: COc1ccc(NC(=O)C(F)(F)F)c(C#Cc2ccnc(NC(C)=O)c2)n1]

To a suspension of Example 76A (80 mg, 0.283 mmol) in Ether:DCM (1:1) (4 mL) was added dropwise a solution of 2,2,2-trifluoroacetic anhydride (0.039 mL, 0.283 mmol) in DCM (1 mL) at −10° C. The reaction mixture was stirred for 30 min at −10° C. to 0° C. The reaction mixture was then diluted with EtOAc, washed with water, and then with saturated aqueous NaCl, dried with MgSO₄ and concentrated to yield Example 76B (90 mg, 0.238 mmol, 84% yield) as an off white solid which was used for the next step without further purification. HPLC: RT=0.69 min (H₂O/acetonitrile with 0.1% TFA, Waters Aquity BEH C18, 1.7-μm particles, 2.0×50 mm, gradient=1.5 min, wavelength=220 nm); m/z=379 [M+H]⁺.

N-(4-(5-Methoxy-3-(6-methoxypyridin-3-yl)-1H-pyrrolo[3,2-b]pyridin-2-yl)pyridin-2-yl)acetamide

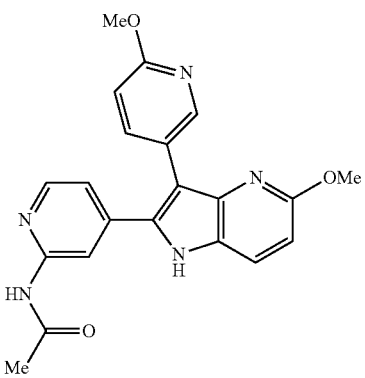 [SMILES: COc1ccc(-c2c(-c3ccnc(NC(C)=O)c3)[nH]c3ccc(OC)nc23)cn1]

Example 76 was prepared from Example 76B and 5-bromo-2-methoxypyridine following the general method for Example 1. HPLC: RT=1.05 min (H₂O/ACN with 0.1% TFA, Waters Acquity UPLC BEH C18, 2.1×50 mm, 1.7-μm particles, gradient=3 min, wavelength=220 nm); MS (ES): m/z=390 [M+H]⁺; ¹H NMR (500 MHz, DMSO-d₆) δ ppm 11.89 (s, 1H), 10.60 (s, 1H), 8.34 (d, J=2.0 Hz, 1H), 8.31-8.23 (m, 2H), 7.95 (s, 1H), 7.80 (d, J=8.8 Hz, 1H), 7.76 (dd, J=8.6, 2.2 Hz, 1H), 7.07 (d, J=4.4 Hz, 1H), 6.84 (d, J=8.8 Hz, 1H), 6.70 (d, J=8.8 Hz, 1H), 3.90-3.86 (m, 3H), 3.85 (s, 3H), 2.09 (s, 3H).

Example 77

N-(4-(5-Methoxy-3-(6-methoxypyridin-3-yl)-1H-pyrrolo[3,2-b]pyridin-2-yl)pyridin-2-yl)acetamide

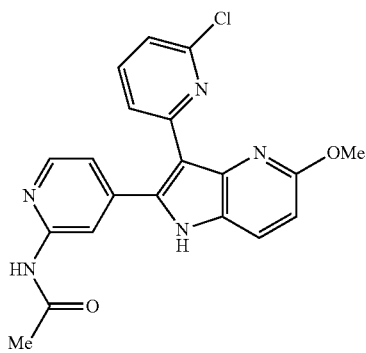 [SMILES: COc1ccc2[nH]c(-c3ccnc(NC(C)=O)c3)c(-c3cccc(Cl)n3)c2n1]

Example 77 was prepared from Example 76B and 2-bromo-6-chloropyridine following the general method for example 1. HPLC: RT=1.21 min (H₂O/ACN with 0.1% TFA, Waters Acquity UPLC BEH C18, 2.1×50 mm, 1.7-μm particles, gradient=3 min, wavelength=220 nm); MS (ES): m/z=394 [M+H]⁺; ¹H NMR (500 MHz, DMSO-d₆) δ ppm 12.14 (s, 1H), 10.66 (s, 1H), 8.34 (d, J=7.7 Hz, 1H), 8.31 (d, J=5.4 Hz, 1H), 8.20 (s, 1H), 7.91 (t, J=7.7 Hz, 1H), 7.83 (d, J=8.8 Hz, 1H), 7.29 (d, J=7.7 Hz, 1H), 7.23 (d, J=4.4 Hz, 1H), 6.75 (d, J=8.8 Hz, 1H), 3.92 (s, 3H), 2.10 (s, 3H).

Example 78

N-(4-(6-Cyano-3-(6-methoxypyridin-3-yl)-1H-pyrrolo[3,2-b]pyridin-2-yl)pyridin-2-yl)acetamide

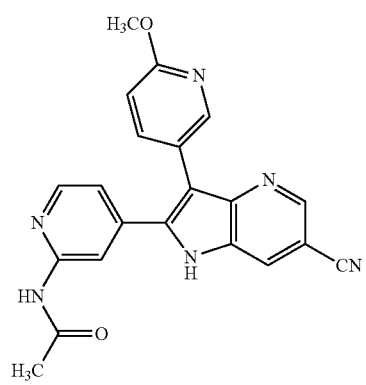 [SMILES: COc1ccc(-c2c(-c3ccnc(NC(C)=O)c3)[nH]c3cc(C#N)cnc23)cn1]

78A): N-(4-((3-Amino-5-bromopyridin-2-yl)ethynyl)pyridin-2-yl)acetamide

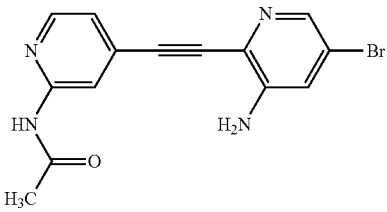 [SMILES: CC(=O)Nc1cc(C#Cc2ncc(Br)cc2N)ccn1]

A mixture of 2,5-dibromopyridin-3-amine (2.16 g, 8.57 mmol, from Combi-Blocks, Inc.), N-(4-ethynylpyridin-2-yl)acetamide (1.373 g, 8.57 mmol), copper(I) iodide (0.082 g, 0.429 mmol) in Et₃N (20 mL, 143 mmol) and DMF (30 mL) was purged with N₂. The resulting mixture was treated with bis(triphenylphosphine)palladium(II) dichloride (0.060 g, 0.086 mmol), purged with N₂ and heated at 75° C. for 90 min. The reaction mixture was concentrated in vacuo. To the residue was added 20 mL of iPrOH, the mixture was sonicated and the solid was filtered and washed with iPrOH. The resulting solid was triturated with CH₂Cl₂ and collected by filtration. The filtrate was concentrated and the residue was triturated with CH₂Cl₂ to obtain a second crop of the title compound. Both solids were combined to obtain 2 g of yellow solid. The filtrate was further concentrated in vacuo and the residue was purified by column chromatography on SiO₂ (gradient hexane/EtOAc) to obtain 640 mg of the title compound, total 2.64 g (93% yield) as a yellow solid. MS (ES): m/z=331, 333 [M+H]⁺; ¹H NMR (500 MHz, DMSO-d₆) 10.62 (s, 1H), 8.35 (d, J=5.0 Hz, 1H), 8.23 (s, 1H), 7.86 (d, J=1.7 Hz, 1H), 7.37-7.33 (m, 2H), 6.13 (s, 1H), 2.11 (s, 3H).

78B): N-(4-((3-Amino-5-cyanopyridin-2-yl)ethynyl)pyridin-2-yl)acetamide

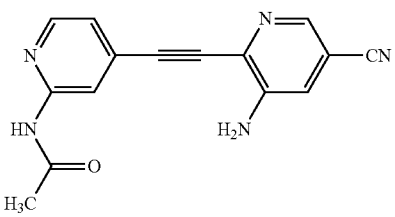 [SMILES: CC(=O)Nc1cc(C#Cc2ncc(C#N)cc2N)ccn1]

A mixture of Example 78A (300 mg, 0.91 mmol) and Zn(CN)₂ (106 mg, 0.91 mmol) in DMF (10 mL) and water (0.5 mL) was purged with N₂, and treated with PdCl₂ (dppf) (60 mg, 0.082 mmol) and Pd₂dba₃ (80 mg, 0.087 mmol). The mixture was again purged with N₂ and heated at 85° C. for 6 h. The reaction mixture was partially concentrated in vacuo and the residue was passed through a column of SiO₂ (gradient CH₂Cl₂ to 10% MeOH in CH₂Cl₂) to obtain the title compound (135 mg, 0.487 mmol, 54% yield) as a yellow solid. MS (ES): m/z=278 [M+H]⁺; ¹H NMR (400 MHz, METHANOL-d₄) δ 8.33 (br. s., 1H), 8.09 (d, J=1.5 Hz, 1H), 8.05 (br. s., 1H), 7.47 (d, J=1.5 Hz, 1H), 7.46-7.43 (m, 1H), 2.24 (br. s., 3H).

101

78C): N-(4-(6-Cyano-1H-pyrrolo[3,2-b]pyridin-2-yl)pyridin-2-yl)acetamide

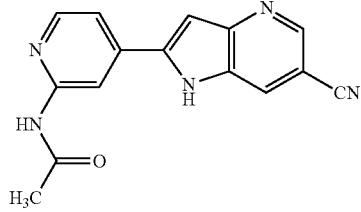 [SMILES: CC(=O)Nc1cc(-c2cc3ncc(C#N)cc3[nH]2)ccn1]

A mixture of Example 78B (530 mg, 1.911 mmol), Cs₂CO₃ (685 mg, 2.103 mmol) and Pd(Ph₃P)₄ (110 mg, 0.096 mmol) in 12 mL DMF was purged with N₂ and the mixture was heated 150° C. for 20 minutes, and then cooled to room temperature. The reaction mixture was partially concentrated in vacuo, and the residue was mixed with 15 mL CH₂Cl₂ and 3 mL water. The solid was filtered and dried to obtain the title compound (350 mg, 1.262 mmol, 66.0% yield) as a light yellow solid. MS (ES): m/z=278 [M+H]⁺; ¹H NMR (400 MHz, METHANOL-d₄) δ 8.63 (d, J=1.8 Hz, 1H), 8.57 (s, 1H), 8.42 (d, J=5.3 Hz, 1H), 8.23 (s, 1H), 7.61 (m, 1H), 7.28 (s, 1H), 2.23 (s, 3H).

78D): N-(4-(6-Cyano-3-iodo-1H-pyrrolo[3,2-b]pyridin-2-yl)pyridin-2-yl)acetamide

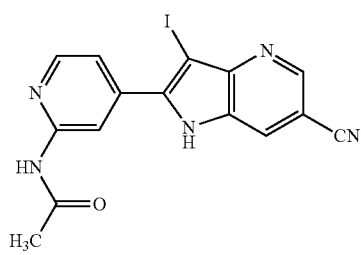 [SMILES: CC(=O)Nc1cc(-c2[nH]c3cc(C#N)cnc3c2I)ccn1]

To a solution of Example 78C (600 mg, 2.164 mmol) in DMF (15 mL) was added N-iodosuccinimde (487 mg, 2.164 mmol) and the mixture was stirred at room temperature for 1 h. The reaction mixture was partially concentrated in vacuo, and the residue was triturated with water and the solid was filtered to obtain the title compound (620 mg, 1.538 mmol, 71.1% yield) as a light brown solid. MS (ES): m/z=403.9 [M+H]⁺; ¹H NMR (400 MHz, DMSO-d₆) δ 12.98 (s, 1H), 10.72 (s, 1H), 8.78 (d, J=1.8 Hz, 1H), 8.69 (s, 1H), 8.52 (d, J=5.1 Hz, 1H), 8.37 (d, J=2.0 Hz, 1H), 7.66-7.56 (m, 1H), 2.15 (s, 3H).

102

N-(4-(6-Cyano-3-(6-methoxypyridin-3-yl)-1H-pyrrolo[3,2-b]pyridin-2-yl)pyridin-2-yl)acetamide

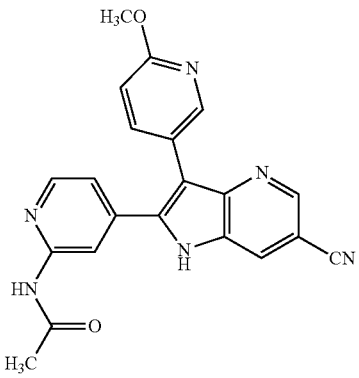 [SMILES: COc1ccc(-c2c(-c3ccnc(NC(C)=O)c3)[nH]c3cc(C#N)cnc23)cn1]

A mixture of Example 78D (35 mg, 0.087 mmol), 2-methoxy-5-(4,4,5,5-tetramethyl-1,3,2-dioxaborolan-2-yl)pyridine (30.6 mg, 0.130 mmol) and 0.2 mL 3M K₃PO₄ in DMF (2 mL) was purged with N₂. The mixture was treated with PdCl₂(dppf) (25.4 mg, 0.035 mmol), purged with N₂ and heated at 80° C. for 60 min. The reaction mixture was concentrated to a volume of 1 mL and 3 mL MeOH was added. The resulting solid was filtered and the filtrate was purified by preparative HPLC (Sunfire C-18 19×150 mm, eluting with 5%-100% aqueous CH₃CN containing 1% TFA gradient over 12 min, 20 mL/min, wavelength=254 nm) to obtain the title compound (27 mg, 56%). HPLC: RT=0.68 min (H₂O/ACN with 0.1% TFA, Waters Acquity UPLC BEH C18, 2.1×50 mm, 1.7-μm particles, gradient=3 min, wavelength=220 nm). MS (ES): m/z=385 [M+H]⁺; ¹H NMR (500 MHz, DMSO-d₆) δ 10.65 (s, 1H), 8.74 (d, J=2.0 Hz, 1H), 8.40 (d, J=2.0 Hz, 1H), 8.38-8.34 (m, 2H), 8.23 (dd, J=2.4, 0.6 Hz, 1H), 7.77 (dd, J=8.5, 2.4 Hz, 1H), 7.15 (dd, J=5.2, 1.7 Hz, 1H), 6.88 (dd, J=8.5, 0.8 Hz, 1H), 3.89 (s, 3H), 2.10 (s, 3H).

Example 79

N-(4-(6-(Aminomethyl)-3-(6-methoxypyridin-3-yl)-1H-pyrrolo[3,2-b]pyridin-2-yl)pyridin-2-yl)acetamide

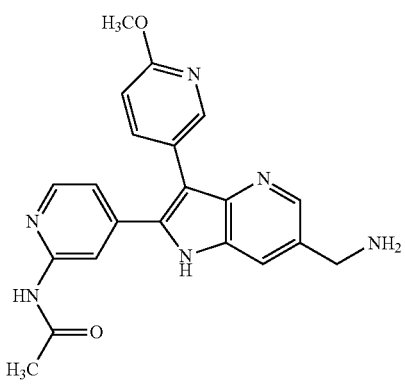 [SMILES: COc1ccc(-c2c(-c3ccnc(NC(C)=O)c3)[nH]c3cc(CN)cnc23)cn1]

A mixture of Example 78 (50 mg, 0.130 mmol) and 20% Pd(OH)₂ on carbon (10 mg) in MeOH (12 mL) was stirred under 1 atm of H₂ at room temperature. After 4 h additional 20% Pd(OH)₂ on carbon (20 mg) was added and stirring was continued under 1 atm H2. After 7 h, the solid was filtered and the filtrate was partially concentrated and the residue was purified by preparative HPLC (Sunfire C-18 19×150 mm, eluting with 10% aqueous CH₃CN to 60% aqueous CH₃CN containing 5 mmol NH₄OAc gradient over 8 min, 20 mL/min, wavelength=254 nm) to obtain the title compound (13 mg, 0.032 mmol, 24.44% yield) as a light yellow solid. HPLC: RT=0.49 min (H₂O/ACN with 0.1% TFA, Waters Acquity UPLC BEH C18, 2.1×50 mm, 1.7-μm particles, gradient=3 min, wavelength=220 nm); MS (ES): m/z=389 [M+H]⁺; ¹H NMR (400 MHz, METHANOL-d₄) δ 8.45 (s, 1H), 8.30 (s, 1H), 8.26 (d, J=5.1 Hz, 1H), 8.17 (d, J=1.8 Hz, 1H), 8.05 (s, 1H), 7.76 (dd, J=8.6, 2.2 Hz, 1H), 7.15-7.11 (m, 1H), 6.88 (d, J=8.4 Hz, 1H), 4.29 (s, 2H), 3.95 (s, 3H), 2.16 (s, 3H).

Example 80 and Example 81 were prepared following similar procedures as described in Examples 78 and 79.

Example 80

N-(4-(7-Cyano-3-(6-methoxypyridin-3-yl)-1H-pyrrolo[3,2-b]pyridin-2-yl)pyridin-2-yl)acetamide

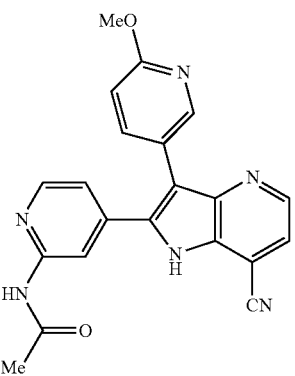 [SMILES: COc1ccc(-c2c(-c3ccnc(NC(C)=O)c3)[nH]c3c(C#N)ccnc23)cn1]

HPLC: RT=0.68 min (H₂O/ACN with 0.1% TFA, Waters Acquity UPLC BEH C18, 2.1×50 mm, 1.7-μm particles, gradient=3 min, wavelength=220 nm); MS (ES): m/z=385 [M+H]⁺; ¹H NMR (400 MHz, METHANOL-d₄) δ 8.60 (d, J=5.1 Hz, 1H), 8.37 (d, J=5.9 Hz, 1H), 8.30-8.28 (m, 1H), 7.96-7.91 (m, 2H), 7.71 (d, J=5.1 Hz, 1H), 7.47 (dd, J=5.7, 1.3 Hz, 1H), 7.03 (dd, J=8.7, 0.6 Hz, 1H), 4.01 (s, 3H), 2.23 (s, 3H).

Example 81

N-(4-(7-(Aminomethyl)-3-(6-methoxypyridin-3-yl)-1H-pyrrolo[3,2-b]pyridin-2-yl)pyridin-2-yl)acetamide

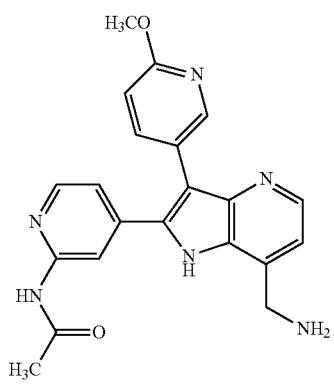 [SMILES: COc1ccc(-c2c(-c3ccnc(NC(C)=O)c3)[nH]c3c(CN)ccnc23)cn1]

HPLC: RT=0.50 min (H₂O/ACN with 0.1% TFA, Waters Acquity UPLC BEH C18, 2.1×50 mm, 1.7-μm particles, gradient=3 min, wavelength=220 nm); MS (ES): m/z=389 [M+H]⁺; ¹H NMR (500 MHz, DMSO-d₆) δ 10.61 (s, 1H), 8.45 (d, J=4.7 Hz, 1H), 8.37-8.33 (m, 2H), 8.24 (d, J=1.7 Hz, 1H), 7.78 (dd, J=8.5, 2.3 Hz, 1H), 7.32 (d, J=4.7 Hz, 1H), 7.14 (dd, J=5.1, 1.6 Hz, 1H), 6.86 (d, J=8.5 Hz, 1H), 4.39 (s, 2H), 3.87 (s, 3H), 2.10 (s, 3H).

Example 82

4-[6-Chloro-3-(5-fluoropyridin-2-yl)-1H-pyrrolo[3,2-b]pyridin-2-yl]-N-methylpyridin-2-amine

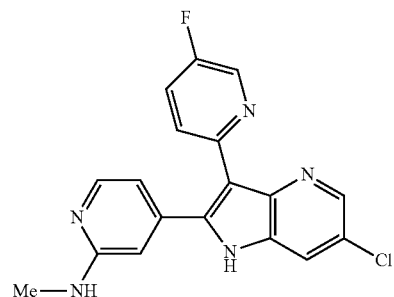 [SMILES: CNc1cc(-c2[nH]c3cc(Cl)cnc3c2-c2ccc(F)cn2)ccn1]

82A): N-(4-(6-Chloro-3-(5-fluoropyridin-2-yl)-1-tosyl-1H-pyrrolo[3,2-b]pyridin-2-yl)pyridin-2-yl)acetamide 82B): N-(4-(6-Chloro-3-(5-fluoropyridin-2-yl)-1-tosyl-1H-pyrrolo[3,2-b]pyridin-2-yl)pyridin-2-yl)-N-methylacetamide

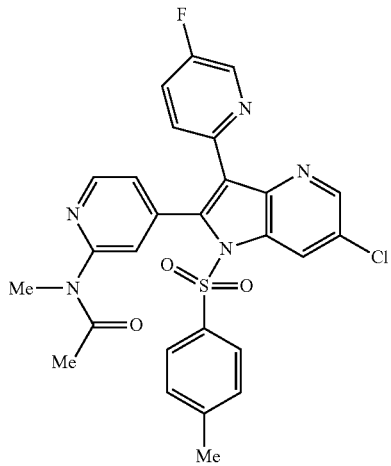

To a suspension of Example 82A (50 mg, 0.093 mmol) in THF (1 mL) was added methyl iodide (0.017 mL, 0.280 mmol) in DMF (0.6 mL) and $Cs_2CO_3$ (61 mg, 0.187 mmol). The reaction mixture was stirred at room temperature for 2 h. The reaction mixture was then diluted with ethyl acetate and saturated $NaHCO_3$ solution. The organic layer was separated and dried over $MgSO_4$ and filtered. The filtrate was concentrated in vacuo to give the desired product, which was used in the next step without purification. HPLC: RT=1.43 min ($H_2O$/ACN with 0.1% TFA, Waters Acquity BEH C18, 2.0×50 mm, 1.7-μm particles, gradient=1.5 min, wavelength=220 nm); MS (ES): m/z=550.3 $[M+H]^+$.

Example 82): 4-[6-Chloro-3-(5-fluoropyridin-2-yl)-1H-pyrrolo[3,2-b]pyridin-2-yl]-N-methylpyridin-2-amine

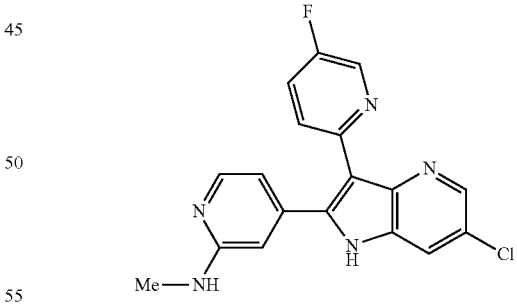

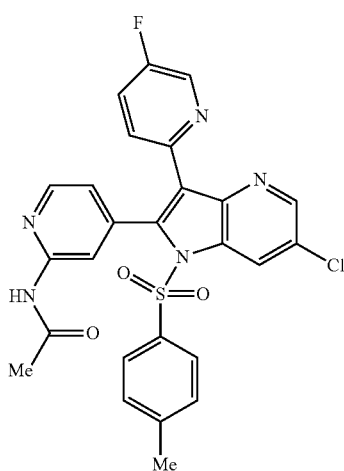 [SMILES: CC(=O)Nc1cc(-c2c(-c3ccc(F)cn3)c3ncc(Cl)cc3n2S(=O)(=O)c2ccc(C)cc2)ccn1]

To a solution of Example 72A (0.45 g, 1.18 mmol) in DMF (8 mL) were added $Cs_2CO_3$ (0.85 g, 2.59 mmol) and p-toluenesulfonyl chloride (0.22 mL, 1.18 mmol). The reaction mixture was stirred at room temperature over night. To the reaction mixture was added ethyl acetate and a saturated $NaHCO_3$ solution. The organic layer was extracted with ethyl acetate (2×) and the combined organic layers were washed with saturated $NaHCO_3$ solution, dried over $MgSO_4$ and filtered. The filtrate was concentrated in vacuo. The residue was purified by silica gel flash chromatography, eluting with 0-10% MeOH in DCM to give the desired product as a yellow solid (0.16 g, 25.3%); HPLC: RT=1.30 min ($H_2O$/ACN with 0.1% TFA, Waters Acquity BEH C18, 2.0×50 mm, 1.7-μm particles, gradient=1.5 min, wavelength=220 nm); MS (ES): m/z=536.3 $[M+H]^+$; $^1H$ NMR (400 MHz, $CDCl_3$) δ ppm 8.68 (d, J=2.2 Hz, 1H), 8.61 (d, J=2.2 Hz, 1H), 8.33 (d, J=3.1 Hz, 1H), 8.30 (dd, J=5.1, 0.7 Hz, 1H), 7.99 (s, 1H), 7.62 (dd, J=8.5, 4.3 Hz, 1H), 7.45 (d, J=8.6 Hz, 2H), 7.36-7.29 (m, 1H), 7.20 (d, J=7.9 Hz, 2H), 7.13 (dd, 1.4 Hz, 1H), 2.37 (s, 3H), 2.20 (s, 3H).

To a solution of crude Example 82B (30 mg, 0.055 mmol) in MeOH (2 mL) was added an aqueous LiOH solution (0.55 mL, 1.10 mmol). The reaction mixture was then heated at 85° C. for 2 h. The reaction mixture was concentrated in vacuo and the residue was dissolved in DMF and purified by preparative HPLC (Sunfire C-18 19×150 mm, eluting with 10%-100% aqueous $CH_3CN$ containing 5 mmol $NH_4OAc$ over 12 min, 20 mL/min, wavelength=220 nm). Fractions containing the desired product were combined, concentrated, and lyophilized to give the desired product as a yellow solid (11 mg, 55%); HPLC: RT=0.67 min ($H_2O$/

ACN with 0.05% TFA, Waters Acquity SDS BEH C18, 2.1×50 mm, 1.7-μm particles, gradient=1.8 min, wavelength=220 nm); MS (ES): m/z=354.0 [M+H]+; 1H NMR (400 MHz, DMSO-d6) δ ppm 8.51 (d, =3.1 Hz, 1H), 8.38 (d, J=2.2 Hz, 1H), 8.05-7.95 (m, 2H), 7.90 (d, J=2.2 Hz, 1H), 7.79 (td, J=8.7, 3.0 Hz, 1H), 6.59 (s, 1H), 6.56-6.48 (m, 2H), 2.75 (d, J=4.8 Hz, 3H).

Example 83

N-{4-[6-Bromo-3-(5-methoxypyridin-2-yl)-1H-pyrrolo[3,2-b]pyridin-2-yl]pyridin-2-yl}acetamide

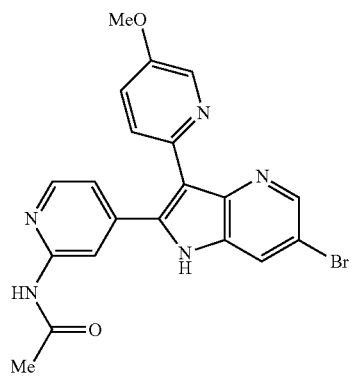 [SMILES: COc1ccc(-c2c(-c3ccnc(NC(C)=O)c3)[nH]c3cc(Br)cnc23)nc1]

83A): N-(4-((3-Amino-5-bromopyridin-2-yl)ethynyl)pyridin-2-yl)acetamide

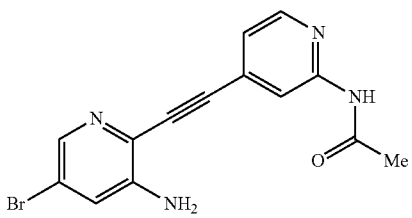 [SMILES: CC(=O)Nc1cc(C#Cc2ncc(Br)cc2N)ccn1]

Example 83A was prepared from Example 1B and 2,5-dibromopyridin-3-amine by methods similar to those shown for Example 1C. HPLC: RT=1.43 min (H2O/MeOH with 0.1% TFA, Chromolith SpeedROD, 4.6×50 mm, gradient=4 min, wavelength=220 nm); MS (ES): m/z=331 [M+H]+; 1H NMR (400 MHz, DMSO-d6) δ 10.61 (s, 1H), 8.36 (dd, J=5.1, 0.7 Hz, 1H), 8.24 (s, 1H), 7.87 (d, J=2.0 Hz, 1H), 7.37-7.34 (m, 2H), 3.31 (s, 2H), 2.12 (s, 3H).

83B): N-(2-((2-Acetamidopyridin-4-yl)ethynyl)-5-bromopyridin-3-yl)-2,2,2-trifluoroacetamide

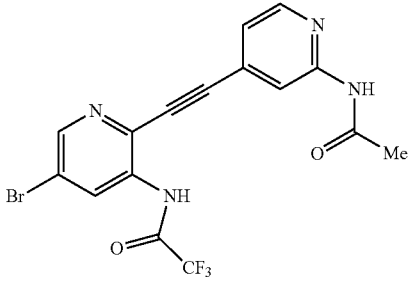 [SMILES: CC(=O)Nc1cc(C#Cc2ncc(Br)cc2NC(=O)C(F)(F)F)ccn1]

Example 83B was prepared from Example 83A by methods similar to those shown for Example 1D. HPLC: RT=1.85 min (H2O/MeOH with 0.1% TFA, Chromolith SpeedROD, 4.6×50 mm, gradient=4 min, wavelength=220 nm); MS (ES): m/z=427 [M+H]+, 1H NMR (400 MHz, DMSO-d) δ ppm 11.72 (s, 1H), 10.68 (s, 1H), 8.79 (d, J=2.0 Hz, 1H), 8.41 (dd, J=5.1, 0.9 Hz, 1H), 8.36 (d, J=2.2 Hz, 1H), 8.25 (s, 1H), 7.19 (dd, J=5.1, 1.5 Hz, 1H), 2.12 (s, 3H).

Example 83): N-{4-[6-Bromo-3-(5-methoxypyridin-2-yl)-1H-pyrrolo[3,2-b]pyridin-2-yl]pyridin-2-yl}acetamide

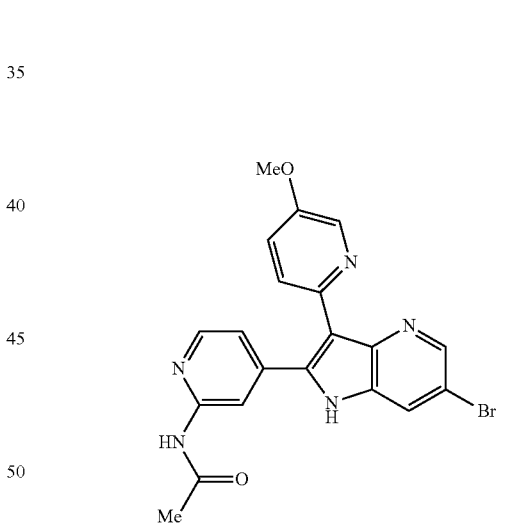

Example 83 was prepared from Example 83B and 2-bromo-5-methoxypyridine by the general methods shown for Example 1. HPLC: RT=0.91 min (H2O/ACN with 0.1% TFA, Waters Acquity UPLC BEH C18, 2.1×50 mm, 1.7-μm particles, gradient=3 min, wavelength=220 nm); MS (ES): m/z=438 [M+H]+; 1H NMR (500 MHz, DMSO-d6) δ ppm 12.20 (s, 1H), 10.56 (s, 1H), 8.49 (s, 1H), 8.35-8.25 (m, 2H), 8.20 (d, J=2.5 Hz, 1H), 8.08 (s, 1H), 7.93 (d, J=8.7 Hz, 1H), 7.50 (dd, J=8.6, 2.7 Hz, 1H), 7.13 (d, J=4.9 Hz, 1H), 3.86 (s, 3H), 2.10 (s, 3H).

Example 84

Methyl N-{4-[3-(6-methoxypyridin-3-yl)-1H-pyrrolo[3,2-b]pyridin-2-yl]pyridin-2-yl}carbamate

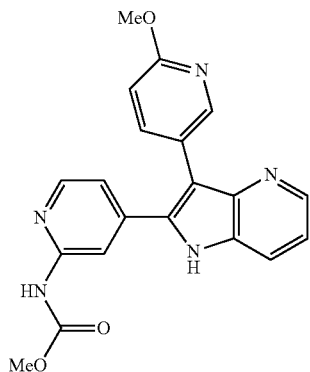 [SMILES: COC(=O)Nc1cc(-c2[nH]c3cccnc3c2-c2ccc(OC)nc2)ccn1]

To a suspension of Example 52 (28.8 mg, 0.091 mmol) in CH$_2$Cl$_2$ (2 mL) was added TEA (0.038 mL, 0.272 mmol) and methyl chloroformate (0.014 mL, 0.182 mmol). The mixture was stirred at room temperature overnight, and then MeOH (1 mL) and concentrated NH$_4$OH (1 drop) were added. The resulting reaction mixture was stirred at room temperature overnight. The mixture was then concentrated, diluted with DMF, and purified by preparative HPLC (Column: Waters XBridge C18, 19×200 mm, 5-μm particles; Mobile Phase A: 5:95 acetonitrile: water with 10 mM ammonium acetate; Mobile Phase B: 95:5 acetonitrile: water with 10-mM ammonium acetate; Gradient: 10-50% B over 20 minutes, then a 5-minute hold at 100% B; Flow: 20 mL/min.) to give Example 84 (10.5 mg, 31%). HPLC: RT=0.73 min (H$_2$O/ACN with 0.1% TFA, Waters Acquity UPLC BEH C18, 2.1×50 mm, 1.7-μm particles, gradient=3 min, wavelength=220 nm); MS (ES): m/z=376 [M+H]$^+$; $^1$H NMR (500 MHz, DMSO-d$_6$) δ ppm 12.07 (br. s., 1H), 10.33 (s, 1H), 8.42 (d, J=4.1 Hz, 1H), 8.34-8.17 (m, 2H), 8.08 (s, 1H), 7.94-7.71 (m, 2H), 7.27 (dd, 4.5 Hz, 1H), 7.10 (d, J=5.0 Hz, 1H), 6.89 (d, J=8.4 Hz, 1H), 3.89 (s, 3H), 3.66 (s, 2H).

Example 85

Methyl N-{4-[6-chloro-3-(5-fluoropyridin-2-yl)-1H-pyrrolo[3,2-b]pyridin-2-yl]pyridin-2-yl}carbamate

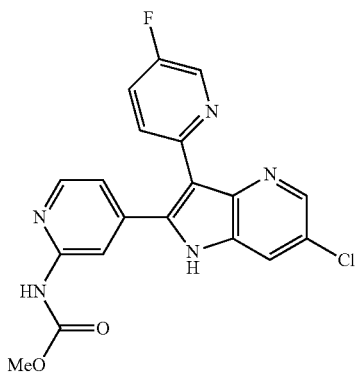 [SMILES: COC(=O)Nc1cc(-c2[nH]c3cc(Cl)cnc3c2-c2ccc(F)cn2)ccn1]

To a suspension of Example 72A (68 mg, 0.20 mmol) in DCE (3 mL) were added methyl chloroformate (0.04 mL, 0.52 mmol) and 4-methylmorpholine (0.13 mL, 1.20 mmol). The reaction mixture was stirred at room temperature for 1 h. Additional methyl chloroformate (0.04 mL, 0.52 mmol) and 4-methylmorpholine (0.13 mL, 1.201 mmol) was added to the reaction mixture. The reaction mixture was stirred at room temperature for another 0.5 h. To the mixture was added ammonium hydroxide (0.6 mL) and MeOH (3 mL). The resulting mixture was stirred at room temperature for 20 h. The reaction mixture was then diluted with a saturated NaHCO$_3$ solution and CHCl$_3$: 2-propanol (2.5:1). The layers were separated and the aqueous layer was extracted with CHCl$_3$: 2-propanol (2.5:1). The combined organic layers were dried over MgSO$_4$ and filtered. The filtrate was concentrated in vacuo to give a yellow solid. To the extract was added DCM, the mixture was sonicated and then filtered to give the desired product as a yellow solid (35 mg, 42%). HPLC: RT=0.72 min (H$_2$O/ACN with 0.05% TFA, Waters Acquity SDS BEH C18, 2.1×50 mm, 1.7-μm particles, gradient=1.8 min, wavelength=220 nm); MS (ES): m/z=397.9 [M+H]$^+$; $^1$H NMR (400 MHz, DMSO-d$_6$) δ ppm 12.31 (s, 1H), 10.25 (s, 1H), 8.46 (dd, J=6.2, 2.6 Hz, 2H), 8.28 (d, J=5.3 Hz, 1H), 8.11 (dd, J=8.8, 4.6 Hz, 1H), 8.02 (s, 1H), 7.97 (d, J=2.2 Hz, 1H), 7.83 (td, J=8.8, 2.9 Hz, 1H), 7.13 (dd, 1.3 Hz, 1H), 3.68-3.63 (m, 3H).

Example 86

4-[6-Chloro-3-(5-methoxypyridin-2-yl)-1H-pyrrolo[3,2-b]pyridin-2-yl]pyridin-2-amine

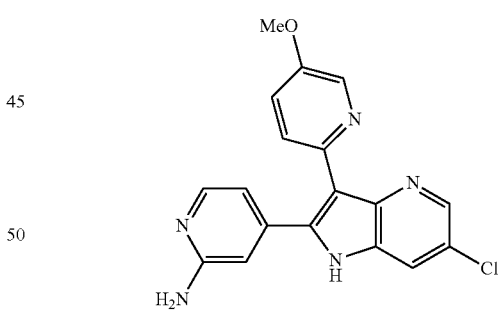

Example 86 was prepared from Example 47 by the general methods shown for Example 52. HPLC: RT=0.86 min (H$_2$O/ACN with 0.1% TFA, Waters Acquity BEH C18, 2.0×50 mm, 1.7-μm particles, gradient=1.5 min, wavelength=220 nm); MS (ES): m/z=352.2 [M+H]$^+$; $^1$H NMR (500 MHz, DMSO-d$_6$) δ ppm 8.37 (d, J=2.2 Hz, 1H), 8.24 (d, J=2.6 Hz, 1H), 7.95-7.78 (m, 3H), 7.47 (dd, J=8.8, 3.1 Hz, 1H), 6.62 (s, 1H), 6.53 (dd, J=5.3, 1.5 Hz, 1H), 5.97 (s, 2H), 3.86 (s, 3H).

Example 87

Methyl N-{4-[6-chloro-3-(5-methoxypyridin-2-yl)-1H-pyrrolo[3,2-b]pyridin-2-yl]pyridin-2-yl}carbamate

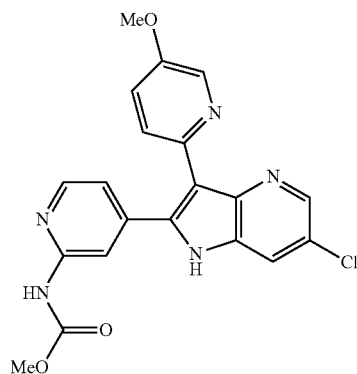 [SMILES: COC(=O)Nc1cc(-c2[nH]c3cc(Cl)cnc3c2-c2ccc(OC)cn2)ccn1]

Example 87 was prepared from Example 86 by the general methods shown for Example 85. HPLC: RT=0.98 min (H$_2$O/ACN with 0.1% TFA, Waters Acquity UPLC BEH C18, 2.1×50 mm, 1.7-μm particles, gradient=3 min, wavelength=220 nm); MS (ES): m/z=410.0 [M+H]$^+$; $^1$H NMR (500 MHz, DMSO-d$_6$) δ ppm 10.25 (s, 1H), 8.42 (d, J=1.9 Hz, 1H), 8.24 (d, J=5.1 Hz, 1H), 8.21 (d, J=2.8 Hz, 1H), 8.04 (s, 1H), 7.95 (d, J=1.9 Hz, 1H), 7.92 (d, J=8.6 Hz, 1H), 7.50 (dd, J=8.7, 2.9 Hz, 1H), 7.09 (d, J=5.1 Hz, 1H), 3.85 (s, 3H), 3.65 (s, 3H).

Example 88

N-{4-[6-Chloro-3-(5-fluoropyridin-2-yl)-1H-pyrrolo[3,2-b]pyridin-2-yl]pyridin-2-yl}-2-(4-methylpiperazin-1-yl)acetamide

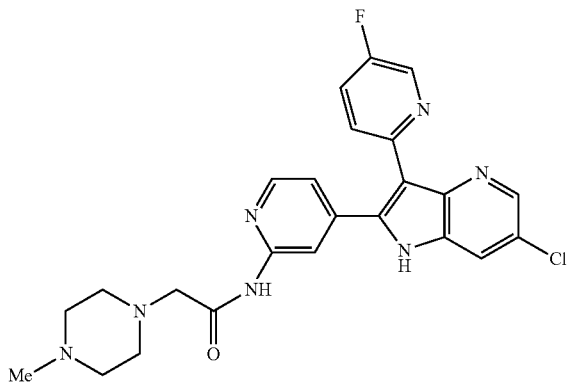

Example 88 was prepared from 74A and 1-methylpiperazine by the general methods shown for Example 74. HPLC: RT=0.85 min (H$_2$O/ACN with 0.1% TFA, Waters Acquity UPLC BEH C18, 2.1×50 mm, 1.7-μm particles, gradient=3 min, wavelength=220 nm); MS (ES): m/z=480.1 [M+H]$^+$; $^1$H NMR (500 MHz, DMSO-d$_6$) δ ppm 10.06 (br. s., 1H), 8.45 (br. s., 2H), 8.34 (d, J=5.1 Hz, 1H), 8.28 (s, 1H), 8.10 (dd, J=8.8, 4.5 Hz, 1H), 7.98 (d, J=1.9 Hz, 1H), 7.83 (td, J=8.8, 2.9 Hz, 1H), 7.22 (d, J=5.0 Hz, 1H), 2.63-2.51 (m., 10H), 2.39 (br. s, 3H).

Example 89

N-{4-[6-Chloro-3-(5-fluoropyridin-2-yl)-1H-pyrrolo[3,2-b]pyridin-2-yl]pyridin-2-yl}-2-{[3-(morpholin-4-yl)propyl]amino}acetamide

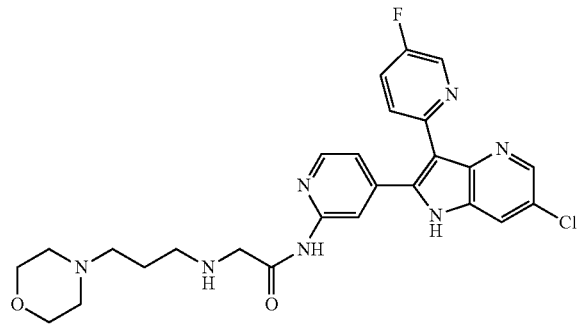 [SMILES: O=C(CNCCCN1CCOCC1)Nc1cc(-c2[nH]c3cc(Cl)cnc3c2-c2ccc(F)cn2)ccn1]

Example 89 was prepared from 74A and 3-morpholinopropan-1-amine by the general methods shown for Example 74. HPLC: RT=0.82 min (H$_2$O/ACN with 0.1% TFA, Waters Acquity UPLC BEH C18, 2.1×50 mm, 1.7-μm particles, gradient=3 min, wavelength=220 nm); MS (ES): m/z=524.1 [M+H]$^+$; $^1$H NMR (500 MHz, DMSO-d$_6$) δ ppm 8.45 (br. s., 2H), 8.37-8.26 (m, 2H), 8.11 (dd, J=8.5, 4.5 Hz, 1H), 7.98 (s, 1H), 7.87-7.76 (m, 1H), 7.20 (d, J=5.0 Hz, 1H), 3.54-3.4 (br. s., 6H), 3.29 (br. s., 4H), 2.32 (t, J=6.8 Hz, 2H), 1.90 (s, 2H), 1.58 (t, J=6.9 Hz, 2H).

Example 90

N-{4-[6-Chloro-3-(5-fluoropyridin-2-yl)-1H-pyrrolo[3,2-b]pyridin-2-yl]pyridin-2-yl}-2-{[2-(morpholin-4-yl)ethyl]amino}acetamide

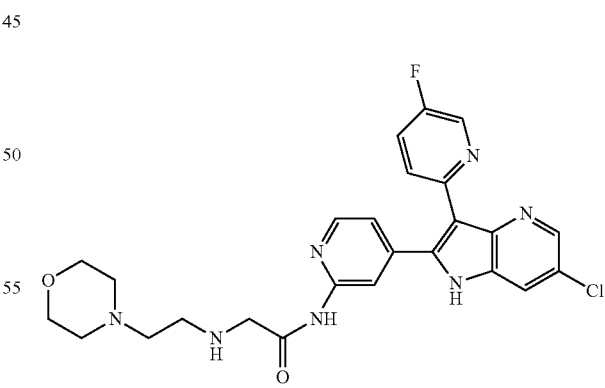

Example 90 was prepared from 74A and 2-morpholinoethanamine by the general methods shown for Example 74. HPLC: RT=0.82 min (H$_2$O/ACN with 0.1% TFA, Waters Acquity UPLC BEH C18, 2.1×50 mm, 1.7-μm particles, gradient=3 min, wavelength=220 nm); MS (ES): m/z=510.1 [M+H]$^+$; $^1$H NMR (500 MHz, DMSO-d$_6$) δ ppm 12.47 (s, 1H), 8.55-8.39 (m, 3H), 8.27-8.12 (m, 2H), 8.01 (s, 1H), 7.89-7.77 (m, 1H), 7.35 (d, J=4.9 Hz, 1H), 4.29-3.59 (m, 2H), 3.45-2.80 (m, 4H), 2.54 (br.s, 8H).

Example 91

N-{4-[6-Methanesulfonyl-3-(5-methoxypyridin-2-yl)-1H-pyrrolo[3,2-b]pyridin-2-yl]pyridin-2-yl}acetamide

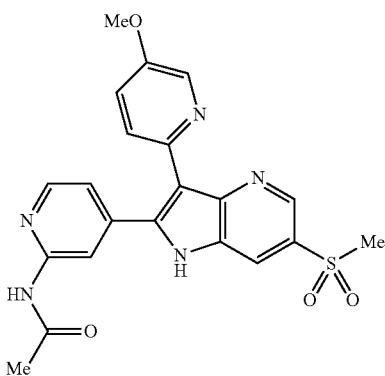 [SMILES: COc1ccc(-c2c(-c3ccnc(NC(C)=O)c3)[nH]c3cc(S(C)(=O)=O)cnc23)nc1]

91A): N-(4-(6-Bromo-3-(5-methoxypyridin-2-yl)-1-((2-(trimethylsilyl)ethoxy)methyl)-1H-pyrrolo[3,2-b]pyridin-2-yl)pyridin-2-yl)-N-((2-(trimethylsilyl)ethoxy)methyl)acetamide

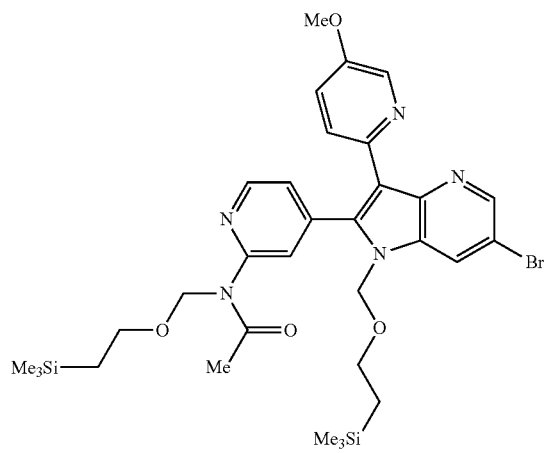 [SMILES: COc1ccc(-c2c(-c3ccnc(N(COCC[Si](C)(C)C)C(C)=O)c3)n(COCC[Si](C)(C)C)c3cc(Br)cnc23)nc1]

To a suspension of Example 83 (200 mg, 0.456 mmol) in THF (15 mL)/DMF (7 mL) was added 60% NaH (146 mg, 3.65 mmol), and the mixture was stirred for 15 min. SEM-Cl (0.324 mL, 1.825 mmol) was then added, and the resulting mixture was stirred at room temperature for 1.5 h. The reaction was carefully quenched with water, and the mixture was then extracted with EtOAc. The organic layer was separated and washed with 10% LiOH and brine, dried (MgSO$_4$) and concentrated. The residue was purified by silica gel flash chromatography (24 g, MeOH/DCM=0-5%) to give Example 91A (196 mg, 62%). HPLC: RT=3.32 min (H$_2$O/MeOH with 0.1% TFA, Chromolith SpeedROD, 4.6× 50 mm, gradient=4 min, wavelength=220 nm); MS (ES): m/z=698 [M+H]$^+$.

Example 91): N-{4-[6-Methanesulfonyl-3-(5-methoxypyridin-2-yl)-1H-pyrrolo[3,2-b]pyridin-2-yl]pyridin-2-yl}acetamide

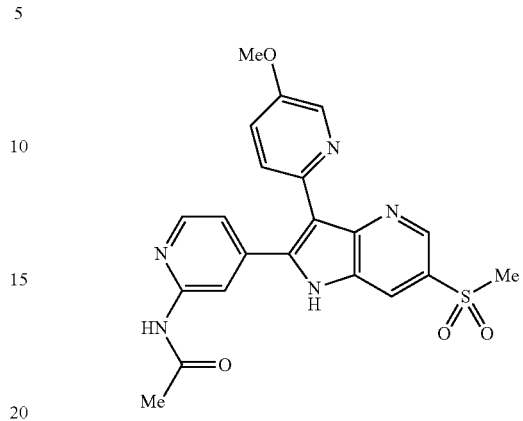

A mixture of Example 91A (25 mg, 0.036 mmol), sodium methanesulfinate (7.30 mg, 0.072 mmol), copper (I) iodide (10.22 mg, 0.054 mmol), L-proline (8.24 mg, 0.072 mmol) and Cs$_2$CO$_3$ (23.31 mg, 0.072 mmol) in DMSO (0.7 mL) in a 2 dram vial was purged with nitrogen and then heated at 100° C. overnight. The mixture was cooled to room temperature, and then diluted with MeOH and purified by preparative HPLC (Luna 5 u C18, 20×100 mm, eluting with 20%-100% aqueous acetonitrile over 15 minutes containing 5 mM NH$_4$OAc, 20 mL/min, monitor 254 nm). The desired fractions were combined and concentrated, and the residue was then treated with 50% TFA/DCM (2 mL) and stirred at room temperature for 2 h. The mixture was concentrated and purified by preparative HPLC (XBridge C18, 5 u, 19×200 mm, eluting with 5%-50% aqueous acetonitrile over 20 minutes containing 10 mM ammonium acetate, 20 mL/min, monitor 254 nm) to give Example 91 (3.4 mg, 21%). HPLC: RT=0.62 min (H$_2$O/ACN with 0.1% TFA, Waters Acquity UPLC BEH C18, 2.1×50 mm, 1.7-μm particles, gradient=3 min, wavelength=220 nm); MS (ES): m/z=438 [M+H]$^+$; $^1$H NMR (500 MHz, DMSO-d$_6$) δ ppm 10.62 (s, 1H), 8.91 (s, 1H), 8.41-8.27 (m, 3H), 8.22 (d, J=2.7 Hz, 1H), 7.99 (d, J=8.6 Hz, 1H), 7.53 (dd, J=8.7, 2.8 Hz, 1H), 7.16 (d, J=4.5 Hz, 1H), 3.87 (s, 3H), 2.55 (s, 3H), 2.11 (s, 3H).

Example 92

N-{4-[6-Cyano-3-(5-methoxypyridin-2-yl)-1H-pyrrolo[3,2-b]pyridin-2-yl]pyridin-2-yl}acetamide

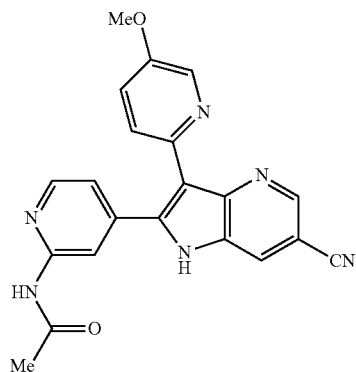 [SMILES: COc1ccc(-c2c(-c3ccnc(NC(C)=O)c3)[nH]c3cc(C#N)cnc23)nc1]

Example 92 was prepared from Example 83 using conditions similar to those described for Example 78B. HPLC: RT=0.59 min (H₂O/ACN with 0.05% TFA, Waters Acquity BEH C18, 2.0×50 mm, 1.7-μm particles, gradient=1.8 min, wavelength=220 nm); MS (ES): m/z=385 [M+H]$^+$; $^1$H NMR (400 MHz, DMSO-d$_6$) δ 12.75 (s, 1H), 10.60 (s, 1H), 8.78 (d, J=1.8 Hz, 1H), 8.41 (d, J=1.8 Hz, 1H), 8.35-8.30 (m, 3H), 8.26 (d, J=2.6 Hz, 1H), 7.95 (d, J=8.8 Hz, 1H), 7.17 (dd, J=5.2, 1.7 Hz, 1H), 3.88 (s, 3H), 2.09, 2.07 (s, 3H).

Example 93

N-{4-[6-(Dimethyl-1,2-oxazol-4-yl)-3-(5-methoxy-pyridin-2-yl)-1H-pyrrolo[3,2-b]pyridin-2-yl]pyridin-2-yl}acetamide

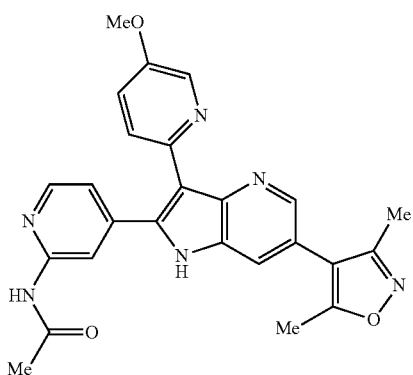 [SMILES: COc1ccc(-c2c(-c3ccnc(NC(C)=O)c3)[nH]c3cc(-c4c(C)noc4C)cnc23)nc1]

A mixture of Example 83 (20 mg, 0.046 mmol), (3,5-dimethylisoxazol-4-yl)boronic acid (9.65 mg, 0.068 mmol), PdCl₂(dppf)-CH₂Cl₂ adduct (1.863 mg, 2.282 μmol) and 2M potassium phosphate tribasic (0.068 mL, 0.137 mmol) in THF (2 mL) was purged with N₂, and then heated in a sealed vial at 85° C. for 30 min. The mixture was cooled to room temperature, then concentrated and purified by preparative HPLC (XBridge C18, 5 u, 19×200 mm, eluting with 5%-80% aqueous acetonitrile over 20 minutes containing 10 mM ammonium acetate, 20 mL/min, monitor 254 nm) to give Example 93 (12.3 mg, 59%). HPLC: RT=0.97 min (H₂O/ACN with 0.1% TFA, Waters Acquity UPLC BEH C18, 2.1×50 mm, 1.7-μm particles, gradient=3 min, wavelength=220 nm); MS (ES): m/z=455 [M+H]$^+$; $^1$H NMR (500 MHz, DMSO-d$_6$) δ ppm 10.56 (s, 1H), 8.44 (s, 1H), 8.34 (br. s., 1H), 8.30 (d, J=5.0 Hz, 1H), 8.21 (d, J=2.8 Hz, 1H), 8.04 (d, J=8.7 Hz, 1H), 7.84 (s, 1H), 7.51 (dd, J=8.7, 2.9 Hz, 1H), 7.16 (d, J=5.1 Hz, 1H), 3.87 (s, 3H), 2.47 (s, 3H), 2.29 (s, 3H), 2.10 (s, 3H).

Example 94

N-{4-[6-(Dimethyl-1H-1,2,3-triazol-5-yl)-3-(5-methoxypyridin-2-yl)-1H-pyrrolo[3,2-b]pyridin-2-yl]pyridin-2-yl}acetamide

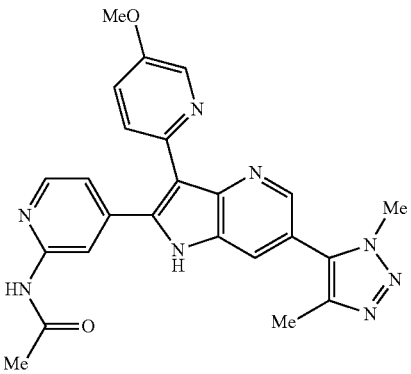 [SMILES: COc1ccc(-c2c(-c3ccnc(NC(C)=O)c3)[nH]c3cc(-c4c(C)nnn4C)cnc23)nc1]

A mixture of Example 84 (20 mg, 0.046 mmol), 1,4-dimethyl-5-(tributylstannyl)-1H-1,2,3-triazole (35.2 mg, 0.091 mmol) [Seefeld, M. A. et al. PCT Int. Appl., 2008, WO2008098104], Pd(Ph₃P)₄ (5.27 mg, 4.56 μmol), copper (I) iodide (1.738 mg, 9.13 μmol) and TEA (0.013 mL, 0.091 mmol) in DMF (1 mL) was purged with N₂, and then heated at 90° C. overnight. The mixture was cooled to room temperature and purified by preparative HPLC (XBridge C18, 5 u, 19×200 mm, eluting with 10%-50% aqueous acetonitrile over 20 minutes containing 10 mM ammonium acetate, 20 mL/min, monitor 254 nm) to give Example 94 (1.7 mg, 8%). HPLC: RT=0.75 min (H₂O/ACN with 0.1% TFA, Waters Acquity UPLC BEH C18, 2.1×50 mm, 1.7-μm particles, gradient=3 min, wavelength=220 nm); MS (ES): m/z=455 [M+H]$^+$.

Example 95

N-(4-(6-(2-Methoxy ethoxy)-3-(5-methoxypyridin-2-yl)-1H-pyrrolo[3,2-b]pyridin-2-yl)pyridin-2-yl)acetamide

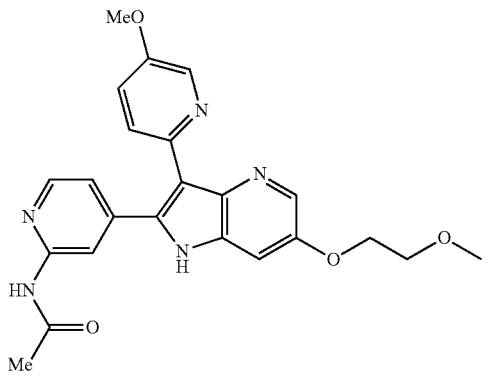 [SMILES: COCCOc1cnc2c(-c3ccc(OC)cn3)c(-c3ccnc(NC(C)=O)c3)[nH]c2c1]

95A) N-(4-(6-Bromo-3-(5-methoxypyridin-2-yl)-1-((2-(trimethylsilyl)ethoxy)methyl)-1H-pyrrolo[3,2-b]pyridin-2-yl)pyridin-2-yl)acetamide

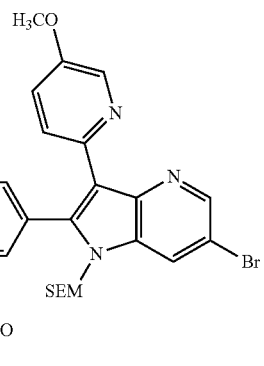

To a suspension of N-(4-(6-bromo-3-(5-methoxypyridin-2-yl)-1H-pyrrolo[3,2-b]pyridin-2-yl)pyridin-2-yl)acetamide (Example 83, 125 mg, 0.285 mmol) and cesium carbonate (139 mg, 0.428 mmol) in DMF (1 mL) and THF (1 mL) was added (2-(chloromethoxy)ethyl) trimethylsilane (57.1 mg, 0.342 mmol). The reaction was stirred at room temperature for 1 h before it was quenched with brine, and extracted with EtOAc (3×). The combined organic layers were concentrated and purified on ISCO (0-10% MeOH/DCM, 24 g column) to give N-(4-(6-bromo-3-(5-methoxypyridin-2-yl)-1-((2-(trimethylsilyl)ethoxy)methyl)-1H-pyrrolo[3,2-b]pyridin-2-yl)pyridin-2-yl)acetamide (143 mg, 0.252 mmol, 88% yield). MS (ES): m/z=569.9 [M+H]$^+$.

95B) N-(4-(6-hydroxy-3-(5-methoxypyridin-2-yl)-1-((2-(trimethylsilyl)ethoxy)methyl)-1H-pyrrolo[3,2-b]pyridin-2-yl)pyridin-2-yl)acetamide

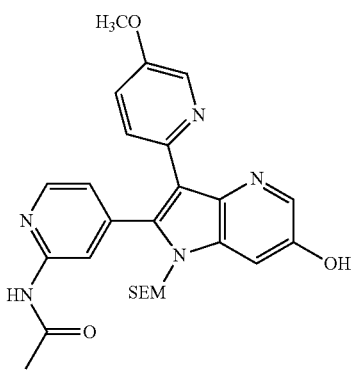 [SMILES: COc1ccc(-c2c(-c3ccnc(NC(C)=O)c3)n(COCC[Si](C)(C)C)c3cc(O)cnc23)nc1]

To a vial was added bis(pinacolato)diboron (156 mg, 0.616 mmol), N-(4-(6-bromo-3-(5-methoxypyridin-2-yl)-1-((2-(trimethylsilyl)ethoxy)methyl)-1H-pyrrolo[3,2-b]pyridin-2-yl)pyridin-2-yl)acetamide (140 mg, 0.246 mmol, Pd$_2$(dba)$_3$ (4.51 mg, 4.92 µmol), XPhos (4.70 mg, 9.85 µmol), and potassium acetate (72.5 mg, 0.739 mmol). The vial was evacuated and refilled with N$_2$. Dioxane (3 mL) was then added. The reaction was then heated to 100° C. for 2 h. The reaction was then cooled to room temperature, diluted with EtOAC, filtered through a pad of Celite, washing with 10% MeOH/DCM. The combined filtrated was concentrated and taken up in THF (5 mL) and water (2 mL). To the mixture was added sodium perborate (100 mg). The resulting suspension was stirred at room temperature overnight before it was diluted with EtOAc, washed with brine, dried and concentrated in vacuo. The crude product was purified on ISCO (0-7% MeOH/DCM, 24 g column) to give N-(4-(6-hydroxy-3-(5-methoxypyridin-2-yl)-1-((2-(trimethylsilyl)ethoxy)methyl)-1H-pyrrolo[3,2-b]pyridin-2-yl)pyridin-2-yl)acetamide (79 mg, 0.156 mmol, 63.4% yield). MS (ES): m/z=506.0 [M+H]$^+$.

95C) N-(4-(6-(2-Methoxyethoxy)-3-(5-methoxypyridin-2-yl)-1-((2-(trimethylsilyl)ethoxy)methyl)-1H-pyrrolo[3,2-b]pyridin-2-yl)pyridin-2-yl)acetamide

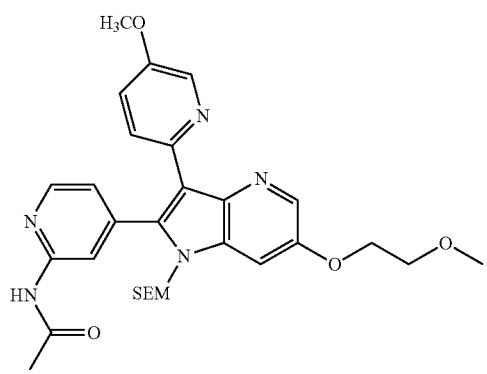 [SMILES: COCCOc1cnc2c(-c3ccc(OC)cn3)c(-c3ccnc(NC(C)=O)c3)n(COCC[Si](C)(C)C)c2c1]

To a solution of N-(4-(6-hydroxy-3-(5-methoxypyridin-2-yl)-1-((2-(trimethylsilyl)ethoxy)methyl)-1H-pyrrolo[3,2-b]pyridin-2-yl)pyridin-2-yl)acetamide (32 mg, 0.063 mmol), triphenylphosphine (16.60 mg, 0.063 mmol), and 2-methoxyethanol (14.45 mg, 0.190 mmol) in THF (0.5 mL) at 0° C. was added DIAD (0.012 mL, 0.063 mmol). The reaction was then heated to 50° C. for 1 h before it was cooled to room temperature and purified on ISCO (0-10% MeOH/DCM, 12 g column) to give N-(4-(6-(2-methoxyethoxy)-3-(5-methoxypyridin-2-yl)-1-((2-(trimethylsilyl)ethoxy)methyl)-1H-pyrrolo[3,2-b]pyridin-2-yl)pyridin-2-yl)acetamide (25 mg, 0.044 mmol, 70.1% yield). MS (ES): m/z=564 [M+H]$^+$.

Example 95) N-(4-(6-(2-Methoxyethoxy)-3-(5-methoxypyridin-2-yl)-1H-pyrrolo[3,2-b]pyridin-2-yl)pyridin-2-yl)acetamide To a solution of N-(4-(6-(2-methoxyethoxy)-3-(5-methoxypyridin-2-yl)-1-((2-(trimethylsilyl)ethoxy)methyl)-1H-pyrrolo[3,2-b]pyridin-2-yl)pyridin-2-yl)acetamide (26 mg, 0.046 mmol) in DCM (0.2 mL) was added TFA (0.3 mL). The resulting reaction was stirred at room temperature for 4 h before it was concentrated. The resulting mixture was then dissolved in 0.4 M NH$_3$ in 20% MeOH/DCM (0.5 mL) and stirred at room temperature for 1 h. The reaction was then concentrated and purified on ISCO (0-10% MeOH/DCM, 12 g Gold column) to give N-(4-(6-(2-methoxyethoxy)-3-(5-methoxypyridin-2-yl)-1H-pyrrolo[3,2-b]pyridin-2-yl)pyridin-2-yl)acetamide (13.5 mg, 0.030 mmol, 64.2% yield). HPLC: RT=0.59 min (H$_2$O/ACN with 0.1% TFA, Waters Acquity UPLC BEH C18, 2.1×50 mm, 1.7-µm particles, gradient=1 min, wavelength=220 nm); MS (ES): m/z=434 [M+H]$^+$; $^1$H NMR (400 MHz, METHANOL-d$_4$) δ 8.28 (dd, J=3.0, 0.6 Hz, 1H), 8.24-8.20 (m, 2H), 8.18 (d, J=2.6 Hz, 1H), 7.63 (dd, J=8.6, 0.6 Hz, 1H), 7.54 (dd, J=8.6, 3.0 Hz, 1H), 7.50 (d, J=2.6 Hz, 1H), 7.10-7.05 (m, 1H), 4.38-4.22 (m, 2H), 3.97 (s, 3H), 3.88-3.77 (m, 2H), 3.48 (s, 3H).

TABLE 1

| Example # | Structure | Name | HPLC ret. time (min) | LC/MS (M + H)+ |
|---|---|---|---|---|
| 96 | 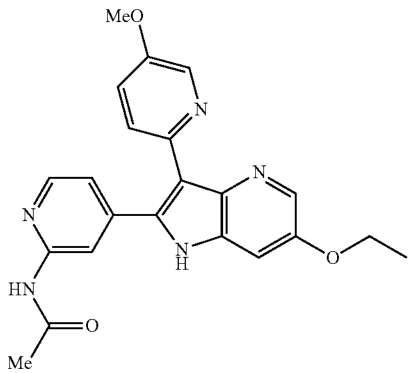 [SMILES: CCOc1cnc2c(-c3ccc(OC)cn3)c(-c3ccnc(NC(C)=O)c3)[nH]c2c1] | N-(4-(6-Ethoxy-3-(5-methoxypyridin-2-yl)-1H-pyrrolo[3,2-b]pyridin-2-yl)pyridin-2-yl)acetamide | 0.61 | 404 |
| 97 | 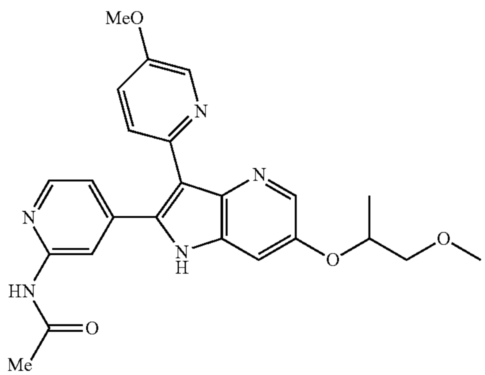 [SMILES: COCC(C)Oc1cnc2c(-c3ccc(OC)cn3)c(-c3ccnc(NC(C)=O)c3)[nH]c2c1] | N-(4-(6-((1-Methoxypropan-2-yl)oxy)-3-(5-methoxypyridin-2-yl)-1H-pyrrolo[3,2-b]pyridin-2-yl)pyridin-2-yl)acetamide | 0.62 | 448 |
| 98 | 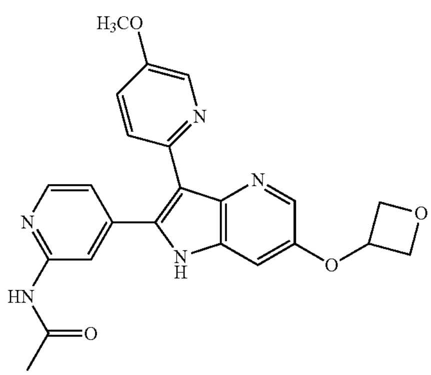 [SMILES: COc1ccc(-c2c(-c3ccnc(NC(C)=O)c3)[nH]c3cc(OC4COC4)cnc23)nc1] | N-(4-(3-(5-Methoxypyridin-2-yl)-6-(oxetan-3-yloxy)-1H-pyrrolo[3,2-b]pyridin-2-yl)pyridin-2-yl)acetamide | 0.60 | 432 |
| 99 | 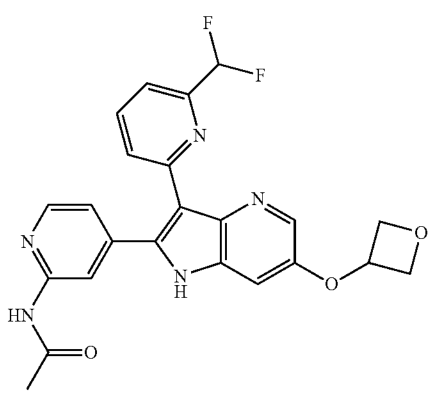 [SMILES: CC(=O)Nc1cc(-c2[nH]c3cc(OC4COC4)cnc3c2-c2cccc(C(F)F)n2)ccn1] | N-(4-(3-(6-(Difluoromethyl)pyridin-2-yl)-6-(oxetan-3-yloxy)-1H-pyrrolo[3,2-b]pyridin-2-yl)pyridin-2-yl)acetamide | 0.62 | 452 |

TABLE 1-continued
| Example # | Structure | Name | HPLC ret. time (min) | LC/MS (M + H)+ |
|---|---|---|---|---|
| 100 | 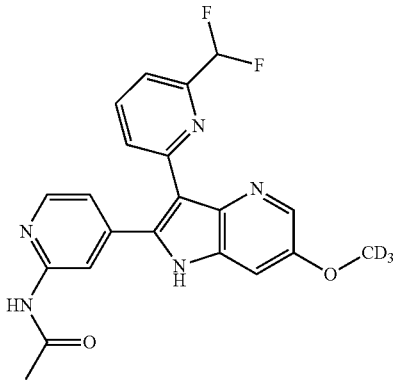 [SMILES: [2H]C([2H])([2H])Oc1cnc2c(-c3cccc(C(F)F)n3)c(-c3ccnc(NC(C)=O)c3)[nH]c2c1] | N-(4-(3-(6-(Difluoromethyl)pyridin-2-yl)-6-(methoxy-d3)-1H-pyrrolo[3,2-b]pyridin-2-yl)pyridin-2-yl)acetamide | 0.63 | 413 |
| 101 | 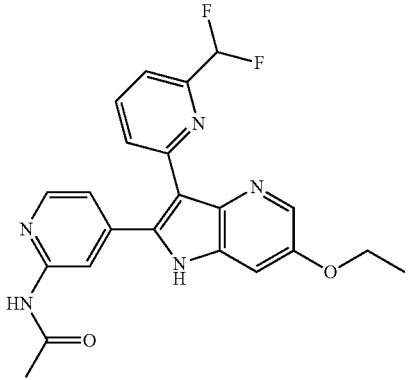 [SMILES: CCOc1cnc2c(-c3cccc(C(F)F)n3)c(-c3ccnc(NC(C)=O)c3)[nH]c2c1] | N-(4-(3-(6-(Difluoromethyl)pyridin-2-yl)-6-ethoxy-1H-pyrrolo[3,2-b]pyridin-2-yl)pyridin-2-yl)acetamide | 0.67 | 424 |
| 102 | 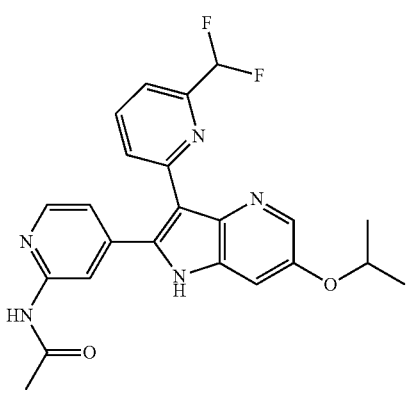 | N-(4-(3-(6-(Difluoromethyl)pyridin-2-yl)-6-isopropoxy-1H-pyrrolo[3,2-b]pyridin-2-yl)pyridin-2-yl)acetamide | 0.72 | 438 |

TABLE 1-continued

| Example # | Structure | Name | HPLC ret. time (min) | LC/MS (M + H)+ |
|---|---|---|---|---|
| 103 | 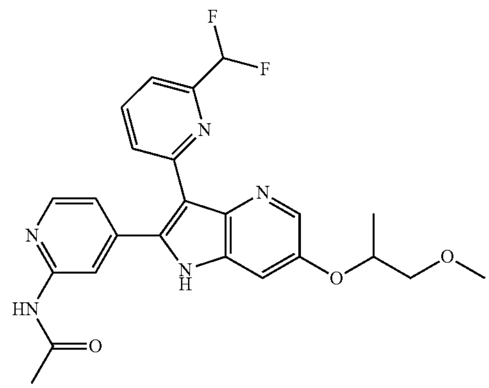 [SMILES: COCC(C)Oc1cnc2c(-c3cccc(C(F)F)n3)c(-c3ccnc(NC(C)=O)c3)[nH]c2c1] | N-(4-(3-(6-(Difluoromethyl)pyridin-2-yl)-6-1-methoxypropan-2-yl)oxy)-1H-pyrrolo[3,2-b]pyridin-2-yl)pyridin-2-yl)acetamide | 0.70 | 468 |

HPLC/LCMS Column conditions: Waters Acquity UPLC BEH C18, 2.1 × 50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 1 minutes, then a 0.75-minute hold at 100% B; Flow: 1.0 mL/min; Detection: UV at 220 nm.

The Examples found in Table 1 were prepared according to the general methods shown for Example 95 from the appropriate starting materials.

Example 104

N-(4-(3-(5-(Methoxy-d3)pyridin-2-yl)-1H-pyrrolo[3,2-b]pyridin-2-yl)pyridin-2-yl)acetamide

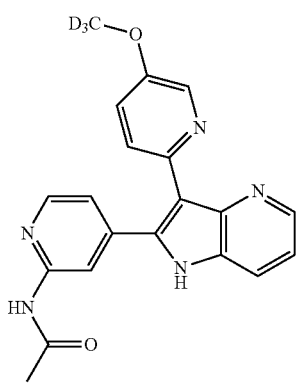 [SMILES: [2H]C([2H])([2H])Oc1ccc(-c2c(-c3ccnc(NC(C)=O)c3)[nH]c3cccnc23)nc1]

104A) 2-Bromo-5-(methoxy-d3)pyridine

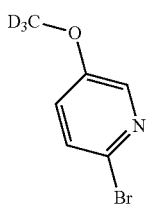

To a solution of 6-bromopyridin-3-ol (10.00 g, 57.5 mmol), d4-MeOD (12.44 g, 345 mmol), and triphenylphosphine (15.83 g, 60.3 mmol) in dioxane (80 mL) at 0° C. was added dropwise DIAD (11.73 mL, 60.3 mmol). The reaction was stirred at 0° C. for 10 min before warmed to room temperature and stirred overnight. The reaction was then concentrated and then triturated with DCM (60 mL). The mixture was filtered to remove phosphine oxide by-product. The filtrate was concentrated and purified on ISCO (0-10% MeOH/DCM, 120 g column) to give 2-bromo-5-(methoxy-d3)pyridine (7.1 g, 37.2 mmol, 64.7% yield). MS (ES): m/z=191 [M+H]+. $^1$H NMR (400 MHz, CHLOROFORM-d) δ 8.08 (dd, J=3.2, 0.4 Hz, 1H), 7.39 (dd, J=8.7, 0.6 Hz, 1H), 7.12 (dd, J=8.7, 3.2 Hz, 1H)

Example 104) N-(4-(3-(5-(Methoxy-d3)pyridin-2-yl)-1H-pyrrolo[3,2-b]pyridin-2-yl)pyridin-2-yl)acetamide A mixture of Example 1D (1.2 g, 3.45 mmol) and cesium carbonate (2.245 g, 6.89 mmol) was evacuated and back-filled with $N_2$. MeCN (17.23 ml) and 2-bromo-5-(methoxy-d3)pyridine (1.316 g, 6.89 mmol) were added. The mixture was sparged with $N_2$ for 5 min before tetrakis(triphenylphosphine)palladium(0) (0.199 g, 0.172 mmol) was added. The reaction was sparged with $N_2$ for 1 min, then it was sealed and stirred at 110° C. for 2 h. The resulting mixture was cooled to room temperature diluted with 10% MeOH—$CH_2Cl_2$ (20 mL) and filtered through Celite (washed with 10% MeOH—$CH_2Cl_2$). The filtrate was concentrated in vacuo. The crude material was purified by ISCO (120 g column, 0-8% MeOH/DCM) and dried under vacuum give N-(4-(3-(5-(methoxy-$d_3$)pyridin-2-yl)-1H-pyrrolo[3,2-b]pyridin-2-yl)pyridin-2-yl)acetamide (540 mg, 1.460 mmol, 42.4% yield). HPLC: RT=0.56 min ($H_2O$/ACN with 0.1% TFA, Waters Acquity UPLC BEH C18, 2.1×50 mm, 1.7-μm particles, gradient=1 min, wavelength=220 nm); MS (ES): m/z=363 [M+H]+; $^1$H NMR (400 MHz, DMSO-$d_6$) δ 11.98 (s, 1H), 10.52 (s, 1H), 8.44 (d, J=4.4 Hz, 1H), 8.36-8.25 (m, 2H), 8.19 (d, J=2.9 Hz, 1H), 8.03 (d, J=8.7 Hz, 1H), 7.87 (d, J=8.2 Hz, 1H), 7.50 (dd, J=8.7, 2.9 Hz, 1H), 7.26 (dd, J=8.1, 4.6 Hz, 1H), 7.14 (d, J=5.1 Hz, 1H), 2.10 (s, 3H)

Example 105

N-(4-(6-Chloro-3-(5-(methoxy-d3)pyridin-2-yl)-1H-pyrrolo[3,2-b]pyridin-2-yl)pyridin-2-yl)acetamide

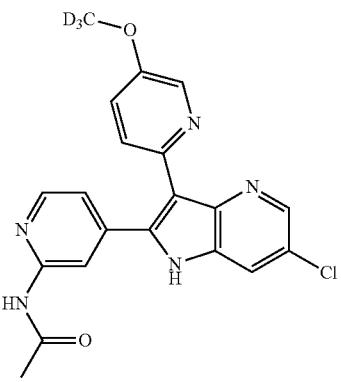 [SMILES: [2H]C([2H])([2H])Oc1ccc(-c2c(-c3ccnc(NC(C)=O)c3)[nH]c3cc(Cl)cnc23)nc1]

A mixture of Example 41B (110 mg, 0.287 mmol) and cesium carbonate (187 mg, 0.575 mmol) was evacuated and backfilled with $N_2$. MeCN (2874 µl) and 2-bromo-5-(methoxy-d3)pyridine (110 mg, 0.575 mmol) were added. The mixture was sparged with $N_2$ for 5 min, then tetrakis(triphenylphosphine)palladium(0) (16.61 mg, 0.014 mmol) was added. The reaction was sparged with $N_2$ for 1 min, then it was sealed and stirred at 110° C. for 2 h. The reaction was then cooled to room temperature, diluted with 10% MeOH—$CH_2Cl_2$ (20 mL), and filtered through Celite (washed with 10% MeOH—$CH_2Cl_2$). The filtrate was concentrated in vacuo. The crude material was purified by ISCO (40 g gold column, 0-8% MeOH/DCM, dry-loaded on Celite) and dried under vacuum give the desired product (48 mg, 0.119 mmol, 41.2% yield). HPLC: RT=0.61 min ($H_2O$/ACN with 0.1% TFA, Waters Acquity UPLC BEH C18, 2.1×50 mm, 1.7-µm particles, gradient=1 min, wavelength=220 nm); MS (ES): m/z=397 [M+H]$^+$ $^1$H NMR (400 MHz, DMSO-$d_6$) δ 12.19 (s, 1H), 10.55 (s, 1H), 8.44 (d, J=2.2 Hz, 1H), 8.32 (s, 1H), 8.29 (d, J=5.3 Hz, 1H), 8.21 (d, J=3.1 Hz, 1H), 7.95 (dd, J=5.4, 3.2 Hz, 2H), 7.50 (dd, J=8.7, 3.1 Hz, 1H), 7.13 (dd, J=5.2, 1.5 Hz, 1H), 2.10 (s, 3H)

Example 106

N-(4-(6-Fluoro-3-(5-(methoxy-d3)pyridin-2-yl)-1H-pyrrolo[3,2-b]pyridin-2-yl)pyridin-2-yl)acetamide

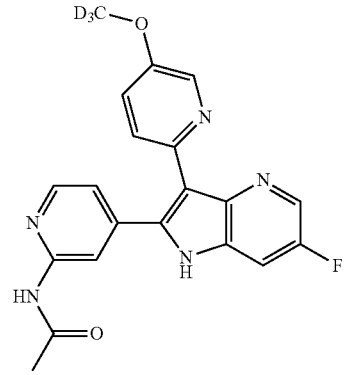 [SMILES: [2H]C([2H])([2H])Oc1ccc(-c2c(-c3ccnc(NC(C)=O)c3)[nH]c3cc(F)cnc23)nc1]

A mixture of Example 38B (110 mg, 0.300 mmol) and cesium carbonate (196 mg, 0.601 mmol) was evacuated and backfilled with $N_2$. MeCN (3003 µl) and 2-bromo-5-(methoxy-d3)pyridine (115 mg, 0.601 mmol) were added. The mixture was sparged with N2 for 5 min, then tetrakis(triphenylphosphine)palladium(0) (17.35 mg, 0.015 mmol) was added. The reaction was sparged with $N_2$ for 1 min, then it was sealed and stirred at 110° C. for 2 h. The reaction was then cooled to room temperature, diluted with 10% MeOH—$CH_2Cl_2$ (20 mL), and filtered through Celite (washed with 10% MeOH—$CH_2Cl_2$). The filtrate was concentrated in vacuo. The crude material was purified by ISCO (40 g gold column, 0-8% MeOH/DCM) and dried to give N-(4-(6-fluoro-3-(5-(methoxy-d3)pyridin-2-yl)-1H-pyrrolo[3,2-b]pyridin-2-yl)pyridin-2-yl)acetamide (50 mg, 0.125 mmol, 41.6% yield). HPLC: RT=0.56 min ($H_2O$/ACN with 0.1% TFA, Waters Acquity UPLC BEH C18, 2.1×50 mm, 1.7-µm particles, gradient=1 min, wavelength=220 nm); MS (ES): m/z=381 [M+H]$^+$; $^1$H NMR (400 MHz, METHANOL-$d_4$) δ 8.33 (t, J=2.2 Hz, 1H), 8.28 (dd, J=3.1, 0.6 Hz, 1H), 8.27-8.22 (m, 2H), 7.71 (dd, J=9.1, 2.5 Hz, 1H), 7.67 (dd, J=8.7, 0.6 Hz, 1H), 7.54 (dd, J=8.7, 3.1 Hz, 1H), 7.15-7.08 (m, 1H), 2.17 (s, 3H).

TABLE 2

| Example # | Structure | Name | HPLC ret. time (min) | LC/MS (M + H)$^+$ |
|---|---|---|---|---|
| 107 | 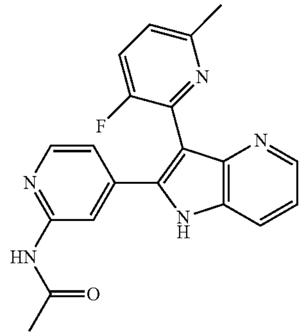 [SMILES: CC(=O)Nc1cc(-c2[nH]c3cccnc3c2-c2nc(C)ccc2F)ccn1] | N-(4-(3-(3-Fluoro-6-methylpyridin-2-yl)-1H-pyrrolo[3,2-b]pyridin-2-yl)pyridin-2-yl)acetamide | 1.03 | 362 |

TABLE 2-continued
| Example # | Structure | Name | HPLC ret. time (min) | LC/MS (M + H)+ |
|---|---|---|---|---|
| 108 | 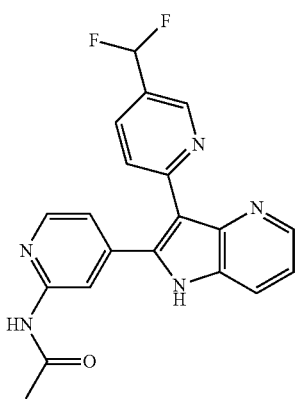 [SMILES: CC(=O)Nc1cc(-c2[nH]c3cccnc3c2-c2ccc(C(F)F)cn2)ccn1] | N-(4-(3-(5-(Difluoromethyl)pyridin-2-yl)-1H-pyrrolo[3,2-b]pyridin-2-yl)pyridin-2-yl)acetamide | 0.91 | 380 |
| 109 | 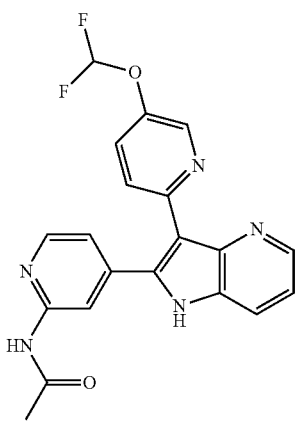 [SMILES: CC(=O)Nc1cc(-c2[nH]c3cccnc3c2-c2ccc(OC(F)F)cn2)ccn1] | N-(4-(3-(5-(Difluoromethoxy)pyridin-2-yl)-1H-pyrrolo[3,2-b]pyridin-2-yl)pyridin-2-yl)acetamide | 0.92 | 396 |
| 110 | 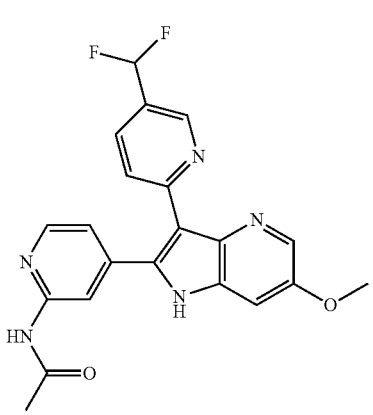 [SMILES: COc1cnc2c(-c3ccc(C(F)F)cn3)c(-c3ccnc(NC(C)=O)c3)[nH]c2c1] | N-(4-(3-(5-(Difluoromethyl)pyridin-2-yl)-6-methoxy-1H-pyrrolo[3,2-b]pyridin-2-yl)pyridin-2-yl)acetamide | 0.97 | 410 |

TABLE 2-continued

| Example # | Structure | Name | HPLC ret. time (min) | LC/MS (M + H)+ |
|---|---|---|---|---|
| 111 | 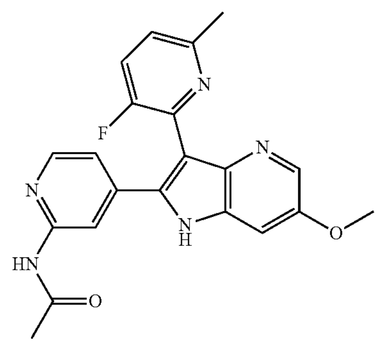 [SMILES: COc1cnc2c(-c3nc(C)ccc3F)c(-c3ccnc(NC(C)=O)c3)[nH]c2c1] | N-(4-(3-(3-Fluoro-6-methylpyridin-2-yl)-6-methoxy-1H-pyrrolo[3,2-b]pyridin-2-yl)pyridin-2-yl)acetamide | 0.79 | 392 |
| 112 | 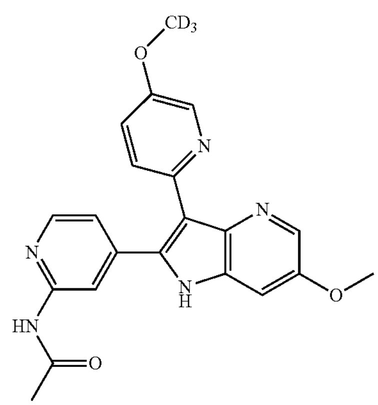 [SMILES: [2H]C([2H])([2H])Oc1ccc(-c2c(-c3ccnc(NC(C)=O)c3)[nH]c3cc(OC)cnc23)nc1] | N-(4-(6-Methoxy-3-(5-(methoxy-d3)pyridin-2-yl)-1H-pyrrolo[3,2-b]pyridin-2-yl)pyridin-2-yl)acetamide | 0.83 | 393 |
| 113 | 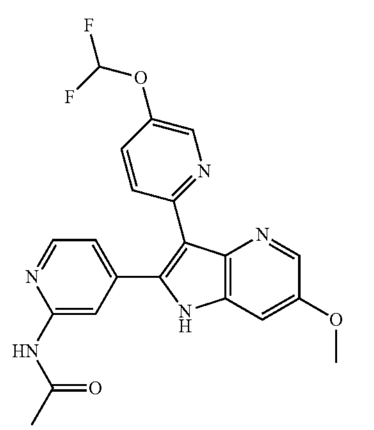 [SMILES: COc1cnc2c(-c3ccc(OC(F)F)cn3)c(-c3ccnc(NC(C)=O)c3)[nH]c2c1] | N-(4-(3-(5-(Difluoromethoxy)pyridin-2-yl)-6-methoxy-1H-pyrrolo[3,2-b]pyridin-2-yl)pyridin-2-yl)acetamide | 1.01 | 426 |

HPLC/LCMS Column conditions: Waters Acquity UPLC BEH C18, 2.1 × 50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

The Examples in the Table 2 were prepared according to the general methods shown for Example 104 from the appropriate starting materials.

Example 114

2-(2-(2-Acetamidopyridin-4-yl)-3-(6-(difluoromethyl)pyridin-2-yl)-1H-pyrrolo[3,2-b]pyridin-1-yl)acetamide

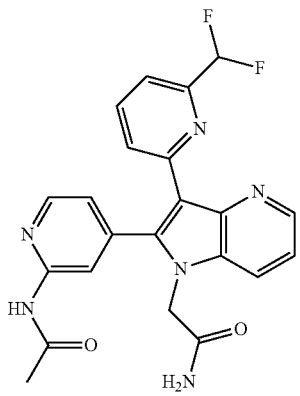 [SMILES: CC(=O)Nc1cc(-c2c(-c3cccc(C(F)F)n3)c3ncccc3n2CC(N)=O)ccn1]

To a solution of Example 281 (20 mg, 0.053 mmol) in DMF (0.3 mL) was added potassium carbonate (14.57 mg, 0.105 mmol) and iodomethane (6.59 μl, 0.105 mmol). The reaction mixture was stirred overnight at room temperature and then filtered and diluted with MeOH. The crude product was then purified by preparative HPLC to give 2-(2-(2-acetamidopyridin-4-yl)-3-(6-(difluoromethyl)pyridin-2-yl)-1H-pyrrolo[3,2-b]pyridin-1-yl)acetamide. HPLC: RT=0.83 min (H$_2$O/ACN with 0.1% TFA, Waters Acquity UPLC BEH C18, 2.1×50 mm, 1.7-μm particles, gradient=3 min, wavelength=220 nm); MS (ES): m/z=437 [M+H]$^+$, $^1$H NMR (500 MHz, DMSO-d$_6$) δ 10.58 (s, 1H), 8.66 (d, J=7.8 Hz, 1H), 8.56 (d, J=4.1 Hz, 1H), 8.37 (d, J=4.8 Hz, 1H), 8.13 (br. s., 1H), 8.01-7.93 (m, 2H), 7.56 (br. s., 1H), 7.41 (d, J=7.5 Hz, 1H), 7.35 (dd, 4.5 Hz, 1H), 7.23 (br. s., 1H), 7.08 (d, J=4.6 Hz, 1H), 6.50-6.17 (m, 1H), 4.76 (s, 2H), 2.07 (s, 3H).

Example 115

2-(Dimethylamino)-N-{4-[6-methoxy-3-(5-methoxypyridin-2-yl)-1H-pyrrolo[3,2-b]pyridin-2-yl]pyridin-2-yl}acetamide

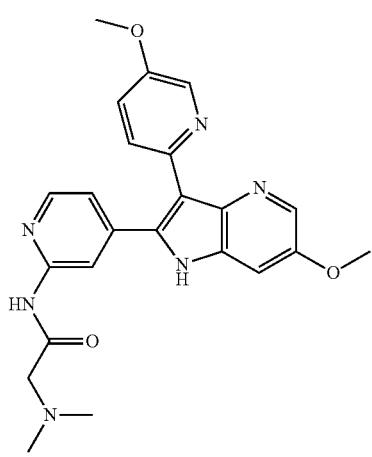 [SMILES: COc1ccc(-c2c(-c3ccnc(NC(=O)CN(C)C)c3)[nH]c3cc(OC)cnc23)nc1]

115A) N-(4-(6-Methoxy-3-(5-methoxypyridin-2-yl)-1H-pyrrolo[3,2-b]pyridin-2-yl)pyridin-2-yl)acetamide

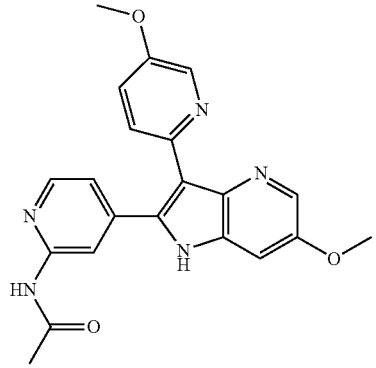 [SMILES: COc1ccc(-c2c(-c3ccnc(NC(C)=O)c3)[nH]c3cc(OC)cnc23)nc1]

A mixture of Example 48B (0.423 g, 1.118 mmol) and cesium carbonate (0.729 g, 2.236 mmol) was evacuated and backfilled with N$_2$, then MeCN (10.16 mL) and 2-bromo-5-methoxypyridine (0.420 g, 2.236 mmol) were added. The mixture was sparged with N$_2$ for 5 min, then tetrakis(triphenylphosphine)palladium(0) (0.065 g, 0.056 mmol) was added. The reaction was sparged with N$_2$ for 1 min, then it was sealed and stirred at 110° C. for 2 h. The reaction was cooled to room temperature, diluted with 10% MeOH—CH$_2$Cl$_2$ (10 mL), and filtered through Celite (washed with 10% MeOH—CH$_2$Cl$_2$). The filtrate was concentrated in vacuo. The crude material was purified by flash chromatography (40 g silica gel with 25 g prepacked load cartridge; linear gradient 0-10% MeOH—CH$_2$Cl$_2$) to provide Example 115A (0.216 g, 50%) as an off-white solid. LC-MS m/z 390 [M+H]$^+$; $^1$H NMR (400 MHz, DMSO-d$_6$) δ 11.78 (s, 1H), 10.47 (s, 1H), 8.29 (s, 1H), 8.24 (dd, J=5.3, 0.7 Hz, 1H), 8.20-8.17 (m, 2H), 7.96 (d, J=8.7 Hz, 1H), 7.47 (dd, J=8.7, 3.1 Hz, 1H), 7.33 (d, J=2.6 Hz, 1H), 7.10 (dd, J=5.3, 1.6 Hz, 1H), 3.89 (s, 3H), 3.85 (s, 3H), 2.09 (s, 3H).

115B) 4-(6-Methoxy-3-(5-methoxypyridin-2-yl)-1H-pyrrolo[3,2-b]pyridin-2-yl)pyridin-2-amine

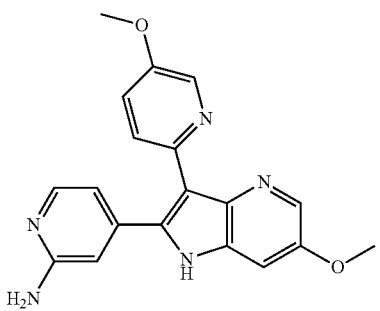 [SMILES: COc1ccc(-c2c(-c3ccnc(N)c3)[nH]c3cc(OC)cnc23)nc1]

To a room temperature solution of Example 115A (215 mg, 0.552 mmol) in MeOH (5.52 mL) was added sodium hydroxide (5.52 mL, 1 M solution in H$_2$O, 5.52 mmol). The reaction was sealed and stirred at 80° C. for 2 h, and then it was cooled to room temperature, causing the precipitation of solids, which were collected by vacuum filtration (washed with H$_2$O) to provide Example 115B (199 mg, quant.).

LC-MS m/z 348 [M+H]+; 1H NMR (400 MHz, DMSO-d6) δ 11.62 (s, 1H), 8.24-8.22 (m, 1H), 8.16 (d, J=2.7 Hz, 1H), 7.88-7.86 (m, 1H), 7.86-7.85 (m, 1H), 7.45 (dd, J=8.7, 3.1 Hz, 1H), 7.29 (d, J=2.6 Hz, 1H), 6.60-6.57 (m, 1H), 6.51 (dd, J=5.3, 1.5 Hz, 1H), 5.92 (s, 2H), 3.88 (s, 3H), 3.86 (s, 3H).

Example 115) 2-(Dimethylamino)-N-{4-[6-methoxy-3-(5-methoxypyridin-2-yl)-1H-pyrrolo[3,2-b]pyridin-2-yl]pyridin-2-yl}acetamide

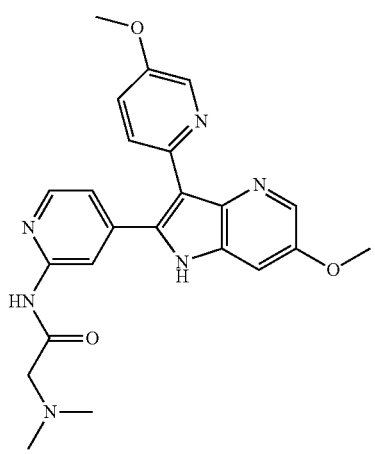 [SMILES: COc1ccc(-c2c(-c3ccnc(NC(=O)CN(C)C)c3)[nH]c3cc(OC)cnc23)nc1]

To a room temperature solution of Example 115B (26.2 mg, 0.075 mmol) in DMF (151 µL) was added 2-(dimethylamino)acetic acid (10.89 mg, 0.106 mmol), N,N-diisopropylethylamine (65.7 µL, 0.377 mmol), and HATU (40.1 mg, 0.106 mmol). The reaction was stirred at room temperature for 5 h, and then it was diluted with DMF, filtered, and purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 5-50% B over 20 minutes, then a 5-minute hold at 100% B; Flow: 20 mL/min. Fractions containing the desired product were combined and dried via centrifugal evaporation to provide Example 115 (26.2 mg, 50%). HPLC Rt=0.725 min (Waters Acquity UPLC BEH C18, 2.1×50 mm, 1.7-µm particles; 5-95% MeCN—H2O with 0.1% TFA over 3 min; wavelength=220 nm); LC-MS m/z 433 [M+H]+; 1H NMR (500 MHz, DMSO-d6) δ 11.84 (s, 1H), 9.91 (s, 1H), 8.30 (s, 1H), 8.25 (d, J=5.2 Hz, 1H), 8.20-8.17 (m, 2H), 7.95 (d, J=8.6 Hz, 1H), 7.48 (dd, J=8.7, 2.9 Hz, 1H), 7.35 (d, J=2.4 Hz, 1H), 7.15 (d, J=5.1 Hz, 1H), 3.88 (s, 3H), 3.84 (s, 3H), 3.11 (s, 2H), 2.29 (s, 6H)

Example 116

2-(Dimethylamino)-N-{4-[6-methoxy-3-(6-methylpyridin-2-yl)-1H-pyrrolo[3,2-b]pyridin-2-yl]pyridin-2-yl}acetamide

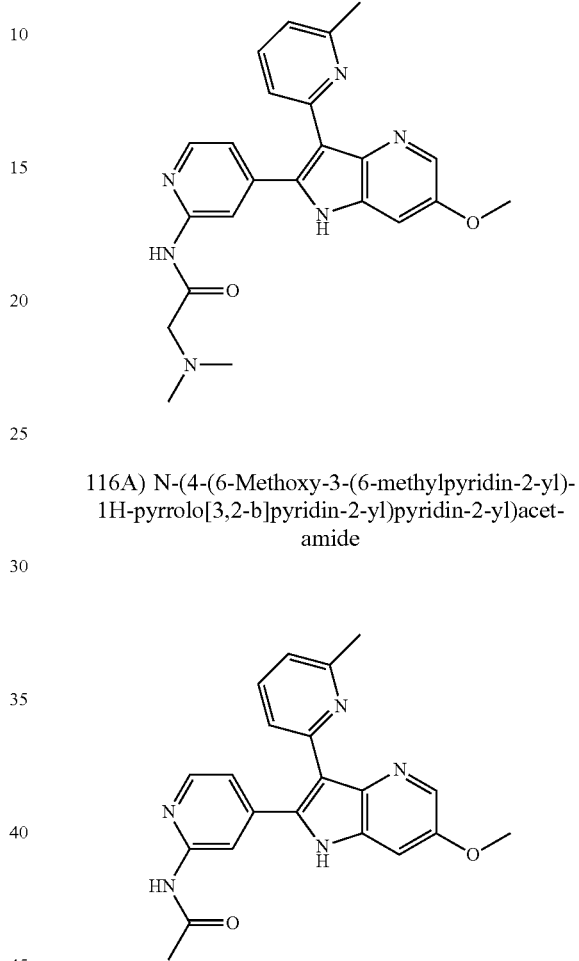

116A) N-(4-(6-Methoxy-3-(6-methylpyridin-2-yl)-1H-pyrrolo[3,2-b]pyridin-2-yl)pyridin-2-yl)acetamide A mixture of Example 48B (0.360 g, 0.952 mmol) and cesium carbonate (0.620 g, 1.903 mmol) was evacuated and backfilled with N2, then MeCN (9.52 mL) and 2-bromo-6-methylpyridine (0.327 g, 1.903 mmol) were added. The mixture was sparged with N2 for 5 min, then tetrakis(triphenylphosphine)palladium(0) (0.055 g, 0.048 mmol) was added. The reaction was sparged with N2 for 1 min, then it was sealed and stirred at 110° C. for 2 h. The reaction was cooled to room temperature, diluted with 10% MeOH—CH2Cl2 (10 mL), and filtered through Celite (washed with 10% MeOH—CH2Cl2). The filtrate was concentrated in vacuo. The crude material was purified by flash chromatography (24 g silica gel with 5 g prepacked load cartridge; linear gradient 0-10% MeOH—CH2Cl2) to provide Example 116A (172 mg, 48%) as an off-white solid. LC-MS m/z 374 [M+H]+; 1H NMR (400 MHz, DMSO-d6) δ 11.83 (s, 1H), 10.47 (s, 1H), 8.34 (s, 1H), 8.25 (dd, J=5.2, 0.7 Hz, 1H), 8.21 (d, J=2.7 Hz, 1H), 7.88 (d, J=7.7 Hz, 1H), 7.71 (t, J=7.7 Hz, 1H), 7.34 (d, J=2.6 Hz, 1H), 7.19 (dd, J=5.3, 1.6 Hz, 1H), 7.10 (d, J=7.6 Hz, 1H), 3.89 (s, 3H), 2.30 (s, 3H), 2.09 (s, 3H).

116B) 4-(6-Methoxy-3-(6-methylpyridin-2-yl)-1H-pyrrolo[3,2-b]pyridin-2-yl)pyridin-2-amine

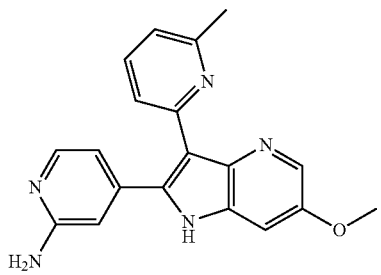 [SMILES: COc1cnc2c(-c3cccc(C)n3)c(-c3ccnc(N)c3)[nH]c2c1]

To a room temperature solution of Example 116A (171 mg, 0.458 mmol) in MeOH (4579 μL) was added sodium hydroxide (4579 μL, 1 M solution in H$_2$O, 4.58 mmol). The reaction was sealed and stirred at 80° C. for 2 h, and then it was cooled to room temperature and partially concentrated under a stream of N$_2$ to remove most of the MeOH, causing precipitation of solids. The mixture was diluted with H$_2$O (10 mL) and the solids were collected by vacuum filtration (washed with H$_2$O) to provide Example 116B (117 mg, 77%) as a yellow solid. LC-MS m/z 332 [M+H]$^+$; $^1$H NMR (400 MHz, DMSO-d$_6$) δ 11.68 (s, 1H), 8.17 (d, J=2.7 Hz, 1H), 7.86 (d, J=5.4 Hz, 1H), 7.79-7.76 (m, 1H), 7.69 (t, J=7.7 Hz, 1H), 7.30 (d, J=2.6 Hz, 1H), 7.10 (d, J=7.2 Hz, 1H), 6.68-6.64 (m, 1H), 6.56 (dd, J=5.4, 1.5 Hz, 1H), 5.91 (s, 2H), 3.88 (s, 3H), 2.36 (s, 3H).

Example 116) 2-(Dimethylamino)-N-{4-[6-methoxy-3-(6-methylpyridin-2-yl)-1H-pyrrolo[3,2-b]pyridin-2-yl]pyridin-2-yl}acetamide

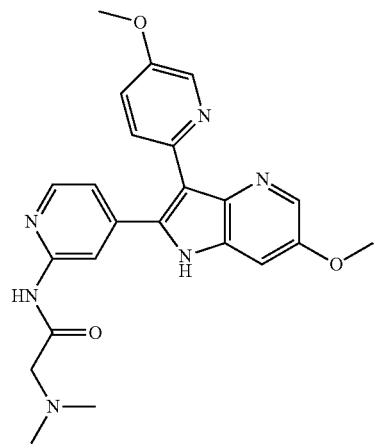 [SMILES: COc1ccc(-c2c(-c3ccnc(NC(=O)CN(C)C)c3)[nH]c3cc(OC)cnc23)nc1]

To a room temperature solution of Example 116B (30.7 mg, 0.093 mmol) and 2-(dimethylamino)acetic acid (13.37 mg, 0.130 mmol) in DMF (185 μL) was added N,N-diisopropylethylamine (81 μL, 0.463 mmol) and HATU (49.3 mg, 0.130 mmol). The reaction was stirred at room temperature for 18 h, and then it was diluted with DMF, filtered, and purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 20 minutes, then a 5-minute hold at 100% B; Flow: 20 mL/min. Fractions containing the desired product were combined and dried via centrifugal evaporation to provide Example 116 (19.8 mg, 51%). HPLC Rt=0.710 min (Waters Acquity UPLC BEH C18, 2.1×50 mm, 1.7-μm particles; 5-95% MeCN H$_2$O with 0.1% TFA over 3 min; wavelength=220 nm); LC-MS 417 [M+H]$^+$; $^1$H NMR (500 MHz, DMSO-d$_6$) δ 11.90 (s, 1H), 9.97 (br s, 1H), 8.34 (s, 1H), 8.27 (d, J=5.2 Hz, 1H), 8.20 (d, J=2.5 Hz, 1H), 7.87 (d, J=7.7 Hz, 1H), 7.71 (t, J=7.7 Hz, 1H), 7.36 (d, J=2.4 Hz, 1H), 7.24 (d, J=4.2 Hz, 1H), 7.10 (d, J=7.7 Hz, 1H), 3.88 (s, 3H), 3.18 (s, 2H), 2.33 (s, 6H), 2.29 (s, 3H).

Example 117

N-(4-{3-[6-(Difluoromethyl)pyridin-2-yl]-6-methoxy-1H-pyrrolo[3,2-b]pyridin-2-yl}pyridin-2-yl)-2-(dimethylamino)acetamide

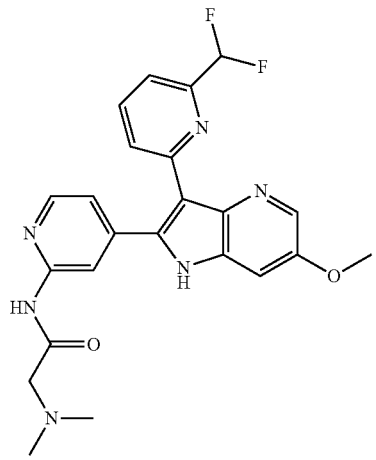 [SMILES: COc1cnc2c(-c3cccc(C(F)F)n3)c(-c3ccnc(NC(=O)CN(C)C)c3)[nH]c2c1]

117A) N-(4-(3-(6-(Difluoromethyl)pyridin-2-yl)-6-methoxy-1H-pyrrolo[3,2-b]pyridin-2-yl)pyridin-2-yl)acetamide

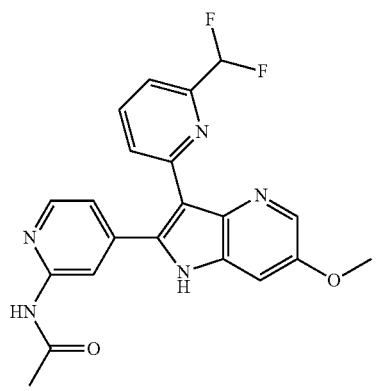 [SMILES: COc1cnc2c(-c3cccc(C(F)F)n3)c(-c3ccnc(NC(C)=O)c3)[nH]c2c1]

A mixture of Example 48B (0.360 g, 0.952 mmol) and cesium carbonate (0.620 g, 1.903 mmol) was evacuated and backfilled with N$_2$, then MeCN (9.52 mL) and 2-bromo-6-(difluoromethyl)pyridine (0.396 g, 1.903 mmol) were added.

The mixture was sparged with N₂ for 5 min, then tetrakis(triphenylphosphine)palladium(0) (0.055 g, 0.048 mmol) was added. The reaction was sparged with N₂ for 1 min, then it was sealed and stirred at 110° C. for 2 h. The reaction was cooled to room temperature, diluted with 10% MeOH—CH₂Cl₂ (10 mL), and filtered through Celite (washed with 10% MeOH—CH₂Cl₂). The filtrate was concentrated in vacuo. The crude material was purified by flash chromatography (24 g silica gel with 5 g prepacked load cartridge; linear gradient 0-10% MeOH—CH₂Cl₂) to provide Example 117A (194 mg, 50%) as an off-white solid. LC-MS m/z 410 [M+H]⁺; ¹H NMR (400 MHz, DMSO-d₆) δ 12.00 (s, 1H), 10.49 (s, 1H), 8.35-8.30 (m, 2H), 8.27 (dd, J=5.3, 0.6 Hz, 1H), 8.24 (d, J=2.7 Hz, 1H), 8.05 (t, J=7.9 Hz, 1H), 7.54 (d, J=7.6 Hz, 1H), 7.37 (d, J=2.6 Hz, 1H), 7.21 (dd, J=5.1, 1.6 Hz, 1H), 6.66 (t, J=55.4 Hz, 1H), 3.90 (s, 3H), 2.08 (s, 3H).

117B) 4-(3-(6-(Difluoromethyl)pyridin-2-yl)-6-methoxy-1H-pyrrolo[3,2-b]pyridin-2-yl)pyridin-2-amine

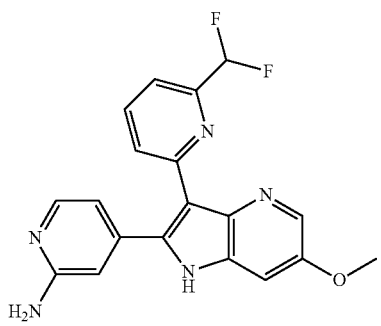 [SMILES: COc1cnc2c(-c3cccc(C(F)F)n3)c(-c3ccnc(N)c3)[nH]c2c1]

To a room temperature solution of Example 117A (193 mg, 0.471 mmol) in MeOH (4714 μL) was added sodium hydroxide (4714 μL, 1 M solution in H₂O, 4.71 mmol). The reaction was sealed and stirred at 80° C. for 2 h, and then it was cooled to room temperature, causing the precipitation of solids. The mixture was diluted with H₂O (10 mL) and the solids were collected by vacuum filtration (washed with H₂O) to provide Example 117B (133 mg, 77%) as an off-white solid. LC-MS m/z 368 [M+H]⁺; ¹H NMR (400 MHz, DMSO-d₆) δ 11.85 (s, 1H), 8.24-8.20 (m, 2H), 8.03 (t, J=7.8 Hz, 1H), 7.88-7.86 (m, 1H), 7.54 (d, J=7.5 Hz, 1H), 7.33 (d, J=2.6 Hz, 1H), 6.70-6.68 (m, 1H), 6.72 (t, J=55.1 Hz, 1H), 6.57 (dd, J=5.4, 1.5 Hz, 1H), 5.93 (s, 2H), 3.89 (s, 3H).

Example 117) N-(4-{3-[6-(Difluoromethyl)pyridin-2-yl]-6-methoxy-1H-pyrrolo[3,2-b]pyridin-2-yl}pyridin-2-yl)-2-(dimethylamino)acetamide

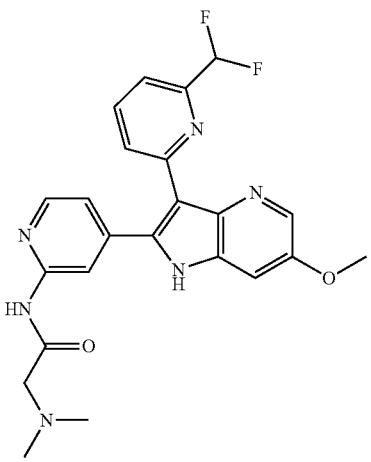 [SMILES: COc1cnc2c(-c3cccc(C(F)F)n3)c(-c3ccnc(NC(=O)CN(C)C)c3)[nH]c2c1]

To a room temperature suspension of Example 117B (33.6 mg, 0.091 mmol) and 2-(dimethylamino)acetic acid (13.20 mg, 0.128 mmol) in DMF (183 μL) was added N,N-diisopropylethylamine (80 μL, 0.457 mmol) and HATU (48.7 mg, 0.128 mmol). The reaction was stirred at room temperature for 18 h, and then it was diluted with DMF, filtered, and purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 15-55% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μM particles; Mobile Phase A: 5:95 acetonitrile: water with 10-mM ammonium acetate; Mobile Phase B: 95:5 acetonitrile: water with 10-mM ammonium acetate; Gradient: 20-60% B over 20 minutes, then a 3-minute hold at 100% B; Flow: 20 mL/min. Fractions containing the desired product were combined and dried via centrifugal evaporation to provide Example 117 (10.7 mg, 26%). HPLC Rt=0.817 min (Waters Acquity UPLC BEH C18, 2.1×50 mm, 1.7-μm particles; 5-95% MeCN—H₂O with 0.1% TFA over 3 min; wavelength=220 nm); LC-MS m/z 453 [M+H]⁺; ¹H NMR (500 MHz, DMSO-d₆) δ 12.06 (s, 1H), 9.91 (br s, 1H), 8.35 (s, 1H), 8.32 (d, J=8.0 Hz, 1H), 8.29 (d, J=5.2 Hz, 1H), 8.25 (d, J=2.4 Hz, 1H), 8.05 (t, J=7.8 Hz, 1H), 7.54 (d, J=7.7 Hz, 1H), 7.39 (d, J=2.5 Hz, 1H), 7.27 (d, J=4.3 Hz, 1H), 6.66 (t, J=55.3 Hz, 1H), 3.90 (s, 3H), 3.10 (s, 2H), 2.29 (s, 6H).

TABLE 3

| Example | Structure | Name | HPLC ret. time (min)[a] | MS m/z [M + H]+ |
|---|---|---|---|---|
| 118 | 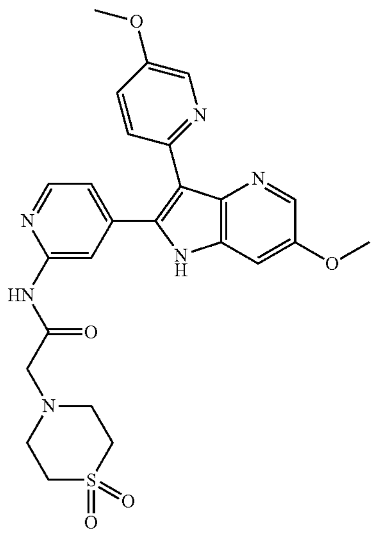 [SMILES: COc1ccc(-c2c(-c3ccnc(NC(=O)CN4CCS(=O)(=O)CC4)c3)[nH]c3cc(OC)cnc23)nc1] | 2-(1,1-Dioxidothiomorpholino)-N-{4-[6-methoxy-3-(5-methoxypyridin-2-yl)-1H-pyrrolo[3,2-b]pyridin-2-yl]pyridin-2-yl}acetamide | 0.876 | 523 |
| 119 | 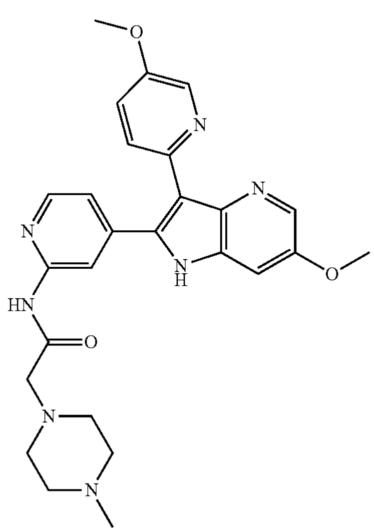 [SMILES: COc1ccc(-c2c(-c3ccnc(NC(=O)CN4CCN(C)CC4)c3)[nH]c3cc(OC)cnc23)nc1] | N-{4-[6-Methoxy-3-(5-methoxypyridin-2-yl)-1H-pyrrolo[3,2-b]pyridin-2-yl]pyridin-2-yl}-2-(4-methylpiperazin-1-yl)acetamide | 0.758 | 488 |

TABLE 3-continued
| Example | Structure | Name | HPLC ret. time (min)[a] | MS m/z [M + H]+ |
|---|---|---|---|---|
| 120 | 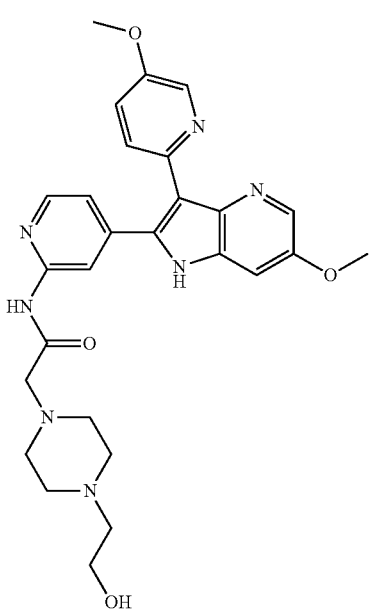 [SMILES: COc1ccc(-c2c(-c3ccnc(NC(=O)CN4CCN(CCO)CC4)c3)[nH]c3cc(OC)cnc23)nc1] | 2-[4-(2-Hydroxyethyl)piperazin-1-yl]-N-{4-[6-methoxy-3-(5-methoxypyridin-2-yl)-1H-pyrrolo[3,2-b]pyridin-2-yl]pyridin-2-yl}acetamide | 0.754 | 518 |
| 121 | 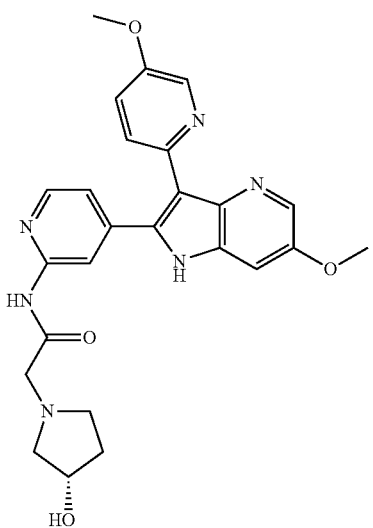 [SMILES: COc1ccc(-c2c(-c3ccnc(NC(=O)CN4CC[C@H](O)C4)c3)[nH]c3cc(OC)cnc23)nc1] | 2-[(3S)-3-Hydroxypyrrolidin-1-yl]-N-{4-[6-methoxy-3-(5-methoxypyridin-2-yl)-1H-pyrrolo[3,2-b]pyridin-2-yl]pyridin-2-yl}acetamide | 0.725 | 475 |

TABLE 3-continued

| Example | Structure | Name | HPLC ret. time (min)[a] | MS m/z [M + H]+ |
|---|---|---|---|---|
| 122 | 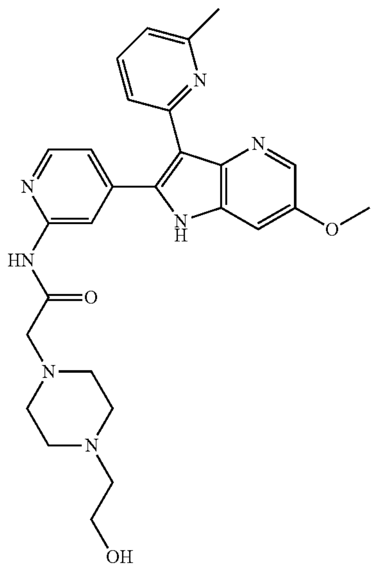 [SMILES: COc1cnc2c(-c3cccc(C)n3)c(-c3ccnc(NC(=O)CN4CCN(CCO)CC4)c3)[nH]c2c1] | 2-[4-(2-Hydroxyethyl)piperazin-1-yl]-N-{4-[6-methoxy-3-(6-methylpyridin-2-yl)-1H-pyrrolo[3,2-b]pyridin-2-yl]pyridin-2-yl}acetamide | 0.738 | 502 |
| 123 | 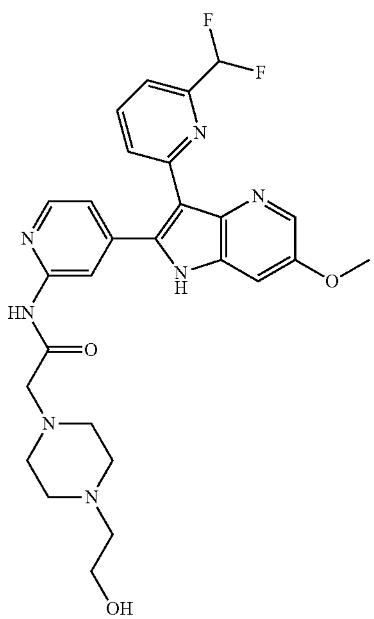 [SMILES: COc1cnc2c(-c3cccc(C(F)F)n3)c(-c3ccnc(NC(=O)CN4CCN(CCO)CC4)c3)[nH]c2c1] | N-(4-{3-[6-(Difluoromethyl)pyridin-2-yl]-6-methoxy-1H-pyrrolo[3,2-b]pyridin-2-yl}pyridin-2-yl)-2-[4-(2-hydroxyethyl)piperazin-1-yl]acetamide | 0.842 | 538 |

[a]HPLC conditions: Waters Acquity UPLC BEH C18, 2.1 × 50 mm, 1.7-µm particles; 5-95% MeCN—$H_2O$ with 0.1% TFA over 3 min; wavelength = 220 nm.

Examples 118-123 in Table 3 were prepared from either Example 115B, Example 116B, or Example 117B using procedures similar to those used for the preparation of Example 115.

Example 124

Methyl N-{4-[6-methoxy-3-(5-methoxypyridin-2-yl)-1H-pyrrolo[3,2-b]pyridin-2-yl]pyridin-2-yl}carbamate

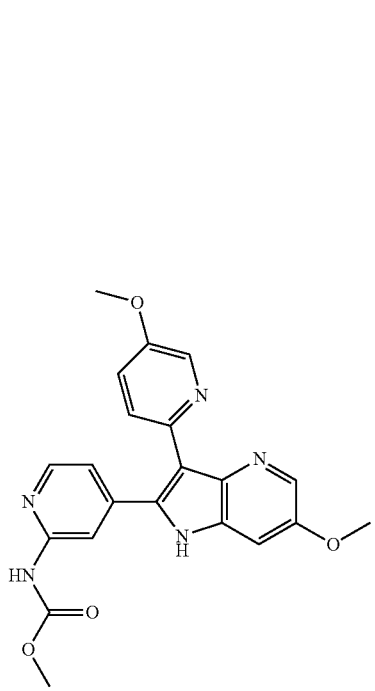 [SMILES: COC(=O)Nc1cc(-c2[nH]c3cc(OC)cnc3c2-c2ccc(OC)cn2)ccn1]

To a 0° C. suspension of Example 115B (32 mg, 0.092 mmol) in CH$_2$Cl$_2$ (921 μL) was added triethylamine (51.4 μL, 0.368 mmol), followed by methyl chloroformate (10.68 μL, 0.138 mmol), dropwise. The reaction was stirred at 0° C. for 5 min, then it was warmed to room temperature and stirred for 18 h. Additional methyl chloroformate (3.6 μL, 0.046 mmol) was added and the reaction was stirred at room temperature for 1 h. Additional methyl chloroformate (3.6 μL, 0.046 mmol) was added and the reaction was stirred at room temperature for 1 h. The reaction was diluted with MeOH (920 μL) and ammonium hydroxide (200 μL), stirred for 3 h, and then concentrated in vacuo. The crude material was triturated with CH$_2$Cl$_2$ to provide Example 124 (23.3 mg, 61%) as a white solid. HPLC Rt=5.27 min (Sunfire C18, 3.0×150 mm, 3.5-μm particles; 5-95% MeCN—H$_2$O with 0.05% TFA over 12 min; wavelength=220 nm); LC-MS m/z 406 [M+H]$^+$; $^1$H NMR (400 MHz, DMSO-d$_6$) δ 11.77 (s, 1H), 10.16 (s, 1H), 8.22-8.18 (m, 3H), 8.03 (s, 1H), 7.95 (d, J=8.7 Hz, 1H), 7.48 (dd, J=8.7, 3.1 Hz, 1H), 7.33 (d, J=2.6 Hz, 1H), 7.08 (dd, J=5.2, 1.5 Hz, 1H), 3.89 (s, 3H), 3.86 (s, 3H), 3.66 (s, 3H).

Example 125

N-(4-{3-[6-(Difluoromethyl)pyridin-2-yl]-7-ethoxy-1H-pyrrolo[3,2-b]pyridin-2-yl}-pyridin-2-yl)acetamide

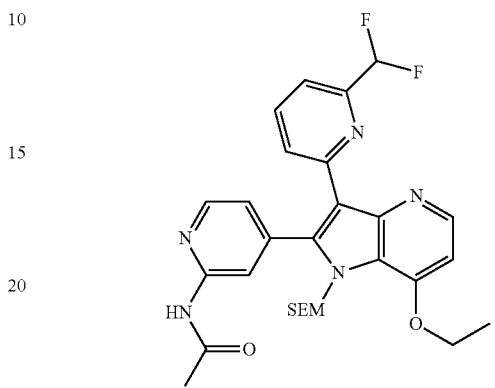

125A) N-(4-(7-Chloro-3-(6-(difluoromethyl)pyridin-2-yl)-1H-pyrrolo[3,2-b]pyridin-2-yl)pyridin-2-yl) acetamide

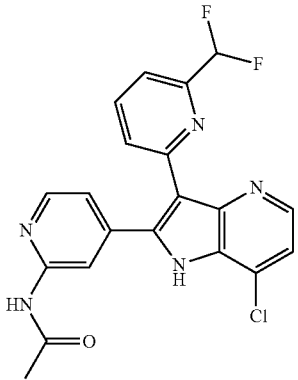 [SMILES: CC(=O)Nc1cc(-c2[nH]c3c(Cl)ccnc3c2-c2cccc(C(F)F)n2)ccn1]

A mixture of Example 61C (1.273 g, 3.33 mmol) and cesium carbonate (2.167 g, 6.65 mmol) was evacuated and backfilled with N$_2$, then DMF (13.30 mL) and 2-bromo-6-(difluoromethyl)pyridine (1.384 g, 6.65 mmol) were added. The mixture was sparged with N$_2$ for 5 min, then 2nd generation XPhos precatalyst (0.131 g, 0.166 mmol) was added. The reaction was sparged with N$_2$ for 2 min, then it was sealed and stirred at 120° C. for 2 h. The reaction was cooled to room temperature, diluted with THF (20 mL), filtered through Celite (washed with 60 mL THF followed by 100 mL 20% MeOH—CH$_2$Cl$_2$), and concentrated in vacuo. The residue was suspended in CH$_2$Cl$_2$ (25 mL) and the solids were collected by vacuum filtration (washed with 10 mL CH$_2$Cl$_2$) to provide crude Example 125A, which was used without further purification. LC-MS m/z 414 [M+H]$^+$.

125B) N-(4-(7-Chloro-3-(6-(difluoromethyl)pyridin-2-yl)-1-((2-(trimethylsilyl)ethoxy)methyl)-1H-pyrrolo[3,2-b]pyridin-2-yl)pyridin-2-yl)acetamide

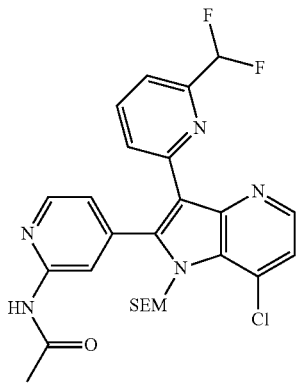 [SMILES: CC(=O)Nc1cc(-c2c(-c3cccc(C(F)F)n3)c3nccc(Cl)c3n2COCC[Si](C)(C)C)ccn1]

To a room temperature solution of crude Example 125A in THF (26.3 mL) and DMF (26.3 mL) was added cesium carbonate (3.43 g, 10.53 mmol), followed by 2-(trimethylsilyl)ethoxymethyl chloride (1.400 mL, 7.89 mmol), dropwise. The reaction was stirred at room temperature for 1 h, and then it was diluted with EtOAc (400 mL), washed with H$_2$O (400 mL) and sat. aq. NaCl (400 mL), dried over Na$_2$SO$_4$, filtered, and concentrated in vacuo. The crude material was purified by flash chromatography (40 g silica gel with 5 g prepacked load cartridge; linear gradient 0-100% EtOAc-CH$_2$Cl$_2$) to provide Example 125B (620 mg, 34% over two steps) as a yellow foam. LC-MS m/z 544 [M+H]$^+$; $^1$H NMR (400 MHz, DMSO-d$_6$) δ 10.60 (s, 1H), 8.50 (d, J=5.1 Hz, 1H), 8.43 (dd, J=8.0, 0.8 Hz, 1H), 8.38 (dd, J=5.1, 0.7 Hz, 1H), 8.22 (s, 1H), 8.03 (t, J=7.8 Hz, 1H), 7.52 (d, J=5.0 Hz, 1H), 7.49 (d, J=7.6 Hz, 1H), 7.16 (dd, J=5.1, 1.5 Hz, 1H), 6.45 (t, J=55.1 Hz, 1H), 5.65 (s, 2H), 3.33-3.27 (m, 2H), 2.07 (s, 3H), 0.75-0.66 (m, 2H), −0.14 (s, 9H).

125C) N-(4-(3-(6-(Difluoromethyl)pyridin-2-yl)-7-hydroxy-1-((2-(trimethylsilyl)ethoxy)methyl)-1H-pyrrolo[3,2-b]pyridin-2-yl)pyridin-2-yl)acetamide

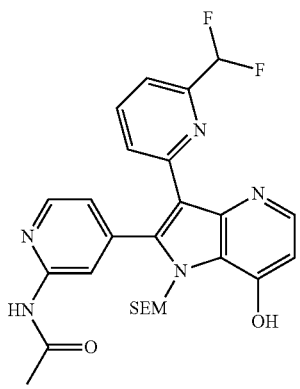 [SMILES: CC(=O)Nc1cc(-c2c(-c3cccc(C(F)F)n3)c3nccc(O)c3n2COCC[Si](C)(C)C)ccn1]

A mixture of Example 125B (20 mg, 0.037 mmol) and cesium carbonate (35.9 mg, 0.110 mmol) was evacuated and backfilled with N$_2$, then 1,4-dioxane (331 μL) and H$_2$O (36.8 μL) were added. The mixture was sparged with N$_2$ for 5 min, then 2nd generation XPhos precatalyst (1.446 mg, 1.838 μmol) was added. The mixture was sparged with N$_2$ for 1 min, then it was sealed and stirred at 100° C. for 4 h. Additional Cs$_2$CO$_3$ (36 mg, 0.11 mmol) and H$_2$O (74 μL) were added and the reaction was sparged with N$_2$ for 5 min, then additional 2nd generation XPhos precatalyst (3 mg, 0.038 mmol) was added. The reaction was sparged with N$_2$ for 1 min, then it was sealed and stirred at 100° C. for 20 h. The reaction was cooled to room temperature, diluted with EtOAc (25 mL), washed with sat. aq. NaCl (25 mL), dried over Na$_2$SO$_4$, filtered, and concentrated in vacuo. The crude material was purified by flash chromatography (12 g silica gel with 5 g prepacked load cartridge; linear gradient 0-10% MeOH—CH$_2$Cl$_2$) to provide Example 125C (5.9 mg, 31%) as a white solid. LC-MS m/z 526 [M+H]$^+$.

125D) N-(4-(3-(6-(Difluoromethyl)pyridin-2-yl)-7-ethoxy-1-((2-(trimethylsilyl)ethoxy)methyl)-1H-pyrrolo[3,2-b]pyridin-2-yl)pyridin-2-yl)acetamide

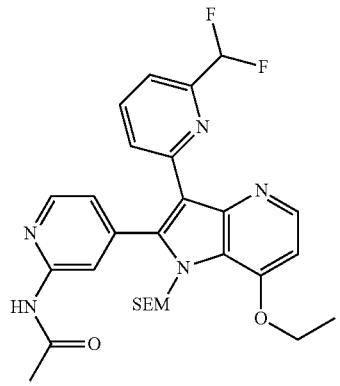 [SMILES: CCOc1ccnc2c(-c3cccc(C(F)F)n3)c(-c3ccnc(NC(C)=O)c3)n(COCC[Si](C)(C)C)c12]

To a 0° C. solution of Example 125C (10.6 mg, 0.020 mmol) in 1,4-dioxane (202 μL) was added triphenylphosphine (6.35 mg, 0.024 mmol) and ethanol (23.55 μL, 0.403 mmol), followed by diisopropyl azodicarboxylate (4.76 μL, 0.024 mmol), dropwise. The reaction was stirred at room temperature for 30 min, then at 50° C. for 1 h. The reaction was cooled to room temperature and concentrated in vacuo. The crude material was purified by flash chromatography (12 g silica gel with 5 g prepacked load cartridge; linear gradient 0-100% EtOAc-CH$_2$Cl$_2$) to provide Example 125D (8.8 mg, 79%) as a yellow film. LC-MS m/z 554 [M+H]$^+$.

Example 125) N-(4-{3-[6-(Difluoromethyl)pyridin-2-yl]-7-ethoxy-1H-pyrrolo[3,2-b]pyridin-2-yl}pyridin-2-yl)acetamide

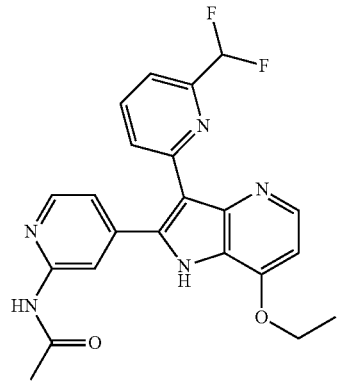 [SMILES: CCOc1ccnc2c(-c3cccc(C(F)F)n3)c(-c3ccnc(NC(C)=O)c3)[nH]c12]

To a room temperature solution of Example 125D (8.8 mg, 0.016 mmol) in CH$_2$Cl$_2$ (79 µL) was added TFA (79 µL). The clear yellow solution was stirred at room temperature for 1 h. Additional TFA (79 µL) was added and the reaction was stirred at room temperature for 5 h. The reaction was concentrated in vacuo. The residue was taken up in 10% 7N NH$_3$/MeOH in CH$_2$Cl$_2$ (500 µL), stirred at room temperature for 1 h, and then it was concentrated in vacuo. The crude material was purified by flash chromatography (4 g silica gel; linear gradient 0-20% MeOH—CH$_2$Cl$_2$) to provide Example 125 (3.6 mg, 53%) as a white solid. HPLC Rt=6.03 min (Sunfire C18, 3.0×150 mm, 3.5-µm particles; 5-95% MeCN—H$_2$O with 0.05% TFA over 12 min; wavelength=220 nm); LC-MS m/z 424 [M+H]$^+$; $^1$H NMR (400 MHz, DMSO-d$_6$) δ 12.21 (s, 1H), 10.47 (s, 1H), 8.41 (d, J=7.9 Hz, 1H), 8.35-8.29 (m, 2H), 8.26 (d, J=5.1 Hz, 1H), 8.03 (t, J=7.8 Hz, 1H), 7.50 (d, J=7.6 Hz, 1H), 7.22 (dd, 1.5 Hz, 1H), 6.91 (d, J=5.4 Hz, 1H), 6.60 (t, J=55.4 Hz, 1H), 4.36 (q, J=7.0 Hz, 2H), 2.07 (s, 3H), 1.49 (t, J=7.0 Hz, 3H).

Example 126

N-(4-{3-[6-(Difluoromethyl)pyridin-2-yl]-7-[2-(pyrrolidin-1-yl)ethoxy]-1H-pyrrolo[3,2-b]pyridin-2-yl}pyridin-2-yl)acetamide

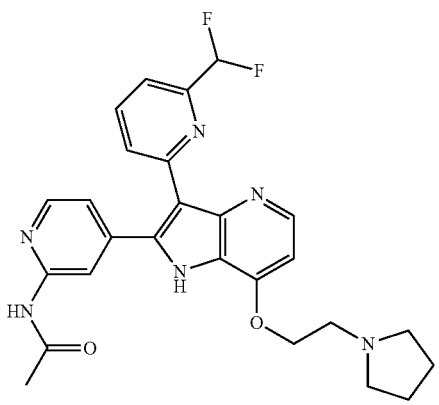 [SMILES: CC(=O)Nc1cc(-c2[nH]c3c(OCCN4CCCC4)ccnc3c2-c2cccc(C(F)F)n2)ccn1]

126A) N-(4-(3-(6-(Difluoromethyl)pyridin-2-yl)-7-(2-(pyrrolidin-1-yl)ethoxy)-1-((2-(trimethylsilyl)ethoxy)methyl)-1H-pyrrolo[3,2-b]pyridin-2-yl)pyridin-2-yl)acetamide

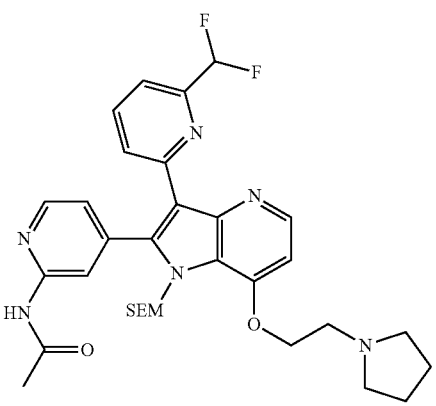 [SMILES: CC(=O)Nc1cc(-c2c(-c3cccc(C(F)F)n3)c3nccc(OCCN4CCCC4)c3n2COCC[Si](C)(C)C)ccn1]

To a 0° C. suspension of Example 125C (21.3 mg, 0.041 mmol) in 1,4-dioxane (405 µL) was added triphenylphosphine (13.82 mg, 0.053 mmol) and 2-(pyrrolidin-1-yl)ethanol (9.48 µL, 0.081 mmol), followed by diisopropyl azodicarboxylate (10.37 µL, 0.053 mmol), dropwise. The reaction was stirred at room temperature for 10 min, then at 50° C. for 50 min. The reaction was cooled to room temperature and concentrated in vacuo. The crude material was purified by flash chromatography (12 g silica gel with 5 g prepacked load cartridge; linear gradient 0-10% MeOH—CH$_2$Cl$_2$) to provide Example 126A (11.0 mg, 44%) as a white solid. LC-MS m/z 623 [M+H]$^+$.

Example 126) N-(4-{3-[6-(Difluoromethyl)pyridin-2-yl]-7-[2-(pyrrolidin-1-yl)ethoxy]-1H-pyrrolo[3,2-b]pyridin-2-yl}pyridin-2-yl)acetamide

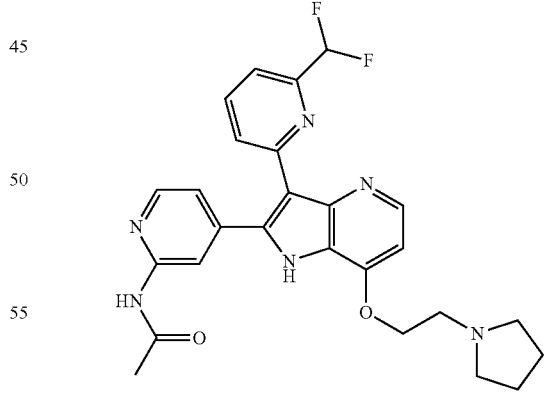

To a room temperature solution of Example 126A (11.0 mg, 0.018 mmol) in CH$_2$Cl$_2$ (58.9 µL) was added TFA (118 µL). The reaction was stirred at room temperature for 17 h, and then it was concentrated in vacuo. The residue was taken up in 10% 7 N NH$_3$/MeOH in CH$_2$Cl$_2$ (2 mL), stirred at room temperature for 5 min, and then concentrated in vacuo, dissolved in DMSO, filtered, and purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 19 minutes, then a 5-minute hold at 100% B; Flow: 20 mL/min. Fractions containing the desired product were combined and dried via centrifugal evaporation to provide Example 126 (15.4 mg). HPLC Rt=0.818 min (Waters Acquity UPLC BEH C18, 2.1×50 mm, 1.7-μm particles; 5-95% MeCN—H$_2$O with 0.1% TFA over 3 min; wavelength=220 nm); LC-MS m/z 493 [M+H]$^+$; $^1$H NMR (500 MHz, DMSO-d$_6$) δ 10.43 (s, 1H), 8.31 (d, J=4.9 Hz, 1H), 8.29-8.23 (m, 3H), 8.02 (t, J=8.0 Hz, 1H), 7.51 (d, J=8.0 Hz, 1H), 7.22 (d, J=5.2 Hz, 1H), 6.91 (d, J=5.3 Hz, 1H), 6.61 (dd, J=55.4, 54.8 Hz, 1H), 4.36 (br t, J=5.3 Hz, 2H), 2.99-2.94 (m, 2H), 2.62-2.57 (m, 4H), 2.04 (s, 3H), 1.74-1.69 (m, 4H).

Example 127

N-(4-{3-[6-(Difluoromethyl)pyridin-2-yl]-7-ethenyl-1H-pyrrolo[3,2-b]pyridin-2-yl}pyridin-2-yl)acetamide

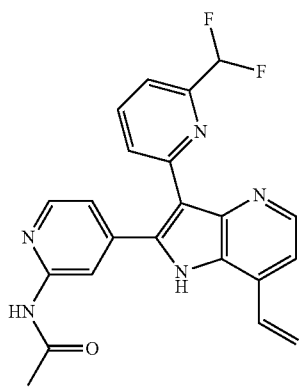 [SMILES: C=Cc1ccnc2c(-c3cccc(C(F)F)n3)c(-c3ccnc(NC(C)=O)c3)[nH]c12]

127A) N-(4-(3-(6-(Difluoromethyl)pyridin-2-yl)-1-((2-(trimethylsilyl)ethoxy)methyl)-7-vinyl-1H-pyrrolo[3,2-b]pyridin-2-yl)pyridin-2-yl)acetamide

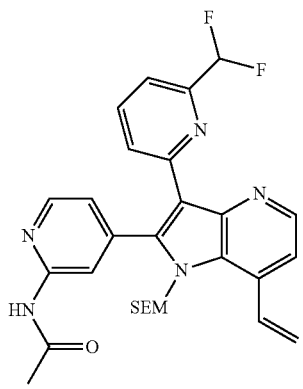 [SMILES: C=Cc1ccnc2c(-c3cccc(C(F)F)n3)c(-c3ccnc(NC(C)=O)c3)n(COCC[Si](C)(C)C)c12]

A mixture of Example 125B (307 mg, 0.564 mmol), potassium vinyltrifluoroborate (113 mg, 0.846 mmol), and cesium carbonate (552 mg, 1.693 mmol) was evacuated and backfilled with N$_2$, then 1,4-dioxane (5078 μL) and H$_2$O (564 μL) were added. The mixture was sparged with N$_2$ for 5 min, then 2nd generation XPhos precatalyst (22.20 mg, 0.028 mmol) was added. The mixture was sparged with N$_2$ for 1 min, then it was sealed and stirred at 80° C. for 1 h. The reaction was cooled to room temperature, diluted with EtOAc (50 mL), washed with sat. aq. NaCl (50 mL), dried over Na$_2$SO$_4$, filtered, and concentrated in vacuo. The crude material was purified by flash chromatography (24 g silica gel with 5 g prepacked load cartridge; linear gradient 0-100% EtOAc-CH$_2$Cl$_2$) to provide Example 127A (270 mg, 0.504 mmol, 89%) as a yellow foam. LC-MS m/z 536 [M+H]$^+$; $^1$H NMR (400 MHz, DMSO-d$_6$) δ 10.60 (s, 1H), 8.56-8.50 (m, 2H), 8.37 (dd, J=5.0, 0.7 Hz, 1H), 8.22 (s, 1H), 8.01 (t, J=7.8 Hz, 1H), 7.52 (dd, J=17.3, 10.9 Hz, 1H), 7.46 (d, J=7.6 Hz, 1H), 7.43 (d, J=4.9 Hz, 1H), 7.13 (dd, 1.5 Hz, 1H), 6.41 (t, J=55.4 Hz, 1H), 6.04 (dd, J=17.2, 1.2 Hz, 1H), 5.70-5.63 (m, 1H), 5.39 (s, 2H), 3.35-3.26 (m, 2H), 2.07 (s, 3H), 0.78-0.73 (m, 2H), −0.12 (s, 9H).

Example 127) N-(4-{3-[6-(Difluoromethyl)pyridin-2-yl]-7-ethenyl-1H-pyrrolo[3,2-b]pyridin-2-yl}pyridin-2-yl)acetamide

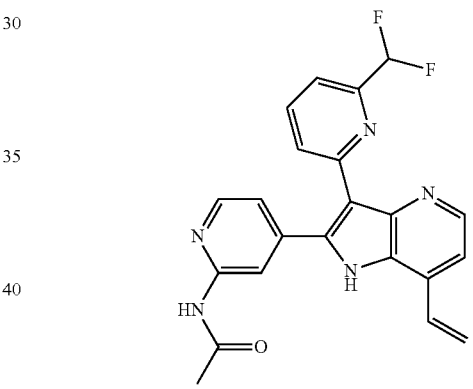

To a room temperature solution of Example 127A (17.1 mg, 0.032 mmol) in CH$_2$Cl$_2$ (106 μL) was added TFA (213 μL). The reaction was stirred at room temperature for 7 h, and then it was concentrated in vacuo. The residue was taken up in 10% 7 N NH$_3$/MeOH in CH$_2$Cl$_2$ (500 μL), stirred at room temperature for 1 h, and then it was concentrated in vacuo. The crude material was purified by flash chromatography (12 g silica gel with 5 g prepacked load cartridge; linear gradient 0-20% MeOH—CH$_2$Cl$_2$). The resulting material was repurified by flash chromatography (12 g silica gel with 5 g prepacked load cartridge; linear gradient 0-10% MeOH—CH$_2$Cl$_2$) to provide Example 127 (7.2 mg, 55%) as a white solid. HPLC Rt=6.19 min (Sunfire C18, 3.0×150 mm, 3.5-μm particles; 5-95% MeCN—H$_2$O with 0.05% TFA over 12 min; wavelength=220 nm); LC-MS m/z 406 [M+H]$^+$; $^1$H NMR (400 MHz, DMSO-d$_6$) δ 12.15 (s, 1H), 10.52 (s, 1H), 8.46 (d, J=4.9 Hz, 1H), 8.42 (d, J=7.9 Hz, 1H), 8.36-8.30 (m, 2H), 8.05 (t, J=7.8 Hz, 1H), 7.54-7.50 (m, 2H), 7.46 (dd, J=17.6, 11.0 Hz, 1H), 7.27 (dd, J=5.1, 1.6 Hz, 1H), 6.62 (t, J=55.1 Hz, 1H), 6.29 (d, J=17.7 Hz, 1H), 5.70 (d, J=11.6 Hz, 1H), 2.08 (s, 3H).

Example 128

N-(4-{3-[6-(Difluoromethyl)pyridin-2-yl]-7-ethyl-1H-pyrrolo[3,2-b]pyridin-2-yl}pyridin-2-yl)acetamide

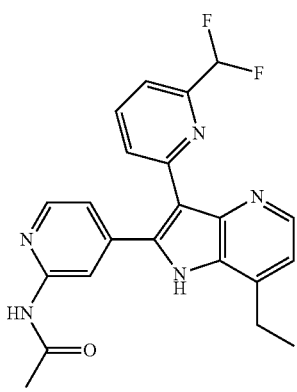 [SMILES: CCc1ccnc2c(-c3cccc(C(F)F)n3)c(-c3ccnc(NC(C)=O)c3)[nH]c12]

To a room temperature solution of Example 127A (37.2 mg, 0.069 mmol) in EtOH (694 μL) was added 10% palladium on carbon (7.39 mg, 6.94 μmol) and ammonium formate (43.8 mg, 0.694 mmol). The reaction was stirred at room temperature for 1 h, then it was filtered through Celite (washed with MeOH) and concentrated in vacuo. This material was taken up in a mixture of $CH_2Cl_2$ (230 μL) and TFA (460 μL). The reaction was stirred at room temperature for 16 h, and then it was concentrated in vacuo. The residue was taken up in 10% 7N $NH_3$/MeOH in $CH_2Cl_2$ (2 mL), stirred at room temperature for 1 h, concentrated in vacuo, dissolved in DMSO, filtered, and purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-100% B over 19 minutes, then a 5-minute hold at 100% B; Flow: 20 mL/min. Fractions containing the desired product were combined and dried via centrifugal evaporation to provide Example 128 (28.6 mg, quant. over two steps). HPLC Rt=1.062 min (Waters Acquity UPLC BEH C18, 2.1×50 mm, 1.7-μm particles; 5-95% MeCN—$H_2O$ with 0.1% TFA over 3 min; wavelength=220 nm); LC-MS m/z 408 $[M+H]^+$; $^1H$ NMR (500 MHz, DMSO-$d_6$) δ 12.05 (s, 1H), 10.49 (s, 1H), 8.37 (d, J=4.7 Hz, 1H), 8.32 (d, J=7.9 Hz, 1H), 8.30-8.27 (m, 2H), 8.02 (t, J=7.9 Hz, 1H), 7.51 (d, J=7.6 Hz, 1H), 7.23 (d, J=5.2 Hz, 1H), 7.14 (d, J=4.7 Hz, 1H), 6.61 (t, J=55.3 Hz, 1H), 2.99 (q, J=7.6 Hz, 2H), 2.06 (s, 3H), 1.30 (t, J=7.6 Hz, 3H).

TABLE 4

| Example | Structure | Name | HPLC ret. time (min)[a] | MS m/z [M + H]+ |
|---|---|---|---|---|
| 129 | 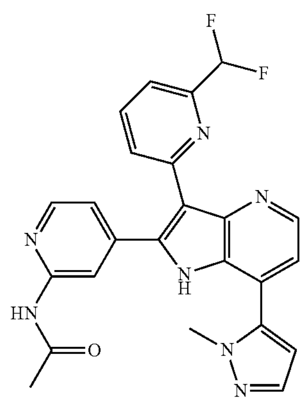 [SMILES: CC(=O)Nc1cc(-c2[nH]c3c(-c4ccnn4C)ccnc3c2-c2cccc(C(F)F)n2)ccn1] | N-(4-{3-[6-(Difluoromethyl)pyridin-2-yl]-7-(1-methyl-1H-pyrazol-5-yl)-1H-pyrrolo[3,2-b]pyridin-2-yl}pyridin-2-yl)acetamide | 1.009 | 460 |
| 130 | 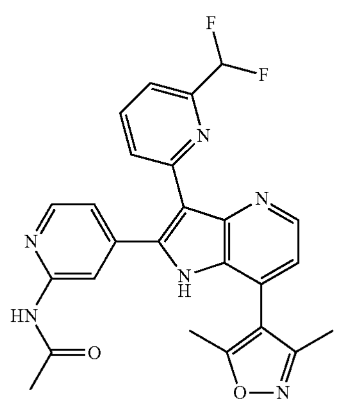 [SMILES: CC(=O)Nc1cc(-c2[nH]c3c(-c4c(C)noc4C)ccnc3c2-c2cccc(C(F)F)n2)ccn1] | N-(4-{3-[6-(Difluoromethyl)pyridin-2-yl]-7-(dimethyl-1,2-oxazol-4-yl)-1H-pyrrolo[3,2-b]pyridin-2-yl}pyridin-2-yl)acetamide | 1.092 | 475 |

[a]HPLC conditions: Waters Acquity UPLC BEH C18, 2.1 × 50 mm, 1.7-μm particles; 5-95% MeCN—$H_2O$ with 0.1% TFA over 3 min; wavelength = 220 nm.

Examples 129 and 130 in Table 4 were prepared from Example 125B and, respectively, 1-methyl-5-(4,4,5,5-tetramethyl-1,3,2-dioxaborolan-2-yl)-1H-pyrazole and potassium (3,5-dimethylisoxazol-4-yl)trifluoroborate, using procedures similar to those used for the preparation of Example 127.

TABLE 5

| Example | Structure | Name | HPLC ret. time (min)[a] | MS m/z [M + H]+ |
|---|---|---|---|---|
| 131 | 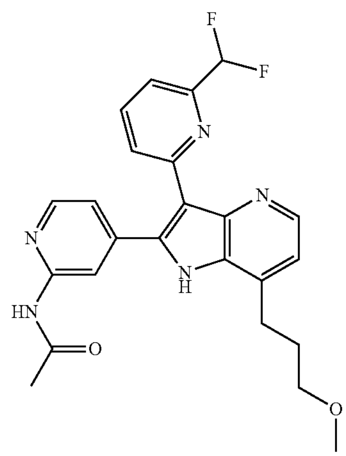 [SMILES: COCCCc1ccnc2c(-c3cccc(C(F)F)n3)c(-c3ccnc(NC(C)=O)c3)[nH]c12] | N-(4-{3-[6-(Difluoromethyl)pyridin-2-yl]-7-(3-methoxypropyl)-1H-pyrrolo[3,2-b]pyridin-2-yl}pyridin-2-yl)acetamide | 1.111 | 452 |
| 132 | 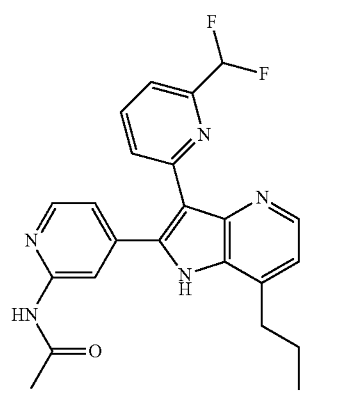 [SMILES: CCCc1ccnc2c(-c3cccc(C(F)F)n3)c(-c3ccnc(NC(C)=O)c3)[nH]c12] | N-(4-{3-[6-(Difluoromethyl)pyridin-2-yl]-7-propyl-1H-pyrrolo[3,2-b]pyridin-2-yl}pyridin-2-yl)acetamide | 1.200 | 422 |
| 133 | 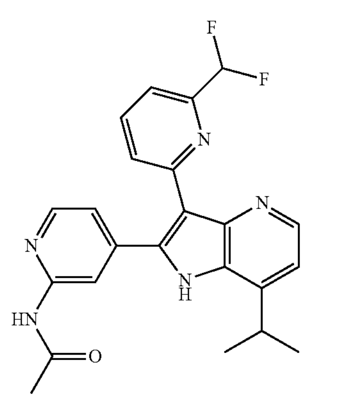 | N-(4-{3-[6-(Difluoromethyl)pyridin-2-yl]-7-(propan-2-yl)-1H-pyrrolo[3,2-b]pyridin-2-yl}pyridin-2-yl)acetamide | 1.150 | 422 |

TABLE 5-continued

| Example | Structure | Name | HPLC ret. time (min)[a] | MS m/z [M + H]+ |
|---|---|---|---|---|
| 134 | 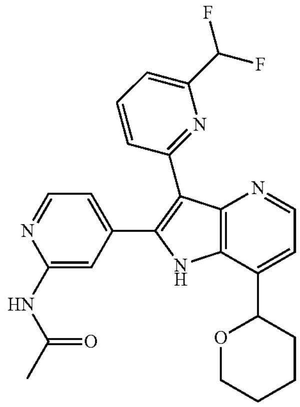 [SMILES: CC(=O)Nc1cc(-c2[nH]c3c(C4CCCCO4)ccnc3c2-c2cccc(C(F)F)n2)ccn1] | N-(4-{3-[6-(Difluoromethyl)pyridin-2-yl]-7-(oxan-2-yl)-1H-pyrrolo[3,2-b]pyridin-2-yl}pyridin-2-yl)acetamide | 1.284 | 464 |

[a]HPLC conditions: Waters Acquity UPLC BEH C18, 2.1 × 50 mm, 1.7-μm particles; 5-95% MeCN—H₂O with 0.1% TFA over 3 min; wavelength = 220 nm.

Examples 131-134 in Table 5 were prepared from Example 125B and the appropriate alkenyl binacol boronate or potassium trifluoroborate using procedures similar to those used for the preparation of Example 127A and Example 128. Temperatures ranging from 60° C. to 100° C. were employed for the cross-coupling reaction. Temperatures ranging from room temperature to 60° C. were employed for the hydrogenation reaction.

Example 135

N-(4-{3-[6-(Difluoromethyl)pyridin-2-yl]-7-(oxan-4-yl)-1H-pyrrolo[3,2-b]pyridin-2-yl}pyridin-2-yl)acetamide and Example 136

N-{4-[3-(6-Methylpyridin-2-yl)-7-(oxan-4-yl)-1H-pyrrolo[3,2-b]pyridin-2-yl]pyridin-2-yl}acetamide

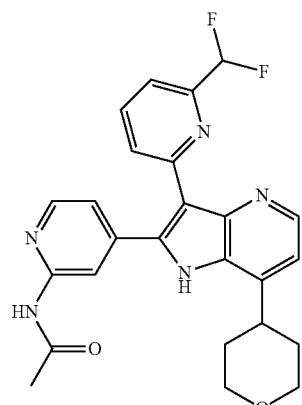

-continued

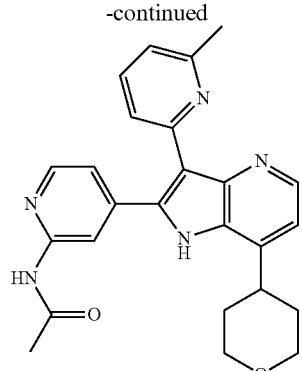

135A) N-(4-(3-(6-(Difluoromethyl)pyridin-2-yl)-7-(3,6-dihydro-2H-pyran-4-yl)-1-((2-(trimethylsilyl)ethoxy)methyl)-1H-pyrrolo[3,2-b]pyridin-2-yl)pyridin-2-yl)acetamide

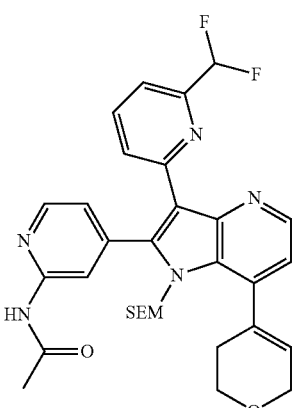

A mixture of Example 125B (40 mg, 0.074 mmol), 2-(3,6-dihydro-2H-pyran-4-yl)-4,4,5,5-tetramethyl-1,3,2-dioxaborolane (23.17 mg, 0.110 mmol), and cesium carbonate (71.9 mg, 0.221 mmol) was evacuated and backfilled with $N_2$, then 1,4-dioxane (662 µL) and $H_2O$ (73.5 µL) were added. The mixture was sparged with $N_2$ for 5 min, then 2nd generation XPhos precatalyst (2.89 mg, 3.68 µmol) was added. The mixture was sparged with $N_2$ for 1 min, then it was sealed and stirred at 60° C. for 2 h. The reaction was cooled to room temperature, diluted with EtOAc (25 mL), washed with sat. aq. NaCl (25 mL), dried over $Na_2SO_4$, filtered, and concentrated in vacuo. The crude material was purified by flash chromatography (12 g silica gel with 5 g prepacked load cartridge; linear gradient 0-100% EtOAc-$CH_2Cl_2$) to provide Example 135A (40.2 mg, 92%) as a yellow foam. LC-MS m/z 592 [M+H]$^+$.

Example 135) N-(4-{3-[6-(Difluoromethyl)pyridin-2-yl]-7-(oxan-4-yl)-1H-pyrrolo[3,2-b]pyridin-2-yl}pyridin-2-yl)acetamide and Example 136 N-{4-[3-(6-methylpyridin-2-yl)-7-(oxan-4-yl)-1H-pyrrolo[3,2-b]pyridin-2-yl]pyridin-2-yl}acetamide

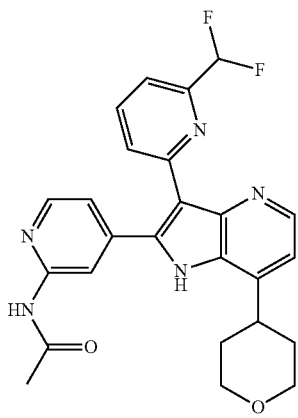 [SMILES: CC(=O)Nc1cc(-c2c(-c3cccc(C(F)F)n3)c3nccc(C4=CCOCC4)c3n2COCC[Si](C)(C)C)ccn1]

To a room temperature suspension of Example 135A (40.2 mg, 0.068 mmol) in EtOH (697 µL) was added THF (348 µL), followed by 10% palladium on carbon (7.23 mg, 6.79 µmol) and ammonium formate (42.8 mg, 0.679 mmol). The reaction was stirred at room temperature for 15 h, then at 60° C. for 1 h, and then at 70° C. for 2 h. Additional ammonium formate (22 mg, 0.35 mmol) was added and the reaction was stirred at 70° C. for 4 h. The reaction was cooled to room temperature, filtered through Celite (washed with THF and MeOH), and concentrated in vacuo. This material was taken up in a mixture of $CH_2Cl_2$ (227 µL) and TFA (453 µL). The reaction was stirred at room temperature for 13 h. Additional TFA (0.453 mL) was added and the reaction was stirred at room temperature for 27 h, and then it was concentrated in vacuo. The residue was taken up in 10% 7N $NH_3$/MeOH in $CH_2Cl_2$ (2 mL), stirred at room temperature for 5 min, concentrated in vacuo, dissolved in DMSO, filtered, and purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 15-55% B over 25 minutes, then a 5-minute hold at 100% B; Flow: 20 mL/min. Fractions containing the desired product were combined and dried via centrifugal evaporation to provide Example 135 (9.0 mg, 29% over two steps) and Example 136 (7.7 mg, 27% over two steps). Characterization data for Example 135: HPLC Rt=1.079 min (Waters Acquity UPLC BEH C18, 2.1×50 mm, 1.7-µm particles; 5-95% MeCN—$H_2O$ with 0.1% TFA over 3 min; wavelength=220 nm); LC-MS m/z 464; $^1$H NMR (500 MHz, DMSO-$d_6$) δ 12.08 (s, 1H), 10.52 (s, 1H), 8.42 (d, J=4.9 Hz, 1H), 8.37 (br d, J=7.7 Hz, 1H), 8.32-8.28 (m, 2H), 8.03 (t, J=7.8 Hz, 1H), 7.50 (d, J=7.6 Hz, 1H), 7.24 (d, J=5.2 Hz, 1H), 7.19 (d, J=4.8 Hz, 1H), 6.60 (t, J=55.2 Hz, 1H), 4.00 (br d, J=10.8 Hz, 2H), 3.64-3.46 (m, 3H), 2.07 (s, 3H), 1.85-1.77 (m, 4H). Characterization data for Example 136: HPLC Rt=0.826 min (Waters Acquity UPLC BEH C18, 2.1×50 mm, 1.7-µm particles; 5-95% MeCN—$H_2O$ with 0.1% TFA over 3 min; wavelength=220 nm); LC-MS m/z 428 [M+H]$^+$; $^1$H NMR (500 MHz, DMSO-$d_6$) δ 11.90 (br s, 1H), 10.43 (s, 1H), 8.35 (d, J=4.6 Hz, 1H), 8.26 (d, J=4.7 Hz, 1H), 8.20 (br s, 1H), 7.77-7.73 (m, 1H), 7.68 (t, J=7.7 Hz, 1H), 7.19 (br d, J=4.5 Hz, 1H), 7.14 (br d, J=4.5 Hz, 1H), 7.08 (br d, J=7.6 Hz, 1H), 4.02-3.78 (m, 2H), 3.63-3.45 (m, 3H), 2.25 (s, 3H), 2.06 (s, 3H), 1.84-1.73 (m, 4H).

Example 137

N-(4-{3-[6-(Difluoromethyl)pyridin-2-yl]-7-(1-methylpiperidin-4-yl)-1H-pyrrolo[3,2-b]pyridin-2-yl}pyridin-2-yl)acetamide and

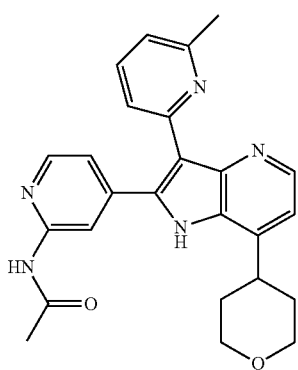

Example 138

N-{4-[7-(1-Methylpiperidin-4-yl)-3-(6-methylpyridin-2-yl)-1H-pyrrolo[3,2-b]pyridin-2-yl]pyridin-2-yl}acetamide

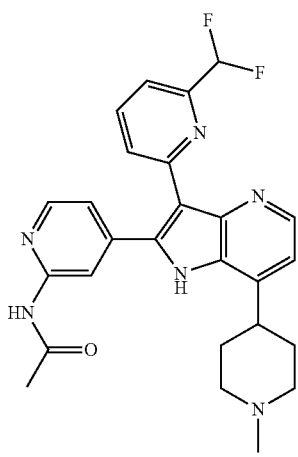

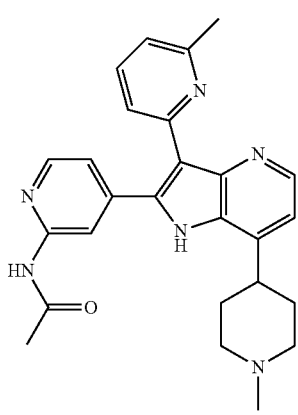

Example 137 and Example 138 were prepared from Example 125B and 1-methyl-4-(4,4,5,5-tetramethyl-1,3,2-dioxaborolan-2-yl)-1,2,3,6-tetrahydropyridine using procedures similar to those used for the preparation of Example 135 and Example 136. Characterization data for Example 137: HPLC Rt=0.831 min (Waters Acquity UPLC BEH C18, 2.1×50 mm, 1.7-μm particles; 5-95% MeCN—H₂O with 0.1% TFA over 3 min; wavelength=220 nm); LC-MS m/z 477 [M+H]⁺; ¹H NMR (500 MHz, DMSO-d₆) δ 12.03 (br s, 1H), 10.52 (s, 1H), 8.43-8.37 (m, 2H), 8.32-8.26 (m, 2H), 8.02 (t, J=7.9 Hz, 1H), 7.50 (d, J=7.7 Hz, 1H), 7.24 (d, J=5.0 Hz, 1H), 7.16 (d, J=4.7 Hz, 1H), 6.59 (t, J=55.3 Hz, 1H), 3.30-3.20 (m, 1H), 2.94 (br d, J=11.4 Hz, 2H), 2.25 (s, 3H), 2.14 (br t, J=11.0 Hz, 2H), 2.07 (s, 3H), 1.90-1.75 (m, 4H). Characterization data for Example 138: HPLC Rt=0.614 min (Waters Acquity UPLC BEH C18, 2.1×50 mm, 1.7-μm particles; 5-95% MeCN—H₂O with 0.1% TFA over 3 min; wavelength=220 nm); LC-MS m/z 441 [M+H]⁺; ¹H NMR (500 MHz, DMSO-d₆) δ 11.85 (br s, 1H), 10.50 (s, 1H), 8.37 (d, J=4.6 Hz, 1H), 8.31-8.26 (m, 2H), 7.94 (br d, J=7.7 Hz, 1H), 7.69 (t, J=7.7 Hz, 1H), 7.21 (d, J=5.0 Hz, 1H), 7.12 (d, J=4.8 Hz, 1H), 7.06 (d, J=7.4 Hz, 1H), 3.28-3.20 (m, 1H), 2.94 (br d, J=10.6 Hz, 2H), 2.27-2.23 (m, 6H), 2.13 (br t, J=11.1 Hz, 2H), 2.08 (s, 3H), 1.88-1.74 (m, 4H).

Example 139

N-(4-{3-[6-(Difluoromethyl)pyridin-2-yl]-7-[(4-methylpiperazin-1-yl)methyl]-1H-pyrrolo[3,2-b]pyridin-2-yl}pyridin-2-yl)acetamide

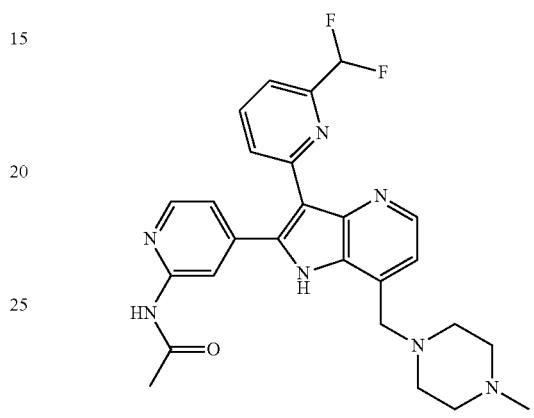

A mixture of Example 125B (40 mg, 0.074 mmol), potassium trifluoro((4-methylpiperazin-1-yl)methyl)borate (24.27 mg, 0.110 mmol), and cesium carbonate (71.9 mg, 0.221 mmol) was evacuated and backfilled with N₂, then THF (331 μL) and H₂O (36.8 μL) were added. The mixture was sparged with N₂ for 5 min, then 2nd generation XPhos precatalyst (2.89 mg, 3.68 μmol) was added. The mixture was sparged with N₂ for 1 min, then it was sealed and stirred at 80° C. for 1 h. The reaction was cooled to room temperature, diluted with EtOAc (25 mL), washed with sat. aq. NaCl (25 mL), dried over Na₂SO₄, filtered, and concentrated in vacuo. This material was taken up in a mixture of CH₂Cl₂ (247 μL) and TFA (493 μL). The reaction was stirred at room temperature for 42 h, and then it was concentrated in vacuo. The residue was taken up in 10% 7N NH₃/MeOH in CH₂Cl₂ (2 mL), stirred at room temperature for 5 min, concentrated in vacuo, dissolved in DMSO, filtered, and purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-100% B over 20 minutes, then a 2-minute hold at 100% B; Flow: 20 mL/min. Fractions containing the desired product were combined and dried via centrifugal evaporation to provide Example 139 (29.3 mg, 81%). HPLC Rt=0.896 min (Waters Acquity UPLC BEH C18, 2.1×50 mm, 1.7-μm particles; 5-95% MeCN—H₂O with 0.1% TFA over 3 min; wavelength=220 nm); LC-MS m/z 492 [M+H]⁺; ¹H NMR (500 MHz, DMSO-d₆) δ 11.78 (br s, 1H), 10.53 (s, 1H), 8.43 (d, J=4.7 Hz, 1H), 8.39 (br d, J=8.0 Hz, 1H), 8.33 (br s, 1H), 8.30 (d, J=5.1 Hz, 1H), 8.04 (t, J=7.9 Hz, 1H), 7.52 (d, J=7.8 Hz, 1H), 7.26-7.20 (m, 2H), 6.62 (t, J=55.2 Hz, 1H), 3.89 (s, 2H), 3.63-3.35 (m, 4H), 2.46-2.29 (m, 4H), 2.18 (s, 3H), 2.07 (s, 3H).

TABLE 6

| Example | Structure | Name | HPLC ret. time (min)[a] | MS m/z [M + H]+ |
|---|---|---|---|---|
| 140 | 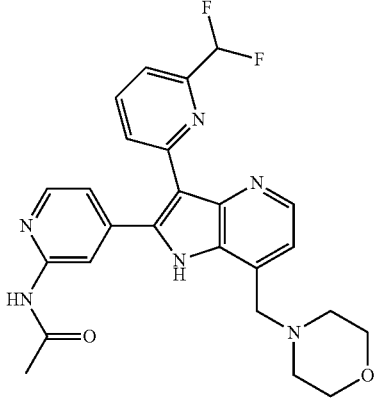 [SMILES: CC(=O)Nc1cc(-c2[nH]c3c(CN4CCOCC4)ccnc3c2-c2cccc(C(F)F)n2)ccn1] | N-(4-{3-[6-(Difluoromethyl)pyridin-2-yl]-7-(morpholin-4-ylmethyl)-1H-pyrrolo[3,2-b]pyridin-2-yl}pyridin-2-yl)acetamide | 0.796 | 479 |
| 141 | 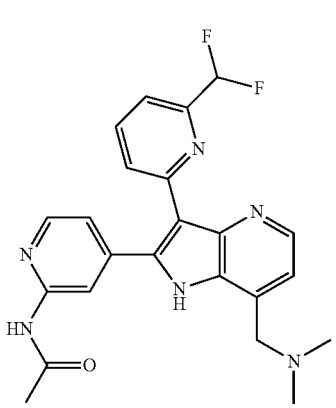 [SMILES: CC(=O)Nc1cc(-c2[nH]c3c(CN(C)C)ccnc3c2-c2cccc(C(F)F)n2)ccn1] | N-(4-{3-[6-(Difluoromethyl)pyridin-2-yl]-7-[(dimethylamino)methyl]-1H-pyrrolo[3,2-b]pyridin-2-yl}pyridin-2-yl)acetamide | 0.805 | 437 |

[a]HPLC conditions: Waters Acquity UPLC BEH C18, 2.1 × 50 mm, 1.7-μm particles; 5-95% MeCN—H₂O with 0.1% TFA over 3 min; wavelength = 220 nm.

Example 140 and Example 141 in Table 6 were prepared from Example 125B and, respectively, potassium trifluoro(morpholinomethyl)borate and potassium ((dimethylamino)methyl)trifluoroborate using procedures similar to those used for the preparation of Example 139.

Example 142

N-(4-{3-[6-(Difluoromethyl)pyridin-2-yl]-7-(hydroxymethyl)-1H-pyrrolo[3,2-b]pyridin-2-yl}pyridin-2-yl)acetamide

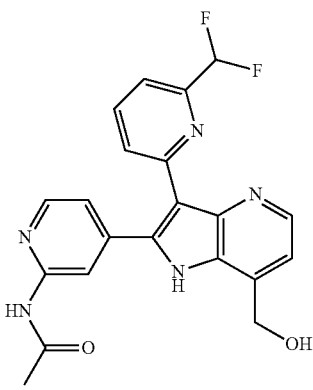 [SMILES: CC(=O)Nc1cc(-c2[nH]c3c(CO)ccnc3c2-c2cccc(C(F)F)n2)ccn1]

142A) N-(4-(3-(6-(Difluoromethyl)pyridin-2-yl)-7-formyl-1-((2-(trimethylsilyl)ethoxy)methyl)-1H-pyrrolo[3,2-b]pyridin-2-yl)pyridin-2-yl)acetamide

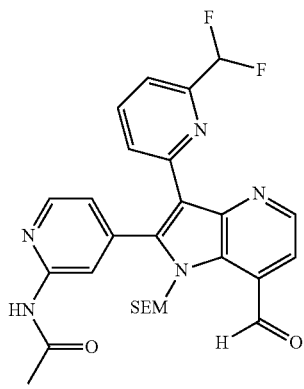 [SMILES: CC(=O)Nc1cc(-c2c(-c3cccc(C(F)F)n3)c3nccc(C=O)c3n2COCC[Si](C)(C)C)ccn1]

To a room temperature solution of Example 127A (187.8 mg, 0.351 mmol) in 1,4-dioxane (2805 μL) was added H$_2$O (701 μL), 2,6-lutidine (82 μL, 0.701 mmol), osmium tetroxide (111 μL, 4 wt % solution in H$_2$O, 0.018 mmol), and sodium periodate (300 mg, 1.402 mmol). The reaction was stirred at room temperature for 2 h, and then it was diluted with H$_2$O (30 mL) and extracted with CH$_2$Cl$_2$ (2×30 mL). The combined organic layers were dried over Na$_2$SO$_4$, filtered, and concentrated in vacuo. The crude material was purified by flash chromatography (12 g silica gel with 5 g prepacked load cartridge; linear gradient 0-100% EtOAc-CH$_2$Cl$_2$) to provide Example 142A (179 mg, 95%) as a yellow solid. LC-MS m/z 538 [M+H]$^+$; $^1$H NMR (400 MHz, DMSO-d$_6$) δ 10.64 (s, 1H), 10.60 (s, 1H), 8.81 (d, J=4.6 Hz, 1H), 8.47 (dd, J=7.9, 0.9 Hz, 1H), 8.40 (dd, J=5.1, 0.7 Hz, 1H), 8.23 (s, 1H), 8.04 (t, J=7.8 Hz, 1H), 7.78 (d, J=4.8 Hz, 1H), 7.50 (d, J=7.6 Hz, 1H), 7.16 (dd, J=5.1, 1.5 Hz, 1H), 6.46 (t, J=55.3 Hz, 1H), 5.68 (s, 2H), 3.25-3.19 (m, 2H), 2.08 (s, 3H), 0.69-0.60 (m, 2H), −0.17 (s, 9H).

Example 142) N-(4-{3-[6-(Difluoromethyl)pyridin-2-yl]-7-(hydroxymethyl)-1H-pyrrolo[3,2-b]pyridin-2-yl}pyridin-2-yl)acetamide

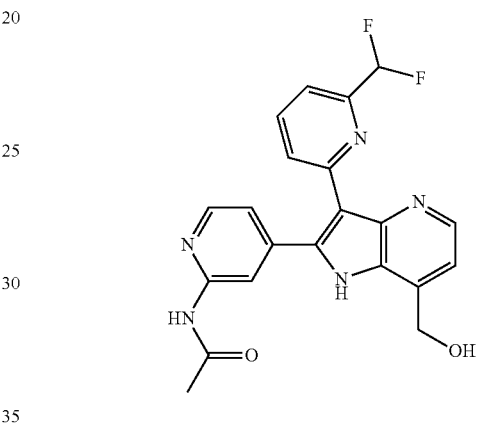

To a room temperature solution of Example 142A (19.3 mg, 0.036 mmol) in MeOH (359 μL) was added sodium borohydride (2.72 mg, 0.072 mmol). The reaction was stirred at room temperature for 30 min, and then it was quenched by the addition of H$_2$O (20 mL) and extracted with CH$_2$Cl$_2$ (2×20 mL). The combined organic layers were dried over Na$_2$SO$_4$, filtered, and concentrated in vacuo. This material was taken up in a mixture of CH$_2$Cl$_2$ (98 μL) and TFA (196 μL). The reaction was stirred at room temperature for 16 h, and then it was concentrated in vacuo. The residue was taken up in 10% 7N NH$_3$/MeOH in CH$_2$Cl$_2$ (2 mL), stirred at room temperature for 5 min, concentrated in vacuo, dissolved in DMSO, filtered, and purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 20 minutes, then a 4-minute hold at 100% B; Flow: 20 mL/min. Fractions containing the desired product were combined and dried via centrifugal evaporation to provide Example 142 (8.6 mg, 71%). HPLC Rt=0.882 min (Waters Acquity UPLC BEH C18, 2.1×50 mm, 1.7-μm particles; 5-95% MeCN—H$_2$O with 0.1% TFA over 3 min; wavelength=220 nm); LC-MS m/z 410 [M+H]$^+$; $^1$H NMR (500 MHz, DMSO-d$_6$) δ 12.02 (br s, 1H), 10.48 (s, 1H), 8.45 (br d, J=4.6 Hz, 1H), 8.29 (br d, J=5.2 Hz, 1H), 8.27-8.24 (m, 2H), 8.02 (t, J=7.9 Hz, 1H), 7.52 (d, J=7.6 Hz, 1H), 7.34 (br d, J=4.4 Hz, 1H), 7.22 (br d, J=5.2 Hz, 1H), 6.63 (t, J=55.5 Hz, 1H), 5.73 (br s, 1H), 4.92 (s, 2H), 2.05 (s, 3H).

Example 143

N-(4-{3-[6-(Difluoromethyl)pyridin-2-yl]-7-(1-hydroxyethyl)-1H-pyrrolo[3,2-b]pyridin-2-yl}pyridin-2-yl)acetamide

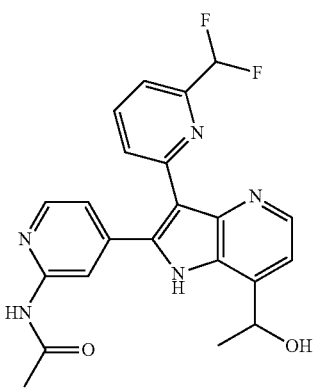 [SMILES: CC(=O)Nc1cc(-c2[nH]c3c(C(C)O)ccnc3c2-c2cccc(C(F)F)n2)ccn1]

To a 0° C. solution of Example 142A (21.1 mg, 0.039 mmol) in THF (392 μL) was added methylmagnesium bromide (26.2 μL, 3 M solution in Et$_2$O, 0.078 mmol). The reaction was stirred at 0° C. for 1 h, and then it was quenched by the addition of H$_2$O (25 mL) and extracted with EtOAc (25 mL). The organic layer was washed with sat. aq. NaCl (25 mL), dried over Na$_2$SO$_4$, filtered, and concentrated in vacuo. This material was taken up in a mixture of CH$_2$Cl$_2$ (130 μL) and TFA (260 μL). The reaction was stirred at room temperature for 3 h, and then it was concentrated in vacuo. The residue was taken up in 10% 7N NH$_3$/MeOH in CH$_2$Cl$_2$ (2 mL), stirred at room temperature for 5 min, concentrated in vacuo, dissolved in DMSO, filtered, and purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-100% B over 20 minutes, then a 2-minute hold at 100% B; Flow: 20 mL/min. Fractions containing the desired product were combined and dried via centrifugal evaporation to provide Example 143 (8.3 mg, 50%). HPLC Rt=1.007 min (Waters Acquity UPLC BEH C18, 2.1×50 mm, 1.7-μm particles; 5-95% MeCN—H$_2$O with 0.1% TFA over 3 min; wavelength=220 nm); LC-MS m/z 424 [M+H]$^+$; $^1$H NMR (500 MHz, DMSO-d$_6$) δ 11.88 (s, 1H), 10.46 (s, 1H), 8.43 (d, J=4.7 Hz, 1H), 8.30-8.24 (m, 3H), 8.02 (t, J=7.8 Hz, 1H), 7.51 (d, J=7.6 Hz, 1H), 7.33 (d, J=4.7 Hz, 1H), 7.22 (br d, J=4.9 Hz, 1H), 6.60 (t, J=55.2 Hz, 1H), 5.74-5.69 (m, 1H), 5.39-5.33 (m, 1H), 2.05 (s, 3H), 1.45 (br d, J=6.4 Hz, 3H).

TABLE 7

| Example | Structure | Name | HPLC ret. time (min)[a] | MS m/z [M + H]$^+$ |
|---|---|---|---|---|
| 144 | 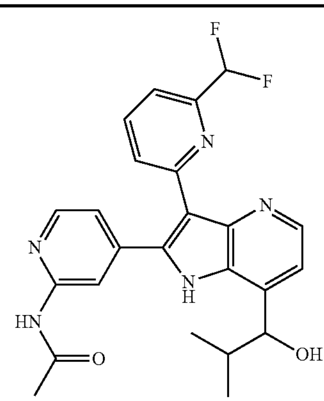 | N-(4-{3-[6-(Difluoromethyl)pyridin-2-yl]-7-(1-hydroxy-2-methylpropyl)-1H-pyrrolo[3,2-b]pyridin-2-yl}pyridin-2-yl)acetamide | 1.222 | 452 |
| 145 | 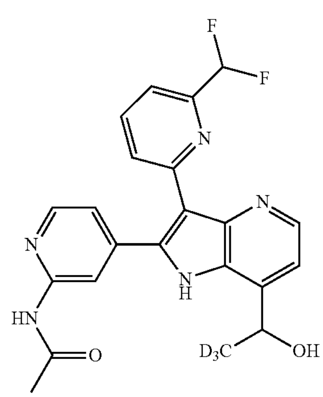 [SMILES: [2H]C([2H])([2H])C(O)c1ccnc2c(-c3cccc(C(F)F)n3)c(-c3ccnc(NC(C)=O)c3)[nH]c12] | N-(4-{3-[6-(Difluoromethyl)pyridin-2-yl]-7-[1-hydroxy(2,2,2-2H)ethyl]-1H-pyrrolo[3,2-b]pyridin-2-yl}pyridin-2-yl)acetamide | 0.963 | 427 |

[a]HPLC conditions: Waters Acquity UPLC BEH C18, 2.1 × 50 mm, 1.7-μm particles; 5-95% MeCN—H$_2$O with 0.1% TFA over 3 min; wavelength = 220 nm.

Example 144 and Example 145 in Table 7 were prepared from Example 142A and, respectively, isopropylmagnesium bromide and methyl-d3-magnesium iodide, using procedures similar to those used for the preparation of Example 143.

Example 146

N-(4-{3-[6-(Difluoromethyl)pyridin-2-yl]-7-[(1R)-1-hydroxyethyl]-1H-pyrrolo[3,2-b]pyridin-2-yl}pyridin-2-yl)acetamide and Example 147

N-(4-{3-[6-(Difluoromethyl)pyridin-2-yl]-7-[(1S)-1-hydroxyethyl]-1H-pyrrolo[3,2-b]pyridin-2-yl}pyridin-2-yl)acetamide

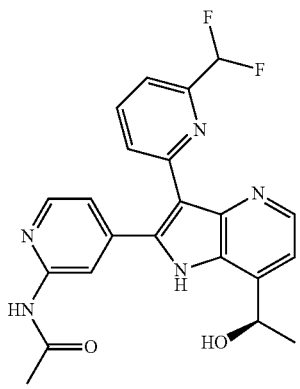

To a 0° C. solution of Example 142A (82.4 mg, 0.153 mmol) in THF (1533 µL) was added methylmagnesium bromide (102 µL, 3 M solution in Et$_2$O, 0.307 mmol). The reaction was stirred at 0° C. for 1 h, and then it was quenched by the addition of H$_2$O (30 mL) and extracted with EtOAc (30 mL). The organic layer was washed with sat. aq. NaCl (30 mL), dried over Na$_2$SO$_4$, filtered, and concentrated in vacuo. This material was taken up in mixture of CH$_2$Cl$_2$ (510 µL) and TFA (1020 µL). The reaction was stirred at room temperature for 5 h, and then it was concentrated in vacuo. The residue was taken up in 10% 7N NH$_3$/MeOH in CH$_2$Cl$_2$ (2 mL), stirred at room temperature for 5 min, and concentrated in vacuo. The crude material was purified via preparative SFC with the following conditions: Column: Chiral AD-H 25×3 cm ID, 5-µm particles; Mobile Phase 75:25 CO$_2$/MeOH; Flow: 85 mL/min. Fractions containing peak 1 were combined and concentrated in vacuo to provide Example 146 (23.9 mg, 37%). Fractions containing peak 2 were combined and concentrated in vacuo to provide Example 147 (24.0 mg, 35%). The stereochemistry of these two enantiomers was arbitrarily assigned. Characterization data for Example 146: HPLC Rt=5.43 min (Sunfire C18, 3.0×150 mm, 3.5-µm particles; 5-95% MeCN—H$_2$O with 0.05% TFA over 12 min; wavelength=220 nm); LC-MS m/z 424 [M+H]$^+$; $^1$H NMR (400 MHz, DMSO-d$_6$) δ 11.85 (br s, 1H), 10.51 (s, 1H), 8.45 (d, J=4.8 Hz, 1H), 8.43 (d, J=7.9 Hz, 1H), 8.34 (s, 1H), 8.30 (d, J=5.1 Hz, 1H), 8.04 (t, J=7.8 Hz, 1H), 7.51 (d, J=7.7 Hz, 1H), 7.33 (d, J=4.6 Hz, 1H), 7.24 (dd, J=5.2, 1.5 Hz, 1H), 6.61 (t, J=55.0 Hz, 1H), 5.54-5.48 (m, 1H), 5.43-5.34 (m, 1H), 2.08 (s, 3H), 1.47 (d, J=6.5 Hz, 3H). Characterization data for Example 147: HPLC Rt=5.42 min (Sunfire C18, 3.0×150 mm, 3.5-µm particles; 5-95% MeCN—H$_2$O with 0.05% TFA over 12 min; wavelength=220 nm); LC-MS m/z 424 [M+H]$^+$; $^1$H NMR (400 MHz, DMSO-d$_6$) δ 11.85 (s, 1H), 10.51 (s, 1H), 8.46 (d, J=4.8 Hz, 1H), 8.43 (d, J=7.2 Hz, 1H), 8.34 (s, 1H), 8.30 (d, J=5.1 Hz, 1H), 8.04 (t, J=7.8 Hz, 1H), 7.51 (d, J=7.6 Hz, 1H), 7.34 (d, J=4.8 Hz, 1H), 7.24 (dd, J=5.1, 1.6 Hz, 1H), 6.61 (t, J=55.3 Hz, 1H), 5.51 (br d, J=4.2 Hz, 1H), 5.42-5.35 (m, 1H), 2.08 (s, 3H), 1.47 (d, J=6.5 Hz, 3H).

Example 148

N-{4-[7-(2,2-Difluoro-1-hydroxyethyl)-3-[6-(difluoromethyl)pyridin-2-yl]-1H-pyrrolo[3,2-b]pyridin-2-yl]pyridin-2-yl}acetamide

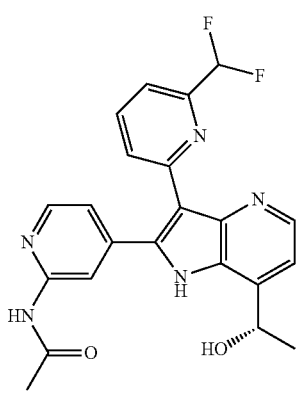

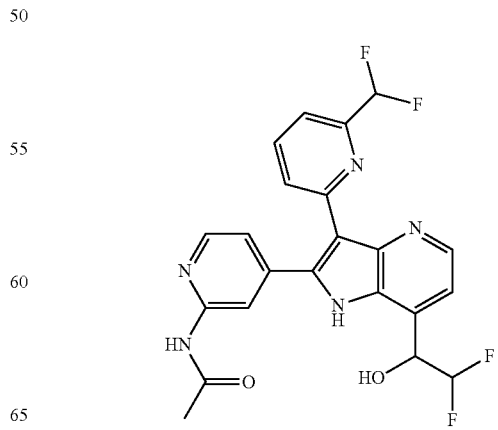

148A) N-(4-(7-(2,2-Difluoro-1-hydroxyethyl)-3-(6-(difluoromethyl)pyridin-2-yl)-1-((2-(trimethylsilyl)ethoxy)methyl)-1H-pyrrolo[3,2-b]pyridin-2-yl)pyridin-2-yl)acetamide

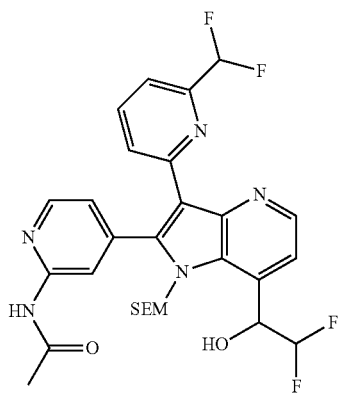 [SMILES: CC(=O)Nc1cc(-c2c(-c3cccc(C(F)F)n3)c3nccc(C(O)C(F)F)c3n2COCC[Si](C)(C)C)ccn1]

To a room temperature solution of Example 142A (19.9 mg, 0.037 mmol) in DMF (370 μL) was added (difluoromethyl)trimethylsilane (9.19 mg, 0.074 mmol), followed by cesium fluoride (0.787 mg, 5.18 μmol). The reaction was stirred at room temperature for 21 h, and then tetrabutylammonium fluoride (185 μL, 1 M solution in THF, 0.185 mmol) was added and the reaction was stirred at room temperature for 1 h. The reaction was diluted with EtOAc (25 mL), washed with $H_2O$ (25 mL) and sat. aq. NaCl (25 mL), dried over $Na_2SO_4$, filtered, and concentrated in vacuo. The crude material was purified by flash chromatography (12 g silica gel with 5 g prepacked load cartridge; linear gradient 0-100% EtOAc-$CH_2Cl_2$) to provide Example 148A (9.5 mg, 44%) as a white film. LC-MS m/z 590 [M+H]$^+$.

Example 148) N-{4-[7-(2,2-Difluoro-1-hydroxyethyl)-3-[6-(difluoromethyl)pyridin-2-yl]-1H-pyrrolo[3,2-b]pyridin-2-yl]pyridin-2-yl}acetamide

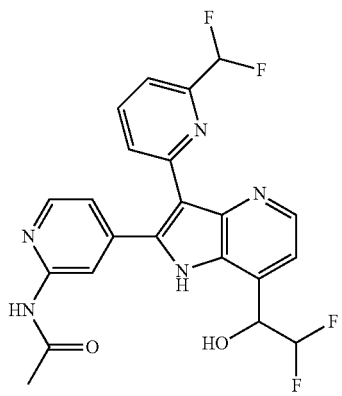 [SMILES: CC(=O)Nc1cc(-c2[nH]c3c(C(O)C(F)F)ccnc3c2-c2cccc(C(F)F)n2)ccn1]

To a room temperature solution of Example 148A (9.5 mg, 0.016 mmol) in $CH_2Cl_2$ (53.7 μL) was added TFA (107 μL). The reaction was stirred at room temperature for 18 h, and then it was concentrated in vacuo. The residue was taken up in 10% 7N $NH_3$/MeOH in $CH_2Cl_2$ (2 mL), stirred at room temperature for 5 min, and then it was concentrated in vacuo, dissolved in DMSO, filtered, and purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 0-100% B over 15 minutes, then a 3-minute hold at 100% B; Flow: 20 mL/min. Fractions containing the desired product were combined and dried via centrifugal evaporation to provide Example 148 (7.1 mg, 95%). HPLC Rt=1.042 min (Waters Acquity UPLC BEH C18, 2.1×50 mm, 1.7-μm particles; 5-95% MeCN—$H_2O$ with 0.1% TFA over 3 min; wavelength=220 nm); LC-MS m/z 460 [M+H]$^+$; $^1$H NMR (500 MHz, DMSO-$d_6$) δ 12.06 (s, 1H), 10.46 (s, 1H), 8.49 (d, J=4.6 Hz, 1H), 8.29 (br d, J=5.1 Hz, 1H), 8.27-8.23 (m, 2H), 8.03 (t, J=7.8 Hz, 1H), 7.53 (d, J=7.7 Hz, 1H), 7.39 (d, J=4.6 Hz, 1H), 7.22 (br d, J=4.5 Hz, 1H), 6.76 (br d, J=5.0 Hz, 1H), 6.73-6.47 (m, 1H), 6.32-6.05 (m, 1H), 5.60-5.49 (m, 1H), 2.05 (s, 3H).

Example 149

N-{4-[7-(Difluoromethyl)-3-[6-(difluoromethyl)pyridin-2-yl]-1H-pyrrolo[3,2-b]pyridin-2-yl]pyridin-2-yl}acetamide

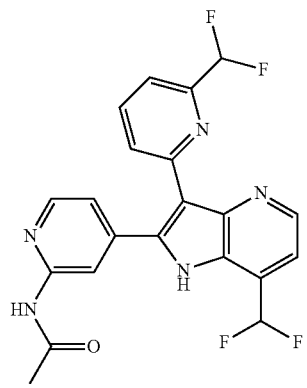 [SMILES: CC(=O)Nc1cc(-c2[nH]c3c(C(F)F)ccnc3c2-c2cccc(C(F)F)n2)ccn1]

To a 0° C. solution of Example 142A (20.9 mg, 0.039 mmol) in $CH_2Cl_2$ (389 μL) was added diethylaminosulfur trifluoride (7.70 μL, 0.058 mmol). The reaction was stirred at 0° C. for 1 h, then at room temperature for 2 h. The reaction was diluted with sat. aq. $NaHCO_3$ (25 mL) and extracted with $CH_2Cl_2$ (25 mL). The organic layer was dried over $Na_2SO_4$, filtered, and concentrated in vacuo. This material was taken up in a mixture of $CH_2Cl_2$ (130 μL) and TFA (260 μL). The reaction was stirred at room temperature for 16 h, and then it was concentrated in vacuo. The residue was taken up in 10% 7N $NH_3$/MeOH in $CH_2Cl_2$ (2 mL), stirred at room temperature for 5 min, concentrated in vacuo, dissolved in DMSO, filtered, and purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 15-55% B over 20 minutes, then a 5-minute hold at 100% B; Flow: 20 mL/min. Fractions containing the desired product were combined and dried via centrifugal evaporation to provide Example 149 (10.3 mg, 62%). HPLC Rt=1.086 min (Waters Acquity UPLC BEH C18, 2.1×50 mm, 1.7-μm particles; 5-95% MeCN—$H_2O$ with 0.1% TFA over 3 min; wavelength=220 nm); LC-MS m/z 430 [M+H]$^+$; $^1$H NMR (500 MHz, DMSO-$d_6$) δ 12.50 (br s, 1H), 10.56 (s, 1H), 8.63 (br d, J=3.9 Hz, 1H), 8.34-8.26 (m, 3H), 8.06 (br t, J=7.6 Hz, 1H), 7.66-7.40 (m, 3H), 7.27-7.20 (m, 1H), 6.65 (t, J=55.1 Hz, 1H), 2.07 (s, 3H).

Example 150

N-(4-{3-[6-(Difluoromethyl)pyridin-2-yl]-7-(fluoromethyl)-1H-pyrrolo[3,2-b]pyridin-2-yl}-pyridin-2-yl)acetamide

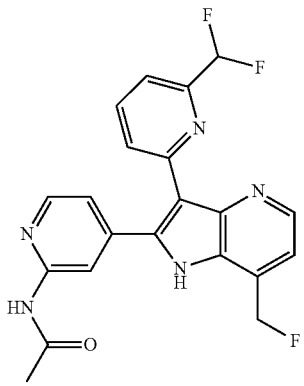 [SMILES: CC(=O)Nc1cc(-c2[nH]c3c(CF)ccnc3c2-c2cccc(C(F)F)n2)ccn1]

150A) N-(4-(3-(6-(Difluoromethyl)pyridin-2-yl)-7-(hydroxymethyl)-1-((2-(trimethylsilyl)ethoxy)methyl)-1H-pyrrolo[3,2-b]pyridin-2-yl)pyridin-2-yl)acetamide

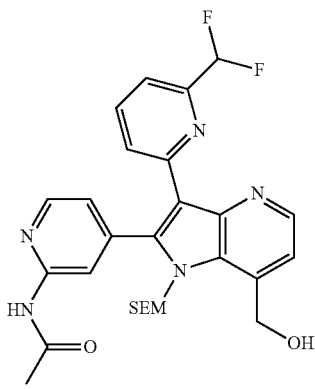 [SMILES: CC(=O)Nc1cc(-c2c(-c3cccc(C(F)F)n3)c3nccc(CO)c3n2COCC[Si](C)(C)C)ccn1]

To a room temperature solution of Example 142A (20 mg, 0.037 mmol) in MeOH (372 μl) was added sodium borohydride (2.81 mg, 0.074 mmol). The reaction was stirred at room temperature for 15 min, and then it was quenched by the addition of H₂O (20 mL) and extracted with CH₂Cl₂ (2×20 mL). The combined organic layers were dried over Na₂SO₄, filtered, and concentrated in vacuo. The aqueous layer was diluted with sat. aq. NH₄Cl (20 mL) and extracted with CH₂Cl₂ (2×20 mL). The combined organic layers were dried over Na₂SO₄, filtered, and concentrated in vacuo. Each of the crude isolates was purified by flash chromatography (12 g silica gel with 5 g prepacked load cartridge; linear gradient 0-10% MeOH—CH₂Cl₂). The product-containing fractions from each column were combined to provide Example 150A (18 mg, 90%) as a white foam. LC-MS m/z 540 [M+H]⁺.

Example 150) N-(4-{3-[6-(Difluoromethyl)pyridin-2-yl]-7-(fluoromethyl)-1H-pyrrolo[3,2-b]pyridin-2-yl}pyridin-2-yl)acetamide

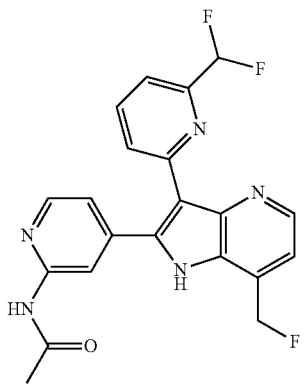 [SMILES: CC(=O)Nc1cc(-c2[nH]c3c(CF)ccnc3c2-c2cccc(C(F)F)n2)ccn1]

To a −78° C. solution of Example 150A (18 mg, 0.033 mmol) in CH₂Cl₂ (334 μL) was added diethylaminosulfur trifluoride (6.61 μL, 0.050 mmol). The reaction was stirred at −78° C. for 10 min, then the reaction was stirred at room temperature for 35 min. The reaction was diluted with sat. aq. NaHCO₃ (25 mL) and extracted with CH₂Cl₂ (25 mL). The organic layer was dried over Na₂SO₄, filtered, and concentrated in vacuo. This material was taken up in a mixture of CH₂Cl₂ (110 μL) and TFA (220 μL). The reaction was stirred at room temperature for 16 h, and then it was concentrated in vacuo. The residue was taken up in 10% 7N NH₃/MeOH in CH₂Cl₂ (2 mL), stirred at room temperature for 5 min, concentrated in vacuo, dissolved in DMSO, filtered, and purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 15-55% B over 25 minutes, then a 5-minute hold at 100% B; Flow: 20 mL/min. Fractions containing the desired product were combined and dried via centrifugal evaporation to provide Example 150 (3.4 mg, 25%). HPLC Rt=1.007 min (Waters Acquity UPLC BEH C18, 2.1×50 mm, 1.7-μm particles; 5-95% MeCN—H₂O with 0.1% TFA over 3 min; wavelength=220 nm); LC-MS m/z 412 [M+H]⁺; ¹H NMR (500 MHz, DMSO-d₆) δ 12.28 (br s, 1H), 10.52 (s, 1H), 8.52 (d, J=4.5 Hz, 1H), 8.35 (br d, J=7.8 Hz, 1H), 8.33-8.29 (m, 2H), 8.05 (t, J=7.8 Hz, 1H), 7.54 (d, J=7.7 Hz, 1H), 7.34 (br d, J=4.5 Hz, 1H), 7.24 (br d, J=5.0 Hz, 1H), 6.63 (t, J=55.2 Hz, 1H), 5.87 (d, J=46.9 Hz, 2H), 2.07 (s, 3H)

Example 151

N-(4-{3-[6-(Difluoromethyl)pyridin-2-yl]-7-[(methylamino)methyl]-1H-pyrrolo[3,2-b]pyridin-2-yl}pyridin-2-yl)acetamide

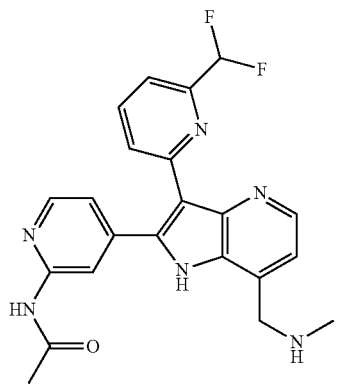

To a room temperature solution of Example 142A (22.1 mg, 0.041 mmol) in DCE (411 μL) was added methylamine (123 μL, 2.0 M solution in THF, 0.247 mmol), followed by sodium triacetoxyborohydride (13.94 mg, 0.066 mmol). The reaction was stirred at room temperature for 17 h. Additional sodium triacetoxyborohydride (30 mg, 0.14 mmol) was added and the reaction was stirred at room temperature for 3 days. The reaction was diluted with sat. aq. NaHCO$_3$ (25 mL) and extracted with CH$_2$Cl$_2$ (25 mL). The organic layer was dried over Na$_2$SO$_4$, filtered, and concentrated in vacuo. This material was taken up in a mixture of CH$_2$Cl$_2$ (137 pt) and TFA (273 μL). The reaction was stirred at room temperature for 2 days, and then it was concentrated in vacuo. The residue was taken up in 10% 7N NH$_3$/MeOH in CH$_2$Cl$_2$ (2 mL), stirred at room temperature for 5 min, concentrated in vacuo, dissolved in DMSO, filtered, and purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 5-45% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 5-35% B over 25 minutes, then a 2-minute hold at 35% B; Flow: 20 mL/min. Fractions containing the desired product were combined and dried via centrifugal evaporation to provide Example 151 (2.3 mg, 13%). HPLC Rt=0.764 min (Waters Acquity UPLC BEH C18, 2.1×50 mm, 1.7-μm particles; 5-95% MeCN—H$_2$O with 0.1% TFA over 3 min; wavelength=220 nm); LC-MS m/z 423 [M+H]$^+$; $^1$H NMR (500 MHz, DMSO-d$_6$) δ 10.50 (s, 1H), 8.43 (d, J=4.8 Hz, 1H), 8.36 (d, J=8.1 Hz, 1H), 8.30 (d, J=4.9 Hz, 2H), 8.04 (t, J=7.9 Hz, 1H), 7.52 (d, J=7.8 Hz, 1H), 7.28 (d, J=4.7 Hz, 1H), 7.24 (d, J=5.0 Hz, 1H), 6.75-6.47 (m, 1H), 4.09 (s, 2H), 2.35 (s, 3H), 2.06 (s, 3H).

Example 152

N-(4-{7-[(3,3-Difluoroazetidin-1-yl)methyl]-3-[6-(difluoromethyl)pyridin-2-yl]-1H-pyrrolo[3,2-b]pyridin-2-yl}pyridin-2-yl)acetamide

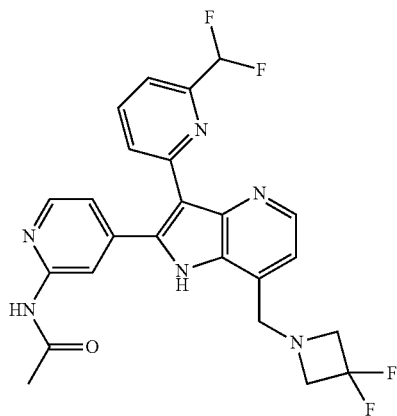 [SMILES: CC(=O)Nc1cc(-c2[nH]c3c(CN4CC(F)(F)C4)ccnc3c2-c2cccc(C(F)F)n2)ccn1]

To a room temperature solution of Example 142A (23.0 mg, 0.043 mmol) in DCE (428 μL) was added 3,3-difluoroazetidine hydrochloride (8.31 mg, 0.064 mmol) and triethylamine (13.42 μL, 0.096 mmol), followed by sodium triacetoxyborohydride (14.51 mg, 0.068 mmol). The reaction was stirred at room temperature for 16 h, and then it was diluted with sat. aq. NaHCO$_3$ (25 mL) and extracted with CH$_2$Cl$_2$ (25 mL). The organic layer was dried over Na$_2$SO$_4$, filtered, and concentrated in vacuo. This material was taken up in a mixture of CH$_2$Cl$_2$ (143 μL) and TFA (287 μL). The reaction was stirred at room temperature for 4 days, and then it was concentrated in vacuo. The residue was taken up in 10% 7N NH$_3$/MeOH in CH$_2$Cl$_2$ (2 mL), stirred at room temperature for 5 min, concentrated in vacuo, dissolved in DMSO, filtered, and purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-60% B over 19 minutes, then a 5-minute hold at 100% B; Flow: 20 mL/min. Fractions containing the desired product were combined and dried via centrifugal evaporation to provide Example 152 (8.7 mg, 42%). HPLC Rt=1.113 min (Waters Acquity UPLC BEH C18, 2.1×50 mm, 1.7-μm particles; 5-95% MeCN—H$_2$O with 0.1% TFA over 3 min; wavelength=220 nm); LC-MS m/z 485 [M+H]$^+$; $^1$H NMR (500 MHz, DMSO-d$_6$) δ 12.03 (br s, 1H), 10.50 (s, 1H), 8.42 (d, J=4.7 Hz, 1H), 8.33 (br d, J=8.1 Hz, 1H), 8.31-8.27 (m, 2H), 8.03 (t, J=7.8 Hz, 1H), 7.51 (d, J=7.6 Hz, 1H), 7.27-7.22 (m, 2H), 6.61 (t, J=55.2 Hz, 1H), 4.13 (s, 2H), 3.76-3.68 (m, 4H), 2.06 (s, 3H).

Example 153

N-(4-{3-[6-(Difluoromethyl)pyridin-2-yl]-7-[(3-hydroxyazetidin-1-yl)methyl]-1H-pyrrolo[3,2-b]pyridin-2-yl}pyridin-2-yl)acetamide

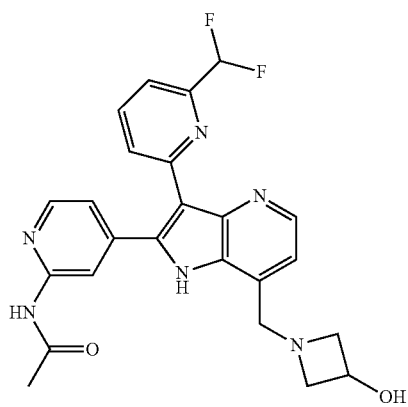 [SMILES: CC(=O)Nc1cc(-c2[nH]c3c(CN4CC(O)C4)ccnc3c2-c2cccc(C(F)F)n2)ccn1]

To a room temperature solution of Example 142A (19.4 mg, 0.036 mmol) in DCE (361 μL) was added azetidin-3-ol hydrochloride (5.93 mg, 0.054 mmol), followed by triethylamine (11.32 μL, 0.081 mmol) and sodium triacetoxyborohydride (12.24 mg, 0.058 mmol). The reaction was stirred at room temperature for 16 h, and then it was diluted with sat. aq. NaHCO$_3$ (25 mL) and extracted with CH$_2$Cl$_2$ (25 mL). The organic layer was dried over Na$_2$SO$_4$, filtered, and concentrated in vacuo. This material was taken up in a mixture of CH$_2$Cl$_2$ (120 μL) and TFA (240 μL). The reaction was stirred at room temperature for 2 days, and then it was concentrated in vacuo. The residue was taken up in 10% 7N NH$_3$/MeOH in CH$_2$Cl$_2$ (2 mL), stirred at room temperature for 5 min, concentrated in vacuo, dissolved in DMSO, filtered, and purified via preparative LC/MS with the following conditions: Column: waters xbridge shield rp18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-35% B over 25 minutes, then a 2-minute hold at 35% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 0-45% B over 20 minutes, then a 3-minute hold at 100% B; Flow: 20 mL/min. Fractions containing the desired product were combined and dried via centrifugal evaporation to provide Example 153 (0.7 mg, 4%). HPLC Rt=0.944 min (Waters Acquity UPLC BEH C18, 2.1×50 mm, 1.7-μm particles; 5-95% MeCN H$_2$O with 0.1% TFA over 3 min; wavelength=220 nm); LC-MS m/z 465 [M+H]$^+$; $^1$H NMR (500 MHz, DMSO-d$_6$) δ 11.95 (br s, 1H), 10.54 (s, 1H), 8.44-8.39 (m, 2H), 8.34-8.29 (m, 2H), 8.04 (t, J=7.9 Hz, 1H), 7.52 (d, J=7.3 Hz, 1H), 7.24 (d, J=5.2 Hz, 1H), 7.20 (d, J=4.6 Hz, 1H), 6.62 (t, J=55.4 Hz, 1H), 5.40 (br s, 1H), 4.30-4.22 (m, 1H), 4.05-3.97 (m, 2H), 3.68-3.57 (m, 2H), 2.97-2.86 (m, 2H), 2.08 (s, 3H).

Example 154

N-(4-{3-[6-(Difluoromethyl)pyridin-2-yl]-7-(2-hydroxypropan-2-yl)-1H-pyrrolo[3,2-b]pyridin-2-yl}pyridin-2-yl)acetamide

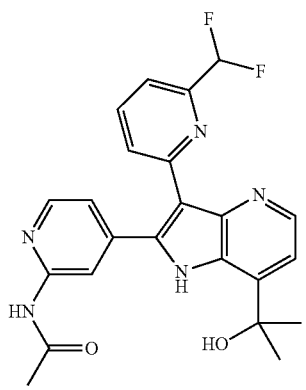

154A) N-(4-(7-Acetyl-3-(6-(difluoromethyl)pyridin-2-yl)-1-((2-(trimethylsilyl)ethoxy)methyl)-1H-pyrrolo[3,2-b]pyridin-2-yl)pyridin-2-yl)acetamide

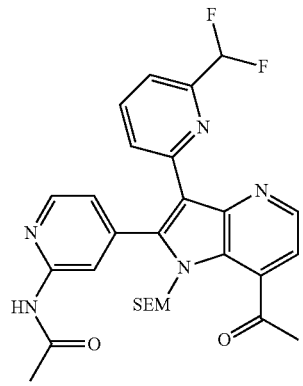 [SMILES: CC(=O)Nc1cc(-c2c(-c3cccc(C(F)F)n3)c3nccc(C(C)=O)c3n2COCC[Si](C)(C)C)ccn1]

To a 0° C. solution of Example 142A (50.3 mg, 0.094 mmol) in THF (936 μL) was added methylmagnesium bromide (62.4 μl, 3 M solution in Et$_2$O, 0.187 mmol), dropwise. The reaction was stirred at 0° C. for 30 min, then it was quenched by the addition of H$_2$O (30 mL) and extracted with EtOAc (30 mL). The organic layer was washed with sat. aq. NaCl (30 mL), dried over Na$_2$SO$_4$, filtered, and concentrated in vacuo. This material was taken up CH$_2$Cl$_2$ (889 μL), and Dess-Martin periodinane (45.2 mg, 0.107 mmol) was added. The reaction was stirred at room temperature for 30 min, and then it was diluted with CH$_2$Cl$_2$ (25 mL), washed with sat. aq. NaHCO$_3$ (25 mL), dried over Na$_2$SO$_4$, filtered, and concentrated in vacuo. The crude material was purified by flash chromatography (12 g silica gel with 5 g prepacked load cartridge; linear gradient 0-100% EtOAc-CH$_2$Cl$_2$) to provide Example 154A (44.5 mg, 91%) as a white foam. LC-MS m/z 552 [M+H]$^+$; $^1$H NMR (400 MHz, DMSO-d$_6$) δ 10.61 (s, 1H), 8.71 (d, J=4.9 Hz, 1H), 8.49 (d, J=7.9 Hz, 1H), 8.38 (d, J=5.0 Hz, 1H), 8.17 (s, 1H), 8.03 (t, J=7.9 Hz, 1H), 7.70 (d, J=4.8 Hz, 1H), 7.48

(d, J=7.6 Hz, 1H), 7.15 (dd, J=5.1, 1.4 Hz, 1H), 6.45 (t, J=55.1 Hz, 1H), 5.28 (s, 2H), 3.05-2.96 (m, 2H), 2.72 (s, 3H), 2.07 (s, 3H), 0.60-0.53 (m, 2H), −0.17 (s, 9H).

Example 154) N-(4-{3-[6-(Difluoromethyl)pyridin-2-yl]-7-(2-hydroxypropan-2-yl)-1H-pyrrolo[3,2-b]pyridin-2-yl}pyridin-2-yl)acetamide

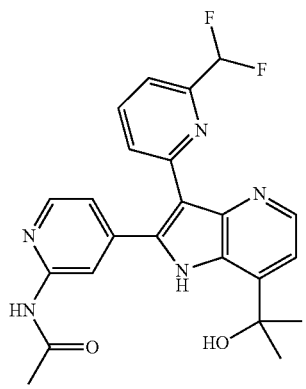 [SMILES: CC(=O)Nc1cc(-c2[nH]c3c(C(C)(C)O)ccnc3c2-c2cccc(C(F)F)n2)ccn1]

To a 0° C. solution of Example 154A (27.2 mg, 0.049 mmol) in THF (493 µL) was added methylmagnesium bromide (32.9 µL, 3 M solution in Et₂O, 0.099 mmol), dropwise. The reaction was stirred at 0° C. for 1.25 h, and then additional methylmagnesium bromide (17 µL, 0.051 mmol) was added and the reaction was stirred at 0° C. for 15 min. Additional methylmagnesium bromide (17 µL, 0.051 mmol) was added and the reaction was stirred at 0° C. for 15 min. The reaction was quenched by the addition of H₂O (30 mL) and extracted with EtOAc (30 mL). The organic layer was washed with sat. aq. NaCl (30 mL), dried over Na₂SO₄, filtered, and concentrated in vacuo. This material was taken up in a mixture of CH₂Cl₂ (163 µL) and TFA (327 µL). The reaction was stirred at room temperature for 15 h, and then it was concentrated in vacuo. The residue was taken up in 10% 7N NH₃/MeOH in CH₂Cl₂ (2 mL), stirred at room temperature for 5 min, concentrated in vacuo, dissolved in DMSO, filtered, and purified via preparative LC/MS with the following conditions: Column: XBridge Phenyl, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 20-45% B over 25 minutes, then a 2-minute hold at 45% B; Flow: 20 mL/min. Fractions containing the desired product were combined and dried via centrifugal evaporation to provide Example 154 (7.9 mg, 37%). HPLC Rt=1.021 min (Waters Acquity UPLC BEH C18, 2.1×50 mm, 1.7-µm particles; 5-95% MeCN—H₂O with 0.1% TFA over 3 min; wavelength=220 nm); LC-MS m/z 438 [M+H]⁺; ¹H NMR (500 MHz, DMSO-d₆) δ 11.07 (s, 1H), 10.48 (s, 1H), 8.40 (d, J=4.8 Hz, 1H), 8.30 (d, J=7.9 Hz, 1H), 8.28-8.25 (m, 2H), 8.02 (t, J=7.8 Hz, 1H), 7.51 (d, J=7.7 Hz, 1H), 7.23-7.18 (m, 2H), 6.61 (t, J=55.3 Hz, 1H), 5.83 (s, 1H), 2.06 (s, 3H), 1.64 (s, 6H).

Example 155

N-(4-{3-[6-(Difluoromethyl)pyridin-2-yl]-7-(2-hydroxyethyl)-1H-pyrrolo[3,2-b]pyridin-2-yl}pyridin-2-yl)acetamide

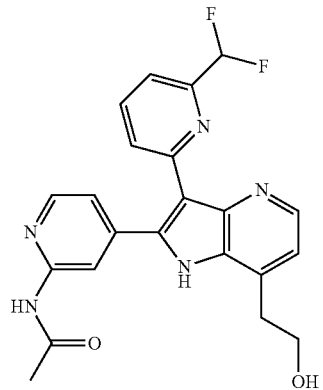 [SMILES: CC(=O)Nc1cc(-c2[nH]c3c(CCO)ccnc3c2-c2cccc(C(F)F)n2)ccn1]

155A) (E)-N-(4-(3-(6-(Difluoromethyl)pyridin-2-yl)-7-(2-ethoxyvinyl)-1-((2-(trimethylsilyl)ethoxy)methyl)-1H-pyrrolo[3,2-b]pyridin-2-yl)pyridin-2-yl)acetamide

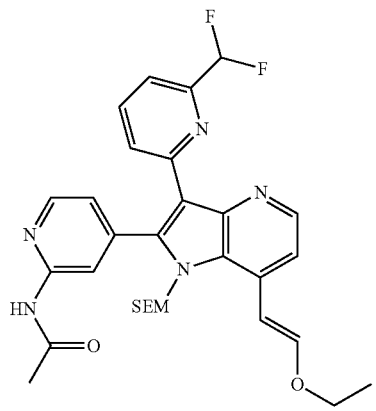 [SMILES: CCO/C=C/c1ccnc2c(-c3cccc(C(F)F)n3)c(-c3ccnc(NC(C)=O)c3)n(COCC[Si](C)(C)C)c12]

A mixture of Example 125B (90.0 mg, 0.165 mmol) and cesium carbonate (216 mg, 0.662 mmol) was evacuated and backfilled with N₂, then 1,4-dioxane (1489 µL) and H₂O (165 µL) were added. The mixture was sparged with N₂ for 5 min, then 2nd generation XPhos precatalyst (6.51 mg, 8.27 µmol) and (E)-2-(2-ethoxyvinyl)-4,4,5,5-tetramethyl-1,3,2-dioxaborolane (98 mg, 0.496 mmol) were added. The mixture was sparged with N₂ for 1 min, then it was sealed and stirred at 80° C. for 1 h. The reaction was cooled to room temperature, diluted with EtOAc (30 mL), washed with sat. aq. NaCl (30 mL), dried over Na₂SO₄, filtered, and concentrated in vacuo. The crude material was purified by flash chromatography (24 g silica gel with 5 g prepacked load cartridge; linear gradient 0-100% EtOAc-CH₂Cl₂) to provide Example 155A (67.2 mg, 70%) as a light yellow solid. LC-MS m/z 580 [M+H]⁺; ¹H NMR (400 MHz, DMSO-d₆) δ 10.58 (s, 1H), 8.52 (d, J=8.1 Hz, 1H), 8.40 (d, J=4.9 Hz, 1H), 8.35 (d, J=5.1 Hz, 1H), 8.23 (s, 1H), 8.00 (t, J=7.9 Hz, 1H), 7.44 (d, J=7.7 Hz, 1H), 7.40 (d, J=12.7 Hz, 1H), 7.30 (d, J=5.0 Hz, 1H), 7.11 (dd, J=5.1, 1.5 Hz, 1H), 6.57-6.26 (m, 2H), 5.40 (s, 2H), 4.02 (q, J=7.0 Hz, 2H), 3.37-3.32 (m, 2H), 2.07 (s, 3H), 1.31 (t, J=7.0 Hz, 3H), 0.85-0.75 (m, 2H), −0.09 (s, 9H).

Example 155) N-(4-{3-[6-(Difluoromethyl)pyridin-2-yl]-7-(2-hydroxyethyl)-1H-pyrrolo[3,2-b]pyridin-2-yl}pyridin-2-yl)acetamide

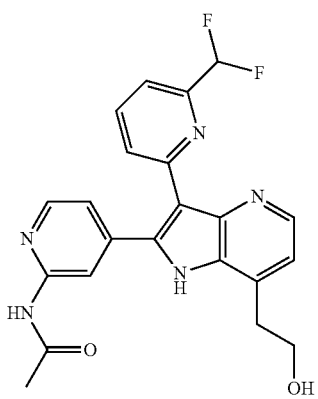

A room temperature suspension of Example 155A (66 mg, 0.114 mmol) in a mixture of CH$_2$Cl$_2$ (379 µL) and TFA (759 µL) was stirred for 6 h, and then H$_2$O (5 drops) was added and the reaction was stirred for 16 h. The reaction was concentrated in vacuo. The residue was taken up in CH$_2$Cl$_2$ (20 mL) and washed with sat. aq. NaHCO$_3$ (20 mL). The aqueous layer was extracted with CH$_2$Cl$_2$ (2×20 mL). The combined organic layers were dried over Na$_2$SO$_4$, filtered, and concentrated in vacuo. This material was taken up in MeOH (1140 µL) and sodium borohydride (8.63 mg, 0.228 mmol) was added. The reaction was stirred at room temperature for 15 min, and then it was diluted with sat. aq. NH$_4$Cl (25 mL) and extracted with CH$_2$Cl$_2$ (2×25 mL). The combined organic layers were dried over Na$_2$SO$_4$, filtered, and concentrated in vacuo. The crude material was dissolved in DMSO, filtered, and purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 5-45% B over 20 minutes, then a 5-minute hold at 100% B; Flow: 20 mL/min. Fractions containing the desired product were combined and dried via centrifugal evaporation to provide Example 155 (4.9 mg, 10%). HPLC Rt=0.929 min (Waters Acquity UPLC BEH C18, 2.1×50 mm, 1.7-µm particles; 5-95% MeCN—H$_2$O with 0.1% TFA over 3 min; wavelength=220 nm); LC-MS m/z 424 [M+H]$^+$; $^1$H NMR (500 MHz, DMSO-d$_6$) δ 12.04 (br s, 1H), 10.52 (s, 1H), 8.39-8.33 (m, 2H), 8.32-8.28 (m, 2H), 8.03 (t, J=7.7 Hz, 1H), 7.52 (d, J=7.6 Hz, 1H), 7.24 (br d, J=5.0 Hz, 1H), 7.16 (br d, J=4.7 Hz, 1H), 6.63 (t, J=55.5 Hz, 1H), 4.86 (br s, 1H), 3.83-3.77 (m, 2H), 3.15 (br t, J=6.6 Hz, 2H), 2.07 (s, 3H).

Example 156

N-(4-{3-[6-(Difluoromethyl)pyridin-2-yl]-7-(pyrrolidin-1-yl)-1H-pyrrolo[3,2-b]pyridin-2-yl}pyridin-2-yl)acetamide

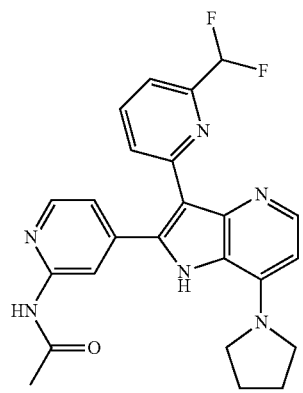 [SMILES: CC(=O)Nc1cc(-c2[nH]c3c(N4CCCC4)ccnc3c2-c2cccc(C(F)F)n2)ccn1]

To a room temperature solution of Example 125B (20 mg, 0.037 mmol) in DMF (184 µL) was added pyrrolidine (61.4 µL, 0.735 mmol). The reaction was sealed and stirred at 110° C. for 6 h, and then it was cooled to room temperature, diluted with EtOAc (25 mL), washed with H$_2$O (25 mL) and sat. aq. NaCl (25 mL), dried over Na$_2$SO$_4$, filtered, and concentrated in vacuo. This material was taken up in a mixture of CH$_2$Cl$_2$ (123 µL) and TFA (247 µL). The reaction was stirred at room temperature for 22 h, and then it was concentrated in vacuo. The residue was taken up in 10% 7N NH$_3$/MeOH in CH$_2$Cl$_2$ (2 mL), stirred at room temperature for 5 min, concentrated in vacuo, dissolved in DMSO, filtered, and purified via preparative LC/MS with the following conditions: Column: XBridge Shield RP18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 15-55% B over 20 minutes, then a 4-minute hold at 100% B; Flow: 20 mL/min. Fractions containing the desired product were combined and dried via centrifugal evaporation to provide Example 156 (3.6 mg, 21%). HPLC Rt=1.252 min (Waters Acquity UPLC BEH C18, 2.1×50 mm, 1.7-µm particles; 5-95% MeCN—H$_2$O with 0.1% TFA over 3 min; wavelength=220 nm); LC-MS m/z 449 [M+H]$^+$; $^1$H NMR (500 MHz, DMSO-d$_6$) δ 12.00 (br s, 1H), 10.50 (br s, 1H), 8.35-8.26 (m, 2H), 7.91-7.83 (m, 1H), 7.81-7.75 (m, 1H), 7.47-7.32 (m, 2H), 7.26 (br d, J=4.7 Hz, 1H), 7.24-6.97 (m, 1H), 6.32 (br d, J=6.2 Hz, 1H), 3.49-3.30 (m, 4H), 2.07 (s, 3H), 2.02-1.98 (m, 4H).

Example 157

N-(4-(6-Acetamido-3-(5-methoxypyridin-2-yl)-1H-pyrrolo[3,2-b]pyridin-2-yl)pyridin-2-yl)acetamide

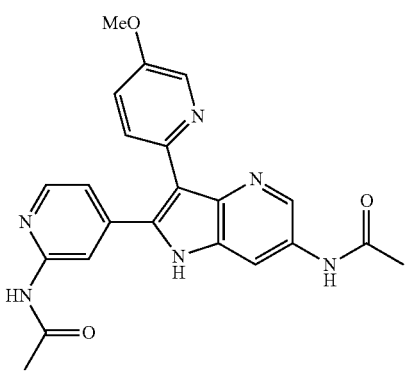 [SMILES: COc1ccc(-c2c(-c3ccnc(NC(C)=O)c3)[nH]c3cc(NC(C)=O)cnc23)nc1]

157A) N-(4-(6-Bromo-3-(5-methoxypyridin-2-yl)-1-((2-(trimethylsilyl)ethoxy)methyl)-1H-pyrrolo[3,2-b]pyridin-2-yl)pyridin-2-yl)acetamide

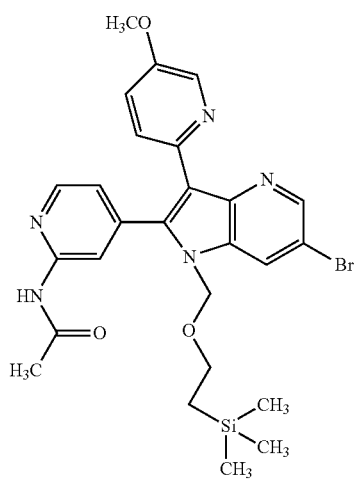 [SMILES: COc1ccc(-c2c(-c3ccnc(NC(C)=O)c3)n(COCC[Si](C)(C)C)c3cc(Br)cnc23)nc1]

A mixture of Example 83 (765 mg, 1.745 mmol), cesium carbonate (1137 mg, 3.49 mmol) and (2-(chloromethoxy)ethyl)trimethylsilane (437 mg, 2.62 mmol) in THF (12 mL) and DMF (12 mL) was stirred at room temperature for 30 min. To the reaction mixture were added $CH_2Cl_2$ and water, $CH_2Cl_2$ layer was separated, dried over $MgSO_4$, concentrated in vacuo and the residue was purified by flash column on $SiO_2$ (gradient of 100% $CH_2Cl_2$ to 80% EtOAc in $CH_2Cl_2$, product was eluted at 30-40% EtOAc in $CH_2Cl_2$) to obtain 6 (625 mg, 1.099 mmol, 63%) as a glassy material. MS (ES): m/z=568, 570 [M+H]$^+$; $^1$H NMR (400 MHz, CHLOROFORM-d) δ 8.65 (d, J=2.0 Hz, 1H), 8.33 (s, 1H), 8.28-8.24 (m, 2H), 8.05 (d, J=2.0 Hz, 1H), 7.80 (d, J=8.6 Hz, 1H), 7.30 (dd, J=8.7, 3.0 Hz, 1H), 7.14 (dd, J=5.2, 1.4 Hz, 1H), 5.43 (s, 2H), 3.85 (s, 3H), 3.42-3.36 (m, 2H), 2.19 (s, 3H), 0.85-0.80 (m, 2H), −0.08 (s, 9H).

Example 157) N-(4-(6-Acetamido-3-(5-methoxypyridin-2-yl)-1H-pyrrolo[3,2-b]pyridin-2-yl)pyridin-2-yl)acetamide

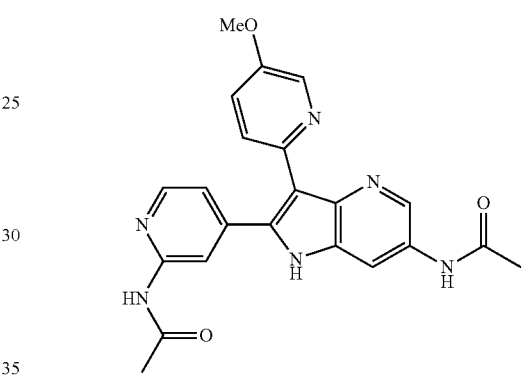

To a solution of N-(4-(6-bromo-3-(5-methoxypyridin-2-yl)-1-((2-(trimethylsilyl)ethoxy)methyl)-1H-pyrrolo[3,2-b]pyridin-2-yl)pyridin-2-yl)acetamide (40 mg, 0.070 mmol) in dioxane (2 ml) was added acetamide (41.6 mg, 0.704 mmol), xantphos (8.14 mg, 0.014 mmol), cesium carbonate (45.8 mg, 0.141 mmol) and $Pd_2(dba)_3$ (12.89 mg, 0.014 mmol). The suspension was purged with nitrogen for 5 minutes and the heated to 110° C. for 1 hr. The reaction mixture was concentrated to dryness and resuspended in 1 mL EtOAc and filtered through on a small silica gel plug, eluted with Hex:EtOAc (1:1) then with EtOAc. The EtOAc fractions were concentrated to give crude product which was treated with 4N HCl in Dioxane 1.5 (mL) for 30 minutes at 60° C. The reaction mixture is concentrated, diluted with DMF and purified by preparative HPLC to give N-(4-(6-acetamido-3-(5-methoxypyridin-2-yl)-1H-pyrrolo[3,2-b]pyridin-2-yl)pyridin-2-yl)acetamide. HPLC: RT=0.85 min ($H_2O$/ACN with 0.1% TFA, Waters Acquity UPLC BEH C18, 2.1×50 mm, 1.7-μm particles, gradient=3 min, wavelength=220 nm); MS (ES): m/z=417 [M+H]$^+$; $^1$H NMR (500 MHz, DMSO-$d_6$) δ ppm 10.50 (s, 1H), 10.27 (s, 1H), 8.42-8.45 (m, 1H), 8.43 (s, 1H), 8.40 (s, 1H), 8.27 (br. s., 1H), 8.24 (d, J=5.05 Hz, 1H), 8.18 (d, J=1.60 Hz, 1H), 7.93 (d, J=8.58 Hz, 1H), 7.48 (dd, J=2.19, 8.50 Hz, 1H), 7.10 (d, J=4.88 Hz, 1H), 3.85 (s, 3H), 2.10 (s, 3H), 2.08 (s, 3H)

Example 158

N-(4-(6-(4-Methoxypiperidin-1-yl)-3-(5-methoxy-pyridin-2-yl)-1H-pyrrolo[3,2-b]pyridin-2-yl)pyridin-2-yl)acetamide

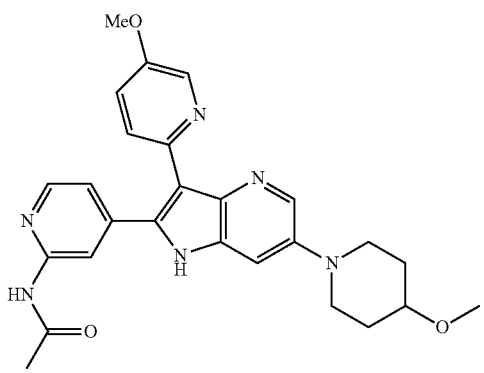 [SMILES: COc1ccc(-c2c(-c3ccnc(NC(C)=O)c3)[nH]c3cc(N4CCC(OC)CC4)cnc23)nc1]

To a solution of Example 157A (30 mg, 0.053 mmol) in DMSO (2 mL) was added (S)-pyrrolidine-2-carboxylic acid (6.68 mg, 0.058 mmol), K$_2$CO$_3$ (14.59 mg, 0.106 mmol), 4-methoxypiperidine (42.5 mg, 0.369 mmol) and copper (I) iodide (5.33 mg, 0.028 mmol). The reaction mixture was purged with nitrogen for 2 min. and stirred at 100° C. for 3 h. The reaction mixture was concentrated to dryness over a stream of nitrogen and treated with 4N HCl in dioxane (3 mL) at 60° C. for 30 minutes. The reaction mixture was concentrated and redissolved in DMF and purified by preparative HPLC to give N-(4-(6-(4-methoxypiperidin-1-yl)-3-(5-methoxypyridin-2-yl)-1H-pyrrolo[3,2-b]pyridin-2-yl)pyridin-2-yl)acetamide. HPLC: RT=0.92 min (H$_2$O/ACN with 0.1% TFA, Waters Acquity UPLC BEH C18, 2.1×50 mm, 1.7-μm particles, gradient=3 min, wavelength=220 nm); MS (ES): m/z=473 [M+H]$^+$; $^1$H NMR (500 MHz, DMSO-d$_6$) d 12.66 (br. s., 1H), 10.71 (br. s., 1H), 8.42 (s, 1H), 8.40 (d, J=5.55 Hz, 1H), 8.34 (br. s., 1H), 8.30 (br. s., 1H), 7.81 (br. s., 1H), 7.43-7.59 (m, 2H), 7.10-7.31 (m, H), 3.89 (s, 3H), 3.51-3.67 (m, J=5.39 Hz, 2H), 3.42 (br. s., 1H), 3.11 (t, J=9.47 Hz, 2H), 3.10 (s, 3H) 2.10 (s, 3H), 2.00 (br. s., 2H), 1.55-1.72 (m, 2H)

TABLE 8

| # | Structure | Name | HPLC ret. time (min) | LC/MS) (M + H)$^+$ |
|---|---|---|---|---|
| 159 | 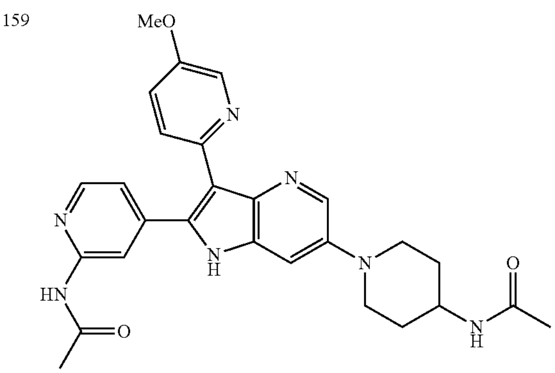 | N-(4-(6-(4-Acetamidopiperidin-1-yl)-3-(5-methoxypyridin-2-yl)-1H-pyrrolo[3,2-b]pyridin-2-yl)pyridin-2-yl)acetamide | 0.79 | 500 |
| 160 | 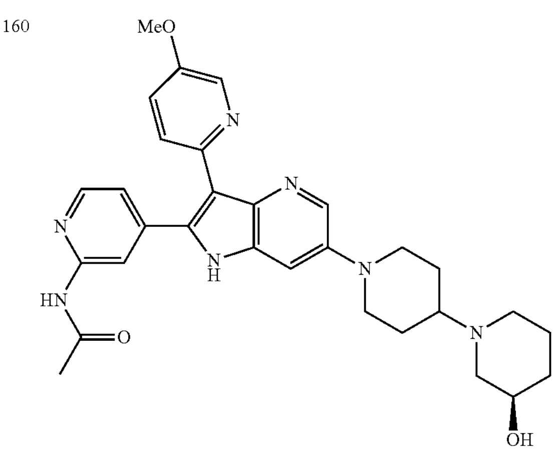 | (R)-N-(4-(6-(3-Hydroxypiperidin-1-yl)-3-(5-methoxypyridin-2-yl)-1H-pyrrolo[3,2-b]pyridin-2-yl)pyridin-2-yl)acetamide | 0.76 | 459 |

TABLE 8-continued

| # | Structure | Name | HPLC ret. time (min) | LC/MS) (M + H)+ |
|---|---|---|---|---|
| 161 | 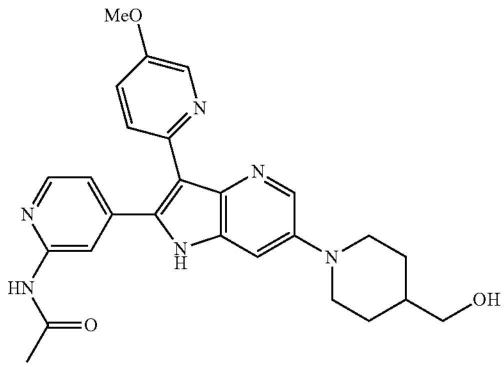 [SMILES: COc1ccc(-c2c(-c3ccnc(NC(C)=O)c3)[nH]c3cc(N4CCC(CO)CC4)cnc23)nc1] | N-(4-(6-(4-(Hydroxymethyl)piperidin-1-yl)-3-(5-methoxypyridin-2-yl)-1H-pyrrolo[3,2-b]pyridin-2-yl)pyridin-2-yl)acetamide | 0.92 | 473 |
| 162 | 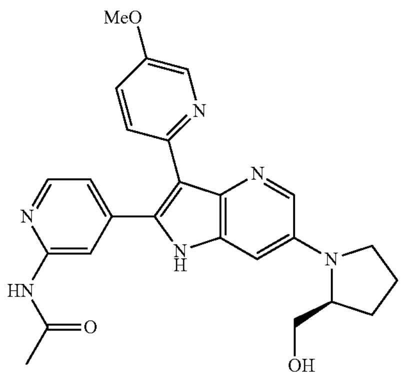 [SMILES: COc1ccc(-c2c(-c3ccnc(NC(C)=O)c3)[nH]c3cc(N4CCC[C@H]4CO)cnc23)nc1] | (S)-N-(4-(6-(2-(Hydroxymethyl)pyrrolidin-1-yl)-3-(5-methoxypyridin-2-yl)-1H-pyrrolo[3,2-b]pyridin-2-yl)pyridin-2-yl)acetamide | 1.02 | 459 |
| 163 | 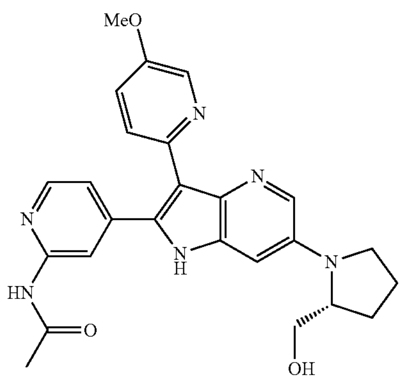 [SMILES: COc1ccc(-c2c(-c3ccnc(NC(C)=O)c3)[nH]c3cc(N4CCC[C@@H]4CO)cnc23)nc1] | (R)-N-(4-(6-(2-(Hydroxymethyl)pyrrolidin-1-yl)-3-(5-methoxypyridin-2-yl)-1H-pyrrolo[3,2-b]pyridin-2-yl)pyridin-2-yl)acetamide | 1.16 | 459 |
| 164 | 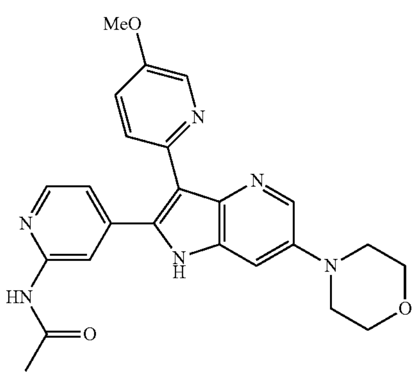 [SMILES: COc1ccc(-c2c(-c3ccnc(NC(C)=O)c3)[nH]c3cc(N4CCOCC4)cnc23)nc1] | N-(4-(3-(5-Methoxypyridin-2-yl)-6-morpholino-1H-pyrrolo[3,2-b]pyridin-2-yl)pyridin-2-yl)acetamide | 0.86 | 445 |

TABLE 8-continued

| # | Structure | Name | HPLC ret. time (min) | LC/MS (M + H)+ |
|---|---|---|---|---|
| 165 | 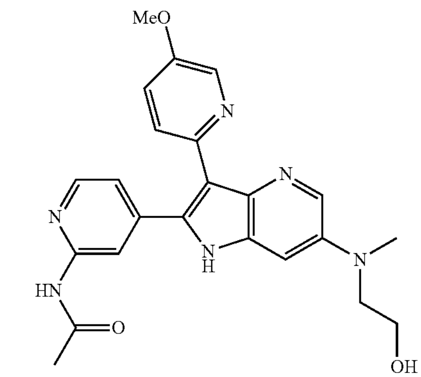 [SMILES: COc1ccc(-c2c(-c3ccnc(NC(C)=O)c3)[nH]c3cc(N(C)CCO)cnc23)nc1] | N-(4-(6-((2-Hydroxyethyl)(methyl)amino)-3-(5-methoxypyridin-2-yl)-1H-pyrrolo[3,2-b]pyridin-2-yl)pyridin-2-yl)acetamide | 1.08 | 433 |
| 166 | 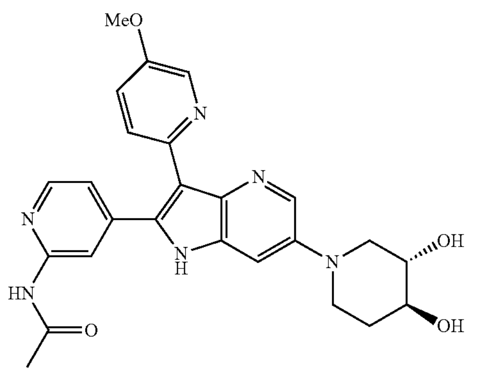 [SMILES: COc1ccc(-c2c(-c3ccnc(NC(C)=O)c3)[nH]c3cc(N4CC[C@H](O)[C@@H](O)C4)cnc23)nc1] | N-(4-(6-((3S,4S)-3,4-Dihydroxypiperidin-1-yl)-3-(5-methoxypyridin-2-yl)-1H-pyrrolo[3,2-b]pyridin-2-yl)pyridin-2-yl)acetamide | 0.90 | 497 |

HPLC/LCMS Column conditions: Waters Acquity UPLC BEH C18, 2.1 × 50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

Examples in Table 8 were prepared in the same general way as Example 158 and the corresponding amine by the general methods shown.

Example 167

N-(4-(3-(5-Methoxypyridin-2-yl)-6-(pyrrolidin-1-yl)-1H-pyrrolo[3,2-b]pyridin-2-yl)pyridin-2-yl)acetamide

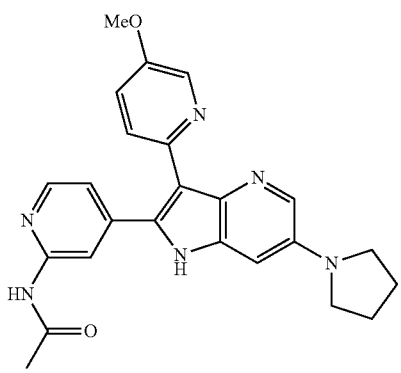 [SMILES: COc1ccc(-c2c(-c3ccnc(NC(C)=O)c3)[nH]c3cc(N4CCCC4)cnc23)nc1]

167A) tert-Butyl 2-(2-acetamidopyridin-4-yl)-3-(5-methoxypyridin-2-yl)-6-(pyrrolidin-1-yl)-1H-pyrrolo[3,2-b]pyridine-1-carboxylate

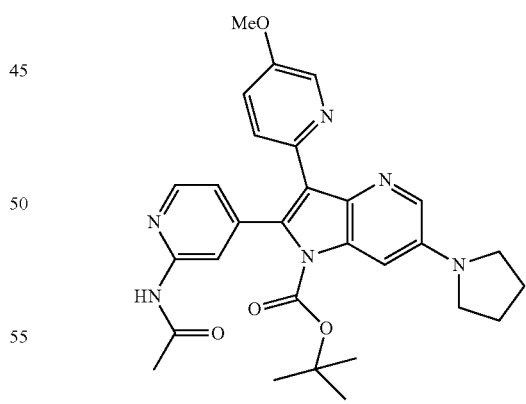

To a suspension of Example 83 (100 mg, 0.228 mmol) and DMAP (5.57 mg, 0.046 mmol) in THF (3 mL) was added di-tert-butyl dicarbonate (100 mg, 0.456 mmol). The reaction mixture was stirred at room temperature for overnight. The reaction mixture was diluted water (10 ml) and extract with EtOAc (3×10 ml). The organics were combined, dry over sodium sulfate, filtered and concentrated to give tert-butyl 2-(2-acetamidopyridin-4-yl)-3-(5-methoxypyridin-2-yl)-6-(pyrrolidin-1-yl)-1H-pyrrolo[3,2-b]pyridine-1-carboxylate as clear yellow oil which was used as is in the next reaction. HPLC: RT=3.11 min (MeOH/H₂O with 0.1% TFA, column: Sun-Fire 5 u 4.6×30 mm, 1.7-μm particles, gradient=4 min, wavelength=220 nm); MS (ES): m/z=529 [M+H]⁺.

Example 167) N-(4-(3-(5-Methoxypyridin-2-yl)-6-(pyrrolidin-1-yl)-1H-pyrrolo[3,2-b]pyridin-2-yl)pyridin-2-yl)acetamide

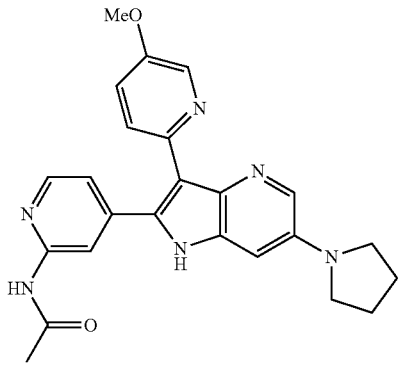 [SMILES: COc1ccc(-c2c(-c3ccnc(NC(C)=O)c3)[nH]c3cc(N4CCCC4)cnc23)nc1]

To a solution tert-butyl 2-(2-acetamidopyridin-4-yl)-6-bromo-3-(5-methoxypyridin-2-yl)-1H-pyrrolo[3,2-b]pyridine-1-carboxylate (20 mg, 0.037 mmol) in DMSO (2 mL) was added (S)-pyrrolidine-2-carboxylic acid (4.70 mg, 0.041 mmol), K₂CO₃ (10.27 mg, 0.074 mmol), pyrrolidine (13.21 mg, 0.186 mmol) and copper (I) iodide (3.75 mg, 0.020 mmol). The reaction mixture was purged with nitrogen for 2 min. and stirred at 90° C. for over the weekend. The Boc group fell off during the reaction to give the desired product. The reaction mixture was filtered and purified by preparative HPLC to give N-(4-(3-(5-methoxypyridin-2-yl)-6-(pyrrolidin-1-yl)-1H-pyrrolo[3,2-b]pyridin-2-yl)pyridin-2-yl)acetamide. HPLC: RT=1.01 min (H₂O/ACN with 0.1% TFA, Waters Acquity UPLC BEH C18, 2.1×50 mm, 1.7-μm particles, gradient=3 min, wavelength=220 nm); MS (ES): m/z=429 [M+H]⁺.

TABLE 9

| # | Structure | Name | HPLC ret. time (min) | LC/MS) (M + H)⁺ |
|---|---|---|---|---|
| 168 | 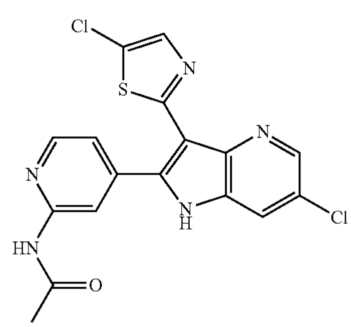 [SMILES: CC(=O)Nc1cc(-c2[nH]c3cc(Cl)cnc3c2-c2ncc(Cl)s2)ccn1] | N-(4-(6-Chloro-3-(5-chlorothiazol-2-yl)-1H-pyrrolo[3,2-b]pyridin-2-yl)pyridin-2-yl)acetamide | 1.57 | 404 |
| 169 | 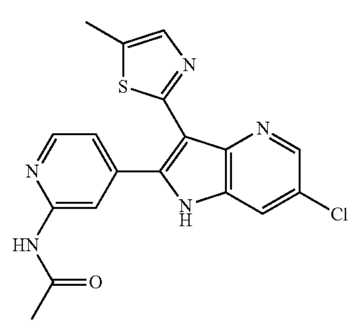 [SMILES: CC(=O)Nc1cc(-c2[nH]c3cc(Cl)cnc3c2-c2ncc(C)s2)ccn1] | (N-(4-(6-Chloro-3-(5-methylthiazol-2-yl)-1H-pyrrolo[3,2-b]pyridin-2-yl)pyridin-2-yl)acetamide | 1.50* | 384 |

TABLE 9-continued

| # | Structure | Name | HPLC ret. time (min) | LC/MS) (M + H)+ |
|---|---|---|---|---|
| 170 | 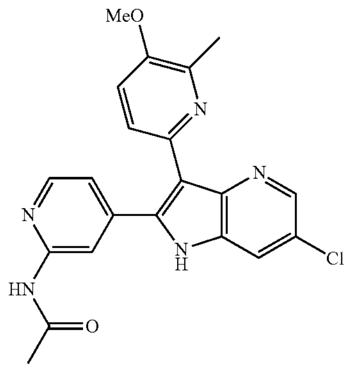 [SMILES: COc1ccc(-c2c(-c3ccnc(NC(C)=O)c3)[nH]c3cc(Cl)cnc23)nc1C] | N-(4-(6-Chloro-3-(5-methoxy-6-methylpyridin-2-yl)-1H-pyrrolo[3,2-b]pyridin-2-yl)pyridin-2-yl)acetamide | 0.99 | 408 |
| 171 | 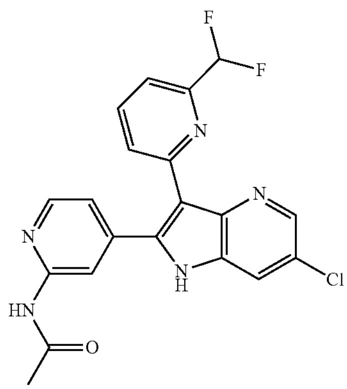 [SMILES: CC(=O)Nc1cc(-c2[nH]c3cc(Cl)cnc3c2-c2cccc(C(F)F)n2)ccn1] | N-(4-(6-Chloro-3-(6-(difluoromethyl)pyridin-2-yl)-1H-pyrrolo[3,2-b]pyridin-2-yl)pyridin-2-yl)acetamide | 1.23 | 414 |

HPLC/LCMS Column conditions: Waters Acquity UPLC BEH C18, 2.1 × 50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

Examples in table 9 were prepared the same way as Example 46 (from Example 41B and heteroaryl bromide by the general methods shown for Example 1)

Example 172

N-(4-(6-Chloro-3-(4-(difluoromethyl)thiazol-2-yl)-1H-pyrrolo[3,2-b]pyridin-2-yl)pyridin-2-yl)acetamide

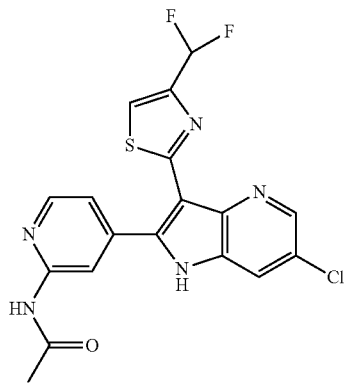 [SMILES: CC(=O)Nc1cc(-c2[nH]c3cc(Cl)cnc3c2-c2nc(C(F)F)cs2)ccn1]

172A) 2-Bromo-4-(difluoromethyl)thiazole

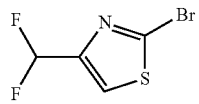

To a solution of 2-bromothiazole-4-carbaldehyde (0.3 g, 1.562 mmol) in DCM (10 mL) under a nitrogen atmosphere was added DAST (0.826 mL, 6.25 mmol) dropwise. The reaction mixture was stirred overnight at room temperature and then diluted with EtOAc (10 mL) and quenched with MeOH added dropwise (1 mL) until bubbling stopped. The reaction mixture was washed with aq. $K_3PO_4$. The organic phase was washed with brine, dried over magnesium sulphate, filtered and concentrated under reduced pressure to afford light yellow oil which was and purified by silica gel flash chromatography, eluting with 0-50% ethyl acetate in hexane to afford 2-bromo-4-(difluoromethyl)thiazole (0.2 g, 0.934 mmol, 59.8% yield) as a yellow oil. $^1$H NMR (400 MHz, METHANOL-$d_4$) δ ppm 7.92 (t, J=1.5 Hz, 1H), 6.75 (t, J=54.6 Hz, 1H) which does not show [M+H]+ under LCMS.

Example 172) N-(4-(6-Chloro-3-(4-(difluoromethyl) thiazol-2-yl)-1H-pyrrolo[3,2-b]pyridin-2-yl)pyridin-2-yl)acetamide

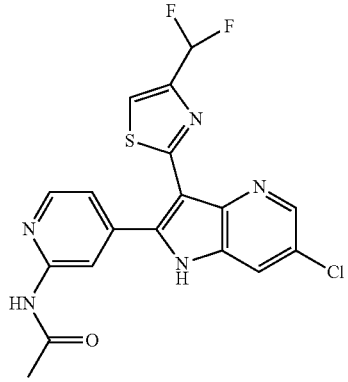

A mixture of Example 41B (54 mg, 0.141 mmol), 2-bromo-4-(difluoromethyl)thiazole (60.4 mg, 0.282 mmol) and Cs$_2$CO$_3$ (69.0 mg, 0.212 mmol) in Acetonitrile (2 mL) was purged with nitrogen for a few minutes. Xphos (6.73 mg, 0.014 mmol) and Pd$_2$(dba)$_3$ (3.88 mg, 4.23 μmol) were added and the mixture was heated at 120° C. in a sealed vial for 1 h. The reaction mixture was cooled, filtered and purified by preparative HPLC to give N-(4-(6-chloro-3-(4-(difluoromethyl)thiazol-2-yl)-1H-pyrrolo[3,2-b]pyridin-2-yl)pyridin-2-yl)acetamide. HPLC: RT=1.42 min (H$_2$O/ACN with 0.1% TFA, Waters Acquity UPLC BEH C18, 2.1×50 mm, 1.7-μm particles, gradient=3 min, wavelength=220 nm); MS (ES): m/z=420 [M+H]$^+$; $^1$H NMR (500 MHz, DMSO-d$_6$) δ ppm 10.63 (s, 1H), 8.57 (d, J=1.94 Hz, 1H), 8.53 (s, 1H), 8.40 (d, J=5.13 Hz, 1H), 8.10 (s, 1H), 8.04 (d, J=1.85 Hz, 1H), 7.49 (d, J=5.13 Hz, 1H), 6.99 (t, J=54.95 Hz, 1H), 6.57 (s, 1H), 2.10 (s, 3H).

Example 173

N-(4-(3-(6-Methoxypyridin-3-yl)-6-methyl-1H-pyrrolo[3,2-b]pyridin-2-yl)pyridin-2-yl)acetamide

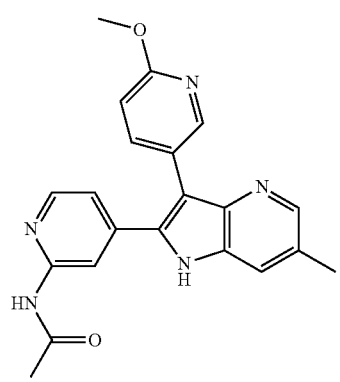 [SMILES: COc1ccc(-c2c(-c3ccnc(NC(C)=O)c3)[nH]c3cc(C)cnc23)cn1]

173A) N-(4-((3-Amino-5-methylpyridin-2-yl)ethynyl)pyridin-2-yl)acetamide

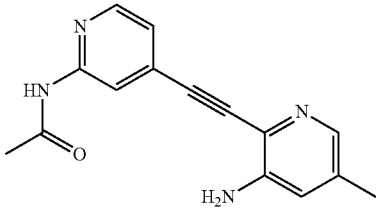 [SMILES: CC(=O)Nc1cc(C#Cc2ncc(C)cc2N)ccn1]

N-(4-((3-Amino-5-methylpyridin-2-yl)ethynyl)pyridin-2-yl)acetamide was prepared from Example 1B and 2-bromo-5-methylpyridin-3-amine by the methods shown for Example 1C. HPLC: RT=0.49 min (H$_2$O/MeOH with 0.05% TFA, Waters Acquity SDS BEH C18 2.1×50 mm 1.7 u, gradient=1.8 min, wavelength=220 nm); MS (ES): m/z=267 [M+H]$^+$; $^1$H NMR (400 MHz, DMSO-d$_6$) δ 10.58 (s, 1H), 8.33 (dd, J=0.77, 5.17 Hz, 1H), 8.21 (s, 1H), 7.64-7.71 (m, 1H), 7.32 (dd, J=1.54, 5.06 Hz, 1H), 6.93 (dd, J=0.88, 1.76 Hz, 1H), 5.72 (s, 2H), 2.20 (s, 3H), 2.11 (s, 3H)

173B) N-(2-((2-Acetamidopyridin-4-yl)ethynyl)-5-methylpyridin-3-yl)-2,2,2-trifluoroacetamide

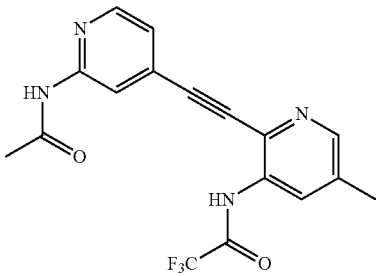 [SMILES: CC(=O)Nc1cc(C#Cc2ncc(C)cc2NC(=O)C(F)(F)F)ccn1]

N-(2-((2-Acetamidopyridin-4-yl)ethynyl)-5-methylpyridin-3-yl)-2,2,2-trifluoroacetamide was prepared by methods shown for Example 1D. HPLC: RT=0.72 min (H$_2$O/MeOH with 0.05% TFA, Waters Acquity SDS BEH C18 2.1×50 mm 1.7 u, gradient=1.8 min, wavelength=220 nm); MS (ES): m/z=363 [M+H]$^+$;

Example 173) N-(4-(3-(6-Methoxypyridin-3-yl)-6-methyl-1H-pyrrolo[3,2-b]pyridin-2-yl)pyridin-2-yl)acetamide

Example 174
N-(4-(3-(6-(Difluoromethoxy)pyridin-2-yl)-1H-pyrrolo[3,2-b]pyridin-2-yl)pyridin-2-yl)acetamide

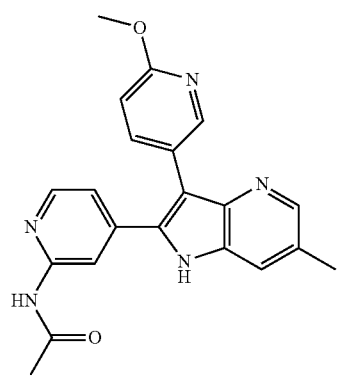

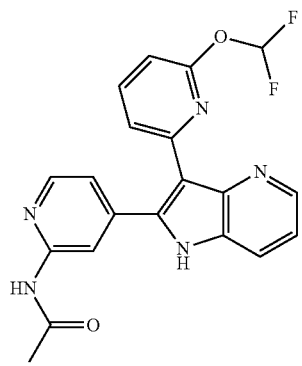 [SMILES: CC(=O)Nc1cc(-c2[nH]c3cccnc3c2-c2cccc(OC(F)F)n2)ccn1]

N-(4-(3-(6-Methoxypyridin-3-yl)-6-methyl-1H-pyrrolo[3,2-b]pyridin-2-yl)pyridin-2-yl)acetamide was prepared from N-(2-((2-acetamidopyridin-4-yl)ethynyl)-5-methylpyridin-3-yl)-2,2,2-trifluoroacetamide and 5-iodo-2-methoxypyridine by the methods shown for Example 172. HPLC: RT=0.80 min (H$_2$O/ACN with 0.1% TFA, Waters Acquity UPLC BEH C18, 2.1×50 mm, 1.7-μm particles, gradient=3 min, wavelength=220 nm); MS (ES): m/z=374; $^1$H NMR (500 MHz, DMSO-d$_6$) δ ppm 11.85 (s, 1H), 10.50 (s, 1H), 8.28 (d, J=5.19 Hz, 1H), 8.24 (s, 2H), 8.19 (d, J=1.83 Hz, 1H), 7.75 (dd, J=2.29, 8.39 Hz, 1H), 7.65 (s, 1H), 7.09 (d, J=5.19 Hz, 1H), 6.84 (d, J=8.24 Hz, 1H), 3.85 (s, 3H), 2.42 (s, 3H), 2.06 (s, 3H)

N-(4-(3-(6-(Difluoromethoxy)pyridin-2-yl)-1H-pyrrolo[3,2-b]pyridin-2-yl)pyridin-2-yl)acetamide was prepared from Example 1D and 2-bromo-6-(difluoromethoxy)pyridine by the methods shown for Example 172. HPLC: RT=0.93 min (H$_2$O/ACN with 0.1% TFA, Waters Acquity UPLC BEH C18, 2.1×50 mm, 1.7-μm particles, gradient=3 min, wavelength=220 nm); MS (ES): m/z=396; $^1$H NMR (500 MHz, DMSO-d$_6$) δ ppm 12.26 (s, 1H), 10.63 (s, 1H), 8.52 (d, J=4.12 Hz, 1H), 8.35-8.45 (m, 2H), 8.25 (s, 1H), 7.99 (t, J=7.87 Hz, 1H), 7.91 (d, J=7.91 Hz, 1H), 7.31 (dd, J=4.59, 8.20 Hz, 1H), 7.26 (d, J=4.38 Hz, 1H), 6.87 (d, J=7.99 Hz, 1H), 6.65 (t, J=73.55 Hz, 1H), 2.09 (s, 3H)

TABLE 10

| # | Structure | Name | HPLC ret. time (min) | LC/MS) (M + H)$^+$ |
|---|---|---|---|---|
| 175 | 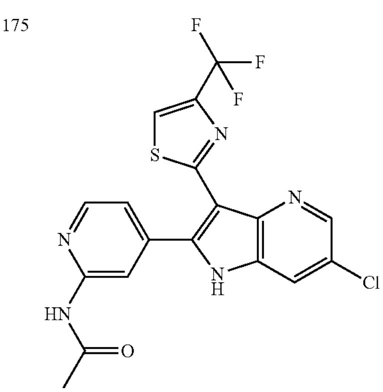 | N-(4-(6-Chloro-3-(4-(trifluoromethyl)thiazol-2-yl)-1H-pyrrolo[3,2-b]pyridin-2-yl)pyridin-2-yl)acetamide | 1.62 | 438 |

TABLE 10-continued

| # | Structure | Name | HPLC ret. time (min) | LC/MS) (M + H)+ |
|---|---|---|---|---|
| 176 | 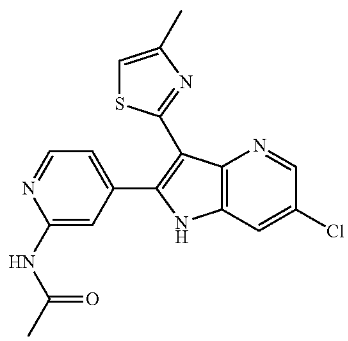 [SMILES: CC(=O)Nc1cc(-c2[nH]c3cc(Cl)cnc3c2-c2nc(C)cs2)ccn1] | N-(4-(6-Chloro-3-(4-methylthiazol-2-yl)-1H-pyrrolo[3,2-b]pyridin-2-yl)pyridin-2-yl)acetamide | 1.13 | 384 |
| 177 | 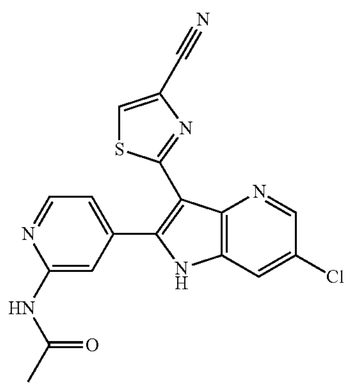 [SMILES: CC(=O)Nc1cc(-c2[nH]c3cc(Cl)cnc3c2-c2nc(C#N)cs2)ccn1] | N-(4-(6-Chloro-3-(4-cyanothiazol-2-yl)-1H-pyrrolo[3,2-b]pyridin-2-yl)pyridin-2-yl)acetamide | 1.37 | 394 |
| 178 | 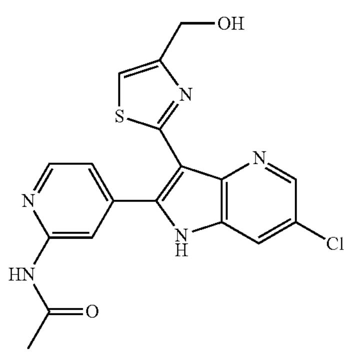 [SMILES: CC(=O)Nc1cc(-c2[nH]c3cc(Cl)cnc3c2-c2nc(CO)cs2)ccn1] | N-(4-(6-Chloro-3-(4-(hydroxymethyl)thiazol-2-yl)-1H-pyrrolo[3,2-b]pyridin-2-yl)pyridin-2-yl)acetamide | 0.94 | 400 |
| 179 | 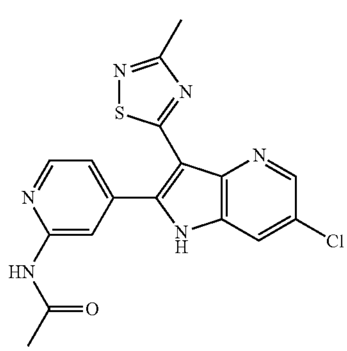 [SMILES: CC(=O)Nc1cc(-c2[nH]c3cc(Cl)cnc3c2-c2nc(C)ns2)ccn1] | N-(4-(6-chloro-3-(3-methyl-1,2,4-thiadiazol-5-yl)-1H-pyrrolo[3,2-b]pyrdin-2-yl)pyridin-2-yl)acetamide | 1.32 | 385 |

TABLE 10-continued

| # | Structure | Name | HPLC ret. time (min) | LC/MS (M + H)+ |
|---|---|---|---|---|
| 180 | 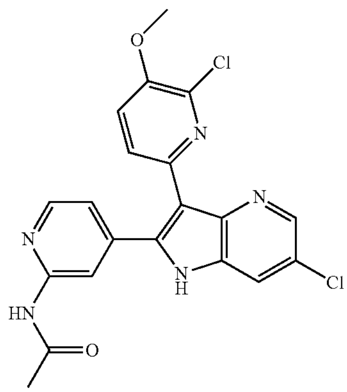 [SMILES: COc1ccc(-c2c(-c3ccnc(NC(C)=O)c3)[nH]c3cc(Cl)cnc23)nc1Cl] | N-(4-(6-Chloro-3-(6-chloro-5-methoxypyridin-2-yl)-1H-pyrrolo[3,2-b]pyridin-2-yl)pyridin-2-yl)acetamide | 1.20 | 428 |
| 181 | 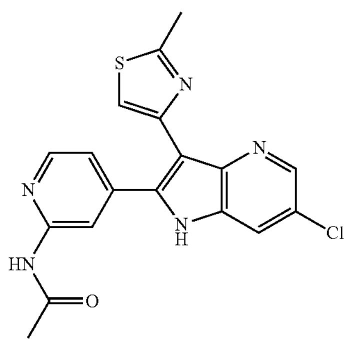 [SMILES: CC(=O)Nc1cc(-c2[nH]c3cc(Cl)cnc3c2-c2csc(C)n2)ccn1] | N-(4-(6-Chloro-3-(2-methylthiazol-4-yl)-1H-pyrrolo[3,2-b]pyridin-2-yl)pyridin-2-yl)acetamide | 1.05 | 384 |
| 182 | 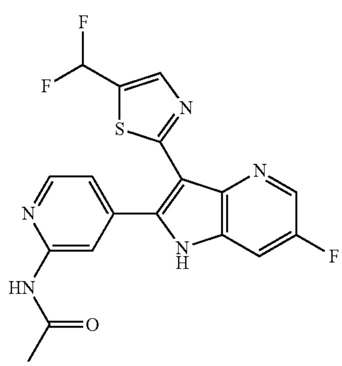 [SMILES: CC(=O)Nc1cc(-c2[nH]c3cc(F)cnc3c2-c2ncc(C(F)F)s2)ccn1] | N-(4-(3-(5-(Difluoromethyl)thiazol-2-yl)-6-fluoro-1H-pyrrolo[3,2-b]pyridin-2-yl)pyridin-2-yl)acetamide | 1.25 | 403 |
| 183 | 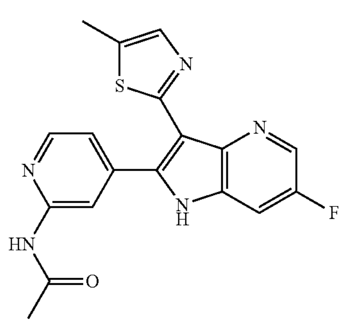 [SMILES: CC(=O)Nc1cc(-c2[nH]c3cc(F)cnc3c2-c2ncc(C)s2)ccn1] | N-(4-(6-Fluoro-3-(5-methylthiazol-2-yl)-1H-pyrrolo[3,2-b]pyridin-2-yl)pyridin-2-yl)acetamide | 0.96 | 368 |

TABLE 10-continued

| # | Structure | Name | HPLC ret. time (min) | LC/MS) (M + H)+ |
|---|---|---|---|---|
| 184 | 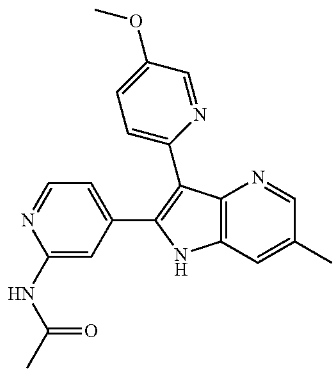 [SMILES: COc1ccc(-c2c(-c3ccnc(NC(C)=O)c3)[nH]c3cc(C)cnc23)nc1] | N-(4-(3-(5-Methoxypyridin-2-yl)-6-methyl-1H-pyrrolo[3,2-b]pyridin-2-yl)pyridin-2-yl)acetamide | 0.67 | 374 |
| 185 | 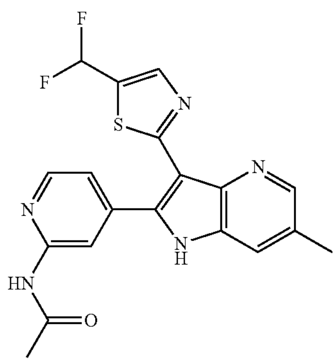 [SMILES: CC(=O)Nc1cc(-c2[nH]c3cc(C)cnc3c2-c2ncc(C(F)F)s2)ccn1] | N-(4-(3-(5-(Difluoromethyl)thiazol-2-yl)-6-methyl-1H-pyrrolo[3,2-b]pyridin-2-yl)pyridin-2-yl)acetamide | 0.92 | 400 |
| 186 | 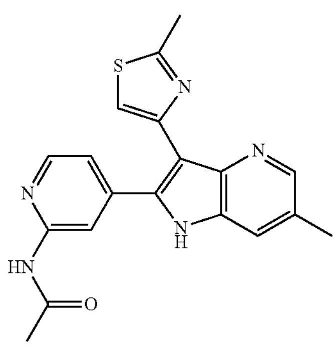 [SMILES: CC(=O)Nc1cc(-c2[nH]c3cc(C)cnc3c2-c2csc(C)n2)ccn1] | N-(4-(6-Methyl-3-(2-methylthiazol-4-yl)-1H-pyrrolo[3,2-b]pyridin-2-yl)pyridin-2-yl)acetamide | 0.84 | 364 |
| 187 | 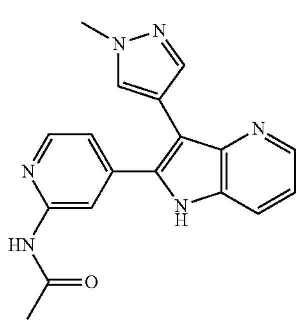 [SMILES: CC(=O)Nc1cc(-c2[nH]c3cccnc3c2-c2cnn(C)c2)ccn1] | N-(4-(3-(1-Methyl-1H-pyrazol-4-yl)-1H-pyrrolo[3,2-b]pyridin-2-yl)pyridin-2-yl)acetamide | 0.51 | 333 |

TABLE 10-continued

| # | Structure | Name | HPLC ret. time (min) | LC/MS) (M + H)+ |
|---|---|---|---|---|
| 188 | 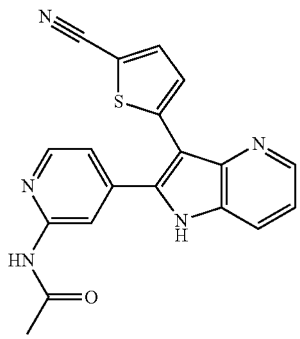 [SMILES: CC(=O)Nc1cc(-c2[nH]c3cccnc3c2-c2ccc(C#N)s2)ccn1] | N-(4-(3-(5-Cyanothiophen-2-yl)-1H-pyrrolo[3,2-b]pyridin-2-yl)pyridin-2-yl)acetamide | 0.76 | 360 |
| 189 | 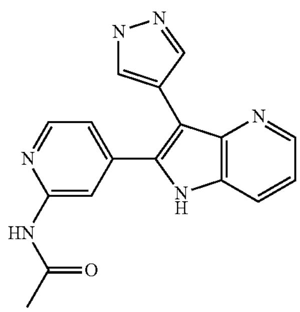 [SMILES: CC(=O)Nc1cc(-c2[nH]c3cccnc3c2-c2cn[nH]c2)ccn1] | N-(4-(3-(1H-Pyrazol-4-yl)-1H-pyrrolo[3,2-b]pyridin-2-yl)pyridin-2-yl)acetamide | 0.51 | 319 |
| 190 | 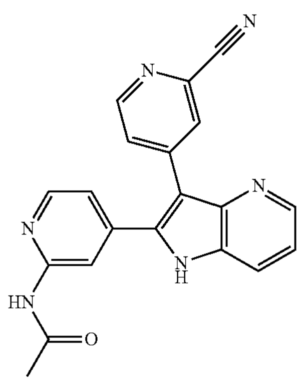 [SMILES: CC(=O)Nc1cc(-c2[nH]c3cccnc3c2-c2ccnc(C#N)c2)ccn1] | N-(4-(3-(2-Cyanopyridin-4-yl)-1H-pyrrolo[3,2-b]pyridin-2-yl)pyridin-2-yl)acetamide | 0.68 | 355 |
| 191 | 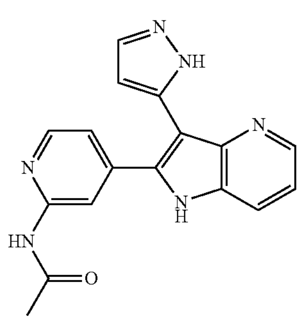 [SMILES: CC(=O)Nc1cc(-c2[nH]c3cccnc3c2-c2ccn[nH]2)ccn1] | N-(4-(3-(1H-Pyrazol-5-yl)-1H-pyrrolo[3,2-b]pyridin-2-yl)pyridin-2-yl)acetamide | 0.54 | 319 |

TABLE 10-continued

| # | Structure | Name | HPLC ret. time (min) | LC/MS) (M + H)+ |
|---|---|---|---|---|
| 192 | 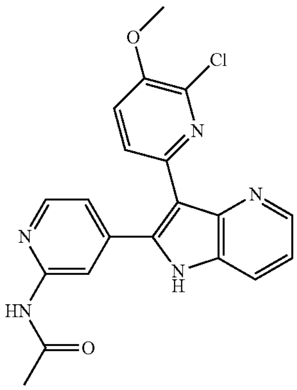 [SMILES: COc1ccc(-c2c(-c3ccnc(NC(C)=O)c3)[nH]c3cccnc23)nc1Cl] | N-(4-(3-(6-Chloro-5-methoxypyridin-2-yl)-1H-pyrrolo[3,2-b]pyridin-2-yl)pyridin-2-yl)acetamide | 0.86 | 394 |
| 193 | 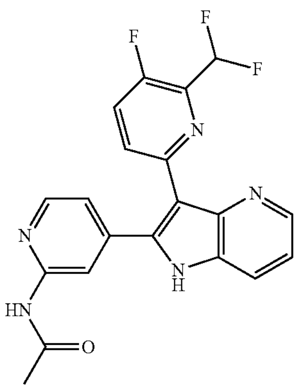 [SMILES: CC(=O)Nc1cc(-c2[nH]c3cccnc3c2-c2ccc(F)c(C(F)F)n2)ccn1] | N-(4-(3-(6-(Difluoromethyl)-5-fluoropyridin-2-yl)-1H-pyrrolo[3,2-b]pyridin-2-yl)pyridin-2-yl)acetamide | 0.92 | 398 |
| 194 | 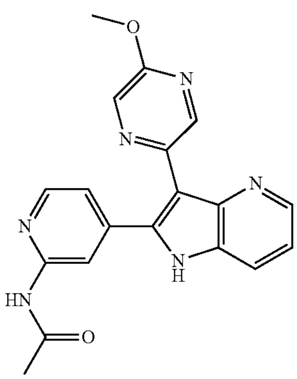 [SMILES: COc1cnc(-c2c(-c3ccnc(NC(C)=O)c3)[nH]c3cccnc23)cn1] | N-(4-(3-(5-Methoxypyrazin-2-yl)-1H-pyrrolo[3,2-b]pyridin-2-yl)pyridin-2-yl)acetamide | 0.74 | 361 |
| 195 | 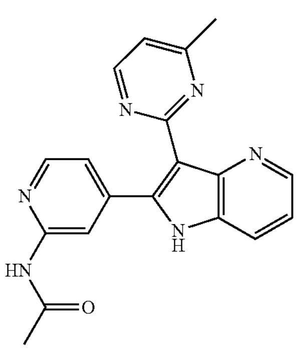 [SMILES: CC(=O)Nc1cc(-c2[nH]c3cccnc3c2-c2nccc(C)n2)ccn1] | N-(4-(3-(4-Methylpyrimidin-2-yl)-1H-pyrrolo[3,2-b]pyridin-2-yl)pyridin-2-yl)acetamide | 0.71 | 345 |

TABLE 10-continued

| # | Structure | Name | HPLC ret. time (min) | LC/MS) (M + H)+ |
|---|---|---|---|---|
| 196 | 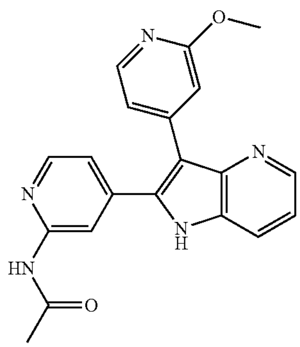 [SMILES: COc1cc(-c2c(-c3ccnc(NC(C)=O)c3)[nH]c3cccnc23)ccn1] | N-(4-(3-(2-Methoxypyridin-4-yl)-1H-pyrrolo[3,2-b]pyridin-2-yl)pyridin-2-yl)acetamide | 0.95 | 360 |
| 197 | 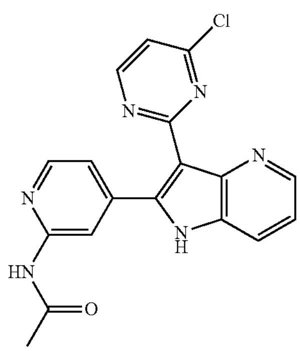 [SMILES: CC(=O)Nc1cc(-c2[nH]c3cccnc3c2-c2nccc(Cl)n2)ccn1] | N-(4-(3-(4-Chloropyrimidin-2-yl)-1H-pyrrolo[3,2-b]pyridin-2-yl)pyridin-2-yl)acetamide | 0.80 | 365 |
| 198 | 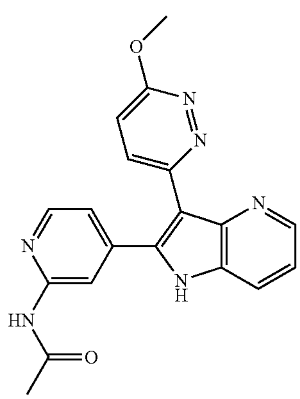 [SMILES: COc1ccc(-c2c(-c3ccnc(NC(C)=O)c3)[nH]c3cccnc23)nn1] | N-(4-(3-(6-Methoxypyridazin-3-yl)-1H-pyrrolo[3,2-b]pyridin-2-yl)pyridin-2-yl)acetamide | 0.71 | 361 |
| 199 | 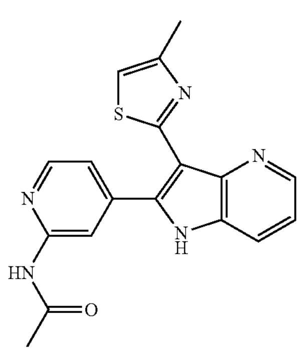 [SMILES: CC(=O)Nc1cc(-c2[nH]c3cccnc3c2-c2nc(C)cs2)ccn1] | N-(4-(3-(4-Methylthiazol-2-yl)-1H-pyrrolo[3,2-b]pyridin-2-yl)pyridin-2-yl)acetamide | 0.83 | 350 |

TABLE 10-continued
| # | Structure | Name | HPLC ret. time (min) | LC/MS) (M + H)+ |
|---|---|---|---|---|
| 200 | 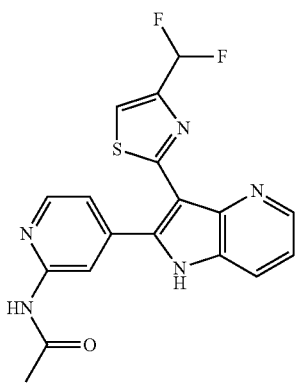 [SMILES: CC(=O)Nc1cc(-c2[nH]c3cccnc3c2-c2nc(C(F)F)cs2)ccn1] | N-(4-(3-(4-(Difluoromethyl)thiazol-2-yl)-1H-pyrrolo[3,2-b]pyridin-2-yl)pyridin-2-yl)acetamide | 0.87 | 386 |
| 201 | 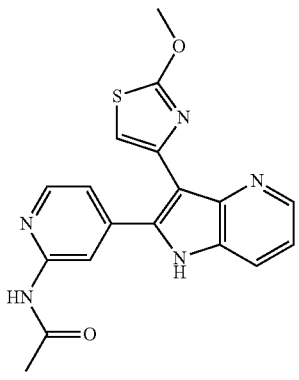 [SMILES: COc1nc(-c2c(-c3ccnc(NC(C)=O)c3)[nH]c3cccnc23)cs1] | N-(4-(3-(2-Methoxythiazol-4-yl)-1H-pyrrolo[3,2-b]pyridin-2-yl)pyridin-2-yl)acetamide | 0.77 | 367 |
| 202 | 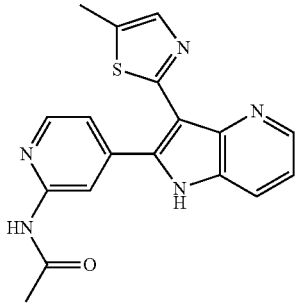 [SMILES: CC(=O)Nc1cc(-c2[nH]c3cccnc3c2-c2ncc(C)s2)ccn1] | N-(4-(3-(5-Methylthiazol-2-yl)-1H-pyrrolo[3,2-b]pyridin-2-yl)pyridin-2-yl)acetamide | 0.82 | 350 |
| 203 | 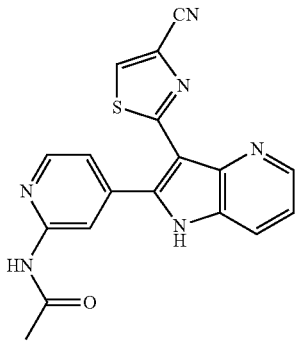 [SMILES: CC(=O)Nc1cc(-c2[nH]c3cccnc3c2-c2nc(C#N)cs2)ccn1] | N-(4-(3-(4-Cyanothiazol-2-yl)-1H-pyrrolo[3,2-b]pyridin-2-yl)pyridin-2-yl)acetamide | 0.75 | 360 |

TABLE 10-continued

| # | Structure | Name | HPLC ret. time (min) | LC/MS $(M + H)^+$ |
|---|---|---|---|---|
| 204 | 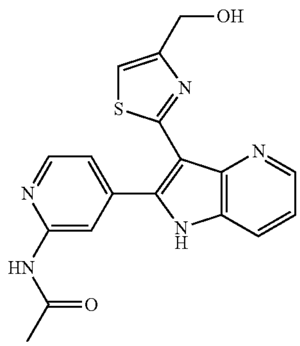 [SMILES: CC(=O)Nc1cc(-c2[nH]c3cccnc3c2-c2nc(CO)cs2)ccn1] | N-(4-(3-(4-(Hydroxymethyl)thiazol-2-yl)-1H-pyrrolo[3,2-b]pyridin-2-yl)pyridin-2-yl)acetamide | 0.66 | 366 |
| 205 | 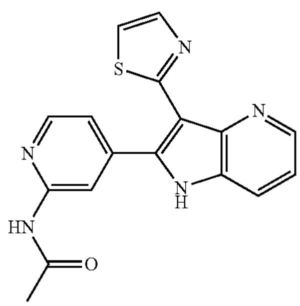 [SMILES: CC(=O)Nc1cc(-c2[nH]c3cccnc3c2-c2nccs2)ccn1] | N-(4-(3-(Thiazol-2-yl)-1H-pyrrolo[3,2-b]pyridin-2-yl)pyridin-2-yl)acetamide | 0.69 | 336 |

HPLC/LCMS Column conditions: Waters Acquity UPLC BEH C18, 2.1 × 50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

Examples in Table 10 below were prepared from Example 41B or Example 38B or Example 1D or from Example 173B and the heteroaryl bromides following the general methods shown for Example 172

Example 206

N-(4-(3-(5-Chlorothiazol-2-yl)-6-fluoro-1H-pyrrolo[3,2-b]pyridin-2-yl)pyridin-2-yl)acetamide

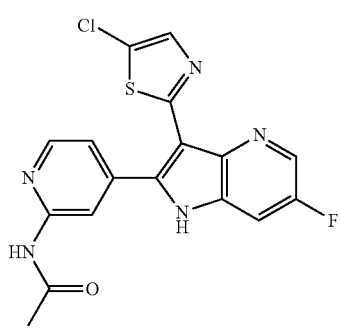 [SMILES: CC(=O)Nc1cc(-c2[nH]c3cc(F)cnc3c2-c2ncc(Cl)s2)ccn1]

A mixture of Example 38B (42 mg, 0.109 mmol), 2-bromo-5-chlorothiazole (43.3 mg, 0.218 mmol) and $Cs_2CO_3$ (53.4 mg, 0.164 mmol) in acetonitrile (2 mL) was purged with nitrogen for a few minutes. Xphos-Pd-G2 (4.30 mg, 5.46 μmol) was added and the reaction mixture was heated at 120° C. in a sealed vial for 1 h. The reaction mixture was cooled, filtered and purified by preparative HPLC to give N-(4-(3-(5-chlorothiazol-2-yl)-6-fluoro-1H-pyrrolo[3,2-b]pyridin-2-yl)pyridin-2-yl)acetamide. HPLC: RT=1.34 min ($H_2O$/MeOH with 0.05% TFA, Waters Acquity SDS BEH C18 2.1×50 mm 1.7 u, gradient=1.8 min, wavelength=220 nm); MS (ES): m/z=388 $[M+H]^+$; $^1H$ NMR (500 MHz, DMSO-$d_6$) δ ppm 10.64 (s, 1H), 8.57 (s, 1H), 8.45 (s, 1H), 8.41 (d, J=4.88 Hz, 1H), 7.84 (d, J=9.26 Hz, 1H), 7.71 (s, 1H), 7.48 (d, J=4.96 Hz, 1H), 2.11 (s, 3H).

TABLE 11

| # | Structure | Name | HPLC ret. time (min) | LC/MS) (M + H)+ |
|---|---|---|---|---|
| 207 | 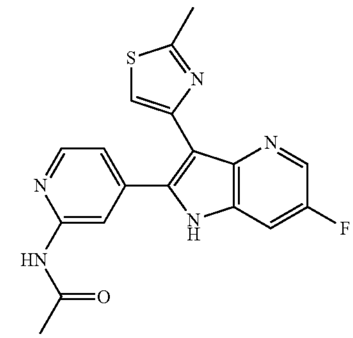 [SMILES: CC(=O)Nc1cc(-c2[nH]c3cc(F)cnc3c2-c2csc(C)n2)ccn1] | N-(4-(6-Fluoro-3-(2-methylthiazol-4-yl)-1H-pyrrolo[3,2-b]pyridin-2-yl)pyridin-2-yl)acetamide | 0.91 | 368 |
| 208 | 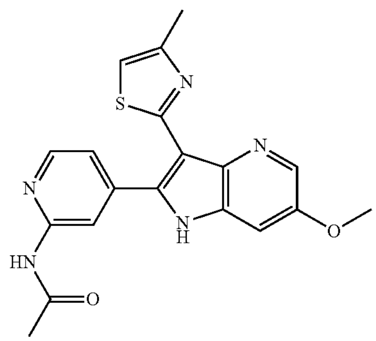 [SMILES: COc1cnc2c(-c3nc(C)cs3)c(-c3ccnc(NC(C)=O)c3)[nH]c2c1] | N-(4-(6-Methoxy-3-(4-methylthiazol-2-yl)-1H-pyrrolo[3,2-b]pyridin-2-yl)pyridin-2-yl)acetamide | 0.96 | 380 |
| 209 | 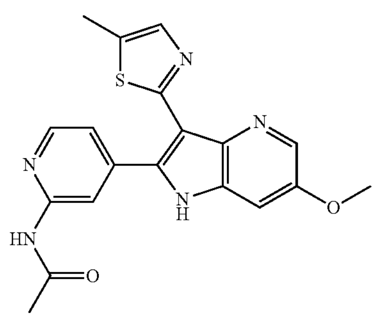 [SMILES: COc1cnc2c(-c3ncc(C)s3)c(-c3ccnc(NC(C)=O)c3)[nH]c2c1] | N-(4-(6-Methoxy-3-(5-methylthiazol-2-yl)-1H-pyrrolo[3,2-b]pyridin-2-yl)pyridin-2-yl)acetamide | 0.92 | 380 |
| 210 | 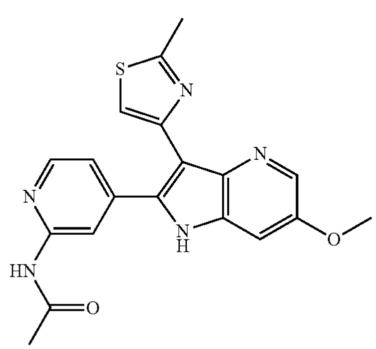 [SMILES: COc1cnc2c(-c3csc(C)n3)c(-c3ccnc(NC(C)=O)c3)[nH]c2c1] | N-(4-(6-Methoxy-3-(2-methylthiazol-4-yl)-1H-pyrrolo[3,2-b]pyridin-2-yl)pyridin-2-yl)acetamide | 0.86 | 380 |

TABLE 11-continued

| # | Structure | Name | HPLC ret. time (min) | LC/MS (M + H)+ |
|---|-----------|------|----------------------|----------------|
| 211 | 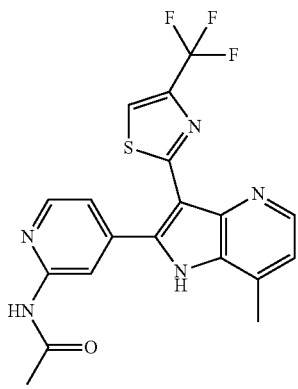 [SMILES: CC(=O)Nc1cc(-c2[nH]c3c(C)ccnc3c2-c2nc(C(F)(F)F)cs2)ccn1] | N-(4-(3-(2-Methylthiazol-4-yl)-1H-pyrrolo[3,2-b]pyridin-2-yl)pyridin-2-yl)acetamide | 0.76 | 350 |

HPLC/LCMS Column conditions: Waters Acquity UPLC BEH C18, 2.1 × 50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

Examples in Table 11 below were prepared from Example 38B or Example 48B and heteroaryl bromide using the general methods shown for Example 206.

Example 212

N-(4-(7-Methyl-3-(4-(trifluoromethyl)thiazol-2-yl)-1H-pyrrolo[3,2-b]pyridin-2-yl)pyridin-2-yl)acetamide

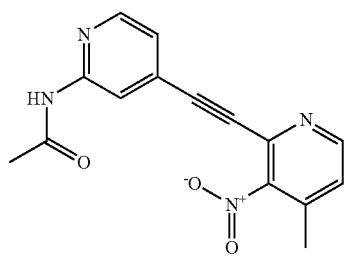

212A) N-(4-((4-Methyl-3-nitropyridin-2-yl)ethynyl)pyridin-2-yl)acetamide

N-(4-((4-Methyl-3-nitropyridin-2-yl)ethynyl)pyridin-2-yl)acetamide was prepared from Example 1B and 2-bromo-4-methyl-3-nitropyridine by the methods shown for Example 1C. HPLC: RT=0.65 min (H₂O/MeOH with 0.05% TFA, Waters Acquity SDS BEH C18 2.1×50 mm 1.7 u, gradient=1.8 min, wavelength=220 nm); MS (ES): m/z=297 [M+H]+; ¹H NMR (400 MHz, DMSO-d₆) δ ppm 10.72 (s, 1H), 8.73 (d, J=5.06 Hz, 1H), 8.41 (dd, J=0.66, 5.06 Hz, 1H), 8.20 (s, 1H), 7.68 (dd, J=0.66, 5.06 Hz, 1H), 7.22 (dd, J=1.54, 5.06 Hz, 1H), 2.41 (s, 3H), 2.12 (s, 3H).

212B) N-(4-((3-Amino-4-methylpyridin-2-yl)ethynyl)pyridin-2-yl)acetamide

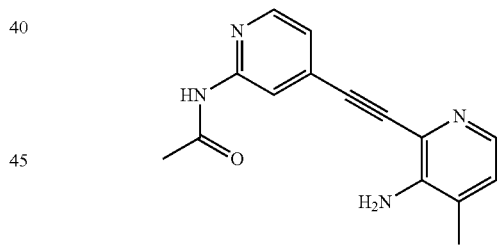

To a solution of N-(4-((4-methyl-3-nitropyridin-2-yl)ethynyl)pyridin-2-yl)acetamide (2 g, 6.75 mmol) in (10:1) EtOH:H₂O (110 ml) was added iron (1.885 g, 33.8 mmol) and ammonium chloride (3.61 g, 67.5 mmol) and the reaction mixture was heated at 70° C. for 2 h. The reaction mixture cooled, stirred with celite for 30 min and then filtered. The filter cake was washed with 10% MeOH in DCM and the filterate was concentrated to give a light brown solid which purified on a short silical gel plug eluted with 10-15% MeOH in DCM to yield N-(4-((3-amino-4-methylpyridin-2-yl)ethynyl)pyridin-2-yl)acetamide (1.7 g, 6.38 mmol, 95% yield) as a light yellow solid. HPLC: RT=0.48 min (H₂O/MeOH with 0.05% TFA, Waters Acquity SDS BEH C18 2.1×50 mm 1.7 u, gradient=1.8 min, wavelength=220 nm); MS (ES): m/z=267 [M+H]+; ¹H NMR (400 MHz, DMSO-d₆) δ ppm 10.61 (br. s., 1H), 8.35 (d, J=4.62 Hz, 1H), 8.23 (s, 1H), 7.75 (d, J=4.40 Hz, 1H), 7.23 (br. s., 1H), 7.06 (d, J=3.96 Hz, 1H), 5.55 (br. s., 2H), 2.14-2.26 (m, 3H), 2.17 (s, 3H), 2.12 (s, 3H).

212C) N-(2-((2-Acetamidopyridin-4-yl)ethynyl)-4-methylpyridin-3-yl)-2,2,2-trifluoroacetamide

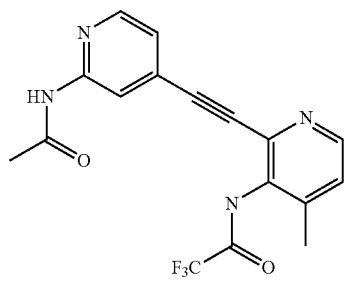 [SMILES: CC(=O)Nc1cc(C#Cc2nccc(C)c2NC(=O)C(F)(F)F)ccn1]

N-(2-((2-Acetamidopyridin-4-yl)ethynyl)-4-methylpyridin-3-yl)-2,2,2-trifluoroacetamide was prepared from N-(4-((3-amino-4-methylpyridin-2-yl)ethynyl)pyridin-2-yl)acetamide by the methods shown for Example 1D. HPLC: RT=0.67 min (H$_2$O/MeOH with 0.05% TFA, Waters Acquity SDS BEH C18 2.1×50 mm 1.7 u, gradient=1.8 min, wavelength=220 nm); MS (ES): m/z=363 [M+H]$^+$, $^1$H NMR (400 MHz, DMSO-d$_6$) δ ppm 11.52 (s, 1H), 10.66 (s, 1H), 8.51 (d, J=4.84 Hz, 1H), 8.39 (dd, J=0.88, 5.06 Hz, 1H), 8.22 (s, 1H), 7.50 (dd, J=0.55, 4.95 Hz, 1H), 7.14 (dd, J=1.54, 5.06 Hz, 1H), 2.26 (s, 3H), 2.12 (s, 3H).

Example 212) N-(4-(7-Methyl-3-(4-(trifluoromethyl)thiazol-2-yl)-1H-pyrrolo[3,2-b]pyridin-2-yl)pyridin-2-yl)acetamide

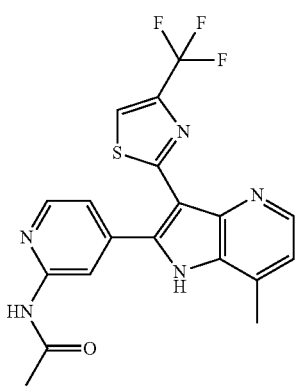 [SMILES: CC(=O)Nc1cc(-c2[nH]c3c(C)ccnc3c2-c2nc(C(F)(F)F)cs2)ccn1]

To a solution of N-(2-((2-acetamidopyridin-4-yl)ethynyl)-4-methylpyridin-3-yl)-2,2,2-trifluoroacetamide (40 mg, 110 mmole) and 2-bromo-4-(trifluoromethyl)thiazole (51.2 mg, 0.221 mmol) in DMF (2 mL) was added Cs$_2$CO$_3$ (53.4 mg, 0.164 mmol) and the reaction mixture was purged with nitrogen for a few minutes. Xphos-Pd-G2 (4.30 mg, 5.46 µmol) was added and the reaction mixture was heated at 120° C. in a sealed vial for 1 h. The reaction mixture was cooled, filtered and purified by preparative HPLC to give N-(4-(7-methyl-3-(4-(trifluoromethyl)thiazol-2-yl)-1H-pyrrolo[3,2-b]pyridin-2-yl)pyridin-2-yl)acetamide. HPLC: RT=1.09 min (H$_2$O/ACN with 0.1% TFA, Waters Acquity SDS BEH C18, 2.1×50 mm, 1.7-µm particles, gradient=3 min, wavelength=220 nm). MS (ES): m/z=418 [M+H]$^+$; $^1$H NMR (500 MHz, DMSO-d$_6$) δ ppm 12.43 (s, 1H), 10.60 (s, 1H), 8.46 (br. s., 1H), 8.44 (d, J=4.71 Hz, 1H), 8.40 (d, J=5.05 Hz, 1H), 8.36 (s, 1H), 7.46 (d, J=4.96 Hz, 1H), 7.18 (d, J=4.63 Hz, 1H), 2.60 (s, 3H), 2.09 (s, 3H).

Example 213

N-(4-(7-(Difluoromethyl)-3-(6-methoxypyridin-3-yl)-1H-pyrrolo[3,2-b]pyridin-2-yl)pyridin-2-yl)acetamide

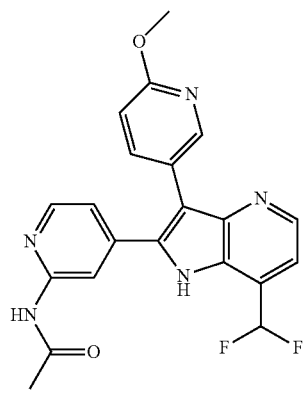 [SMILES: COc1ccc(-c2c(-c3ccnc(NC(C)=O)c3)[nH]c3c(C(F)F)ccnc23)cn1]

213A) (3-Amino-2-chloropyridin-4-yl)methanol

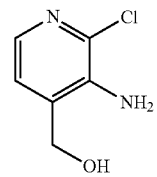

To a solution of methyl 3-amino-2-chloroisonicotinate (0.4 g, 2.144 mmol in THF (5 mL) at −20° C. was added) LAH (2.57 mL, 2.57 mmol) under a nitrogen atmosphere. The mixture was then stirred at 0° C. for 30 min. Ammonium chloride (200 mg) was added and after stirred for 15 min. silica gel (3 mL) was added to the reaction mixture and concentrated in vacuo. The crude was dry loaded over a 3 mL silical gel plug and eluted with 10% MeOH in DCM to give (3-amino-2-chloropyridin-4-yl)methanol (290 mg, 1.829 mmol, 85% yield) as a white flaky solid. HPLC: RT=0.44 min (H$_2$O/ACN with 0.05% TFA, Waters Acquity SDS BEH C18, 2.1×50 mm, 1.7-µm particles, gradient=1.8 min, wavelength=220 nm); MS (ES): m/z=159 [M+H]$^+$; $^1$H NMR (400 MHz, DMSO-d$_6$) δ ppm 7.61 (d, J=4.6 Hz, 1H), 7.18 (d, J=4.6 Hz, 1H), 5.40 (t, J=5.5 Hz, 1H), 5.24 (s, 2H), 4.43 (d, J=5.5 Hz, 2H)

213B) 3-Amino-2-chloroisonicotinaldehyde

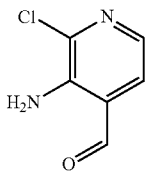

To the solution of (3-amino-2-chloropyridin-4-yl)methanol (0.5 g, 3.15 mmol) in THF (31.5 ml), DCM (31.5 ml) was added Dess-Martin periodinane (2.006 g, 4.73 mmol). The mixture was stirred for 1 h at room temperature. The reaction mixture was diluted with EtOAc (30 mL) and poured into saturated aqueous NaHCO$_3$ containing Na$_2$S$_2$O$_3$ (0.4 g). The mixture was stirred for 30 min. and then diluted with EtOAc (10 mL). The organic layer was separated and washed with water, then washed with brine, dried and evaporated. The crude product was purified by silica gel flash chromatography (12 g column, EtOAc/DCM=0-100%) to yield 3-amino-2-chloroisonicotinaldehyde (260 mg, 1.661 mmol, 52.7% yield) as a yellow solid. HPLC: RT=0.61 min (H$_2$O/ACN with 0.05% TFA, Waters Acquity SDS BEH C18, 2.1×50 mm, 1.7-μm particles, gradient=1.8 min, wavelength=220 nm); MS (ES): m/z=157 [M+H]$^+$; $^1$H NMR (400 MHz, CHLOROFORM-d) δ 9.97 (s, 1H), 7.87 (d, J=5.1 Hz, 1H), 7.36 (d, J=4.8 Hz, 1H)

213C) 2-Chloro-4-(difluoromethyl)pyridin-3-amine

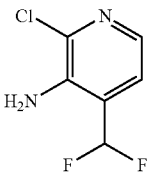

2-Chloro-4-(difluoromethyl)pyridin-3-amine was prepared from 3-amino-2-chloroisonicotinaldehyde following the method shown for Example 173A. HPLC: RT=0.68 min (H$_2$O/ACN with 0.05% TFA, Waters Acquity SDS BEH C18, 2.1×50 mm, 1.7-μm particles, gradient=1.8 min, wavelength=220 nm); MS (ES): m/z=179.0, 181.0 [M+H]$^+$; $^1$H NMR (400 MHz, CHLOROFORM-d) δ ppm 7.87 (d, J=4.8 Hz, 1H), 7.15 (d, J=4.8 Hz, 1H), 6.63 (t, J=54.8 Hz, 1H), 4.58 (br. s., 2H)

213D) N-(4-((3-Amino-4-(difluoromethyl)pyridin-2-yl)ethynyl)pyridin-2-yl)acetamide

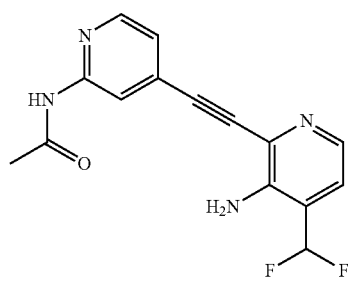 [SMILES: CC(=O)Nc1cc(C#Cc2nccc(C(F)F)c2N)ccn1]

To solution of 2-chloro-4-(difluoromethyl)pyridin-3-amine (0.1 g, 0.560 mmol) in MeCN (5.60 ml) was added K$_2$CO$_3$ (0.232 g, 1.680 mmol). The mixture was bubbled with argon for 5 minutes and then PdCl$_2$(dppf) (0.020 g, 0.028 mmol) was added. After stirring at room temperature for 20 min. Example 1B (0.135 g, 0.840 mmol) was added and the reaction mixture was purged with argon then heated at 80° C. for 5 h. The reaction mixture was concentrated, suspended in 10% MeOH in DCM and filtered. The filtrate was concentrated and purified by silica gel flash chromatography (4 g column, 0-100% gradient; solvent A=DCM; Solvent B: 20% MeOH in DCM) to afford N-(4-((3-amino-4-(difluoromethyl)pyridin-2-yl)ethynyl)pyridin-2-yl)acetamide (100 mg, 0.331 mmol, 59.1% yield). HPLC: RT=0.63 min (H$_2$O/ACN with 0.05% TFA, Waters Acquity SDS BEH C18, 2.1×50 mm, 1.7-μm particles, gradient=1.8 min, wavelength=220 nm); MS (ES): m/z=303.1 [M+H]$^+$; $^1$H NMR (400 MHz, DMSO-d$_6$) δ ppm 10.62 (s, 1H), 8.37 (dd, J=0.88, 5.06 Hz, 1H), 8.27 (s, 1H), 7.94 (d, J=4.84 Hz, 1H), 7.38 (dd, J=1.32, 5.06 Hz, 1H), 7.33 (d, J=4.84 Hz, 1H), 7.12 (t, J=54.40 Hz, 1H), 6.04 (s, 2H), 2.12 (s, 3H).

213E) N-(2-((2-Acetamidopyridin-4-yl)ethynyl)-4-(difluoromethyl)pyridin-3-yl)-2,2,2-trifluoroacetamide

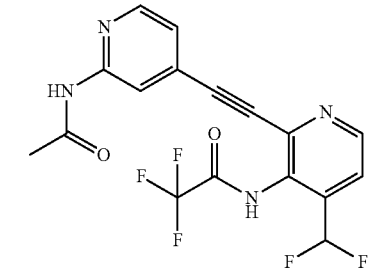 [SMILES: CC(=O)Nc1cc(C#Cc2nccc(C(F)F)c2NC(=O)C(F)(F)F)ccn1]

N-(2-((2-Acetamidopyridin-4-yl)ethynyl)-4-(difluoromethyl)pyridin-3-yl)-2,2,2-trifluoroacetamide was prepared from Example 213D using methods similar to example 1D. HPLC: RT=0.73 min (H$_2$O/ACN with 0.05% TFA, Waters Acquity SDS BEH C18, 2.1×50 mm, 1.7-μm particles, gradient=1.8 min, wavelength=220 nm); MS (ES): m/z=399 [M+H]$^+$; $^1$H NMR (400 MHz, CHLOROFORM-d) δ ppm 8.76 (d, J=5.1 Hz, 1H), 8.58 (br. s., 1H), 8.36 (s, 1H), 8.30 (dd, J=5.2, 0.8 Hz, 1H), 7.99 (br. s., 1H), 7.62 (d, J=5.1 Hz, 1H), 7.14 (dd, J=5.1, 1.3 Hz, 1H), 6.86 (t, J=53.9 Hz, 1H), 2.24 (s, 3H)

Example 213) N-(4-(7-(Difluoromethyl)-3-(6-methoxypyridin-3-yl)-1H-pyrrolo[3,2-b]pyridin-2-yl)pyridin-2-yl)acetamide

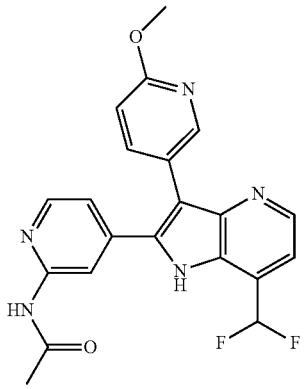

N-(4-(7-(Difluoromethyl)-3-(6-methoxypyridin-3-yl)-1H-pyrrolo[3,2-b]pyridin-2-yl)pyridin-2-yl)acetamide was prepared from N-(2-((2-acetamidopyridin-4-yl)ethynyl)-4-(difluoromethyl)pyridin-3-yl)-2,2,2-trifluoroacetamide and 5-bromo-2-methoxypyridine using the general methods shown for Example 212. HPLC: RT=0.89 min (H₂O/ACN with 0.1% TFA, Waters Acquity SDS BEH C18, 2.1×50 mm, 1.7-μm particles, gradient=3 min, wavelength=220 nm). MS (ES): m/z=410 [M+H]⁺; ¹H NMR (500 MHz, DMSO-d₆) δ 10.59 (s, 1H), 8.54 (d, J=4.46 Hz, 1H), 8.33 (d, J=5.13 Hz, 1H), 8.27 (s, 1H), 8.19 (s, 1H), 7.76 (d, J=8.50 Hz, 1H), 7.44 (d, J=4.38 Hz, 1H), 7.49 (t, J=54.40 Hz, 1H), 7.14 (d, J=5.05 Hz, 1H), 6.86 (d, J=8.58 Hz, 1H), 3.85 (s, 3H), 2.07 (s, 3H).

Example 214

N-(4-(7-(hydroxymethyl)-3-(4-methylthiazol-2-yl)-1H-pyrrolo[3,2-b]pyridin-2-yl)pyridin-2-yl)acetamide

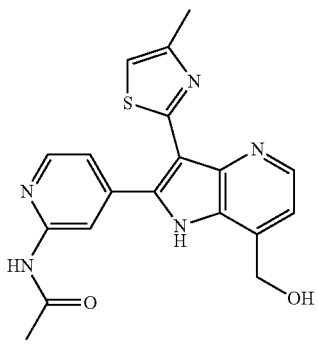 [SMILES: CC(=O)Nc1cc(-c2[nH]c3c(CO)ccnc3c2-c2nc(C)cs2)ccn1]

214A) N-(4-((3-Amino-4-(hydroxymethyl)pyridin-2-yl)ethynyl)pyridin-2-yl)acetamide

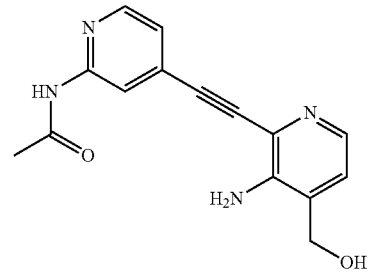 [SMILES: CC(=O)Nc1cc(C#Cc2nccc(CO)c2N)ccn1]

N-(4-((3-Amino-4-(hydroxymethyl)pyridin-2-yl)ethynyl)pyridin-2-yl)acetamide was prepared from (3-amino-2-chloropyridin-4-yl)methanol and Example 1B following the procedure used in Example 213D. HPLC: RT=0.45 min (H₂O/ACN with 0.05% TFA, Waters Acquity SDS BEH C18, 2.1×50 mm, 1.7-μm particles, gradient=1.8 min, wavelength=220 nm); MS (ES): m/z=283 [M+H]⁺; ¹H NMR (400 MHz, METHANOL-d₄) δ ppm 8.32 (dd, J=0.66, 5.06 Hz, 1H), 8.29 (s, 1H), 7.87 (d, J=4.84 Hz, 1H), 7.30 (dd, J=1.43, 5.17 Hz, 1H), 7.27 (d, J=4.62 Hz, 1H), 4.62 (s, 2H), 2.19 (s, 3H)

214B) N-(2-((2-Acetamidopyridin-4-yl)ethynyl)-4-(hydroxymethyl)pyridin-3-yl)-2,2,2-trifluoroacetamide

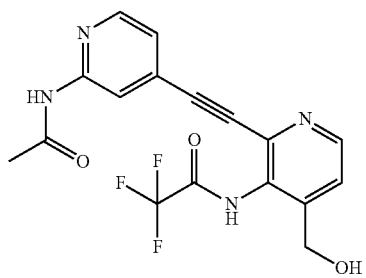 [SMILES: CC(=O)Nc1cc(C#Cc2nccc(CO)c2NC(=O)C(F)(F)F)ccn1]

N-(2-((2-Acetamidopyridin-4-yl)ethynyl)-4-(hydroxymethyl)pyridin-3-yl)-2,2,2-trifluoroacetamide was prepared using methods similar to Example 1D. HPLC: RT=0.58 min (H₂O/ACN with 0.05% TFA, Waters Acquity SDS BEH C18, 2.1×50 mm, 1.7-μm particles, gradient=1.8 min, wavelength=220 nm); MS (ES): m/z=389 [M+H]⁺.

Example 214) N-(4-(7-(Hydroxymethyl)-3-(4-methylthiazol-2-yl)-1H-pyrrolo[3,2-b]pyridin-2-yl)pyridin-2-yl)acetamide

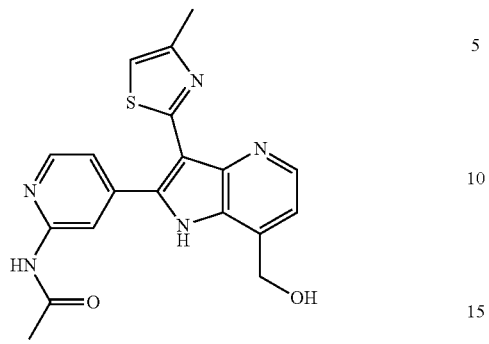

Example 214 was prepared from Example 214B and 2-bromo-4-methylthiazole by methods shown for Example 212. HPLC: RT=0.80 min (H$_2$O/ACN with 0.05% TFA, Waters Acquity SDS BEH C18, 2.1×50 mm, 1.7-μm particles, gradient=1.8 min, wavelength=220 nm); MS (ES): m/z=380 [M+H]$^+$; $^1$H NMR (500 MHz, DMSO-d$_6$) δ 10.62 (s, 1H), 8.54 (d, J=4.80 Hz, 1H), 8.48 (s, 1H), 8.41 (d, J=4.96 Hz, 1H), 7.39-7.49 (m, 2H), 7.21 (s, 1H), 4.95 (s, 2H), 2.32 (s, 3H), 2.11 (s, 3H)

TABLE 12

| Ex. # | Structure | Name | HPLC ret. time (min)* | LC/MS (M + H)$^+$ |
|---|---|---|---|---|
| 215 | 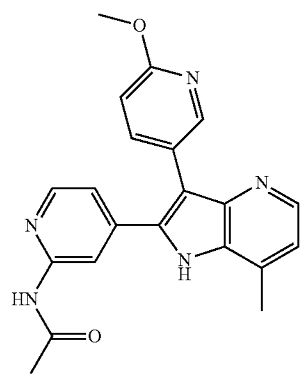 [SMILES: COc1ccc(-c2c(-c3ccnc(NC(C)=O)c3)[nH]c3c(C)ccnc23)cn1] | N-(4-(3-(6-Methoxypyridin-3-yl)-7-methyl-1H-pyrrolo[3,2-b]pyridin-2-yl)pyridin-2-yl)acetamide | 1.17 | 374 |
| 216 | 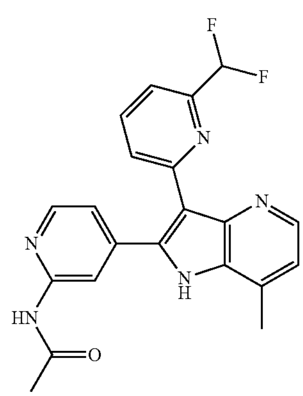 [SMILES: CC(=O)Nc1cc(-c2[nH]c3c(C)ccnc3c2-c2cccc(C(F)F)n2)ccn1] | N-(4-(3-(6-(Difluoromethyl)pyridin-2-yl)-7-methyl-1H-pyrrolo[3,2-b]pyridin-2-yl)pyridin-2-yl)acetamide | 0.97 | 394 |

TABLE 12-continued

| Ex. # | Structure | Name | HPLC ret. time (min)* | LC/MS (M + H)+ |
|---|---|---|---|---|
| 217 | 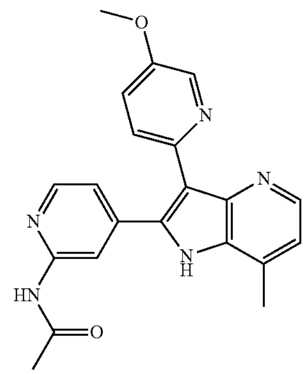 [SMILES: COc1ccc(-c2c(-c3ccnc(NC(C)=O)c3)[nH]c3c(C)ccnc23)nc1] | N-(4-(3-(5-Methoxypyridin-2-yl)-7-methyl-1H-pyrrolo[3,2-b]pyridin-2-yl)pyridin-2-yl)acetamide | 0.64 | 374 |
| 218 | 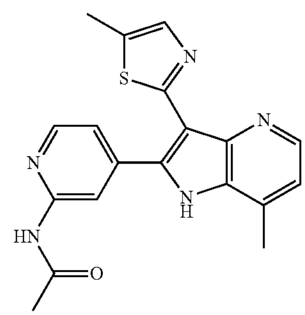 [SMILES: CC(=O)Nc1cc(-c2[nH]c3c(C)ccnc3c2-c2ncc(C)s2)ccn1] | N-(4-(7-Methyl-3-(5-methylthiazol-2-yl)-1H-pyrrolo[3,2-b]pyridin-2-yl)pyridin-2-yl)acetamide | 0.90 | 364 |
| 220 | 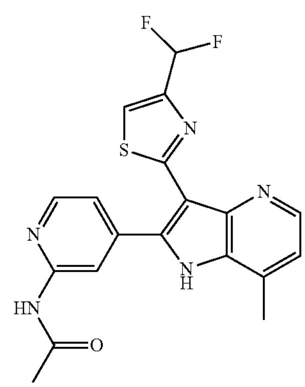 [SMILES: CC(=O)Nc1cc(-c2[nH]c3c(C)ccnc3c2-c2nc(C(F)F)cs2)ccn1] | N-(4-(3-(4-(Difluoromethyl)thiazol-2-yl)-7-methyl-1H-pyrrolo[3,2-b]pyridin-2-yl)pyridin-2-yl)acetamide | 0.95 | 400 |
| 221 | 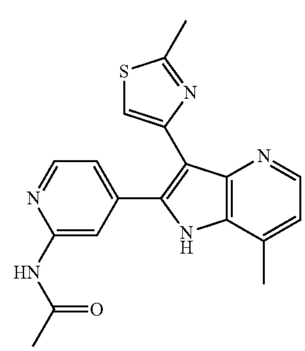 [SMILES: CC(=O)Nc1cc(-c2[nH]c3c(C)ccnc3c2-c2csc(C)n2)ccn1] | N-(4-(7-Methyl-3-(2-methylthiazol-4-yl)-1H-pyrrolo[3,2-b]pyridin-2-yl)pyridin-2-yl)acetamide | 0.90 | 364 |

TABLE 12-continued

| Ex. # | Structure | Name | HPLC ret. time (min)* | LC/MS (M + H)+ |
|---|---|---|---|---|
| 222 | 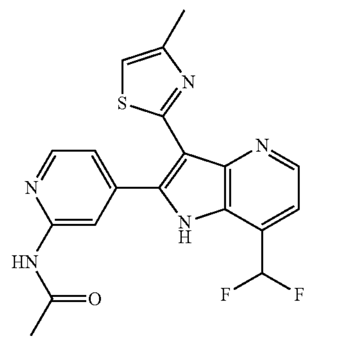 [SMILES: CC(=O)Nc1cc(-c2[nH]c3c(C(F)F)ccnc3c2-c2nc(C)cs2)ccn1] | N-(4-(7-(Difluoromethyl)-3-(4-methylthiazol-2-yl)-1H-pyrrolo[3,2-b]pyridin-2-yl)pyridin-2-yl)acetamide | 1.03 | 400 |
| 223 | 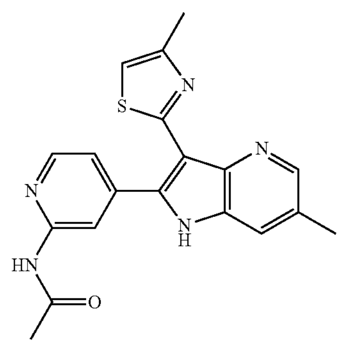 [SMILES: CC(=O)Nc1cc(-c2[nH]c3cc(C)cnc3c2-c2nc(C)cs2)ccn1] | N-(4-(6-Methyl-3-(4-methylthiazol-2-yl)-1H-pyrrolo[3,2-b]pyridin-2-yl)pyridin-2-yl)acetamide | 0.92 | 364 |
| 224 | 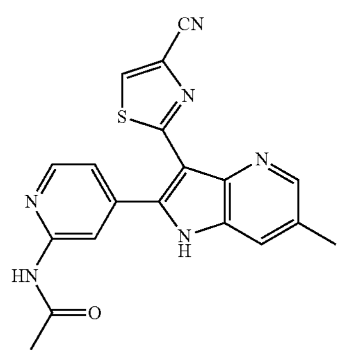 [SMILES: CC(=O)Nc1cc(-c2[nH]c3cc(C)cnc3c2-c2nc(C#N)cs2)ccn1] | N-(4-(3-(4-Cyanothiazol-2-yl)-6-methyl-1H-pyrrolo[3,2-b]pyridin-2-yl)pyridin-2-yl)acetamide | 1.10 | 375 |
| 225 | 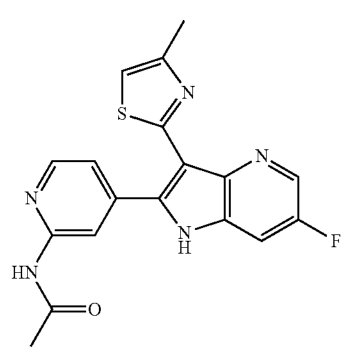 [SMILES: CC(=O)Nc1cc(-c2[nH]c3cc(F)cnc3c2-c2nc(C)cs2)ccn1] | N-(4-(6-Fluoro-3-(4-methylthiazol-2-yl)-1H-pyrrolo[3,2-b]pyridin-2-yl)pyridin-2-yl)acetamide | 0.98 | 368 |

TABLE 12-continued

| Ex. # | Structure | Name | HPLC ret. time (min)* | LC/MS (M + H)+ |
|---|---|---|---|---|
| 226 | 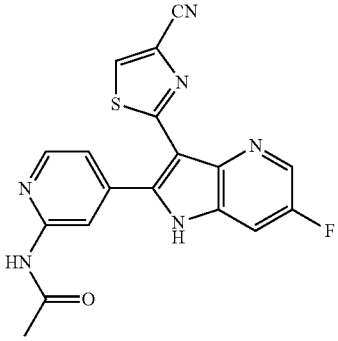 [SMILES: CC(=O)Nc1cc(-c2[nH]c3cc(F)cnc3c2-c2nc(C#N)cs2)ccn1] | N-(4-(3-(4-Cyanothiazol-2-yl)-6-fluoro-1H-pyrrolo[3,2-b]pyridin-2-yl)pyridin-2-yl)acetamide | 1.18 | 379 |
| 227 | 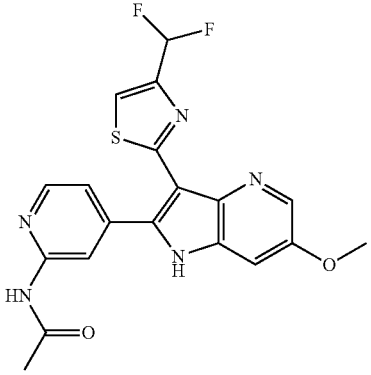 [SMILES: COc1cnc2c(-c3nc(C(F)F)cs3)c(-c3ccnc(NC(C)=O)c3)[nH]c2c1] | N-(4-(3-(4-(Difluoromethyl)thiazol-2-yl)-6-methoxy-1H-pyrrolo[3,2-b]pyridin-2-yl)pyridin-2-yl)acetamide | 1.06 | 416 |
| 228 | 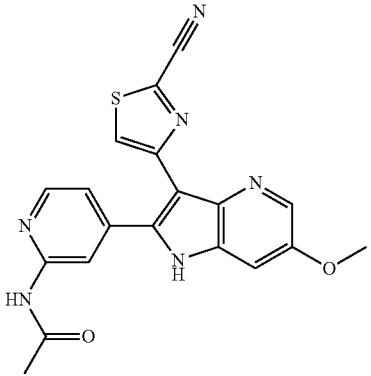 [SMILES: COc1cnc2c(-c3csc(C#N)n3)c(-c3ccnc(NC(C)=O)c3)[nH]c2c1] | N-(4-(3-(2-Cyanothiazol-4-yl)-6-methoxy-1H-pyrrolo[3,2-b]pyridin-2-yl)pyridin-2-yl)acetamide | — | 391 |
| 229 | 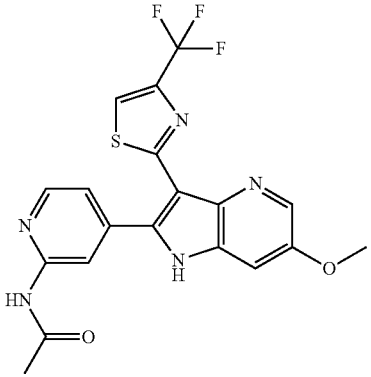 [SMILES: COc1cnc2c(-c3nc(C(F)(F)F)cs3)c(-c3ccnc(NC(C)=O)c3)[nH]c2c1] | N-(4-(6-Methoxy-3-(4-(trifluoromethyl)thiazol-2-yl)-1H-pyrrolo[3,2-b]pyridin-2-yl)pyridin-2-yl)acetamide | 1.30 | 434 |

HPLC/LCMS Column conditions: Waters Acquity UPLC BEH C18, 2.1 × 50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

Examples in Table 12 below were prepared from 212C, 213E or 214B or Example 38B or from Example 48B and the heteroaryl bromide using the general methods shown for Example 212.

Example 230

N-(4-(7-(1-Hydroxyethyl)-3-(6-methoxypyridin-3-yl)-1H-pyrrolo[3,2-b]pyridin-2-yl)pyridin-2-yl)acetamide

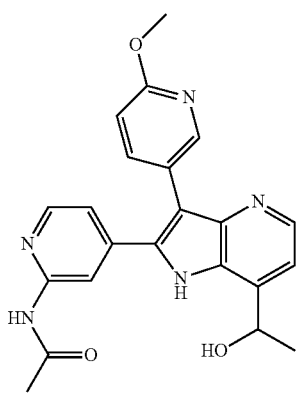 [SMILES: COc1ccc(-c2c(-c3ccnc(NC(C)=O)c3)[nH]c3c(C(C)O)ccnc23)cn1]

230A) 1-(3-Amino-2-chloropyridin-4-yl)ethanol

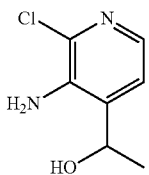

To a solution of 1-(3-amino-2-chloropyridin-4-yl)ethanone (0.5 g, 2.93 mmol) in anhydrous methanol (20 mL) was added NaBH$_4$ (0.222 g, 5.86 mmol). The mixture was stirred at room temperature for 2 h then was quenched with cold water (~1 mL) and concentrated. The crude product was purified on a short flush silica gel plug eluted with 5% MeOH in DCM to yield 1-(3-amino-2-chloropyridin-4-yl)ethanol (0.46 g, 2.66 mmol, 91% yield) as a yellow oil. HPLC: RT=0.49 min (H$_2$O/ACN with 0.05% TFA, Waters Acquity SDS BEH C18, 2.1×50 mm, 1.7-μm particles, gradient=1.8 min, wavelength=220 nm); MS (ES): m/z=173 [M+H]$^+$; $^1$H NMR (400 MHz, METHANOL-d$_4$) δ ppm 7.62 (d, J=5.1 Hz, 1H), 7.16 (d, J=4.8 Hz, 1H), 4.92 (q, J=6.5 Hz, 1H), 1.46 (d, J=6.6 Hz, 3H).

230B) N-(4-((3-Amino-4-(1-hydroxyethyl)pyridin-2-yl)ethynyl)pyridin-2-yl)acetamide

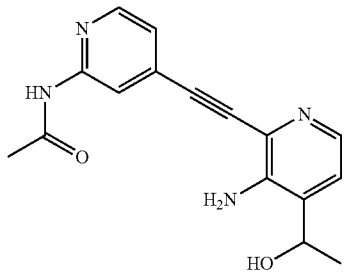 [SMILES: CC(=O)Nc1cc(C#Cc2nccc(C(C)O)c2N)ccn1]

N-(4-((3-Amino-4-(1-hydroxyethyl)pyridin-2-yl)ethynyl)pyridin-2-yl)acetamide was prepared from 1-(3-amino-2-chloropyridin-4-yl)ethanol and Example 1B following the procedure in 213D. HPLC: RT=0.48 min (H$_2$O/ACN with 0.05% TFA, Waters Acquity SDS BEH C18, 2.1×50 mm, 1.7-μm particles, gradient=1.6 min, wavelength=220 nm); MS (ES): m/z=297 [M+H]$^+$; $^1$H NMR (400 MHz, DMSO-d$_6$) δ ppm 10.60 (s, 1H), 8.35 (dd, J=0.66, 5.06 Hz, 1H), 8.24 (s, 1H), 7.85 (d, J=4.62 Hz, 1H), 7.34 (dd, J=1.32, 5.06 Hz, 1H), 7.20 (d, J=4.62 Hz, 1H), 5.56 (s, 2H), 5.47 (d, J=4.18 Hz, 1H), 4.88 (dq, J=4.40, 6.38 Hz, 1H), 2.12 (s, 3H), 1.32 (d, J=6.38 Hz, 3H)

230C) N-(2-((2-Acetamidopyridin-4-yl)ethynyl)-4-(1-hydroxyethyl)pyridin-3-yl)-2,2,2-trifluoroacetamide

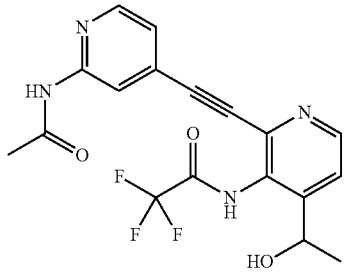 [SMILES: CC(=O)Nc1cc(C#Cc2nccc(C(C)O)c2NC(=O)C(F)(F)F)ccn1]

N-(2-((2-Acetamidopyridin-4-yl)ethynyl)-4-(1-hydroxyethyl)pyridin-3-yl)-2,2,2-trifluoroacetamide was prepared from N-(4-((3-amino-4-(1-hydroxyethyl)pyridin-2-yl)ethynyl)pyridin-2-yl)acetamide (230B) following the procedure in example 1D. HPLC: RT=0.61 min (H$_2$O/ACN with 0.05% TFA, Waters Acquity SDS BEH C18, 2.1×50 mm, 1.7-μm particles, gradient=1.6 min, wavelength=220 nm); MS (ES): m/z=393 [M+H]$^+$; $^1$H NMR (400 MHz, DMSO-d$_6$) δ ppm 11.52 (s, 1H), 10.66 (s, 1H), 8.64 (d, J=5.1 Hz, 1H), 8.39 (dd, J=5.1, 0.7 Hz, 1H), 8.21 (s, 1H), 7.69 (d, J=4.8 Hz, 1H), 7.13 (dd, J=5.1, 1.5 Hz, 1H), 4.83 (q, J=6.4 Hz, 1H), 2.11 (s, 3H), 1.26 (d, J=6.6 Hz, 3H).

Example 230) N-(4-(7-(1-Hydroxyethyl)-3-(6-methoxypyridin-3-yl)-1H-pyrrolo[3,2-b]pyridin-2-yl)pyridin-2-yl)acetamide

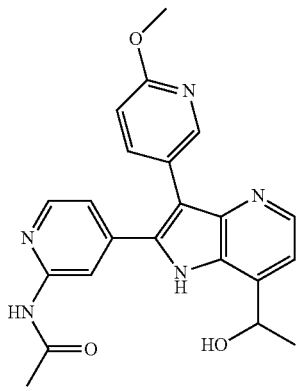 [SMILES: COc1ccc(-c2c(-c3ccnc(NC(C)=O)c3)[nH]c3c(C(C)O)ccnc23)cn1]

N-(4-(7-(1-Hydroxyethyl)-3-(6-methoxypyridin-3-yl)-1H-pyrrolo[3,2-b]pyridin-2-yl)pyridin-2-yl)acetamide was prepared N-(2-((2-acetamidopyridin-4-yl)ethynyl)-4-(1-hydroxyethyl)pyridin-3-yl)-2,2,2-trifluoroacetamide (230C) following procedure used for Example 212. HPLC: RT=0.79 min (H$_2$O/ACN with 0.1% TFA, Waters Acquity UPLC BEH C18, 2.1×50 mm, 1.7-μm particles, gradient=3 min, wavelength=220 nm). MS (ES): m/z=404 [M+H]$^+$; $^1$H NMR (500 MHz, DMSO-d$_6$) δ ppm 11.68 (s, 1H), 10.56 (s, 1H), 8.37 (d, J=4.63 Hz, 1H), 8.31 (d, J=5.05 Hz, 1H), 8.25 (s, 1H), 8.18 (s, 1H), 7.76 (dd, J=1.77, 8.58 Hz, 1H), 7.28 (d, J=4.63 Hz, 1H), 7.13 (d, J=5.05 Hz, 1H), 6.84 (d, J=8.50 Hz, 1H), 5.34 (br. s., 1H), 3.85 (s, 3H), 1.90 (s, 3H), 1.45 (d, J=6.40 Hz, 3H).

TABLE 13

| # | Structure | Name | HPLC ret. time (min)* | LC/MS (M + H)$^+$ |
|---|---|---|---|---|
| 231 | 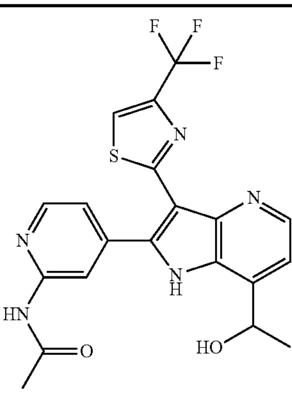 | N-(4-(7-(1-Hydroxyethyl)-3-(4-(trifluoromethyl)thiazol-2-yl)-1H-pyrrolo[3,2-b]pyridin-2-yl)pyridin-2-yl)acetamide | 1.09 | 448 |
| 232 | 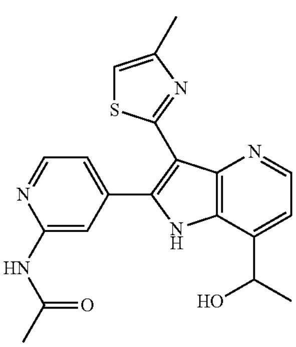 [SMILES: CC(=O)Nc1cc(-c2[nH]c3c(C(C)O)ccnc3c2-c2nc(C)cs2)ccn1] | N-(4-(7-(1-Hydroxyethyl)-3-(4-methylthiazol-2-yl)-1H-pyrrolo[3,2-b]pyridin-2-yl)pyridin-2-yl)acetamide | 0.88 | 394 |

HPLC/LCMS Column conditions: Waters Acquity UPLC BEH C18, 2.1 × 50 mm, 1.7-μm particles; Mobile Phase A: 5:95acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

Examples in Table 13 below were prepared from Example 230C and heteroaryl bromides using the general methods shown for Example 212

Example 233

N-(4-(3-(6-(Difluoromethyl)pyridin-2-yl)-7-(1-fluoroethyl)-1H-pyrrolo[3,2-b]pyridin-2-yl)pyridin-2-yl)acetamide

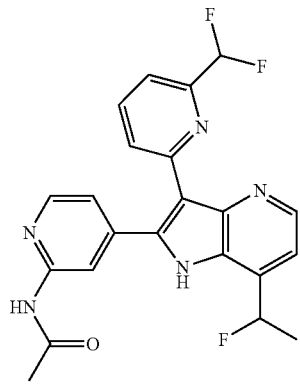 [SMILES: CC(=O)Nc1cc(-c2[nH]c3c(C(C)F)ccnc3c2-c2cccc(C(F)F)n2)ccn1]

233A) N-(4-((3-Amino-4-(1-fluoroethyl)pyridin-2-yl)ethynyl)pyridin-2-yl)acetamide

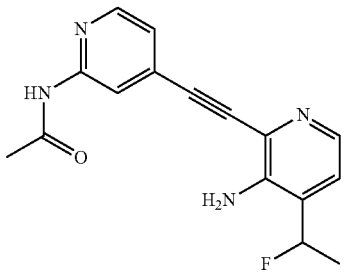 [SMILES: CC(=O)Nc1cc(C#Cc2nccc(C(C)F)c2N)ccn1]

To a solution of N-(4-((3-amino-4-(1-hydroxyethyl)pyridin-2-yl)ethynyl)pyridin-2-yl)acetamide (0.1 g, 0.337 mmol) in CH$_2$Cl$_2$ (334 µl) at −20° C. was added DAST (0.045 ml, 0.337 mmol). The reaction was stirred at −20° C. for 10 min, then stirred warm to room temperature for 45 min. The reaction was quenched with MeOH and concentrated. The crude material was purified by silica gel flash chromatography (4 g column, EtOAc/hexanes=0-100%) to give N-(4-((3-amino-4-(1-fluoroethyl)pyridin-2-yl)ethynyl)pyridin-2-yl)acetamide. HPLC: RT=0.57 min (H$_2$O/ACN with 0.05% TFA, Waters Acquity UPLC BEH C18, 2.1×50 mm, 1.7-µm particles, gradient=1.6 min, wavelength=220 nm). MS (ES): m/z=299 [M+H]$^+$; $^1$H NMR (400 MHz, CHLOROFORM-d) δ ppm 8.37 (s, 1H), 8.27 (dd, J=0.77, 5.17 Hz, 1H), 8.07 (dd, J=1.32, 4.84 Hz, 1H), 7.21 (dd, J=1.43, 5.17 Hz, 1H), 7.03 (dd, J=0.66, 4.84 Hz, 1H), 5.70 (dq, J=6.60, 46.97 Hz, 1H), 4.69 (br. S., 2H), 2.23 (s, 3H), 1.75 (dd, J=6.38, 17.61 Hz, 3H).

233B) N-(2-((2-Acetamidopyridin-4-yl)ethynyl)-4-(1-fluoroethyl)pyridin-3-yl)-2,2,2-trifluoroacetamide N-(2-((2-Acetamidopyridin-4-yl)ethynyl)-4-(1-fluoroethyl)pyridin-3-yl)-2,2,2-trifluoroacetamide was prepared from N-(4-((3-amino-4-(1-fluoroethyl)pyridin-2-yl)ethynyl)pyridin-2-yl)acetamide (233A) by methods similar to those used in example 1D. HPLC: RT=0.74 min (H$_2$O/ACN with 0.05% TFA, Waters Acquity UPLC BEH C18, 2.1×50 mm, 1.7-µm particles, gradient=1.6 min, wavelength=220 nm). MS (ES): m/z=395 [M+H]$^+$;

Example 233) N-(4-(3-(6-(Difluoromethyl)pyridin-2-yl)-7-(1-fluoroethyl)-1H-pyrrolo[3,2-b]pyridin-2-yl)pyridin-2-yl)acetamide N-(4-(3-(6-(Difluoromethyl)pyridin-2-yl)-7-(1-fluoroethyl)-1H-pyrrolo[3,2-b]pyridin-2-yl)pyridin-2-yl)acetamide was prepared from N-(2-((2-acetamidopyridin-4-yl)ethynyl)-4-(1-fluoroethyl)pyridin-3-yl)-2,2,2-trifluoroacetamide (233B) and 2-bromo-6-(difluoromethyl)pyridine using the general methods shown for Example 212. HPLC: RT=1.01 min (H$_2$O/ACN with 0.1% TFA, Waters Acquity UPLC BEH C18, 2.1×50 mm, 1.7-µm particles, gradient=3 min, wavelength=220 nm). MS (ES): m/z=426 [M+H]$^+$; $^1$H NMR (500 MHz, DMSO-d$_6$) δ ppm 12.13 (s, 1H), 10.53 (s, 1H), 8.52 (d, J=4.63 Hz, 1H), 8.35 (d, J=7.91 Hz, 1H), 8.32 (br. s., 1H), 8.31 (d, J=5.22 Hz, 1H), 8.05 (t, J=7.83 Hz, 1H), 7.53 (d, J=7.66 Hz, 1H), 7.33 (d, J=4.71 Hz, 1H), 6.57 (t, J=55.29 Hz, 1H), 6.35 (dq, J=6.60, 46.95 Hz, 1H), 2.07 (s, 3H), 1.73 (dd, J=6.65, 24.66 Hz, 3H).

Example 234

N-(4-(7-Methoxy-3-(4-methylthiazol-2-yl)-1H-pyrrolo[3,2-b]pyridin-2-yl)pyridin-2-yl)acetamide

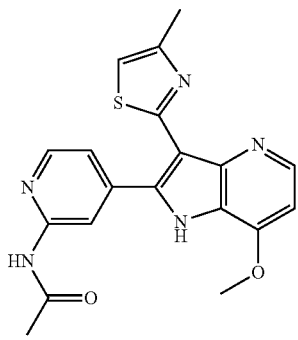 [SMILES: COc1ccnc2c(-c3nc(C)cs3)c(-c3ccnc(NC(C)=O)c3)[nH]c12]

N-(4-(7-Methoxy-3-(4-methylthiazol-2-yl)-1H-pyrrolo[3,2-b]pyridin-2-yl)pyridin-2-yl)acetamide was prepared from N-(2-((2-acetamidopyridin-4-yl)ethynyl)-4-methoxypyridin-3-yl)-2,2,2-trifluoroacetamide and 2-bromo-4-methylthiazole following the same methods shown for Example 212. HPLC: RT=0.90 min (H$_2$O/ACN with 0.1% TFA, Waters Acquity UPLC BEH C18, 2.1×50 mm, 1.7-μm particles, gradient=3 min, wavelength=220 nm). MS (ES): m/z=426 [M+H]$^+$; $^1$H NMR (500 MHz, DMSO-d$_6$) δ ppm 10.54 (s, 1H), 8.50 (s, 1H), 8.39 (d, J=5.30 Hz, 1H), 8.33 (d, J=5.13 Hz, 1H), 7.44 (d, J=5.05 Hz, 1H), 7.20 (s, 1H), 6.95 (d, J=5.30 Hz, 1H), 4.04 (s, 3H), 2.27 (s, 3H), 2.10 (s, 3H).

Example 235

N-(4-(6-Chloro-3-(6-methoxypyridin-3-yl)-1H-pyrrolo[3,2-b]pyridin-2-yl)pyridin-2-yl)-2-(4-(2-hydroxyethyl)piperazin-1-yl)acetamide

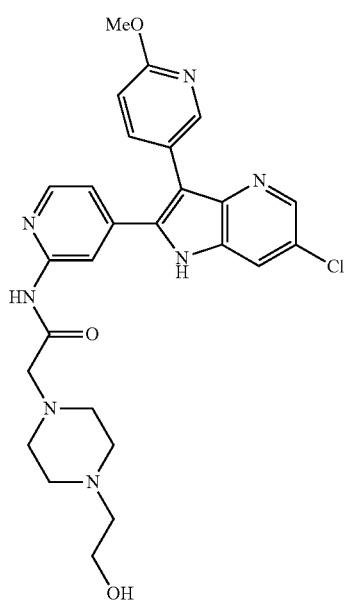 [SMILES: COc1ccc(-c2c(-c3ccnc(NC(=O)CN4CCN(CCO)CC4)c3)[nH]c3cc(Cl)cnc23)cn1]

Example 235 was prepared from Example 290A and 2-(piperazin-1-yl)ethanol by the general methods shown for Example 286. HPLC: RT=1.02 min (H$_2$O/ACN with 0.1% TFA, Waters Acquity UPLC BEH C18, 2.1×50 mm, 1.7-μm particles, gradient=3 min, wavelength=220 nm); MS (ES): m/z=522 [M+H]$^+$.

Example 237

N-(4-(3-(5-Methoxy-6-methylpyridin-2-yl)-1H-pyrrolo[3,2-b]pyridin-2-yl)pyridin-2-yl)acetamide

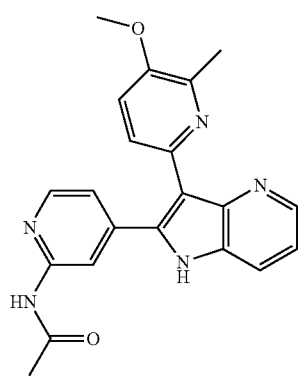 [SMILES: COc1ccc(-c2c(-c3ccnc(NC(C)=O)c3)[nH]c3cccnc23)nc1C]

To a solution of N-(4-(6-chloro-3-(5-methoxy-6-methylpyridin-2-yl)-1H-pyrrolo[3,2-b]pyridin-2-yl)pyridin-2-yl)acetamide (25 mg, 0.061 mmol) (Example 236) and sodium formate (25.01 mg, 0.368 mmol) in MeOH (2 mL) was purged with argon for several minutes. PdOAc$_2$ (5.50 mg, 0.025 mmol) was added and the reaction mixture was purge briefly with argon then heated at 75° C. for 2.5 h in a sealed tube. The reaction mixture was filtered and purified by preparative HPLC to yield N-(4-(3-(5-methoxy-6-methylpyridin-2-yl)-1H-pyrrolo[3,2-b]pyridin-2-yl)pyridin-2-yl)acetamide. HPLC: RT=0.70 min (H$_2$O/ACN with 0.1% TFA, Waters Acquity UPLC BEH C18, 2.1×50 mm, 1.7-μm particles, gradient=3 min, wavelength=220 nm). MS (ES): m/z=374 [M+H]$^+$; $^1$H NMR (500 MHz, DMSO-d$_6$) δ ppm 11.96 (s, 1H), 10.48 (s, 1H), 8.41 (d, J=3.95 Hz, 1H), 8.34 (br. s., 1H), 8.25 (d, J=5.13 Hz, 1H), 7.86 (d, J=8.16 Hz, 2H), 7.40 (d, J=8.50 Hz, 1H), 7.24 (dd, J=4.50, 8.12 Hz, 1H), 7.18 (d, J=4.96 Hz, 1H), 3.83 (s, 3H), 2.20 (s, 3H), 2.08 (s, 3H).

Example 238

N-(4-(6-Chloro-3-(5-methoxy-6-methylpyridin-2-yl)-1H-pyrrolo[3,2-b]pyridin-2-yl)pyridin-2-yl)-2-(4-methylpiperazin-1-yl)acetamide 238B) 2-Chloro-N-(4-(6-chloro-3-(5-methoxy-6-methylpyridin-2-yl)-1H-pyrrolo[3,2-b]pyridin-2-yl)pyridin-2-yl)acetamide

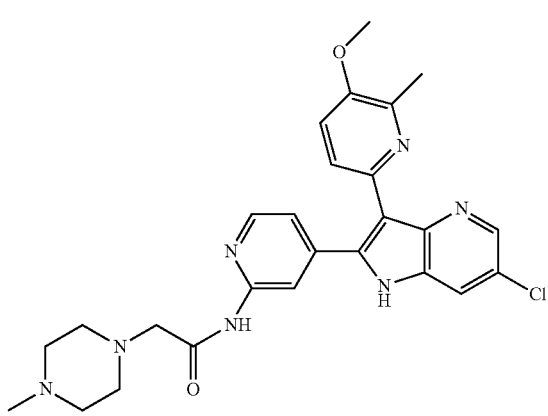 [SMILES: COc1ccc(-c2c(-c3ccnc(NC(=O)CN4CCN(C)CC4)c3)[nH]c3cc(Cl)cnc23)nc1C]

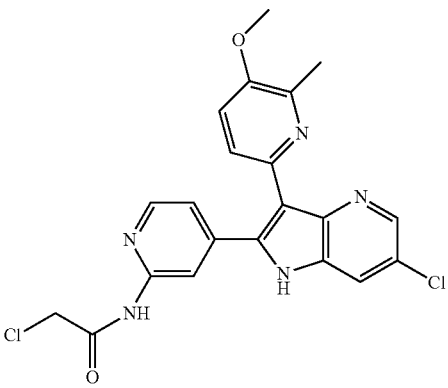

238A) 4-(6-Chloro-3-(5-methoxy-6-methylpyridin-2-yl)-1H-pyrrolo[3,2-b]pyridin-2-yl)pyridin-2-amine 2-Chloro-N-(4-(6-chloro-3-(5-methoxy-6-methylpyridin-2-yl)-1H-pyrrolo[3,2-b]pyridin-2-yl)pyridin-2-yl)acetamide was prepared from 4-(6-chloro-3-(5-methoxy-6-methylpyridin-2-yl)-1H-pyrrolo[3,2-b]pyridin-2-yl)pyridin-2-amine by the general methods shown for Example 74A. HPLC: RT=0.56 min (H₂O/MeOH with 0.05% TFA, Waters Acquity SDS BEH C18 2.1×50 mm 1.7 u, gradient=1.75 min, wavelength=220 nm); MS (ES): m/z=442 [M+H]⁺.

Example 238) N-(4-(6-Chloro-3-(5-methoxy-6-methylpyridin-2-yl)-1H-pyrrolo[3,2-b]pyridin-2-yl)pyridin-2-yl)-2-(4-methylpiperazin-1-yl)acetamide

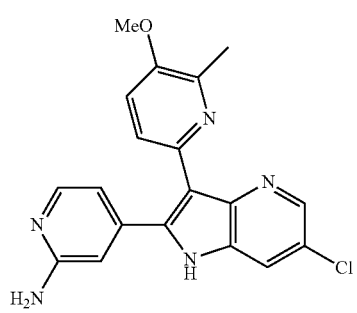 [SMILES: COc1ccc(-c2c(-c3ccnc(N)c3)[nH]c3cc(Cl)cnc23)nc1C]

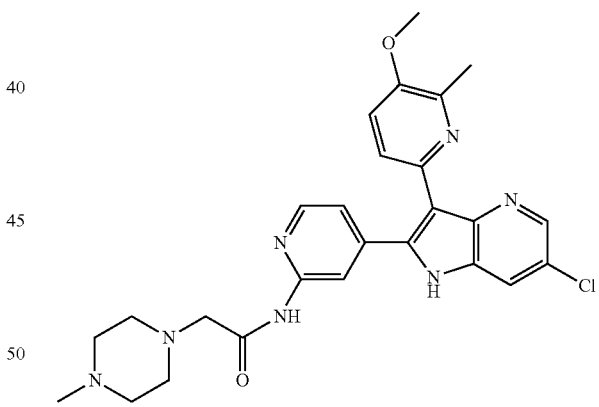

4-(6-Chloro-3-(5-methoxy-6-methylpyridin-2-yl)-1H-pyrrolo[3,2-b]pyridin-2-yl)pyridin-2-amine was prepared from N-(4-(6-chloro-3-(5-methoxy-6-methylpyridin-2-yl)-1H-pyrrolo[3,2-b]pyridin-2-yl)pyridin-2-yl)acetamide (Example 236) by the general methods shown for Example 52. HPLC: RT=0.39 min (H₂O/MeOH with 0.05% TFA, Waters Acquity SDS BEH C18 2.1×50 mm 1.7 u, gradient=1.75 min, wavelength=220 nm); MS (ES): m/z=366 [M+H]⁺.

A solution of 2-chloro-N-(4-(6-chloro-3-(5-methoxy-6-methylpyridin-2-yl)-1H-pyrrolo[3,2-b]pyridin-2-yl)pyridin-2-yl)acetamide (60.6 mg, 0.137 mmol) and 1-methylpiperazine (41.2 mg, 0.411 mmol) in DMF (0.5 mL) was added K₂CO₃ (56.8 mg, 0.411 mmol) and the reaction mixture was stirred at room temperature for 3 h. The reaction mixture was diluted with EtOAc (~3 mL) and filtered through Celite. The celite was washed with 10% MeOH/DCM (~3 mL). The filtrate was concentrated, redissolved in DMF (2 mL) and purified by preparative HPLC to give N-(4-(6-chloro-3-(5-methoxy-6-methylpyridin-2-yl)-1H-pyrrolo[3,2-b]pyridin-2-yl)pyridin-2-yl)-2-(4-methylpiperazin-1-yl)acetamide.
HPLC: RT=0.90 min (H₂O/MeOH with 0.05% TFA, Waters Acquity SDS BEH C18 2.1×50 mm 1.7 u, gradient=1.75 min, wavelength=220 nm); MS (ES): m/z=506 [M+H]⁺. ¹H NMR (500 MHz, DMSO-d₆) δ ppm 9.97 (s, 1H), 8.41 (s, 1H), 8.36 (s, 1H), 8.30 (d, J=5.13 Hz, 1H), 7.94 (d, J=1.60 Hz, 1H), 7.81 (d, J=8.41 Hz, 1H), 7.41 (d, J=8.50 Hz, 1H), 7.23 (d, J=4.63 Hz, 1H), 3.84 (s, 3H), 3.16 (s, 2H), 2.54 (br. s., 8H), 2.20 (s, 6H).

Example 239

N-(4-(6-Chloro-3-(5-methoxythiazol-2-yl)-1H-pyrrolo[3,2-b]pyridin-2-yl)pyridin-2-yl)acetamide

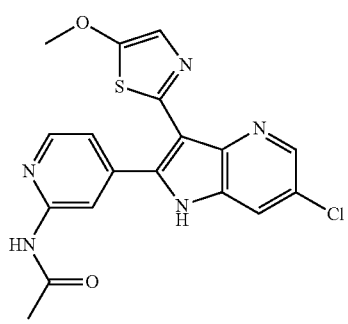 [SMILES: COc1cnc(-c2c(-c3ccnc(NC(C)=O)c3)[nH]c3cc(Cl)cnc23)s1]

N-(4-(6-Chloro-3-(5-methoxythiazol-2-yl)-1H-pyrrolo[3,2-b]pyridin-2-yl)pyridin-2-yl)acetamide was prepared from Example 41B and 2-bromo-5-methoxythiazole by the methods shown for Example 172. HPLC: RT=1.25 min (H₂O/ACN with 0.1% TFA, Waters Acquity UPLC BEH C18, 2.1×50 mm, 1.7-μm particles, gradient=3 min, wavelength=220 nm); MS (ES): m/z=400: ¹H NMR (500 MHz, DMSO-d₆) δ 10.64 (s, 1H), 8.52 (d, J=1.68 Hz, 1H), 8.45 (s, 1H), 8.39 (d, J=5.05 Hz, 1H), 7.98 (d, J=1.94 Hz, 1H), 7.47 (dd, J=1.01, 5.13 Hz, 1H), 7.13 (s, 1H), 3.94 (s, 3H), 2.12 (s, 3H).

Example 240

N-(4-(7-Cyano-3-(4-methylthiazol-2-yl)-1H-pyrrolo[3,2-b]pyridin-2-yl)pyridin-2-yl)acetamide

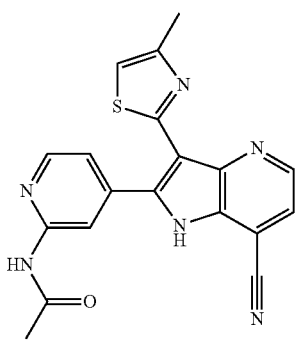 [SMILES: CC(=O)Nc1cc(-c2[nH]c3c(C#N)ccnc3c2-c2nc(C)cs2)ccn1]

240A) N-(4-(5-Bromo-7-cyano-3-(4-methylthiazol-2-yl)-1-((2-(trimethylsilyl)ethoxy)methyl)-1H-pyrrolo[3,2-b]pyridin-2-yl)pyridin-2-yl)acetamide

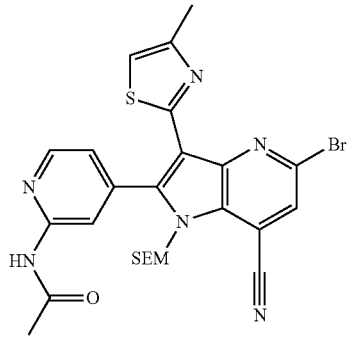 [SMILES: CC(=O)Nc1cc(-c2c(-c3nc(C)cs3)c3nc(Br)cc(C#N)c3n2COCC[Si](C)(C)C)ccn1]

A solution of 2-bromo-4-methylthiazole (145 mg, 0.814 mmol), 4,4,4',4',5,5,5',5'-octamethyl-2,2'-bi(1,3,2-dioxaborolane) (248 mg, 0.977 mmol) in 1,4-dioxane (5 ml) was added potassium acetate (120 mg, 1.222 mmol). The reaction mixture was purged with argon for several minutes and PdCl₂(dppf)-CH₂Cl₂Adduct (20.81 mg, 0.041 mmol) was added. The reaction mixture was bubbled argon for 2 min and heated in a sealed vial at 90° C. for 2 h. To the cooled reaction mixture was added N-(4-(5-bromo-7-cyano-3-iodo-1-((2-(trimethylsilyl)ethoxy)methyl)-1H-pyrrolo[3,2-b]pyridin-2-yl)pyridin-2-yl)acetamide (499 mg, 0.814 mmol) and tripotassium phosphate (0.679 ml, 2.036 mmol). The reaction mixture was bubbled with argon for 5 min and heated at 110° C. for overnight. The reaction mixture was cooled, diluted with EtOAc and washed with water then with brine. The organic phase was dried with MgSO₄, concentrated and purified by silica gel flash chromatography (12 g column, EtOAc/hex=0-50%) to give N-(4-(5-bromo-7-cyano-3-(4-methylthiazol-2-yl)-1-((2-(trimethylsilyl)ethoxy)methyl)-1H-pyrrolo[3,2-b]pyridin-2-yl)pyridin-2-yl)acetamide. HPLC: RT=1.20 min (H₂O/MeOH with 0.05% TFA, Waters Acquity SDS BEH C18 2.1×50 mm 1.7 u, gradient=1.75 min, wavelength=220 nm); MS (ES): m/z=583, 585 [M+H]⁺.

Example 240) N-(4-(7-Cyano-3-(4-methylthiazol-2-yl)-1H-pyrrolo[3,2-b]pyridin-2-yl)pyridin-2-yl)acetamide

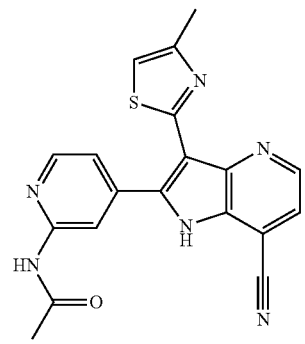 [SMILES: CC(=O)Nc1cc(-c2[nH]c3c(C#N)ccnc3c2-c2nc(C)cs2)ccn1]

A solution of N-(4-(5-bromo-7-cyano-3-(4-methylthiazol-2-yl)-1-((2-(trimethylsilyl)ethoxy)methyl)-1H-pyrrolo[3,2-b]pyridin-2-yl)pyridin-2-yl)acetamide (80 mg, 0.137 mmol) (Example 240A) in methanol (3 mL) was added sodium formate (55.9 mg, 0.823 mmol) and the reaction mixture was purged with argon for several minutes. Pd(OAc)$_2$ (18.47 mg, 0.082 mmol) added and the reaction mixture was stirred at 70° C. in a sealed vial for 16 h. The reaction mixture was filtered and concentrated and then treated with (1:1) DCM:TFA (3 mL) and heated at 50° C. for 2 h. The reaction mixture was then concentrated and dissolved in DMF and purified by preparative HPLC to give N-(4-(7-cyano-3-(4-methylthiazol-2-yl)-1H-pyrrolo[3,2-b]pyridin-2-yl)pyridin-2-yl)acetamide. HPLC: RT=1.34 min (H$_2$O/MeOH with 0.05% TFA, Waters Acquity SDS BEH C18 2.1×50 mm 1.7 u, gradient=1.75 min, wavelength=220 nm); MS (ES): m/z=375 [M+H]$^+$. $^1$H NMR (500 MHz, DMSO-d$_6$) δ ppm 10.64 (s, 1H), 8.58 (s, 1H), 8.44 (d, J=5.13 Hz, 1H), 8.24 (s, 1H), 7.71 (d, J=4.97 Hz, 1H), 7.42 (s, 1H), 7.40 (s, 1H), 2.45 (s, 3H), 2.15 (s, 3H).

Example 241

N-{4-[6-Chloro-3-(5-fluoropyridin-2-yl)-1H-pyrrolo[3,2-b]pyridin-2-yl]pyridin-2-yl}-2-{[2-(morpholin-4-yl)ethyl]amino}acetamide

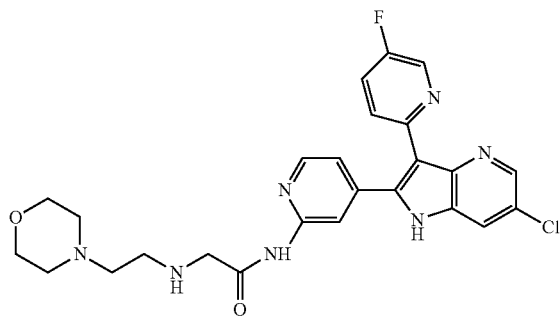 [SMILES: O=C(CNCCN1CCOCC1)Nc1cc(-c2[nH]c3cc(Cl)cnc3c2-c2ccc(F)cn2)ccn1]

Example 241 was prepared from Example 74A and 2-morpholinoethanamine by the general methods shown for Example 74. HPLC: RT=0.82 min (H$_2$O/ACN with 0.1% TFA, Waters Acquity UPLC BEH C18, 2.1×50 mm, 1.7-µm particles, gradient=3 min, wavelength=220 nm); MS (ES): m/z=510.1 [M+H]$^+$; $^1$H NMR (500 MHz, DMSO-d$_6$) δ ppm 12.47 (s, 1H), 8.55-8.39 (m, 3H), 8.27-8.12 (m, 2H), 8.01 (s, 1H), 7.89-7.77 (m, 1H), 7.35 (d, J=4.9 Hz, 1H), 4.29-3.59 (m, 2H), 3.45-2.80 (m, 4H), 2.54 (br.s, 8H).

Example 242

4-(6-Chloro-3-(5-methoxypyridin-2-yl)-1H-pyrrolo[3,2-b]pyridin-2-yl)-N-ethylpyridin-2-amine

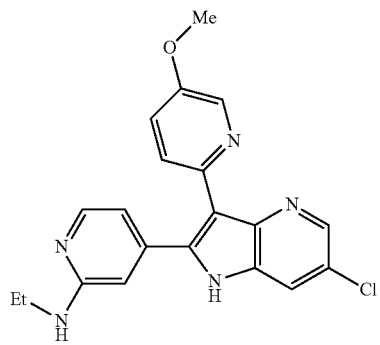 [SMILES: CCNc1cc(-c2[nH]c3cc(Cl)cnc3c2-c2ccc(OC)cn2)ccn1]

Example 242 was prepared by the general methods shown for Example 82. HPLC: RT=1.08 min (H$_2$O/ACN with 0.1% TFA, Waters Acquity UPLC BEH C18, 2.1×50 mm, 1.7-µm particles, gradient=3 min, wavelength=220 nm); MS (ES): m/z=379.9 [M+H]$^+$; $^1$H NMR (500 MHz, DMSO-d$_6$) δ ppm 12.17 (br. s., 1H), 8.41 (br. s., 1H), 8.26 (br. s., 1H), 7.93 (br. s., 2H), 7.87 (d, J=7.0 Hz, 1H), 7.50 (d, J=7.5 Hz, 1H), 6.75 (br. s., 1H), 6.59 (d, J=4.8 Hz, 1H), 3.86 (s, 3H), 2.54 (m, 2H), 1.13 (t, J=7.0 Hz, 3H)

Example 243

4-(6-Chloro-3-(5-methoxypyridin-2-yl)-1H-pyrrolo[3,2-b]pyridin-2-yl)-N-isobutylpyridin-2-amine

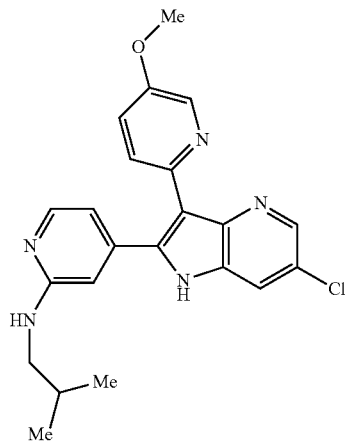 [SMILES: COc1ccc(-c2c(-c3ccnc(NCC(C)C)c3)[nH]c3cc(Cl)cnc23)nc1]

Example 243 was prepared by the general methods shown for Example 82. HPLC: RT=1.01 min (H$_2$O/ACN with 0.1% TFA, Waters Acquity UPLC BEH C18, 2.1×50 mm, 1.7-µm particles, gradient=3 min, wavelength=220 nm); MS (ES): m/z=408.2 [M+H]$^+$; $^1$H NMR (500 MHz, DMSO-d$_6$) δ ppm 12.13 (br. s., 1H), 8.40 (br. s., 1H), 8.25 (br. s., 1H), 7.92 (br. s., 2H), 7.86 (d, J=8.4 Hz, 1H), 7.49 (d, J=8.3 Hz, 1H), 6.69 (br. s., 1H), 6.56 (br. s., 1H), 3.86 (s, 3H), 3.00 (br. s., 2H), 1.83-1.71 (m, 1H), 0.88 (d, J=6.4 Hz, 6H.

Example 244

N-(4-(6-Chloro-3-(5-fluoropyridin-2-yl)-1H-pyrrolo[3,2-b]pyridin-2-yl)pyridin-2-yl)-2-(4-hydroxypiperidin-1-yl)acetamide

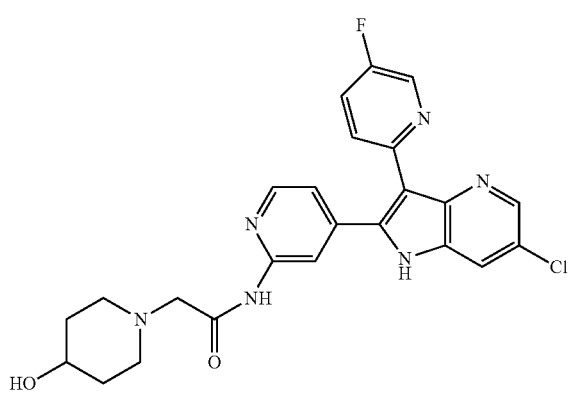 [SMILES: O=C(CN1CCC(O)CC1)Nc1cc(-c2[nH]c3cc(Cl)cnc3c2-c2ccc(F)cn2)ccn1]

Example 244 was prepared from 74A and piperidin-4-ol by the general methods shown for Example 74. HPLC: RT=0.84 min (H$_2$O/ACN with 0.1% TFA, Waters Acquity UPLC BEH C18, 2.1×50 mm, 1.7-μm particles, gradient=3 min, wavelength=220 nm); MS (ES): m/z=481.1 [M+H]; $^1$H NMR (500 MHz, DMSO-d$_6$) δ ppm 12.48 (br. s., 1H), 8.46 (br. s., 2H), 8.42 (d, J=4.5 Hz, 1H), 8.23 (br. s., 1H), 8.12 (dd, J=8.6, 4.5 Hz, 1H), 8.01 (s, 1H), 7.89-7.75 (m, 1H), 7.33 (br. s., 1H), 4.23-3.11 (m, 3H), 2.54 (s, 4H), 1.91 (br. s., 2H), 1.68 (br. s., 2H).

Example 245

N-(4-(6-Chloro-3-(5-fluoropyridin-2-yl)-1H-pyrrolo[3,2-b]pyridin-2-yl)pyridin-2-yl)-2-(4-(dimethylamino)piperidin-1-yl)acetamide

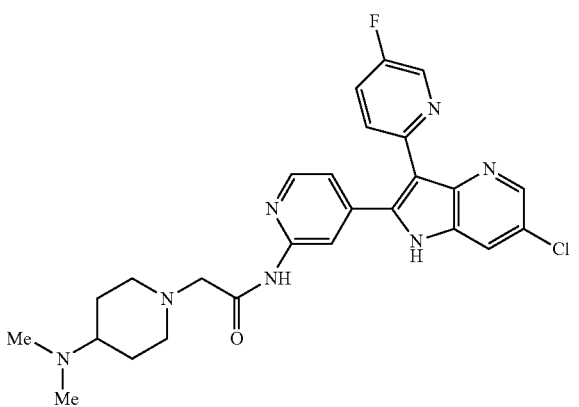 [SMILES: CN(C)C1CCN(CC(=O)Nc2cc(-c3[nH]c4cc(Cl)cnc4c3-c3ccc(F)cn3)ccn2)CC1]

Example 245 was prepared from 74A and N,N-dimethylpiperidin-4-amine by the general methods shown for Example 74. HPLC: RT=0.83 min (H$_2$O/ACN with 0.1% TFA, Waters Acquity UPLC BEH C18, 2.1×50 mm, 1.7-μm particles, gradient=3 min, wavelength=220 nm); MS (ES): m/z=508.3 [M+H]; $^1$H NMR (500 MHz, DMSO-d$_6$) δ ppm 12.43 (s, 1H), 8.44 (br. s., 2H), 8.36 (d, J=5.0 Hz, 1H), 8.22 (br. s., 1H), 8.07 (dd, J=8.7, 4.5 Hz, 1H), 8.01 (s, 1H), 7.87-7.71 (m, 1H), 7.28 (br. s., 1H), 3.87-3.52 (m, 13H), 2.04 (br. s., 2H), 1.76 (br. s., 2H).

Example 246

N-(4-(6-Chloro-3-(5-fluoropyridin-2-yl)-1H-pyrrolo[3,2-b]pyridin-2-yl)pyridin-2-yl)-2-(4-(2-hydroxyethyl)piperazin-1-yl)acetamide

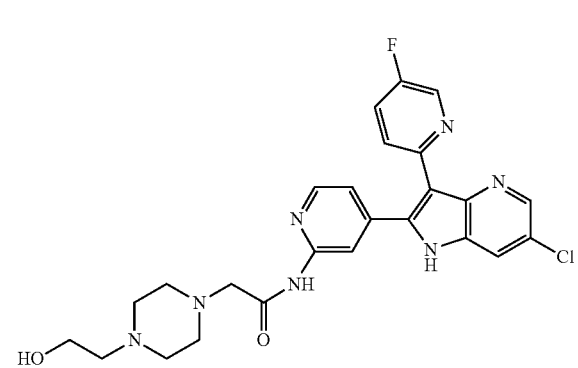 [SMILES: O=C(CN1CCN(CCO)CC1)Nc1cc(-c2[nH]c3cc(Cl)cnc3c2-c2ccc(F)cn2)ccn1]

Example 246 was prepared from example 74A and 2-(piperazin-1-yl)ethanol by the general methods shown for Example 74. HPLC: RT=0.86 min (H$_2$O/ACN with 0.1% TFA, Waters Acquity UPLC BEH C18, 2.1×50 mm, 1.7-μm particles, gradient=3 min, wavelength=220 nm); MS (ES): m/z=510.2 [M+H]; $^1$H NMR (500 MHz, DMSO-d$_6$) δ ppm 12.44 (s, 1H), 10.34 (br. s., 1H), 8.46 (br. s., 2H), 8.36 (d, J=5.0 Hz, 1H), 8.27 (br. s., 1H), 8.16-8.07 (m, 1H), 8.00 (s, 1H), 7.83 (t, J=8.6 Hz, 1H), 7.25 (d, J=4.9 Hz, 1H), 3.73 (br. s., 4H), 3.19 (br. s., 4H), 3.11-2.63 (m, 4H), 2.54 (s, 2H).

Example 247

N-(4-(6-Chloro-3-(5-fluoropyridin-2-yl)-1H-pyrrolo[3,2-b]pyridin-2-yl)pyridin-2-yl)-2-(piperazin-1-yl)acetamide

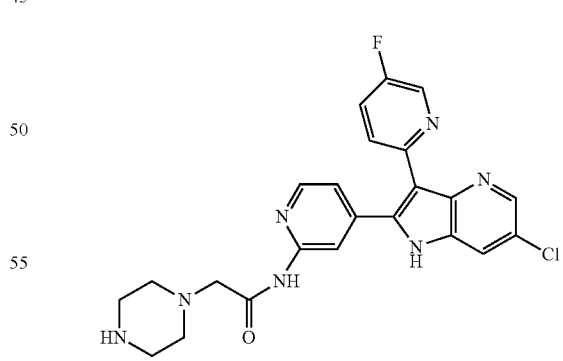

Example 247 was prepared from 74A and tert-butyl piperazine-1-carboxylate by the general methods shown for Example 74. HPLC: RT=0.86 min (H$_2$O/ACN with 0.1% TFA, Waters Acquity UPLC BEH C18, 2.1×50 mm, 1.7-μm particles, gradient=3 min, wavelength=220 nm); MS (ES): m/z=466.0 [M+H]; $^1$H NMR (500 MHz, DMSO-d$_6$) δ ppm 10.13 (s, 1H), 8.46 (br. s., 2H), 8.34 (d, J=5.1 Hz, 1H), 8.28

(s, 1H), 8.15-8.07 (m, 1H), 7.99 (s, 1H), 7.88-7.77 (m, 1H), 7.22 (d, J=5.0 Hz, 1H), 3.23 (s, 2H), 2.98 (br. s., 4H), 2.63 (br. s., 4H).

Example 248

2-(4-Acetylpiperazin-1-yl)-N-(4-(6-chloro-3-(5-fluoropyridin-2-yl)-1H-pyrrolo[3,2-b]pyridin-2-yl)pyridin-2-yl)acetamide

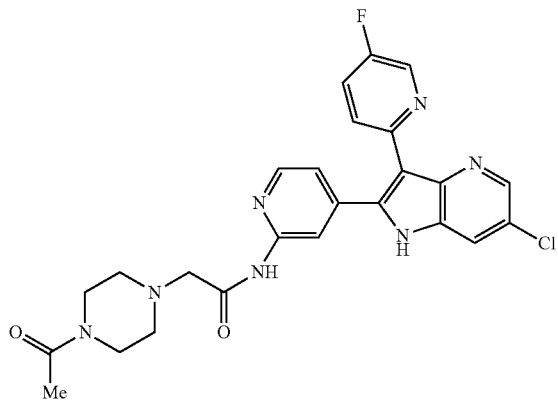 [SMILES: CC(=O)N1CCN(CC(=O)Nc2cc(-c3[nH]c4cc(Cl)cnc4c3-c3ccc(F)cn3)ccn2)CC1]

Example 248 was prepared from 74A and 1-(piperazin-1-yl)ethanone by the general methods shown for Example 74. HPLC: RT=0.86 min (H$_2$O/ACN with 0.1% TFA, Waters Acquity UPLC BEH C18, 2.1×50 mm, 1.7-μm particles, gradient=3 min, wavelength=220 nm); MS (ES): m/z=508.2 [M+H]; $^1$H NMR (500 MHz, DMSO-d$_6$) δ 10.12 (s, 1H), 8.46 (s, 2H), 8.34 (d, J=5.2 Hz, 1H), 8.29 (s, 1H), 8.10 (dd, J=8.5, 4.3 Hz, 1H), 7.99 (s, 1H), 7.88-7.79 (m, 1H), 7.21 (d, J=4.9 Hz, 1H), 3.47 (d, J=4.3 Hz, 4H), 3.41-3.35 (m, 4H), 3.22 (s, 2H), 1.99 (s, 3H).

Example 249

N-(4-(6-Chloro-3-(5-methoxypyridin-2-yl)-1H-pyrrolo[3,2-b]pyridin-2-yl)pyridin-2-yl)-2-(4-methylpiperazin-1-yl)acetamide

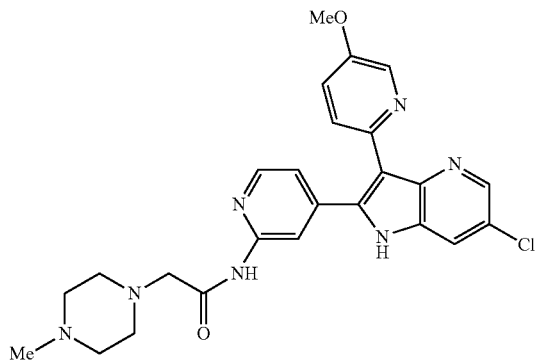 [SMILES: COc1ccc(-c2c(-c3ccnc(NC(=O)CN4CCN(C)CC4)c3)[nH]c3cc(Cl)cnc23)nc1]

249A) 2-Chloro-N-(4-(6-chloro-3-(5-methoxypyridin-2-yl)-1H-pyrrolo[3,2-b]pyridin-2-yl)pyridin-2-yl)acetamide

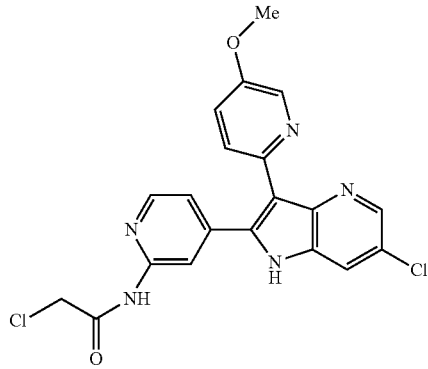 [SMILES: COc1ccc(-c2c(-c3ccnc(NC(=O)CCl)c3)[nH]c3cc(Cl)cnc23)nc1]

To a suspension of 4-(6-chloro-3-(5-methoxypyridin-2-yl)-1H-pyrrolo[3,2-b]pyridin-2-yl)pyridin-2-amine (210 mg, 0.597 mmol) (Example 86) in DCE (8 mL) (sonicated) was added chloroacetyl chloride (0.214 mL, 2.69 mmol) and TEA (0.42 mL, 2.98 mmol) slowly at ice bath temperature. The reaction mixture was stirred at rt for 0.5 h. Then to the reaction mixture was added 2 mL of aqueous ammonia hydroxide solution and the mixture was stirred at room temperature for 2 h. The reaction mixture was then diluted with saturated NaHCO$_3$ solution and the mixture was filtered to give the desired product (255 mg, 99%); HPLC: RT=0.69 min (H$_2$O/ACN with 0.05% TFA, Waters Acquity SDS C18, 2.1×50 mm, 1.7-μm particles, gradient=1.8 min, wavelength=220 nm); MS (ES): m/z=427.9 [M+H]$^+$; $^1$H NMR (400 MHz, DMSO-d$_6$) δ ppm 12.22 (s, 1H), 10.87 (s, 1H), 8.43 (d, J=2.2 Hz, 1H), 8.37-8.28 (m, 2H), 8.20 (d, J=2.9 Hz, 1H), 7.99-7.91 (m, 2H), 7.50 (dd, J=8.8, 3.1 Hz, 1H), 7.20 (dd, J=5.2, 1.4 Hz, 1H), 4.35 (s, 2H), 3.86 (s, 3H).

Example 249) N-(4-(6-Chloro-3-(5-methoxypyridin-2-yl)-1H-pyrrolo[3,2-b]pyridin-2-yl)pyridin-2-yl)-2-(4-methylpiperazin-1-yl)acetamide

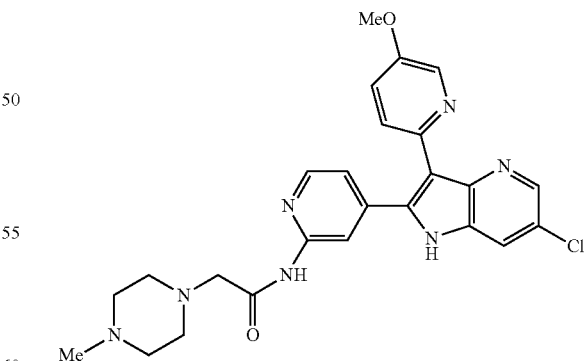

To a mixture of Example 249A (60 mg, 0.140 mmol) in acetonitrile (4 mL) was added 1-methylpiperazine (168 mg, 1.681 mmol) and silver oxide (64.9 mg, 0.280 mmol). The reaction mixture was stirred at room temperature for 3.5 h. The reaction mixture was concentrated in vacuo and the residue was mixed with TFA/MeOH, then concentrated in vacuo. To the residue was added small amount of TFA/ MeOH. The mixture was filtered through a syringe filter, and purified by preparative HPLC. Fractions containing the desired product were combined, and mixed with CHCl$_3$/2-propanol (3:1) and NaHCO$_3$ solution. The organic layer was separated and dried over MgSO$_4$. The filtrate was concentrated in vacuo and lyophilized to give the desired product (43 mg, 61%); HPLC: RT=0.57 min (H$_2$O/ACN with 0.05% TFA, Waters Acquity SDS C18, 2.1×50 mm, 1.7-μm particles, gradient=1.8 min, wavelength=220 nm); MS (ES): m/z=492.0 [M+H]; $^1$H NMR (400 MHz, MeOH-d$_4$) δ ppm 8.35 (d, J=2.2 Hz, 1H), 8.31 (d, J=0.7 Hz, 1H), 8.28-8.23 (m, 2H), 7.94 (d, J=2.0 Hz, 1H), 7.67 (d, J=8.8 Hz, 1H), 7.52 (dd, J=8.7, 3.0 Hz, 1H), 7.16 (dd, J=5.3, 1.5 Hz, 1H), 3.94 (s, 3H), 3.20 (s, 2H), 2.83-2.46 (m, 8H), 2.33 (s, 3H).

Example 250

N-(4-(6-Chloro-3-(5-methoxypyridin-2-yl)-1H-pyr-rolo[3,2-b]pyridin-2-yl)pyridin-2-yl)-2-morpholino-acetamide

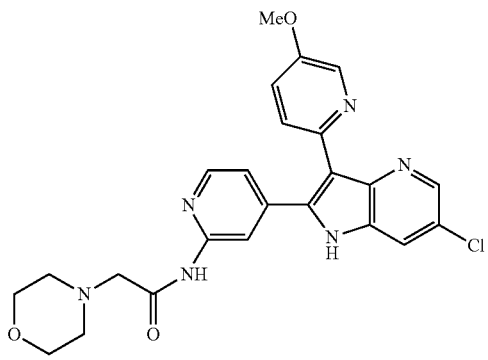 [SMILES: COc1ccc(-c2c(-c3ccnc(NC(=O)CN4CCOCC4)c3)[nH]c3cc(Cl)cnc23)nc1]

Example 250 was prepared from Example 249A and morpholine by the general methods shown for Example 249. HPLC: RT=0.77 min (H$_2$O/ACN with 0.1% TFA, Waters Acquity UPLC BEH C18, 2.1×50 mm, 1.7-μm particles, gradient=3 min, wavelength=220 nm); MS (ES): m/z=479.0 [M+H]; $^1$H NMR (500 MHz, DMSO-d$_6$) δ ppm 10.06 (br. s., 1H), 8.42 (br. s., 1H), 8.31 (br. s., 2H), 8.19 (br. s., 1H), 7.95 (br. s., 1H), 7.91 (d, J=8.6 Hz, 1H), 7.49 (d, J=7.4 Hz, 1H), 7.17 (br. s., 1H), 3.84 (br. s., 3H), 3.62 (br. s., 2H), 2.54 (s, 8H).

Example 251

N-(4-(6-Chloro-3-(5-methoxypyridin-2-yl)-1H-pyr-rolo[3,2-b]pyridin-2-yl)pyridin-2-yl)-2-(4-ethylpip-erazin-1-yl)acetamide

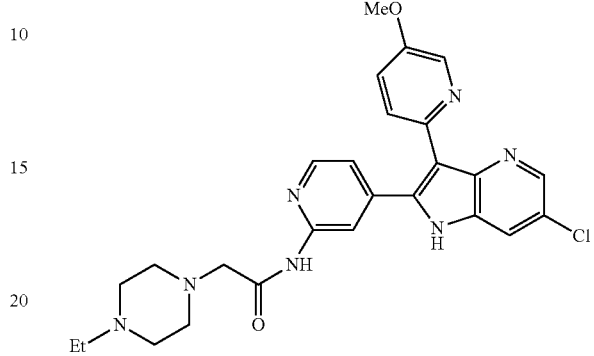

Example 251 was prepared from Example 249A and 1-ethylpiperazine by the general methods shown for Example 249. HPLC: RT=0.85 min (H$_2$O/ACN with 0.1% TFA, Waters Acquity UPLC BEH C18, 2.1×50 mm, 1.7-μm particles, gradient=3 min, wavelength=220 nm); MS (ES): m/z=506.1 [M+H]; $^1$H NMR (500 MHz, DMSO-d$_6$) δ 12.27 (s, 1H), 10.21 (br. s., 1H), 8.42 (s, 1H), 8.35-8.27 (m, 2H), 8.18 (br. s., 1H), 7.97 (s, 1H), 7.91 (d, J=8.7 Hz, 1H), 7.50 (dd, J=8.7, 2.8 Hz, 1H), 7.18 (d, J=4.9 Hz, 1H), 3.84 (s, 3H), 3.53 (m, 10H), 3.20-2.92 (m, 2H), 1.20 (t, J=7.2 Hz, 3H).

Example 252

N-(4-(6-Chloro-3-(5-methoxypyridin-2-yl)-1H-pyr-rolo[3,2-b]pyridin-2-yl)pyridin-2-yl)-2-(4-(2-hy-droxyethyl)piperazin-1-yl)acetamide

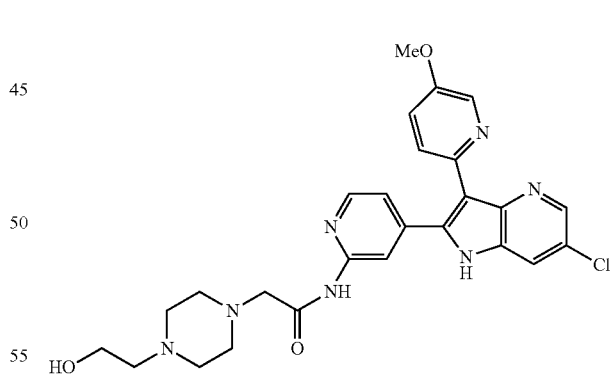

Example 252 was prepared from Example 249A and 2-(piperazin-1-yl)ethanol by the general methods shown for Example 249. HPLC: RT=0.85 min (H$_2$O/ACN with 0.1% TFA, Waters Acquity UPLC BEH C18, 2.1×50 mm, 1.7-μm particles, gradient=3 min, wavelength=220 nm); MS (ES): m/z=522.3 [M+H]; $^1$H NMR (500 MHz, DMSO-d$_6$) δ ppm 9.98 (s, 1H), 8.42 (br. s., 1H), 8.36-8.27 (m, 2H), 8.18 (br. s., 1H), 8.01-7.84 (m, 2H), 7.50 (d, J=8.5 Hz, 1H), 7.17 (d, J=5.0 Hz, 1H), 3.85 (s, 3H), 3.16 (s, 2H), 2.54 (br. s., 6H), 2.43 (br. s., 3H), 1.90 (s, 3H).

Example 253

N-(4-(6-Chloro-3-(5-ethoxypyridin-2-yl)-1H-pyrrolo[3,2-b]pyridin-2-yl)pyridin-2-yl)acetamide

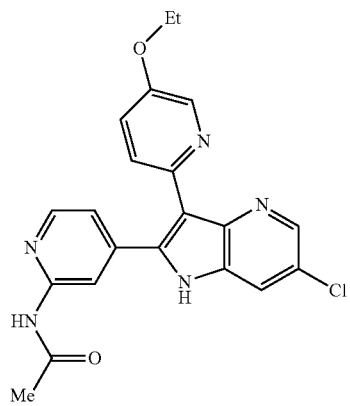

Example 253 was prepared from Example 41B and 2-bromo-5-ethoxypyridine by the general methods shown for Example 1. HPLC: RT=1.05 min (H₂O/ACN with 0.1% TFA, Waters Acquity UPLC BEH C18, 2.1×50 mm, 1.7-μm particles, gradient=3 min, wavelength=220 nm); MS (ES): m/z=408.0 [M+H]⁺; ¹H NMR (500 MHz, DMSO-d₆) δ ppm 12.20 (s, 1H), 10.56 (s, 1H), 8.42 (d, J=1.8 Hz, 1H), 8.35-8.24 (m, 2H), 8.18 (d, J=2.6 Hz, 1H), 8.01-7.85 (m, 2H), 7.48 (dd, J=8.6, 2.7 Hz, 1H), 7.11 (d, J=4.5 Hz, 1H), 4.13 (q, J=6.9 Hz, 2H), 2.09 (s, 3H), 1.36 (t, J=6.9 Hz, 3H)

Example 254

N-(4-(6-Chloro-3-(5-isopropoxypyridin-2-yl)-1H-pyrrolo[3,2-b]pyridin-2-yl)pyridin-2-yl)acetamide

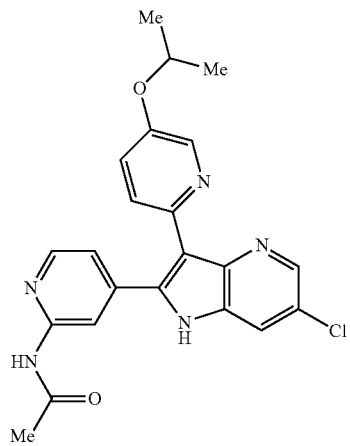 [SMILES: CC(=O)Nc1cc(-c2[nH]c3cc(Cl)cnc3c2-c2ccc(OC(C)C)cn2)ccn1]

Example 254 was prepared from Example 41B and 2-bromo-5-isopropoxypyridine by the general methods shown for Example 1. HPLC: RT=1.16 min (H₂O/ACN with 0.1% TFA, Waters Acquity UPLC BEH C18, 2.1×50 mm, 1.7-μm particles, gradient=3 min, wavelength=220 nm); MS (ES): m/z=422.1 [M+H]⁺; ¹H NMR (500 MHz, DMSO-d₆) δ ppm 12.56 (br. s., 1H), 10.64 (s, 1H), 8.57-8.47 (m, 1H), 8.35 (d, J=5.0 Hz, 2H), 8.21 (br. s., 1H), 8.03 (d, J=1.7 Hz, 1H), 7.93 (d, J=8.8 Hz, 1H), 7.79 (d, J=7.1 Hz, 1H), 7.22 (d, J=5.4 Hz, 1H), 4.81 (dt, J=11.9, 5.8 Hz, 1H), 2.07 (s, 3H), 1.34 (d, J=6.0 Hz, 6H)

Example 255

N-(4-(6-Chloro-3-(6-isopropoxypyridin-2-yl)-1H-pyrrolo[3,2-b]pyridin-2-yl)pyridin-2-yl)acetamide

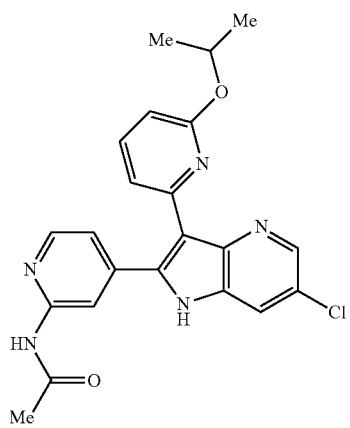 [SMILES: CC(=O)Nc1cc(-c2[nH]c3cc(Cl)cnc3c2-c2cccc(OC(C)C)n2)ccn1]

Example 255 was prepared from Example 41B and 2-bromo-6-isopropoxypyridine by the general methods shown for Example 1. HPLC: RT=1.35 min (H₂O/ACN with 0.1% TFA, Waters Acquity UPLC BEH C18, 2.1×50 mm, 1.7-μm particles, gradient=3 min, wavelength=220 nm); MS (ES): m/z=422.1 [M+H]⁺; ¹H NMR (500 MHz, DMSO-d₆) δ ppm 12.24 (br. s., 1H), 10.59 (br. s., 1H), 8.44 (s, 1H), 8.32 (d, J=4.7 Hz, 1H), 8.23 (br. s., 1H), 7.97 (d, J=7.3 Hz, 1H), 7.91 (s, 1H), 7.68 (t, J=7.7 Hz, 1H), 7.13 (d, J=4.7 Hz, 1H), 6.48 (d, J=8.1 Hz, 1H), 4.47-4.26 (m, 1H), 2.04 (s, 3H), 0.88 (d, J=6.1 Hz, 6H)

Example 256

N-(4-(6-Chloro-3-(6-ethoxypyridin-2-yl)-1H-pyrrolo[3,2-b]pyridin-2-yl)pyridin-2-yl)acetamide

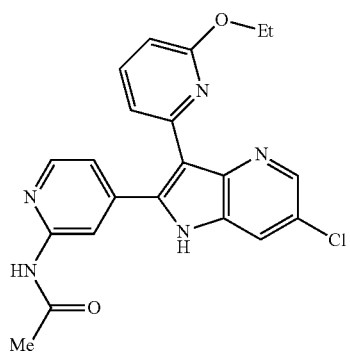 [SMILES: CCOc1cccc(-c2c(-c3ccnc(NC(C)=O)c3)[nH]c3cc(Cl)cnc23)n1]

Example 256 was prepared from Example 41B and 2-bromo-6-ethoxypyridine by the general methods shown for Example 1. HPLC: RT=1.23 min (H₂O/ACN with 0.1% TFA, Waters Acquity UPLC BEH C18, 2.1×50 mm, 1.7-μm particles, gradient=3 min, wavelength=220 nm); MS (ES): m/z=408.0 [M+H]+; 1H NMR (500 MHz, DMSO-d6) δ ppm 12.29 (br. s., 1H), 10.61 (s, 1H), 8.48 (s, 1H), 8.35 (d, J=5.0 Hz, 1H), 8.28 (br. s., 1H), 8.00 (d, J=7.4 Hz, 1H), 7.95 (s, 1H), 7.74 (t, J=7.8 Hz, 1H), 7.18 (d, J=5.0 Hz, 1H), 6.58 (d, J=8.2 Hz, 1H), 3.64 (q, J=6.9 Hz, 2H), 2.09 (s, 3H), 1.00 (t, J=7.0 Hz, 3H)

Example 257

N-(4-(7-Methoxy-3-(6-methylpyridin-2-yl)-1H-pyrrolo[3,2-b]pyridin-2-yl)pyridin-2-yl)acetamide

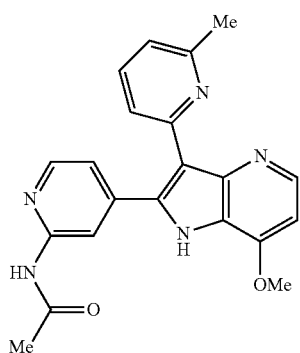 [SMILES: COc1ccnc2c(-c3cccc(C)n3)c(-c3ccnc(NC(C)=O)c3)[nH]c12]

Example 257 was prepared from 2-bromo-6-methylpyridine by the general methods shown for Example 266. HPLC: RT=0.66 min (H2O/ACN with 0.1% TFA, Waters Acquity UPLC BEH C18, 2.1×50 mm, 1.7-μm particles, gradient=3 min, wavelength=220 nm); MS (ES): m/z=374.2 [M+H]+; 1H NMR (500 MHz, DMSO-d6) δ ppm 10.46 (s, 1H), 8.31 (d, J=5.0 Hz, 2H), 8.24 (d, J=5.2 Hz, 1H), 7.93 (d, J=7.7 Hz, 1H), 7.69 (t, J=7.7 Hz, 1H), 7.20 (d, J=5.0 Hz, 1H), 7.07 (d, J=7.6 Hz, 1H), 6.90 (d, J=5.4 Hz, 1H), 4.04 (s, 3H), 2.26 (s, 3H), 2.11-2.03 (m, 3H).

Example 258

N-(4-(6-Chloro-3-(6-ethoxypyridin-3-yl)-1H-pyrrolo[3,2-b]pyridin-2-yl)pyridin-2-yl)acetamide

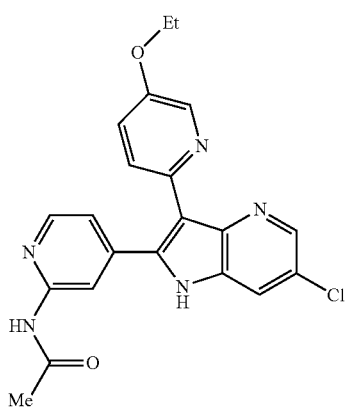 [SMILES: CCOc1ccc(-c2c(-c3ccnc(NC(C)=O)c3)[nH]c3cc(Cl)cnc23)nc1]

Example 258 was prepared from Example 41B and 5-bromo-2-ethoxypyridine by the general methods shown for Example 1. HPLC: RT=1.18 min (H2O/ACN with 0.1% TFA, Waters Acquity UPLC BEH C18, 2.1×50 mm, 1.7-μm particles, gradient=3 min, wavelength=220 nm); MS (ES): m/z=408.2 [M+H]+; 1H NMR (500 MHz, DMSO-d6) δ ppm 12.23 (br. s., 1H), 10.60 (s, 1H), 8.39 (s, 1H), 8.35-8.27 (m, 2H), 8.20 (s, 1H), 7.95 (br. s., 1H), 7.74 (d, J=7.2 Hz, 1H), 7.11 (d, J=4.7 Hz, 1H), 6.83 (d, J=8.5 Hz, 1H), 4.31 (q, J=6.8 Hz, 2H), 1.32 (t, J=6.9 Hz, 3H)

Example 259

N-(4-(6-Chloro-3-(3-methylpyridin-2-yl)-1H-pyrrolo[3,2-b]pyridin-2-yl)pyridin-2-yl)acetamide

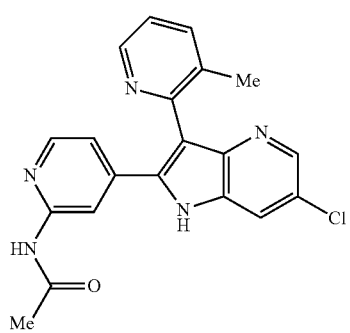 [SMILES: CC(=O)Nc1cc(-c2[nH]c3cc(Cl)cnc3c2-c2ncccc2C)ccn1]

Example 259 was prepared from Example 41B and 2-bromo-3-methylpyridine by the general methods shown for Example 1. HPLC: RT=1.16 min (H2O/ACN with 0.1% TFA, Waters Acquity UPLC BEH C18, 2.1×50 mm, 1.7-μm particles, gradient=3 min, wavelength=220 nm); MS (ES): m/z=378.0 [M+H]+; 1H NMR (500 MHz, DMSO-d6) δ ppm 12.61 (br. s., 1H), 10.51 (s, 1H), 8.54 (br. s., 1H), 8.34 (s, 1H), 8.26 (d, J=5.0 Hz, 1H), 8.10-7.95 (m, 3H), 7.59 (br. s., 1H), 7.05 (d, J=5.1 Hz, 1H), 2.09 (s, 3H), 1.99 (s, 3H)

Example 260

N-(4-(6-Chloro-3-(6-isopropylpyridin-2-yl)-1H-pyrrolo[3,2-b]pyridin-2-yl)pyridin-2-yl)acetamide

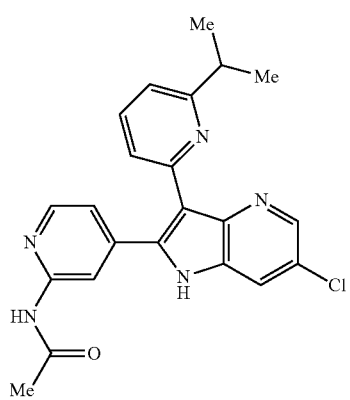 [SMILES: CC(=O)Nc1cc(-c2[nH]c3cc(Cl)cnc3c2-c2cccc(C(C)C)n2)ccn1]

Example 260 was prepared from Example 41B and 2-bromo-6-isopropylpyridine by the general methods shown for Example 1. HPLC: RT=1.06 min (H2O/ACN with 0.1% TFA, Waters Acquity UPLC BEH C18, 2.1×50 mm, 1.7-μm particles, gradient=3 min, wavelength=220 nm); MS (ES):

m/z=406.1 [M+H]+; 1H NMR (500 MHz, DMSO-d6) δ ppm 12.28 (br. s., 1H), 10.53 (br. s., 1H), 8.46 (s, 1H), 8.30 (d, J=4.2 Hz, 1H), 8.23 (br. s., 1H), 8.01 (d, J=7.6 Hz, 1H), 7.97 (s, 1H), 7.77 (t, J=7.5 Hz, 1H), 7.18 (d, J=4.7 Hz, 1H), 7.09 (d, J=7.2 Hz, 1H), 2.87-2.73 (m, 1H), 2.06 (s, 3H), 0.94 (d, J=6.6 Hz, 6H)

Example 261

N-(4-(3-(6-Fluoropyridin-3-yl)-7-(1-hydroxyethyl)-1H-pyrrolo[3,2-b]pyridin-2-yl)pyridin-2-yl)acetamide

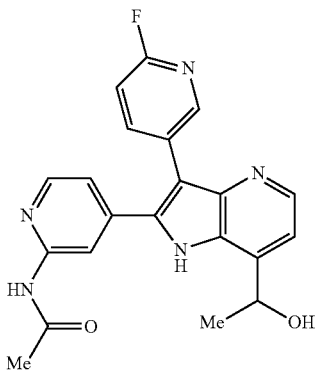 [SMILES: CC(=O)Nc1cc(-c2[nH]c3c(C(C)O)ccnc3c2-c2ccc(F)nc2)ccn1]

261A) 1-(3-Amino-2,6-dibromopyridin-4-yl)ethanone

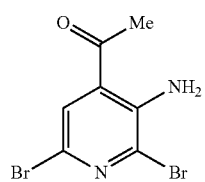 [SMILES: CC(=O)c1cc(Br)nc(Br)c1N]

To a solution of 1-(3-aminopyridin-4-yl)ethanone (0.9 g, 6.61 mmol) in DMF (10 mL) was added NBS (2.53 g, 14.21 mmol). The reaction mixture was stirred at room temperature for 2 h. The reaction mixture was diluted with ethyl acetate and saturated NaHCO3 solution. The organic layers (extracted two times) were washed with saturated NaHCO3 solution, dried over MgSO4. The filtrate was concentrated in vacuo. The residue was purified by flash chromatography. The product was eluted with 0-20% ethyl acetate in hexane to give the desired product as a white solid (1.55 g, 80%); HPLC: RT=0.88 min (H2O/ACN with 0.05% TFA, Waters Acquity SDS C18, 2.1×50 mm, 1.7-μm particles, gradient=1.8 min, wavelength=220 nm); MS (ES): m/z=292.8, 294.8 [M+H]+; 1H NMR (400 MHz, CDCl3) δ ppm 7.65 (s, 1H), 6.73 (br. s., 2H), 2.62 (s, 3H).

261B) N-(4-((4-Acetyl-3-amino-6-bromopyridin-2-yl)ethynyl)pyridin-2-yl)acetamide

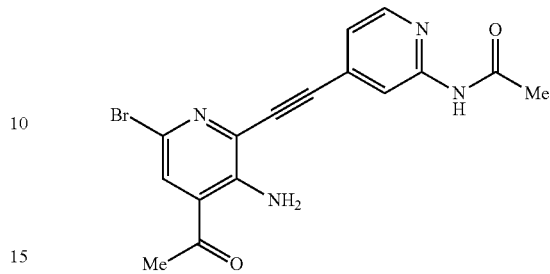

To a solution of 1-(3-amino-2,6-dibromopyridin-4-yl)ethanone (6.2 g, 21.09 mmol) in DMF (30 mL) were added TEA (29.4 mL, 211 mmol), CuI (0.20 g, 1.055 mmol) and N-(4-ethynylpyridin-2-yl)acetamide (3.72 g, 23.20 mmol). The reaction mixture was purged with nitrogen stream for 3 min, followed by addition of bis(triphenlphosphine)Palladium (II) chloride (0.888 g, 1.266 mmol). The reaction mixture was heated at 80° C. for 2 h. The reaction mixture was cooled down and diluted with ethyl acetate and saturated NaHCO3 solution. The ethyl acetate extracts (two times) were combined, washed with saturated NaHCO3 solution, dried over MgSO4. The filtrate was concentrated in vacuo. To the residue was added DCM, and the mixture was filtered to give light tan solid and filtrate. The filtrate was purified by flash chromatography. The product was eluted with DCM to 20% of 10% MeOH in DCM to give the desired product as brown solid, total (3.4 g, 43.2%); HPLC: RT=0.78 min (H2O/ACN with 0.05% TFA, Waters Acquity SDS C18, 2.1×50 mm, 1.7-μm particles, gradient=1.8 min, wavelength=220 nm); MS (ES): m/z=372.8, 374.8 [M+H]+; 1H NMR (400 MHz, DMSO-d6) δ ppm 10.64 (s, 1H), 8.39 (dd, J=5.1, 0.9 Hz, 1H), 8.29 (s, 1H), 7.94 (s, 1H), 7.44-7.31 (m, 3H), 2.63 (s, 3H), 2.12 (s, 3H).

261C) N-(2-((2-Acetamidopyridin-4-yl)ethynyl)-4-acetyl-6-bromopyridin-3-yl)-2,2,2-trifluoroacetamide

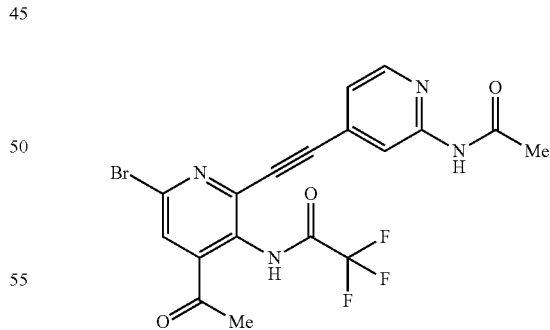

To a suspension of N-(4-((4-acetyl-3-amino-6-bromopyridin-2-yl)ethynyl)pyridin-2-yl)acetamide (2.0 g, 5.36 mmol) in DCE (35 mL) (sonicated) were added TEA (3.73 mL, 26.8 mmol) and trifluoroacetic anhydride (1.29 mL, 9.11 mmol) dropwise at ice bath temperature. The reaction mixture was stirred at 0° C. for 40 min. To the reaction mixture was added more TEA (2.5 ml) and trifluoroacetic anhydride (0.7 mL) and the reaction mixture was stirred at 0° C. for another 40 min. The reaction mixture was diluted with ethyl acetate and saturated NaHCO₃ solution. The organic layer was separated and washed with saturated NaHCO₃ solution, dried over MgSO₄. The filtrate was concentrated in vacuo. The residue was dissolved in DCM and filtered through a syringe filter, purified by flash Chromatography. The product was eluted with DCM to 20% of 10% MeOH in DCM to give the desired product as yellow solid (0.8 g, 32%); HPLC: RT=0.82 min (H₂O/ACN with 0.05% TFA, Waters Acquity SDS C18, 2.1×50 mm, 1.7-μm particles, gradient=1.8 min, wavelength=220 nm); MS (ES): m/z=470.7 [M+H]⁺; ¹H NMR (400 MHz, CHLOROFORM-d) δ ppm 9.46 (br. s., 1H), 8.37 (s, 1H), 8.30 (d, J=5.1 Hz, 1H), 7.94 (br. s., 1H), 7.75 (s, 1H), 7.15 (dd, J=5.1, 1.3 Hz, 1H), 2.68 (s, 3H), 2.23 (s, 3H).

261D) N-(4-(7-Acetyl-5-bromo-1H-pyrrolo[3,2-b]pyridin-2-yl)pyridin-2-yl)acetamide

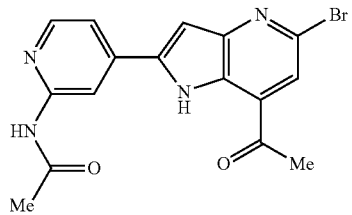 [SMILES: CC(=O)Nc1cc(-c2cc3nc(Br)cc(C(C)=O)c3[nH]2)ccn1]

The reaction mixture of N-(2-((2-acetamidopyridin-4-yl)ethynyl)-4-acetyl-6-bromopyridin-3-yl)-2,2,2-trifluoroacetamide (150 mg, 0.320 mmol), bis(dibenzylideneacetone)palladium (18.4 mg, 0.032 mmol), 2-(dicyclohexylphosphino)-2',4',6'-triisopropylbiphenyl (10.67 mg, 0.022 mmol) and Cs₂CO₃ (208 mg, 0.639 mmol) in acetonitrile (5 mL) in a sealed tube was purged with nitrogen stream for 2 min, then heated at 110° C. for 2 h. The reaction mixture was cooled down and extracted with ethyl acetate. The residue was dissolved in MeOH/TFA solution, purified by preparative HPLC. Fractions containing the desired product were combined, concentrated, and lyophilized to give the desired product as a yellow solid (31 mg, 26%); HPLC: RT=0.67 min (H₂O/ACN with 0.05% TFA, Waters Acquity SDS C18, 2.1×50 mm, 1.7-μm particles, gradient=1.8 min, wavelength=220 nm); MS (ES): m/z=373.1 [M+H]⁺; ¹H NMR (400 MHz, DMSO-d₆) δ ppm 11.82 (s, 1H), 10.66 (s, 1H), 8.51 (s, 1H), 8.41 (d, J=5.3 Hz, 1H), 7.89 (s, 1H), 7.70 (dd, 1.5 Hz, 1H), 7.23 (d, J=2.0 Hz, 1H), 2.76 (s, 3H), 2.15 (s, 3H).

261E) N-(4-(7-(1-Hydroxyethyl)-1H-pyrrolo[3,2-b]pyridin-2-yl)pyridin-2-yl)acetamide

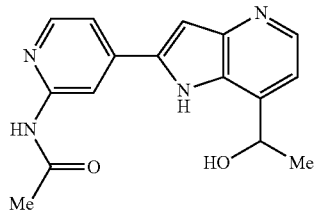 [SMILES: CC(=O)Nc1cc(-c2cc3nccc(C(C)O)c3[nH]2)ccn1]

To the reaction mixture of N-(4-(7-acetyl-5-bromo-1H-pyrrolo[3,2-b]pyridin-2-yl)pyridin-2-yl)acetamide (90 mg, 0.241 mmol) in MeOH (6 mL) was added Pd(OH)₂—C (16.93 mg, 0.024 mmol). The mixture was sonicated, vacuumed, then hydrogenated with hydrogen balloon for 2 h. The reaction mixture was diluted with MeOH, filtered. The filtrate was concentrated in vacuo to give the desired product as yellow solid (60 mg, 84%); HPLC: RT=0.46 min (H₂O/ACN with 0.05% TFA, Waters Acquity SDS C18, 2.1×50 mm, 1.7-μm particles, gradient=1.8 min, wavelength=220 nm); MS (ES): m/z=297.1 [M+H]⁺.

261F) N-(4-(7-(1-Hydroxyethyl)-3-iodo-1H-pyrrolo[3,2-b]pyridin-2-yl)pyridin-2-yl)acetamide

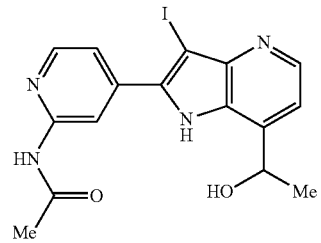 [SMILES: CC(=O)Nc1cc(-c2[nH]c3c(C(C)O)ccnc3c2I)ccn1]

To a solution of N-(4-(7-(1-hydroxyethyl)-1H-pyrrolo[3,2-b]pyridin-2-yl)pyridin-2-yl)acetamide (60 mg, 0.202 mmol) in DMF (2 mL) was added NIS (54.7 mg, 0.243 mmol). The reaction mixture was stirred at room temperature for 1 h. The reaction mixture was extracted with ethyl acetate and brine. The organic layer was separated and concentrated in vacuo. The crude was used in the next step reaction without purification. HPLC: RT=0.50 min (H₂O/ACN with 0.05% TFA, Waters Acquity SDS C18, 2.1×50 mm, 1.7-μm particles, gradient=1.8 min, wavelength=220 nm); MS (ES): m/z=423.1 [M+H]⁺.

Example 261) N-(4-(3-(6-Fluoropyridin-3-yl)-7-(1-hydroxyethyl)-1H-pyrrolo[3,2-b]pyridin-2-yl)pyridin-2-yl)acetamide The solution of N-(4-(7-(1-hydroxyethyl)-3-iodo-1H-pyrrolo[3,2-b]pyridin-2-yl)pyridin-2-yl)acetamide (30 mg, 0.071 mmol) and 2-fluoropyridine-5-boronic acid (12.0 mg, 0.085 mmol) in dioxane (2 mL) in a sealed tube. 1.0 M Na₂CO₃ solution (0.18 mL, 0.18 mmol) was added and the mixture was purged with nitrogen stream for 3 min, followed by addition of PdCl₂(dppf) (5.2 mg, 7.11 μmol). The resulting mixture was heated at 90° C. for 2 h. The reaction mixture was concentrated in vacuo. The residue was dissolved in MeOH+2 drop of TFA and filtered through a syringe filter, purified by preparative HPLC. Fractions containing the desired product were combined, concentrated, and lyophilized to give the desired product 2 TFA salt as a yellow solid (5.3 mg, 12%); HPLC: RT=0.69 min (H₂O/ACN with 0.1% TFA, Waters Acquity UPLC BEH C18, 2.1×50 mm, 1.7-μm particles, gradient=3 min, wavelength=220 nm); MS (ES): m/z=392.2 [M+H]⁺; ¹H NMR (500 MHz, DMSO-d₆) δ ppm 10.65 (s, 1H), 8.53 (d, J=5.3 Hz, 1H), 8.38 (d, J=5.1 Hz, 1H), 8.28 (s, 1H), 8.23 (s, 1H), 8.04 (td, J=8.2, 2.2 Hz, 1H), 7.57 (d, J=5.0 Hz, 1H), 7.27 (br. s., 1H), 7.20 (d, J=5.0 Hz, 1H), 5.49 (q, J=6.2 Hz, 1H), 2.07 (s, 3H), 1.50 (d, J=6.4 Hz, 3H).

Example 262

N-(4-(3-(6-Fluoropyridin-2-yl)-7-(1-hydroxyethyl)-1H-pyrrolo[3,2-b]pyridin-2-yl)pyridin-2-yl)acetamide

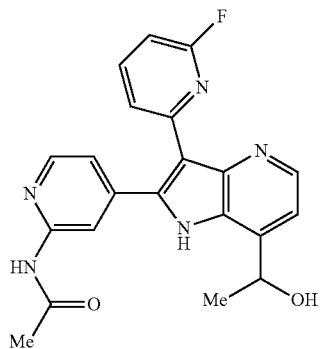 [SMILES: CC(=O)Nc1cc(-c2[nH]c3c(C(C)O)ccnc3c2-c2cccc(F)n2)ccn1]

Example 262 was prepared from 2-bromo-6-fluoropyridine by the general methods shown for Example 261. HPLC: RT=0.79 min (H$_2$O/ACN with 0.1% TFA, Waters Acquity UPLC BEH C18, 2.1×50 mm, 1.7-μm particles, gradient=3 min, wavelength=220 nm); MS (ES): m/z=392.1 [M+H]; $^1$H NMR (500 MHz, DMSO-d$_6$) δ ppm 11.88 (s, 1H), 10.57 (s, 1H), 8.46 (d, J=4.7 Hz, 1H), 8.34 (d, J=5.0 Hz, 1H), 8.28-8.17 (m, 2H), 8.02 (q, J=8.2 Hz, 1H), 7.33 (d, J=4.7 Hz, 1H), 7.22 (d, J=4.1 Hz, 1H), 6.96 (dd, J=8.0, 2.3 Hz, 1H), 5.55 (d, J=4.4 Hz, 1H), 5.43-5.26 (m, 1H), 2.08 (s, 3H), 1.45 (d, J=6.4 Hz, 3H).

Example 263

N-(4-(3-(6-Chloropyridin-2-yl)-7-(1-hydroxyethyl)-1H-pyrrolo[3,2-b]pyridin-2-yl)pyridin-2-yl)acetamide

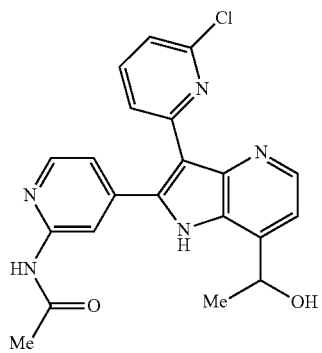 [SMILES: CC(=O)Nc1cc(-c2[nH]c3c(C(C)O)ccnc3c2-c2cccc(Cl)n2)ccn1]

Example 263 was prepared from 2-bromo-6-chloropyridine by the general methods shown for Example 261. HPLC: RT=0.86 min (H$_2$O/ACN with 0.1% TFA, Waters Acquity UPLC BEH C18, 2.1×50 mm, 1.7-μm particles, gradient=3 min, wavelength=220 nm); MS (ES): m/z=408.2 [M+H]; $^1$H NMR (500 MHz, DMSO-d$_6$) δ ppm 10.68 (s, 1H), 8.61 (d, J=5.4 Hz, 1H), 8.42 (d, J=5.0 Hz, 1H), 8.28 (s, 1H), 7.92-7.84 (m, 1H), 7.74 (br. s., 1H), 7.64 (d, J=5.3 Hz, 1H), 7.43 (d, J=7.9 Hz, 1H), 7.26 (s, 1H), 5.49 (d, J=6.5 Hz, 1H), 2.09 (s, 3H), 1.49 (d, J=6.5 Hz, 3H)

Example 264

N-(4-(3-(6-Chloropyridin-3-yl)-7-(1-hydroxyethyl)-1H-pyrrolo[3,2-b]pyridin-2-yl)pyridin-2-yl)acetamide

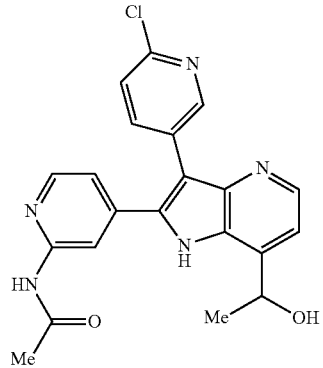

Example 264 was prepared from 5-bromo-2-chloropyridine by the general methods shown for Example 261. HPLC: RT=0.77 min (H$_2$O/ACN with 0.1% TFA, Waters Acquity UPLC BEH C18, 2.1×50 mm, 1.7-μm particles, gradient=3 min, wavelength=220 nm); MS (ES): m/z=408.2 [M+H]; $^1$H NMR (500 MHz, DMSO-d$_6$) δ ppm 10.67 (s, 1H), 8.53 (d, J=5.2 Hz, 1H), 8.46 (d, J=2.0 Hz, 1H), 8.39 (d, J=5.1 Hz, 1H), 8.26 (s, 1H), 7.94 (dd, J=8.2, 2.2 Hz, 1H), 7.68-7.51 (m, 2H), 7.18 (d, J=4.9 Hz, 2H), 5.47 (q, J=6.2 Hz, 1H), 3.00-2.84 (m, 1H), 2.08 (s, 3H), 1.49 (d, J=6.4 Hz, 3H).

Example 265

N-(4-(3-(5-Fluoropyridin-2-yl)-7-(1-hydroxyethyl)-1H-pyrrolo[3,2-b]pyridin-2-yl)pyridin-2-yl)acetamide

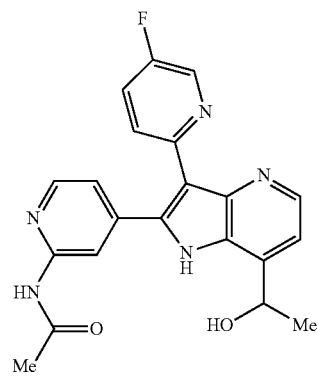 [SMILES: CC(=O)Nc1cc(-c2[nH]c3c(C(C)O)ccnc3c2-c2ccc(F)cn2)ccn1]

Example 265 was prepared from 2-bromo-5-fluoropyridine by the general methods shown for Example 261. HPLC: RT=0.60 min (H$_2$O/ACN with 0.1% TFA, Waters Acquity UPLC BEH C18, 2.1×50 mm, 1.7-μm particles, gradient=3 min, wavelength=220 nm); MS (ES): m/z=392.2 [M+H]; $^1$H NMR (400 MHz, MeOH-d$_4$) ppm 8.45 (d, J=2.9 Hz, 1H), 8.38 (d, J=5.1 Hz, 1H), 8.27 (dd, J=5.3, 0.4 Hz, 1H), 8.19 (s, 1H), 7.81-7.66 (m, 2H), 7.36 (d, J=5.1 Hz, 1H), 7.18 (dd, J=5.3, 1.5 Hz, 1H), 5.44 (q, J=6.6 Hz, 1H), 2.15 (s, 3H), 1.62 (d, J=6.6 Hz, 3H).

Example 266

N-(4-(7-Methoxy-3-(5-methoxypyridin-2-yl)-1H-pyrrolo[3,2-b]pyridin-2-yl)pyridin-2-yl)acetamide

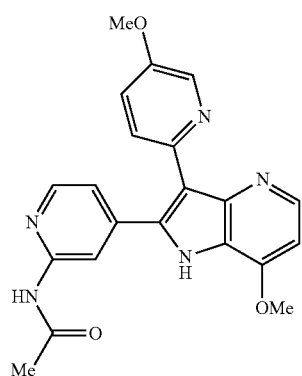 [SMILES: COc1ccc(-c2c(-c3ccnc(NC(C)=O)c3)[nH]c3c(OC)ccnc23)nc1]

266A) 2-Bromo-4-methoxypyridin-3-amine

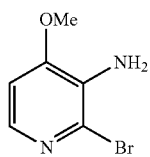

The solution of 4-methoxypyridin-3-amine (3.1 g, 24.97 mmol) in TFA (38.5 ml, 499 mmol) was stirred at ice bath temperature and to the mixture was added NBS (4.89 g, 27.5 mmol) in several batches. The reaction mixture was stirred at room temperature over night. The reaction mixture was concentrated in vacuo and the residue was diluted with saturated NaHCO$_3$ solution and ethyl acetate. The organic layers (twice extracts) were combined and washed with saturated NaHCO$_3$ solution, dried over MgSO$_4$. The filtrate was concentrated in vacuo. The residue was purified by flash chromatography. The product was eluted with 0-20% ethyl acetate in hexane to give the desired product as a white solid (3.9 g, 77%); HPLC: RT=0.47 min (H$_2$O/ACN with 0.05% TFA, Waters Acquity SDS C18, 2.1×50 mm, 1.7-μm particles, gradient=1.8 min, wavelength=220 nm); MS (ES): m/z=202.8, 204.8 [M+H]$^+$; $^1$H NMR (400 MHz, CDCl$_3$) δ ppm 7.75 (d, J=5.5 Hz, 1H), 6.69 (d, J=5.5 Hz, 1H), 4.11 (d, J=6.2 Hz, 2H), 3.92 (s, 3H).

266B) N-(4-((3-Amino-4-methoxypyridin-2-yl)ethynyl)pyridin-2-yl)acetamide

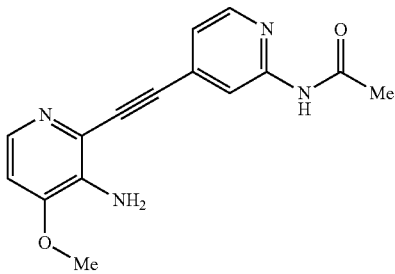 [SMILES: COc1ccnc(C#Cc2ccnc(NC(C)=O)c2)c1N]

To a solution of 2-bromo-4-methoxypyridin-3-amine (2.1 g, 10.34 mmol), N-(4-ethynylpyridin-2-yl)acetamide (1.82 g, 11.38 mmol) in DMF (15 mL) was added TEA (21.62 mL, 155 mmol) and CuI (0.12 g, 0.62 mmol). The reaction mixture was purged with nitrogen for 2 min, followed by addition of Pd(PPh$_3$)$_2$Cl$_2$ (0.73 g, 1.03 mmol). The reaction mixture was then heated at 100° C. for 3 h. The reaction mixture was cooled down and diluted with ethyl acetate and saturated NaHCO$_3$ solution. The organic layer (two times extracts) were combined, washed with saturated NaHCO$_3$ solution, dried over MgSO$_4$. The filtrate was concentrated in vacuo. The residue was purified by flash chromatography. The product was eluted with DCM to 50% of 10% MeOH in DCM to give the desired product as a light yellow (1.0 g, 34%); HPLC: RT=0.48 min (H$_2$O/ACN with 0.05% TFA, Waters Acquity SDS C18, 2.1×50 mm, 1.7-μm particles, gradient=1.8 min, wavelength=220 nm); MS (ES): m/z=283.1 [M+H]$^+$; $^1$H NMR (400 MHz, DMSO-d$_6$) δ ppm 10.59 (s, 1H), 8.34 (dd, J=5.1, 0.7 Hz, 1H), 8.22 (s, 1H), 7.79 (d, J=5.3 Hz, 1H), 7.34 (dd, J=5.2, 1.4 Hz, 1H), 6.91 (d, J=5.3 Hz, 1H), 5.35 (s, 2H), 4.03 (q, J=7.2 Hz, 1H), 3.88 (s, 3H), 2.11 (s, 3H).

266C) N-(2-((2-Acetamidopyridin-4-yl)ethynyl)-4-methoxypyridin-3-yl)-2,2,2-trifluoroacetamide

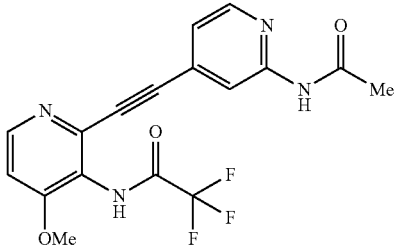 [SMILES: COc1ccnc(C#Cc2ccnc(NC(C)=O)c2)c1NC(=O)C(F)(F)F]

To a suspension of N-(4-((3-amino-4-methoxypyridin-2-yl)ethynyl)pyridin-2-yl)acetamide (0.6 g, 2.13 mmol) in DCE (14 mL) (sonicated) in ice bath temperature was added TEA (1.19 mL, 8.50 mmol), followed by addition of trifluoroacetic anhydride (0.53 mL, 3.83 mmol) slowly. The reaction mixture was stirred at 0° C. for 15 min and it turned into clear solution. The reaction mixture was quenched with cold saturated NaHCO$_3$ solution and the resulting mixture was extracted with ethyl acetate three times. The organic layer was separated and washed with saturated NaHCO$_3$ solution, dried over MgSO$_4$. The filtrate was concentrated in vacuo to give to give brown solid. To the residue was added ether and the solid was filtered to give the desired product as a brown solid (0.42 g, 70%); HPLC: RT=0.63 min (H$_2$O/ACN with 0.05% TFA, Waters Acquity SDS C18, 2.1×50 mm, 1.7-μm particles, gradient=1.8 min, wavelength=220 nm); MS (ES): m/z=379.0 [M+H]$^+$; $^1$H NMR (400 MHz, DMSO-d$_6$) δ ppm 11.32 (s, 1H), 10.66 (s, 1H), 8.52 (d, J=5.7 Hz, 1H), 8.42-8.36 (m, 1H), 8.20 (s, 1H), 7.32 (d, J=5.7 Hz, 1H), 7.13 (dd, J=5.1, 1.5 Hz, 1H), 3.93 (s, 3H), 2.11 (s, 3H).

Example 266) N-(4-(7-Methoxy-3-(5-methoxypyridin-2-yl)-1H-pyrrolo[3,2-b]pyridin-2-yl)pyridin-2-yl)acetamide To a suspension of N-(2-((2-acetamidopyridin-4-yl)ethynyl)-4-methoxypyridin-3-yl)-2,2,2-trifluoroacetamide (70 mg, 0.185 mmol), 2-bromo-5-methoxypyridine (70 mg, 0.37 mmol) in DMF (2 mL) was added Cs$_2$CO$_3$ (121 mg, 0.37 mmol). The reaction mixture was purged with nitrogen and followed by addition of 2$^{nd}$ generation Xphos precatalyst (7.5 mg, 9.3 μmol). The resulting mixture was heated at 120° C. for 3 h. The reaction mixture was cooled down. The residue was concentrated in vacuo and filtered and purified by preparative HPLC. Fractions containing the desired product were combined, concentrated, and lyophilized to give the desired product as a yellow solid (15.3 mg, 20.4%); HPLC: RT=0.77 min (H$_2$O/ACN with 0.1% TFA, Waters Acquity UPLC BEH C18, 2.1×50 mm, 1.7-μm particles, gradient=3 min, wavelength=220 nm); MS (ES): m/z=390.2 [M+H]$^+$; $^1$H NMR (500 MHz, DMSO-d$_6$) δ 10.45 (s, 1H), 8.29 (d, J=5.3 Hz, 1H), 8.22 (d, J=5.3 Hz, 2H), 8.13 (d, J=2.9 Hz, 1H), 7.96 (d, J=8.7 Hz, 1H), 7.46 (dd, J=8.7, 3.0 Hz, 1H), 7.11 (d, J=5.1 Hz, 1H), 6.89 (d, J=5.4 Hz, 1H), 4.03 (s, 3H), 3.83 (s, 3H), 2.07 (s, 3H).

Example 267

N-(4-(3-(6-(Difluoromethyl)pyridin-2-yl)-7-methoxy-1H-pyrrolo[3,2-b]pyridin-2-yl)pyridin-2-yl)acetamide

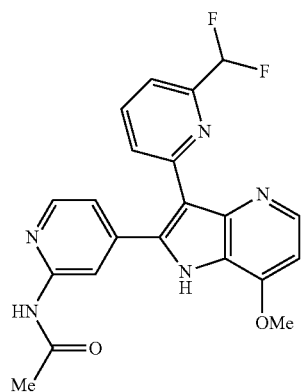 [SMILES: COc1ccnc2c(-c3cccc(C(F)F)n3)c(-c3ccnc(NC(C)=O)c3)[nH]c12]

Example 267 was prepared from 2-bromo-6-(difluoromethyl)pyridine by the general methods shown for Example 266. HPLC: RT=0.94 min (H$_2$O/ACN with 0.1% TFA, Waters Acquity UPLC BEH C18, 2.1×50 mm, 1.7-μm particles, gradient=3 min, wavelength=220 nm); MS (ES): m/z=410.2 [M+H]$^+$; $^1$H NMR (500 MHz, DMSO-d$_6$) δ ppm 10.72 (s, 1H), 8.65 (d, J=6.6 Hz, 1H), 8.43 (d, J=5.0 Hz, 1H), 8.34 (s, 1H), 7.98 (t, J=7.9 Hz, 1H), 7.66 (d, J=7.7 Hz, 1H), 7.54 (d, J=6.6 Hz, 1H), 7.40 (d, J=6.5 Hz, 1H), 7.28 (d, J=4.5 Hz, 1H), 7.23-6.97 (m, 1H), 4.27 (s, 3H), 2.09 (s, 3H).

Example 268

N-(4-(3-(5-Fluoropyridin-2-yl)-7-methoxy-1H-pyrrolo[3,2-b]pyridin-2-yl)pyridin-2-yl)acetamide

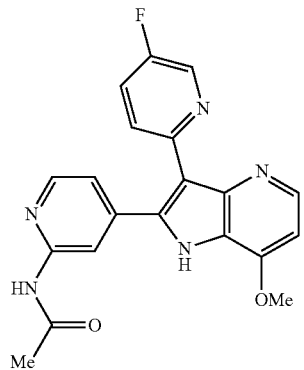

Example 268 was prepared from 2-bromo-5-fluoropyridine by the general methods shown for Example 266. HPLC: RT=0.80 min (H$_2$O/ACN with 0.1% TFA, Waters Acquity UPLC BEH C18, 2.1×50 mm, 1.7-μm particles, gradient=3 min, wavelength=220 nm); MS (ES): m/z=378.2 [M+H]$^+$; $^1$H NMR (500 MHz, DMSO-d$_6$) δ ppm 10.46 (s, 1H), 8.38 (d, J=2.9 Hz, 1H), 8.31 (d, J=5.3 Hz, 1H), 8.25 (d, J=5.1 Hz, 1H), 8.18 (br. s., 1H), 8.11 (dd, J=8.5, 4.6 Hz, 1H), 7.77 (td, J=8.8, 2.9 Hz, 1H), 7.16 (d, J=5.1 Hz, 1H), 6.91 (d, J=5.4 Hz, 1H), 4.03 (s, 3H), 2.06 (s, 3H).

Example 269

N-(4-(7-Methoxy-3-(6-methoxypyridin-3-yl)-1H-pyrrolo[3,2-b]pyridin-2-yl)pyridin-2-yl)acetamide

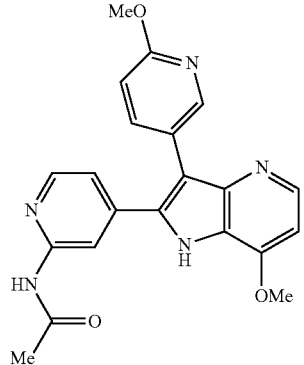

Example 269 was prepared from 5-bromo-2-methoxypyridine by the general methods shown for Example 266. HPLC: RT=0.76 min (H$_2$O/ACN with 0.1% TFA, Waters Acquity UPLC BEH C18, 2.1×50 mm, 1.7-μm particles, gradient=3 min, wavelength=220 nm); MS (ES): m/z=390.3 [M+H]$^+$; $^1$H NMR (500 MHz, DMSO-d$_6$) δ ppm 12.11 (s, 1H), 10.54 (s, 1H), 8.28 (dd, J=5.0, 2.7 Hz, 3H), 8.19 (d, J=2.0 Hz, 1H), 7.75 (dd, J=8.5, 2.3 Hz, 1H), 7.12 (d, J=6.1

Hz, 1H), 6.89 (d, J=5.4 Hz, 1H), 6.83 (d, J=8.5 Hz, 1H), 4.03 (s, 3H), 3.85 (s, 3H), 2.07 (s, 3H).

Example 270

N-(4-(3-(4-(Difluoromethyl)thiazol-2-yl)-7-methoxy-1H-pyrrolo[3,2-b]pyridin-2-yl)pyridin-2-yl)acetamide

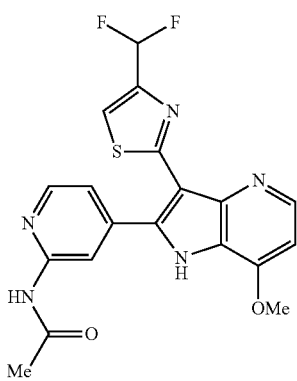 [SMILES: COc1ccnc2c(-c3nc(C(F)F)cs3)c(-c3ccnc(NC(C)=O)c3)[nH]c12]

Example 270 was prepared from 2-bromo-4-(difluoromethyl)thiazole by the general methods shown for Example 266. HPLC: RT=0.94 min (H₂O/ACN with 0.1% TFA, Waters Acquity UPLC BEH C18, 2.1×50 mm, 1.7-μm particles, gradient=3 min, wavelength=220 nm); MS (ES): m/z=416.0 [M+H]$^+$; $^1$H NMR (500 MHz, DMSO-d$_6$) δ ppm 12.59 (s, 1H), 10.56 (s, 2H), 8.50 (s, 2H), 8.44 (d, J=5.4 Hz, 2H), 8.35 (d, J=5.2 Hz, 2H), 8.04 (s, 2H), 7.46 (d, J=4.0 Hz, 2H), 7.00 (d, J=5.5 Hz, 2H), 7.12-6.80 (m, 2H), 4.06 (s, 3H), 2.10 (s, 3H).

Example 271

N-(4-(7-Chloro-3-(6-methoxypyridin-3-yl)-1H-pyrrolo[3,2-b]pyridin-2-yl)pyridin-2-yl)acetamide

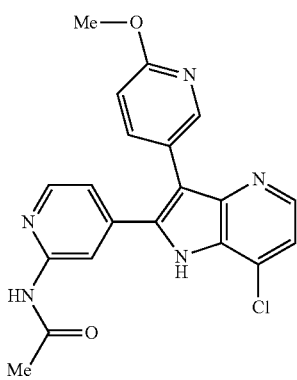 [SMILES: COc1ccc(-c2c(-c3ccnc(NC(C)=O)c3)[nH]c3c(Cl)ccnc23)cn1]

Example 271 was prepared from 6-methoxypyridin-3-ylboronic acid by the general methods shown for Example 266. HPLC: RT=0.57 min (H₂O/ACN with 0.1% TFA, Waters Acquity UPLC BEH C18, 2.1×50 mm, 1.7-μm particles, gradient=3 min, wavelength=220 nm); MS (ES): m/z=394.1[M+H]$^+$; $^1$H NMR (400 MHz, DMSO-d$_6$) δ ppm 12.38 (br. s., 1H), 10.59 (s, 1H), 8.36 (d, J=5.1 Hz, 1H), 8.35-8.28 (m, 2H), 8.25-8.15 (m, 1H), 7.76 (dd, J=8.6, 2.4 Hz, 1H), 7.41 (d, J=5.1 Hz, 1H), 7.16 (dd, J=5.3, 1.5 Hz, 1H), 6.85 (dd, J=8.6, 0.7 Hz, 1H), 3.87 (s, 3H), 2.09 (s, 3H)

Example 272

N-(4-(6-Bromo-3-(6-(difluoromethyl)pyridin-2-yl)-1H-pyrrolo[3,2-b]pyridin-2-yl)pyridin-2-yl)acetamide

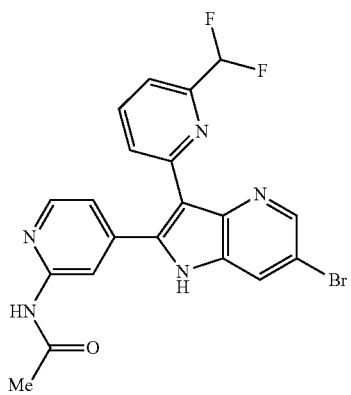 [SMILES: CC(=O)Nc1cc(-c2[nH]c3cc(Br)cnc3c2-c2cccc(C(F)F)n2)ccn1]

Example 272 was prepared from 2-bromo-6-(difluoromethyl)pyridine by the general methods shown for Example 1. HPLC: RT=0.75 min (H₂O/ACN with 0.1% TFA, Waters Acquity UPLC BEH C18, 2.1×50 mm, 1.7-μm particles, gradient=3 min, wavelength=220 nm); MS (ES): m/z=458, 460.1[M+H]$^+$; $^1$H NMR (400 MHz, DMSO-d$_6$) δ ppm 12.39 (s, 1H), 10.53 (s, 1H), 8.54 (d, J=2.2 Hz, 1H), 8.35 (s, 1H), 8.32-8.25 (m, 2H), 8.11 (d, J=2.0 Hz, 1H), 8.07 (t, J=7.9 Hz, 1H), 7.56 (d, J=7.7 Hz, 1H), 7.23 (dd, J=5.2, 1.7 Hz, 1H), 6.85-6.51 (m, 1H), 2.08 (s, 3H)

Example 273

N-(4-(3-(6-Fluoropyridin-2-yl)-7-methoxy-1H-pyrrolo[3,2-b]pyridin-2-yl)pyridin-2-yl)acetamide

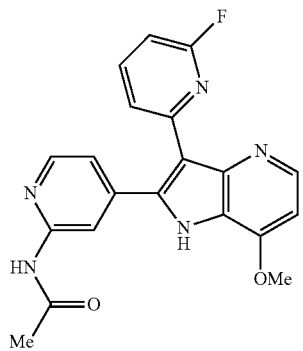

Example 273 was prepared from 2-bromo-6-fluoropyridine by the general methods shown for Example 266. HPLC: RT=0.80 min (H₂O/ACN with 0.1% TFA, Waters Acquity UPLC BEH C18, 2.1×50 mm, 1.7-μm particles, gradient=3 min, wavelength=220 nm); MS (ES): m/z=378.2 [M+H]$^+$; $^1$H NMR (500 MHz, DMSO-d$_6$) δ ppm 10.51 (s, 1H), 8.35 (d, J=5.3 Hz, 1H), 8.30 (d, J=5.1 Hz, 1H), 8.20 (s, 1H), 8.15

(d, J=5.7 Hz, 1H), 8.01 (q, J=8.1 Hz, 1H), 7.20 (d, J=5.1 Hz, 1H), 7.04-6.88 (m, 2H), 4.04 (s, 3H), 2.07 (s, 3H).

Example 274

N-(4-(7-(Hydroxymethyl)-3-(6-methoxypyridin-3-yl)-1H-pyrrolo[3,2-b]pyridin-2-yl)pyridin-2-yl)acetamide

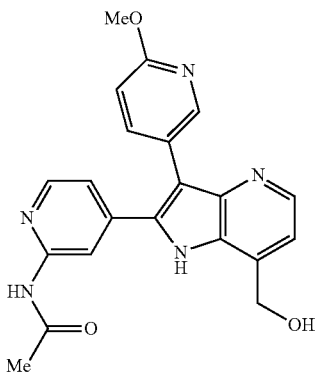 [SMILES: COc1ccc(-c2c(-c3ccnc(NC(C)=O)c3)[nH]c3c(CO)ccnc23)cn1]

274A) Ethyl 3-amino-2,6-dibromoisonicotinate

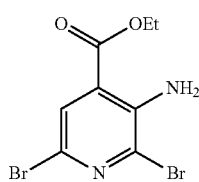 [SMILES: CCOC(=O)c1cc(Br)nc(Br)c1N]

To a solution of ethyl 3-aminoisonicotinate (7.0 g, 42.1 mmol) in DMF (40 mL) was added NBS (15.74 g, 88 mmol). The reaction mixture was stirred at room temperature for 20 h. The reaction mixture was diluted with saturated NaHCO₃ solution and ethyl acetate. The organic layer was separated and washed with saturated NaHCO₃ solution, dried over MgSO₄. The filtrate was concentrated in vacuo. The crude product was dissolved in DCM and purified by flash chromatography. The product was eluted with 0-15% ethyl acetate in hexane to give the desired product as a white solid (9.6 g, 70%); HPLC: RT=1.02 min (H₂O/ACN with 0.05% TFA, Waters Acquity SDS C18, 2.1×50 mm, 1.7-μm particles, gradient=1.8 min, wavelength=220 nm); MS (ES): m/z=278.9, 280.9 [M+H]⁺; ¹H NMR (400 MHz, CDCl₃) δ ppm 7.81 (s, 1H), 6.26 (br. s., 2H), 4.39 (q, J=7.0 Hz, 2H), 1.42 (t, J=7.2 Hz, 3H).

274B) Ethyl 2-((2-acetamidopyridin-4-yl)ethynyl)-3-amino-6-bromoisonicotinate

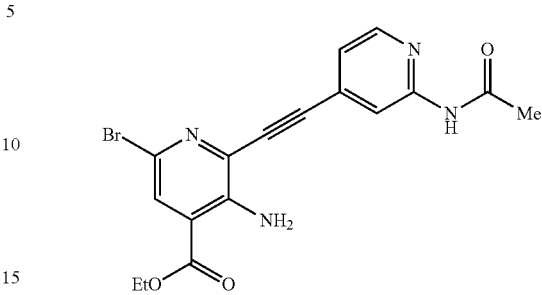

To a solution of ethyl 3-amino-2,6-dibromoisonicotinate (4.0 g, 12.35 mmol) and N-(4-ethynylpyridin-2-yl)acetamide (2.18 g, 13.6 mmol) in DMF (20 mL) were added CuI (0.19 g, 0.99 mmol) and TEA (17.21 mL, 123 mmol). The reaction mixture was purged with nitrogen stream for 3 min, followed by addition of Pd(PPh₃)₂Cl₂ (0.52 g, 0.74 mmol). The resulting mixture was heated at 80° C. for 2 h under nitrogen stream. The reaction mixture was cooled down and diluted with ethyl acetate and saturated NaHCO₃ solution. The ethyl acetate extracts (two times) were combined, washed with saturated NaHCO₃ solution, dried over MgSO₄. The filtrate was concentrated in vacuo. To the residue was added DCM, and the mixture was filtered to give light tan solid as the desired product (3.5 g). The filtrate was purified by flash chromatography. The product was eluted with 0-30% ethyl acetate in DCM to give the desired product as a yellow solid, total weight (4.0 g, 80%); HPLC: RT=0.92 min (H₂O/ACN with 0.05% TFA, Waters Acquity SDS C18, 2.1×50 mm, 1.7-μm particles, gradient=1.8 min, wavelength=220 nm); MS (ES): m/z=402.9, 404.9 [M+H]⁺; ¹H NMR (400 MHz, CDCl₃) δ ppm 8.37 (s, 1H), 8.29 (d, J=5.1 Hz, 1H), 8.01 (s, 1H), 7.85 (s, 1H), 7.20 (dd, J=5.2, 1.4 Hz, 1H), 6.36 (br. s., 2H), 4.41 (q, J=7.0 Hz, 2H), 2.24 (s, 3H), 1.43 (t, J=7.2 Hz, 3H).

274C) Ethyl 2-(2-acetamidopyridin-4-yl)-5-bromo-1H-pyrrolo[3,2-b]pyridine-7-carboxylate To a suspension of ethyl 2-((2-acetamidopyridin-4-yl)ethynyl)-3-amino-6-bromoisonicotinate (2.0 g, 4.96 mmol) and Cs₂CO₃ (2.42 g, 7.44 mmol) in CH₃CN (30 mL) was purged with nitrogen stream for 2 min, was added Pd(PPh₃)₄ (0.344 g, 0.298 mmol). The reaction mixture was heated at 95° C. for 2 h. The reaction mixture was diluted with ethyl acetate and filtered to give black filtrate. The solid on the funnel was washed with ethyl acetate. The total filtrate was concentrated in vacuo to give black solid. To the solid on the funnel was added water. The mixture was stirred with a spatula and filtered to give black solid 2, dried on high vacuum. The black solid 2 was mixed with THF+MeOH, sonicated and filtered. The filtrate was concentrated in vacuo to give black solid 3 as the desired product of ethyl and methyl ester mixture (1.0 g, 50%); HPLC: RT=0.80 min (H₂O/ACN with 0.05% TFA, Waters Acquity SDS C18, 2.1×50 mm, particles, gradient=1.8 min, wavelength=220 nm); MS (ES): m/z=403.0, 405.0 [M+H]⁺; ¹H NMR (400 MHz, DMSO-d₆) δ ppm 11.70 (s, 1H), 10.62 (s, 1H), 8.55 (s, 1H), 8.43 (d, J=5.3 Hz, 1H), 7.76-7.62 (m, 2H), 7.25 (s, 1H), 4.49 (q, J=7.2 Hz, 2H), 2.14 (s, 3H), 1.43 (t, J=7.2 Hz, 3H).

274D) Methyl 2-(2-acetamidopyridin-4-yl)-1H-pyrrolo[3,2-b]pyridine-7-carboxylate

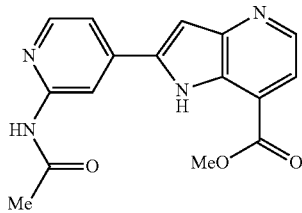 [SMILES: COC(=O)c1ccnc2cc(-c3ccnc(NC(C)=O)c3)[nH]c12]

To the reaction mixture of methyl 2-(2-acetamidopyridin-4-yl)-5-bromo-1H-pyrrolo[3,2-b]pyridine-7-carboxylate (110 mg, 0.283 mmol) in MeOH (8 mL) and THF (4 mL) was added Pd—C (20 mg, 0.028 mmol) and the mixture was sonicated, evacuated, then hydrogenated with hydrogen balloon for 4 h. The reaction mixture was filtered and the filtrate was concentrated in vacuo. The residue was extracted with CHCl₃:2-propanol (2.5:1). The organic layer was washed with saturated NaHCO₃ solution, dried over MgSO₄. The filtrate was concentrated in vacuo to give yellow solid as the desired product (60 mg, 68%); HPLC: RT=0.51 min (H₂O/ACN with 0.05% TFA, Waters Acquity SDS C18, 2.1×50 mm, 1.7-μm particles, gradient=1.8 min, wavelength=220 nm); MS (ES): m/z=311.0 [M+H]⁺; ¹H NMR (400 MHz, DMSO-d₆) δ ppm 11.44 (s, 1H), 10.60 (s, 1H), 8.60-8.51 (m, 2H), 8.42 (d, J=5.3 Hz, 1H), 7.69 (dd, 1.5 Hz, 1H), 7.64 (d, J=4.8 Hz, 1H), 7.25 (d, J=2.0 Hz, 1H), 4.07-4.00 (m, 3H), 2.15 (s, 3H).

274E) N-(4-(7-(Hydroxymethyl)-1H-pyrrolo[3,2-b]pyridin-2-yl)pyridin-2-yl)acetamide

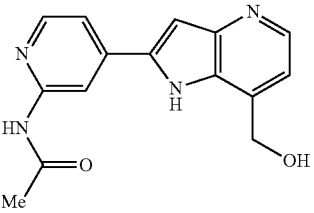 [SMILES: CC(=O)Nc1cc(-c2cc3nccc(CO)c3[nH]2)ccn1]

To a solution of methyl 2-(2-acetamidopyridin-4-yl)-1H-pyrrolo[3,2-b]pyridine-7-carboxylate (0.6 g, 1.93 mmol) in MeOH (15 mL) and THF (15 mL) was added LiBr (0.34 g, 3.87 mmol) and NaBH₄ (0.37 g, 9.67 mmol) in several batches. The reaction mixture was stirred at room temperature for 3 h. The reaction mixture was concentrated in vacuo. The residue was extracted with CHCl₃:2-propanol (2:1). The organic layer was washed with saturated NaHCO₃ solution, dried over MgSO₄, concentrated in vacuo to give the desired product as a yellow solid (0.28 g, 51%). HPLC: RT=0.44 min (H₂O/ACN with 0.05% TFA, Waters Acquity SDS C18, 2.1×50 mm, 1.7-μm particles, gradient=1.8 min, wavelength=220 nm); MS (ES): m/z=283.1 [M+H]⁺; ¹H NMR (400 MHz, MeOH-d₄) δ ppm 8.58 (d, J=5.9 Hz, 1H), 8.48 (d, J=5.3 Hz, 1H), 7.84 (d, J=6.2 Hz, 1H), 7.70 (dd, J=5.4, 1.7 Hz, 1H), 7.37 (s, 1H), 5.27 (s, 2H), 2.25 (s, 3H).

274F) N-(4-(7-(Hydroxymethyl)-3-iodo-1H-pyrrolo[3,2-b]pyridin-2-yl)pyridin-2-yl)acetamide

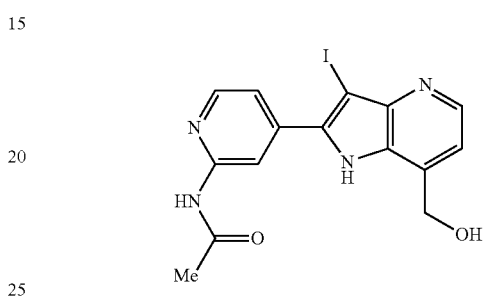

To a solution of N-(4-(7-(hydroxymethyl)-1H-pyrrolo[3,2-b]pyridin-2-yl)pyridin-2-yl)acetamide (25 mg, 0.089 mmol) in DMF (1 mL) was added NIS (22 mg, 0.097 mmol). The reaction mixture was stirred at room temperature for 1 h. The reaction mixture was purified by preparative HPLC. Fractions containing the desired product were combined, concentrated, and lyophilized to give the desired product as a yellow solid (13 mg, 36%); HPLC: RT=0.48 min (H₂O/ACN with 0.05% TFA, Waters Acquity SDS C18, 2.1×50 mm, 1.7-μm particles, gradient=1.8 min, wavelength=220 nm); MS (ES): m/z=408.8 [M+H]⁺; ¹H NMR (400 MHz, MeOH-d₄) δ ppm 8.64 (s, 1H), 8.60 (d, J=6.2 Hz, 1H), 8.52 (d, J=5.3 Hz, 1H), 7.89 (d, J=6.2 Hz, 1H), 7.59 (dd, J=5.2, 1.7 Hz, 1H), 5.23 (s, 2H), 2.24 (s, 3H).

Example 274 N-(4-(7-(Hydroxymethyl)-3-(6-methoxypyridin-3-yl)-1H-pyrrolo[3,2-b]pyridin-2-yl)pyridin-2-yl)acetamide The suspension of N-(4-(7-(hydroxymethyl)-3-iodo-1H-pyrrolo[3,2-b]pyridin-2-yl)pyridin-2-yl)acetamide (60 mg, 0.147 mmol) and (6-methoxypyridin-3-yl)boronic acid (27.0 mg, 0.176 mmol) in dioxane (2 mL) and aqueous Na₂CO₃ solution (0.37 mL, 0.37 mmol) was purged with nitrogen stream for 3 min, followed by addition of PdCl₂(dppf) (10.8 mg, 0.015 mmol). The resulting mixture was heated at 90° C. for 2 h. The reaction mixture was concentrated in vacuo. The residue was purified by preparative HPLC. Fractions containing the desired product were combined, concentrated, and lyophilized to give the desired product as a yellow solid (23 mg, 39%); HPLC: RT=0.71 min (H₂O/ACN with 0.1% TFA, Waters Acquity UPLC BEH C18, 2.1×50 mm, 1.7-μm particles, gradient=3 min, wavelength=220 nm); MS (ES): m/z=390.1 [M+H]⁺; ¹H NMR (500 MHz, DMSO-d₆) δ ppm 11.75 (s, 1H), 10.58 (s, 1H), 8.38 (d, J=4.6 Hz, 1H), 8.31 (d, J=5.1 Hz, 1H), 8.28 (s, 1H), 8.21 (d, J=1.9 Hz, 1H), 7.77 (dd, J=8.5, 2.3 Hz, 1H), 7.28 (d, J=4.5 Hz, 1H), 7.12 (d, J=4.0 Hz, 1H), 6.85 (d, J=8.5 Hz, 1H), 5.55 (t, J=5.7 Hz, 1H), 4.90 (d, J=5.6 Hz, 2H), 3.86 (s, 3H), 2.08 (s, 3H).

Example 275

N-(4-(3-(6-Fluoropyridin-2-yl)-7-(hydroxymethyl)-1H-pyrrolo[3,2-b]pyridin-2-yl)pyridin-2-yl)acetamide

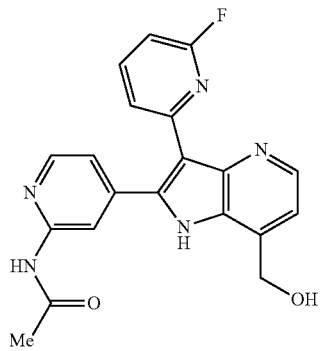 [SMILES: CC(=O)Nc1cc(-c2[nH]c3c(CO)ccnc3c2-c2cccc(F)n2)ccn1]

Example 275 was prepared from 2-bromo-6-fluoropyridine by the general methods shown for Example 274. HPLC: RT=0.72 min (H$_2$O/ACN with 0.1% TFA, Waters Acquity UPLC BEH C18, 2.1×50 mm, 1.7-μm particles, gradient=3 min, wavelength=220 nm); MS (ES): m/z=377.9 [M+H]$^+$; $^1$H NMR (500 MHz, DMSO-d$_6$) δ ppm 10.57 (s, 1H), 8.46 (d, J=4.7 Hz, 1H), 8.34 (d, J=5.1 Hz, 1H), 8.24 (d, J=4.2 Hz, 2H), 8.03 (q, J=8.1 Hz, 1H), 7.32 (d, J=4.6 Hz, 1H), 7.22 (d, J=5.1 Hz, 1H), 6.97 (dd, J=8.1, 2.4 Hz, 1H), 4.91 (s, 2H), 2.08 (s, 3H).

Example 276

N-(4-(3-(6-Chloropyridin-2-yl)-7-(hydroxymethyl)-1H-pyrrolo[3,2-b]pyridin-2-yl)pyridin-2-yl)acetamide

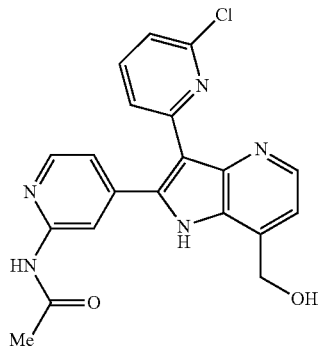 [SMILES: CC(=O)Nc1cc(-c2[nH]c3c(CO)ccnc3c2-c2cccc(Cl)n2)ccn1]

Example 276 was prepared from 2-bromo-6-chloropyridine by the general methods shown for Example 274. HPLC: RT=0.80 min (H$_2$O/ACN with 0.1% TFA, Waters Acquity UPLC BEH C18, 2.1×50 mm, 1.7-μm particles, gradient=3 min, wavelength=220 nm); MS (ES): m/z=394.1 [M+H]$^+$; $^1$H NMR (500 MHz, DMSO-d$_6$) δ ppm 10.59 (s, 1H), 8.49 (d, J=4.8 Hz, 1H), 8.35 (d, J=5.1 Hz, 1H), 8.28 (s, 1H), 8.22 (d, J=6.9 Hz, 1H), 7.90 (t, J=7.8 Hz, 1H), 7.38 (d, J=4.6 Hz, 1H), 7.33 (d, J=7.8 Hz, 1H), 7.23 (d, J=5.1 Hz, 1H), 4.94 (s, 2H), 2.09 (s, 3H).

Example 277

N-(4-(3-(6-Fluoropyridin-3-yl)-7-(hydroxymethyl)-1H-pyrrolo[3,2-b]pyridin-2-yl)pyridin-2-yl)acetamide

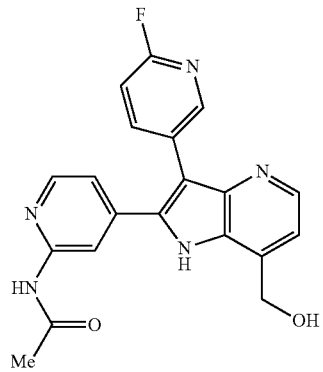 [SMILES: CC(=O)Nc1cc(-c2[nH]c3c(CO)ccnc3c2-c2ccc(F)nc2)ccn1]

Example 277 was prepared from 5-bromo-2-fluoropyridine by the general methods shown for Example 274. HPLC: RT=0.63 min (H$_2$O/ACN with 0.1% TFA, Waters Acquity UPLC BEH C18, 2.1×50 mm, 1.7-μm particles, gradient=3 min, wavelength=220 nm); MS (ES): m/z=378.2 [M+H]$^+$; $^1$H NMR (500 MHz, DMSO-d$_6$) δ ppm 10.61 (s, 1H), 8.45-8.33 (m, 2H), 8.27 (br. s., 2H), 8.13-7.99 (m, 1H), 7.31 (d, J=4.5 Hz, 1H), 7.25-7.12 (m, 2H), 4.92 (s, 2H), 2.08 (s, 3H).

Example 278

N-(4-(3-(6-Chloropyridin-3-yl)-7-(hydroxymethyl)-1H-pyrrolo[3,2-b]pyridin-2-yl)pyridin-2-yl)acetamide

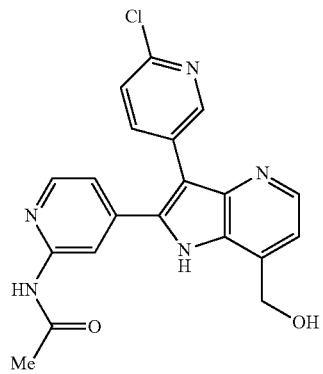 [SMILES: CC(=O)Nc1cc(-c2[nH]c3c(CO)ccnc3c2-c2ccc(Cl)nc2)ccn1]

Example 278 was prepared from 5-bromo-2-chloropyridine by the general methods shown for Example 274. HPLC: RT=0.71 min (H$_2$O/ACN with 0.1% TFA, Waters Acquity UPLC BEH C18, 2.1×50 mm, 1.7-μm particles, gradient=3 min, wavelength=220 nm); MS (ES): m/z=394.1 [M+H]$^+$; $^1$H NMR (500 MHz, DMSO-d$_6$) δ ppm 13.01 (br. s., 1H), 10.70 (s, 1H), 8.60 (d, J=5.6 Hz, 1H), 8.47 (d, J=2.1 Hz, 1H), 8.40 (d, J=5.0 Hz, 1H), 8.26 (s, 1H), 7.92 (dd, J=8.2, 2.3 Hz, 1H), 7.68 (d, J=5.4 Hz, 1H), 7.61 (d, J=8.2 Hz, 1H), 7.17 (d, J=3.5 Hz, 1H), 5.10 (s, 2H), 2.08 (s, 3H).

Example 279

N-(4-(7-(Hydroxymethyl)-3-(6-methylpyridin-2-yl)-1H-pyrrolo[3,2-b]pyridin-2-yl)pyridin-2-yl)acetamide

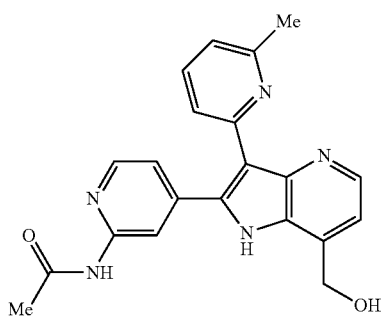 [SMILES: CC(=O)Nc1cc(-c2[nH]c3c(CO)ccnc3c2-c2cccc(C)n2)ccn1]

Example 279 was prepared from 2-bromo-6-methylpyridine by the general methods shown for Example 274. HPLC: RT=0.58 min (H$_2$O/ACN with 0.1% TFA, Waters Acquity UPLC BEH C18, 2.1×50 mm, 1.7-μm particles, gradient=3 min, wavelength=220 nm); MS (ES): m/z=374.2 [M+H]$^+$.

Example 280

N-(4-(7-(Hydroxymethyl)-3-(6-methylpyridin-3-yl)-1H-pyrrolo[3,2-b]pyridin-2-yl)pyridin-2-yl)acetamide

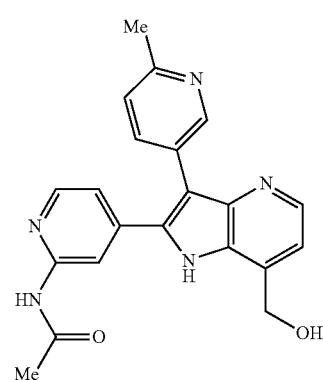 [SMILES: CC(=O)Nc1cc(-c2[nH]c3c(CO)ccnc3c2-c2ccc(C)nc2)ccn1]

Example 280 was prepared from 5-bromo-2-methylpyridine by the general methods shown for Example 274. HPLC: RT=0.47 min (H$_2$O/ACN with 0.1% TFA, Waters Acquity UPLC BEH C18, 2.1×50 mm, 1.7-μm particles, gradient=3 min, wavelength=220 nm); MS (ES): m/z=374.2 [M+H]$^+$; $^1$H NMR (500 MHz, DMSO-d$_6$) δ ppm 10.66 (s, 1H), 8.68 (br. s., 1H), 8.48 (d, J=4.9 Hz, 1H), 8.36 (d, J=5.0 Hz, 1H), 8.27 (br. s., 1H), 8.03 (br. s., 1H), 7.54 (d, J=8.2 Hz, 1H), 7.45 (br. s., 1H), 7.16 (d, J=4.5 Hz, 1H), 4.98 (s, 2H), 2.59 (s, 3H), 2.08 (s, 3H).

Example 281

N-(4-(3-(6-(Difluoromethyl)pyridin-2-yl)-1H-pyrrolo[3,2-b]pyridin-2-yl)pyridin-2-yl)acetamide

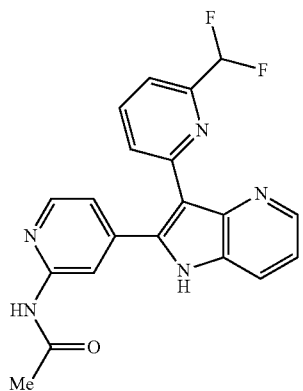 [SMILES: CC(=O)Nc1cc(-c2[nH]c3cccnc3c2-c2cccc(C(F)F)n2)ccn1]

Example 281 was prepared from Example 1D and 2-bromo-6-(difluoromethyl)pyridine by the general methods shown for Example 1. HPLC: RT=0.83 min (H$_2$O/ACN with 0.1% TFA, Waters Acquity UPLC BEH C18, 2.1×50 mm, 1.7-μm particles, gradient=3 min, wavelength=220 nm); MS (ES): m/z=380 [M+H]$^+$; $^1$H NMR (500 MHz, DMSO-d$_6$) δ ppm 10.56 (s, 1H), 8.49 (d, J=4.3 Hz, 1H), 8.44-8.26 (m, 3H), 8.07 (t, J=7.8 Hz, 1H), 7.93 (d, J=8.1 Hz, 1H), 7.55 (d, J=7.7 Hz, 1H), 7.38-7.22 (m, 2H), 6.84-6.48 (m, 1H), 2.09 (s, 3H)

Example 282

N-(4-(3-(6-(Difluoromethyl)pyridin-2-yl)-6-methoxy-1H-pyrrolo[3,2-b]pyridin-2-yl)pyridin-2-yl)acetamide

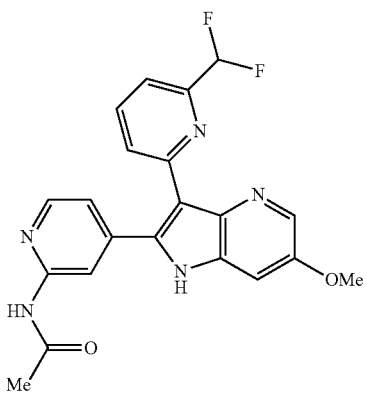 [SMILES: COc1cnc2c(-c3cccc(C(F)F)n3)c(-c3ccnc(NC(C)=O)c3)[nH]c2c1]

282A): N-(4-((3-Amino-5-methoxypyridin-2-yl)ethynyl)pyridin-2-yl)acetamide

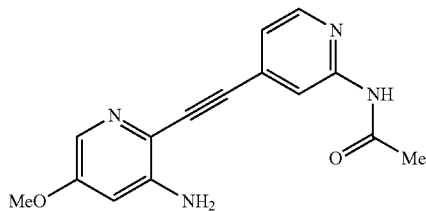 [SMILES: COc1cnc(C#Cc2ccnc(NC(C)=O)c2)c(N)c1]

Example 282A was prepared from Example 1B and 2-bromo-5-methoxypyridin-3-amine by similar methods as shown for Example 1C. HPLC: RT=0.80 min (H$_2$O/ACN with 0.1% TFA, Waters Acquity UPLC BEH C18, 2.0×50 mm, 1.7-μm particles, gradient=2 min, wavelength=220 nm); MS (ES): m/z=283 [M+H]$^+$.

282B): N-(2-((2-Acetamidopyridin-4-yl)ethynyl)-5-methoxypyridin-3-yl)-2,2,2-trifluoroacetamide

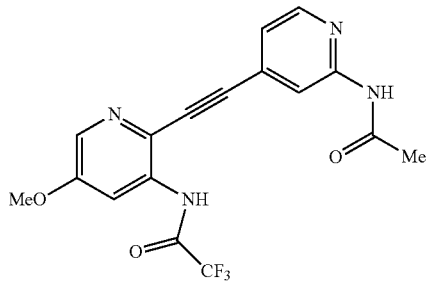

Example 282B was prepared from Example 282A by methods similar to those shown for Example 1D. HPLC: RT=0.97 min (H$_2$O/ACN with 0.1% TFA, Waters Acquity UPLC BEH C18, 2.0×50 mm, 1.7-μm particles, gradient=2 min, wavelength=220 nm); MS (ES): m/z=379 [M+H]$^+$.

Example 282 was prepared from Example 282B and 2-bromo-6-(difluoromethyl)pyridine by the general methods shown for Example 1. HPLC: RT=0.94 min (H$_2$O/ACN with 0.1% TFA, Waters Acquity UPLC BEH C18, 2.1×50 mm, 1.7-μm particles, gradient=3 min, wavelength=220 nm); MS (ES): m/z=410 [M+H]$^+$; $^1$H NMR (500 MHz, DMSO-d$_6$) δ ppm 10.65 (s, 1H), 8.46-8.24 (m, 4H), 8.14 (br. s., 1H), 8.09-7.99 (m, 1H), 7.79-7.49 (m, 3H), 7.25 (d, J=4.9 Hz, 2H), 6.97-6.56 (m, 2H), 3.94 (s, 3H), 2.09 (s, 3H)

Example 283

N-(4-(6-Methoxy-3-(6-methylpyridin-2-yl)-1H-pyrrolo[3,2-b]pyridin-2-yl)pyridin-2-yl)acetamide

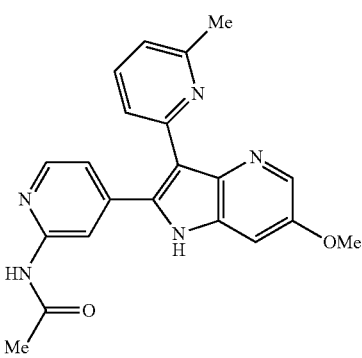 [SMILES: COc1cnc2c(-c3cccc(C)n3)c(-c3ccnc(NC(C)=O)c3)[nH]c2c1]

Example 283 was prepared from Example 282B and 2-bromo-6-methylpyridine by the general methods shown for Example 1. HPLC: RT=0.74 min (H$_2$O/ACN with 0.1% TFA, Waters Acquity UPLC BEH C18, 2.1×50 mm, 1.7-μm particles, gradient=3 min, wavelength=220 nm); MS (ES): m/z=374 [M+H]$^+$; $^1$H NMR (500 MHz, DMSO-d$_6$) δ ppm 10.67 (s, 1H), 8.42 (d, J=5.0 Hz, 1H), 8.38-8.26 (m, 2H), 8.19 (br. s., 1H), 7.84 (d, J=7.9 Hz, 1H), 7.71 (d, J=6.8 Hz, 1H), 7.53 (s, 1H), 7.30 (d, J=4.7 Hz, 1H), 3.94 (s, 3H), 2.66 (s, 3H), 2.08 (s, 3H)

Example 284

N-(4-(6-Methoxy-3-(5-methoxypyridin-2-yl)-1H-pyrrolo[3,2-b]pyridin-2-yl)pyridin-2-yl)acetamide

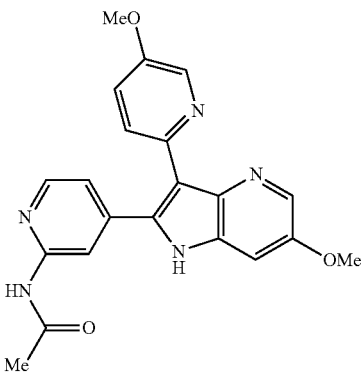 [SMILES: COc1ccc(-c2c(-c3ccnc(NC(C)=O)c3)[nH]c3cc(OC)cnc23)nc1]

Example 284 was prepared from Example 282B and 2-bromo-5-methoxypyridine by the general methods shown for Example 1. HPLC: RT=0.82 min (H$_2$O/ACN with 0.1% TFA, Waters Acquity UPLC BEH C18, 2.1×50 mm, 1.7-μm particles, gradient=3 min, wavelength=220 nm); MS (ES): m/z=390 [M+H]$^+$; $^1$H NMR (500 MHz, DMSO-d$_6$) δ ppm 11.81 (br. s., 1H), 10.51 (br. s., 1H), 8.40-8.07 (m, 4H), 7.95 (d, J=4.8 Hz, 1H), 7.49 (br. s., 1H), 7.35 (br. s., 1H), 7.11 (br. s., 1H), 3.99-3.76 (m, 6H), 2.09 (br. s., 3H)

Example 285

N-(4-(6-Methoxy-3-(6-methoxypyridin-3-yl)-1H-pyrrolo[3,2-b]pyridin-2-yl)pyridin-2-yl)acetamide

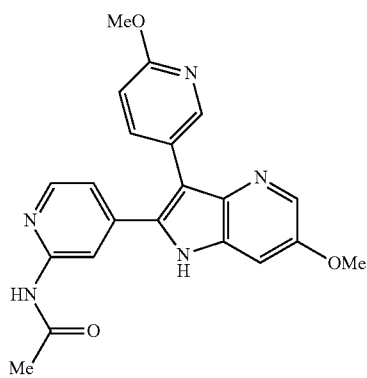 [SMILES: COc1cnc2c(-c3ccc(OC)nc3)c(-c3ccnc(NC(C)=O)c3)[nH]c2c1]

285A): N-(4-(6-Methoxy-1H-pyrrolo[3,2-b]pyridin-2-yl)pyridin-2-yl)acetamide

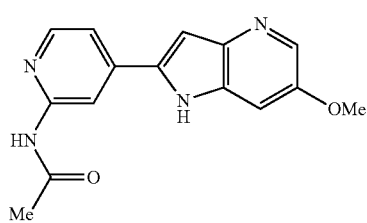 [SMILES: COc1cnc2cc(-c3ccnc(NC(C)=O)c3)[nH]c2c1]

To a solution of 282A in THF (4 mL) was added 1M potassium tert-butoxide in THF (2.1 mL, 2.1 mmol). The mixture was heated to 70° C. and stirred for 2.5 h, then cooled to room temperature. The semi-solid was dissolved in MeOH, and dry loaded on celite, and then purified by silica gel chromatography (24 g, MeOH/DCM=0-10%) to give 285A (187 mg, 94%). HPLC: RT=0.82 min (H$_2$O/ACN with 0.1% TFA, Waters Acquity UPLC BEH C18, 2.0×50 mm, 1.7-μm particles, gradient=2 min, wavelength=220 nm); MS (ES): m/z=283 [M+H]$^+$; $^1$H NMR (400 MHz, DMSO-d$_6$) δ ppm 11.84 (s, 1H), 10.53 (s, 1H), 8.46 (s, 1H), 8.35 (dd, J=5.3, 0.7 Hz, 1H), 8.15 (d, J=2.6 Hz, 1H), 7.54 (dd, J=5.3, 1.5 Hz, 1H), 7.33-7.26 (m, 1H), 7.11 (d, J=1.5 Hz, 1H), 3.87 (s, 3H), 2.15 (s, 3H).

285B): N-(4-(3-Bromo-6-methoxy-1H-pyrrolo[3,2-b]pyridin-2-yl)pyridin-2-yl)acetamide

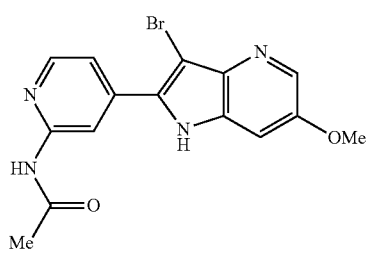 [SMILES: COc1cnc2c(Br)c(-c3ccnc(NC(C)=O)c3)[nH]c2c1]

Example 285B was prepared from Example 285A by the general methods shown for Example 14B. HPLC: RT=0.84 min (H$_2$O/ACN with 0.1% TFA, Waters Acquity UPLC BEH C18, 2.0×50 mm, 1.7-μm particles, gradient=2 min, wavelength=220 nm); MS (ES): m/z=361 [M+H]$^+$; $^1$H NMR (400 MHz, DMSO-d$_6$) δ ppm 12.10 (s, 1H), 10.62 (s, 1H), 8.73 (s, 1H), 8.49-8.39 (m, 1H), 8.23 (d, J=2.4 Hz, 1H), 7.57 (dd, 1.8 Hz, 1H), 7.33 (d, J=2.4 Hz, 1H), 3.90 (s, 3H), 2.15 (s, 3H)

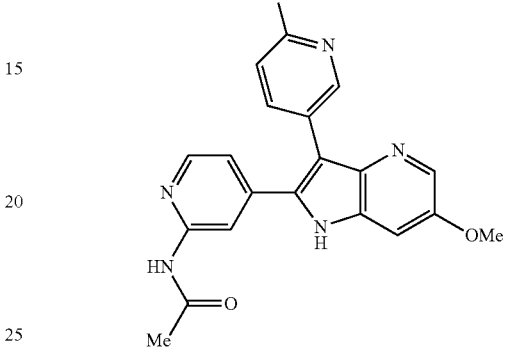

Example 285 was prepared from Example 285B and (6-methoxypyridin-3-yl)boronic acid by the general methods shown for Example 14. HPLC: RT=1.19 min (H$_2$O/CAN with 10 mM ammonium acetate, Waters Acquity UPLC BEH C18, 2.0×50 mm, 1.7-μm particles, gradient=3 min, wavelength=220 nm); MS (ES): m/z=390 [M+H]$^+$; $^1$H NMR (500 MHz, DMSO-d$_6$) δ ppm 11.86 (s, 1H), 10.56 (s, 1H), 8.29 (d, J=5.0 Hz, 2H), 8.23 (s, 1H), 8.17 (s, 1H), 7.77 (d, J=8.5 Hz, 1H), 7.36 (s, 1H), 7.09 (d, J=5.1 Hz, 1H), 6.86 (d, J=8.5 Hz, 1H), 3.88 (br. s., 3H), 3.87 (br. s., 3H), 2.09 (s, 3H)

Example 286

N-(4-(3-(6-Methoxypyridin-3-yl)-1H-pyrrolo[3,2-b]pyridin-2-yl)pyridin-2-yl)-2-morpholinoacetamide

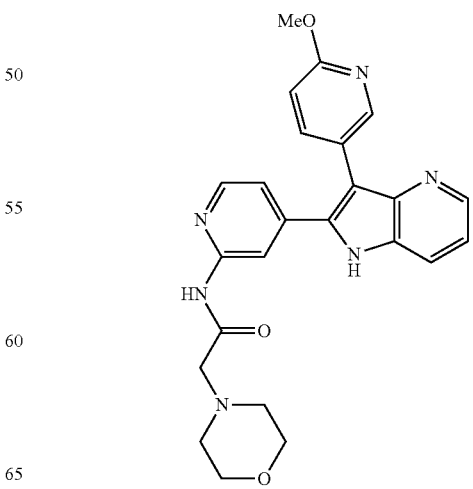

286A): 2-Chloro-N-(4-(3-(6-methoxypyridin-3-yl)-1H-pyrrolo[3,2-b]pyridin-2-yl)pyridin-2-yl)acetamide

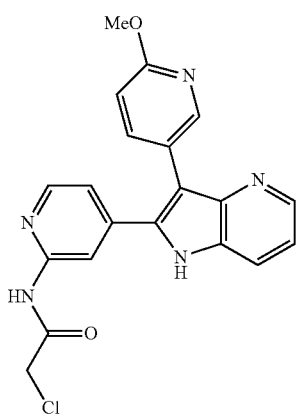 [SMILES: COc1ccc(-c2c(-c3ccnc(NC(=O)CCl)c3)[nH]c3cccnc23)cn1]

Example 286A was prepared from Example 52 by the general methods shown for Example 74A. HPLC: RT=0.87 min (H₂O/CAN with 0.1% TFA, Waters Acquity UPLC BEH C18, 2.0×50 mm, 1.7-μm particles, gradient=2 min, wavelength=220 nm); MS (ES): m/z=394 [M+H]⁺.

N-(4-(3-(6-Methoxypyridin-3-yl)-1H-pyrrolo[3,2-b]pyridin-2-yl)pyridin-2-yl)-2-morpholinoacetamide

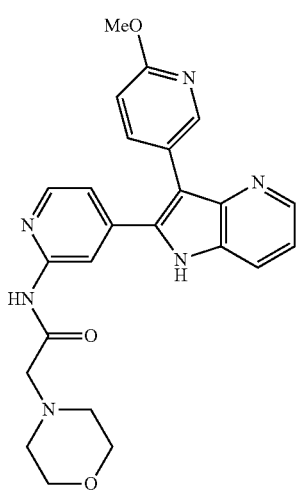 [SMILES: COc1ccc(-c2c(-c3ccnc(NC(=O)CN4CCOCC4)c3)[nH]c3cccnc23)cn1]

A mixture of 286A (30 mg, 0.076 mmol), morpholine (19.91 mg, 0.229 mmol) and K₂CO₃ (31.6 mg, 0.229 mmol) in DMF (0.5 mL) was stirred at room temperature for 3. h. Diluted with EtOAc, the resulting mixture was filtered through celite, and eluted with 10% MeOH/DCM. The filtrate was concentrated. The residue was purified by preparative HPLC (Column: Waters XBridge C18, 19×200 mm, 5-μm particles; Mobile Phase A: 5:95 acetonitrile: water with 10 mM ammonium acetate; Mobile Phase B: 95:5 acetonitrile: water with 10-mM ammonium acetate; Gradient: 10-60% B over 15 minutes, then a 5 minute hold at 100% B; Flow: 20 mL/min.) to give Example 286 (19.6 mg, 58%). HPLC: RT=0.62 min (H₂O/CAN with 0.1% TFA, Waters Acquity UPLC BEH C18, 2.1×50 mm, 1.7-μm particles, gradient=3 min, wavelength=220 nm); MS (ES): m/z=445 [M+H]⁺; ¹H NMR (500 MHz, DMSO-d₆) δ ppm 12.08 (br. s., 1H), 10.12 (s, 1H), 8.50-8.30 (m, 4H), 8.25 (br. s., 1H), 7.88 (d, J=8.2 Hz, 1H), 7.80 (d, J=8.5 Hz, 1H), 7.26 (dd, J=7.8, 4.5 Hz, 1H), 7.18 (d, J=4.8 Hz, 1H), 6.87 (d, J=8.4 Hz, 1H), 3.88 (s, 3H), 3.63 (br. s., 3H), 3.44 (br. s., 4H), 3.20 (s, 2H)

Example 287

N-(4-(3-(6-Methoxypyridin-3-yl)-1H-pyrrolo[3,2-b]pyridin-2-yl)pyridin-2-yl)-2-(4-methylpiperazin-1-yl)acetamide

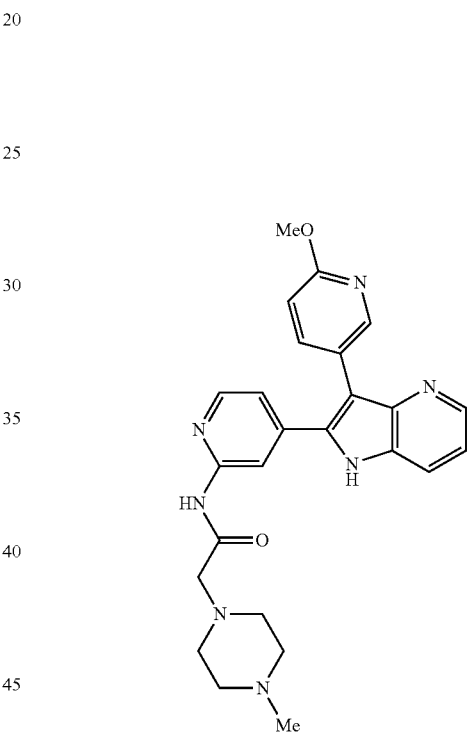

Example 287 was prepared from Example 286A and 1-methylpiperazine by the general methods shown for Example 286. HPLC: RT=0.59 min (H₂O/ACN with 0.1% TFA, Waters Acquity UPLC BEH C18, 2.1×50 mm, 1.7-μm particles, gradient=3 min, wavelength=220 nm); MS (ES): m/z=458 [M+H]⁺; ¹H NMR (500 MHz, DMSO-d₆) δ ppm 10.04 (s, 1H), 8.50-8.31 (m, 3H), 8.26 (s, 1H), 7.88 (d, J=8.2 Hz, 1H), 7.84-7.74 (m, 1H), 7.26 (dd, J=8.1, 4.5 Hz, 1H), 7.18 (d, J=5.0 Hz, 1H), 6.87 (d, J=8.5 Hz, 1H), 3.88 (s, 3H), 2.53-2.36 (m, 10H), 2.21 (s, 3H)

Example 288

2-(4-(2-Hydroxyethyl)piperazin-1-yl)-N-(4-(3-(6-methoxypyridin-3-yl)-1H-pyrrolo[3,2-b]pyridin-2-yl)pyridin-2-yl)acetamide

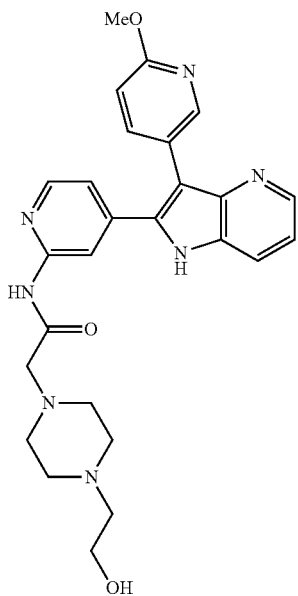 [SMILES: COc1ccc(-c2c(-c3ccnc(NC(=O)CN4CCN(CCO)CC4)c3)[nH]c3cccnc23)cn1]

Example 288 was prepared from Example 286A and 2-(piperazin-1-yl)ethanol by the general methods shown for Example 286. HPLC: RT=0.62 min (H$_2$O/ACN with 0.1% TFA, Waters Acquity UPLC BEH C18, 2.1×50 mm, 1.7-μm particles, gradient=3 min, wavelength=220 nm); MS (ES): m/z=488 [M+H]$^+$; $^1$H NMR (500 MHz, DMSO-d$_6$) δ ppm 8.41 (d, J=4.0 Hz, 1H), 8.37-8.30 (m, 2H), 8.24 (s, 1H), 7.88 (d, J=7.9 Hz, 1H), 7.83-7.70 (m, 1H), 7.26 (dd, J=8.1, 4.5 Hz, 1H), 7.18 (d, J=5.5 Hz, 1H), 6.87 (d, J=8.5 Hz, 1H), 3.88 (s, 3H), 3.51 (br. s., 2H), 2.51 (br. s., 12H), 1.91 (s, 2H)

Example 289

4-(6-Chloro-3-(6-methoxypyridin-3-yl)-1H-pyrrolo[3,2-b]pyridin-2-yl)pyridin-2-amine

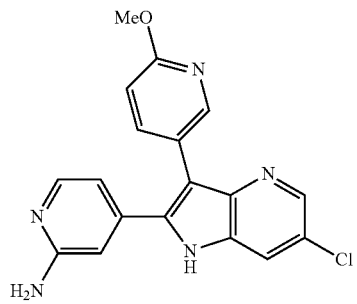 [SMILES: COc1ccc(-c2c(-c3ccnc(N)c3)[nH]c3cc(Cl)cnc23)cn1]

Example 289 was prepared from Example 43 by the general methods shown for Example 14. HPLC: RT=0.91 min (H$_2$O/CAN with 0.1% TFA, Waters Acquity UPLC BEH C18, 2.0×50 mm, 1.7-μm particles, gradient=2 min, wavelength=220 nm); MS (ES): m/z=352 [M+H]$^+$; $^1$H NMR (400 MHz, DMSO-d$_6$) δ ppm 12.07 (s, 1H), 8.39 (d, J=2.2 Hz, 1H), 8.28 (d, J=1.8 Hz, 1H), 7.96 (d, J=5.3 Hz, 1H), 7.89 (d, J=2.2 Hz, 1H), 7.79 (dd, J=8.6, 2.4 Hz, 1H), 6.88 (d, J=8.6 Hz, 1H), 6.62-6.50 (m, 2H), 6.09 (s, 2H), 3.89 (s, 3H).

Example 290

N-(4-(6-Chloro-3-(6-methoxypyridin-3-yl)-1H-pyrrolo[3,2-b]pyridin-2-yl)pyridin-2-yl)-2-morpholinoacetamide

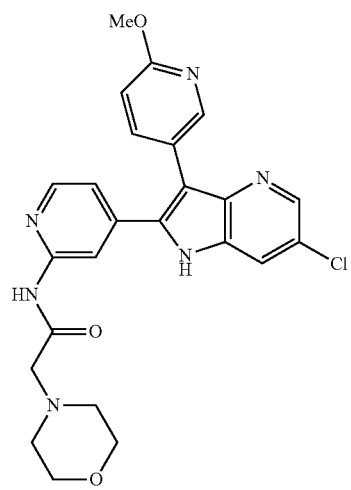 [SMILES: COc1ccc(-c2c(-c3ccnc(NC(=O)CN4CCOCC4)c3)[nH]c3cc(Cl)cnc23)cn1]

290A): 2-Chloro-N-(4-(6-chloro-3-(6-methoxypyridin-3-yl)-1H-pyrrolo[3,2-b]pyridin-2-yl)pyridin-2-yl)acetamide

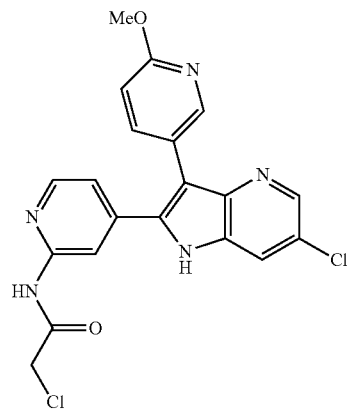 [SMILES: COc1ccc(-c2c(-c3ccnc(NC(=O)CCl)c3)[nH]c3cc(Cl)cnc23)cn1]

Example 290A was prepared from Example 289 by the general methods shown for Example 74A. HPLC: RT=0.98 min (H$_2$O/CAN with 0.1% TFA, Waters Acquity UPLC BEH C18, 2.0×50 mm, 1.7-μm particles, gradient=2 min, wavelength=220 nm); MS (ES): m/z=428 [M+H]$^+$.

Example 290 was prepared from Example 290A and morpholine by the general methods shown for Example 286. HPLC: RT=1.01 min (H$_2$O/ACN with 0.1% TFA, Waters Acquity UPLC BEH C18, 2.1×50 mm, 1.7-μm particles, gradient=3 min, wavelength=220 nm); MS (ES): m/z=479 [M+H]$^+$; $^1$H NMR (500 MHz, DMSO-d$_6$) δ ppm 12.28 (s, 1H), 10.14 (br. s., 1H), 8.42 (s, 1H), 8.38-8.30 (m, 2H), 8.23 (s, 1H), 7.97 (s, 1H), 7.77 (d, J=8.5 Hz, 1H), 7.17 (d, J=5.0 Hz, 1H), 6.88 (d, J=8.6 Hz, 1H), 3.88 (s, 3H), 3.63 (br. s., 4H), 3.24-3.13 (m, 2H).

Example 291

N-(4-(6-chloro-3-(6-methoxypyridin-3-yl)-1H-pyrrolo[3,2-b]pyridin-2-yl)pyridin-2-yl)-2-(4-ethylpiperazin-1-yl)acetamide

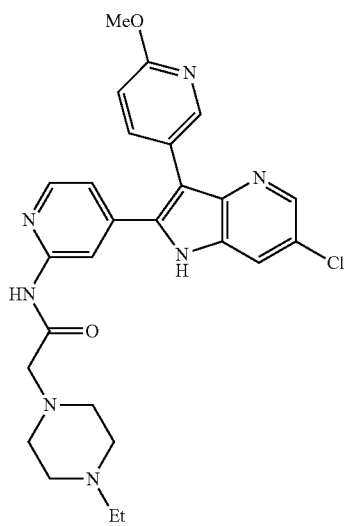 [SMILES: CCN1CCN(CC(=O)Nc2cc(-c3[nH]c4cc(Cl)cnc4c3-c3ccc(OC)nc3)ccn2)CC1]

Example 291 was prepared from Example 290A and 1-ethylpiperazine by the general methods shown for Example 286. HPLC: RT=1.05 min (H$_2$O/ACN with 0.1% TFA, Waters Acquity UPLC BEH C18, 2.1×50 mm, 1.7-μm particles, gradient=3 min, wavelength=220 nm); MS (ES): m/z=506 [M+H]$^+$.

Example 292

N-(4-(6-chloro-3-(6-methoxypyridin-3-yl)-1H-pyrrolo[3,2-b]pyridin-2-yl)pyridin-2-yl)-2-(4-methylpiperazin-1-yl)acetamide

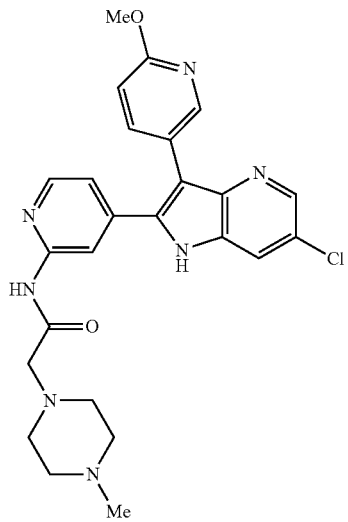 [SMILES: COc1ccc(-c2c(-c3ccnc(NC(=O)CN4CCN(C)CC4)c3)[nH]c3cc(Cl)cnc23)cn1]

Example 292 was prepared from Example 290A and 1-methylpiperazine by the general methods shown for Example 286. HPLC: RT=1.03 min (H$_2$O/ACN with 0.1% TFA, Waters Acquity UPLC BEH C18, 2.1×50 mm, 1.7-μm particles, gradient=3 min, wavelength=220 nm); MS (ES): m/z=492 [M+H]$^+$.

Example 293

N-(4-(3-(5-Methoxypyridin-2-yl)-6-((methylamino)methyl)-1H-pyrrolo[3,2-b]pyridin-2-yl)pyridin-2-yl)acetamide

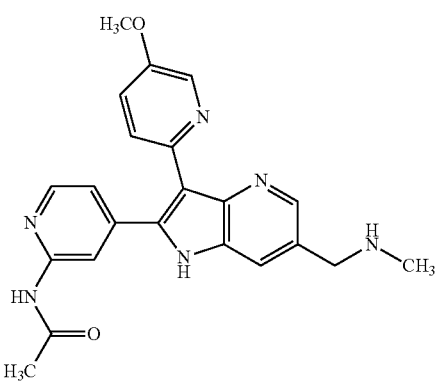 [SMILES: CNCc1cnc2c(-c3ccc(OC)cn3)c(-c3ccnc(NC(C)=O)c3)[nH]c2c1]

293A) N-(4-((3-Amino-5-bromopyridin-2-yl)ethynyl)pyridin-2-yl)acetamide

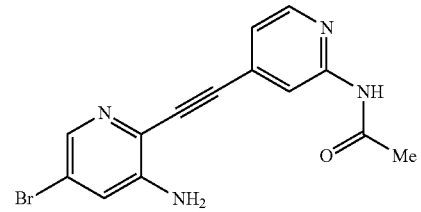 [SMILES: CC(=O)Nc1cc(C#Cc2ncc(Br)cc2N)ccn1]

A mixture of 2,5-dibromopyridin-3-amine (6.89 g, 27.3 mmol, from Combi-Blocks, Inc.), N-(4-ethynylpyridin-2-yl)acetamide (3.98 g, 24.85 mmol), copper(I) iodide (0.237 g, 1.242 mmol) in triethylamine (90 mL) and DMF (70 mL) was purged with N$_2$. Solid PdCl$_2$(PPh$_3$)$_2$ (0.174 g, 0.248 mmol) was added and the reaction mixture was purged with N$_2$. The reaction mixture was heated at 75° C. for 90 min under a N$_2$ atm and then concentrated in vacuo. To the residue was added 100 mL of CH$_2$Cl$_2$ and the resulting mixture was sonicated briefly and stirred at room temperature for 10 minutes. The solid was filtered and washed with CH$_2$Cl$_2$ to obtain the desired compound (5.1 g,) after drying. The filtrate was concentrated and residue was mixed with Celite which was passed through a flash column on SiO$_2$ (solid load, gradient of 100% CH$_2$Cl$_2$ to 10% MeOH in CH$_2$Cl$_2$) to obtain additional desired product (0.9 g). Total 6 g (73%). MS (ES): m/z=331, 333 [M+H]$^+$; $^1$H NMR (500 MHz, DMSO-d$_6$) δ 10.62 (s, 1H), 8.35 (d, J=5.0 Hz, 1H), 8.23 (s, 1H), 7.86 (d, J=1.7 Hz, 1H), 7.37-7.33 (m, 2H), 6.13 (s, 1H), 2.11 (s, 3H).

293B) N-(2-((2-Acetamidopyridin-4-yl)ethynyl)-5-bromopyridin-3-yl)-2,2,2-trifluoroacetamide

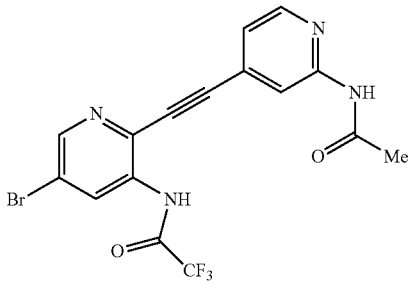 [SMILES: CC(=O)Nc1cc(C#Cc2ncc(Br)cc2NC(=O)C(F)(F)F)ccn1]

To a heterogeneous mixture of 293A (4 g, 12.08 mmol) and Et$_3$N (6 mL) in CH$_2$Cl$_2$ (100 mL) at ice bath temperature was added 2,2,2-trifluoroacetic anhydride (1.4 mL, 10.07 mmol) slowly and it was stirred at the ice bath temperature for 1 h. The reaction mixture was mixed with di-basic phosphate buffer (4.5 g of K$_2$HPO$_4$ in 30 mL water), the organic layer was separated, dried over MgSO$_4$, concentrated in vacuo and the residue was passed through a flash column on SiO$_2$ (gradient of 100% CH$_2$Cl$_2$ to 100% EtOAc, product was eluted at 40-55% EtOAc) to obtain 293B (2.8 g, 6.55 mmol, 54%) as a white solid. MS (ES): m/z=427, 429 [M+H]$^+$; $^1$H NMR (400 MHz, CHLOROFORM-d) δ 8.94 (d, J=2.0 Hz, 1H), 8.69 (br. s., 1H), 8.58 (d, J=2.0 Hz, 1H), 8.50 (br. s., 1H), 8.31 (d, J=4.6 Hz, 1H), 2.27 (s, 3H).

293C) N-{4-[6-Bromo-3-(5-methoxypyridin-2-yl)-1H-pyrrolo[3,2-b]pyridin-2-yl]pyridin-2-yl}acetamide

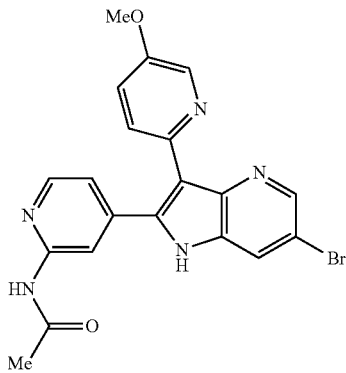

A mixture of 293B (1.5 g, 3.51 mmol), 2-bromo-5-methoxypyridine (1.651 g, 8.78 mmol) and cesium carbonate (2.86 g, 8.78 mmol) in MeCN (13 mL) in a sealed tube was purged with N$_2$. Pd(Ph$_3$P)$_4$ (0.406 g, 0.351 mmol) was added and the mixture was purged with N$_2$ again. The reaction mixture was put in a preheated heater at 110° C., stirred at that temperature for 3 h and cooled to room temperature. To the reaction mixture was added 15 mL water, the mixture was stirred and then the solid was collected by filtration, washed with water and then CH$_2$Cl$_2$ to obtain 293C (1 g, 2.282 mmol, 65%). MS (ES): m/z=438, 440 [M+H]$^+$; $^1$H NMR (400 MHz, DMSO-d$_6$) δ 12.16 (s, 1H), 10.53 (s, 1H), 8.49 (d, J=2.0 Hz, 1H), 8.31 (s, 1H), 8.28 (d, J=5.3 Hz, 1H), 8.20 (d, J=2.9 Hz, 1H), 8.06 (d, J=2.0 Hz, 1H), 7.95-7.92 (m, 1H), 7.49 (dd, J=8.6, 3.1 Hz, 1H), 7.12 (dd, J=5.1, 1.5 Hz, 1H), 3.86 (s, 3H), 2.09 (s, 3H).

293D) N-(4-(6-Bromo-3-(5-methoxypyridin-2-yl)-1-((2-(trimethylsilyl)ethoxy)methyl)-1H-pyrrolo[3,2-b]pyridin-2-yl)pyridin-2-yl)acetamide

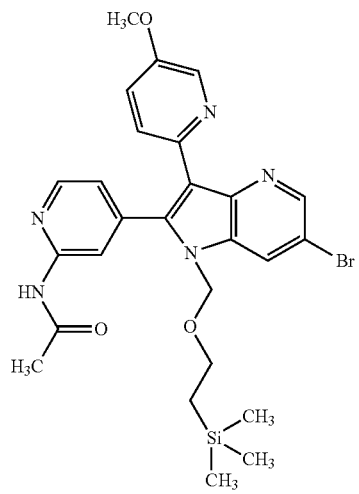 [SMILES: COc1ccc(-c2c(-c3ccnc(NC(C)=O)c3)n(COCC[Si](C)(C)C)c3cc(Br)cnc23)nc1]

A mixture of 293C (765 mg, 1.745 mmol), cesium carbonate (1137 mg, 3.49 mmol) and (2-(chloromethoxy)ethyl)trimethylsilane (437 mg, 2.62 mmol) in THF (12 mL) and DMF (12 mL) was stirred at room temperature for 30 min. To the reaction mixture were added CH$_2$Cl$_2$ and water. The CH$_2$Cl$_2$ layer was separated, dried over MgSO$_4$, concentrated in vacuo and the residue was purified by flash column on SiO$_2$ (gradient of 100% CH$_2$Cl$_2$ to 80% EtOAc in CH$_2$Cl$_2$, product was eluted at 30-40% EtOAc in CH$_2$Cl$_2$) to obtain 294D (625 mg, 1.099 mmol, 63%). MS (ES): m/z=568, 570 [M+H]$^+$; $^1$H NMR (400 MHz, CHLOROFORM-d) δ 8.65 (d, J=2.0 Hz, 1H), 8.33 (s, 1H), 8.28-8.24 (m, 2H), 8.05 (d, J=2.0 Hz, 1H), 7.80 (d, J=8.6 Hz, 1H), 7.30 (dd, J=8.7, 3.0 Hz, 1H), 7.14 (dd, J=5.2, 1.4 Hz, 1H), 5.43 (s, 2H), 3.85 (s, 3H), 3.42-3.36 (m, 2H), 2.19 (s, 3H), 0.85-0.80 (m, 2H), −0.08 (s, 9H).

293E) N-(4-(6-Formyl-3-(5-methoxypyridin-2-yl)-1-((2-(trimethylsilyl)ethoxy)methyl)-1H-pyrrolo[3,2-b]pyridin-2-yl)pyridin-2-yl)acetamide

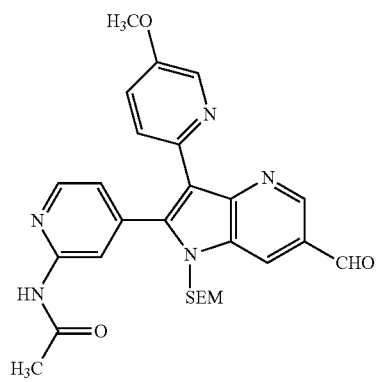 [SMILES: COc1ccc(-c2c(-c3ccnc(NC(C)=O)c3)n(COCC[Si](C)(C)C)c3cc(C=O)cnc23)nc1]

To a solution of 293D (740 mg, 1.302 mmol) in THF (8 mL) at −78° C. was added 1 mL of 1.6M MeLi in ether under $N_2$ with stirring. In 15 minutes was added 0.8 mL of 2M nBuLi solution at −78° C., stirred for 15 minutes. To the resulting heterogeneous mixture was added 1 mL DMF and it was stirred for 40 minutes. HOAc (1 mL) was added, and the mixture was concentrated to a volume of ~4 mL and then the residue was passed through a flash column on $SiO_2$ eluting with a gradient of 100% $CH_2Cl_2$ to 10% MeOH in $CH_2Cl_2$ (product was eluted at ~50% of 10% MeOH in $CH_2Cl_2$) to obtain 293E (130 mg, 0.251 mmol, 19%). MS (ES): m/z=518 [M+H]$^+$; $^1$H NMR (400 MHz, CHLOROFORM-d) δ 10.18 (s, 1H), 9.43 (s, 1H), 9.04 (d, J=1.5 Hz, 1H), 8.42-8.40 (m, 2H), 8.32-8.38 (m, 2H), 7.84 (d, J=8.6 Hz, 1H), 7.18 (dd, J=8.7, 3.0 Hz, 1H), 7.04 (dd, J=5.2, 1.2 Hz, 1H), 5.53 (s, 2H), 3.81 (s, 3H), 3.44-3.37 (m, 2H), 2.09 (s, 3H), 0.86-0.77 (m, 2H), −0.45 (s, 9H).

Example 293) N-(4-(3-(5-Methoxypyridin-2-yl)-6-((methylamino)methyl)-1H-pyrrolo[3,2-b]pyridin-2-yl)pyridin-2-yl)acetamide A mixture of 293E (40 mg, 0.077 mmol) and 0.6 mL of 2M $MeNH_2$ in THF in $CH_2Cl_2$ (2 mL) and iPrOH (2 mL) was stirred at room temperature for 20 min. The reaction mixture was cooled in an ice bath and $NaBH_4$ (~50 mg) was added. The reaction mixture was stirred for 30 min. Acetone (5 mL) was added, and the mixture was stirred for 10 minutes. TFA (~1 mL) was added and the mixture was concentrated in vacuo and the residue was purified by Prep HPLC to obtain ~17 mg of the SEM-protected methylaminomethyl intermediate as a TFA salt. Prep HPLC: Column #1, 20% B to 100% B over 8 min, RT=3.6 min. Column #1=Waters Sunfire C-18, 19×150 mm; Solvent A=10% $CH_3CN$/90% $H_2O$—0.1% TFA; Solvent B=90% $CH_3CN$/10% $H_2O$—0.1% TFA. MS (ES): m/z=533 [M+H]$^+$; $^1$H NMR (400 MHz, METHANOL-$d_4$) δ 8.84 (d, J=1.5 Hz, 1H), 8.64 (d, J=1.8 Hz, 1H), 8.59 (dd, J=5.1, 0.9 Hz, 1H), 8.55 (d, J=2.6 Hz, 1H), 8.35 (s, 1H), 7.76 (dd, J=9.1, 3.0 Hz, 1H), 7.38 (d, J=9.0 Hz, 1H), 7.34 (dd, J=5.1, 1.5 Hz, 1H), 4.55 (s, 2H), 3.99 (s, 3H), 3.48 (dd, J=8.8, 7.7 Hz, 2H), 2.84 (s, 4H), 2.18 (s, 3H), 0.88-0.67 (m, 2H), −0.07 (s, 9H).

The SEM-protected methylaminomethyl intermediate obtained above was mixed with 1.5 mL $CH_2Cl_2$ and 1.5 mL TFA at room temperature and was stirred for 1 h at room temperature. The mixture was concentrated in vacuo and the residue was purified by prep HPLC to obtain Example 294 (1.6 mg, 5% overall yield). Prep HPLC: Column #1, 10% B to 60% B over 8 min, RT=2.7-4 min. Column #1=Waters Sunfire C-18, 19×150 mm; Solvent A=10% $CH_3CN$/90% $H_2O$—5 mmol $NH_4OAc$; Solvent B=90% $CH_3CN$/10% $H_2O$—5 mmol $NH_4OAc$. Analytical HPLC: RT=0.48 min ($H_2O$/MeCN with 0.1% TFA, Waters Acquity BEH C18, 2.0×50 mm, 1.7-μm particles, gradient=1.5 min, wavelength=220 nm). MS (ES): m/z=403 [M+H]$^+$; $^1$H NMR (400 MHz, METHANOL-$d_4$) δ 8.47 (d, J=2.0 Hz, 1H), 8.28 (d, J=2.6 Hz, 1H), 8.27-8.24 (m, 2H), 8.08 (d, J=2.0 Hz, 1H), 7.63 (dd, J=8.6, 0.4 Hz, 1H), 7.53 (dd, J=8.7, 3.0 Hz, 1H), 7.11-7.08 (m, 1H), 4.37 (s, 2H), 3.95 (s, 3H), 2.77 (s, 3H), 2.16 (s, 3H).

Example 294

N-(4-(3-(5-methoxypyridin-2-yl)-6-((propylamino)methyl)-1H-pyrrolo[3,2-b]pyridin-2-yl)pyridin-2-yl)acetamide

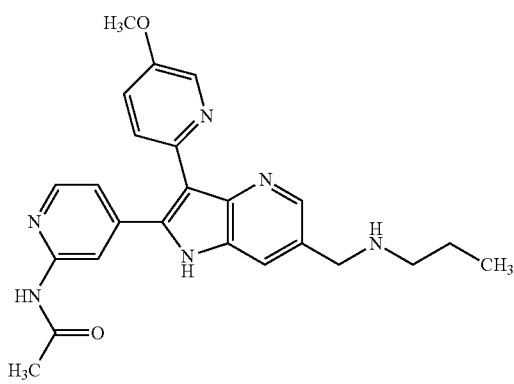 [SMILES: CCCNCc1cnc2c(-c3ccc(OC)cn3)c(-c3ccnc(NC(C)=O)c3)[nH]c2c1]

Example 294 was prepared in a similar way as Example 293. HPLC: RT=0.55 min ($H_2O$/MeCN with 0.1% TFA, Waters Acquity BEH C18, 2.0×50 mm, 1.7-μm particles, gradient=1.5 min, wavelength=220 nm). MS (ES): m/z=431 [M+H]$^+$; $^1$H NMR (500 MHz, DMSO-$d_6$) δ 10.54 (s, 1H), 8.43 (s, 1H), 8.31 (br. s., 1H), 8.27 (d, J=5.0 Hz, 1H), 8.18 (d, J=2.5 Hz, 1H), 8.00 (d, J=8.7 Hz, 1H), 7.88 (s, 1H), 7.49 (dd, J=8.5, 2.7 Hz, 1H), 7.12 (d, J=4.9 Hz, 1H), 4.04 (s., 2H), 3.44 (br. s., 3H), 2.66 (t, J=7.3 Hz, 2H), 2.54 (s, 2H), 2.09 (s, 3H), 1.58-1.48 (m, 2H), 0.89 (t, J=7.4 Hz, 3H).

Example 295

3-(2-(2-Acetamidopyridin-4-yl)-3-(5-methoxypyridin-2-yl)-1H-pyrrolo[3,2-b]pyridin-6-yl)-2,2-difluoro-3-hydroxypropanamide

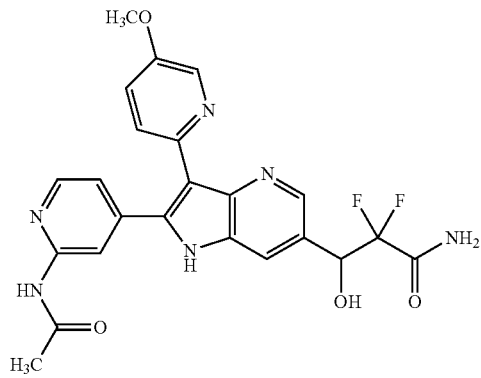 [SMILES: COc1ccc(-c2c(-c3ccnc(NC(C)=O)c3)[nH]c3cc(C(O)C(F)(F)C(N)=O)cnc23)nc1]

295A) 3-(2-(2-Acetamidopyridin-4-yl)-3-(5-methoxypyridin-2-yl)-1-((2-(trimethylsilyl)ethoxy)methyl)-1H-pyrrolo[3,2-b]pyridin-6-yl)-2,2-difluoro-3-hydroxypropanamide

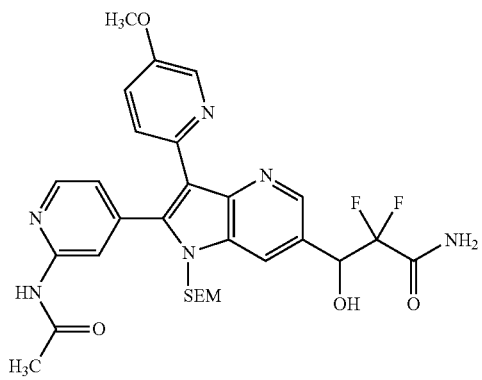 [SMILES: COc1ccc(-c2c(-c3ccnc(NC(C)=O)c3)n(COCC[Si](C)(C)C)c3cc(C(O)C(F)(F)C(N)=O)cnc23)nc1]

To a solution of aldehyde 293E (100 mg, 0.193 mmol) in THF (3 mL) was added 7 mL of (2-ethoxy-1,1-difluoro-2-oxoethyl)zinc(II) bromide (0.5 M solution in THF from Rieke Metals, RiekeMetals.com) under a N2 atm. The reaction mixture was stirred at room temperature for 4 h. 7N NH$_3$ in MeOH solution (4 mL) was added at room temperature. The resulting solid was filtered and the filtrate was concentrated in vacuo. The residue was passed through a flash column on SiO$_2$ eluting with a gradient of 10% MeOH in CH$_2$Cl$_2$—CH$_2$Cl$_2$ solvent system to obtain Example 295A (20 mg, 0.033 mmol, 17%). MS (ES): m/z=613 [M+H]$^+$; $^1$H NMR (400 MHz, METHANOL-d$_4$) δ 8.56 (d, J=5.1 Hz, 1H), 8.54 (br. s., 1H), 8.34 (br. s., 1H), 8.02 (br. s., 1H), 7.94 (s, 1H), 7.34 (dd, J=9.2, 2.9 Hz, 1H), 7.28 (d, J=4.0 Hz, 1H), 7.10 (d, J=9.2 Hz, 1H), 5.58 (s, 2H), 3.77 (s, 3H), 3.45-3.39 (m, 2H), 3.27 (dt, J=3.2, 1.6 Hz, 1H), 2.17 (s, 3H), 0.81-0.75 (m, 2H), −0.12 (s, 9H).

Example 295) 3-(2-(2-Acetamidopyridin-4-yl)-3-(5-methoxypyridin-2-yl)-1H-pyrrolo[3,2-b]pyridin-6-yl)-2,2-difluoro-3-hydroxypropanamide To a solution of 295A (20 mg, 0.033 mmol) in CH$_2$Cl$_2$ (5 mL) was added 1 mL of TFA at room temperature and it was stirred for 3 h. The reaction mixture was concentrated, and to the residue was added 0.3 mL Et$_3$N. The mixture was concentrated and the residue was mixed with 0.3 mL of Et$_3$N and then passed through a flash column on SiO$_2$ eluting with CH$_2$Cl$_2$— 10% MeOH in a CH$_2$Cl$_2$ gradient. Followed by elution with 20% MeOH and 1% Et$_3$N in CH$_2$Cl$_2$ to provide 24 mg of the slightly impure product. This material was repurified by prep HPLC (RT=2.7-3.4 min) to obtain Example 295 (4.5 mg, 8.39 μmol, 26%). Prep HPLC: Column #1, 20% B to 100% B over 8 min; Column #1=Waters Sunfire C-18, 19×150 mm; Solvent A=10% CH$_3$CN/90% H$_2$O—5 mmol NH$_4$OAc; Solvent B=90% CH$_3$CN/10% H$_2$O—5 mmol NH$_4$OAc. Analytical HPLC: RT=0.54 min (H$_2$O/MeCN with 0.1% TFA, Waters Acquity BEH C18, 2.0×50 mm, 1.7-μm particles, gradient=1.5 min, wavelength=220 nm). MS (ES): m/z=483 [M+H]$^+$; $^1$H NMR (400 MHz, METHANOL-d$_4$) δ 8.45 (s, 1H), 8.27 (d, J=2.9 Hz, 1H), 8.25-8.22 (m, 2H), 8.05 (d, J=1.1 Hz, 1H), 7.64 (d, J=8.6 Hz, 1H), 7.53 (dd, J=8.6, 2.9 Hz, 1H), 7.12-7.09 (m, 1H), 5.37 (dd, J=16.3, 8.6 Hz, 1H), 3.95 (s, 3H), 2.15 (s, 3H).

Example 296

N-(4-(3-(5-Methoxypyridin-2-yl)-6-(2,2,2-trifluoroacetyl)-1H-pyrrolo[3,2-b]pyridin-2-yl)pyridin-2-yl)acetamide

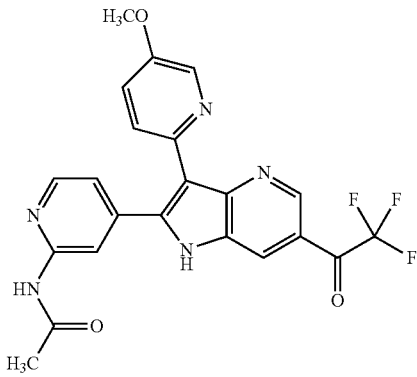 [SMILES: COc1ccc(-c2c(-c3ccnc(NC(C)=O)c3)[nH]c3cc(C(=O)C(F)(F)F)cnc23)nc1]

296A) N-(4-(3-(5-Methoxypyridin-2-yl)-6-(2,2,2-trifluoroacetyl)-1-((2-(trimethylsilyl)ethoxy)methyl)-1H-pyrrolo[3,2-b]pyridin-2-yl)pyridin-2-yl)acetamide, 2 (99893-307)

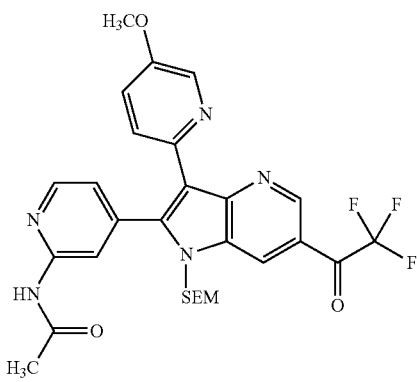 [SMILES: COc1ccc(-c2c(-c3ccnc(NC(C)=O)c3)n(COCC[Si](C)(C)C)c3cc(C(=O)C(F)(F)F)cnc23)nc1]

To a solution of Example 293D (300 mg, 0.528 mmol) in THF (5 mL) at −78° C. was added 0.4 mL of 1.6M MeLi solution in ether. After 10 minutes was added 0.25 mL of 2.5M nBuLi solution in hexane and the mixture was stirred for 30 min at −78° C. 2,2,2-trifluoro-N-methyl-N-(2,2,2-trifluoroacetyl)acetamide (0.2 mL, 0.528 mmol) (from TCI company) was added and the mixture was stirred for 1 h. To the reaction mixture was added MeOH and 100 uL of TFA. The mixture was warmed to room temperature and directly purified by prep HPLC to obtain a partially purified product, which was used for the next step as it is. Prep HPLC: Column #1, 20% B to 100% B over 8 min, RT=5.2-6 min. Column #1=Waters Sunfire C-18, 19×150 mm; Solvent A=10% CH$_3$CN/90% H$_2$O—0.1% TFA; Solvent B=90% CH$_3$CN/10% H$_2$O—0.1% TFA. LCMS shows a hydrated mass, MS (ES): m/z=604 [M+H$_2$O+H]$^+$

Example 296) N-(4-(3-(5-Methoxypyridin-2-yl)-6-(2,2,2-trifluoroacetyl)-1H-pyrrolo[3,2-b]pyridin-2-yl)pyridin-2-yl)acetamide The partially purified material obtained above (Example 296A) was mixed with 5 mL CH$_2$Cl$_2$ and 2 mL TFA at room temperature and stirred for 7.5 h. The reaction mixture was then concentrated in vacuo and the residue was purified by prep HPLC: RT=3.1 min. Prep HPLC: Column #1, 20% B to 100% B over 8 min, Column #1=Waters Sunfire C-18, 19×150 mm; Solvent A=10% CH$_3$CN/90% H$_2$O—0.1% TFA; Solvent B=90% CH$_3$CN/10% H$_2$O—0.1% TFA. The material obtained was repurified by prep HPLC to afford Example 297 (9 mg, 0.018 mmol, 3%). Column #1=Waters Sunfire C-18, 19×150 mm; Solvent A=10% CH$_3$CN/90% H$_2$O—5 mmol NH$_4$OAc; Solvent B=90% CH$_3$CN/10% H$_2$O—5 mmol NH$_4$OAc, 9 mg, (0.018 mmol, 3.37% yield). Analytical HPLC: RT=0.63 min (H$_2$O/MeCN with 0.1% TFA, Waters Acquity BEH C18, 2.0×50 mm, 1.7-μm particles, gradient=1.5 min, wavelength=220 nm). LCMS shows a hydrated mass, MS (ES): m/z=474 [M+H$_2$O+H]$^+$; $^1$H NMR (400 MHz, METHANOL-d$_4$) δ 8.70 (d, J=1.1 Hz, 1H), 8.31-8.23 (m, 4H), 7.67-7.60 (m, 1H), 7.55-7.50 (m, 1H), 7.13 (dd, J=5.2, 1.7 Hz, 1H), 3.94 (s, 3H), 2.14 (s, 3H).

Example 297

N-(4-(3-(5-Methoxypyridin-2-yl)-6-(2,2,2-trifluoro-1-hydroxyethyl)-1H-pyrrolo[3,2-b]pyridin-2-yl)pyridin-2-yl)acetamide

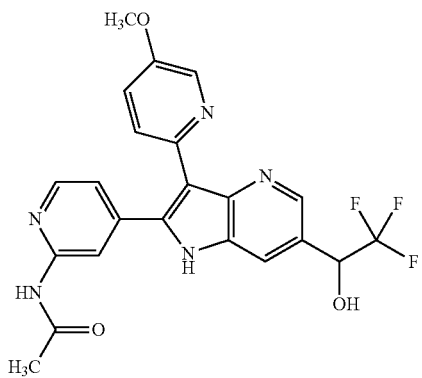 [SMILES: COc1ccc(-c2c(-c3ccnc(NC(C)=O)c3)[nH]c3cc(C(O)C(F)(F)F)cnc23)nc1]

297A) N-(4-(3-(5-Methoxypyridin-2-yl)-6-(2,2,2-trifluoro-1-hydroxyethyl)-1-((2-(trimethylsilyl)ethoxy)methyl)-1H-pyrrolo[3,2-b]pyridin-2-yl)pyridin-2-yl)acetamide To a partially purified Example 296A (110 mg) in MeOH (5 mL) at ice bath temp was added 50 mg of NaBH$_4$ in small portions with stirring. After 1 h, the reaction mixture was treated with 3 mL acetone, stirred for 10 min, and quenched with 0.4 mL HOAc. The mixture was concentrated in vacuo and the residue was purified by prep HPLC to obtain 65 mg of the alcohol as a TFA salt. Prep HPLC: Column #1, 20% B to 100% B over 8 min, RT=5.6 min Column #1=Waters Sunfire C-18, 19×150 mm; Solvent A=10% CH$_3$CN/90% H$_2$O—0.1% TFA; Solvent B=90% CH$_3$CN/10% H$_2$O—0.1% TFA MS (ES): m/z=588 [M+H]$^+$; $^1$H NMR (400 MHz, METHANOL-d$_4$) δ 8.86 (s, 1H), 8.78 (s, 1H), 8.59 (dd, J=5.1, 0.4 Hz, 1H), 8.51 (d, J=2.6 Hz, 1H), 8.36 (s, 1H), 7.58 (dd, J=9.1, 3.0 Hz, 1H), 7.35 (dd, J=5.1, 1.5 Hz, 1H), 7.23 (d, J=9.0 Hz, 1H), 5.63 (s, 2H), 5.55 (q, J=6.8 Hz, 1H), 3.94 (s, 3H), 3.52-3.47 (m, 2H), 2.20 (s, 3H), 0.87-0.81 (m, 2H), −0.09 (s, 9H).

Example 297: N-(4-(3-(5-Methoxypyridin-2-yl)-6-(2,2,2-trifluoro-1-hydroxyethyl)-1H-pyrrolo[3,2-b]pyridin-2-yl)pyridin-2-yl)acetamide

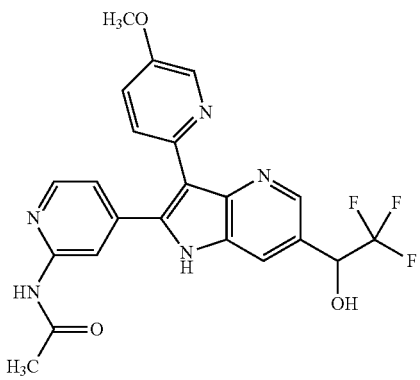 [SMILES: COc1ccc(-c2c(-c3ccnc(NC(C)=O)c3)[nH]c3cc(C(O)C(F)(F)F)cnc23)nc1]

To a solution of the TFA salt of Example 297A (65 mg, 0.093 mmol) in CH$_2$Cl$_2$ (4 mL) at room temperature was added 2 mL TFA. After 4 h at rt the mixture was concentrated in vacuo and the residue was purified by prep HPLC to obtain Example 297 (23 mg, 0.048 mmol, 52% yield). Prep HPLC: Column #1, 20% B to 100% B over 8 min, RT=4.8 min; Column #1=Waters Sunfire C-18, 19×150 mm; Solvent A=10% CH$_3$CN/90% H$_2$O—5 mmol NH$_4$OAc; Solvent B=90% CH$_3$CN/10% H$_2$O—5 mmol NH$_4$OAc. Analytical HPLC: RT=0.64 min (H$_2$O/MeCN with 0.1% TFA, Waters Acquity BEH C18, 2.0×50 mm, 1.7-μm particles, gradient=1.5 min, wavelength=220 nm). MS (ES): m/z=458 [M+H]$^+$; $^1$H NMR (400 MHz, METHANOL-d$_4$) δ 8.46 (d, J=1.1 Hz, 1H), 8.27 (d, J=2.9 Hz, 1H), 8.23 (d, J=4.8 Hz, 2H), 8.08 (s, 1H), 7.65 (d, J=8.6 Hz, 1H), 7.52 (dd, J=8.7, 3.0 Hz, 1H), 7.12-7.09 (m, 1H), 5.29 (q, J=7.0 Hz, 1H), 3.94 (s, 3H), 2.15 (s, 3H).

Example 298

N-(4-(7-Acetyl-3-(6-methoxypyridin-3-yl)-1H-pyrrolo[3,2-b]pyridin-2-yl)pyridin-2-yl)acetamide

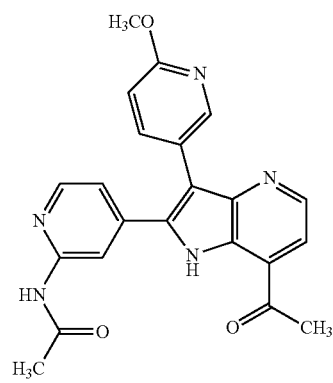 [SMILES: COc1ccc(-c2c(-c3ccnc(NC(C)=O)c3)[nH]c3c(C(C)=O)ccnc23)cn1]

298A) 3-Amino-2,6-dibromoisonicotinonitrile

To a solution of 3-aminoisonicotinonitrile (9 g, 76 mmol) in MeOH (120 mL) at room temperature was added solid N-bromosuccinimide (26.9 g, 151 mmol) in several portions over 45 min with stirring. The reaction mixture was stirred at room temperature for 2 h. To the reaction mixture was added an additional 5 g of NBS and stirring continued at room temperature for 1 h. The reaction mixture was concentrated in vacuo and to the residue was added iPrOH (~120 mL). The resulting solid was filtered and washed with Et$_2$O to obtain 15 g of a yellow solid. The solid was mixed with water (45 mL), sonicated and stirred. Then the resulting solid was collected by filtration and washed with water to obtain 10 g of the desired product. The original iPrOH filtrate was concentrated in vacuo and the residue was mixed with water, the solid was filtered, washed with Et$_2$O to obtain brownish black solid. It was suspended in CHCl$_3$, the insoluble black solid was removed by filtration and the Titrate was concentrated. The residue was mixed with water, sonicated, stirred, and the solid was collected by filtration to obtain 2.78 g of a second crop of Example 298A. Total 12.8 g (61%). MS (ES): m/z=276, 278, 280 [M+H]$^+$; $^1$H NMR (400 MHz, CDCl$_3$) δ 7.29 (s, 1H), 2.80 (s, 2H).

298B) N-(4-((3-Amino-6-bromo-4-cyanopyridin-2-yl)ethynyl)pyridin-2-yl)acetamide

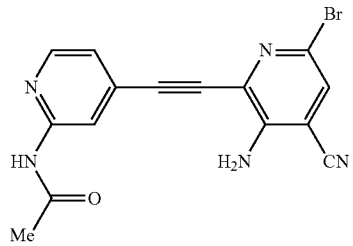 [SMILES: CC(=O)Nc1cc(C#Cc2nc(Br)cc(C#N)c2N)ccn1]

A mixture of Example 298A (7.4 g, 26.7 mmol), Example 1B (3.85 g, 24.05 mmol) and copper(I) iodide (0.254 g, 1.336 mmol) in DMF (60 mL) and Et$_3$N (60 mL) was purged with N$_2$. Solid PdCl$_2$(Ph$_3$P)$_2$ (0.938 g, 1.336 mmol) was added and the mixture was heated at 75° C. for 30 min under a N$_2$ atm. The resulting solid was filtered, washed with CH$_2$Cl$_2$ and dried to obtain the 1st crop of Example 298B (6.8 g). The filtrate was concentrated to a volume of 25 mL. Water (100 mL) and CH$_2$Cl$_2$ (100 mL) were added and the mixture was stirred for 20 minutes. The resulting solid was filtered and washed successively with water, CH$_2$Cl$_2$ and iPrOH to obtain an impure product (~2.1 g). This impure material was triturated again with CH$_2$Cl$_2$ to obtain the 2nd crop of the product (900 mg). Total 7.7 g (81%). MS (ES): m/z=356, 358 [M+H]$^+$; $^1$H NMR (400 MHz, CHLOROFORM-d) δ 8.38 (s, 1H), 8.31 (dd, J=5.2, 0.8 Hz, 1H), 7.97 (br. s., 1H), 7.46 (s, 1H), 7.21 (dd, J=5.1, 1.5 Hz, 1H), 5.10 (br. s., 2H), 2.25 (s, 3H).

298C) N-(4-(5-Bromo-7-cyano-1H-pyrrolo[3,2-b]pyridin-2-yl)pyridin-2-yl)acetamide

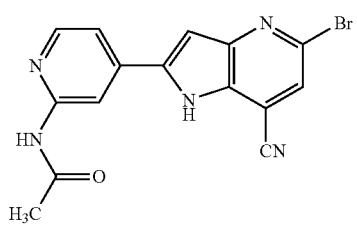 [SMILES: CC(=O)Nc1cc(-c2cc3nc(Br)cc(C#N)c3[nH]2)ccn1]

A heterogeneous mixture of Example 298B (6.4 g, 17.97 mmol) and cesium carbonate (6.44 g, 19.77 mmol) in DMF (100 mL) was purged with N$_2$ and treated with Pd(Ph$_3$P)$_4$ (1.038 g, 0.898 mmol). The mixture was purged with N$_2$ again and heated at 80° C. under N$_2$ atm for 1 h. It was then concentrated to a volume of 60 mL and water (350 mL) and 40 mL CH$_2$Cl$_2$ (40 mL) were added. The mixture was stirred at rt, and the resulting solid was collected and washed with a small amount of iPrOH, and then CH$_2$Cl$_2$ to obtain Example 298C (5.3 g, 14.88 mmol, 83%) after drying. MS (ES): m/z=356, 358 [M+H]$^+$; $^1$H NMR (400 MHz, DMSO-d$_6$) δ 13.08 (br. s., 1H), 10.65 (br. s., 1H), 8.57 (br. s., 1H), 8.44 (br. s., 1H), 7.92 (br. s., 1H), 7.72 (s., 1H), 7.32 (s., 1H), 2.15 (s., 3H).

298D) N-(4-(5-Bromo-7-cyano-3-iodo-1H-pyrrolo[3,2-b]pyridin-2-yl)pyridin-2-yl)acetamide

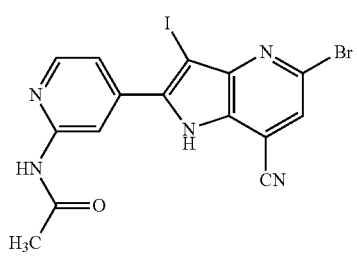 [SMILES: CC(=O)Nc1cc(-c2[nH]c3c(C#N)cc(Br)nc3c2I)ccn1]

A heterogeneous mixture of Example 298C (600 mg, 1.685 mmol) and N-iodosuccinimide (379 mg, 1.685 mmol) in THF (10 mL) was stirred at room temperature for 1 h. The reaction mixture was mostly concentrated in vacuo, and the residue was mixed with CH$_2$Cl$_2$ and water and the solid was filtered. The solid was washed with water and CH$_2$Cl$_2$ to obtain Example 298D (670 mg, 1.390 mmol, 83%). MS (ES): m/z=482, 484 [M+H]$^+$; $^1$H NMR (400 MHz, DMSO-d$_6$) δ 13.49 (s, 1H), 10.72 (s, 1H), 8.65 (s, 1H), 8.51 (d, J=5.1 Hz, 1H), 8.05 (s, 1H), 7.55 (dd, J=5.1, 1.5 Hz, 1H), 2.15 (s, 3H).

298E) N-(4-(5-Bromo-7-cyano-3-iodo-1-((2-(trimethylsilyl)ethoxy)methyl)-1H-pyrrolo[3,2-b]pyridin-2-yl)pyridin-2-yl)acetamide

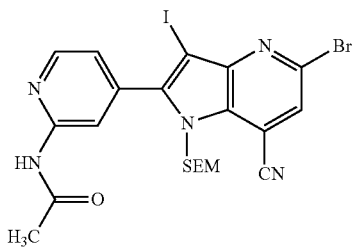 [SMILES: CC(=O)Nc1cc(-c2c(I)c3nc(Br)cc(C#N)c3n2COCC[Si](C)(C)C)ccn1]

A heterogeneous mixture of Example 298D (4.5 g, 9.33 mmol), Hunig's Base (2.119 mL, 12.14 mmol) and (2-(chloromethoxy)ethyl)trimethylsilane (1.712 g, 10.27 mmol) in $CH_2Cl_2$ (70 mL) was stirred at room temperature. It slowly became a homogeneous solution and the reaction was complete in 1 h. To the reaction mixture was added water, the $CH_2Cl_2$ layer was separated, dried over $MgSO_4$, and concentrated in vacuo. The resulting residue was passed through a flash column on $SiO_2$ eluting with hexane-EtOAc gradient to obtain Example 298E (4.2 g, 6.86 mmol, 74%). The desired product was eluted at 40-55% EtOAc in hexane. MS (ES): m/z=612, 614 [M+H]$^+$; $^1$H NMR (400 MHz, CHLOROFORM-d) δ 8.51 (br. s., 1H), 8.46 (d, J=5.3 Hz, 1H), 7.69 (s, 1H), 7.34 (d, J=4.4 Hz, 1H), 7.28-7.28 (m, 1H), 5.65 (s, 2H), 3.56-3.35 (m, 2H), 2.29 (s, 3H), 0.97-0.77 (m, 2H), 0.00--0.19 (m, 9H).

298F) N-(4-(5-Bromo-7-cyano-3-(6-methoxypyridin-3-yl)-1-((2-(trimethylsilyl)ethoxy)methyl)-1H-pyrrolo[3,2-b]pyridin-2-yl)pyridin-2-yl)acetamide

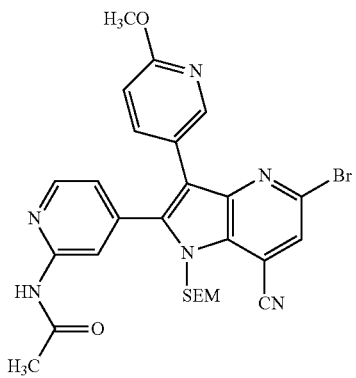 [SMILES: COc1ccc(-c2c(-c3ccnc(NC(C)=O)c3)n(COCC[Si](C)(C)C)c3c(C#N)cc(Br)nc23)cn1]

A mixture of Example 298E (1.8 g, 2.94 mmol), (6-methoxypyridin-3-yl)boronic acid (0.899 g, 5.88 mmol) and 0.25 mL of 3M $K_3PO_4$ in dioxane (20 mL) was purged with $N_2$. $PdCl_2$(dppf) (0.215 g, 0.294 mmol) was added, the reaction was purged with $N_2$ again and the mixture was put into a preheated heater at 100° C. It was stirred at 100° C. under $N_2$ for 60 min., and then cooled to rt. The reaction mixture was mixed with $CH_2Cl_2$ and anhydrous $Na_2SO_4$, stirred, the solid was filtered, washed with $CH_2Cl_2$ and the filtrate was concentrated in vacuo. The residue was purified by flash column on $SiO_2$ eluting with gradient (Hexane-EtOAc) to obtain Example 298F (800 mg, 1.348 mmol, 46%). MS (ES): m/z=593, 595 [M+H]$^+$; $^1$H NMR (400 MHz, CHLOROFORM-d) δ 8.32 (br. s., 1H), 8.03 (s, 1H), 7.95 (d, J=4.6 Hz, 1H), 7.77 (d, J=2.2 Hz, 1H), 7.33 (dd, J=8.6, 2.2 Hz, 1H), 6.89 (s, 1H), 6.66 (d, J=4.4 Hz, 1H), 6.36 (d, J=8.6 Hz, 1H), 5.27 (s, 2H), 3.54 (s, 3H), 3.16-3.10 (m, 2H), 1.85 (s, 3H), 0.56-0.50 (m, 2H), −0.43 (s, 9H).

298G) N-(4-(7-Acetyl-3-(6-methoxypyridin-3-yl)-1-((2-(trimethylsilyl)ethoxy)methyl)-1H-pyrrolo[3,2-b]pyridin-2-yl)pyridin-2-yl)acetamide

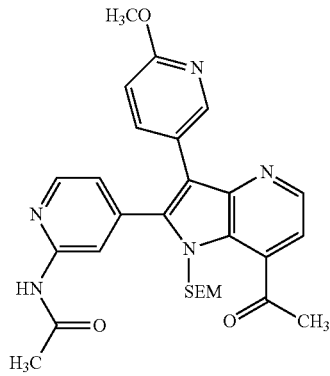 [SMILES: COc1ccc(-c2c(-c3ccnc(NC(C)=O)c3)n(COCC[Si](C)(C)C)c3c(C(C)=O)ccnc23)cn1]

To a solution of Example 298F (45 mg, 0.076 mmol) in THF at −78° C. under $N_2$ was added a MeLi solution (0.5 mL of 1.6M in ether) and it was stirred for 30 min. nBuLi solution (0.2 mL of 2.5M in hexane) was added and the mixture was stirred for 6 min. To the reaction mixture was added 0.5 mL of HOAc, and it was stirred for 5 min. $CH_2Cl_2$ and water were added, organic layer was separated, concentrated in vacuo and prep HPLC provided Example 298G (7 mg, 0.013 mmol, 17%). Prep HPLC: Column #1, 20% B to 100% B over 8 min, Column #1=Waters Sunfire C-18, 19×150 mm; Solvent A=10% $CH_3CN$/90% $H_2O$—0.1% TFA; Solvent B=90% $CH_3CN$/10% $H_2O$—0.1% TFA. MS (ES): m/z=532 [M+H]$^+$; $^1$H NMR (400 MHz, CHLOROFORM-d) δ 12.01 (br. s., 1H), 8.81 (d, J=4.2 Hz, 1H), 8.67 (s, 1H), 8.27 (br. s., 1H), 8.18 (br. s., 1H), 7.98 (d, J=7.0 Hz, 1H), 7.61 (d, J=3.3 Hz, 1H), 7.22 (br. s., 1H), 7.00 (d, J=6.2 Hz, 1H), 5.44 (s, 2H), 4.04 (s, 3H), 3.26-3.19 (m, 2H), 2.80 (s, 3H), 2.33 (s, 3H), 0.80-0.73 (m, 2H), −0.05 (s, 9H).

Example 298) N-(4-(7-Acetyl-3-(6-methoxypyridin-3-yl)-1H-pyrrolo[3,2-b]pyridin-2-yl)pyridin-2-yl)acetamide A mixture of Example 298G (7 mg, 0.013 mmol) and TFA (0.5 mL) in $CH_2Cl_2$ (7 mL) was stirred at room temperature for 5 h, and then concentrated in vacuo. The residue was purified by prep HPLC to obtain the TFA salt of Example 298 (4 mg, 6.98 μmol, 53%). Prep HPLC: Column #1, 20% B to 100% B over 8 min, RT=2.5 min.; Column #1=Waters Sunfire C-18, 19×150 mm; Solvent A=10% $CH_3CN$/90% $H_2O$—0.1% TFA; Solvent B=90% $CH_3CN$/10% $H_2O$—0.1% TFA. Analytical HPLC: RT=0.62 min ($H_2O$/MeCN with 0.1% TFA, Waters Acquity BEH C18, 2.0×50 mm, 1.7-μm particles, gradient=1.5 min, wavelength=220 nm). MS (ES): m/z=402 [M+H]$^+$; $^1$H NMR (400 MHz, DMSO-$d_6$) δ 11.74 (br.s., 1H), 10.58 (s, 1H), 8.66-8.60 (m, 1H), 8.34-8.27 (m, 2H), 8.22 (d, J=2.0 Hz, 1H), 7.81 (d, J=5.1 Hz, 1H), 7.77 (dd, J=8.5, 2.3 Hz, 1H), 7.14 (d, J=4.0 Hz, 1H), 6.85 (d, J=8.6 Hz, 1H), 3.87 (s, 3H), 2.77 (s, 3H), 2.09 (s, 3H).

Example 299

N-(4-(7-(2-Hydroxypropan-2-yl)-3-(6-methoxypyridin-3-yl)-1H-pyrrolo[3,2-b]pyridin-2-yl)pyridin-2-yl)acetamide

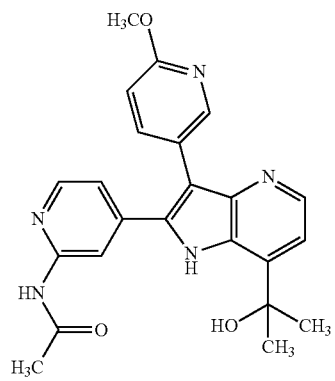 [SMILES: COc1ccc(-c2c(-c3ccnc(NC(C)=O)c3)[nH]c3c(C(C)(C)O)ccnc23)cn1]

To a solution of TFA salt of Example 298 (50 mg, 0.097 mmol) in THF (2.5 mL) at ice bath temp under N₂ atm was added MeMgCl (0.8 mL of 3M solution in THF) slowly with stirring. After 40 minutes, was added TFA in MeOH (0.4 mL in 3 mL MeOH) slowly and the reaction mixture was concentrated in vacuo. The residue was mixed with EtOAc (15 mL), concentrated in vacuo and was purified by preparative HPLC to obtain Example 299 (10.9 mg, 0.026 mmol, 27%). Prep HPLC: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 20 minutes, then a 5-minute hold at 100% B; Flow: 20 mL/min. Analytical HPLC: RT=0.55 min (H₂O/MeCN with 0.1% TFA, Waters Acquity BEH C18, 2.0×50 mm, 1.7-μm particles, gradient=1.5 min, wavelength=220 nm). MS (ES): m/z=418 [M+H]⁺; ¹H NMR (500 MHz, DMSO-d₆) δ 10.96-10.91 (br. s, 1H), 10.60 (s, 1H), 8.34 (d, J=4.8 Hz, 1H), 8.30 (m, 1H), 8.27 (s., 1H), 8.19 (, 1H), 7.80-7.74 (m, 1H), 7.18 (d, J=4.8 Hz, 1H), 7.10 (d, J=4.5 Hz, 1H), 6.84 (d, J=8.5 Hz, 1H), 3.85 (s, 3H), 2.54 (s, 1H), 2.08 (s, 3H), 1.64 (s, 6H).

Example 300

N-(4-(7-(1-Hydroxy-2-methylpropyl)-3-(6-methoxypyridin-3-yl)-1H-pyrrolo[3,2-b]pyridin-2-yl)pyridin-2-yl)acetamide

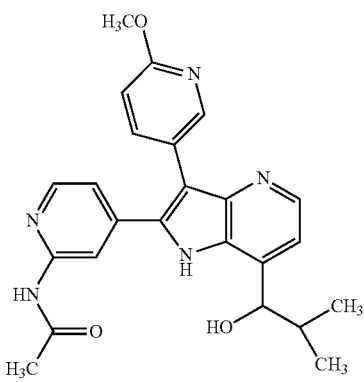 [SMILES: COc1ccc(-c2c(-c3ccnc(NC(C)=O)c3)[nH]c3c(C(O)C(C)C)ccnc23)cn1]

300A) N-(4-(5-Bromo-7-cyano-3-(6-methoxypyridin-3-yl)-1H-pyrrolo[3,2-b]pyridin-2-yl)pyridin-2-yl)acetamide

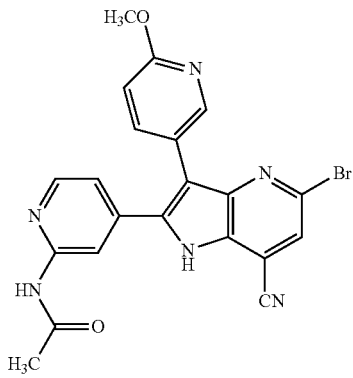 [SMILES: COc1ccc(-c2c(-c3ccnc(NC(C)=O)c3)[nH]c3c(C#N)cc(Br)nc23)cn1]

A mixture of Example 298F (100 mg, 0.168 mmol) and TFA (1 mL) in CH₂Cl₂ (5 mL) was stirred at room temperature for 8 h. The mixture was concentrated in vacuo to obtain ~100 mg of the crude product. This material was used directly in the next step. HPLC: RT=0.86 min (H₂O/CAN with 0.1% TFA, Waters Acquity UPLC BEH C18, 2.0×50 mm, 1.7-μm particles, gradient=2 min, wavelength=220 nm); MS (ES): m/z=462.9, 464.9 [M+H]⁺.

300B) N-(4-(5-Bromo-7-isobutyryl-3-(6-methoxy-pyridin-3-yl)-1H-pyrrolo[3,2-b]pyridin-2-yl)pyridin-2-yl)acetamide

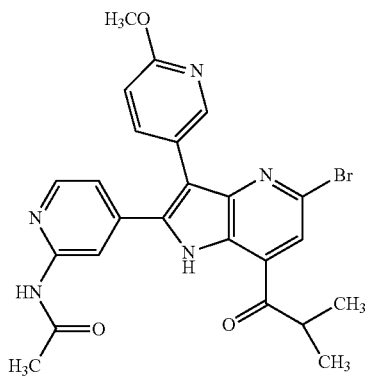 [SMILES: COc1ccc(-c2c(-c3ccnc(NC(C)=O)c3)[nH]c3c(C(=O)C(C)C)cc(Br)nc23)cn1]

To a solution of Example 300A TFA salt (110 mg, 0.191 mmol) in THF (3 mL) at −78° C. was added 2 mL of 2 M iPrMgCl solution in THF with stirring. After 2 h, the mixture was slowly warmed to room temperature over 2 h. The reaction mixture was again cooled to −78° C. and additional 2 mL of 2M iPrMgCl solution was added and then the mixture was warmed to rt over 1 h. To the reaction mixture were added EtOAc (5 mL) and HOAc (2 mL) and it was stirred for 10 min. The mixture was mixed with CH$_2$Cl$_2$ and aq NaHCO$_3$. The CH$_2$Cl$_2$ layer was separated, then aq layer was washed with CH$_2$Cl$_2$ and the combined CH$_2$Cl$_2$ layers were concentrated in vacuo. The residue was purified by prep HPLC to obtain the TFA salt of Example 300B (25 mg, 21%) as a yellow solid. Column #1, 20% B to 100% B over 8 min, RTt=6.8 min. Column #1=Waters Sunfire C-18, 19×150 mm; Solvent A=10% CH$_3$CN/90% H$_2$O—0.1% TFA; Solvent B=90% CH$_3$CN/10% H$_2$O—0.1% TFA. MS (ES): m/z=508, 510 [M+H]$^+$; $^1$H NMR (400 MHz, CHLOROFORM-d) δ 12.65 (br. s., 1H), 10.59 (br. s., 1H), 8.91 (s, 1H), 8.29 (br. s., 1H), 8.08 (br. s., 1H), 7.89-7.85 (m, 1H), 7.84 (s, 1H), 7.29 (d, J=4.2 Hz, 1H), 6.92 (d, J=8.6 Hz, 1H), 4.01 (s, 3H), 3.66 (hept, J=6.6 Hz, 1H), 2.35 (s, 3H), 1.33 (d, J=6.6 Hz, 6H)

Example 300) N-(4-(7-(1-Hydroxy-2-methylpropyl)-3-(6-methoxypyridin-3-yl)-1H-pyrrolo[3,2-b]pyridin-2-yl)pyridin-2-yl)acetamide A mixture of bromoketone Example 300B (25 mg) and 20% Pd(OH)$_2$/C (25 mg) in MeOH (10 mL) was stirred under 1 atm H$_2$ gas at room temperature for 1.5 h. The solid was filtered, washed with MeOH, and the filtrate was concentrated in vacuo. The residue was purified by prep HPLC to obtain Example 300 (14.9 mg, 0.035 mmol, 86%). Prep HPLC: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 20 minutes, then a 5-minute hold at 100% B; Flow: 20 mL/min. Analytical HPLC: RT=0.61 min (H$_2$O/MeCN with 0.1% TFA, Waters Acquity BEH C18, 2.0×50 mm, 1.7-μm particles, gradient=1.5 min, wavelength=220 nm). MS (ES): m/z=432 [M+H]$^+$; $^1$H NMR (500 MHz, DMSO-d$_6$) δ 11.63 (s, 1H), 10.60 (br. s., 1H), 8.37 (d, J=4.6 Hz, 1H), 8.32 (d, J=5.1 Hz, 1H), 8.27 (br. s., 1H), 8.21 (br. s., 1H), 7.78 (d, J=8.3 Hz, 1H), 7.23 (d, J=4.6 Hz, 1H), 7.12 (d, J=4.6 Hz, 1H), 6.84 (d, J=8.6 Hz, 1H), 5.45 (br. s., 1H), 4.96 (t, J=5.0 Hz, 1H, should be a dd, but shows it as if it is a triplet), 3.85 (s, 3H), 2.08 (s, 3H), 1.90 (m, 1H), 0.89 (t, J=6.5 Hz, 6H, should be d or dd, but shows it as if it is a triplet).

Example 301

N-(4-(7-(1-Hydroxypropyl)-3-(6-methoxypyridin-3-yl)-1H-pyrrolo[3,2-b]pyridin-2-yl)pyridin-2-yl)acetamide

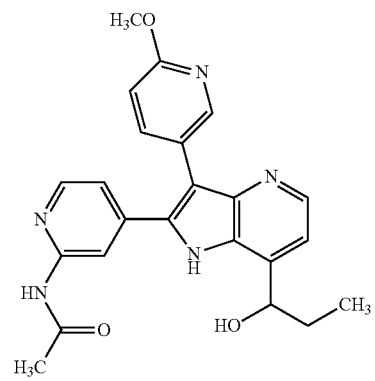 [SMILES: CCC(O)c1ccnc2c(-c3ccc(OC)nc3)c(-c3ccnc(NC(C)=O)c3)[nH]c12]

301A) N-(4-(5-Bromo-3-(6-methoxypyridin-3-yl)-7-propionyl-1-((2-(trimethylsilyl)ethoxy)methyl)-1H-pyrrolo[3,2-b]pyridin-2-yl)pyridin-2-yl)acetamide

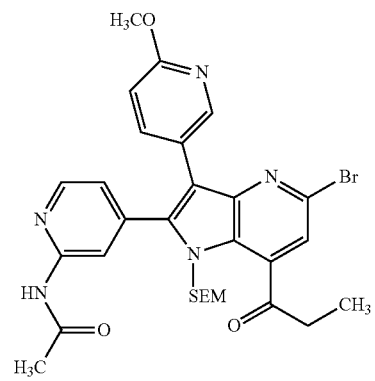 [SMILES: CCC(=O)c1cc(Br)nc2c(-c3ccc(OC)nc3)c(-c3ccnc(NC(C)=O)c3)n(COCC[Si](C)(C)C)c12]

To a solution of Example 298F (358 mg, 0.603 mmol) in THF (3 mL) at room temperature was added 3 mL of 1 M EtMgBr solution in THF slowly with stirring. After 30 min, the reaction mixture was cooled to −78° C. and an additional 2 mL of 2M iPrMgCl solution was added. The mixture was warmed to room temperature over 1 h. To the reaction mixture were added EtOAc (5 mL) and HOAc (2 mL), and it was stirred for 10 min. The reaction mixture was mixed with CH$_2$Cl$_2$ and aq NaHCO$_3$, the organic layer was separated, and the aq layer was washed with CH$_2$Cl$_2$. The combined CH$_2$Cl$_2$ layers were concentrated in vacuo. The residue was purified by prep HPLC to obtain Example 301A (80 mg, 0.155 mmol, 26%). Column #1, 20% B to 100% B over 8 min, RT=11 min. Column #1=Waters Sunfire C-18, 19×150 mm; Solvent A=10% CH₃CN/90% H₂O—0.1% TFA; Solvent B=90% CH₃CN/10% H₂O—0.1% TFA. MS (ES): m/z=624, 626 [M+H]⁺; ¹H NMR (400 MHz, CHLOROFORM-d) δ 11.92 (br.s., 1H), 8.71 (s, 1H), 8.17 (d, J=5.7 Hz, 1H), 8.08 (d, J=2.2 Hz, 1H), 7.82 (dd, J=8.6, 2.4 Hz, 1H), 7.46 (s, 1H), 7.13 (dd, J=5.7, 1.3 Hz, 1H), 6.85 (d, J=8.6 Hz, 1H), 5.33 (s, 2H), 3.95 (s, 3H), 3.15-3.13 (m, 2H), 3.06 (q, J=7.2 Hz, 2H), 2.31 (s, 3H), 1.29 (t, J=7.2 Hz, 3H), 0.74-0.69 (m, 2H), −0.08 (s, 9H).

301B) N-(4-(5-Bromo-3-(6-methoxypyridin-3-yl)-7-propionyl-1H-pyrrolo[3,2-b]pyridin-2-yl)pyridin-2-yl)acetamide

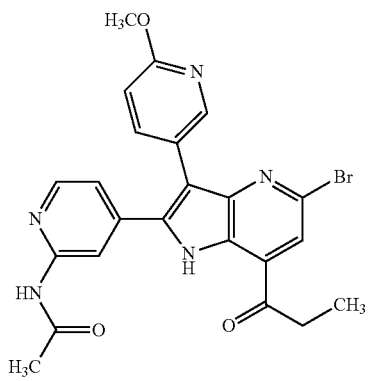 [SMILES: CCC(=O)c1cc(Br)nc2c(-c3ccc(OC)nc3)c(-c3ccnc(NC(C)=O)c3)[nH]c12]

To a solution of Example 301A (40 mg, 0.064 mmol) in CH₂Cl₂ (5 mL) at room temperature was added 1 mL TFA. The mixture was stirred for 6 h, and then concentrated in vacuo and the residue was purified by prep HPLC to obtain the TFA salt of Example 301B (20 mg, 0.033 mmol, 51%). Column #1, 20% B to 100% B over 8 min, RT=6.3 min.; Column #1=Waters Sunfire C-18, 19×150 mm; Solvent A=10% CH₃CN/90% H₂O—0.1% TFA; Solvent B=90% CH₃CN/10% H₂O—0.1% TFA. MS (ES): m/z=494, 496 [M+H]⁺; ¹H NMR (400 MHz, METHANOL-d₄) δ 8.35 (br. s., 1H), 8.29 (d, J=1.8 Hz, 1H), 8.00 (s, 1H), 7.94 (dd, J=8.7, 2.3 Hz, 1H), 7.78 (br. s., 1H), 7.52 (br. s., 1H), 7.03 (d, J=8.8 Hz, 1H), 4.01 (s, 3H), 3.22 (q, J=7.1 Hz, 2H), 2.26 (s., 3H), 1.28 (t, J=7.0 Hz, 3H).

Example 301) N-(4-(7-(1-Hydroxypropyl)-3-(6-methoxypyridin-3-yl)-1H-pyrrolo[3,2-b]pyridin-2-yl)pyridin-2-yl)acetamide A mixture of Example 301B (20 mg, 0.033 mmol) and 12 mg of 20% Pd(OH)₂/C in MeOH (10 mL) was stirred at rt under 1 atm of H₂ for 3.5 h. The reaction mixture was filtered, and the solid was washed with MeOH. The filtrate was concentrated in vacuo and the residue was purified by prep HPLC to obtain Example 301 (9.5 mg, 67%). Prep HPLC: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 20 minutes, then a 5-minute hold at 100% B; Flow: 20 mL/min. Analytical HPLC: RT=0.57 min (H₂O/MeCN with 0.1% TFA, Waters Acquity BEH C18, 2.0×50 mm, 1.7-μm particles, gradient=1.5 min, wavelength=220 nm). MS (ES): m/z=418 [M+H]⁺; ¹H NMR (500 MHz, DMSO-d₆) δ 11.66 (s, 1H), 10.61 (s, 1H), 8.37 (d, J=4.7 Hz, 1H), 8.33 (d, J=5.0 Hz, 1H), 8.29 (br. s., 1H), 8.21 (s, 1H), 7.80-7.76 (m, 1H), 7.26 (d, J=4.6 Hz, 1H), 7.12 (d, J=4.8 Hz, 1H), 6.84 (d, J=8.5 Hz, 1H), 5.46 (d, J=4.4 Hz, 1H), 5.13 (br. s., 1H), 3.86 (s, 3H), 2.09 (s, 3H), 1.84-1.69 (m, 2H), 0.92 (t, J=7.2 Hz, 3H).

Example 302

1-(2-(2-Acetamidopyridin-4-yl)-3-(6-methoxypyridin-3-yl)-1H-pyrrolo[3,2-b]pyridin-7-yl)propyl carbamate

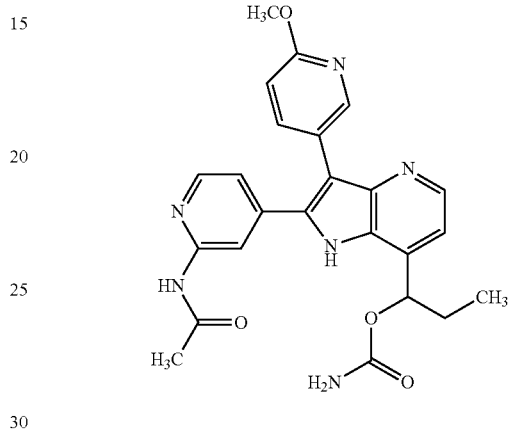

302A) N-(4-(3-(6-Methoxypyridin-3-yl)-7-propionyl-1-((2-(trimethylsilyl)ethoxy)methyl)-1H-pyrrolo[3,2-b]pyridin-2-yl)pyridin-2-yl)acetamide

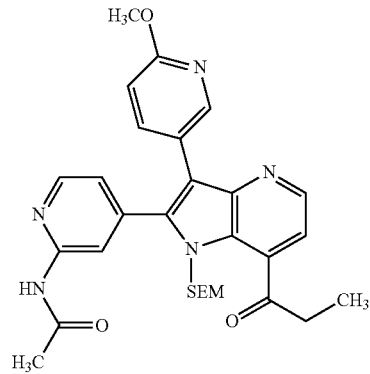 [SMILES: CCC(=O)c1ccnc2c(-c3ccc(OC)nc3)c(-c3ccnc(NC(C)=O)c3)n(COCC[Si](C)(C)C)c12]

To a solution of Example 298F (1.6 g, 2.70 mmol) in THF (30 mL) at −78° C. under N₂ atm was added an EtLi solution (30 mL of 0.5M solution in benzene-cyclohexane, Aldrich) with stirring. After 1.5 h, the mixture was warmed to −20° C. and 3 mL HOAc was added, along with 15 mL methanol and 1.5 mL water. The mixture was stirred, mostly concentrated in vacuo and the residue was passed through a flash column on SiO₂ eluting with hexane-EtOAc gradient to obtain Example 302A (400 mg, 0.733 mmol, 27%). MS (ES): m/z=546 [M+H]⁺; ¹H NMR (400 MHz, CHLOROFORM-d) δ 8.85 (s, 1H), 8.64 (d, J=4.8 Hz, 1H), 8.35 (br. s., 1H), 8.29 (d, J=5.1 Hz, 1H), 8.15-8.13 (m, 1H), 7.81 (dd, J=8.6, 2.4 Hz, 1H), 7.28 (s, 1H), 6.98 (dd, J=5.1, 1.5 Hz, 1H), 6.76 (dd, J=8.6, 0.4 Hz, 1H), 5.38 (s, 2H), 3.91 (s, 3H), 3.11-3.05 (m, 4H), 2.20 (s, 3H), 1.29 (t, J=7.0 Hz, 3H), 0.69-0.64 (m, 2H), −0.11 (s, 9H).

303B) N-(4-(7-(1-Hydroxypropyl)-3-(6-methoxypyridin-3-yl)-1-((2-(trimethylsilyl)ethoxy)methyl)-1H-pyrrolo[3,2-b]pyridin-2-yl)pyridin-2-yl)acetamide

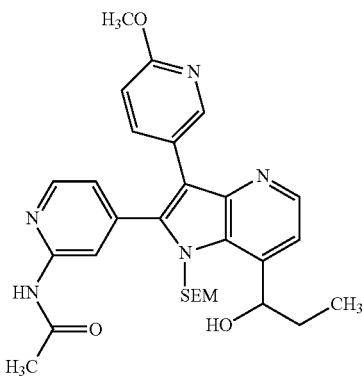 [SMILES: CCC(O)c1ccnc2c(-c3ccc(OC)nc3)c(-c3ccnc(NC(C)=O)c3)n(COCC[Si](C)(C)C)c12]

To a solution of Example 302A (400 mg, 0.733 mmol) in MeOH (15 mL) at ice bath temp was added NaBH$_4$ solid (160 mg) in several portions. The mixture was stirred for 2 h and 2 mL of acetone was added. The mixture was stirred for 10 min. and 2 mL HOAc was added. The mixture was concentrated in vacuo and the residue was passed through a flash column on SiO$_2$ eluting with CH$_2$Cl$_2$-EtOAc gradient (product was eluted at 80-100% EtOAc in CH$_2$Cl$_2$) to obtain Example 302B (310 mg, 0.566 mmol, 77%). MS (ES): m/z=548 [M+H]$^+$; $^1$H NMR (400 MHz, CHLOROFORM-d) δ 9.34 (br. s., 1H), 8.47 (d, J=4.8 Hz, 1H), 8.34 (br. s., 1H), 8.22-8.19 (m, 1H), 8.04 (d, J=2.2 Hz, 1H), 7.76 (dd, J=8.6, 2.4 Hz, 1H), 7.36 (d, J=5.4 Hz, 1H), 6.95 (dd, J=5.2, 1.2 Hz, 1H), 6.70 (d, J=8.6 Hz, 1H), 5.53-5.41 (m, 2H), 5.30 (dd, J=7.9, 4.6 Hz, 1H), 3.86 (s, 3H), 3.19 (dd, J=9.2, 7.5 Hz, 2H), 2.15 (s, 3H), 1.99-1.86 (m, 2H), 1.07 (t, J=7.4 Hz, 3H), 0.73 (t, J=8.5 Hz, 2H), −0.14 (s, 9H).

302C) 1-(2-(2-Acetamidopyridin-4-yl)-3-(6-methoxypyridin-3-yl)-1-((2-(trimethylsilyl)ethoxy)methyl)-1H-pyrrolo[3,2-b]pyridin-7-yl)propyl carbamate

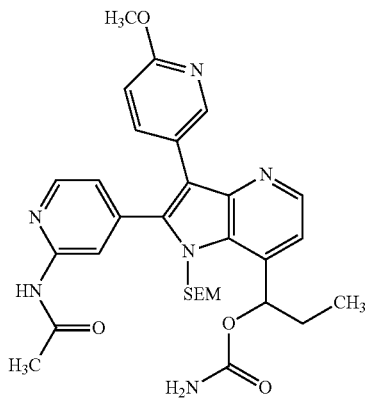 [SMILES: CCC(OC(N)=O)c1ccnc2c(-c3ccc(OC)nc3)c(-c3ccnc(NC(C)=O)c3)n(COCC[Si](C)(C)C)c12]

To a solution of Example 302B (165 mg, 0.301 mmol) in CH$_2$Cl$_2$ (5 mL) at ice bath temp was added 200 uL of trichloroacetylisocyanate slowly with stirring. In 30 min a solution of aq NH$_3$ in MeOH (0.6 mL of 28% NH$_3$ in water+4 mL MeOH) was added, stirring continued for 30 minutes at ice bath temp and then 5 h at room temperature. The mixture was mostly concentrated in vacuo and the residue was purified by prep HPLC to obtain the TFA salt of Example 302C (124 mg, 0.151 mmol, 50.3% yield). Prep HPLC: Column #1, 20% A to 100% B over 8 min, RT=5.2 min; Column #1=Waters Sunfire C-18, 19×150 mm; Solvent A=10% CH$_3$CN/90% H$_2$O—0.1% TFA; Solvent B=90% CH$_3$CN/10% H$_2$O—0.1% TFA. MS (ES): m/z=591 [M+H]$^+$; $^1$H NMR (400 MHz, CHLOROFORM-d) δ 10.91 (br. s., 1H), 8.67 (s, 1H), 8.64 (d, J=5.7 Hz, 1H), 8.19 (d, J=5.7 Hz, 1H), 8.01 (d, J=2.2 Hz, 1H), 7.65 (dd, J=8.6, 2.4 Hz, 1H), 7.61 (d, J=5.7 Hz, 1H), 7.09 (dd, J=5.6, 1.4 Hz, 1H), 6.81 (d, J=8.6 Hz, 1H), 6.30 (dd, J=7.9, 5.1 Hz, 1H), 6.06 (d, J=10.8 Hz, 1H), 5.25 (d, J=10.6 Hz, 1H), 5.11 (br. s, 2H), 3.93 (s, 3H), 3.50 (dd, J=9.1, 8.3 Hz, 2H), 2.27 (s, 3H), 2.04-1.95 (m, 2H), 1.12 (t, J=7.3 Hz, 3H), 1.07-0.90 (m, 2H), −0.01 (s, 9H).

Example 302) 1-(2-(2-Acetamidopyridin-4-yl)-3-(6-methoxypyridin-3-yl)-1H-pyrrolo[3,2-b]pyridin-7-yl)propyl carbamate To a solution of 2 TFA salt of Example 302C (124 mg, 0.151 mmol) in CH$_2$Cl$_2$ (5 mL) at room temperature was added 2.3 mL of TFA. The mixture was stirred for 7 h, and then concentrated and the residue was purified by prep HPLC to obtain partially purified material. Prep HPLC: Column #1, 20% A to 100% B over 8 min; Column #1=Waters Sunfire C-18, 19×150 mm; Solvent A=10% CH$_3$CN/90% H$_2$O—0.1% TFA; Solvent B=90% CH$_3$CN/10% H$_2$O—0.1% TFA. This material was repurified by prep HPLC to obtain Example 302 (13 mg, 0.028 mmol, 18.64% yield). Prep HPLC: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 10-50% B over 20 minutes, then a 5-minute hold at 100% B; Flow: 20 mL/min. Analytical HPLC: RT=0.59 min (H$_2$O/MeCN with 0.1% TFA, Waters Acquity BEH C18, 2.0×50 mm, 1.7-µm particles, gradient=1.5 min, wavelength=220 nm). MS (ES): m/z=461 [M+H]$^+$; $^1$H NMR (500 MHz, DMSO-d$_6$) δ 11.87 (s, 1H), 10.57 (s, 1H), 8.35 (d, J=4.7 Hz, 1H), 8.30 (d, J=5.1 Hz, 1H), 8.27 (s, 1H), 8.18 (d, J=1.9 Hz, 1H), 7.74 (dd, J=8.5, 2.1 Hz, 1H), 7.11 (d, J=4.8 Hz, 2H), 6.81 (d, J=8.6 Hz, 1H), 6.07 (m, 1H), 3.82 (s, 3H),), 2.05 (s, 3H), 1.91-1.75 (m, 2H), 0.91 (t, J=7.2 Hz, 3H).

Biological Assays

Assays are conducted in 1536-well plates and 2 µL reactions are prepared from addition of HIS-TGFβR1 T204D or HIS-TGFβR2 WT, anti-HIS detection antibody, a labeled small molecule probe (K$_d$=<100 nM; k$_{off}$=<0.001 s$^{-1}$) and test compounds in assay buffer (20 mM HEPES pH 7.4, 10 mM MgCl$_2$, 0.015% Brij35, 4 mM DTT, and 0.05 mg/ml BSA). The reaction is incubated for 1 hour at room temperature and the HTRF signal was measured on an Envision plate reader (Ex: 340 nm; Em: 520 nm/495 nm). Inhibition data were calculated by comparison to no enzyme control reactions for 100% inhibition and vehicle-only reactions for 0% inhibition. The final concentration of reagents in the assay are 1 nM HIS-TGFβR1 T204D or HIS-TGFβR2

WT, 0.2 nM anti-HIS detection antibody, labeled small molecule probe (at $K_d$) and 0.5% DMSO. Dose response curves were generated to determine the concentration required inhibiting 50% of kinase activity ($IC_{50}$). Compounds were dissolved at 10 mM in dimethylsulfoxide (DMSO) and evaluated at eleven concentrations. $IC_{50}$ values were derived by non-linear regression analysis.

Table 14 shows the TGFβR1 and TGFβR2 $IC_{50}$ values for the Examples of this invention.

TABLE 14

| Example # | TGFβR1 (μM) | TGFβR2 (μM) |
| --- | --- | --- |
| 1 | 0.002 | 0.73 |
| 2 | 0.006 | 7.85 |
| 3 | 0.001 | 0.089 |
| 4 | 0.022 | 0.007 |
| 5 | 0.002 | 14.61 |
| 6 | 0.003 | 0.39 |
| 7 | 0.002 | >15 |
| 8 | 0.009 | 2.03 |
| 9 | 0.023 | 0.33 |
| 10 | 0.057 | 0.01 |
| 11 | 0.027 | 0.009 |
| 12 | 0.058 | 1.31 |
| 13 | 0.002 | >15 |
| 14 | 0.002 | 0.027 |
| 15 | 0.017 | 13.1 |
| 16 | 0.002 | 0.087 |
| 17 | 0.014 | >15 |
| 18 | 0.005 | >15 |
| 19 | 0.023 | 0.19 |
| 20 | 0.005 | 1.69 |
| 21 | 1.49 | >15 |
| 22 | 0.039 | >15 |
| 23 | 0.003 | 0.68 |
| 24 | 0.018 | 0.21 |
| 26 | 0.006 | >15 |
| 27 | 0.72 | >15 |
| 28 | 0.2 | 6.05 |
| 29 | 0.017 | >15 |
| 30 | 0.32 | 0.49 |
| 31 | 0.019 | 0.66 |
| 32 | 0.049 | 0.44 |
| 33 | 0.005 | >15 |
| 34 | 0.002 | 0.13 |
| 36 | 0.002 | 0.06 |
| 37 | 0.002 | >15 |
| 38 | 0.002 | 0.11 |
| 39 | 0.002 | >15 |
| 40 | 0.005 | 0.067 |
| 41 | 0.002 | 0.13 |
| 42 | 0.004 | 0.46 |
| 43 | 0.002 | 0.068 |
| 44 | 0.027 | 0.34 |
| 45 | 0.003 | 0.11 |
| 46 | 0.008 | >15 |
| 47 | 0.004 | >15 |
| 48 | 0.001 | 0.076 |
| 49 | 0.003 | 0.24 |
| 50 | 0.003 | 6.57 |
| 51 | 0.002 | 0.61 |
| 52 | 0.041 | 0.45 |
| 53 | 0.002 | 0.005 |
| 54 | 0.021 | 3.61 |
| 55 | 0.003 | 0.069 |
| 56 | 0.017 | 1.1 |
| 57 | 0.019 | 0.11 |
| 58 | 0.017 | 9.23 |
| 59 | 0.021 | 6.37 |
| 60 | 0.32 | 6.65 |
| 61 | 0.005 | 0.98 |
| 62 | 0.009 | >15 |
| 63 | 0.019 | >15 |
| 64 | 0.009 | 0.3 |
| 65 | 0.01 | >15 |
| 66 | 0.002 | 3.72 |
| 67 | 0.037 | 0.36 |
| 68 | 0.96 | >15 |

TABLE 14-continued

| Example # | TGFβR1 (μM) | TGFβR2 (μM) |
| --- | --- | --- |
| 69 | 0.76 | >15 |
| 70 | 7.73 | >15 |
| 71 | 0.27 | 4.38 |
| 72 | 0.008 | 1.55 |
| 73 | 0.019 | 15.5 |
| 74 | 0.001 | 2.6 |
| 75 | 0.005 | 1.03 |
| 76 | 0.016 | 0.93 |
| 77 | 0.033 | >15 |
| 78 | 0.003 | 0.16 |
| 79 | 0.007 | 0.16 |
| 80 | 0.007 | 0.083 |
| 81 | 0.014 | 0.26 |
| 82 | 0.006 | 4.05 |
| 83 | 0.002 | >15 |
| 84 | 0.002 | 0.13 |
| 85 | 0.01 | 4.05 |
| 86 | 0.008 | >15 |
| 87 | 0.002 | >15 |
| 88 | 0.001 | 9.92 |
| 89 | 0.003 | 4.81 |
| 90 | 0.004 | 3.67 |
| 91 | 0.019 | >15 |
| 92 | 0.002 | >15 |
| 93 | 0.003 | >15 |
| 94 | 0.004 | >15 |
| 95 | 0.002 | >15 |
| 96 | 0.001 | >15 |
| 97 | 0.001 | >15 |
| 98 | 0.002 | >15 |
| 99 | n/a | 2.75 |
| 100 | n/a | 2.62 |
| 101 | n/a | 4.29 |
| 102 | n/a | 3.45 |
| 103 | n/a | 4.92 |
| 104 | 0.002 | 6.29 |
| 105 | 0.005 | >15 |
| 106 | 0.003 | >15 |
| 107 | 0.001 | 8.14 |
| 108 | 0.145 | >15 |
| 109 | 0.011 | 14.1 |
| 110 | 0.053 | >15 |
| 111 | 0.002 | 2.42 |
| 112 | 0.001 | 8.75 |
| 113 | 0.003 | 14.6 |
| 114 | 0.55 | >15 |
| 115 | 0.001 | 8.68 |
| 116 | 0.005 | 7.35 |
| 117 | 0.003 | 11.3 |
| 118 | 0.002 | >15 |
| 119 | <0.001 | >15 |
| 120 | 0.001 | >15 |
| 121 | 0.001 | >15 |
| 122 | 0.001 | >15 |
| 123 | <0.001 | >15 |
| 124 | 0.001 | 12.8 |
| 125 | 0.003 | >15 |
| 126 | 0.009 | >15 |
| 127 | 0.001 | 6.65 |
| 128 | n/a | 5.26 |
| 129 | 0.007 | >15 |
| 130 | 0.004 | >15 |
| 131 | 0.001 | 3.84 |
| 132 | 0.001 | >15 |
| 133 | 0.001 | >15 |
| 134 | 0.004 | 8.66 |
| 135 | 0.003 | >15 |
| 136 | 0.006 | >15 |
| 137 | 0.058 | >15 |
| 138 | 0.200 | >15 |
| 139 | 0.001 | 8.47 |
| 140 | 0.001 | 7.60 |
| 141 | 0.003 | 27.3 |
| 142 | 0.001 | 7.81 |
| 143 | 0.001 | 2.53 |
| 144 | 0.001 | 0.361 |
| 145 | 0.002 | 2.94 |
| 146 | 0.001 | 1.78 |

TABLE 14-continued

| Example # | TGFβR1 (μM) | TGFβR2 (μM) |
| --- | --- | --- |
| 147 | 0.002 | 0.750 |
| 148 | 0.001 | 0.484 |
| 149 | 0.002 | 8.37 |
| 150 | 0.001 | 6.08 |
| 151 | 0.010 | >15 |
| 152 | 0.002 | 4.09 |
| 153 | n/a | n/a |
| 154 | 0.001 | 1.77 |
| 155 | 0.001 | 3.47 |
| 156 | 0.188 | >15 |
| 157 | 0.0013 | >15 |
| 158 | 0.0163 | >15 |
| 159 | 0.0311 | >15 |
| 160 | 0.0110 | >15 |
| 161 | 0.0126 | >15 |
| 162 | 0.0279 | >15 |
| 163 | 0.0304 | >15 |
| 164 | 0.0053 | >15 |
| 165 | 0.0353 | >15 |
| 166 | 0.0132 | >15 |
| 167 | 0.0171 | >15 |
| 168 | 0.0138 | 1.188 |
| 169 | 0.0023 | 0.882 |
| 170 | 0.0320 | >15 |
| 171 | 0.0010 | 10.763 |
| 172 | 0.0004 | 3.982 |
| 173 | 0.1498 | 1.352 |
| 174 | 0.0034 | >15 |
| 175 | 0.0004 | >15 |
| 176 | 0.0005 | 0.037 |
| 177 | 0.0014 | >15 |
| 178 | 0.0035 | 0.176 |
| 179 | 0.0580 | >15 |
| 180 | 0.0274 | >15 |
| 181 | n/a | 1.068 |
| 182 | 0.1822 | >15 |
| 183 | 0.0030 | 0.407 |
| 184 | 6.5186 | >15 |
| 185 | 7.0006 | >15 |
| 186 | 0.0029 | 0.821 |
| 187 | 0.0587 | 0.424 |
| 188 | 0.0104 | 0.240 |
| 189 | 0.2489 | 0.089 |
| 190 | 0.0443 | 7.556 |
| 191 | 0.0939 | 1.996 |
| 192 | 0.1095 | >15 |
| 193 | 0.0006 | >15 |
| 194 | 0.0050 | 4.309 |
| 195 | 0.0048 | >15 |
| 196 | 0.0951 | 1.211 |
| 197 | 3.5430 | >15 |
| 198 | 0.0011 | 1.478 |
| 199 | 0.0006 | 0.041 |
| 200 | 0.0007 | 0.548 |
| 201 | 0.0275 | 1.533 |
| 202 | 0.0015 | 0.225 |
| 203 | 0.7743 | >15 |
| 204 | 0.0055 | 0.111 |
| 205 | 0.0029 | 0.147 |
| 206 | 0.0068 | 0.325 |
| 207 | n/a | 5.655 |
| 208 | 0.0006 | 0.044 |
| 209 | 0.0009 | 0.218 |
| 210 | 0.0025 | 0.815 |
| 211 | 0.0049 | 1.043 |
| 212 | 0.0005 | 8.822 |
| 213 | 0.0061 | 0.118 |
| 214 | 0.0014 | 0.173 |
| 215 | 0.0885 | 0.999 |
| 216 | 0.0013 | 3.773 |
| 217 | >15 | >15 |
| 218 | 0.0017 | 0.594 |
| 219 | 0.0006 | 0.082 |
| 220 | 0.0005 | 1.379 |
| 221 | 0.0037 | 1.357 |
| 222 | 0.0015 | 0.129 |
| 223 | 0.0008 | 0.043 |
| 224 | 0.0012 | 0.544 |
| 225 | 0.0007 | 0.057 |
| 226 | 0.0041 | 1.551 |
| 227 | 0.0006 | 0.725 |
| 228 | n/a | 4.241 |
| 229 | 0.0014 | 10.934 |
| 230 | 0.0024 | 0.037 |
| 231 | 0.0010 | 9.108 |
| 232 | 0.0030 | 0.115 |
| 233 | 0.0014 | 4.062 |
| 234 | 0.0016 | 0.572 |
| 235 | 0.001 | 0.176 |
| 237 | 0.1112 | >15 |
| 238 | 0.0882 | >15 |
| 239 | 0.0746 | 3.276 |
| 240 | 0.5942 | >15 |
| 241 | 0.004 | 3.67 |
| 242 | 0.033 | 15 |
| 243 | 0.361 | 15 |
| 244 | 0.003 | 7.82 |
| 245 | 0.002 | 4.07 |
| 246 | 0.001 | 5.99 |
| 247 | 0.003 | 15 |
| 248 | 0.002 | 14.45 |
| 249 | 0.007 | >15 |
| 250 | 0.007 | >15 |
| 251 | 0.005 | >15 |
| 252 | 0.001 | >15 |
| 253 | 0.004 | >15 |
| 254 | 0.065 | >15 |
| 255 | 0.433 | >15 |
| 256 | 0.020 | >15 |
| 257 | 0.003 | 6.21 |
| 258 | 0.002 | 6.29 |
| 259 | 0.535 | >15 |
| 260 | 0.049 | >15 |
| 261 | 0.005 | 0.011 |
| 262 | 0.002 | 0.267 |
| 263 | 0.001 | 0.279 |
| 264 | 0.001 | 0.681 |
| 265 | 0.004 | 1.054 |
| 266 | 0.005 | >15 |
| 267 | 0.002 | >15 |
| 268 | 0.005 | 2.45 |
| 269 | 0.067 | 1.038 |
| 270 | n/a | 7.545 |
| 271 | 0.002 | 0.352 |
| 272 | 0.001 | 1.85 |
| 273 | n/a | 1.359 |
| 274 | 0.001 | 0.114 |
| 275 | 0.003 | 0.637 |
| 276 | 0.001 | 0.503 |
| 277 | 0.006 | 0.010 |
| 278 | 0.011 | 0.709 |
| 279 | 0.006 | 9.90 |
| 280 | 0.023 | 4.12 |
| 281 | 0.001 | 0.984 |
| 282 | 0.001 | 1.850 |
| 283 | 0.001 | 1.122 |
| 284 | 0.003 | 5.222 |
| 285 | 0.002 | 0.016 |
| 286 | 0.001 | 0.253 |
| 287 | 0.001 | 0.668 |
| 288 | 0.002 | 0.487 |
| 289 | 0.002 | 0.794 |
| 290 | 0.002 | 1.124 |
| 291 | 0.001 | 1.664 |
| 292 | 0.001 | 1.514 |
| 293 | 0.016 | >15 |
| 294 | 0.063 | >15 |
| 295 | 0.001 | >15 |
| 296 | 0.002 | 7.780 |
| 297 | 0.004 | 4.328 |
| 298 | 0.008 | 0.120 |
| 299 | 0.002 | 0.038 |
| 300 | 0.003 | 0.017 |
| 301 | 0.001 | 0.031 |
| 302 | 0.001 | 0.723 |

What is claimed is:

1. The compound of the formula

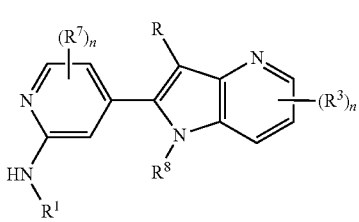

wherein:

R is

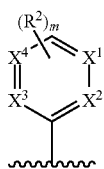

or a heterocyclic or heterobicyclic group substituted with 0-4 $R^2$;

$X^1$, $X^2$, $X^3$ and $X^4$ are independently —CH— or —N—, wherein at least one is —N—;

$R^1$ is hydrogen, $(C_1$-$C_6)$alkyl, $(C_3$-$C_8)$cycloalkyl, —$CONHR^9$, —$COOR^9$, —$COR^9$ or —$SO_2R^9$, any of which except the hydrogen is substituted with 0-3 $R^x$;

$R^x$ is hydrogen, halogen, —OH, halo$(C_1$-$C_3)$alkyl, hydroxy$(C_1$-$C_3)$alkyl, -amino$(C_1$-$C_3)$alkyl, or —CN;

$R^2$ is independently one or more hydrogen, —$CD_3$, $OCD_3$, halogen, —$CF_3$, —$CHF_2$, —CN, $(C_1$-$C_6)$alkyl, $(C_1$-$C_6)$alkoxy or —$SO_2$ $(C_1$-$C_6)$alkyl;

$R^3$ is independently one or more hydrogen, $CD_3$, $OCD_3$, halogen, —CN, $(C_1$-$C_6)$alkyl, $(C_2$-$C_6)$alkenyl, $(C_1$-$C_6)$ alkoxy, $(C_3$-$C_8)$cycloalkyl, hydroxy$(C_1$-$C_3)$alkyl, $(C_1$-$C_6)$alkylamino-, $(C_1$-$C_6)$alkylamino$(C_1$-$C_6)$alkyl, 5-6 membered heteroaryl, heterocyclyl, O-heterocyclyl, —$NR^5R^6$, —$CONR^5R^6$, —$COOR^4$, —$COR^4$, —$SO_2R^4$, —$CHCF_2COOCH_2OH$ or —$CHCF_2CONH_2$, any of which except the hydrogen is substituted with 0-4 $R^y$;

$R^y$ is hydrogen, halogen, —OH, $(C_1$-$C_3)$alkyl, halo$(C_1$-$C_3)$alkyl, hydroxy$(C_1$-$C_3)$alkyl, -amino$(C_1$-$C_3)$alkyl, —NHCOOH, or —CN;

$R^4$ is hydrogen or $(C_1$-$C_6)$alkyl;

$R^5$ and $R^6$ are independently hydrogen, —C(O)alkyl or $(C_1$-$C_6)$alkyl; or $R^5$ and $R^6$ can be taken together with the nitrogen atom to which they are attached to form a 5-7 membered heterocyclo ring;

$R^7$ is independently one or more hydrogen, halogen, halo$(C_1$-$C_6)$alkyl or —CN;

$R^8$ is hydrogen, $(C_1$-$C_6)$alkyl, $(C_3$-$C_8)$cycloalkyl, —$CONHR^9$, —$COOR^9$, —$COR^9$ or —$SO_2R^9$;

$R^9$ is hydrogen, $(C_1$-$C_6)$alkyl, $(C_3$-$C_8)$cycloalkyl, heterocyclylalkyl-, heterocyclyl$(C_1$-$C_3)$alkylamino$(C_1$-$C_3)$alkyl- or $(C_1$-$C_3)$alkylamino$(C_1$-$C_3)$alkyl;

m is 0, 1, 2, 3, or 4;

n is 0, 1, 2 or 3;

and/or a pharmaceutically acceptable salt, tautomer or stereoisomer thereof.

2. A compound according to claim 1 of formula (II)

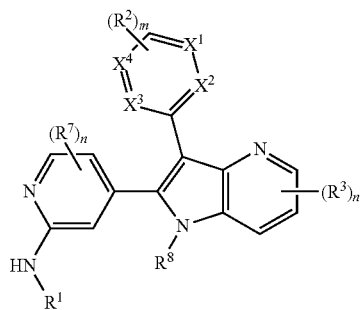

wherein:

$X^1$, $X^2$, $X^3$ and $X^4$ are independently —CH— or —N—, wherein at least one is —N—;

$R^1$ is hydrogen, $(C_1$-$C_6)$alkyl, $(C_3$-$C_8)$cycloalkyl, —$CONHR^9$, —$COOR^9$, —$COR^9$ or —$SO_2R^9$, any of which except the hydrogen is substituted with 0-3 $R^x$;

$R^x$ is hydrogen, halogen, —OH, halo$(C_1$-$C_3)$alkyl, hydroxy$(C_1$-$C_3)$alkyl, -amino$(C_1$-$C_3)$alkyl, or —CN;

$R^2$ is independently one or more hydrogen, —$CD_3$, $OCD_3$, halogen, —$CF_3$, —$CHF_2$, —CN, $(C_1$-$C_6)$alkyl, $(C_1$-$C_6)$alkoxy or —$SO_2$ $(C_1$-$C_6)$alkyl;

$R^3$ is independently one or more hydrogen, $CD_3$, $OCD_3$, halogen, —CN, $(C_1$-$C_6)$alkyl, $(C_2$-$C_6)$alkenyl, $(C_1$-$C_6)$ alkoxy, $(C_3$-$C_8)$cycloalkyl, hydroxy$(C_1$-$C_3)$alkyl, $(C_1$-$C_6)$alkylamino-, $(C_1$-$C_6)$alkylamino$(C_1$-$C_6)$alkyl, 5-6 membered heteroaryl, heterocyclyl, O-heterocyclyl, —$NR^5R^6$, —$CONR^5R^6$, —$COOR^4$, —$COR^4$, —$SO_2R^4$, —$CHCF_2COOCH_2OH$ or —$CHCF_2CONH_2$, any of which except the hydrogen is substituted with 0-4 $R^y$;

$R^y$ is hydrogen, halogen, —OH, $(C_1$-$C_3)$alkyl, halo$(C_1$-$C_3)$alkyl, hydroxy$(C_1$-$C_3)$alkyl, -amino$(C_1$-$C_3)$alkyl, —NHCOOH, or —CN;

$R^4$ is hydrogen or $(C_1$-$C_6)$alkyl;

$R^5$ and $R^6$ are independently hydrogen, —C(O)alkyl or $(C_1$-$C_6)$alkyl; or $R^5$ and $R^6$ can be taken together with the nitrogen atom to which they are attached to form a 5-7 membered heterocyclo ring;

$R^7$ is independently one or more hydrogen, halogen, halo$(C_1$-$C_6)$alkyl or —CN;

$R^8$ is hydrogen, $(C_1$-$C_6)$alkyl, $(C_3$-$C_8)$cycloalkyl, —$CONHR^9$, —$COOR^9$, —$COR^9$ or —$SO_2R^9$;

$R^9$ is hydrogen, $(C_1$-$C_6)$alkyl, $(C_3$-$C_8)$cycloalkyl, heterocyclylalkyl-, heterocyclyl$(C_1$-$C_3)$alkylamino$(C_1$-$C_3)$alkyl- or $(C_1$-$C_3)$alkylamino$(C_1$-$C_3)$alkyl;

m is 0, 1, 2, 3, or 4;

n is 0, 1, 2 or 3;

and/or a pharmaceutically acceptable salt, tautomer or stereoisomer thereof.

3. A compound according to claim 2 of the formula

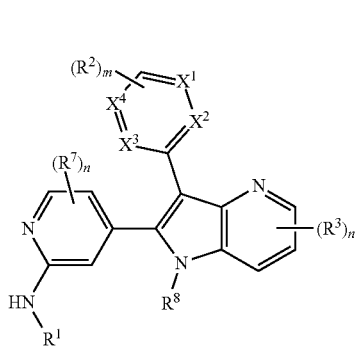

(II)

wherein:

$X^1$, $X^2$, $X^3$ and $X^4$ are independently —CH— or —N—, wherein at least one is —N—;

$R^1$ is hydrogen, $(C_1-C_6)$alkyl, $(C_3-C_8)$cycloalkyl, —CONHR$^9$, —COOR$^9$, —COR$^9$ or —SO$_2$R$^9$, any of which except the hydrogen is substituted with 0-3 R$^x$;

$R^x$ is hydrogen, halogen, —OH, halo$(C_1-C_3)$alkyl, hydroxy$(C_1-C_3)$alkyl, -amino$(C_1-C_3)$alkyl, or —CN;

$R^2$ is independently one or more hydrogen, —CD$_3$, OCD$_3$, halogen, —CF$_3$, —CHF$_2$, —CN, $(C_1-C_3)$alkyl, $(C_1-C_3)$alkoxy or —SO$_2(C_1-C_3)$alkyl;

$R^3$ is independently one or more hydrogen, CD$_3$, OCD$_3$, halogen, —CN, $(C_1-C_3)$alkyl, $(C_2-C_6)$alkenyl, $(C_1-C_3)$alkoxy, $(C_3-C_8)$cycloalkyl, hydroxy$(C_1-C_3)$alkyl, $(C_1-C_3)$alkylamino-, $(C_1-C_3)$alkylamino$(C_1-C_3)$alkyl, 5-6 membered heteroaryl, heterocyclyl, O-heterocyclyl, —NR$^5$R$^6$, —CONR$^5$R$^6$, —COOR$^4$, —COR$^4$, —SO$_2$R$^4$, —CHCF$_2$COOCH$_2$OH or —CHCF$_2$CONH$_2$, any Of which except the hydrogen is substituted with 0-4 R$^y$;

$R^y$ is hydrogen, halogen, —OH, $(C_1-C_3)$alkyl, halo$(C_1-C_3)$alkyl, hydroxy$(C_1-C_3)$alkyl, -amino$(C_1-C_3)$alkyl, —NHCOOH, or —CN;

$R^4$ is hydrogen or $(C_1-C_6)$alkyl;

$R^5$ and $R^6$ are independently hydrogen, —C(O)alkyl or $(C_1-C_6)$alkyl; or $R^5$ and $R^6$ can be taken together with the nitrogen atom to which they are attached to form a 5-7 membered heterocyclo ring;

$R^7$ is independently one or more hydrogen, halogen, halo$(C_1-C_6)$alkyl or —CN;

$R^8$ is hydrogen, $(C_1-C_6)$alkyl, $(C_3-C_5)$cycloalkyl, —CONHR$^9$, —COOR$^9$, —COR$^9$ or —SO$_2$R$^9$;

$R^9$ is hydrogen, $(C_1-C_6)$alkyl, $(C_3-C_8)$cycloalkyl, heterocyclylalkyl-, heterocyclyl$(C_1-C_3)$alkylamino$(C_1-C_3)$alkyl- or $(C_1-C_3)$alkylamino$(C_1-C_3)$alkyl;

m is 0, 1, 2, 3, or 4;

n is 0, 1, 2 or 3;

and/or a pharmaceutically acceptable salt, tautomer or stereoisomer thereof.

4. A compound according to claim 3 of the formula

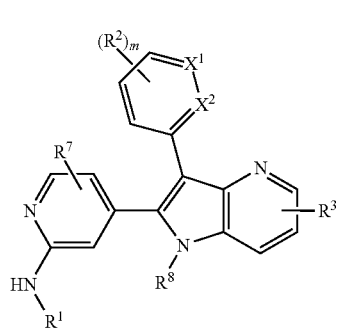

(II')

wherein:

$X^1$ and $X^2$ are independently —CH or —N—, wherein at least one is —N—;

$R^1$ is hydrogen, $(C_1-C_3)$alkyl, $(C_3-C_8)$cycloalkyl, —CONHR$^9$, —COOR$^9$, —COR$^9$ or —SO$_2$R$^9$, any of which except the hydrogen is substituted with 0-3 R$^x$;

$R^x$ is hydrogen, halogen, —OH, halo$(C_1-C_3)$alkyl, hydroxy$(C_1-C_3)$alkyl, -amino$(C_1-C_3)$alkyl, or —CN;

$R^2$ is independently one or more hydrogen, —CD$_3$, OCD$_3$, halogen, —CF$_3$, —CHF$_2$, —CN, $(C_1-C_3)$alkyl, $(C_1-C_3)$alkoxy or —SO$_2$ $(C_1-C_3)$alkyl;

$R^3$ is independently one or more hydrogen, CD$_3$, OCD$_3$, halogen, —CN, $(C_1-C_3)$alkyl, $(C_2-C_6)$alkenyl, $(C_1-C_3)$alkoxy, $(C_3-C_8)$cycloalkyl, hydroxy$(C_1-C_3)$alkyl, $(C_1-C_3)$alkylamino-, $(C_1-C_3)$alkylamino$(C_1-C_3)$alkyl, 5-6 membered heteroaryl, heterocyclyl, O-heterocyclyl, —NR$^5$R$^6$, —CONR$^5$R$^6$, —COOR$^4$, —COR$^4$, —SO$_2$R$^4$, —CHCF$_2$COOCH$_2$OH or —CHCF$_2$CONH$_2$, any of which except the hydrogen is substituted with 0-4 R$^y$;

$R^y$ is hydrogen, halogen, —OH, $(C_1-C_3)$alkyl, halo$(C_1-C_3)$alkyl, hydroxy$(C_1-C_3)$alkyl, -amino$(C_1-C_3)$alkyl, —NHCOOH, or —CN;

$R^4$ is hydrogen or $(C_1-C_3)$alkyl;

$R^5$ and $R^6$ are independently hydrogen, —C(O)alkyl or $(C_1-C_3)$alkyl; or $R^5$ and $R^6$ can be taken together with the nitrogen atom to which they are attached to form a 5-7 membered heterocyclo ring;

$R^7$ is independently one or more hydrogen, halogen, halo$(C_1-C_3)$alkyl or —CN;

$R^8$ is hydrogen, $(C_1-C_3)$alkyl, $(C_3-C_6)$cycloalkyl, —CONHR$^9$, —COOR$^9$, —COR$^9$ or —SO$_2$R$^9$;

$R^9$ is hydrogen, $(C_1-C_3)$alkyl, $(C_3-C_6)$cycloalkyl, heterocyclylalkyl-, heterocyclyl$(C_1-C_3)$alkylamino$(C_1-C_3)$alkyl- or $(C_1-C_3)$alkylamino$(C_1-C_3)$alkyl;

m is 0, 1, 2, 3, or 4;

and/or a pharmaceutically acceptable salt, tautomer or stereoisomer thereof.

5. A compound according to claim 4 of the formula

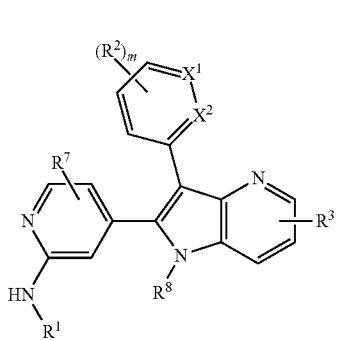

(II')

wherein:
- $X^1$ and $X^2$ are independently —CH or —N—, wherein at least one is —N—;
- $R^1$ is hydrogen, $(C_1\text{-}C_3)$alkyl, $(C_4\text{-}C_6)$cycloalkyl, —CONHR$^9$, —COOR$^9$, —COR$^9$ or —SO$_2$R$^9$, any of which except the hydrogen is substituted with 0-3 R$^x$;
- $R^x$ is hydrogen, halogen, —OH, halo$(C_1\text{-}C_3)$alkyl, hydroxy$(C_1\text{-}C_3)$alkyl, -amino$(C_1\text{-}C_3)$alkyl, or —CN;
- $R^2$ is independently one or more hydrogen, —CD$_3$, OCD$_3$, halogen, —CF$_3$, —CHF$_2$, —CN, $(C_1\text{-}C_3)$alkyl, $(C_1\text{-}C_3)$alkoxy or —SO$_2$ $(C_1\text{-}C_3)$alkyl;
- $R^3$ is independently one or more hydrogen, CD$_3$, OCD$_3$, halogen, —CN, $(C_1\text{-}C_3)$alkyl, $(C_2\text{-}C_6)$alkenyl, $(C_1\text{-}C_3)$alkoxy, $(C_3\text{-}C_8)$cycloalkyl, hydroxy$(C_1\text{-}C_3)$alkyl, $(C_1\text{-}C_3)$alkylamino-, $(C_1\text{-}C_3)$alkylamino$(C_1\text{-}C_3)$alkyl, 5-6 membered heteroaryl, heterocyclyl, O-heterocyclyl, —NR$^5$R$^6$, —CONR$^5$R$^6$, —COOR$^4$, —COR$^4$, —SO$_2$R$^4$, —CHCF$_2$COOCH$_2$OH or —CHCF$_2$CONH$_2$, any of which except the hydrogen is substituted with 0-4 R$^y$;
- $R^y$ is hydrogen, halogen, —OH, $(C_1\text{-}C_3)$alkyl, halo$(C_1\text{-}C_3)$alkyl, hydroxy$(C_1\text{-}C_3)$alkyl, -amino$(C_1\text{-}C_3)$alkyl, —NHCOOH, or —CN;
- $R^4$ is hydrogen or methyl;
- $R^5$ and $R^6$ are independently hydrogen, —C(O)alkyl or $(C_1\text{-}C_3)$alkyl; or
- $R^5$ and $R^6$ can be taken together with the nitrogen atom to which they are attached to form a 5-7 membered heterocyclo ring;
- $R^7$ is independently one or more hydrogen, halogen, halo$(C_1\text{-}C_3)$alkyl or —CN;
- $R^8$ is hydrogen, $(C_1\text{-}C_3)$alkyl, or —COR$^9$;
- $R^9$ is hydrogen, $(C_1\text{-}C_3)$alkyl, $(C_3\text{-}C_6)$cycloalkyl, heterocyclylalkyl-, heterocyclyl$(C_1\text{-}C_3)$alkylamino$(C_1\text{-}C_3)$alkyl- or $(C_1\text{-}C_3)$alkylamino$(C_1\text{-}C_3)$alkyl;
- m is 0, 1 or 2;

and/or a pharmaceutically acceptable salt, tautomer or stereoisomer thereof.

6. A compound according to claim 1 wherein:
- R is thiazole, thiadiazole, thiophene, pyrazole, isoquinoline, indole or quinoline substituted with 0-4 R$^2$;
- $R^1$ is hydrogen, $(C_1\text{-}C_3)$alkyl, $(C_3\text{-}C_6)$cycloalkyl, —CONHR$^9$, —COOR$^9$, —COR$^9$ or —SO$_2$R$^9$, any of which except the hydrogen is substituted with 0-3 R$^x$;
- $R^x$ is hydrogen, halogen, —OH, halo$(C_1\text{-}C_3)$alkyl, hydroxy$(C_1\text{-}C_3)$alkyl, -amino$(C_1\text{-}C_3)$alkyl, or —CN;
- $R^2$ is independently one or more hydrogen, —CD$_3$, OCD$_3$, halogen, —CF$_3$, —CHF$_2$, —CN, $(C_1\text{-}C_6)$alkyl, $(C_1\text{-}C_6)$alkoxy or —SO$_2$ $(C_1\text{-}C_6)$alkyl;
- $R^3$ is independently one or more hydrogen, CD$_3$, OCD$_3$, halogen, —CN, $(C_1\text{-}C_3)$alkyl, $(C_2\text{-}C_6)$alkenyl, $(C_1\text{-}C_3)$alkoxy, $(C_3\text{-}C_8)$cycloalkyl, hydroxy$(C_1\text{-}C_3)$alkyl, $(C_1\text{-}C_3)$alkylamino-, $(C_1\text{-}C_3)$alkylamino$(C_1\text{-}C_3)$alkyl, 5-6 membered heteroaryl, heterocyclyl, O-heterocyclyl, —NR$^5$R$^6$, —CONR$^5$R$^6$, —COOR$^4$, —COR$^4$, —SO$_2$R$^4$, —CHCF$_2$COOCH$_2$OH or —CHCF$_2$CONH$_2$, any of which except the hydrogen is substituted with 0-4 R$^y$;
- $R^y$ is hydrogen, halogen, —OH, $(C_1\text{-}C_3)$alkyl, halo$(C_1\text{-}C_3)$alkyl, hydroxy$(C_1\text{-}C_3)$alkyl, -amino$(C_1\text{-}C_3)$alkyl, —NHCOOH, or —CN;
- $R^4$ is hydrogen or methyl;
- $R^5$ and $R^6$ are independently hydrogen, —C(O)alkyl or $(C_1\text{-}C_3)$alkyl;
- $R^7$ is independently one or more hydrogen, halogen, halo$(C_1\text{-}C_3)$alkyl or —CN;
- $R^8$ is hydrogen, $(C_1\text{-}C_3)$alkyl, $(C_3\text{-}C_6)$cycloalkyl, —CONHR$^9$, —COOR$^9$, —COR$^9$ or —SO$_2$R$^9$;
- $R^9$ is hydrogen, $(C_1\text{-}C_3)$alkyl, $(C_3\text{-}C_6)$cycloalkyl, heterocyclylalkyl-, heterocyclyl$(C_1\text{-}C_3)$alkylamino$(C_1\text{-}C_3)$alkyl- or $(C_1\text{-}C_3)$alkylamino$(C_1\text{-}C_3)$alkyl;
- n is 0, 1, 2 or 3;

and/or a pharmaceutically acceptable salt, tautomer or stereoisomer thereof.

7. A compound according to claim 6 wherein:
- R is thiazole, pyrazole, isoquinoline, indole or quinoline substituted with 0-4 R$^2$;
- $R^1$ is —COR$^9$ substituted with 0-2 R$^x$;
- $R^x$ is hydrogen, halogen, —OH, halo$(C_1\text{-}C_3)$alkyl, hydroxy$(C_1\text{-}C_3)$alkyl, -amino$(C_1\text{-}C_3)$alkyl, or —CN;
- $R^2$ is independently one or more hydrogen, —CD$_3$, OCD$_3$, halogen, —CF$_3$, —CHF$_2$, —CN, $(C_1\text{-}C_3)$alkyl, $(C_1\text{-}C_3)$alkoxy or —SO$_2$ $(C_1\text{-}C_3)$alkyl;
- $R^3$ is independently one or more hydrogen, halogen, —CN, $(C_1\text{-}C_3)$alkyl, $(C_1\text{-}C_3)$alkoxy, $(C_3\text{-}C_6)$cycloalkyl, 5-6 membered heteroaryl, heterocyclo, —NR$^5$R$^6$, —CONR$^5$R$^6$, —COOR$^4$, —SO$_2$R$^4$ or $(C_1\text{-}C_3)$alkylamino substituted with 0-2 R$^y$;
- $R^y$ is hydrogen, halogen, —OH, $(C_1\text{-}C_3)$alkyl, halo$(C_1\text{-}C_3)$alkyl, hydroxy$(C_1\text{-}C_3)$alkyl, -amino$(C_1\text{-}C_3)$alkyl, —NHCOOH, or —CN;
- $R^4$ is hydrogen or methyl;
- $R^5$ and $R^6$ are independently hydrogen, —C(O)alkyl or $(C_1\text{-}C_3)$alkyl;
- $R^7$ is independently one or more hydrogen, halogen, halo$(C_1\text{-}C_3)$alkyl or —CN;
- $R^8$ is hydrogen;
- $R^9$ is hydrogen, $(C_1\text{-}C_3)$alkyl or $(C_3\text{-}C_6)$cycloalkyl;
- n is 0, 1 or 2;

and/or a pharmaceutically acceptable salt, tautomer or stereoisomer thereof.

8. A compound according to claim 7 wherein:
- R is thiazole, isoquinoline, indole or quinoline substituted with 0-4 R$^2$;
- $R^1$ is —COR$^9$;
- $R^2$ is independently one or more hydrogen, halogen, —CF$_3$, —CN, $(C_1\text{-}C_3)$alkyl, $(C_1\text{-}C_3)$alkoxy or —SO$_2$ $(C_1\text{-}C_3)$alkyl;
- $R^3$ is independently one or more hydrogen, halogen, —CN or $(C_1\text{-}C_3)$alkyl;
- $R^7$ is independently one or more hydrogen, halogen, halo$(C_1\text{-}C_3)$alkyl or —CN;
- $R^8$ is hydrogen;
- $R^9$ is hydrogen or $(C_1\text{-}C_3)$alkyl;
- n is 0, 1 or 2;

or a pharmaceutically acceptable salt, tautomer or stereoisomer thereof.

9. A compound according to claim 1 selected from the following
N-{4-[6-Fluoro-3-(6-methoxypyridin-3-yl)-H-pyrrolo[3,2-b]pyridin-2-yl]pyridin-2-yl}acetamide,
N-{4-[6-Chloro-3-(5-fluoropyridin-2-yl)-1H-pyrrolo[3,2-b]pyridin-2-yl]pyridin-2-yl}-2-{[3-(morpholin-4-yl)propyl]amino}acetamide,
N-(4-(3-(6-(Difluoromethyl)pyridin-2-yl)-6-(methoxy-d3)-1H-pyrrolo[3,2-b]pyridin-2-yl)pyridin-2-yl)acetamide,
N-(4-(3-(6-(Difluoromethyl)pyridin-2-yl)-6-ethoxy-1H-pyrrolo[3,2-b]pyridin-2-yl)pyridin-2-yl)acetamide,
N-(4-{3-[6-(Difluoromethyl)pyridin-2-yl]-7-ethoxy-1H-pyrrolo[3,2-b]pyridin-2-yl}pyridin-2-yl)acetamide,
N-(4-{3-[6-(Difluoromethyl)pyridin-2-yl]-7-[(dimethylamino)methyl]-1H-pyrrolo[3,2-b]pyridin-2-yl}pyridin-2-yl)acetamide,
N-(4-{3-[6-(Difluoromethyl)pyridin-2-yl]-7-(hydroxymethyl)-1H-pyrrolo[3,2-b]pyridin-2-yl}pyridin-2-yl)acetamide,
N-(4-{3-[6-(Difluoromethyl)pyridin-2-yl]-7-(1-hydroxyethyl)-1H-pyrrolo[3,2-b]pyridin-2-yl}pyridin-2-yl)acetamide,
N-(4-{3-[6-(Difluoromethyl)pyridin-2-yl]-7-[(1R)-1-hydroxyethyl]-1H-pyrrolo[3,2-b]pyridin-2-yl}pyridin-2-yl)acetamide,
N-(4-{3-[6-(Difluoromethyl)pyridin-2-yl]-7-[(1 S)-1-hydroxyethyl]-1H-pyrrolo[3,2-b]pyridin-2-yl}pyridin-2-yl)acetamide,
N-(4-{3-[6-(Difluoromethyl)pyridin-2-yl]-7-[(methylamino)methyl]-1H-pyrrolo[3,2-b]pyridin-2-yl}pyridin-2-yl)acetamide,
N-(4-{3-[6-(Difluoromethyl)pyridin-2-yl]-7-(2-hydroxypropan-2-yl)-1H-pyrrolo[3,2-b]pyridin-2-yl}pyridin-2-yl)acetamide,
N-(4-(7-(1-Hydroxyethyl)-3-(6-methoxypyridin-3-yl)-1H-pyrrolo[3,2-b]pyridin-2-yl)pyridin-2-yl)acetamide,
N-(4-(3-(6-(Difluoromethyl)pyridin-2-yl)-6-methoxy-1H-pyrrolo[3,2-b]pyridin-2-yl)pyridin-2-yl)acetamide, or
N-(4-(6-Methoxy-3-(6-methoxypyridin-3-yl)-1H-pyrrolo[3,2-b]pyridin-2-yl)pyridin-2-yl)acetamide;
or a pharmaceutically acceptable salt, tautomer or stereoisomer thereof.

10. A compound according to claim 1 selected from the following
N-{4-[3-(6-Methoxypyridin-3-yl)-1H-pyrrolo[3,2-b]pyridin-2-yl]pyridin-2-yl}acetamide,
N-{4-[6-Chloro-3-(5-methoxypyridin-2-yl)-1H-pyrrolo[3,2-b]pyridin-2-yl]pyridin-2-yl}acetamide,
N-(4-(3-(5-(Methoxy-d₃)pyridin-2-yl)-1H-pyrrolo[3,2-b]pyridin-2-yl)pyridin-2-yl)acetamide,
N-(4-(6-Chloro-3-(5-(methoxy-d3)pyridin-2-yl)-1H-pyrrolo[3,2-b]pyridin-2-yl)pyridin-2-yl)acetamide,
N-(4-(6-Fluoro-3-(5-(methoxy-d3)pyridin-2-yl)-1H-pyrrolo[3,2-b]pyridin-2-yl)pyridin-2-yl)acetamide,
N-(4-(6-Methoxy-3-(5-(methoxy-d3)pyridin-2-yl)-1H-pyrrolo[3,2-b]pyridin-2-yl)pyridin-2-yl)acetamide,
N-(4-(3-(6-(Difluoromethyl)pyridin-2-yl)-1H-pyrrolo[3,2-b]pyridin-2-yl)pyridin-2-yl)acetamide, or
N-(4-(6-Methoxy-3-(5-methoxypyridin-2-yl)-1H-pyrrolo[3,2-b]pyridin-2-yl)pyridin-2-yl)acetamide
or a pharmaceutically acceptable salt, tautomer or stereoisomer thereof.

11. A pharmaceutical composition which comprises a compound according to claim 1 or a pharmaceutically acceptable salt thereof and one or more pharmaceutically acceptable carriers, diluents or excipients.

12. A combination pharmaceutical product comprising a compound according to claim 1 or a pharmaceutically acceptable salt thereof together with one or more other therapeutically active agents.

13. A method of treating cancer in a subject in need thereof which comprises administering a therapeutically effective amount of compound according to claim 1 or a pharmaceutically acceptable salt thereof, wherein the cancer is small cell lung cancer, non-small cell lung cancer, triple-negative breast cancer, ovarian cancer, colorectal cancer, prostate cancer, melanoma, pancreatic cancer, multiple myeloma, T-acute lymphoblastic leukemia or AML.

* * * * *